(12) United States Patent
Adams et al.

(10) Patent No.: US 7,652,041 B2
(45) Date of Patent: Jan. 26, 2010

(54) CINNAMIDE AND HYDROCINNAMIDE DERIVATIVES WITH KINASE INHIBITORY ACTIVITY

(75) Inventors: Ruth S. Adams, Medford, MA (US); Emily F. Calderwood, Framingham, MA (US); Alexandra E. Gould, Cambridge, MA (US); Paul D. Greenspan, Acton, MA (US); Matthew J LaMarche, Reading, MA (US); Yuan Tian, Newton, MA (US); Tricia J. Vos, Medford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 576 days.

(21) Appl. No.: 11/332,674

(22) Filed: Jan. 12, 2006

(65) Prior Publication Data

US 2006/0160803 A1    Jul. 20, 2006

Related U.S. Application Data

(60) Provisional application No. 60/643,928, filed on Jan. 14, 2005, provisional application No. 60/710,635, filed on Aug. 23, 2005.

(51) Int. Cl.
C07D 403/02 (2006.01)
C07D 413/02 (2006.01)
A61K 31/44 (2006.01)

(52) U.S. Cl. .................. 514/341; 514/269; 514/336; 544/298; 546/268.1; 546/274.4

(58) Field of Classification Search .................. None
See application file for complete search history.

(56) References Cited

U.S. PATENT DOCUMENTS

| | | | |
|---|---|---|---|
| 2,415,554 | A | 2/1947 | Friedheim |
| 4,895,842 | A | 1/1990 | Okamoto et al. |
| 5,116,717 | A | 5/1992 | Matsushita et al. |
| 5,356,894 | A | 10/1994 | Rodney et al. |
| 5,554,624 | A | 9/1996 | Almansa et al. |
| 5,614,521 | A | 3/1997 | Naruto et al. |
| 5,763,463 | A | 6/1998 | Takefuji et al. |
| 5,990,147 | A | 11/1999 | Aslanian |
| 6,034,251 | A | 3/2000 | Aslanian et al. |
| 6,040,339 | A | 3/2000 | Yoshida et al. |
| 2003/0144278 | A1 | 7/2003 | Riedl et al. |
| 2004/0186118 | A1 | 9/2004 | Bryant et al. |
| 2004/0198743 | A1 | 10/2004 | Hey et al. |
| 2005/0049145 | A1 | 3/2005 | Bickers et al. |

FOREIGN PATENT DOCUMENTS

| | | |
|---|---|---|
| BE | 668367 | 12/1965 |
| EP | 0284632 A1 | 10/1988 |
| EP | 0369035 A1 | 5/1990 |
| EP | 0459702 A1 | 12/1991 |
| EP | 0508432 B1 | 10/1992 |
| EP | 0430884 B1 | 1/1995 |
| EP | 1028947 B1 | 8/2000 |
| EP | 1028948 B1 | 8/2000 |
| EP | 1218357 B1 | 7/2002 |
| EP | 1431267 A1 | 6/2004 |
| JP | 10-101658 | 4/1998 |
| WO | WO 93/15043 A1 | 8/1993 |
| WO | WO 96/28427 A1 | 9/1996 |
| WO | WO 96/33975 A1 | 10/1996 |
| WO | WO 98/22103 A1 | 5/1998 |
| WO | WO 99/24405 A1 | 5/1999 |
| WO | WO 01/21595 A1 | 3/2001 |
| WO | WO 01/66098 A2 | 9/2001 |
| WO | WO 01/70741 A1 | 9/2001 |
| WO | WO 02/24653 A1 | 3/2002 |
| WO | WO 02/42273 A2 | 5/2002 |
| WO | WO 03/024395 A2 | 3/2003 |
| WO | WO 2004/002977 A1 | 1/2004 |
| WO | WO 2004/019941 A1 | 3/2004 |
| WO | WO 2004/048343 A1 | 6/2004 |
| WO | WO 2004/080996 A1 | 9/2004 |
| WO | WO 2005/016870 A1 | 2/2005 |
| WO | WO 2005/020921 A2 | 3/2005 |
| WO | WO 2005/028467 A1 | 3/2005 |
| WO | WO 2006/014012 A2 | 2/2006 |

OTHER PUBLICATIONS

Atwell, G. J., et al., "Potential Antitumor Agents. 13. Bisquaternary Salts," *Journal of Medicinal Chemistry*, vol. 16, No. 6 (1973) pp. 673-678.
Okada, Yoshio, et al., "Development of Potent and Selective Plasmin and Plasma Kallikrein Inhibitors and Studies on the Structure-Activity Relationship," *Chemical & Pharmaceutical Bulletin*, vol. 48, No. 12 (2000) pp. 1964-1972.
Okada, Yoshio, et al., "Development of Plasmin and Plasma Kallikrein Selective Inhibitors and their Effect on M1 (Melanoma) and HT29 Cell Lines," *Bioorganic & Medicinal Chemistry Letters*, vol. 10 (2000) pp. 2217-2221.
International Search Report dated Jun. 22, 2006 cited in corresponding PCT application PCT/US06/001490.
"Quinolinium, 1-methyl-4-[[4-[3-[[4-[(1-methylpyridinium-4-yl)amino]phenyl]amino]-3-oxo-1-propenyl]phenyl]amino]-(CA Index Name)," CAS Registry No. 746552-49-8, entered Sep. 17, 2004.
"Propanediamide,N,N'-bis(4-methylphenyl)-2-[[3-nitro-4-(2-pyrimidinylthio)phenyl]methylene]-(CA Index Name)," CAS Registry No. 732988-78-2, entered Aug. 26, 2004.

(Continued)

Primary Examiner—Zinna N Davis

(57) ABSTRACT

The present invention provides novel cinnamide compounds useful as inhibitors of protein kinases. The invention also provides pharmaceutical compositions comprising the compounds of the invention and methods of using the compositions in the treatment of various diseases.

39 Claims, No Drawings

OTHER PUBLICATIONS

"Propanediamide, N,N'-bis(4-nitrophenyl)-2-[[3-nitro-4-(2-pyrimidinylthio)phenyl]methylene]-(CA Index Name)," CAS Registry No. 569314-01-8, entered Aug. 19, 2003.

"Propanediamide,N,N'-bis(2-methylphenyl)-2-[[3-nitro-4-(2-pyrimidinylthio)phenyl]methylene]-(CA Index Name)," CAS Registry No. 562092-83-5, entered Aug. 7, 2003.

"Propanediamide, 2-[[3-nitro-4-(2-pyrimidinylthio)phenyl]methylene]-N,N'-diphenyl- (CA Index Name)," CAS Registry No. 562060-93-9, entered Aug. 7, 2003.

"Propanediamide, N,N'-bis(2-fluorophenyl)-2-[[3-nitro-4-(2-pyrimidinylthio)phenyl]methylene]-(CA Index Name)," CAS Registry No. 562054-50-6, entered Aug. 7, 2003.

"Propanediamide, N,N'-bis(3,4-dimethylphenyl)-2-[[3-nitro-4-(2-pyrimidinylthio)phenyl]methylene]-(CA Index Name)," CAS Registry No. 562052-19-1, entered Aug. 7, 2003.

"Propanediamide, N,N'-bis(2-nitrophenyl)-2-[[3-nitro-4-(2-pyrimidinylthio)phenyl]methylene]-(CA Index Name)," CAS Registry No. 556818-85-0, entered Jul. 29, 2003.

"Propanediamide, N,N'-bis(2,4-dimethylphenyl)-2-[[3-nitro-4-(2-pyrimidinylthio)phenyl]methylene]-(CA Index Name)," CAS Registry No. 556790-23-9, entered Jul. 29, 2003.

"Quinolinium, 1-methyl-4-[[4-[3-[[4-[(1-methylpyridinium-4-yl)amino]phenyl]amino]-3-oxo-1-propenyl]phenyl]amino]-6-nitro-(9Cl) - (CA Index Name)," CAS Registry No. 50576-56-2, entered Nov. 16, 1984.

CINNAMIDE AND HYDROCINNAMIDE DERIVATIVES WITH KINASE INHIBITORY ACTIVITY

RELATED APPLICATIONS

This application claims priority from U.S. Provisional Patent Application No. 60/643,928, filed on Jan. 14, 2005, and U.S. Provisional Patent Application No. 60/710,635, filed on Aug. 23, 2005, each of which is hereby incorporated by reference in its entirety.

BACKGROUND OF THE INVENTION

1. Field of the Invention

The present invention relates to protein kinase inhibitors, particularly inhibitors of Raf-kinase. The invention also provides pharmaceutical compositions comprising the compounds of the invention and methods of using the compositions in the treatment of various diseases.

2. Background of the Invention

Protein kinases constitute a large family of structurally related enzymes that effect the transfer of a phosphate group from a nucleoside triphosphate to a Ser, Thr or Tyr residue on a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of disease states, including cancers. Of the >100 dominant oncogenes known to date, many encode receptor and cytoplasmic tyrosine kinases known to be mutated and/or over expressed in human cancers (Blume-Jensen and Hunter, *Nature*, 411:355-365 (2001)). Accordingly, protein kinase targets have attracted substantial drug discovery efforts in recent years, with several protein kinase inhibitors achieving regulatory approval (reviewed in Fischer, *Curr. Med. Chem.*, 11:1563 (2004); Dancey and Sausville, *Nature Rev. Drug Disc.*, 2:296 (2003)).

Intracellular signaling pathways activated in response to growth factor/cytokine stimulation are known to control functions such as proliferation, differentiation and cell death (Chiloeches and Marais, In *Targets for Cancer Therapy; Transcription Factors and Other Nuclear Proteins*, 179-206 (La Thangue and Bandara, eds., Totowa, Humana Press 2002)). One example is the Ras-Raf-MEK-ERK pathway which is controlled by receptor tyrosine kinase activation. Activation of Ras proteins at the cell membrane leads to phosphorylation and recruitment of accessory factors and Raf which is then activated by phosphorylation. Activation of Raf leads to downstream activation of MEK and ERK. ERK has several cytoplasmic and nuclear substrates, including ELK and Ets-family transcription factor, which regulates genes involved in cell growth, survival and migration (Marais et al., *J. Biol. Chem.*, 272:4378-4383 (1997); Peyssonnaux and Eychene, *Biol. Cell*, 93-53-62 (2001)). As a result, this pathway is an important mediator of tumor cell proliferation and angiogenesis. For instance, overexpression of constitutively active B-Raf can induce an oncogenic event in untransformed cells (Wellbrock et al., *Cancer Res.*, 64:2338-2342 (2004)). Aberrant activation of the pathway, such as by activating Ras and/or Raf mutations, is known to be associated with a malignant phenotype in a variety of tumor types (Bos, *Hematol. Pathol.*, 2:55-63 (1988); Downward, *Nature Rev. Cancer*, 3:11-22 (2003); Karasarides et al., *Oncogene*, 23:6292-6298 (2004); Tuveson, *Cancer Cell*, 4:95-98 (2003); Bos, *Cancer Res*, 49:4682-4689 (1989)). Activating mutations in B-Raf are found in 60-70% of melanomas. Melanoma cells that carry mutated B-Raf-V599E are transformed, and cell growth, ERK signaling and cell viability are dependent on mutant B-Raf function (Karasarides et al., *Oncogene*, 23:6292-6298 (2004)). Although this mutation historically has been referred to in the literature as V599E, the mutated valine actually is located at position 600 (Wellbrock et al., *Cancer Res.*, 64:2338-2342 (2004)).

There are three Raf isoforms, A-Raf, B-Raf and C-Raf (Raf-1), all of which can act as downstream effectors of Ras. Although they show significant sequence similarities, they also exhibit distinct roles in development, in addition to significant biochemical and functional differences. In particular, the high basal kinase activity of B-Raf may explain why mutated forms of only this isoform have been found in human cancers. Nevertheless, the isoforms show redundant functions in facilitating oncogenic Ras-induced activation of the MEK-ERK signaling cascade (Wellbrock, *Cancer Res*, 64:2338-2342 (2004)). In addition to Raf signaling via the MEK-ERK pathway, there is some evidence that C-Raf (and possibly B-Raf and A-Raf) may signal via alternative pathways directly involved in cell survival by interaction with the BH3 family of anti-apoptotic proteins (Wellbrock et al., *Nature Rev.: Mol. Cell Biol.*, 5:875 (2004)).

Inhibitors of the Raf kinases may be expected to interrupt the Ras-Raf signaling cascade and thereby provide new methods for the treatment of proliferative disorders, such as cancer. There is thus a need for new inhibitors of Raf kinase activity.

DESCRIPTION OF THE INVENTION

The present invention provides compounds that are effective inhibitors of Raf-kinase. These compounds are useful for inhibiting kinase activity in vitro and in vivo, and are especially useful for the treatment of various cell proliferative diseases.

Compounds useful for the methods of the invention are represented by formula (I):

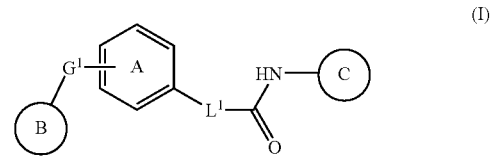

(I)

or a pharmaceutically acceptable salt thereof;

wherein:

G is —C(R$^{e'}$)(R$^e$)—, —C(O)—, —O—, —S—, —S(O)—, —S(O)$_2$—, or —N(R$^f$)—, wherein G$^1$ is attached to Ring A at the position meta or para to L$^1$;

L$^1$ is —[C(R$^g$)(R$^h$)]$_m$—C(R$^j$)(R$^k$)— or —C(R$^m$)=C(R$^n$)—;

Ring A is substituted with 0-2 occurrences of R$^a$;

Ring B is an optionally substituted mono- or bicyclic aromatic ring system having one to four ring nitrogen atoms and optionally one or two additional ring heteroatoms independently selected from oxygen and sulfur;

Ring C is an optionally substituted 5- or 6-membered aryl or heteroaryl ring having 0-3 ring nitrogen atoms and optionally one additional ring heteroatom selected from oxygen and sulfur;

$R^a$ is halo, —$NO_2$, —CN, —$OR^5$, —$SR^6$, —$S(O)R^6$, —$SO_2R^6$, $SO_2N(R^4)_2$, —$N(R^4)_2$, —$OC(O)R^5$, —$CO_2R^5$, —$C(O)N(R^4)_2$, —$N(R^4)SO_2R^6$, —$N(R^4)SO_2N(R^4)_2$, or an optionally substituted $C_{1-4}$ aliphatic;

$R^{e'}$ is hydrogen, fluoro, $C_{1-4}$ aliphatic, $C_{1-4}$ fluoroaliphatic, —$NH_2$, —$NH(C_{1-4}$ alkyl), —$N(C_{1-4}$ alkyl$)_2$, OH, or —$O(C_{1-4}$ alkyl);

$R^e$ is hydrogen, fluoro, $C_{1-4}$ aliphatic, or $C_{1-4}$ fluoroaliphatic; or $R^{e'}$ and $R^e$, taken together with the carbon atom to which they are attached, form a 3- to 6-membered cycloaliphatic or heterocyclyl ring;

$R^f$ is —H, —$C(O)R^5$, —$C(O)N(R^4)_2$, —$CO_2R^6$, —$SO_2R^6$, —$SO_2N(R^4)_2$, or an optionally substituted $C_{1-6}$ aliphatic;

$R^g$ is hydrogen, fluoro, $C_{1-4}$ aliphatic, or $C_{1-4}$ fluoroaliphatic; and $R^h$ is hydrogen, fluoro, $C_{1-4}$ aliphatic, $C_{1-4}$ fluoroaliphatic, —OH, —$O(C_{1-4}$ alkyl), —$N(R^4)_2$, —$N(R^4)C(O)(C_{1-4}$ aliphatic), —$C(O)(C_{1-4}$ alkyl), —$CO_2H$, —$CO_2(C_{1-4}$ alkyl), or —$C(O)N(R^4)_2$; or $R^g$ and $R^h$, taken together with the carbon atom to which they are attached, form a 3- to 6-membered cycloaliphatic ring;

$R^j$ is hydrogen, fluoro, $C_{1-4}$ aliphatic, or $C_{1-4}$ fluoroaliphatic; and $R^k$ is hydrogen, fluoro, $C_{1-4}$ aliphatic, $C_{1-4}$ fluoroaliphatic, —OH, —$O(C_{1-4}$ alkyl), —$C(O)(C_{1-4}$ alkyl), —$CO_2H$, —$CO_2(C_{1-4}$ alkyl), or —$C(O)N(R^4)_2$; or $R^j$ and $R^k$, taken together with the carbon atom to which they are attached, form a 3- to 6-membered cycloaliphatic ring; or each of $R^g$ and $R^j$ is hydrogen, fluoro, $C_{1-4}$ aliphatic, or $C_{1-4}$ fluoroaliphatic; and $R^h$ and $R^k$, taken together with the intervening carbon atoms, form a 3- to 6-membered cycloaliphatic ring;

$R^m$ is hydrogen, fluoro, —$OR^5$, —$C(O)R^5$, —$C(O)N(R^4)_2$, —$CO_2R^5$, —$SO_2R^6$, —$SO_2N(R^4)_2$, or an optionally substituted $C_{1-4}$ aliphatic;

$R^n$ is hydrogen, fluoro, —$C(O)R^5$, —$C(O)N(R^4)_2$, —$CO_2R^5$, —$SO_2R^6$, —$SO_2N(R^4)_2$, or an optionally substituted $C_{1-4}$ aliphatic;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

each $R^5$ independently is hydrogen or an optionally substituted aliphatic, aryl, heteroaryl, or heterocyclyl group;

each $R^6$ independently is an optionally substituted aliphatic, aryl group, or heteroaryl group; and m is 1 or 2.

Compounds of this invention include those described generally above, and are further illustrated by the classes, subclasses, and species disclosed herein. Terms used herein shall be accorded the following defined meanings, unless otherwise indicated.

The terms "Raf" and "Raf kinase" are used interchangeably, and unless otherwise specified refer to any member of the Raf family of kinase enzymes, including without limitation, the isoforms A-Raf, B-Raf, and C-Raf. These enzymes, and the corresponding genes, also may be referred to in the literature by variants of these terms, e.g., RAF, raf, BRAF, B-raf, b-raf. The isoform C-Raf also is referred to by the terms Raf-1 and C-Raf-1.

The term "aliphatic" or "aliphatic group", as used herein, means a substituted or unsubstituted straight-chain, branched, or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight or branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aryl ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, radicals derived from thiophene, furan, pyrrole, imidazole, pyrazole, triazole, tetrazole, oxazole, isoxazole, oxadiazole, thiazole, isothiazole, thiadiazole, pyridine, pyridazine, pyrimidine, pyrazine, indolizine, naphthyridine, pteridine, pyrrolopyridine, imidazopyridine, oxazolopyridine, thiazolopyridine, triazolopyridine, pyrrolopyrimidine, purine, and triazolopyrimidine. As used herein, the phrase "radical derived from" means a monovalent radical produced by removal of a hydrogen radical from the parent heteroaromatic ring system. The radical (i.e., the point of attachment of the heteroaryl to the rest of the molecule) may be created at any substitutable position on any ring of the parent heteroaryl ring system.

In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1, 2-trifluoroethyl, 1,2,2-trifluoroethyl, and pentafluoroethyl.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a C$_{1-6}$ alkylene chain.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)C(=NR$^+$)—N(R$^+$)—, —N(R$^+$)—C(=NR$^+$)—, —N(R$^+$)CO$_2$—, —N(R$^+$)SO$_2$—, —N(R$^+$)SO$_2$N(R$^+$)—, —OC(O)—, —OC(O)O—, —OC(O)N(R$^+$)—, —C(O)—, —CO$_2$—, —C(O)N(R$^+$)—, —C(O)—C(O)—, —C(=NR$^+$)—N(R$^+$)—, —C(NR$^+$)=N—, —C(=NR$^+$)—O—, —C(OR*)=N—, —C(R$^o$)=N—O—, or —N(R$^+$)—N(R$^+$)—. Each R$^+$, independently, is hydrogen or an optionally substituted aliphatic, aryl, heteroaryl, or heterocyclyl group, or two R$^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group.

Examples of C$_{3-6}$ alkylene chains that have been "interrupted" with —O— include —CH$_2$OCH$_2$—, —CH$_2$O(CH$_2$)$_2$—, —CH$_2$O(CH$_2$)$_3$—, —CH$_2$O(CH$_2$)$_4$—, —(CH$_2$)$_2$OCH$_2$—, —(CH$_2$)$_2$O(CH$_2$)$_2$—, —(CH$_2$)$_2$O(CH$_2$)$_3$—, —(CH$_2$)$_3$ O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$ZCH$_2$—, —CH$_2$Z(CH$_2$)$_2$—, —CH$_2$Z(CH$_2$)$_3$—, —CH$_2$Z(CH$_2$)$_4$—, —(CH$_2$)$_2$ZCH$_2$—, —(CH$_2$)$_2$Z(CH$_2$)$_2$—, —(CH$_2$)$_2$Z(CH$_2$)$_3$—, —(CH$_2$)$_3$Z(CH$_2$)—, —(CH$_2$)$_3$Z(CH$_2$)$_2$—, and —(CH$_2$)$_4$Z(CH$_2$)—, wherein Z is one of the "interrupting functional groups" listed above.

For purposes of clarity, all bivalent groups described herein, including, e.g., the alkylene chain linkers described above and the variables G$^1$, L$^1$, T$^1$, T$^2$, T$^3$, V$^1$, and V$^3$, are intended to be read from left to right, with a corresponding left-to-right reading of the formula or structure in which the variable appears.

One of ordinary skill in the art will recognize that when an alkylene chain having an interruption is attached to a functional group, certain combinations are not sufficiently stable for pharmaceutical use. Similarly, certain combinations of V$^1$, T$^1$ and R$^{2b}$, and certain combinations of V$^3$, T$^3$, and R$^{2d}$ would not be sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound. By way of example, in a compound of formula (I), if Ring B is substituted with two substituents —R$^b$, each substituent is selected from the group of defined values for R$^b$, and the two values selected may be the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —C≡C—R*, —OR*, —SR$^o$, —S(O)R$^o$, —SO$_2$R$^o$, —SO$_3$R*, —SO$_2$N(R$^+$)$_2$, —N(R$^+$)$_2$, —NR$^+$C(O)R*, —NR$^+$C(O)N(R$^+$)$_2$, —N(R$^+$)C(=NR$^+$)—N(R$^+$)$_2$, —N(R$^+$)C(=NR$^+$)—R$^o$, —NR$^+$CO$_2$R$^o$, —NR$^+$SO$_2$R$^o$, —NR$^+$SO$_2$N(R$^+$)$_2$, —O—C(O)R*, —O—CO$_2$R*, —OC(O)N(R$^+$)$_2$, —C(O)R*, —CO$_2$R*, —C(O)—C(O)R*, —C(O)N(R$^+$)$_2$, —C(O)N(R$^+$)—OR*, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)—C(=NR$^+$)—N(R$^+$)—OR*, —C(R$^o$)=N—OR*, —P(O)(R*)$_2$, —P(O)(OR*)$_2$, —O—P(O)—OR*, and —P(O)(NR$^+$)—N(R$^+$)$_2$, wherein R$^o$ is an optionally substituted aliphatic, aryl, or heteroaryl group, and R$^+$ and R* are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R$^o$, =N—NHSO$_2$R$^o$, or =N—R*, where each R* and R$^o$ is as defined above. Additionally, two substituents on the same carbon atom, taken together with the carbon atom to which they are attached may form an optionally substituted spirocyclic 3- to 6-membered cycloaliphatic ring.

Suitable substituents on a substitutable nitrogen atom of a heteroaryl or non-aromatic heterocyclic ring include —R*, —N(R*)$_2$, —C(O)R*, —CO$_2$R*, —C(O)—C(O)R* —C(O)

$CH_2C(O)R^*$, $-SO_2R^*$, $-SO_2N(R^*)_2$, $-C(=S)N(R^*)_2$, $-C(=NH)-N(R^*)_2$, and $-NR^*SO_2R^*$; wherein each $R^*$ is as defined above. A ring nitrogen atom of a heteroaryl or non-aromatic heterocyclic ring also may be oxidized to form the corresponding N-hydroxy or N-oxide compound. A non-limiting example of such a heteroaryl having an oxidized ring nitrogen atom is N-oxidopyridyl.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all geometric (or conformational) isomers, i.e., (Z) and (E) double bond isomers and (Z) and (E) conformational isomers, as well as all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one stereoisomer relative to another stereoisomer, the mixture may contain, for example, an enantiomeric excess of at least 50%, 75%, 90%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

In the compounds of formula (I), Ring A is additionally substituted with 0, 1, or 2 substituents $R^a$, where $R^a$ is as defined above. Preferably, $R^a$ is selected from the group consisting of halo, $C_{1-4}$ aliphatic, $C_{1-4}$ fluoroaliphatic, $-NO_2$, $-CN$, $-CO_2H$, $-O(C_{1-4}$ alkyl), $-O(C_{1-4}$ fluoroalkyl), $-S(C_{1-4}$ alkyl), $-SO_2(C_{1-4}$ alkyl), $-NH_2$, $-NH(C_{1-4}$ alkyl), $-N(C_{1-4}$ alkyl)$_2$, $-C(O)NH_2$, $-C(O)NH(C_{1-4}$ alkyl), and $-C(O)N(C_{1-4}$ alkyl)$_2$. More preferably, $R^a$ is selected from the group consisting of, $-F$, $-Cl$, $-NO_2$, $-CH_3$, $-CF_3$, $-OCH_3$, $-SCH_3$, $-SO_2CH_3$, $-CN$, $-CO_2H$, $-C(O)NH_2$, $-C(O)NHCH_3$, and $-C(O)N(CH_3)_2$. In certain preferred embodiments Ring A has no substituents $R^a$.

In one embodiment, the linker $L^1$ is a two-carbon alkenylene chain having the formula $-C(R^m)=C(R^n)-$, where $R^m$ and $R^n$ are as defined above. The substituents $R^m$ and $R^n$ may be in a cis or trans configuration relative to each other. In some embodiments, $R^m$ and $R^n$ are trans to each other. In some embodiments, $R^m$ and $R^n$ are each independently hydrogen, fluoro, $C_{1-4}$ fluoroaliphatic, or a $C_{1-4}$ aliphatic optionally substituted with one substituent selected from $-NH_2$, $-NH(C_{1-4}$ alkyl), $-N(C_{1-4}$ alkyl)$_2$, $-OH$, or $-O(C_{1-4}$ alkyl). In certain embodiments, $R^m$ is hydrogen and $R^n$ is hydrogen, fluoro, $-CH_3$, or $-CH_2OH$. As mentioned above, the bivalent group $L^1$ is intended to be read from left to right, with the carbon atom bearing $R^m$ attached to Ring A, and the carbon atom bearing $R^n$ attached to the amide carbonyl.

In another embodiment, the linker $L^1$ is a two- or three-carbon alkylene chain having the formula $-[C(R^g)(R^h)]_m-C(R^j)(R^k)-$, where each of $R^g$, $R^h$, $R^j$, $R^k$, and m is as defined above. In some embodiments, $R^h$ and $R^k$ are each independently selected from the group consisting of hydrogen, fluoro, $C_{1-4}$ alkyl, or $C_{1-4}$ fluoroalkyl. In some embodiments, the carbon atoms in $L^1$ are substituted with 0, 1, or 2, preferably 0 or 1, non-hydrogen substituents. In certain preferred embodiments, $L^1$ is $-CH_2-CH_2-$ or $-CH_2-CH_2-CH_2-$. As mentioned above, the bivalent group $L^1$ is intended to be read from left to right, with the carbon atom bearing W and $R^h$ attached to Ring A, and the carbon atom bearing $R^j$ and $R^k$ attached to the amide carbonyl.

The linker $G^1$ is a one-atom linker selected from the group consisting of $-C(R^{e'})(R^e)-$, $-C(O)-$, $-O-$, $-S-$, $-S(O)-$, $-S(O)_2-$, or $-N(R^f)-$, where each of $R^{e'}$, $R^e$, and $R^f$ is as defined above. The linker $G^1$ is attached to Ring A at the positional meta or para to $L^1$. When $L^1$ is $-C(R^m)=C(R^n)-$, $G^1$ preferably is attached to Ring A at the position meta to $L^1$.

When $G^1$ is a carbon linker, $R^{e'}$ and $R^e$ preferably are each independently hydrogen, fluoro, $C_{1-4}$ aliphatic, or $C_{1-4}$ fluoroaliphatic. Alternatively, $R^{e'}$ and $R^e$, taken together with the carbon atom to which they are attached, form a 3- to 6-membered cycloaliphatic or heterocyclyl ring, preferably a cyclopropyl ring. In some embodiments, each of $R^{e'}$ and $R^e$ is hydrogen. When $G^1$ is a nitrogen linker, $R^f$ preferably is hydrogen, $-C(O)R^5$, or an optionally substituted $C_{1-4}$ aliphatic. More preferably, $R^f$ is hydrogen. Most preferably, $G^1$ is $-O-$ or $-NH-$.

In some embodiments of the present invention, the compound of formula (I) is characterized by one or more of the following features:

(a) each $R^a$ independently is $-F$, $-Cl$, $-CN$, $-NO_2$, $C_{1-4}$ alkyl, $-CF_3$, $-O(C_{1-4}$ alkyl), $-OCF_3$, $-S(C_{1-4}$ alkyl), $-SO_2(C_{-4}$ alkyl), $-NH_2$, $-NH(C_{1-4}$ alkyl), $-N(C_{1-4}$ alkyl)$_2$, $-CO_2H$, $-C(O)NH_2$, or $-C(O)NH(C_{1-4}$ alkyl);

(b) $R^h$ and $R^k$ are each independently hydrogen, fluoro, $C_{1-4}$ alkyl, or $C_{1-4}$ fluoroalkyl;

(c) $L^1$ is $-C(R^m)=C(R^n)-$, and $R^m$ and $R^n$ are trans to each other;

(d) $R^m$ and $R^n$ are each independently hydrogen, fluoro, $C_{1-4}$ fluoroaliphatic, or a $C_{1-4}$ aliphatic optionally substituted with one substituent selected from $-NH_2$, $-NH(C_{1-4}$ alkyl), $-N(C_{1-4}$ alkyl)$_2$, $-OH$, or $-O(C_{1-4}$ alkyl);

(e) $L^1$ is $-CH_2-CH_2-$ or $-CH_2-CH_2-CH_2-$; and (f) $G^1$ is $-O-$ or $-NH-$.

In the compounds of formula (I), Ring B is an optionally substituted mono- or bicyclic heteroaryl having one to four ring nitrogen atoms and optionally one or two additional ring heteroatoms selected from oxygen and sulfur. Each substitutable ring nitrogen atom in Ring B is unsubstituted or substituted, preferably with $-C(O)R^5$, $-C(O)N(R^4)_2$, $-CO_2R^6$, $-SO_2R^6$, $-SO_2N(R^4)_2$, $C_{1-4}$ aliphatic, an optionally substituted $C_{6-10}$ aryl, or a $C_{6-10}$ ar($C_{1-4}$)alkyl, the aryl portion of which is optionally substituted. One ring nitrogen atom in Ring B optionally is oxidized. In some embodiments, the substitutable ring nitrogen atoms in Ring B all are unsubstituted, and one ring nitrogen atom optionally is oxidized.

In some embodiments, Ring B is a radical derived from an aromatic ring system selected from the group consisting of pyrrole, oxazole, thiazole, imidazole, pyrazole, isoxazole, isothiazole, oxadiazole, triazole, thiadiazole, pyridine, pyridazine, pyrimidine, pyrazine, triazine, indolizine, indole, isoindole, imidazole, benzimidazole, benzthiazole, benzoxazole, pyrrolopyridine, imidazopyridine, oxazolopyridine, thiazolopyridine, triazolopyridine, pyrrolopyrimidine, purine, triazolopyrimidine, quinoline, isoquinoline, cinnoline, phthalazine, quinazoline, quinoxaline, naphthyridine, and pteridine. Any such ring system optionally is substituted on any substitutable ring carbon or ring nitrogen atom, one ring nitrogen atom optionally is oxidized, and the point of attachment connecting Ring B to $G^1$ may be on either ring when Ring B is a radical derived from a bicyclic ring system.

Preferably, Ring B is a radical derived from pyrrole, oxazole, thiazole, imidazole, pyrazole, isoxazole, pyridine, pyridazine, pyrimidine, pyrazine, pyrrolopyridine, imidazolopyridine, pyrazolopyridine, triazolopyridine, pyrrolopyrimidine, purine, pyrazolopyrimidine, triazolopyrimidine, benzimidazole, or benzthiazole, wherein Ring B optionally is substituted on any substitutable ring carbon or ring nitrogen atom, and one ring nitrogen atom optionally is oxidized. In certain preferred embodiments, Ring B is an optionally substituted pyridyl or N-oxidopyridyl.

Substitutable ring carbon atoms in Ring B preferably are substituted with 0-2 $R^b$ and 0-2 $R^{8b}$. Each $R^{8b}$ independently is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$. Each $R^b$ independently is halo, —NO$_2$, —CN, —C($R^5$)=C($R^5$)$_2$, —C≡C—$R^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, —C(R$^6$)=N—OR$^5$, or an optionally substituted aliphatic, aryl, heteroaryl, or heterocyclyl.

In some embodiments, each $R^b$ independently is selected from the group consisting of $C_{1-6}$ aliphatic, $C_{1-6}$ fluoroaliphatic, halo, —$R^{1b}$, —$R^{2b}$, -T$^1$-$R^{1b}$, -T$^1$-$R^{2b}$, —V$^1$-T$^1$-$R^{1b}$, and —V$^1$-T$^1$-$R^{2b}$. The variables $T^1$, $V^1$, $R^{1b}$, and $R^{2b}$ have the values described below.

$T^1$ is a $C_{1-4}$ alkylene chain optionally substituted with $R^{3a}$ or $R^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)C(=NR$^4$)—N(R$^4$)—, —N(R$^4$)C(=NR$^4$)—, —N(R$^4$)CO$_2$—, —N(R$^4$)SO$_2$—, —N(R$^4$)SO$_2$N(R$^4$)—, —OC(O)—, —OC(O)N(R$^4$)—, —C(O)—, —CO$_2$—, —C(O)N(R$^4$)—, —C(=NR$^4$)—N(R$^4$)—, —C(NR$^4$)=N(R$^4$)—, —C(=NR$^4$)—O—, or —C(R$^6$)=N—O—, and wherein $T^1$ or a portion thereof optionally forms part of a 3-7 membered ring. In some embodiments, $T^1$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —CO$_2$H, —CO$_2$($C_{1-4}$ alkyl), —C(O)NH$_2$, and —C(O)NH($C_{1-4}$ alkyl), wherein the alkylene chain optionally is interrupted with —N(R$^4$)—, —C(=NR$^4$)—N(R$^4$)—, —C(NR$^4$)=N(R$^4$)—, —N(R$^4$)—C(=NR$^4$)—, —N(R$^4$)—C(O)—, or —C(O)N(R$^4$)—. In some particular embodiments, $T^1$ is a $C_{1-6}$ or $C_{1-4}$ alkylene chain optionally substituted with —F, $C_{1-3}$ alkyl, or $C_{1-3}$ fluoroalkyl, wherein the alkylene chain optionally is interrupted by —N(R$^4$)—, —C(O)—N(R$^4$)—, —C(=NR$^4$)—N(R$^4$)—, —C(NR$^4$)=N(R$^4$)—, —N(R$^4$)—C(O)—, or —N(R$^4$)—C(=NR$^4$)—. In certain particular embodiments, $T^1$ is a $C_{1-4}$ alkylene chain optionally substituted with —F, $C_{1-3}$ alkyl, or $C_{1-3}$ fluoroalkyl.

$V^1$ is —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)C(=NR$^4$)—N(R$^4$)—, —N(R$^4$)C(=NR$^4$)—, —N(R$^4$)CO$_2$—, —N(R$^4$)SO$_2$—, —N(R$^4$)SO$_2$N(R$^4$)—, —OC(O)—, —OC(O)N(R$^4$)—, —C(O)—, —CO$_2$—, —C(O)N(R$^4$)—, —C(O)N(R$^4$)—, —C(O)N(R$^4$)—O—, —C(O)N(R$^4$)C(=NR$^4$)—N(R$^4$)—, —N(R$^4$)C(=NR$^4$)—N(R$^4$)—C(O)—, —C(=NR$^4$)—N(R$^4$)—, —C(NR$^4$)=N(R$^4$)—, —C(=NR$^4$)—O—, or —C(R$^6$)=N—O—. In some embodiments, $V^1$ is —C(R$^5$)=C(R$^5$)—, —C≡C—, —O—, —N(R$^4$)—, —N(R$^4$)C(O)—, —C(O)N(R$^4$)—, —C(=NR$^4$)—N(R$^4$)—, —C(NR$^4$)=N(R$^4$)—, or —N(R$^4$)—C(=NR$^4$)—. In certain preferred embodiments, $V^1$ is —N(R$^4$)—, —N(R$^4$)—C(O)—, —C(O)N(R$^4$)—, —C(=NR$^4$)N(R$^4$)—, or —N(R$^4$)—C(=NR$^4$)—. In certain particular embodiments, $V^1$ is —N(R$^{4x}$)—, —N(R$^{4x}$)—C(O)—, —C(O)N(R$^{4x}$)—, —C(=NR$^{4x}$)N(R$^{4x}$)—, or —N(R$^{4x}$)—C(=NR$^{4x}$)—, where $R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted. In some embodiments, $V^1$ is —C(O)NH—, —NH—C(O)—, or —C(=NH)NH—.

Each $R^{1b}$ independently is an optionally substituted aryl, heteroaryl, heterocyclyl, or cycloaliphatic ring. In some embodiments, $R^{1b}$ is an optionally substituted $C_{3-6}$ cycloaliphatic or an optionally substituted phenyl, azetidinyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl. In certain preferred embodiments, $R^{1b}$ is an optionally substituted $C_{3-6}$ cycloaliphatic or an optionally substituted pyrrolidinyl, piperidinyl, morpholinyl, or piperazinyl ring.

Each $R^{2b}$ independently is —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$), —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^5$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, or —C(R$^6$)=N—OR$^5$. In some embodiments, each $R^{2b}$ independently is —OR$^5$, —N(R$^4$)$_2$, —NR$^4$C(O)R$^5$, —NR$^4$C(O)N(R$^4$)$_2$, —C(O)N(R$^4$)—OR$^5$, —C(O)N(R$^4$)$_2$, —N(R$^4$)—CO$_2$R$^5$, —N(R$^4$)—C(=NR$^4$)—R$^5$ or —C(=NR$^4$)—N(R$^4$)$_2$. In some embodiments, each $R^{2b}$ independently is —N(R$^4$)$_2$, —NR$^4$C(O)R$^5$, —C(O)N(R$^4$)$_2$, —CO$_2$R$^5$, or —OR$^5$.

Each $R^{3a}$ independently is selected from the group consisting of —F, —OH, —O($C_{1-4}$ alkyl), —CN, —N(R$^4$)$_2$, —C(O)($C_{1-4}$ alkyl), —CO$_2$H, —CO$_2$($C_{1-4}$ alkyl), —C(O)NH$_2$, and —C(O)NH($C_{1-4}$ alkyl).

Each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6 membered cycloaliphatic ring.

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group.

Each $R^6$ independently is an optionally substituted aliphatic, aryl, or heteroaryl group.

Each $R^7$ independently is an optionally substituted aryl or heteroaryl ring.

In some embodiments, the substitutable ring carbon atoms in Ring B are substituted with 0-1 $R^b$ and 0-2 $R^{8b}$. More preferably, the substitutable ring carbon atoms in Ring B are substituted with 0-1 $R^b$ and 0-1 $R^{8b}$. In such embodiments, $R^b$ preferably is selected from the group consisting of $C_{1-4}$ aliphatic, $C_{1-4}$ fluoroaliphatic, halo, —$R^{1b}$, —$R^{2b}$, -$T^1$-$R^{1b}$-$T^1$-$R^{2b}$, —$V^1$-$T^1$-$R^{1b}$, and —$V^1$-$T^1$-$R^{2b}$, where:

$T^1$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —$CO_2H$, —$CO_2$($C_{1-4}$ alkyl), —C(O)$NH_2$, and —C(O)NH($C_{1-4}$ alkyl), wherein the alkylene chain optionally is interrupted with —N($R^4$)—, —C(=N$R^4$)—N($R^4$)—, —C(N$R^4$)=N($R^4$)—, —N($R^4$)—C(=N$R^4$)—, —N($R^4$)—C(O)—, or —C(O)N($R^4$)—;

$V^1$ is —C($R^5$)=C($R^5$)—, —C≡C—, —O—, —N($R^4$)—, —N($R^4$)C(O)—, —C(O)N($R^4$)—, —C(=N$R^4$)—N($R^4$)—, —C(N$R^4$)=N($R^4$)—, or —N($R^4$)—C(=N$R^4$)—;

each $R^{1b}$ independently is an optionally substituted aryl, heteroaryl, heterocyclyl, or cycloaliphatic ring; and each $R^{2b}$ independently is —$NO_2$, —CN, —C($R^5$)=C($R^5$)$_2$, —C≡C—$R^5$, —$OR^5$, —$SO_2R^6$, —$SO_2N(R^4)_2$, —N($R^4$)$_2$, —$NR^4C(O)R^5$, —$NR^4C(O)N(R^4)_2$, —N($R^4$)C(=N$R^4$)—N($R^4$)$_2$, —N($R^4$)C(=N$R^4$)—$R^6$, —$NR^4CO_2R^6$, —N($R^4$)$SO_2R^6$, —N($R^4$)$SO_2N(R^4)_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^4$, —C(=N$R^4$)—N($R^4$)$_2$, —C(=N$R^4$)—$OR^5$, —C(=N$R^4$)—N($R^4$)—$OR^5$, or —C($R^6$)=N—$OR^5$.

In the compounds of formula (I), Ring C is an optionally substituted 5- or 6-membered aryl or heteroaryl ring having 0-3 ring nitrogen atoms and optionally one additional ring heteroatom selected from oxygen and sulfur. In some embodiments, two adjacent substituents on Ring C, taken together with the intervening ring atoms, form an optionally substituted fused 5- or 6-membered aromatic or non-aromatic ring having 0-3 ring heteroatoms selected from the group consisting of O, N, and S.

In some embodiments, Ring C is an optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, or triazinyl, wherein one ring nitrogen atom in Ring C optionally is oxidized.

Each substitutable ring nitrogen atom in Ring C is unsubstituted or is substituted with —C(O)$R^5$, —C(O)N($R^4$)$_2$, —$CO_2R^6$, —$SO_2R^6$, —$SO_2N(R^4)_2$, or a $C_{1-4}$ aliphatic optionally substituted with —F, —OH, —O($C_{1-4}$ alkyl), —CN, —N($R^4$)$_2$, —C(O)($C_{1-4}$ alkyl), —$CO_2H$, —$CO_2$($C_1$, alkyl), —C(O)$NH_2$, —C(O)NH($C_{1-4}$ alkyl), or an optionally substituted $C_{6-10}$ aryl ring. One ring nitrogen atom in Ring C optionally is oxidized. In some embodiments, each substitutable ring nitrogen atom in Ring C is unsubstituted, and one ring nitrogen atom optionally is oxidized.

Substitutable ring carbon atoms in Ring C preferably are substituted with 0-2 $R^c$ and 0-2 $R^{8c}$. Each $R^{8c}$ independently is selected from the group consisting of $C_{1-4}$ aliphatic, $C_{1-4}$ fluoroaliphatic, —O($C_{1-4}$ alkyl), —O($C_{1-4}$ fluoroalkyl), and halo. In some embodiments, $R^{8c}$ is selected from the group consisting of halo, methyl, trifluoromethyl, ethyl, isopropyl, cyclopropyl, tert-butyl, methoxy, and trifluoromethoxy.

Each $R^c$ independently is halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2R^6$, —$SO_2N(R^4)_2$, —N($R^4$)$_2$, —$NR^4C(O)R^5$, —$NR^4C(O)N(R^4)_2$, —N($R^4$)C(=N$R^4$)—N($R^4$)$_2$, —N($R^4$)C(=N$R^4$)—$R^6$, —$NR^4CO_2R^6$, —N($R^4$)$SO_2R^6$, —N($R^4$)$SO_2N(R^4)_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—$OR^5$, —C(=N$R^4$)—N($R^4$)—$OR^5$, —C($R^6$)=N—$OR^5$, or an optionally substituted aliphatic, aryl, heteroaryl, or heterocyclyl; or two adjacent $R^c$, taken together with the intervening ring atoms, form an optionally substituted fused 5- or 6 membered aromatic or non-aromatic ring having 0-3 ring heteroatoms independently selected from the group consisting of O, N, and S.

In some embodiments, each $R^c$ independently is selected from the group consisting of $C_{1-6}$ aliphatic, $C_{1-6}$ fluoroaliphatic, halo, —$R^{1c}$, —$R^{2c}$, -$T^2$-$R^{2c}$, and -$T^2$-$R^{1c}$. The variables $T^2$, $R^{1c}$, and $R^{2c}$ have the values described below.

$T^2$ is a $C_{1-6}$ alkylene chain optionally substituted with $R^{3a}$ or $R^{3b}$, wherein the alkylene chain optionally is interrupted by —C($R^5$)=C($R^5$)—, —C≡C—, —O—, —S—, —S(O)—, —S(O)$_2$—, —$SO_2N(R^4)$—, —N($R^4$)—, —N($R^4$)C(O)—, —$NR^4C(O)N(R^4)$—, —N($R^4$)$CO_2$—, —N($R^4$)$SO_2$—, —C(O)N($R^4$)—, —C(O)—, —$CO_2$—, —OC(O)—, or —OC(O)N($R^4$)—, and wherein $T^2$ or a portion thereof optionally forms part of a 3-7 membered ring. In some embodiments, $T^2$ is a $C_{1-4}$ or $C_{2-4}$ alkylene chain optionally substituted with $R^{1a}$ or $R^{3b}$. In some embodiments, $T^2$ is a $C_{1-4}$ alkylene chain optionally substituted with one or two groups independently selected from —F, $C_{1-4}$ aliphatic, and $C_{1-4}$ fluoroaliphatic.

Each $R^{1c}$ independently is an optionally substituted aryl, heteroaryl, heterocyclyl, or cycloaliphatic ring.

Each $R^{2c}$ independently is —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4C(O)R^5$, —$NR^4C(O)N(R^4)_2$, —N($R^4$)C(=N$R^4$)—N($R^4$)$_2$, —N($R^4$)C(=N$R^4$)—$R^6$, —$NR^4CO_2R^6$, —N($R^4$)$SO_2R^6$, —N($R^4$)$SO_2N(R^4)_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—$OR^5$, —C(=N$R^4$)—N($R^4$)—$OR^{51}$, or —C($R^6$)=N—$OR^5$. In some embodiments, each $R^{2c}$ independently is —CN, —C($R^5$)=C($R^5$)$_2$, —C≡C—$R^5$, —$OR^5$, —$SR^6$, —N($R^4$)$_2$, —$NR^4C(O)R^5$, —$NR^4C(O)N(R^4)_2$, —$NR^4CO_2R^6$, —$CO_2R^5$, or —C(O)N($R^4$)$_2$.

The variables $R^{3a}$, $R^{3b}$, $R^4$, $R^5$, $R^6$, and $R^7$ have the values described above for Ring B.

In some embodiments, the substitutable ring carbon atoms in Ring C are substituted with 0-2 $R^c$ and 0-1 $R^{8c}$, where:

each $R^c$ preferably is selected from the group consisting of $C_{1-4}$ aliphatic, $C_{1-4}$ fluoroaliphatic, halo, —$R^{2c}$ and -$T^2$-$R^{2c}$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$T^2$ is a $C_{1-4}$ alkylene chain optionally substituted with one or two groups independently selected from —F, $C_{1-4}$ aliphatic, and $C_{1-4}$ fluoroaliphatic;

each $R^{2c}$ independently is —CN, —C($R^5$)=C($R^4$)$_2$, —C≡C—$R^5$, —$OR^5$, —$SR^6$, —N($R^4$)$_2$, —$NR^4C(O)R^5$, —$NR^4C(O)N(R^4)_2$, —$NR^4CO_2R^6$, —$CO_2R^5$, and —C(O)N($R^4$)$_2$; and each $R^{8c}$ independently is selected from the group consisting of $C_{1-4}$ aliphatic, $C_{1-4}$ fluoroaliphatic, —O($C_{1-4}$ alkyl), —O($C_{1-4}$ fluoroaliphatic), and halo.

In some embodiments, the substitutable ring carbon atoms in Ring C are substituted with 0-2 $R^c$ and 0-1 $R^{8c}$, where:

each $R^c$ independently is halo, —CN, —C($R^{5x}$)=C($R^{5x}$)($R^{5y}$), —C≡C—$R^{5y}$, —O$R^{5y}$, —S$R^{6x}$, —N($R^{4x}$)($R^{4y}$), —CO$_2R^{5x}$, —C(O)N($R^{4x}$)($R^{4y}$), or a $C_{1-4}$ aliphatic or $C_{1-4}$ fluoroaliphatic optionally substituted with one or two substituents independently selected from the group consisting of —O$R^{5x}$, —N($R^{4x}$)($R^{4y}$), —S$R^{6x}$, —CO$_2R^{5x}$, or —C(O)N($R^{4x}$)($R^{4y}$); or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted, or two $R^{4x}$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

$R^{4y}$ is hydrogen, $C_{6-10}$ ar($C_{1-4}$)alkyl, the aryl portion of which may be optionally substituted, an optionally substituted 5- or 6-membered aryl, heteroaryl, or heterocyclyl ring, or a $C_{1-4}$ alkyl or $C_{1-4}$ fluoroalkyl optionally substituted with one or two substituents independently selected from the group consisting of —O$R^{5x}$, —N($R^{4x}$)$_2$, —CO$_2R^{5x}$, or —C(O)N($R^{4x}$)$_2$; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring;

each $R^{5y}$ independently is hydrogen, an optionally substituted $C_{6-10}$ aryl, a $C_{6-10}$ar($C_{1-4}$)alkyl, the aryl portion of which may be optionally substituted, or a $C_{1-4}$ alkyl or $C_{1-4}$ fluoroalkyl optionally substituted with one or two substituents independently selected from the group consisting of —O$R^{5x}$, —N($R^{4x}$)$_2$, —CO$_2R^{5x}$, or —C(O)N($R^{4x}$)$_2$; and each $R^{6x}$ independently is $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

In some embodiments, Ring C is a 5- or 6-membered heteroaryl substituted with 0-2 $R^c$. In some such embodiments, each $R^c$ independently is selected from the group consisting of -halo, $C_{1-4}$ alkyl, $C_{1-4}$ fluoroalkyl, —O($C_{1-4}$ alkyl), and —O($C_{1-4}$ fluoroalkyl), or two adjacent $R^c$, taken together with the intervening ring atoms, form an optionally substituted fused 5- or 6-membered aromatic or non-aromatic ring having 0-3 ring heteroatoms selected from the group consisting of O, N, and S.

In certain such embodiments, Ring C is selected from the group consisting of:

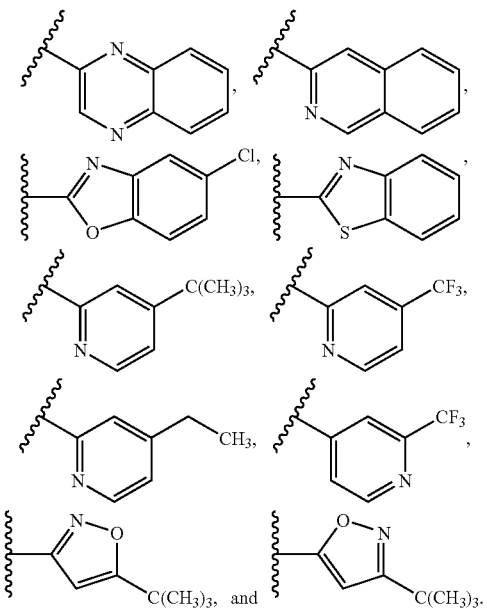

Another embodiment of the invention relates to a compound of formula (I), wherein Ring C is an optionally substituted phenyl. Such compounds have the formula (II):

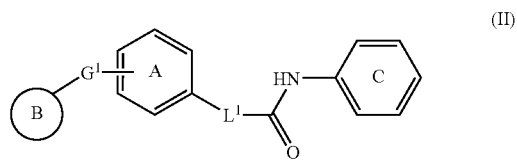

or a pharmaceutically acceptable salt thereof, wherein:

Ring C is substituted with 0-2 $R^c$ and 0-1 $R^{8c}$; and

Ring A, Ring B, and the variables $G^1$, $L^1$, $R^a$, $R^c$, and $R^{8c}$ have the values and preferred values described above for formula (I).

In the compounds of formula (II), when $L^1$ is —[C($R^g$)($R^h$)]$_m$—C($R^j$)($R^k$)—, and $G^1$ is —CH$_2$— in the para position, Ring B preferably is other than imidazole.

In some embodiments, Ring C in formula (II) is selected from the group consisting of:

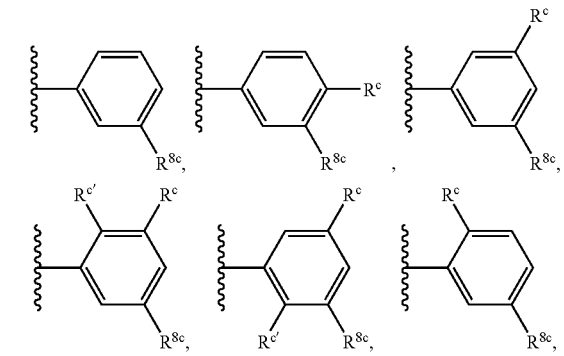

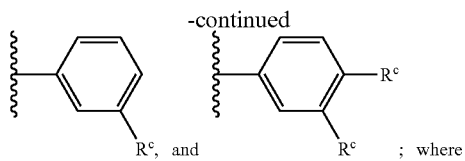

each $R^c$ independently is halo, —CN, —C($R^{5x}$)=C($R^{5x}$)($R^{5y}$), —C≡C—$R^{5y}$, —O$R^{5y}$, —S$R^{6x}$, —N($R^{4x}$)($R^{4y}$), —CO$_2R^{5x}$, —C(O)N($R^{4x}$)($R^{4y}$), or a $C_{1-4}$ aliphatic or $C_{1-4}$ fluoroaliphatic optionally substituted with one or two substituents independently selected from the group consisting of —O$R^{5x}$, —N($R^{4x}$)($R^{4y}$), —S$R^{6x}$, —CO$_2R^{5x}$, or —C(O)N($R^{4x}$)($R^{4y}$); or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$R^{c'}$ is $C_{1-4}$ aliphatic, $C_{1-4}$ fluoroaliphatic, halo, —CN, —OH, —O($C_{1-4}$ alkyl), —O($C_{1-4}$ fluoroalkyl), —S($C_{1-4}$ alkyl), —NH$_2$, —NH($C_{1-4}$ alkyl), or —N($C_{1-4}$ alkyl)$_2$;

$R^{8c}$ is $C_{1-4}$ aliphatic, $C_{1-4}$ fluoroaliphatic, or halo; and the variables $R^{4x}$, $R^{4y}$, $R^{5x}$, $R^{5y}$, and $R^{6x}$ have the values described above for formula (I).

In certain embodiments, Ring C is selected from the group consisting of:

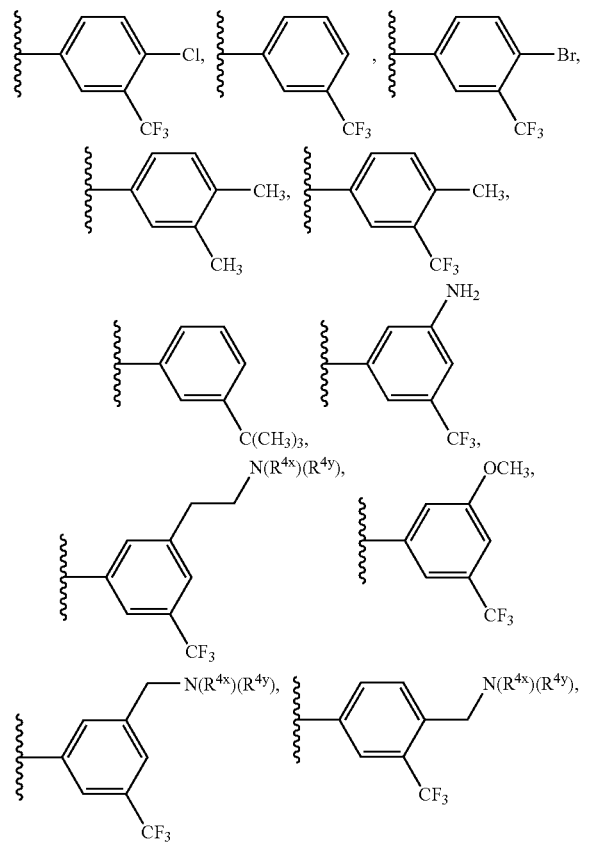

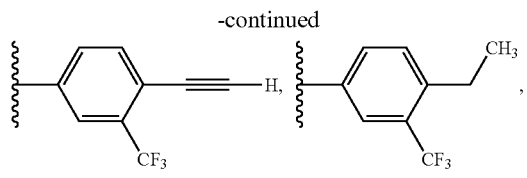

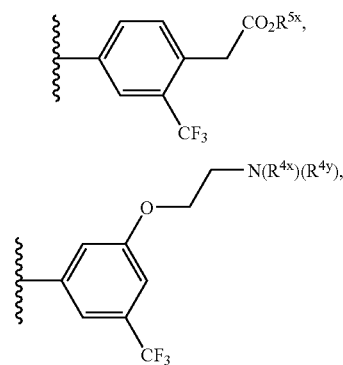

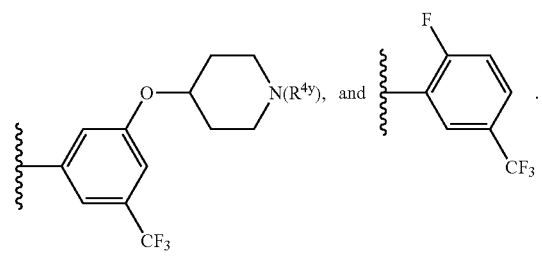

In certain other embodiments, Ring C is selected from the group consisting of:

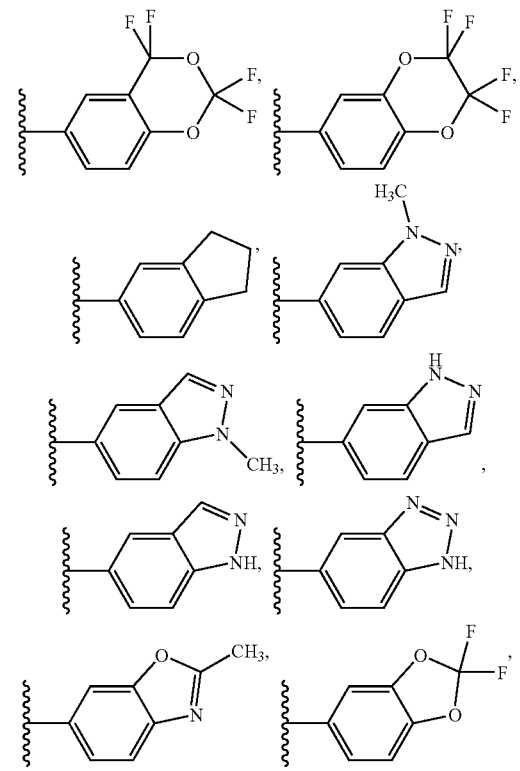

-continued

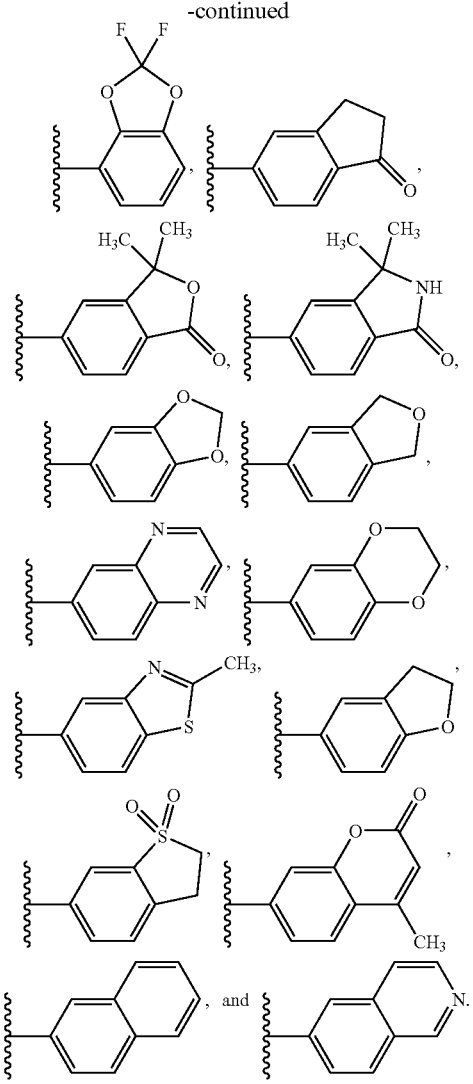

The invention also relates to a subgenus of the compounds of formula (I), characterized by formula (III):

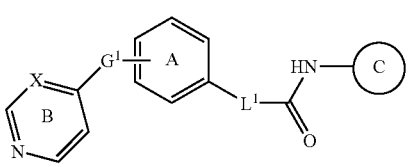

(III)

or a pharmaceutically acceptable salt thereof, wherein:
X is CH or N;
Ring B is substituted with 0-1 $R^b$ and 0-1 $R^{8b}$, and one nitrogen atom in Ring B optionally is oxidized; and
Ring A, Ring C, and the variables $G^1$, $L^1$, $R^b$, and $R^{8b}$ have the values and preferred values described above for formulae (I) and (II).

In a more particular embodiment, the invention relates to a compound of formula (IV):

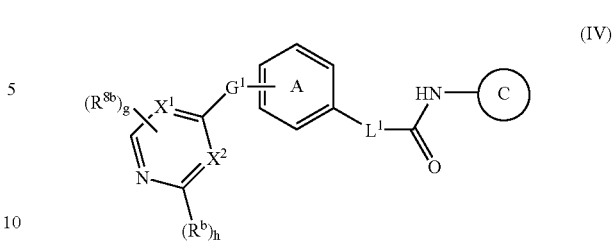

(IV)

or a pharmaceutically acceptable salt thereof;

wherein:
$X^1$ and $X^2$ are each independently CH or N, provided that $X^1$ and $X^2$ are not both N;
g is 0 or 1;
h is 0 or 1; and
Rings A and C, and the variables $L^1$, $G^1$, $R^b$, and $R^{8b}$ have the values and preferred values described above for formulae (I) and (II).

In some embodiments, the invention relates to a compound of formula (IV) or a pharmaceutically acceptable salt thereof, wherein $R^b$ is selected from the group consisting of halo, —N($R^4$)$_2$, —CO$_2$R$^5$, —C(O)—N($R^4$)$_2$, —C(O)—N($R^4$)—OR$^5$, —N($R^4$)C(O)R$^5$, —N($R^4$)C(O)—OR$^5$, —N($R^4$)C(O)—N($R^4$)$_2$, —N($R^4$)SO$_2$R$^6$, —C(=N$R^4$)N($R^4$)$_2$, and —C(=N$R^4$)N($R^4$)—OR$^5$. In some embodiments, $R^b$ is —N($R^4$)$_2$, —C(O)—N($R^4$)$_2$, —N($R^4$)C(O)R$^5$, —C(=N$R^4$)N($R^4$)$_2$, or —C(=N$R^4$)N($R^4$)—OR$^5$.

In some embodiments, $R^b$ is selected from the group consisting of halo, —N($R^{4x}$)($R^{4z}$), —CO$_2$R$^{5x}$, —C(O)—N($R^{4x}$)($R^{4z}$), —C(O)—N($R^{4x}$)—OR$^{5x}$, —N($R^{4x}$)C(O)R$^{5x}$, —N($R^{4x}$)C(O)—OR$^{5x}$, —N($R^{4x}$)C(O)—N($R^{4x}$)($R^{4z}$), —N($R^{4x}$)SO$_2$R$^{6x}$, —C(=N$R^{4x}$)N($R^{4x}$)($R^{4z}$), and —C(=N$R^{4x}$)N($R^{4x}$)—OR$^{5x}$. In certain such embodiments, $R^b$ is selected from the group consisting of halo, —NH($R^{4z}$), —N($R^{4x}$)($R^{4z}$), —CO$_2$R$^{5x}$, —C(O)—NH($R^{4z}$), —C(O)—N($R^{4x}$)($R^{4z}$), —C(O)—NH—OR$^{5x}$, —NHC(O)R$^{5x}$, —NHC(O)—OR$^{5x}$, —NHC(O)—N($R^{4x}$)($R^{4z}$), —NHSO$_2$R$^{6x}$, —C(=NH)N($R^{4x}$)($R^{4z}$), —C(=NH)N($R^{4x}$)($R^{4z}$), and —C(=NH)NH—OR$^{5x}$.

In these embodiments, each $R^{4x}$ independently is hydrogen, $C_{1-4}$ alkyl, $C_{1-4}$ fluoroalkyl, or $C_{6-10}$ ar($C_{1-4}$)alkyl, the aryl portion of which may be optionally substituted, and each $R^{4z}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted 4- to 8 membered heterocyclyl ring having, in addition to the nitrogen atom, 0-2 ring heteroatoms independently selected from N, O, and S. In some embodiments, $R^{4x}$ and $R^{4z}$, taken together with the nitrogen atom to which they are attached, form an optionally substituted morpholinyl, piperidinyl, piperazinyl, or pyrrolidinyl ring.

Each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

Each $R^{6x}$ independently is $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

In some embodiments, $R^b$ is —N($R^{4x}$)($R^{4z}$), —C(O)—N($R^{4x}$)($R^{4z}$), or —C(=NH)N($R^{4x}$)($R^{4z}$), where $R^{4x}$ and $R^{4z}$, taken together with the nitrogen atom to which they are attached, form a morpholinyl, piperidinyl, piperazinyl, or pyrrolidinyl ring.

In other embodiments, the invention relates to a compound of formula (IV) or a pharmaceutically acceptable salt thereof, wherein $R^b$ is —$V^1$-$T^1$-$R^{1b}$ or —$V^1$-$T^1$-$R^{2b}$, where the variables $V^1$, $T^1$, $R^{1b}$, and $R^{2b}$ have the values described below.

$V^1$ is —N($R^4$)—, —N($R^4$)—C(O)—, —N($R^4$)SO$_2$$R^6$, —N($R^4$)C(O)—OR$^5$, —C(O)N($R^4$)—, —C(=N$R^4$)N($R^4$)—, or —N($R^4$)—C(=N$R^4$)—. In some embodiments, $V^1$ is —N($R^{4x}$)—, —N($R^{4x}$)—C(O)—, —C(O)N($R^{4x}$)—, —C(=N$R^{4x}$)N($R^{4x}$)—, or —N($R^{4x}$)—C(=N$R^{4x}$)—, where $R^{4x}$ has the values described above in connection with formula (IV). In some embodiments, $V^1$ is —C(O)—NH—, —NH—C(O)—, or —C(=NH)NH—.

$T^1$ is a $C_{1-4}$ alkylene chain optionally substituted with —F, $C_{1-3}$ alkyl, or $C_{1-3}$ fluoroalkyl.

$R^{1b}$ is an optionally substituted $C_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring. In some embodiments, $R^{1b}$ is an optionally substituted $C_{3-6}$ cycloaliphatic or an optionally substituted pyrrolidinyl, piperidinyl, morpholinyl, or piperazinyl.

$R^{2b}$ is —N($R^4$)$_2$, —NR$^4$C(O)R$^5$, —C(O)N($R^4$)$_2$, —CO$_2$R$^5$, or —OR$^5$.

In certain such embodiments, $R^b$ is selected from the group consisting of:

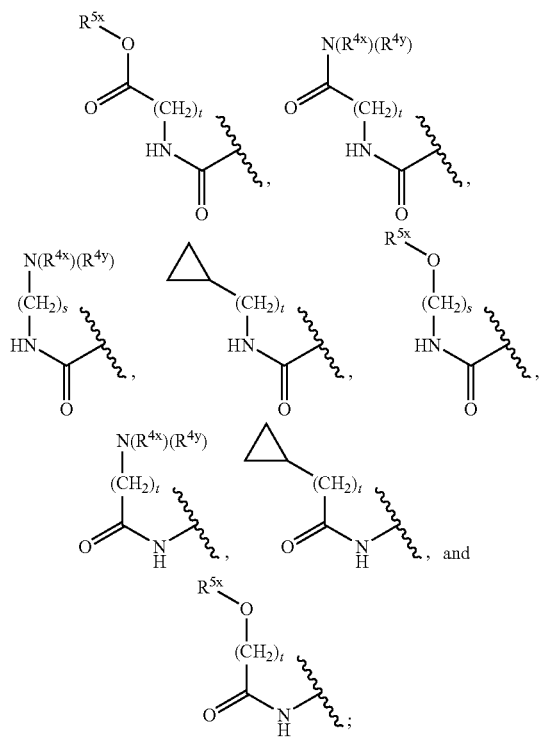

s is 2 or 3, and t is 1, 2, or 3.

In some other embodiments, the invention relates to a compound of formula (IV), wherein $R^b$ is -$T^1$-$R^{1b}$ or -$T^1$-$R^{2b}$. $T^1$ is a $C_{1-6}$ alkylene chain optionally substituted with —F, $C_{1-3}$ alkyl, or $C_{1-3}$ fluoroalkyl, wherein the alkylene chain optionally is interrupted by —N($R^4$)—, —C(O)—N($R^4$)—, —C(=N$R^4$)—N($R^4$)—, —C(N$R^4$)=N($R^4$)—, —N($R^4$)—C(O)—, or —N($R^4$)—C(=N$R^4$)—. $R^{1b}$ is an optionally substituted $C_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring. $R^{2b}$ is —OR$^5$, —N($R^4$)$_2$, —NR$^4$C(O)R$^5$, —NR$^4$C(O)N($R^4$)$_2$, —C(O)N($R^4$)—OR$^5$, —C(O)N($R^4$)$_2$, —N($R^4$)—CO$_2$R$^5$, —N($R^4$)—C(=N$R^4$)—R$^5$ or —C(=N$R^4$)—N($R^4$)$_2$.

In some such embodiments, $R^b$ is selected from the group consisting of —(CH$_2$)$_q$—R$^{1x}$, —(CH$_2$)$_q$—R$^{2x}$, (CH$_2$)$_q$—R$^{2y}$ —(CH$_2$)$_q$—N($R^{4x}$)—(CH$_2$)$_q$—R$^{1x}$, —(CH$_2$)$_q$—N($R^{4x}$)(CH$_2$)$_q$—R$^{2x}$, —(CH$_2$)$_q$—N($R^{4x}$)—(CH$_2$)$_s$—R$^{2y}$ —(CH$_2$)$_q$—N($R^{4x}$)C(=N$R^{4x}$)—(CH$_2$)$_q$—R$^{1x}$, —(CH$_2$)$_q$—N($R^{4x}$)C(=N$R^{4x}$)—(CH$_2$)$_q$—R$^{2x}$, —(CH$_2$)$_q$—N($R^{4x}$)C(=N$R^{4x}$)—(CH$_2$)$_q$—R$^{2y}$, wherein q is 1, 2, or 3, and s is 2 or 3. $R^{1x}$ is an optionally substituted phenyl, piperidinyl, piperazinyl, morpholinyl, or pyrrolidinyl ring. $R^{2x}$ is —C(O)N($R^{4x}$)($R^{4z}$). $R^{2y}$ is —N($R^{4x}$)($R^{4z}$), —NR$^{4x}$C(O)R$^{5x}$, —N($R^{4x}$)—CO$_2$R$^{5x}$, —N($R^{4x}$)—C(=N$R^{4x}$)R$^{5x}$ or —OR$^{5x}$. $R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted; $R^{4z}$ is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted morpholinyl, piperidinyl, piperazinyl, or pyrrolidinyl ring. $R^{5x}$ is hydrogen, $C_{1-4}$ alkyl, $C_{1-4}$ fluoroalkyl, or $C_{6-10}$ ar($C_{1-4}$)alkyl, the aryl portion of which may be optionally substituted.

Another embodiment of the invention relates to a compound of formula (IV) wherein $R^b$ is —$R^{1b}$. In such embodiments, the compound has formula (V):

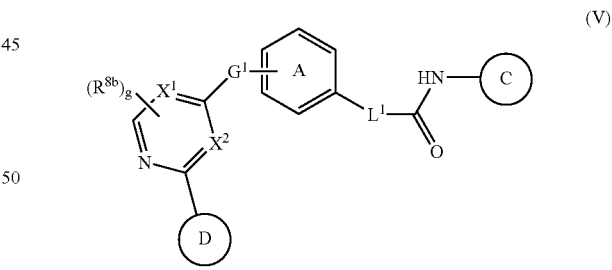

or a pharmaceutically acceptable salt thereof;

wherein:
  $X^1$ and $X^2$ are each independently CH or N, provided that $X^1$ and $X^2$ are not both N;
  Ring D is an optionally substituted aryl, heteroaryl, heterocyclyl, or cycloaliphatic ring;
  Ring A, Ring C, and the variables $R^{8b}$, $G^1$, and $L^1$ have the values and preferred values described above for formulae (I)-(IV); and
  g is 0 or 1.

In some embodiments, $X^1$ and $X^2$ are each CH.

Each substitutable ring nitrogen atom in Ring D preferably is unsubstituted or is substituted with —C(O)R$^5$, —C(O)N(R$^4$)$_2$, —CO$_2$R$^6$, —SO$_2$R$^6$, —SO$_2$(NR$^4$)$_2$, an optionally substituted C$_{6-10}$ aryl, or a C$_{1-4}$ aliphatic optionally substituted with R$^3$ or R$^7$; and one ring nitrogen atom in Ring D optionally is oxidized.

In some embodiments, Ring D is an optionally substituted heteroaryl or heterocyclyl selected from the group consisting of azetidinyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, and tetrahydropyrimidinyl. In certain embodiments, Ring D is an optionally substituted imidazolyl, oxazolyl, thiazolyl, oxadiazolyl, thiadiazolyl, tetrazolyl, imidazolinyl, or tetrahydropyrimidinyl.

Each substitutable saturated ring carbon atom in Ring D preferably is unsubstituted or is substituted with =O, =S, =C(R$^5$)$_2$, =N—OR$^5$, =N—R$^5$, or —R$^d$.

Each substitutable unsaturated ring carbon atom in Ring D preferably is unsubstituted or is substituted with —R$^d$.

Each R$^d$ independently is halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$), —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, —C(R$^6$)=N—OR$^5$, or an optionally substituted aliphatic, aryl, heteroaryl, or heterocyclyl.

In some embodiments, Ring D is substituted with 0-1 R$^d$ and 0-1 R$^{8d}$. R$^{8d}$ is C$_{1-4}$ aliphatic, C$_{1-4}$ fluoroaliphatic, halo, —OH, —O(C$_{1-4}$ aliphatic), —NH$_2$, —NH(C$_{1-4}$ aliphatic), or —N(C$_{1-4}$ aliphatic)$_2$. R$^d$ is selected from the group consisting of C$_{1-4}$ aliphatic, C$_{1-4}$ fluoroaliphatic, halo, —R$^{1d}$, —R$^{2d}$, -T$^3$-R$^{1d}$, -T$^3$-R$^{2d}$, —V$^3$-T$^3$-R$^{1d}$, and —V$^3$-T$^3$R$^{2d}$. The variables T$^3$, V$^3$, R$^{1d}$, and R$^{2d}$ have the values described below.

T$^3$ is a C$_{1-4}$ alkylene chain optionally substituted with one or two substituents independently selected from the group consisting of C$_{1-3}$ aliphatic, C$_{1-3}$ fluoroaliphatic, —F, —OH, —O(C$_{1-4}$ alkyl), —CO$_2$H, —CO$_2$(C$_{1-4}$ alkyl), —C(O)NH$_2$, and —C(O)NH(C$_{1-4}$ alkyl). In some embodiments, T$^3$ is —(CH$_2$)— or —(CH$_2$)$_2$—.

V$^3$ is —O—, —N(R$^4$)—, —N(R$^4$)C(O)—, —C(O)N(R$^4$)—, —C(=NR$^4$)—N(R$^4$)—, —C(NR$^4$)=N(R$^4$)—, or —N(R$^4$)C(=NR$^4$)—.

Each R$^{1d}$ independently is an optionally substituted aryl, heteroaryl, heterocyclyl, or cycloaliphatic ring. In some embodiments, R$^{1d}$ is an optionally substituted phenyl, pyridyl, or pyrimidinyl group.

Each R$^{2d}$ independently is —NO$_2$, —CN, —C(R$^5$)=C(R$^5$)$_2$, —C≡C—R$^5$, —OR$^5$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, or —C(R$^6$)=N—OR$^5$. In some embodiments, each R$^{2d}$ independently is selected from the group consisting of —OR$^5$, —N(R$^4$)$_2$, —NR$^4$C(O)R$^5$, —NR$^4$C(O)N(R$^4$)$_2$, —O—C(O)R$^5$, —CO$_2$R$^5$, —C(O)R$^5$, —C(O)N(R$^4$)$_2$, —C(O)N(R$^4$)—OR$^5$, and —C(=NR$^4$)—N(R$^4$)$_2$. In some embodiments, each R$^{2d}$ is selected from the group consisting of —OR$^5$, —N(R$^4$)$_2$, —CO$_2$R$^5$, or —C(O)N(R$^4$)$_2$.

In some embodiments, Ring D is selected from the group consisting of:

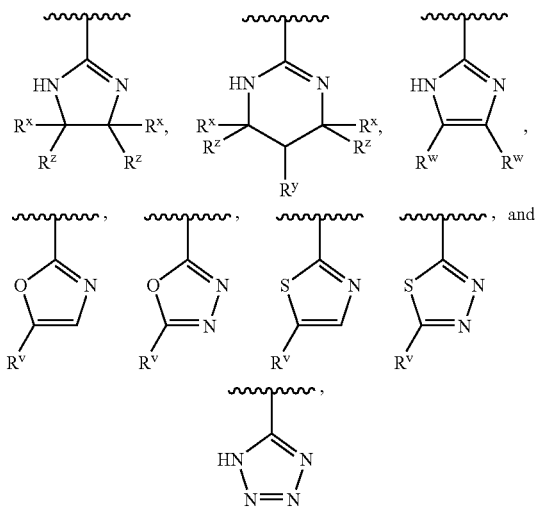

where R$^v$, R$^w$, R$^x$, R$^y$, and R$^z$ have the values described below.

R$^v$ is hydrogen, halo, C$_{1-4}$ aliphatic, C$_{1-4}$ fluoroaliphatic, —OR$^5$, —N(R$^4$)$_2$—C$_2$R$^5$, —C(O)N(R$^4$)$_2$, -T$^3$-OR$^5$, -T$^3$-N(R$^4$)$_2$, -T$^3$-CO$_2$R$^5$, -T$^3$-C(O)N(R$^4$)$_2$, or an optionally substituted 5- or 6-membered aryl or heteroaryl. In certain embodiments, R$^v$ is hydrogen, halo, C$_{1-4}$ aliphatic, C$_{1-4}$ fluoroaliphatic, —(CH$_2$)$_p$—OR$^{5x}$, (CH$_2$)$_p$—N(R$^{4x}$)(R$^{4z}$), (CH$_2$)$_p$—CO$_2$R$^{5x}$, —(CH$_2$)$_p$—C(O)N(R$^{4x}$)(R$^{4z}$), or an optionally substituted phenyl, pyridyl, or pyrimidinyl group.

Each R$^w$ independently is hydrogen, halo, C$_{1-4}$ aliphatic, C$_{1-4}$ fluoroaliphatic, —OR$^5$, —N(R$^4$)$_2$, —CO$_2$R$^5$, —C(O)N(R$^4$)$_2$, -T$^3$-OR$^5$, -T$^3$-CO$_2$R$^5$, -T$^3$-C(O)N(R$^4$)$_2$, or an optionally substituted 5- or 6-membered aryl or heteroaryl. In some embodiments, each R$^w$ independently is hydrogen, an optionally substituted phenyl, pyridyl, or pyrimidinyl group, halo, C$_{1-4}$ aliphatic, C$_{1-4}$ fluoroaliphatic, —(CH$_2$)$_p$—OR$^{5x}$, —(CH$_2$)$_p$—N(R$^{4x}$)(R$^{4z}$), —(CH$_2$)$_p$—CO$_2$R$^{5x}$, —(CH$_2$)$_p$—C(O)N(R$^{4x}$)(R$^{4z}$), —(CH$_2$)$_q$—N(R$^{4x}$)—(CH$_2$)$_q$—R$^{1x}$, (CH$_2$)$_q$—N(R$^{4x}$)—(CH$_2$)$_q$—R$^{2x}$, —(CH$_2$)$_q$—N(R$^{4x}$)—(CH$_2$)—R$^{2y}$ —(CH$_2$)$_q$—N(R$^{4x}$)C(=NR$^{4x}$)—(CH$_2$)$_q$—R$^{1x}$, —(CH$_2$)$_q$—N(R$^{4x}$)C(=NR$^{4x}$)—(CH$_2$)$_q$—R$^{2x}$, or —(CH$_2$)$_q$N(R$^{4x}$)C(=NR$^{4x}$)—(CH$_2$)$_q$—R$^{2y}$. In certain embodiments, each R$^w$ independently is hydrogen, halo, C$_{1-4}$ aliphatic, C$_{1-4}$ fluoroaliphatic, —(CH$_2$)$_p$—OR$^{5x}$, —(CH$_2$)$_p$—N(R$^{4x}$)(R$^{4z}$), —(CH$_2$)$_p$—CO$_2$R$^{5x}$, —(CH$_2$)$_p$—C(O)N(R$^{4x}$)(R$^{4z}$), or an optionally substituted phenyl, pyridyl, or pyrimidinyl group.

Each R$^x$ independently is hydrogen, fluoro, C$_{1-4}$ aliphatic, C$_{1-4}$ fluoroaliphatic, —CO$_2$R$^5$, —C(O)N(R$^4$)$_2$, -T$^3$-N(R$^4$)$_2$, -T$^3$-R$^5$, -T$^3$-CO$_2$R$^5$, or -T$^3$-C(O)N(R$^4$)$_2$—In certain embodiments, each R$^x$ independently is hydrogen, fluoro, C$_{1-4}$ aliphatic, C$_{1-4}$ fluoroaliphatic, —(CH$_2$)$_p$—CO$_2$R$^{5x}$, —(CH$_2$)—C(O)N(R$^{4x}$)(R$^{4z}$), —(CH$_2$)—N(R$^{4x}$)(R$^{4z}$), or —(CH$_2$)$_p$—OR$^{5x}$.

R$^y$ is hydrogen, halo, C$_{1-4}$ aliphatic, C$_{1-4}$ fluoroaliphatic, —OR$^5$, —N(R$^4$)$_2$, —CO$_2$R$^5$, —C(O)N(R$^4$)$_2$, -T$^3$-OR$^5$, -T$^3$-N(R$^4$)$_2$, -T$^3$-CO$_2$R$^5$, or -T$^3$-C(O)N(R$^4$)$_2$. In certain embodiments, R$^y$ is hydrogen, fluoro, C$_{1-4}$ aliphatic, C$_{1-4}$ fluoroaliphatic, —(CH$_2$)$_p$—N(R$^{4x}$)(R$^{2z}$), —(CH$_2$)$_p$—OR$^{5x}$, —(CH$_2$)$_p$—CO$_2$R$^{5x}$, —(CH$_2$)$_p$—C(O)N(R$^{4x}$)(R$^{4z}$).

Each $R^z$ independently is hydrogen, fluoro, $C_{1-4}$ aliphatic, or $C_{1-14}$ fluoroaliphatic.

$T^3$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —CO$_2$H, —CO$_2$($C_{1-4}$ alkyl), —C(O)NH$_2$, and —C(O)NH($C_{1-4}$ alkyl).

Each $R^{1x}$ independently is an optionally substituted phenyl, piperidinyl, piperazinyl, morpholinyl, or pyrrolidinyl ring.

Each $R^{2x}$ independently is —C(O)N($R^{4x}$)($R^{4z}$).

Each $R^{2y}$ independently is —N($R^{4x}$)($R^{4z}$), —NR$^{4x}$C(O)R$^{5x}$, —N($R^{4x}$)—CO$_2$R$^{5x}$, —N($R^{4x}$)—C(=NR$^{4x}$)—R$^{5x}$ or —OR$^{5x}$.

Each $R^{4x}$ independently is hydrogen, $C_{1-4}$ alkyl, $C_{1-4}$ fluoroalkyl, or $C_{6-10}$ ar($C_{1-4}$)alkyl, the aryl portion of which may be optionally substituted, and each $R^{4z}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted 4- to 8-membered heterocyclyl ring having, in addition to the nitrogen atom, 0-2 ring heteroatoms independently selected from N, O, and S.

Each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

The variable p is 0, 1, or 2; q is 1, 2, or 3, r is 1 or 2, and s is 2 or 3.

In more particular embodiments, Ring D is selected from the group consisting of:

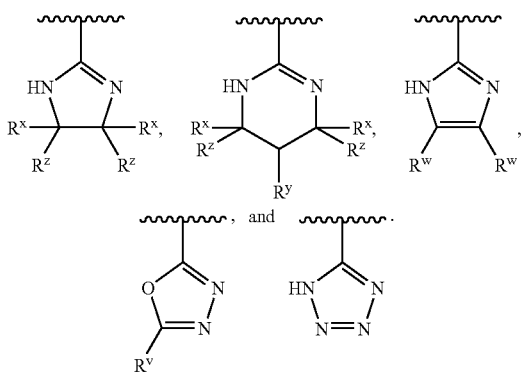

In still more particular embodiments, Ring D is selected from the group consisting of:

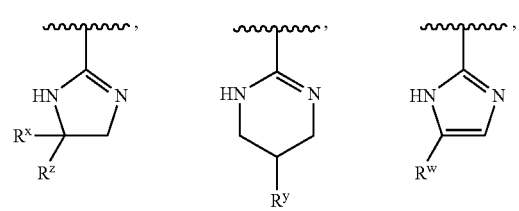

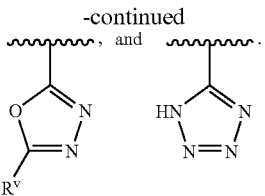

The invention also relates to a compound of formula (VI):

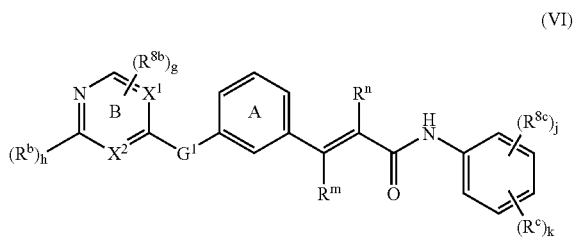

(VI)

or a pharmaceutically acceptable salt thereof;

wherein:
$G^1$ is —O— or —NH—;
$X^1$ and $X^2$ are each independently CH or N, provided that $X^1$ and $X^2$ are not both N;
one ring nitrogen atom in Ring B optionally is oxidized;
g is 0 or 1;
h is 0 or 1;
j is 0 or 1;
k is 0, 1, or 2; and
Ring A and the variables $R^b$, $R^{8b}$, $R^m$, $R^n$, $R^c$, and $R^{8c}$ have the values and preferred values described above for formulae (I)-(V).

In some embodiments, the invention relates to a compound of formula (VI), wherein:
$R^m$ is hydrogen, and $R^n$ is hydrogen, fluoro, —CH$_3$, or —CH$_2$OH;
$X^1$ and $X^2$ are each CH;
Ring A is substituted with zero occurrences of $R^a$;
each $R^c$ independently is halo, —CN, —C($R^{5x}$)=C($R^{5x}$)($R^{5y}$), —C≡C—R$^{5y}$, —OR$^{5y}$, —SR$^{6x}$, —CO$_2$R$^{5x}$, —C(O)N($R^{4x}$)($R^{4y}$), or a $C_{1-4}$ aliphatic or $C_{1-4}$ fluoroaliphatic optionally substituted with one or two substituents independently selected from the group consisting of —OR$^{5x}$, —N($R^{4x}$)($R^{4y}$), —SR$^{6x}$, —CO$_2$R$^{5x}$, or —C(O)N($R^{4x}$)($R^{4y}$); or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;
$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted, or two $R^{4x}$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;
$R^{4y}$ is hydrogen, $C_{6-10}$ ar($C_{1-4}$)alkyl, the aryl portion of which may be optionally substituted, an optionally substituted 5- or 6-membered aryl, heteroaryl, or heterocyclyl ring, or a $C_{1-4}$ alkyl or $C_{1-4}$ fluoroalkyl optionally substituted with one or two substituents independently selected from the group consisting of —$OR^{5x}$, —$N(R^{4x})_2$, —$CO_2R^{5x}$, or —$C(O)N(R^{4x})_2$; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, $C_{(6-10)}$ ar($C_{1-4}$)alkyl, the aryl portion of which may be optionally substituted, or an optionally substituted 5- or 6-membered aryl, heteroaryl, or heterocyclyl ring;

each $R^{5y}$ independently is hydrogen, an optionally substituted $C_{6-10}$ aryl, a $C_{6-10}$ar($C_{1-4}$)alkyl, the aryl portion of which may be optionally substituted, or a $C_{1-4}$ alkyl or $C_{1-4}$ fluoroalkyl optionally substituted with one or two substituents independently selected from the group consisting of —$OR^{5x}$, —$N(R^{4x})_2$, —$CO_2R^{5x}$, or —$C(O)N(R^{4x})_2$; and each $R^{6x}$ independently is $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

The invention also relates to a compound of formula (VII):

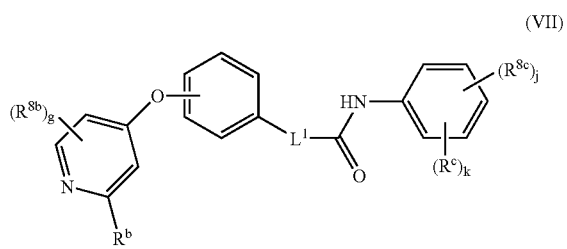

(VII)

or a pharmaceutically acceptable salt thereof;

wherein:

g is 0 or 1;
j is 0 or 1;
k is 0, 1, or 2; and the variables $L^1$, $R^b$, $R^{8b}$, $R^c$, and $R^{8c}$ have the values and preferred values described above for formulae (I)-(VI).

In preferred embodiments, the compound of formula (I) is other than:

N-(3-chloro-2-ethyl-4-pyridinyl)-4-[[5-(trifluoromethyl)-2-pyridinyl]oxy]-benzenepropanamide;

4-[[3-cyano-6-(1-methylethyl)$_2$-pyridinyl]oxy]-N-(2,6-diethylphenyl)benzenepropanamide;

4-[[5-bromo-4-(2-propynyloxy)-2-pyrinidinyl]amino-N-(4-hydroxyphenyl)benzenebutanamide;

4-[(4,5-dihydro-2-thiazolyl)amino]-N-phenyl-benzenebutanamide;

N-(3-chloro-2-ethyl-4-pyridinyl)-4-[[5-(trifluoromethyl)-2-pyridinyl]oxy]-benzenebutanamide; or 4-[[4,6-bis-(3,5-diamino-1-piperidinyl)-1,3,5-triazin-2-yl]amino]-β-hydroxy-N-[2-(trifluoromethyl)phenyl]benzenebutanamide.

Specific examples of compounds of formula (I) are shown below in Table 1.

TABLE 1

Raf Kinase Inhibitors

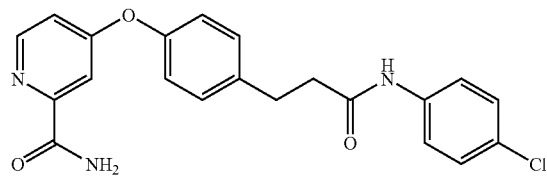

A-1

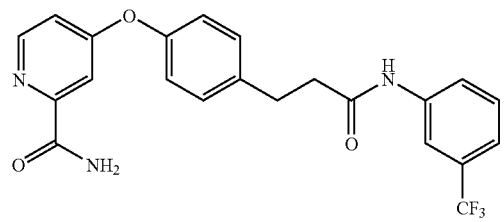

A-2

TABLE 1-continued
Raf Kinase Inhibitors
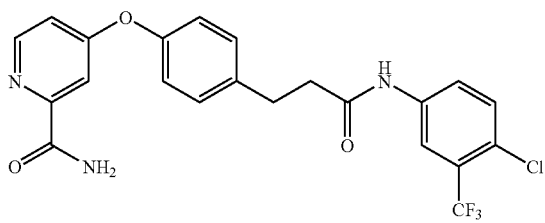
A-3
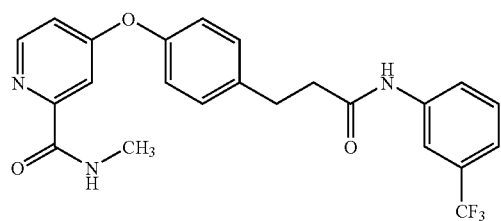
A-4
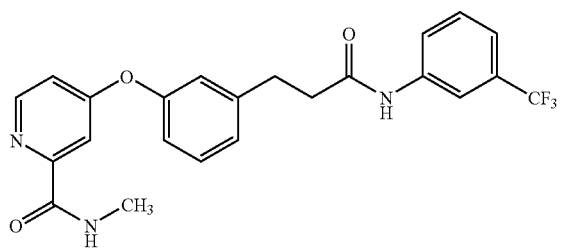
A-5
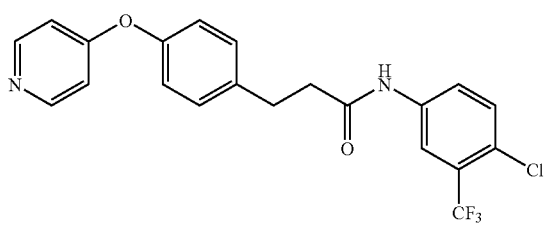
A-6
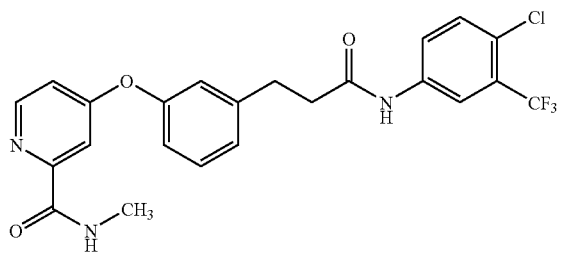
A-7
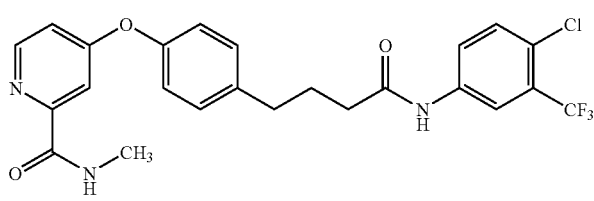
A-8

TABLE 1-continued
Raf Kinase Inhibitors
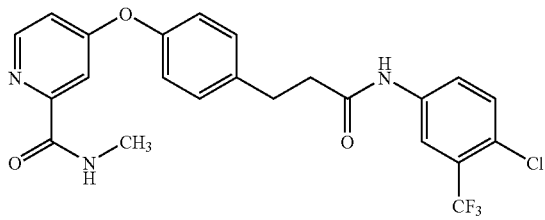
A-9
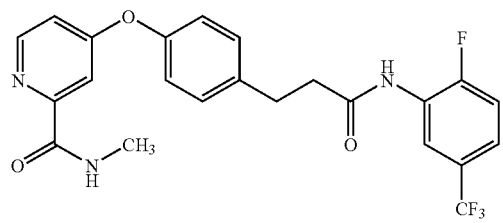
A-10
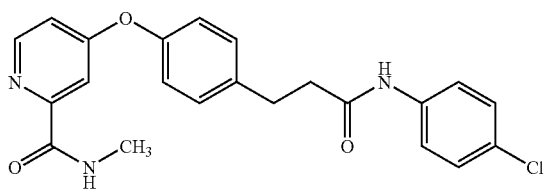
A-11
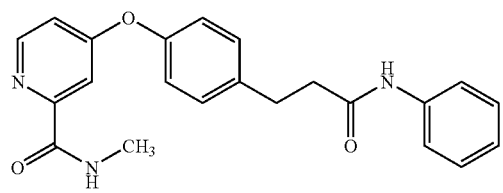
A-12
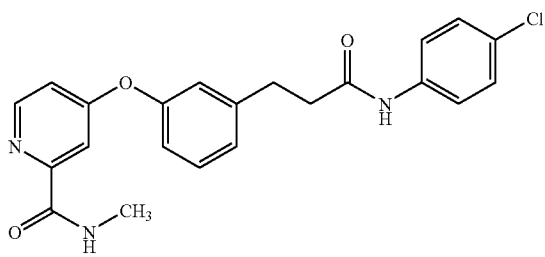
A-13
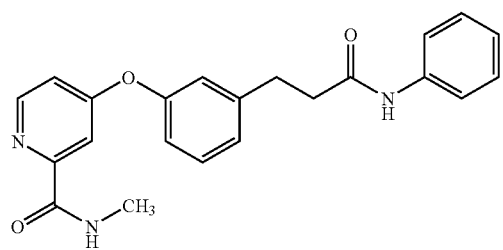
A-14

TABLE 1-continued
Raf Kinase Inhibitors
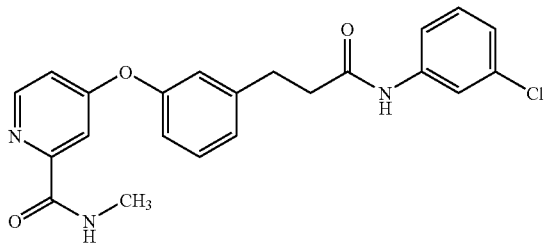
A-15
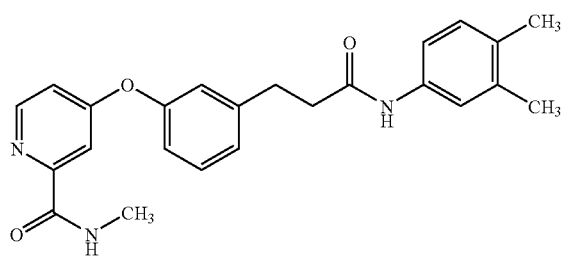
A-16
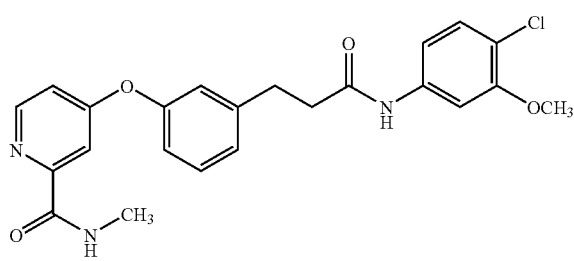
A-17
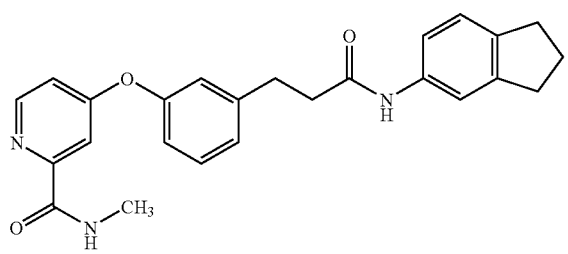
A-18
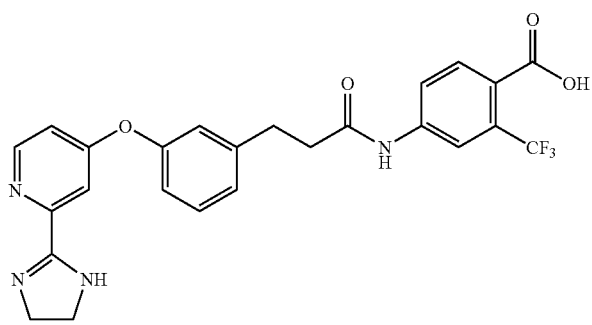
A-19

TABLE 1-continued
Raf Kinase Inhibitors
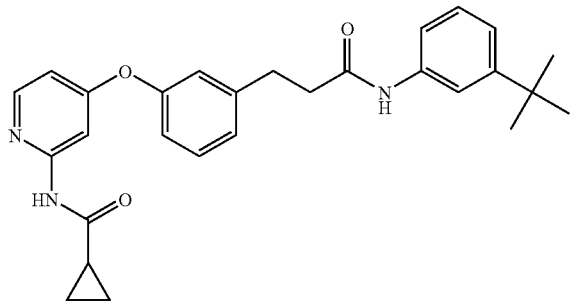
A-20
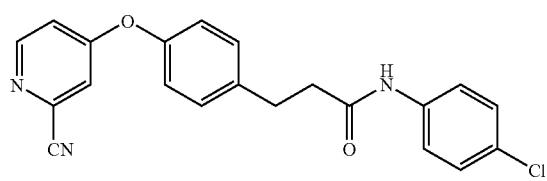
A-21
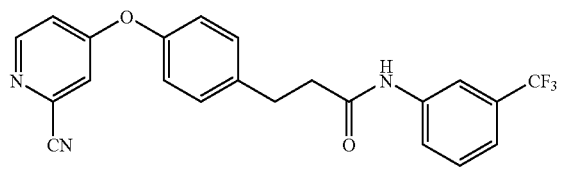
A-22
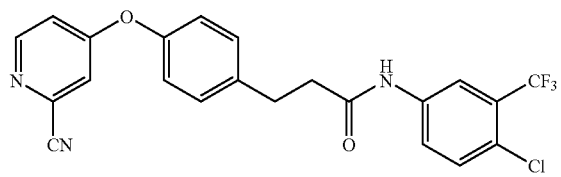
A-23
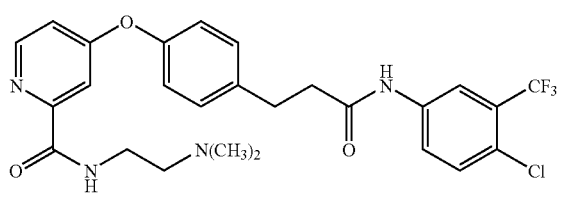
A-24
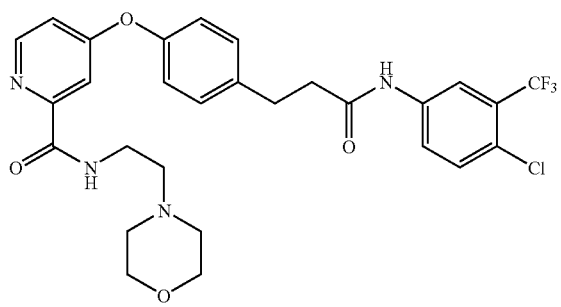
A-25

TABLE 1-continued
Raf Kinase Inhibitors
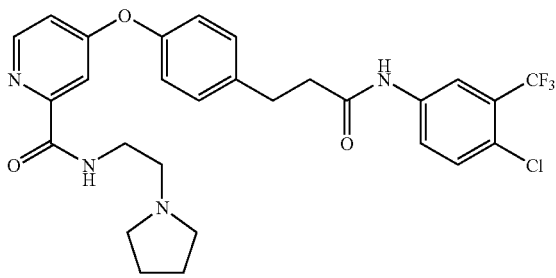
A-26
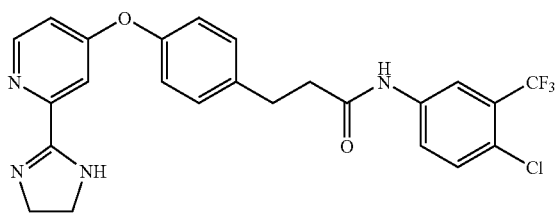
A-27
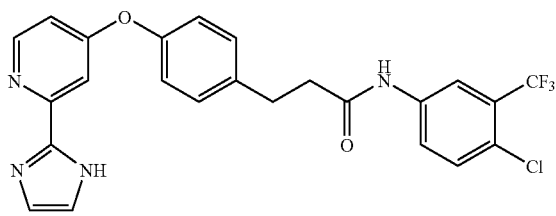
A-28
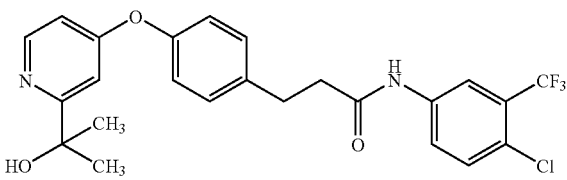
A-29
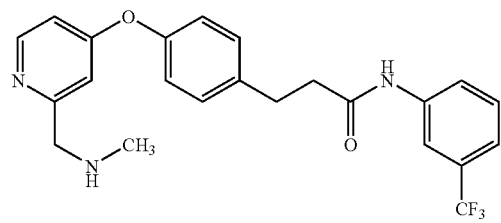
A-30
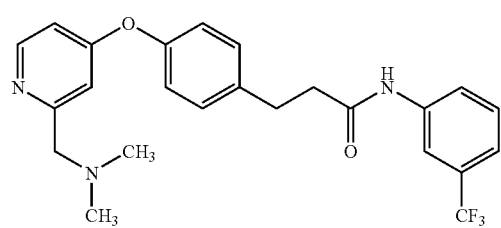
A-31

TABLE 1-continued
Raf Kinase Inhibitors
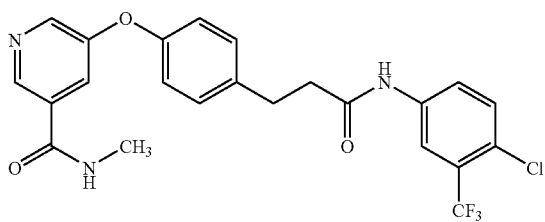
A-32
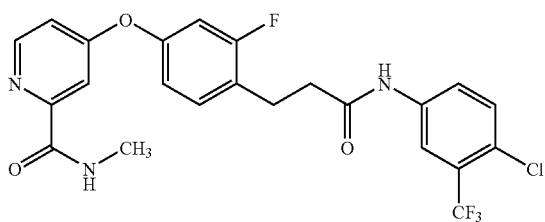
A-33
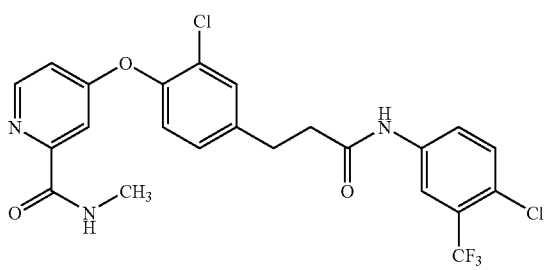
A-34
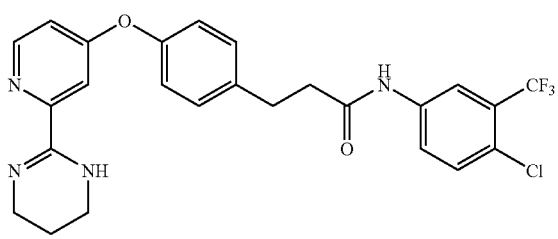
A-35
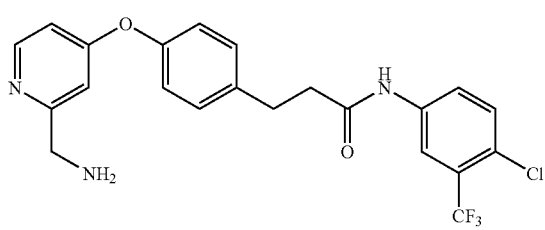
A-36
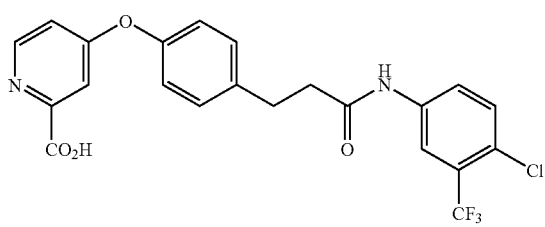
A-37

TABLE 1-continued
Raf Kinase Inhibitors
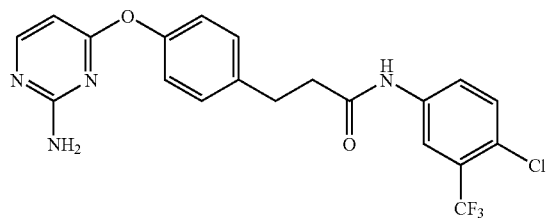
A-38
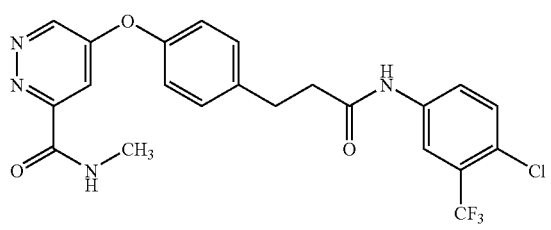
A-39
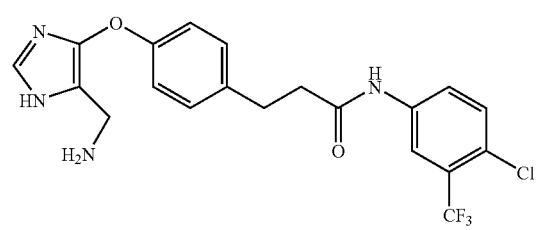
A-40
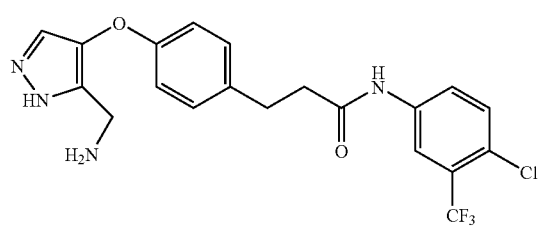
A-41
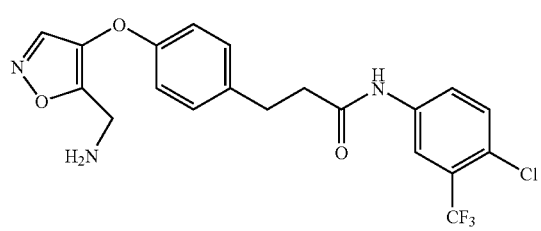
A-42
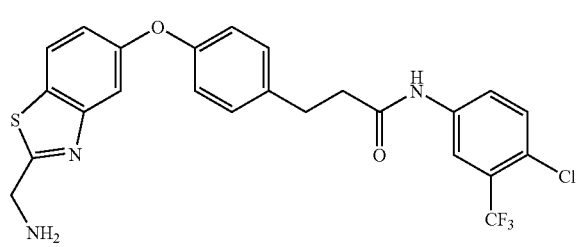
A-43

TABLE 1-continued
Raf Kinase Inhibitors
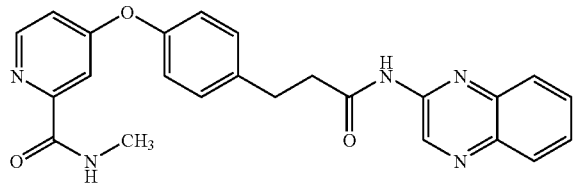
A-44
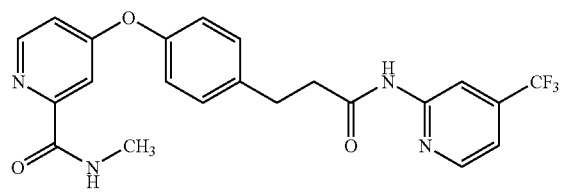
A-45
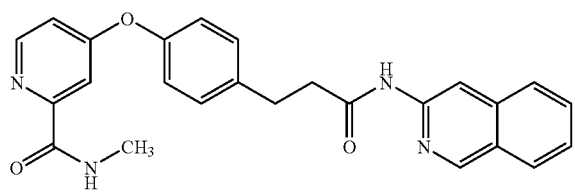
A-46
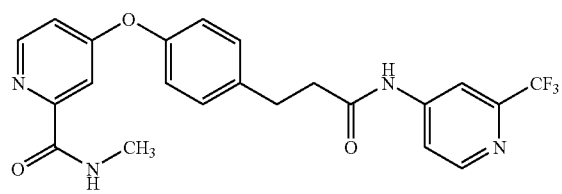
A-47
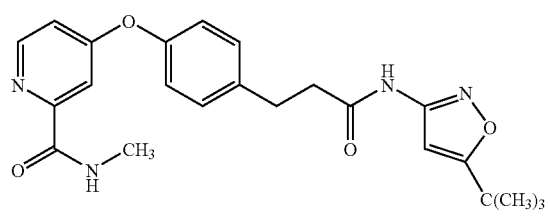
A-48
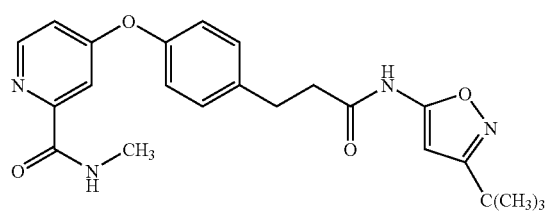
A-49

TABLE 1-continued
Raf Kinase Inhibitors
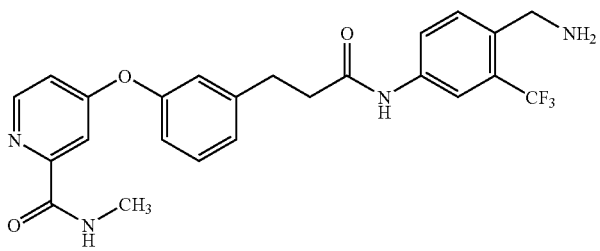
A-50
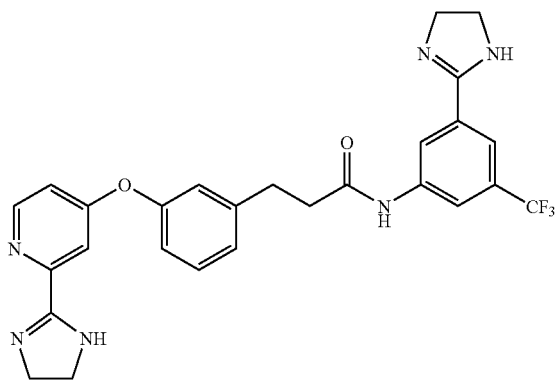
A-51
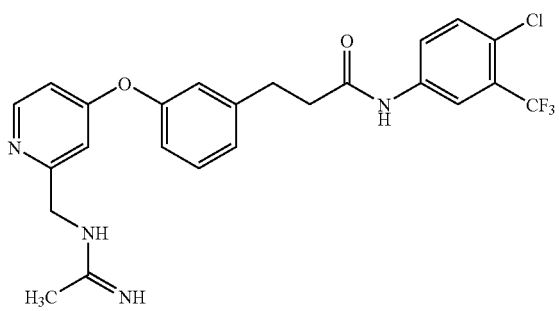
A-52
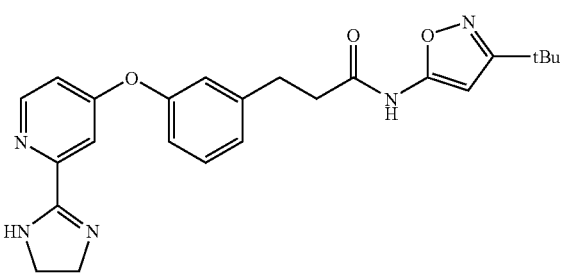
A-53

TABLE 1-continued
Raf Kinase Inhibitors
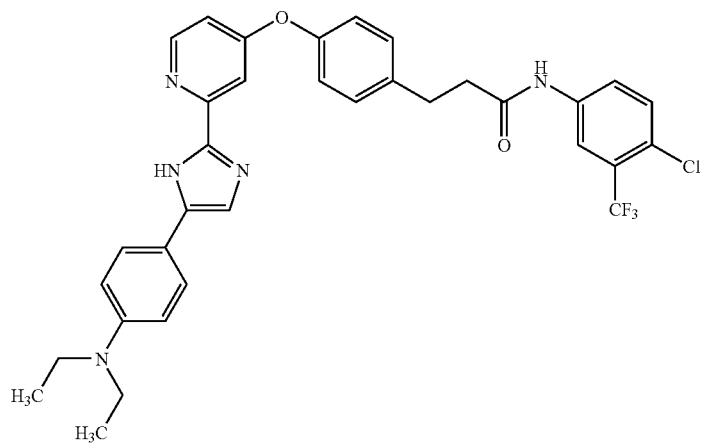
A-54
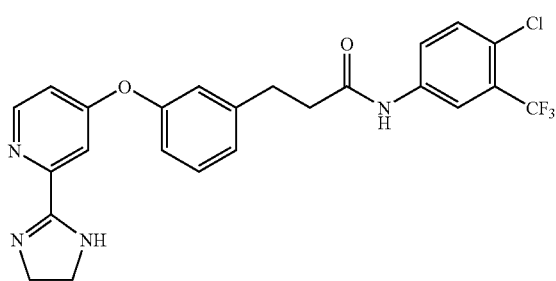
A-55
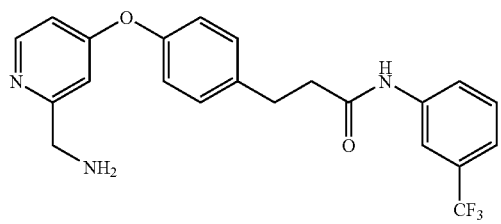
A-56
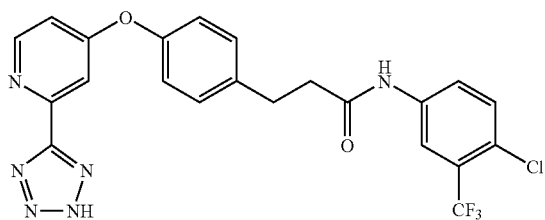
A-57

TABLE 1-continued
Raf Kinase Inhibitors
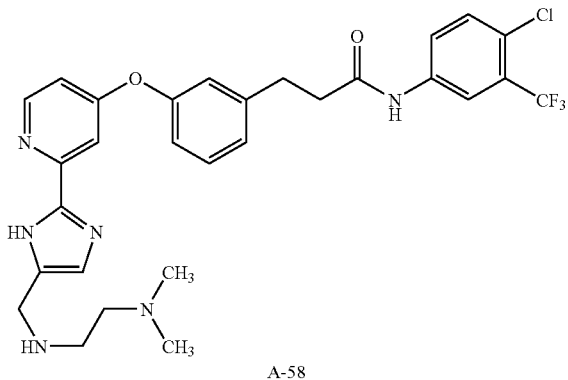
A-58
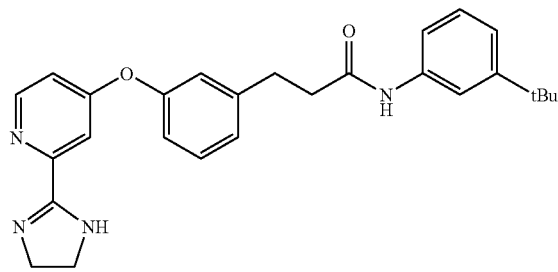
A-59
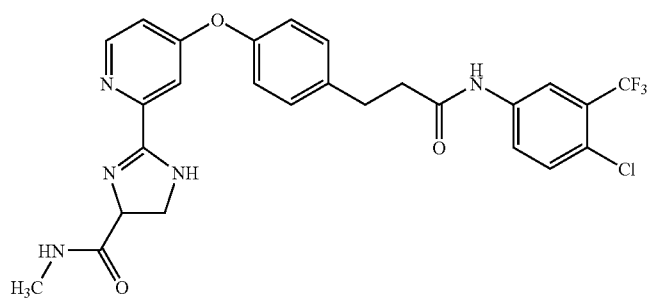
A-60
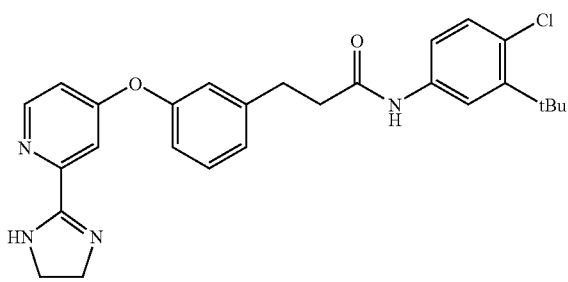
A-61
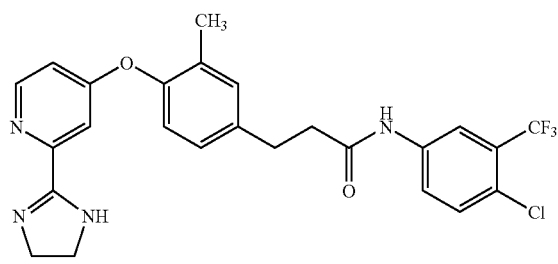
A-62

TABLE 1-continued
Raf Kinase Inhibitors
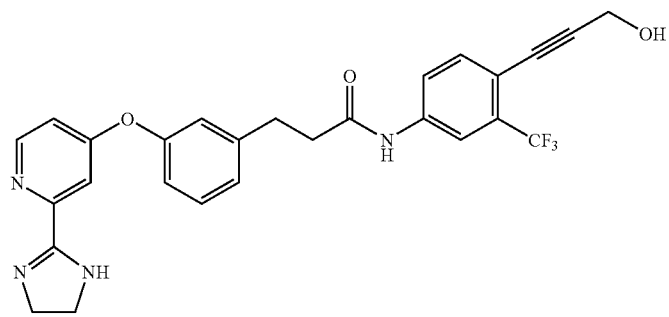
A-63
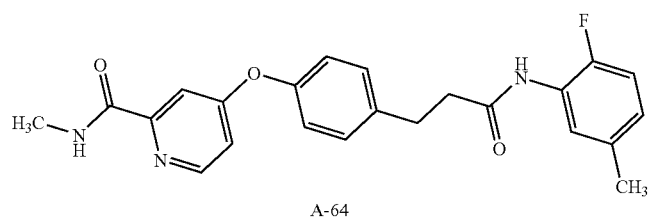
A-64
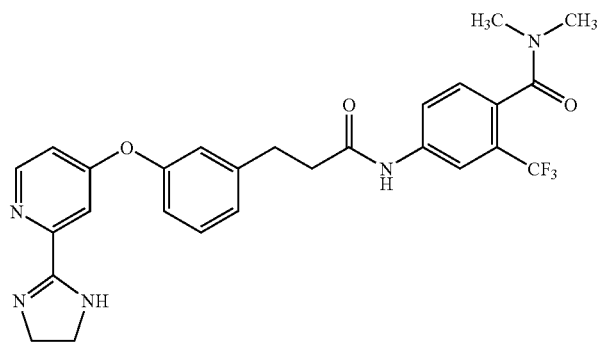
A-65
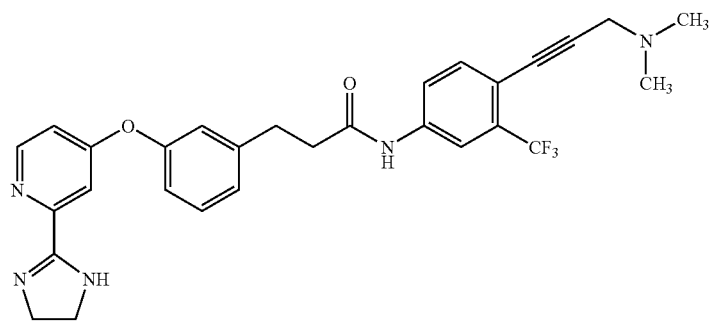
A-66
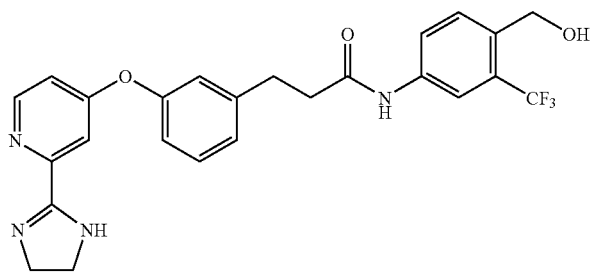
A-67

TABLE 1-continued
Raf Kinase Inhibitors
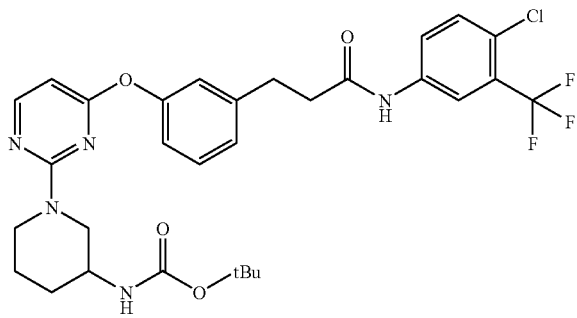
A-68
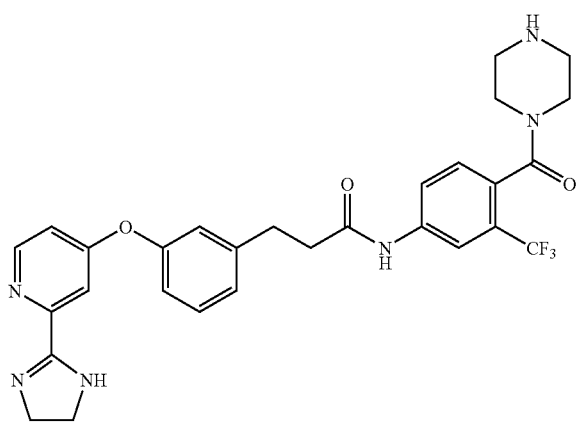
A-69
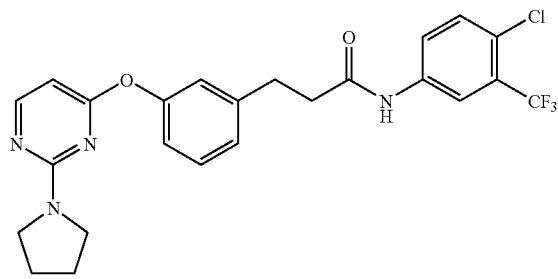
A-70
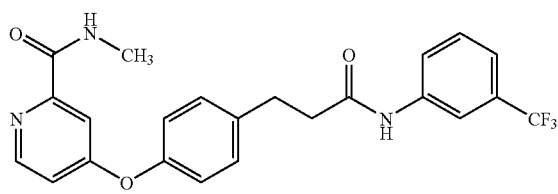
A-71

TABLE 1-continued
Raf Kinase Inhibitors
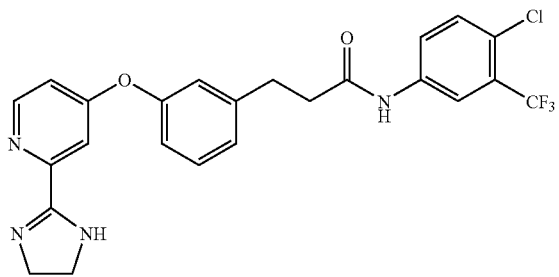
A-72
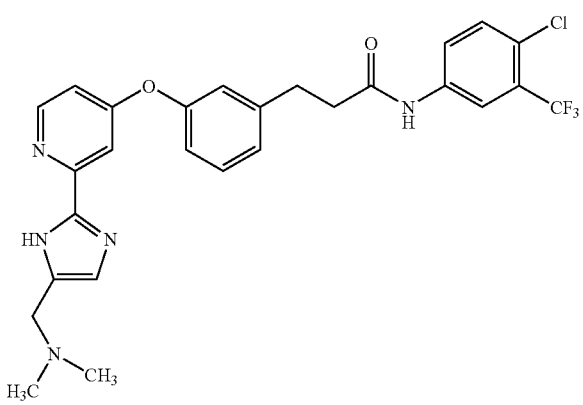
A-73
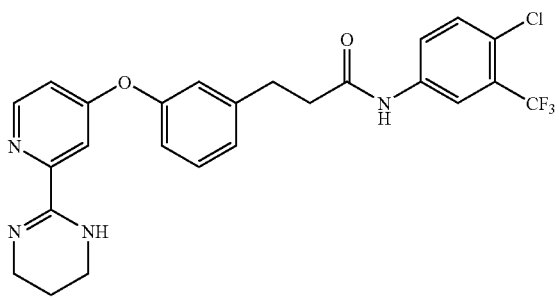
A-74
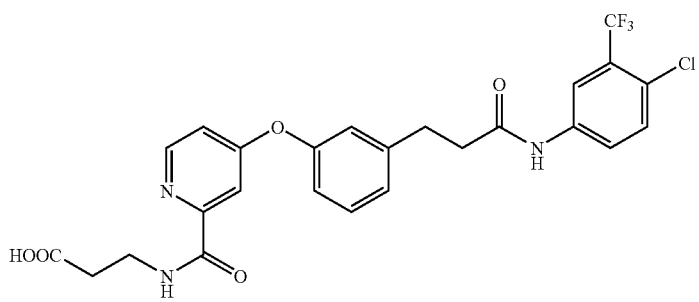
A-75

TABLE 1-continued
Raf Kinase Inhibitors
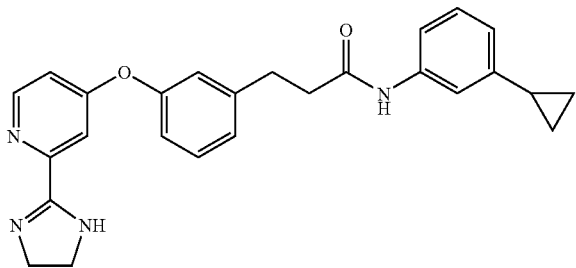
A-76
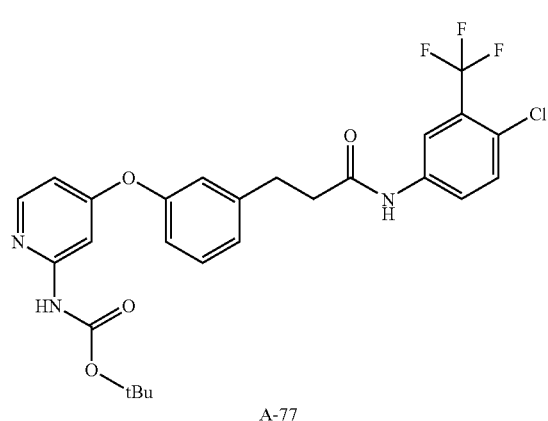
A-77
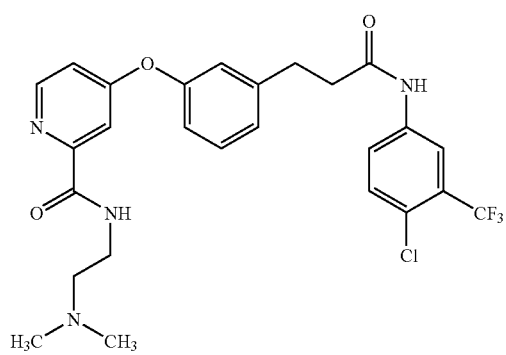
A-78
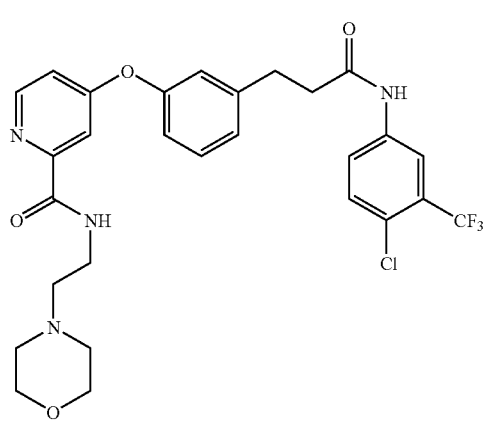
A-79

TABLE 1-continued
Raf Kinase Inhibitors
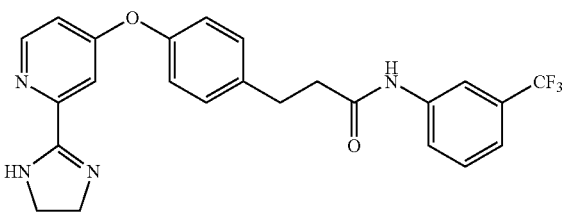
A-80
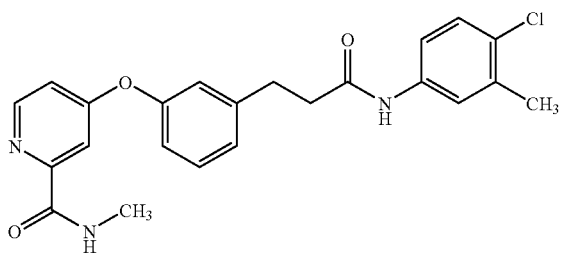
A-81
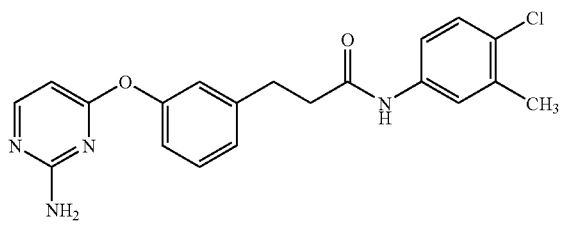
A-82
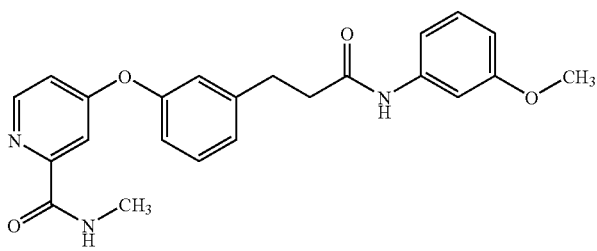
A-83
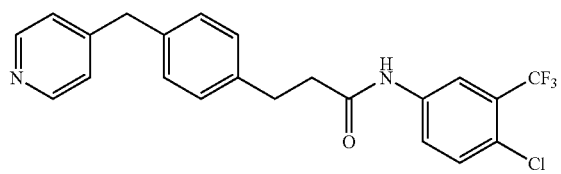
A-84
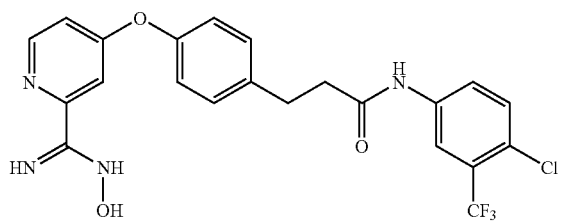
A-85

TABLE 1-continued
Raf Kinase Inhibitors
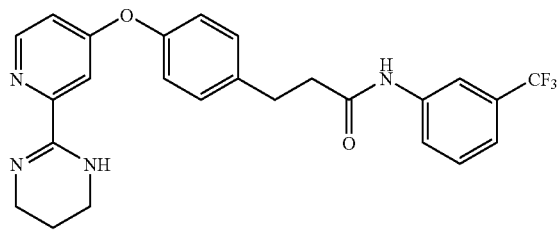
A-86
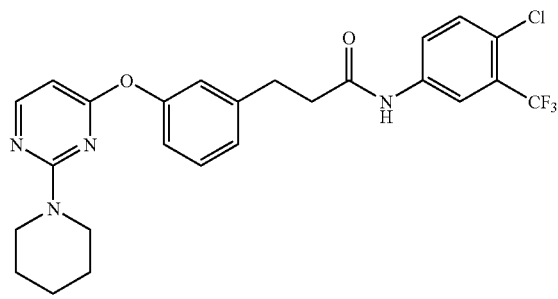
A-87
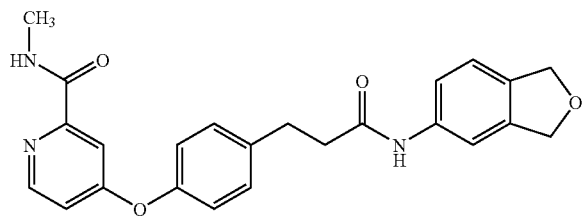
A-88
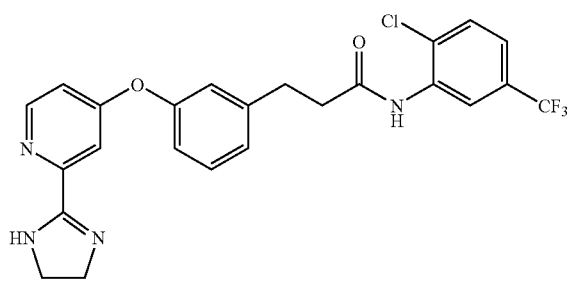
A-89
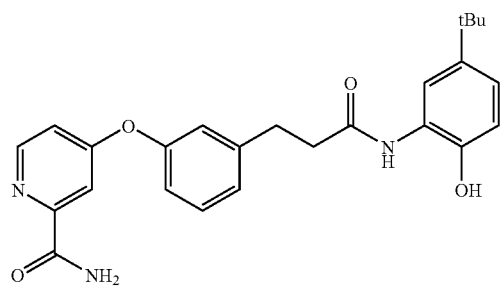
A-90

TABLE 1-continued
Raf Kinase Inhibitors
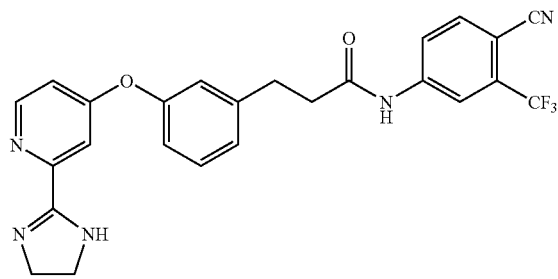
A-91
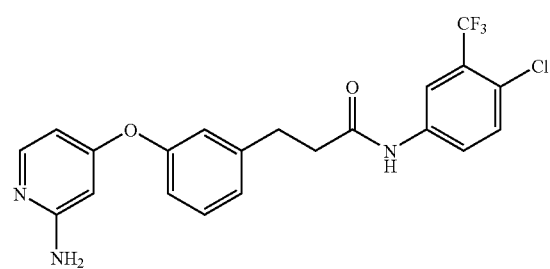
A-92
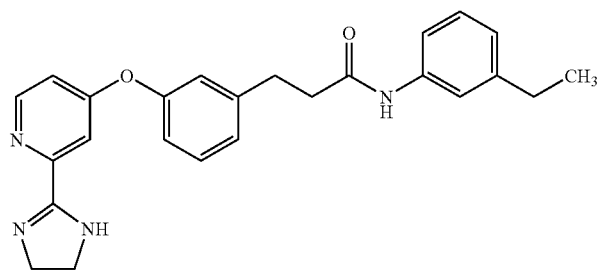
A-93
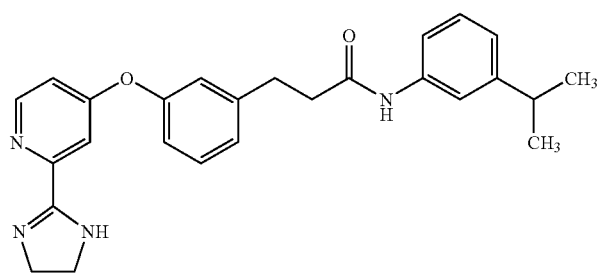
A-94
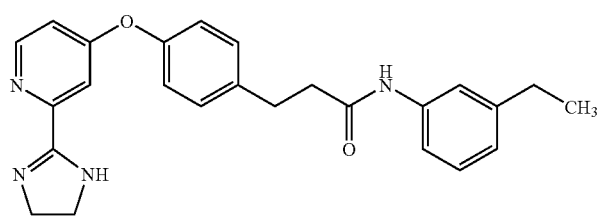
A-95

TABLE 1-continued
Raf Kinase Inhibitors
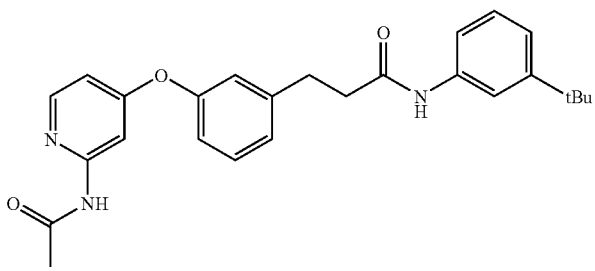
A-96
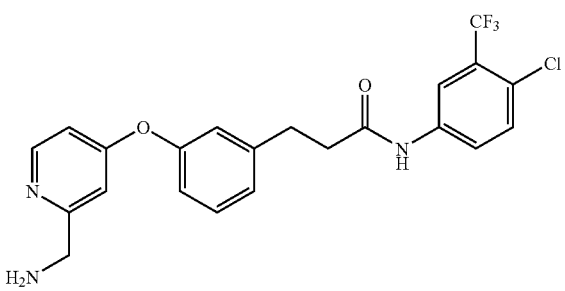
A-97
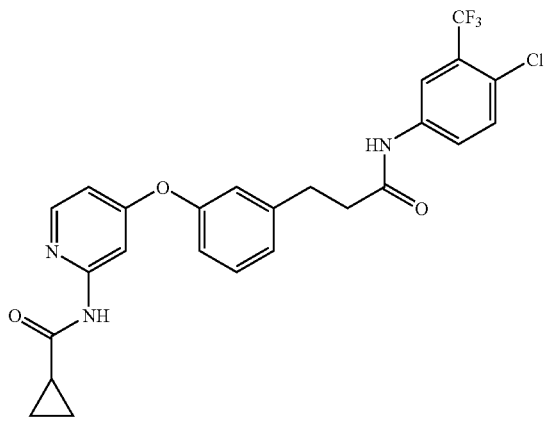
A-98
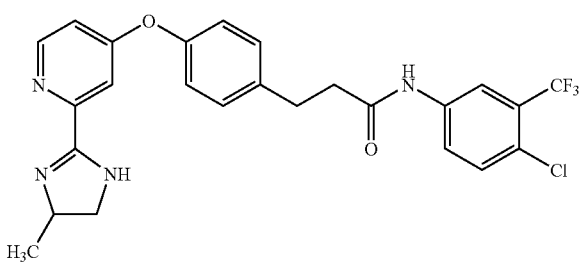
A-99

TABLE 1-continued
Raf Kinase Inhibitors
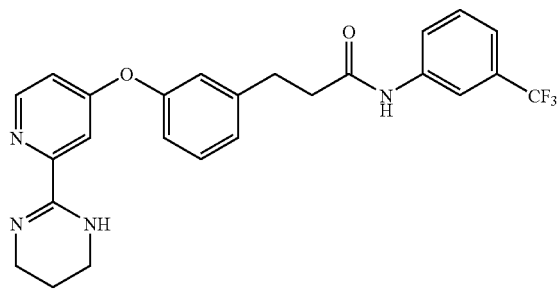
A-100
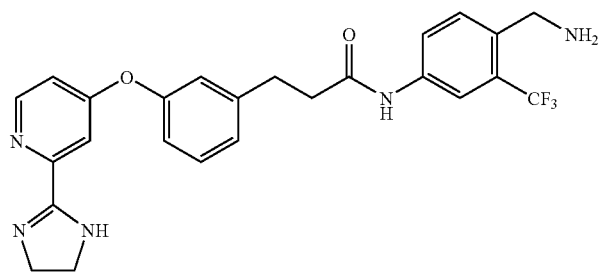
A-101
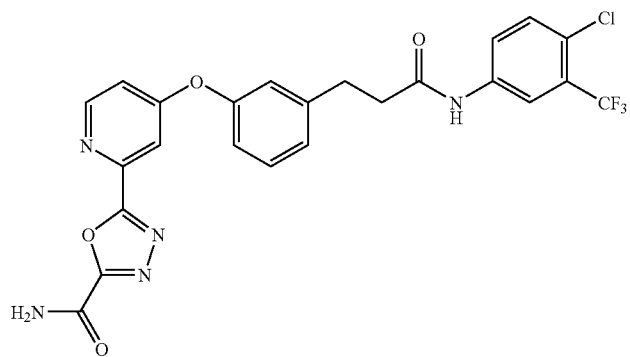
A-102
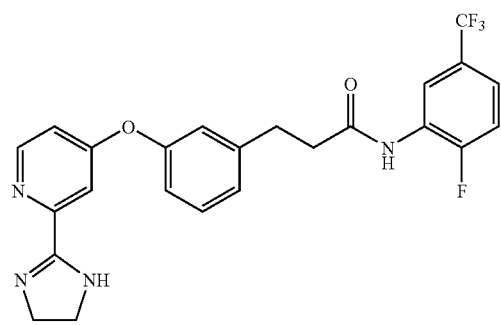
A-103

TABLE 1-continued
Raf Kinase Inhibitors
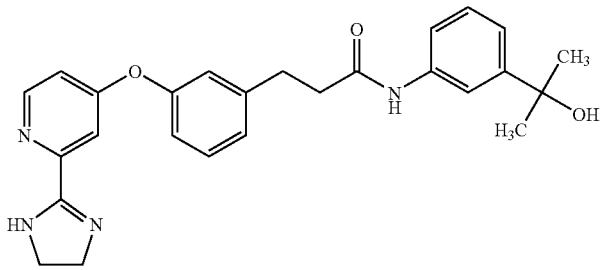
A-104
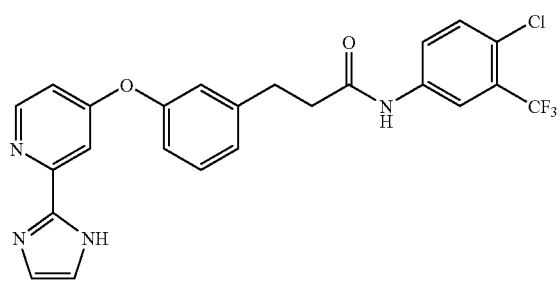
A-105
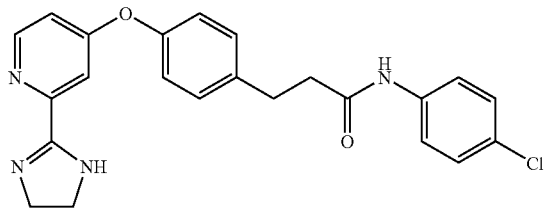
A-106
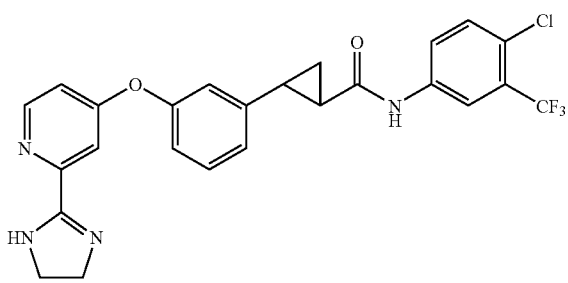
A-107
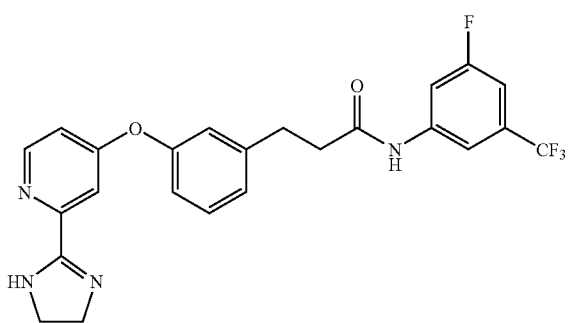
A-108

TABLE 1-continued
Raf Kinase Inhibitors
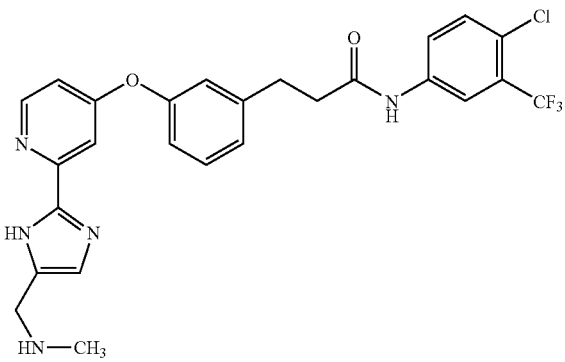
A-109
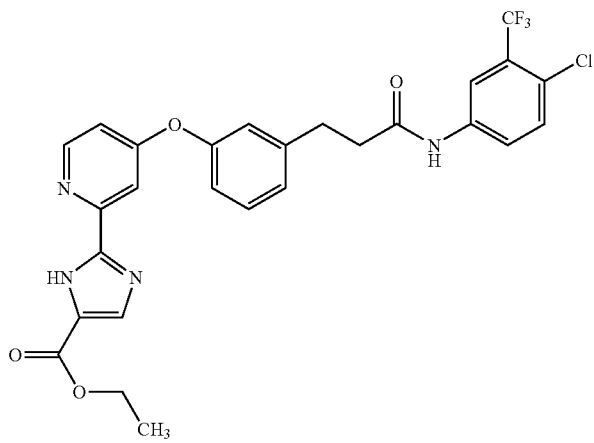
A-110
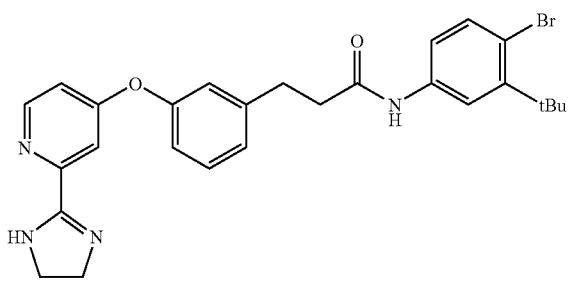
A-111
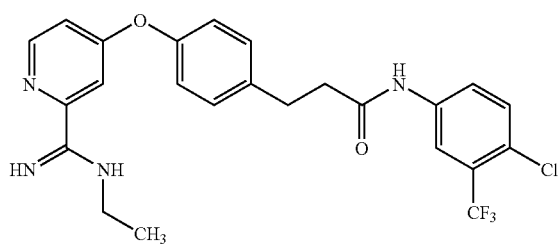
A-112

TABLE 1-continued
Raf Kinase Inhibitors
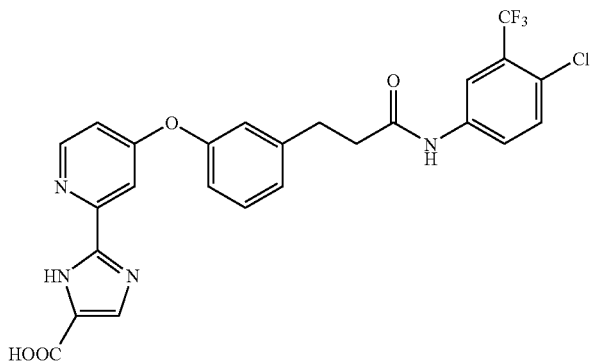
A-113
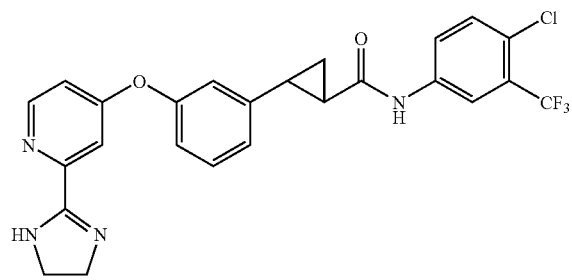
A-114
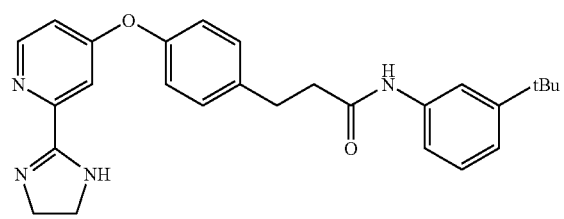
A-115
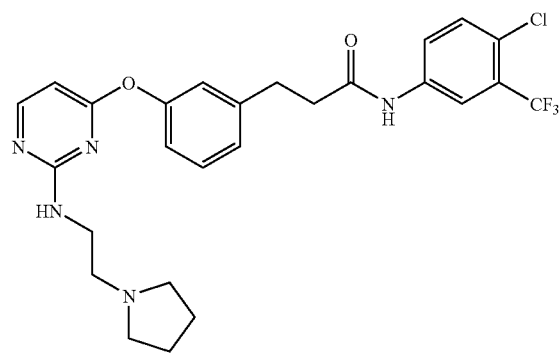
A-116

TABLE 1-continued
Raf Kinase Inhibitors
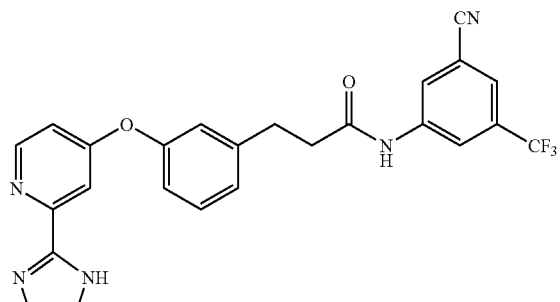
A-117
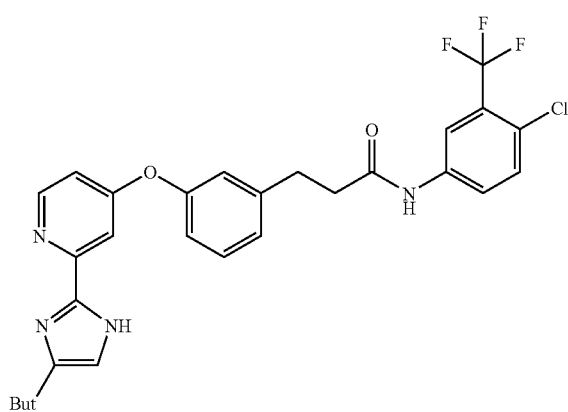
A-118
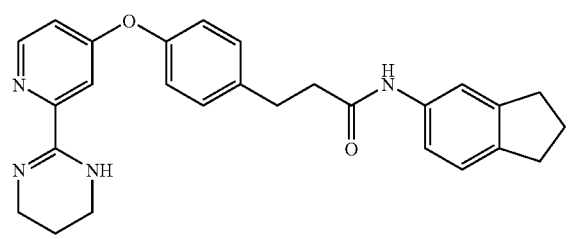
A-119
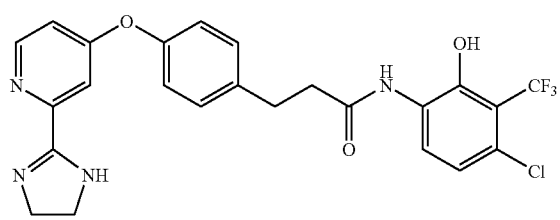
A-120
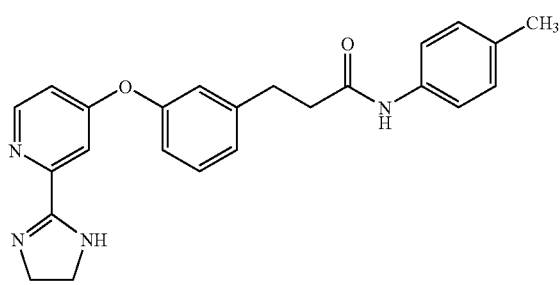
A-121

TABLE 1-continued
Raf Kinase Inhibitors
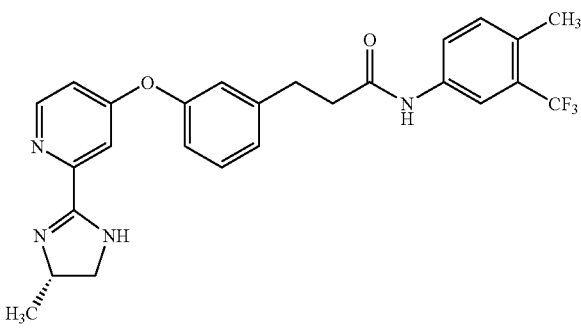
A-122
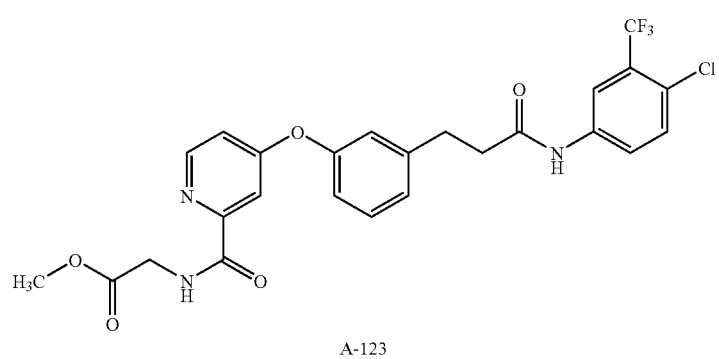
A-123
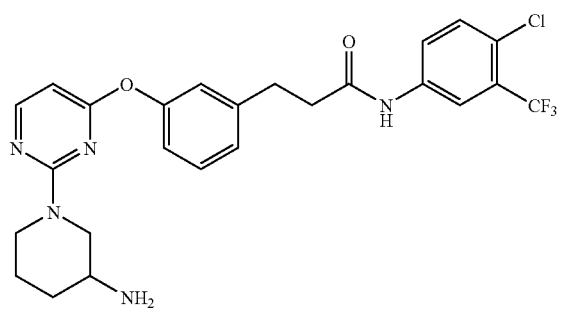
A-124
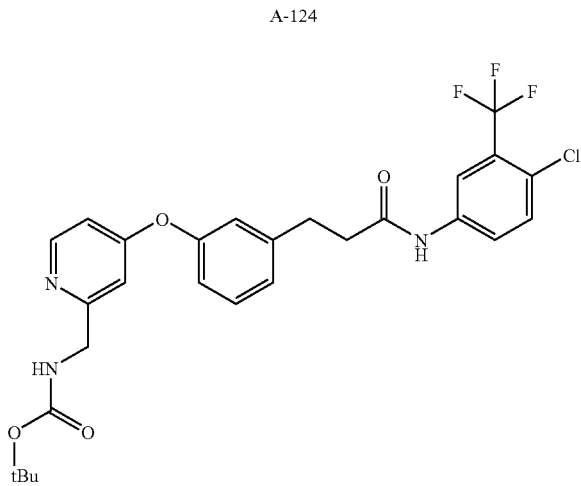
A-125

TABLE 1-continued
Raf Kinase Inhibitors
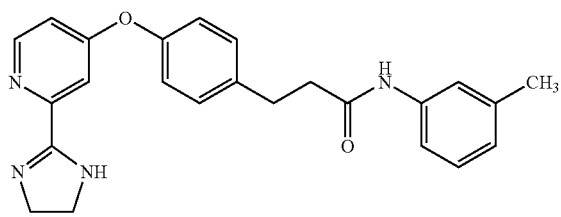
A-126
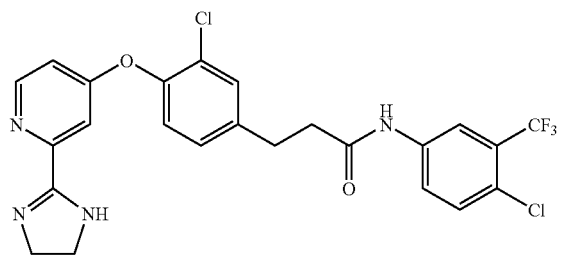
A-127
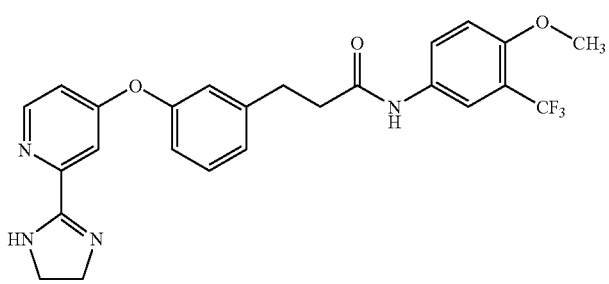
A-128
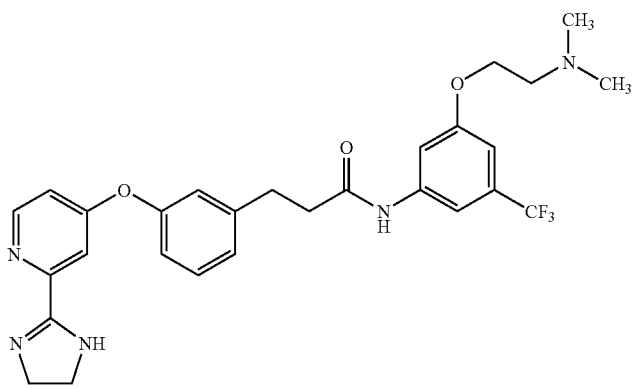
A-129
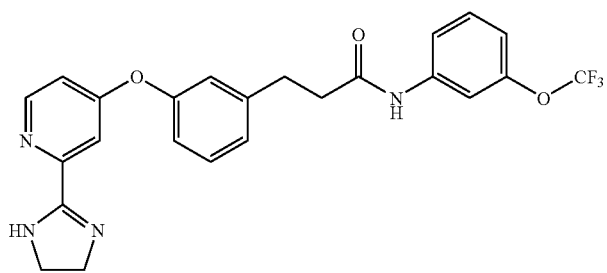
A-130

TABLE 1-continued
Raf Kinase Inhibitors
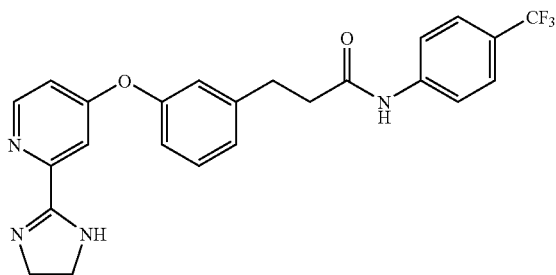
A-131
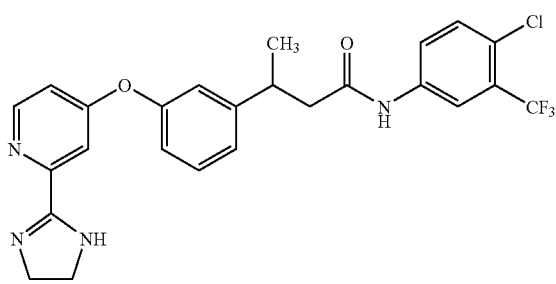
A-132
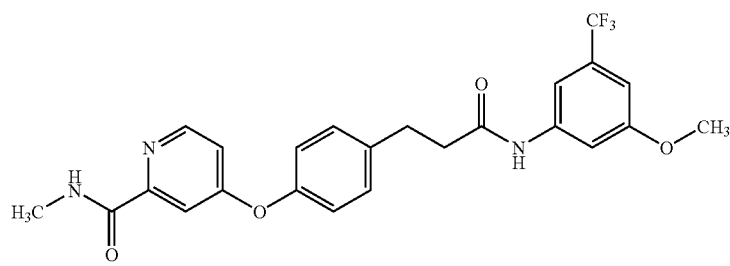
A-133
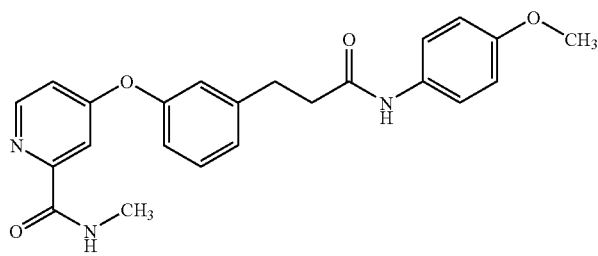
A-134
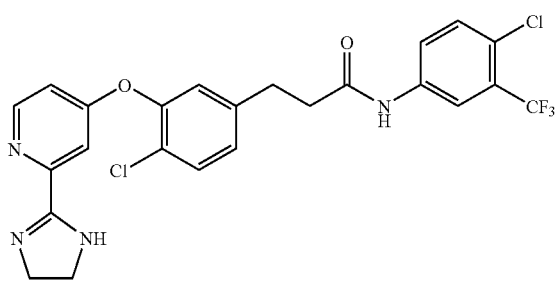
A-135

TABLE 1-continued
Raf Kinase Inhibitors
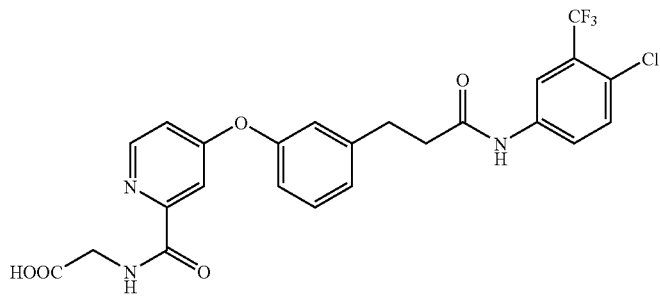
A-136
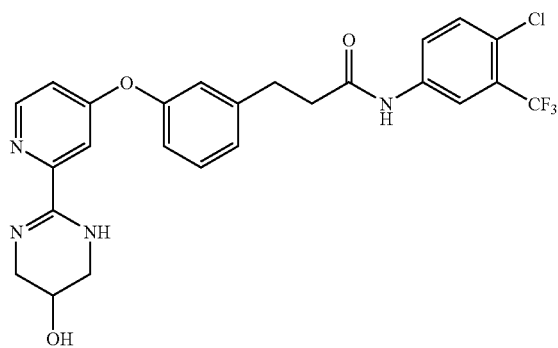
A-137
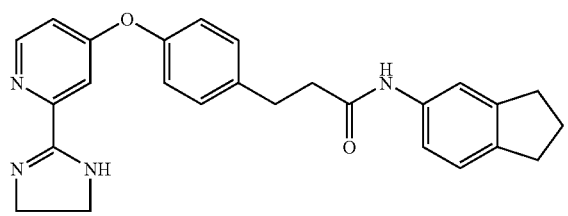
A-138
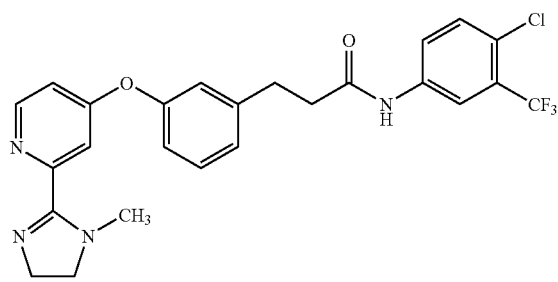
A-139

TABLE 1-continued
Raf Kinase Inhibitors
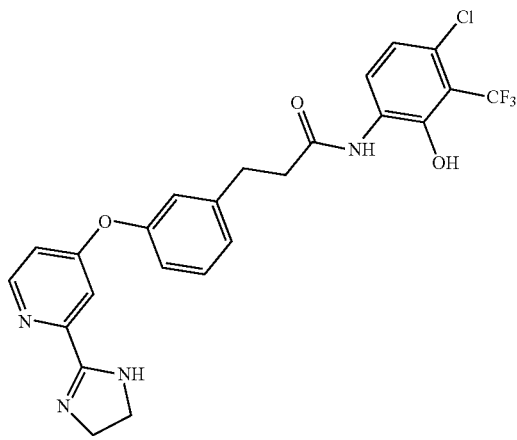
A-140
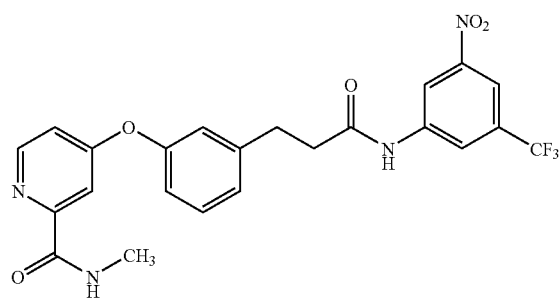
A-141
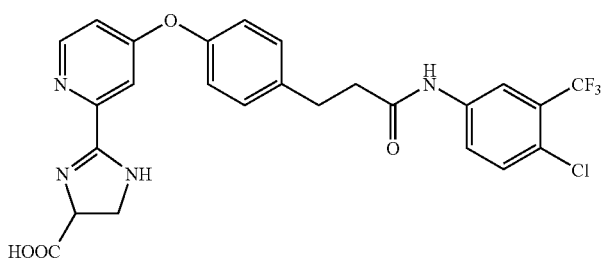
A-142
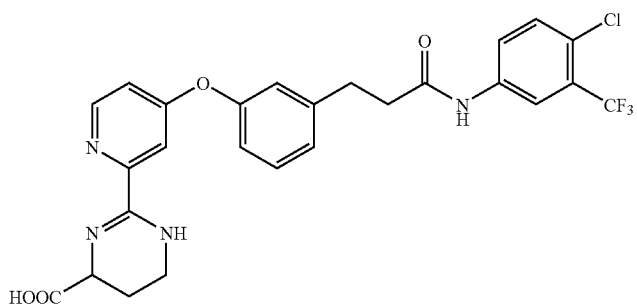
A-143

TABLE 1-continued
Raf Kinase Inhibitors
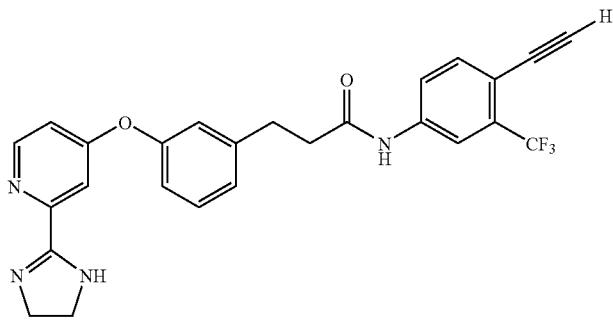
A-144
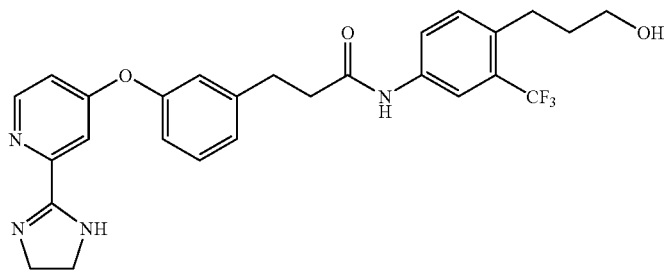
A-145
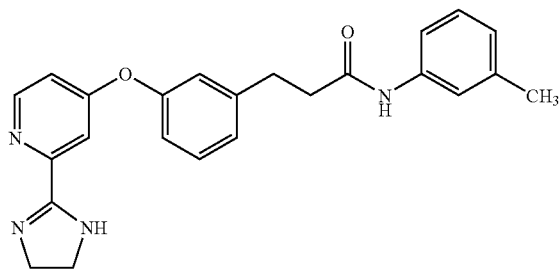
A-146
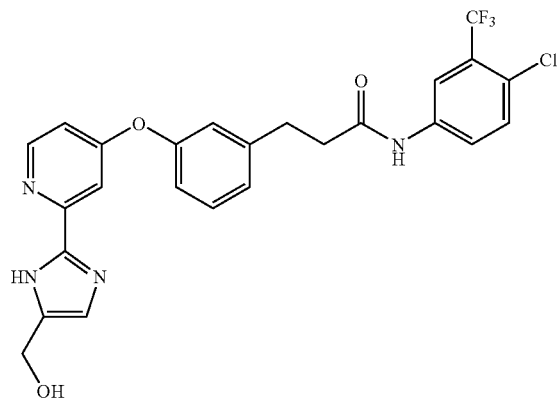
A-147

TABLE 1-continued
Raf Kinase Inhibitors
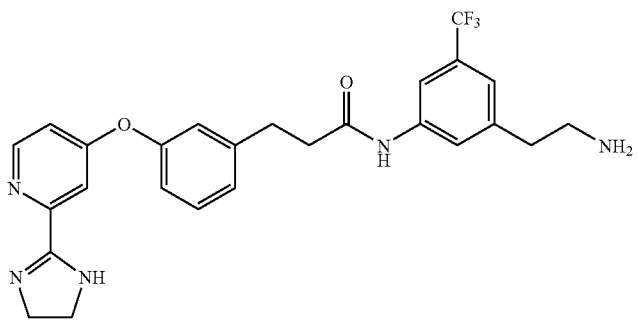
A-148
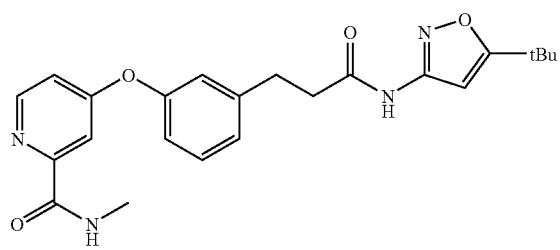
A-149
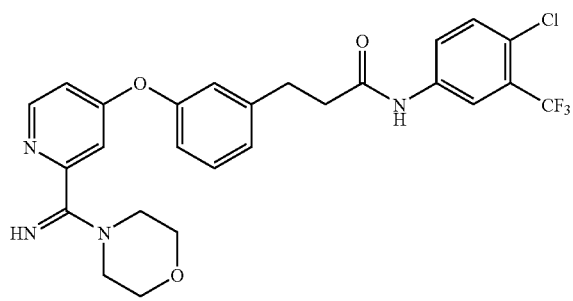
A-150
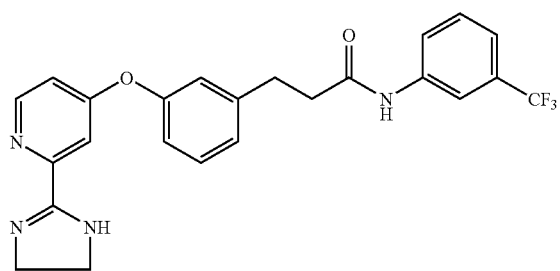
A-151

TABLE 1-continued
Raf Kinase Inhibitors
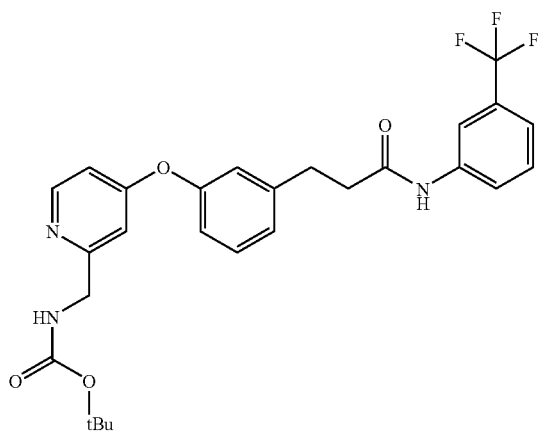
A-152
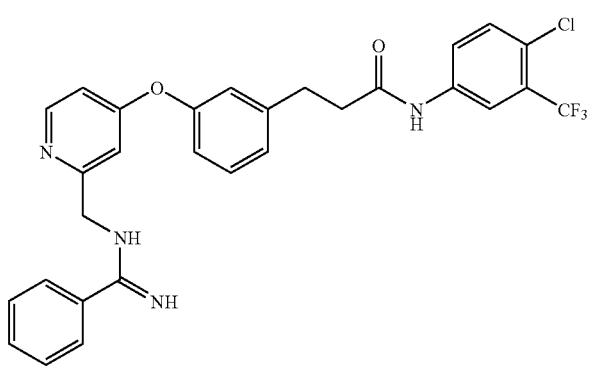
A-153
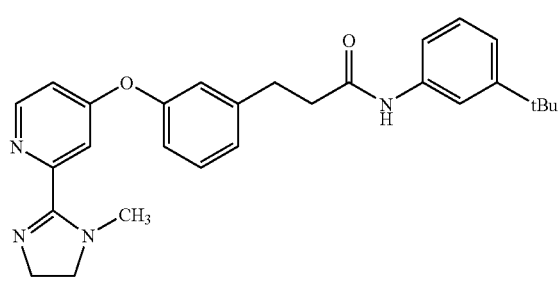
A-154
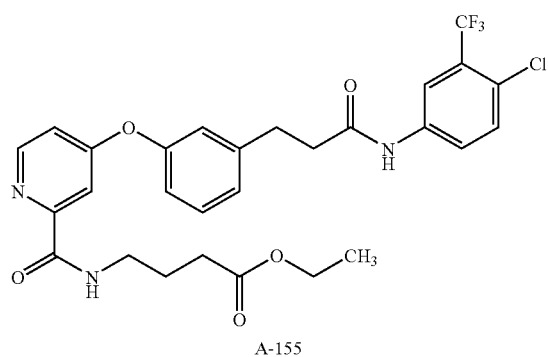
A-155

TABLE 1-continued
Raf Kinase Inhibitors
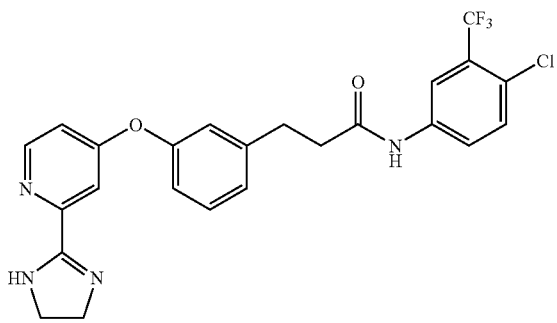
A-156
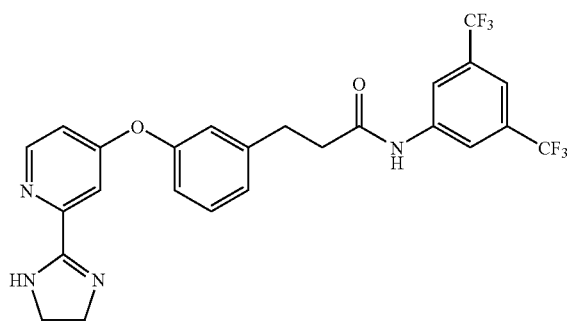
A-157
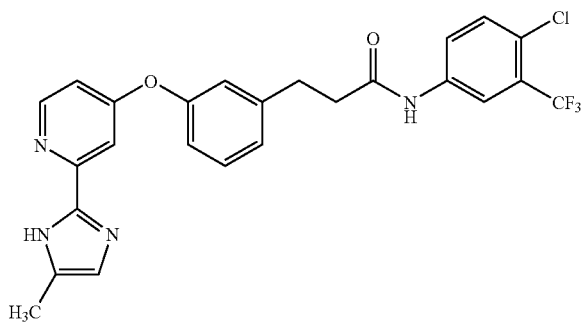
A-158
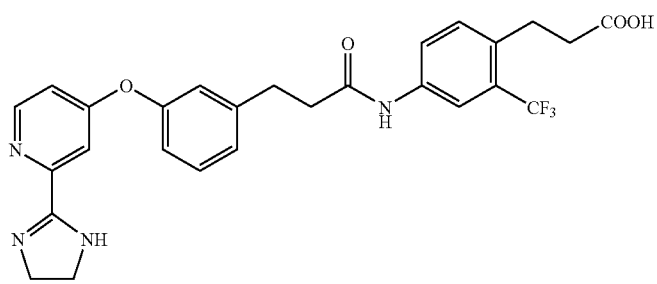
A-159

TABLE 1-continued
Raf Kinase Inhibitors
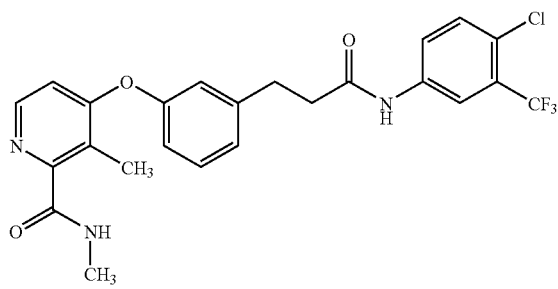
A-160
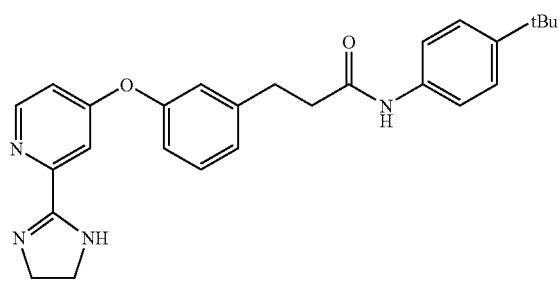
A-161
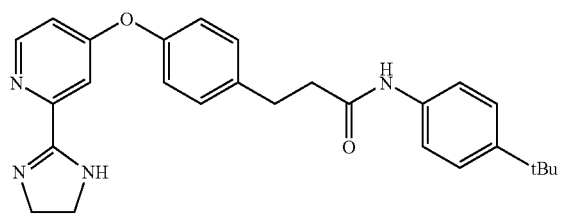
A-162
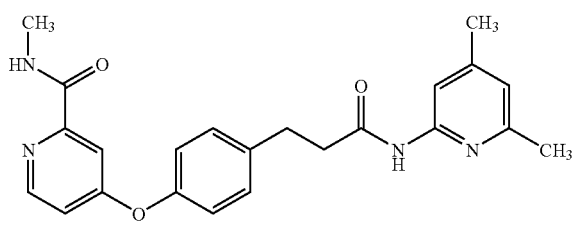
A-163
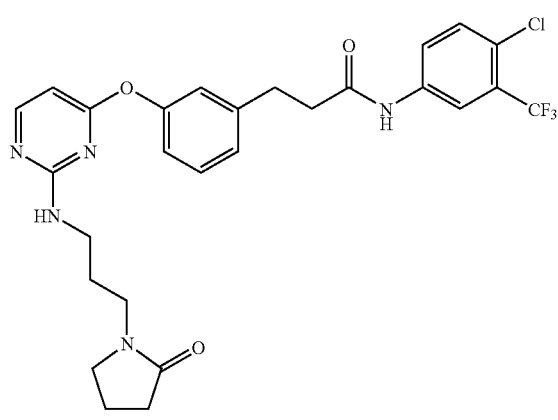
A-164

TABLE 1-continued
Raf Kinase Inhibitors
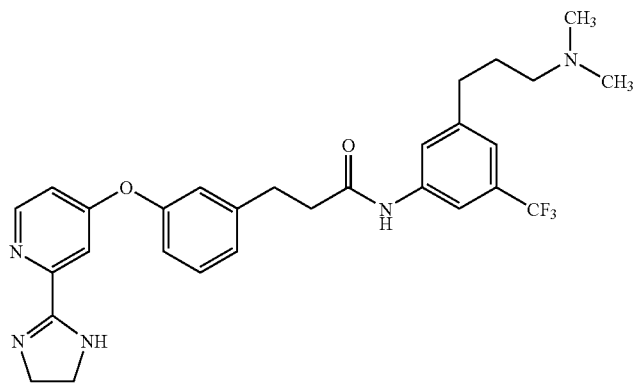
A-165
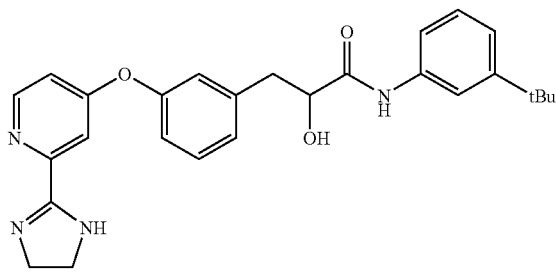
A-166
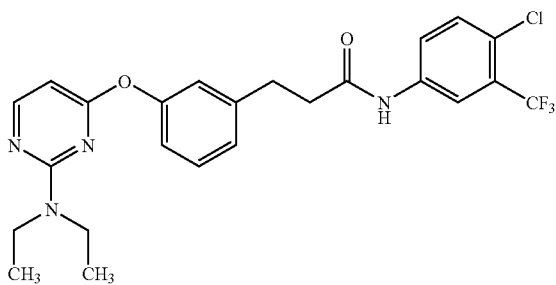
A-167
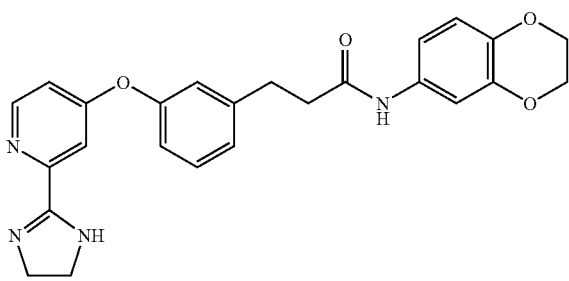
A-168

TABLE 1-continued
Raf Kinase Inhibitors
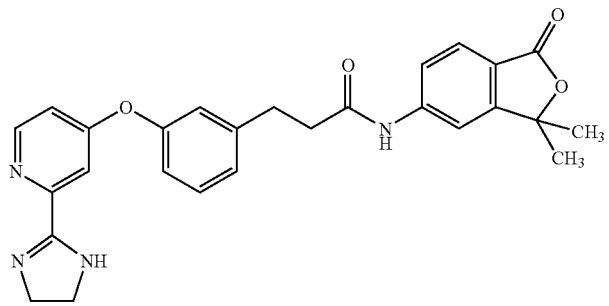
A-169
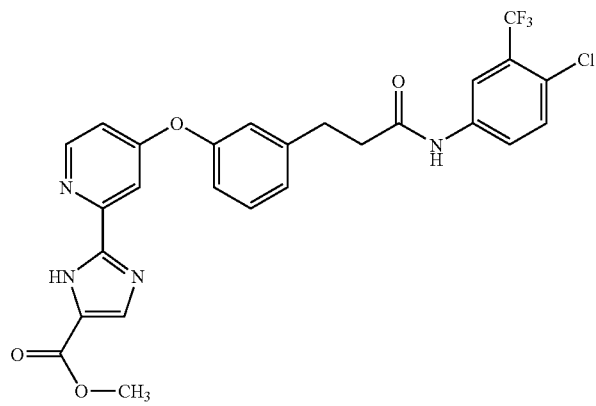
A-170
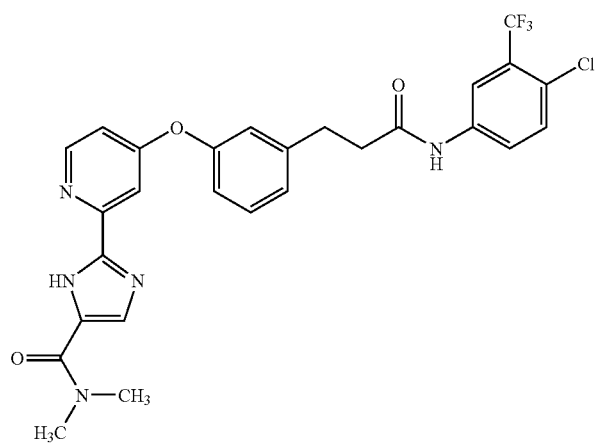
A-171

TABLE 1-continued
Raf Kinase Inhibitors
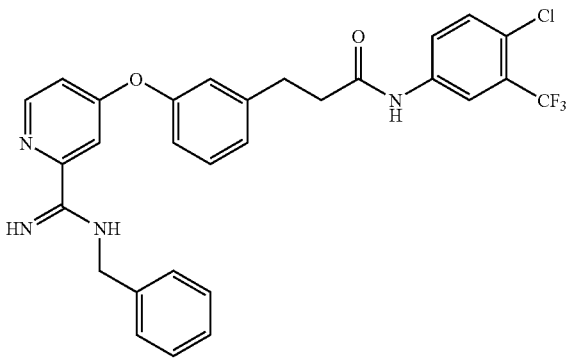
A-172
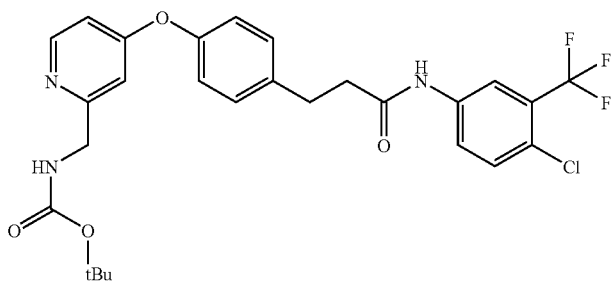
A-173
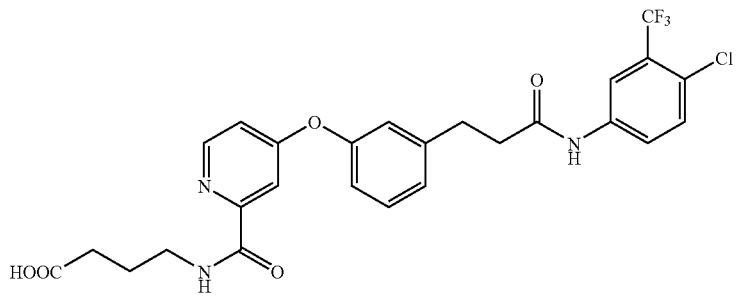
A-174
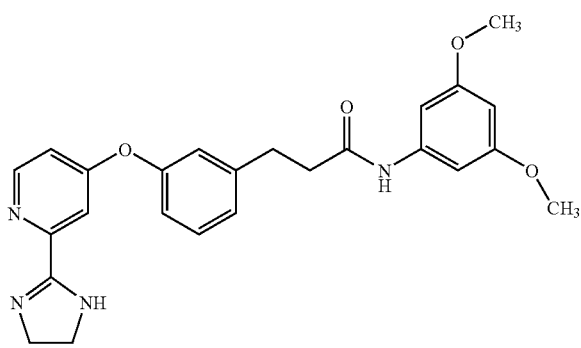
A-175

TABLE 1-continued
Raf Kinase Inhibitors
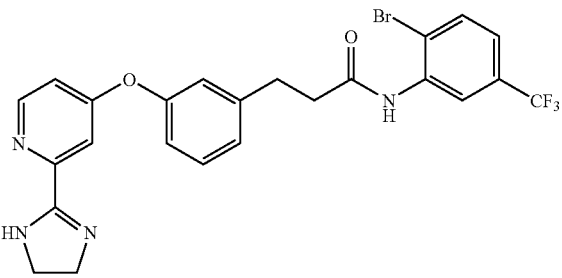
A-176
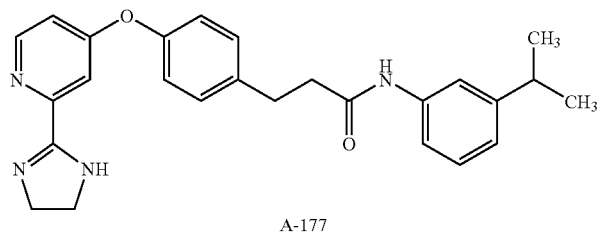
A-177
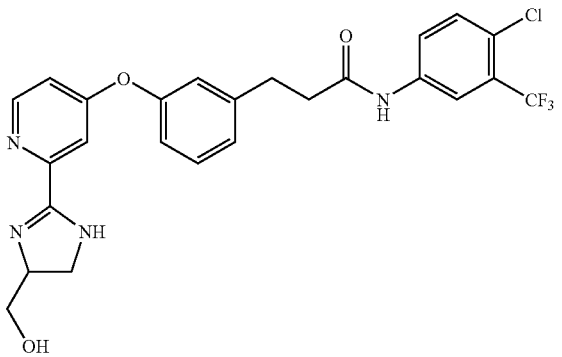
A-178
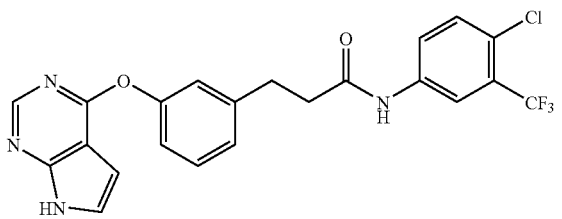
A-179
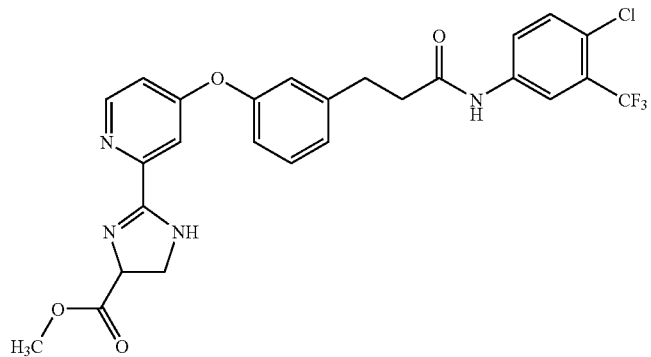
A-180

TABLE 1-continued
Raf Kinase Inhibitors
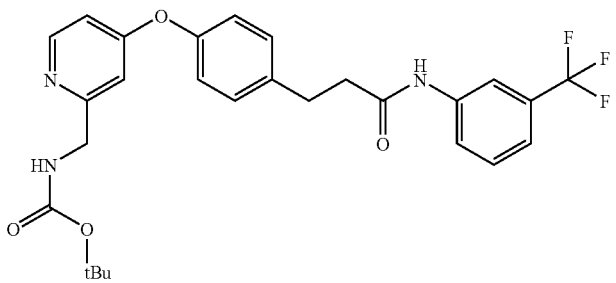
A-181
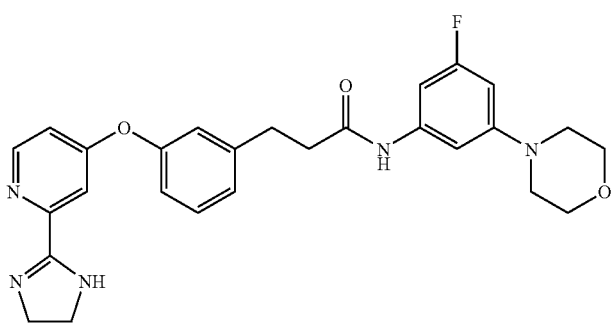
A-182
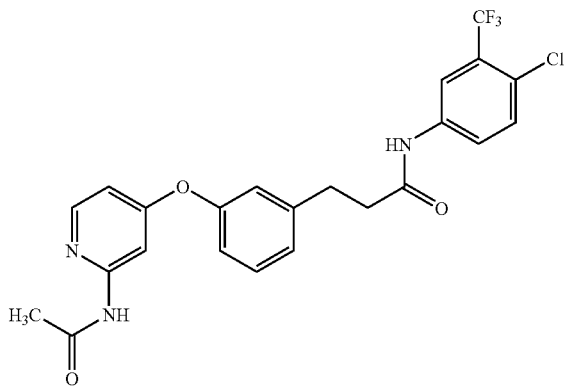
A-183
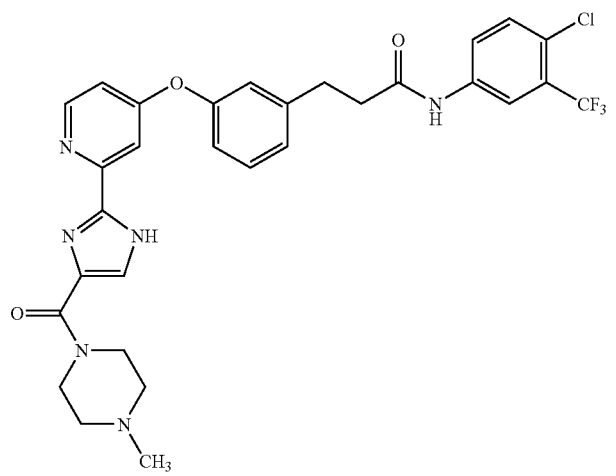
A-184

TABLE 1-continued
Raf Kinase Inhibitors
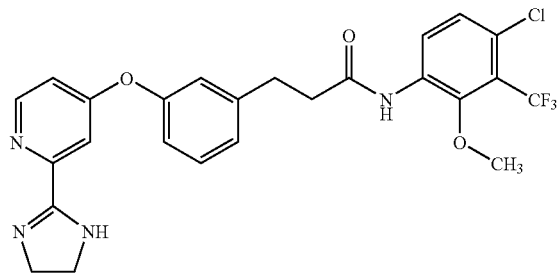
A-185
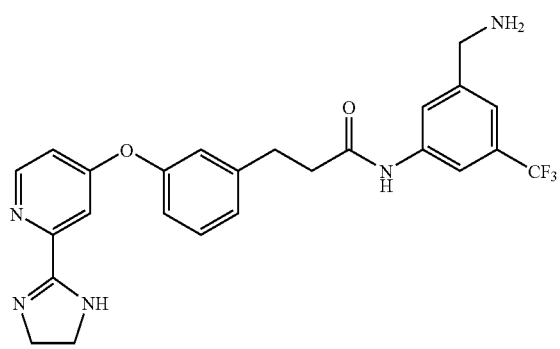
A-186
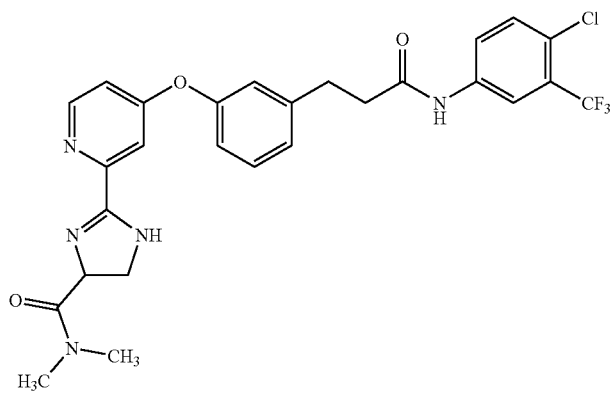
A-187
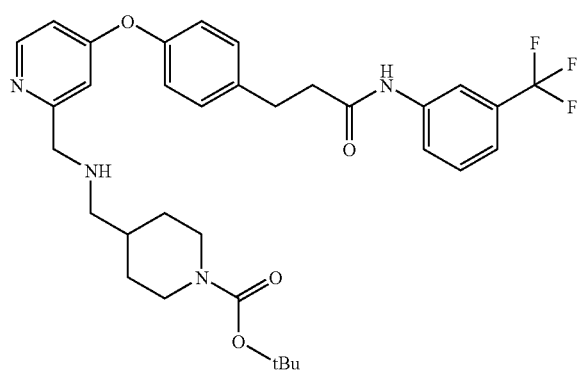
A-188

TABLE 1-continued
Raf Kinase Inhibitors
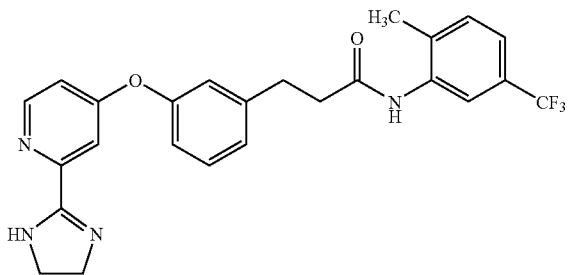
A-189
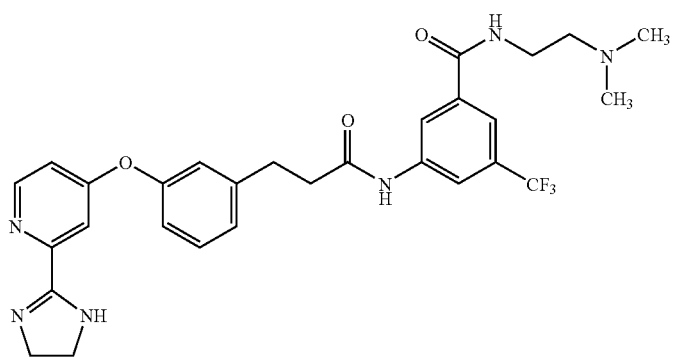
A-190
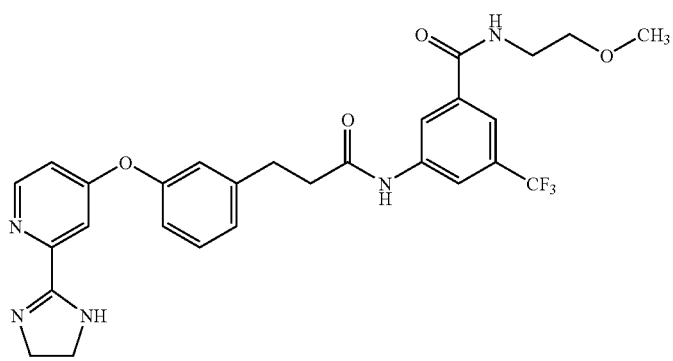
A-191
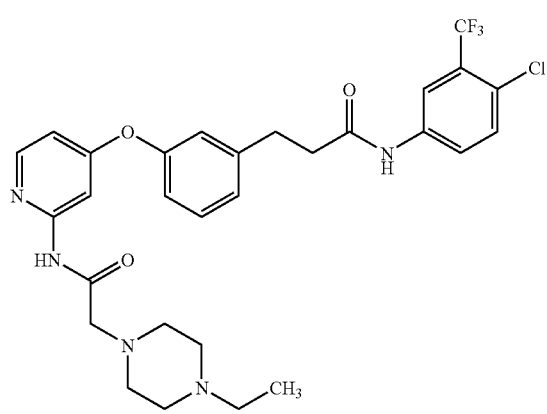
A-192

TABLE 1-continued
Raf Kinase Inhibitors
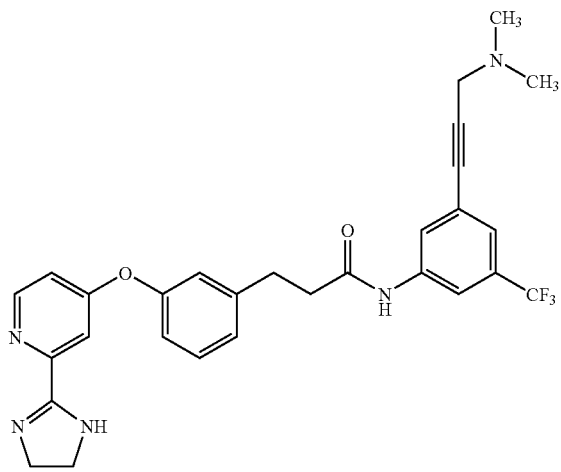
A-193
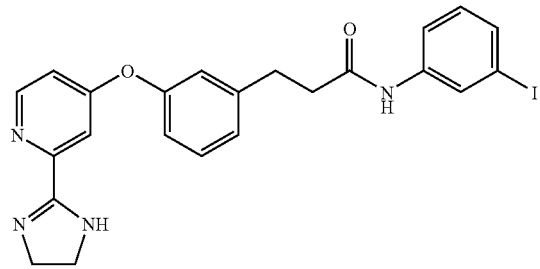
A-194
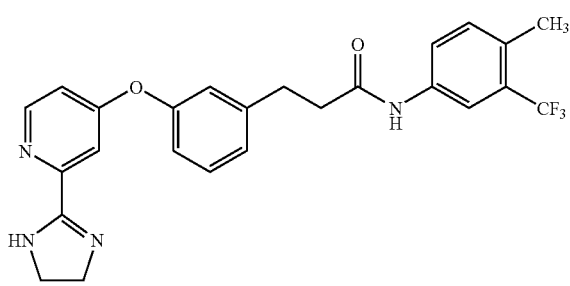
A-195
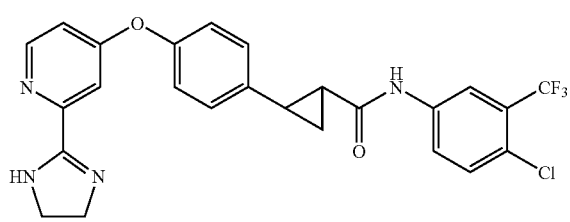
A-196

-continued
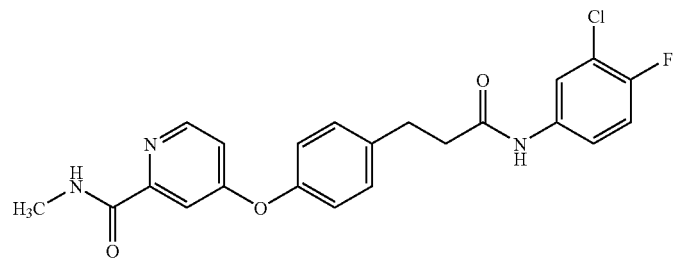
A-197
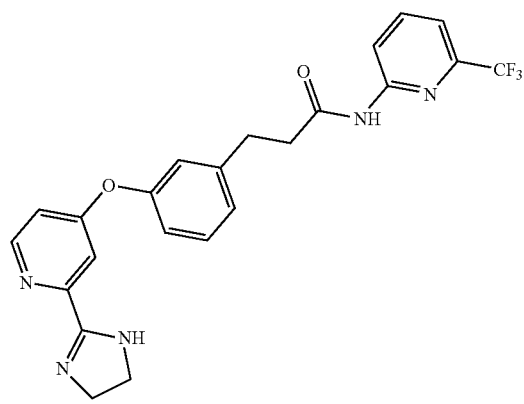
A-198
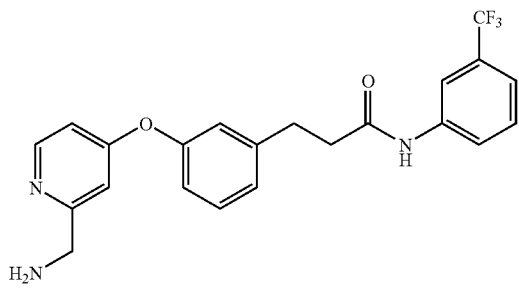
A-199
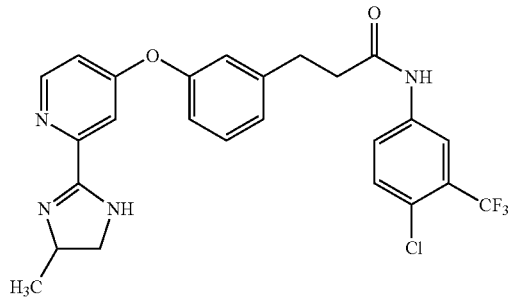
A-200

-continued
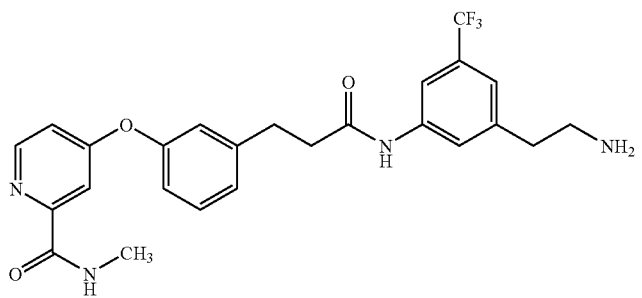
A-201
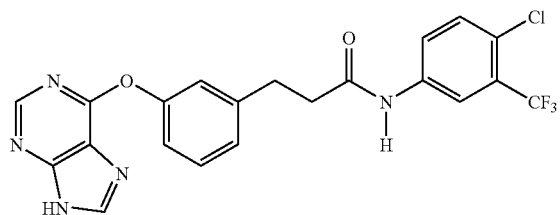
A-202
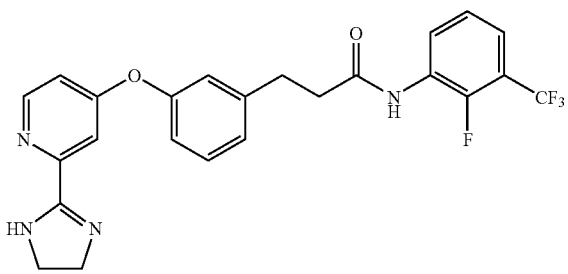
A-203
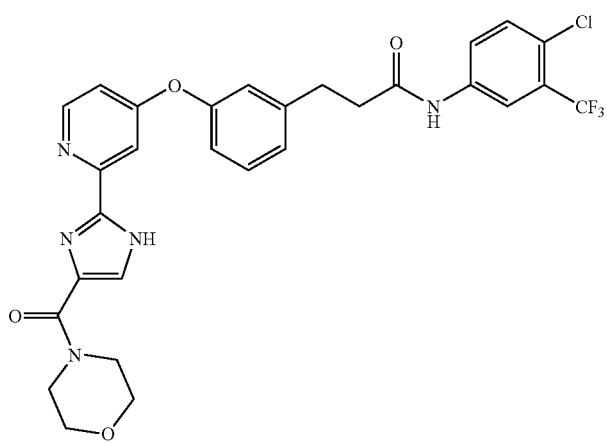
A-204
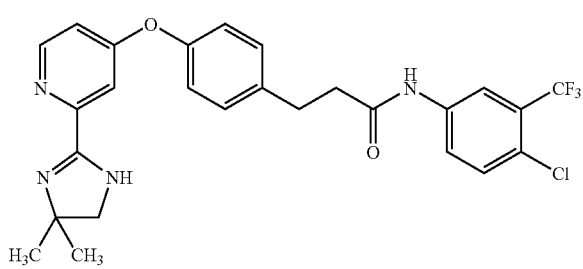
A-205

-continued
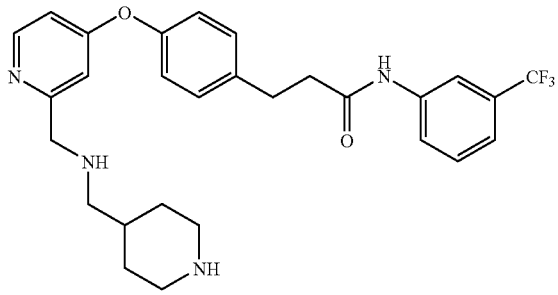
A-206
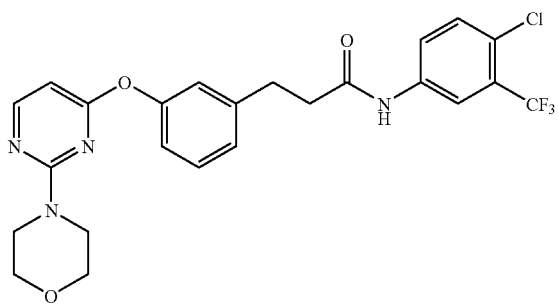
A-207
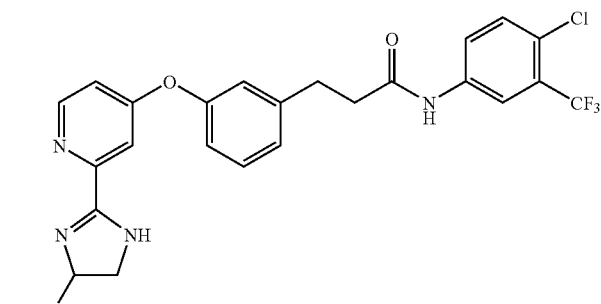
A-208
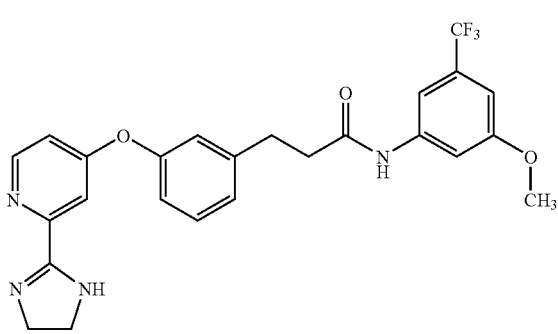
A-209
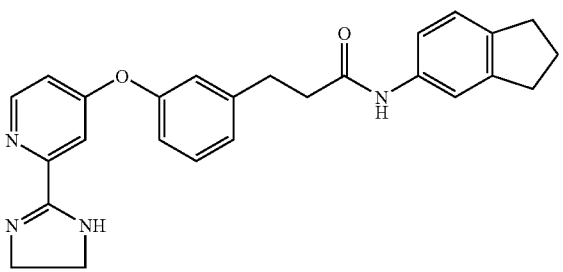
A-210

-continued
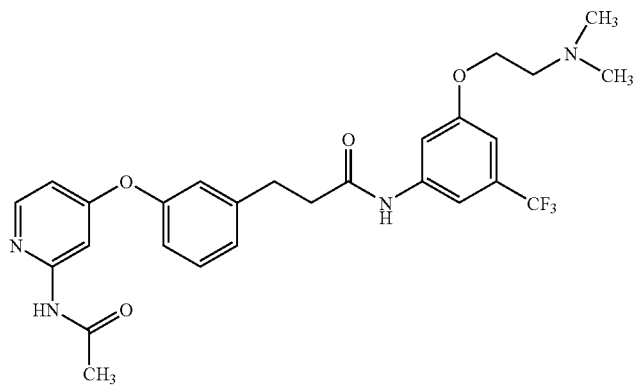
A-211
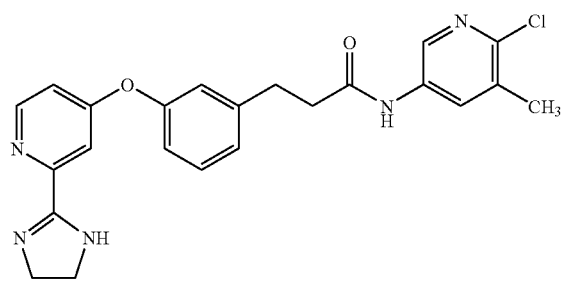
A-212
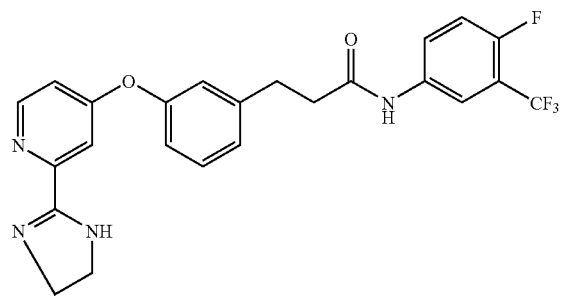
A-213
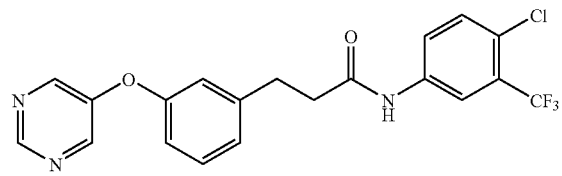
A-214
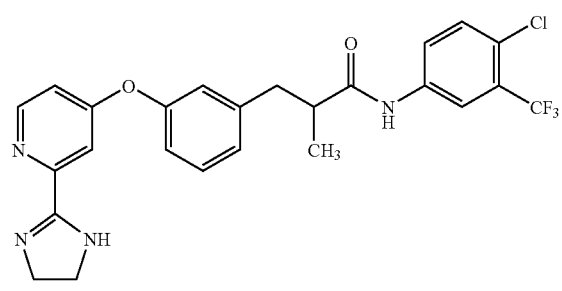
A-215

-continued
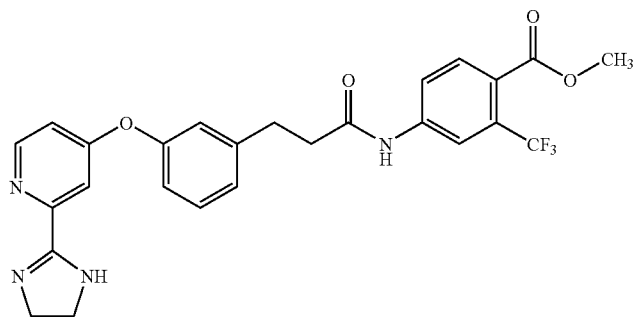
A-216
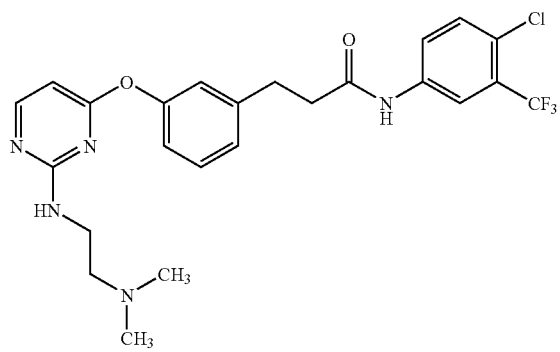
A-217
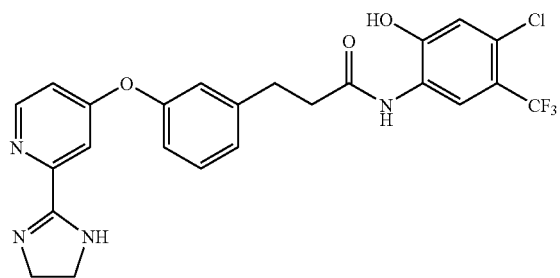
A-218
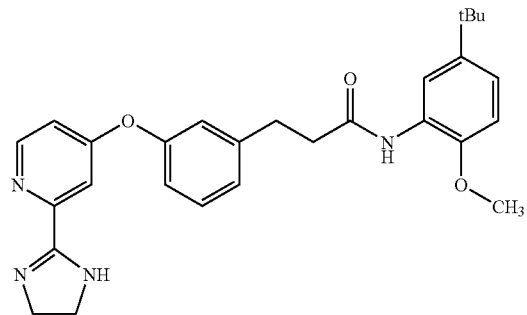
A-219

-continued
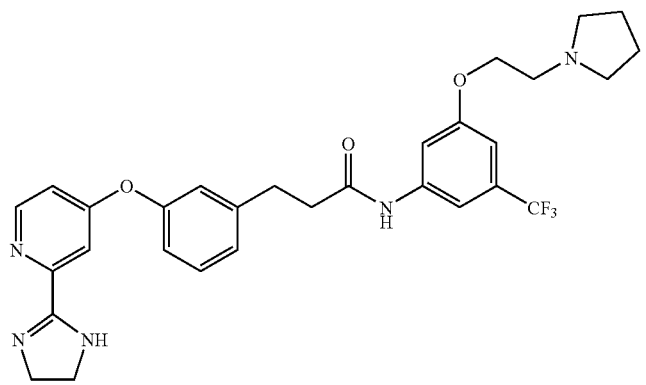
A-220
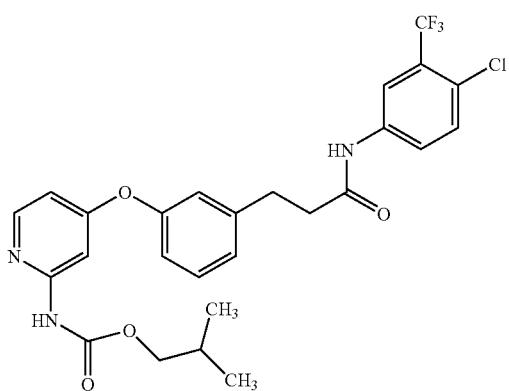
A-221
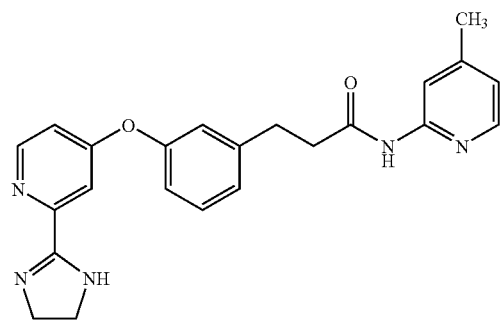
A-222
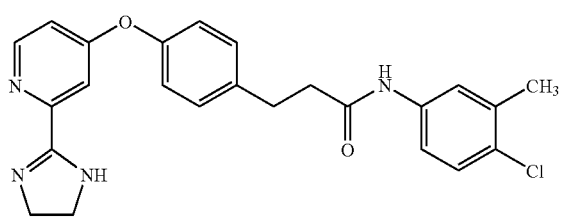
A-223

-continued
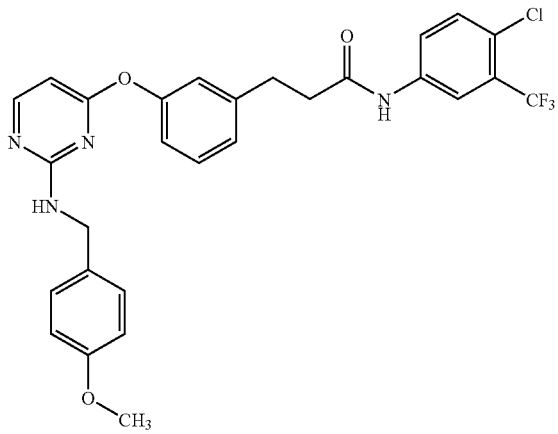
A-224
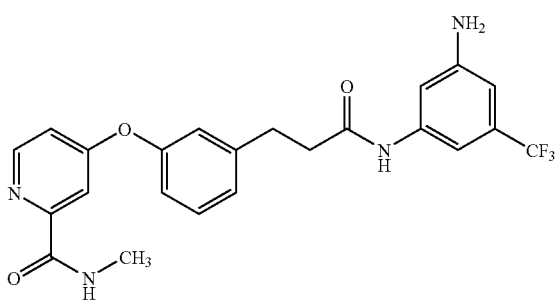
A-225
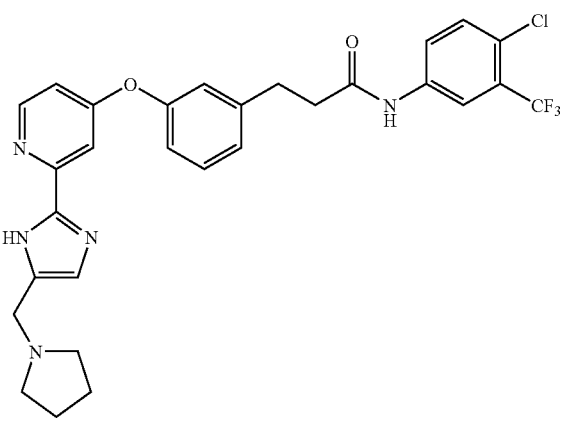
A-226
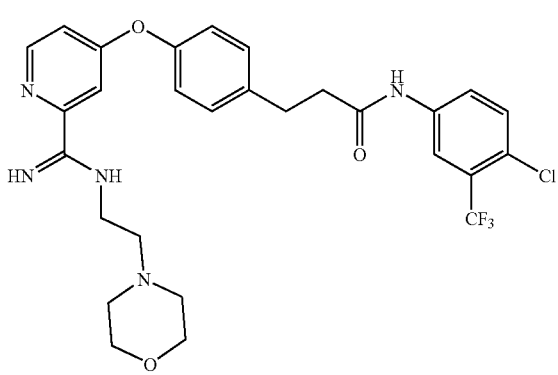
A-227

-continued
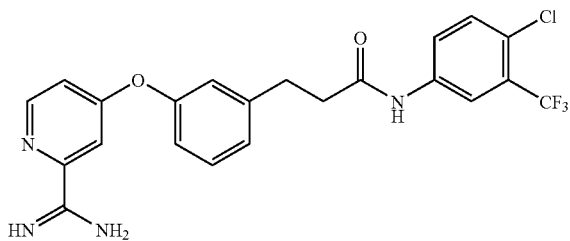
A-228
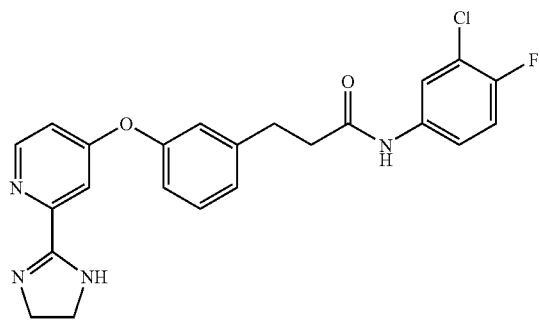
A-229
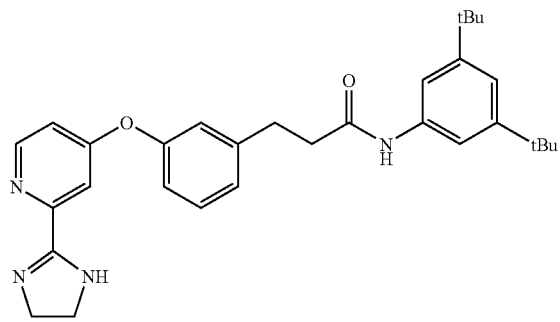
A-230
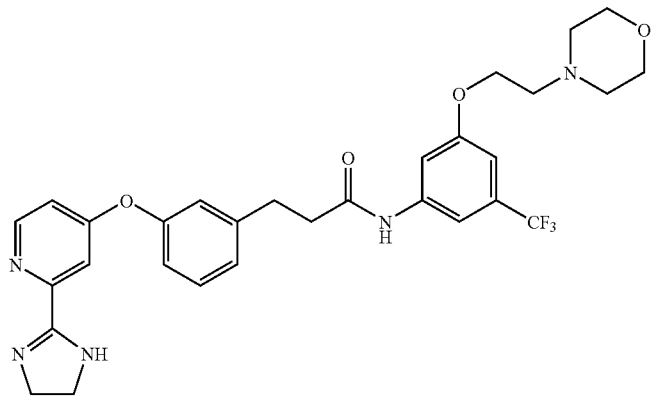
A-231

-continued
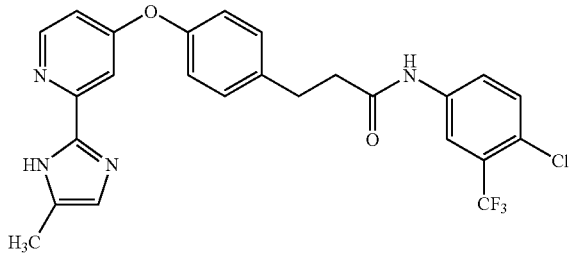
A-232
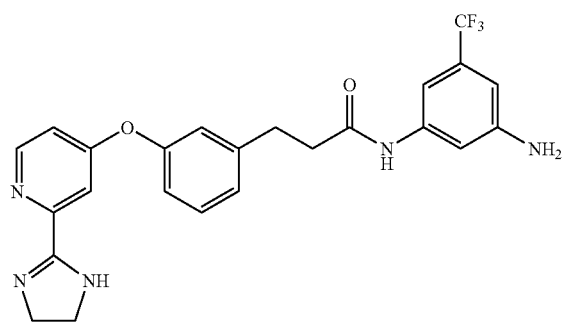
A-233
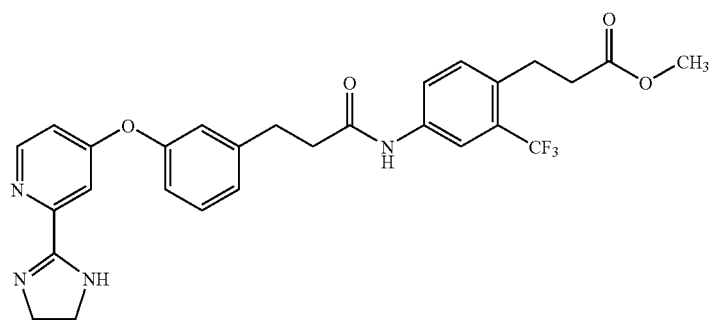
A-234
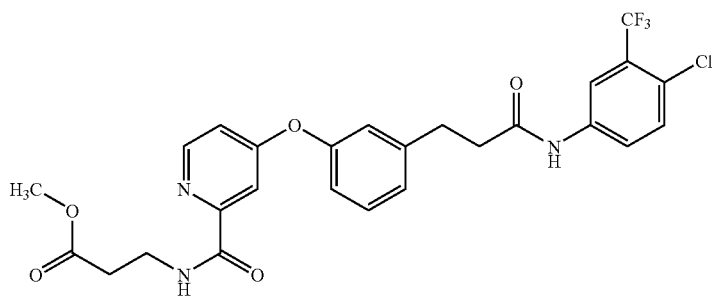
A-235
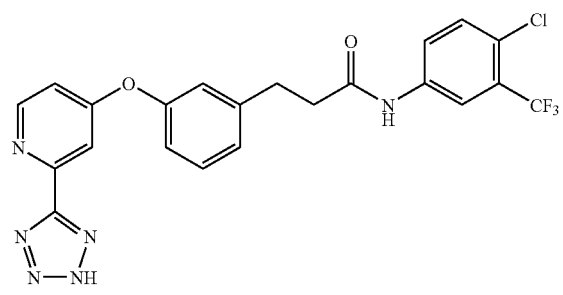
A-236

-continued
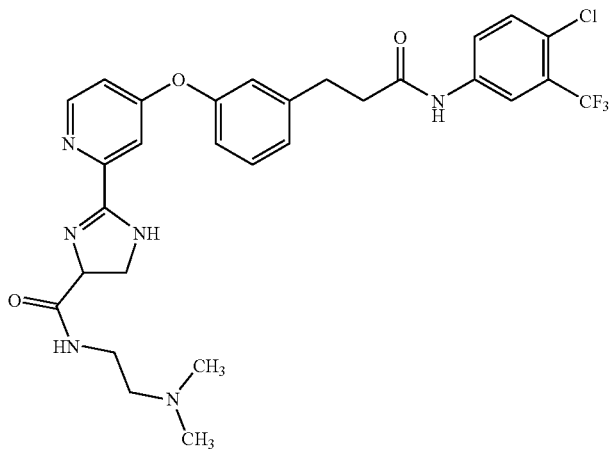
A-237
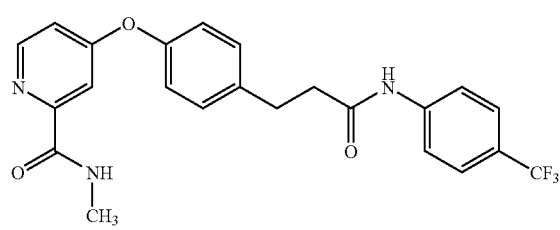
A-238
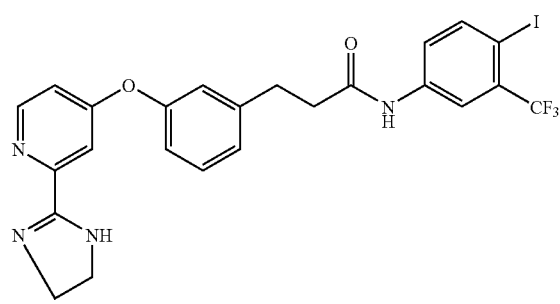
A-239
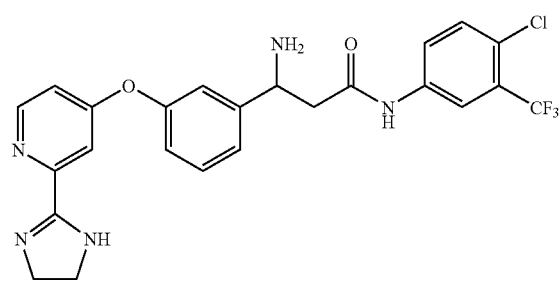
A-240

-continued
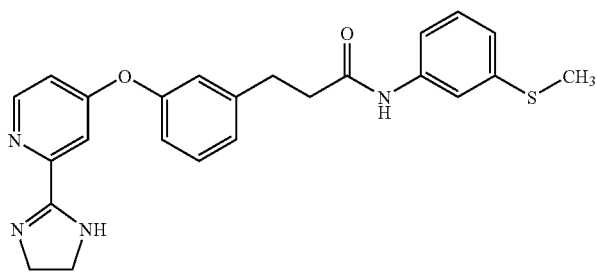
A-241
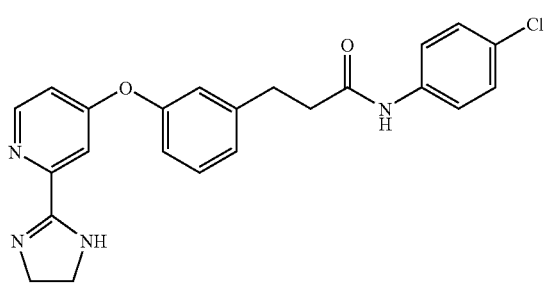
A-242
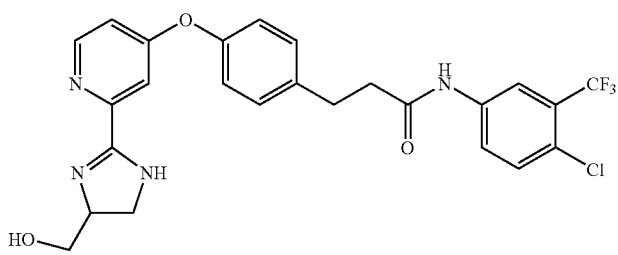
A-243
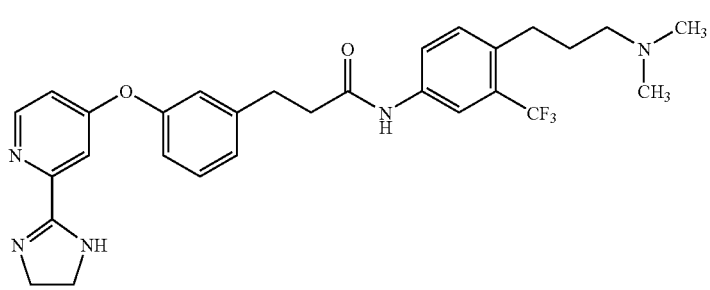
A-244
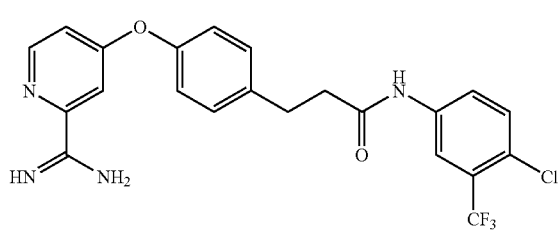
A-245

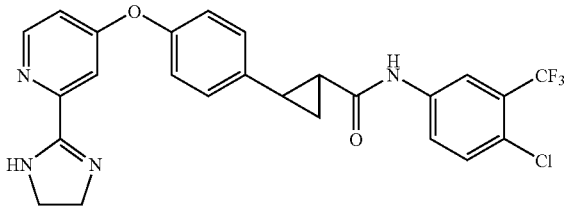
A-246
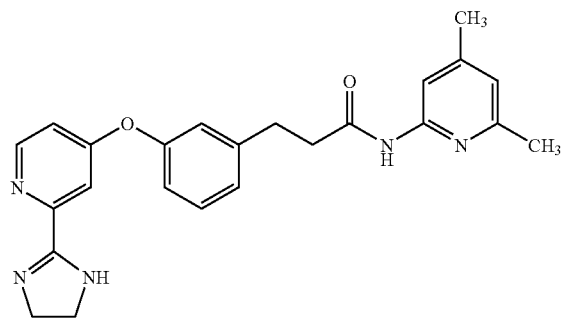
A-247
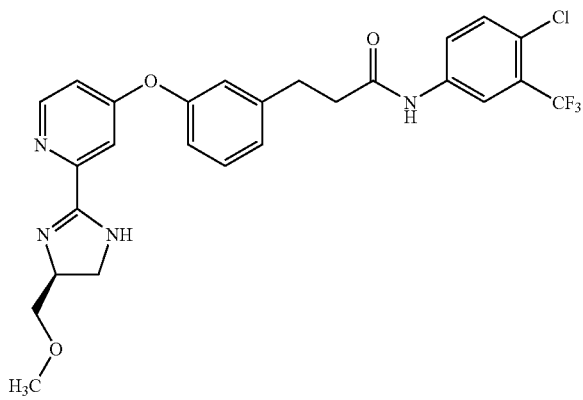
A-248
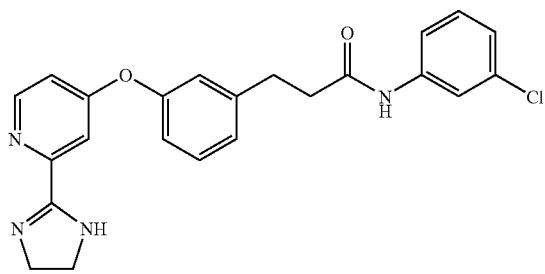
A-249
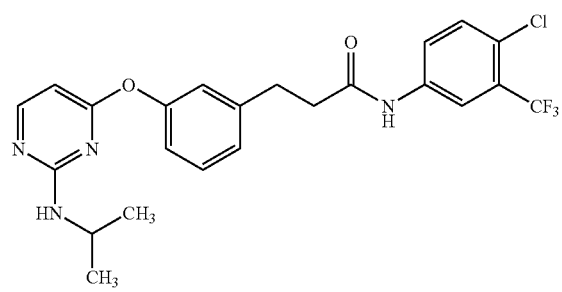
A-250

-continued
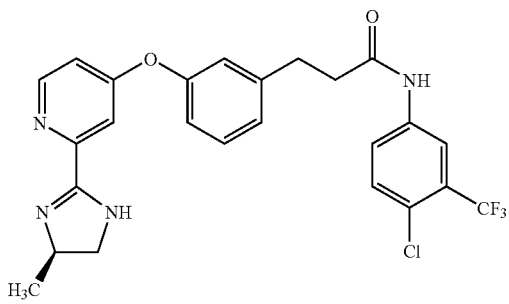
A-251
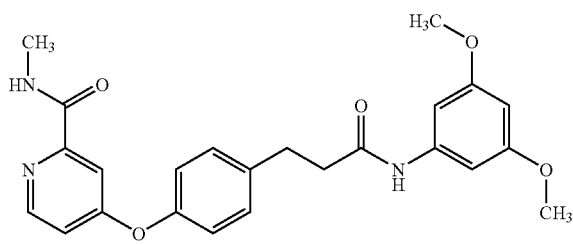
A-252
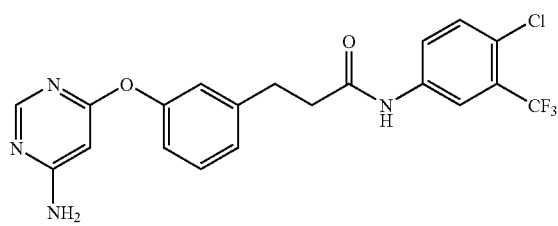
A-253
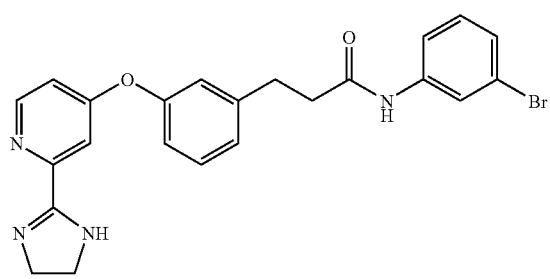
A-254
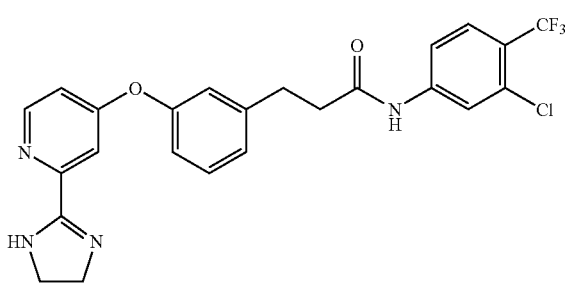
A-255

-continued
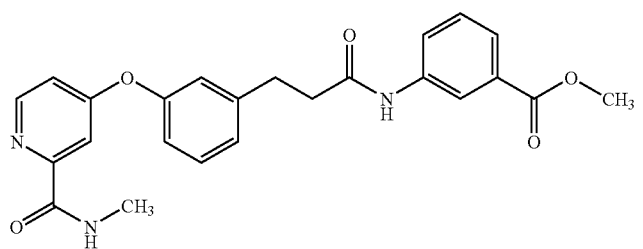
A-256
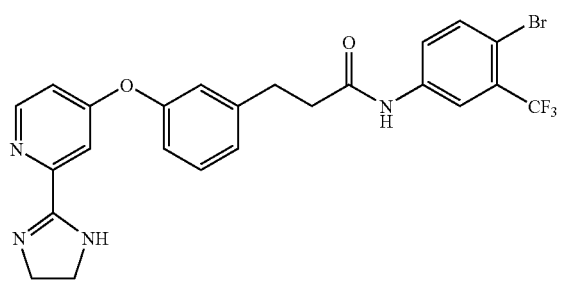
A-257
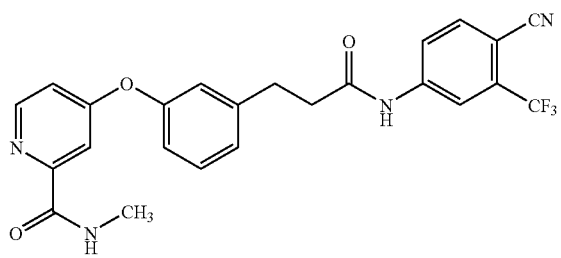
A-258
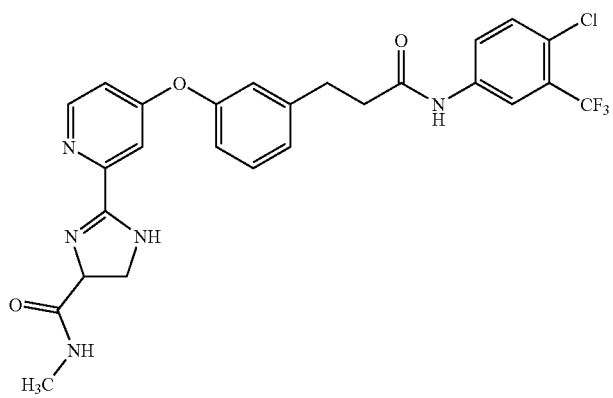
A-259

-continued
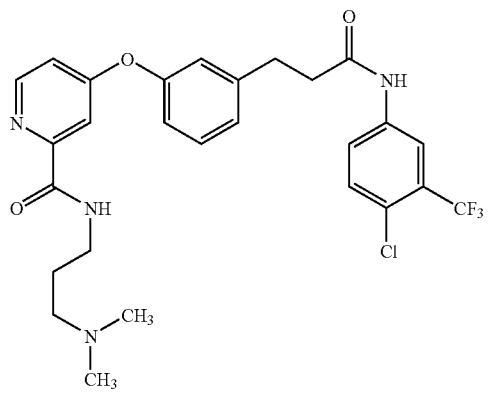
A-260
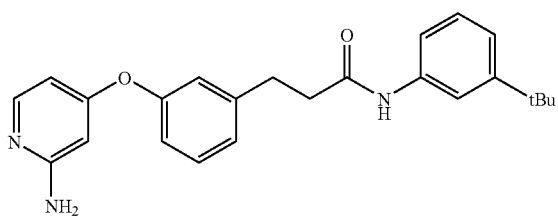
A-261
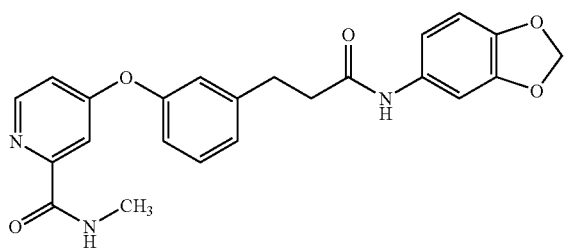
A-262
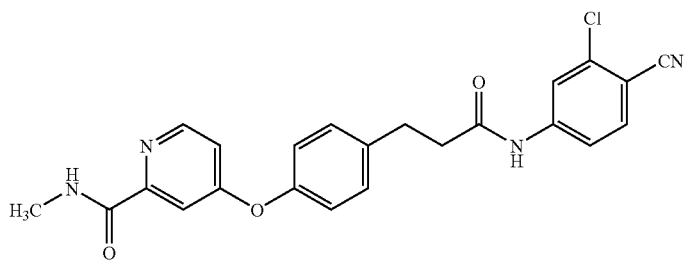
A-263
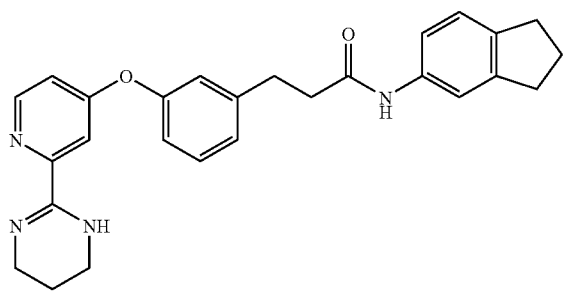
A-264

-continued
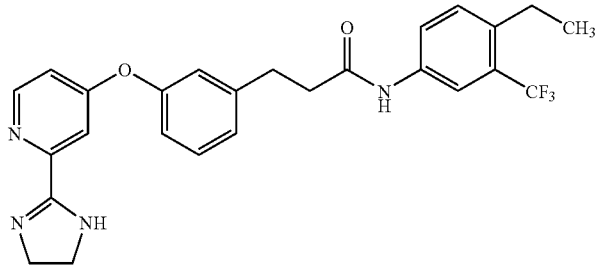
A-265
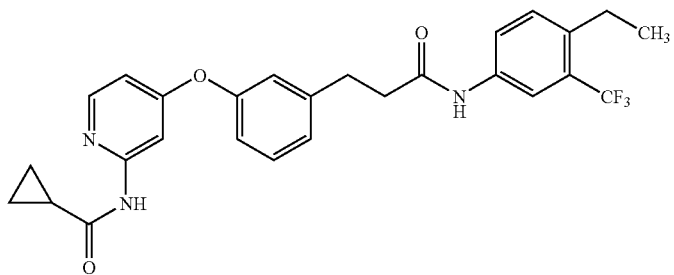
A-266
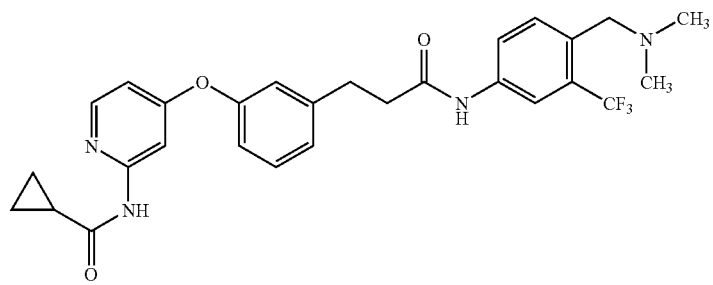
A-267
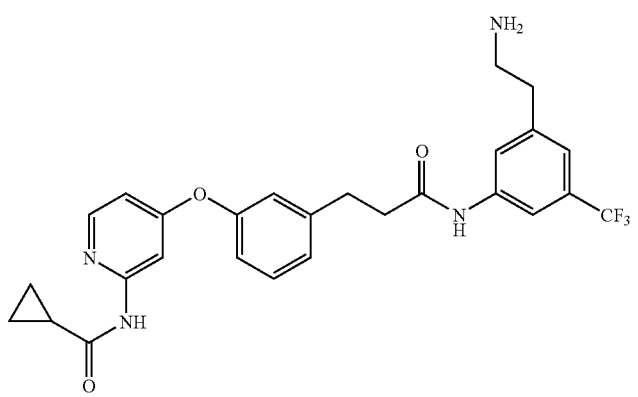
A-268
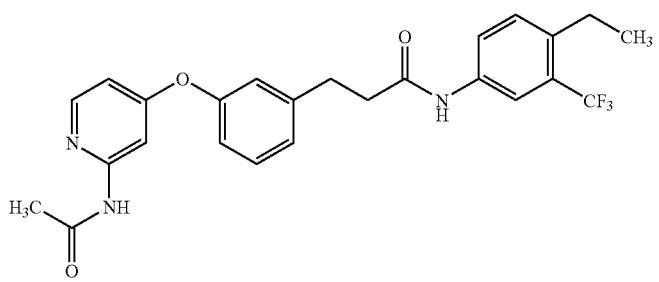
A-269

-continued

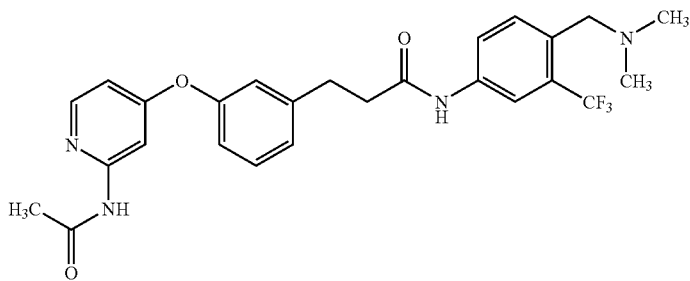

A-270

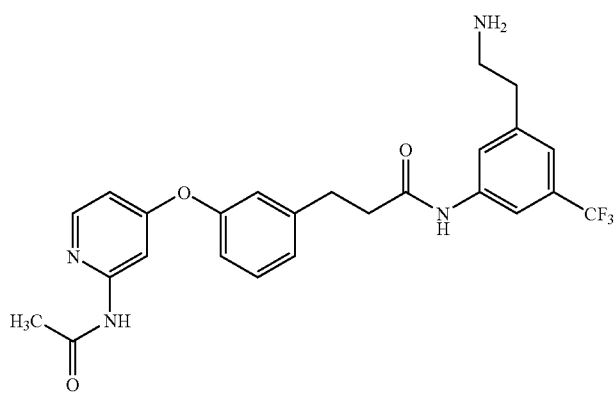

A-271

The compounds in Table 1 above also may be identified by the following chemical names:

| | Chemical Name |
|---|---|
| A-1: | 4-(4-{3-[(4-chlorophenyl)amino]-3-oxopropyl}phenoxy)pyridine-2-carboxamide |
| A-2: | 4-[4-(3-oxo-3-{[3-(trifluoromethyl)phenyl]amino}propyl)phenoxy]pyridine-2-carboxamide |
| A-3: | 4-[4-(3-{[4-chloro-3-(trifluoromethyl)phenyl]amino}-3-oxopropyl)-phenoxy]pyridine-2-carboxamide |
| A-4: | N-methyl-4-[4-(3-oxo-3-{[3-(trifluoromethyl)phenyl]amino}propyl)-phenoxy]pyridine-2-carboxamide |
| A-5: | N-methyl-4-[3-(3-oxo-3-{[3-(trifluoromethyl)phenyl]amino}-propyl)phenoxy]pyridine-2-carboxamide |
| A-6: | N-[4-chloro-3-(trifluoromethyl)phenyl]-3-[4-(pyridin-4-yloxy)-phenyl]propanamide |
| A-7: | 4-[3-(3-{[4-chloro-3-(trifluoromethyl)phenyl]amino}-3-oxopropyl)phenoxy]-N-methylpyridine-2-carboxamide |
| A-8: | 4-[4-(4-{[4-chloro-3-(trifluoromethyl)phenyl]amino}-4-oxobutyl)phenoxy]-N-methylpyridine-2-carboxamide |
| A-9: | 4-[4-(3-{[4-chloro-3-(trifluoromethyl)phenyl]amino}-3-oxopropyl)phenoxy]-N-methylpyridine-2-carboxamide |
| A-10 | 4-[4-(3-{[2-fluoro-5-(trifluoromethyl)phenyl]amino}-3-oxopropyl)phenoxy]-N-methylpyridine-2-carboxamide |
| A-11: | 4-(4-{3-[(4-chlorophenyl)amino]-3-oxopropyl}phenoxy)-N-methylpyridine-2-carboxamide |
| A-12: | 4-[4-(3-anilino-3-oxopropyl)phenoxy]-N-methylpyridine-2-carboxamide |
| A-13: | 4-(3-{3-[(4-chlorophenyl)amino]-3-oxopropyl}phenoxy)-N-methylpyridine-2-carboxamide |
| A-14: | 4-[3-(3-anilino-3-oxopropyl)phenoxy]-N-methylpyridine-2-carboxamide |
| A-15: | N-methyl-4-(3-{3-[(3-chlorophenyl)amino]-3-oxopropyl}phenoxy)pyridine-2-carboxamide |
| A-16: | 4-(3-{3-[(3,4-dimethylphenyl)amino]-3-oxopropyl}phenoxy)-N-methylpyridine-2-carboxamide |
| A-17: | 4-(3-{3-[(4-chloro-3-methoxyphenyl)amino]-3-oxopropyl}phenoxy)-N-methylpyridine-2-carboxamide |

|       | Chemical Name |
|-------|---------------|
| A-18: | 4-{3-[3-(2,3-dihydro-1H-inden-5-ylamino)-3-oxopropyl]phenoxy}-N-methylpyridine-2-carboxamide |
| A-19: | 4-{[3-(3-{[2-(4,5-dihydro-1H-imidazol-2-yl)pyridin-4-yl]oxy}phenyl)propanoyl]amino}-2-(trifluoromethyl)benzoic acid |
| A-20: | N-[4-(3-{3-[(3-tert-butylphenyl)amino]-3-oxopropyl}phenoxy)pyridin-2-yl]cyclopropanecarboxamide |
| A-21: | N-(4-chlorophenyl)-3-{4-[(2-cyanopyridin-4-yl)oxy]phenyl}propanamide |
| A-22: | 3-{4-[(2-cyanopyridin-4-yl)oxy]phenyl}-N-[3-(trifluoromethyl)-phenyl]propanamide |
| A-23: | N-[4-chloro-3-(trifluoromethyl)phenyl]-3-{4-[(2-cyanopyridin-4-yl)oxy]-phenyl}propanamide |
| A-24: | 4-[4-(3-{[4-chloro-3-(trifluoromethyl)phenyl]amino}-3-oxopropyl)phenoxy]-N-[2-(dimethylamino)ethyl]pyridine-2-carboxamide |
| A-25: | 4-[4-(3-{[4-chloro-3-(trifluoromethyl)phenyl]amino}-3-oxopropyl)phenoxy]-N-(2-morpholin-4-ylethyl)pyridine-2-carboxamide |
| A-26: | 4-[4-(3-{[4-chloro-3-(trifluoromethyl)phenyl]amino}-3-oxopropyl)phenoxy]-N-(2-pyrrolidin-1-ylethyl)pyridine-2-carboxamide |
| A-27: | N-[4-chloro-3-(trifluoromethyl)phenyl]-3-(4-{[2-(4,5-dihydro-1H-imidazol-2-yl)pyridin-4-yl]oxy}phenyl)propanamide |
| A-28: | N-[4-chloro-3-(trifluoromethyl)phenyl]-3-(4-{[2-(1H-imidazol-2-yl)pyridin-4-yl]oxy}phenyl)propanamide |
| A-29: | 3-[4-({2-[(methylamino)methyl]pyridin-4-yl}oxy)phenyl]-N-[3-(trifluoromethyl)phenyl]propanamide |
| A-30: | 3-[4-({2-[(methylamino)methyl]pyridin-4-yl}oxy)phenyl]-N-[3-(trifluoromethyl)phenyl]propanamide |
| A-31: | 3-[4-({2-[(dimethylamino)methyl]pyridin-4-yl}oxy)phenyl]-N-[3-(trifluoromethyl)phenyl]propanamide |
| A-32: | 5-[4-(3-{[4-chloro-3-(trifluoromethyl)phenyl]amino}-3-oxopropyl)phenoxy]-N-methylnicotinamide |
| A-33: | 4-[4-(3-{[4-chloro-3-(trifluoromethyl)phenyl]amino}-3-oxopropyl)-3-fluorophenoxy]-N-methylpyridine-2-carboxamide |
| A-34: | 4-[2-chloro-4-(3-{[4-chloro-3-(trifluoromethyl)phenyl]amino}-3-oxopropyl)phenoxy]-N-methylpyridine-2-carboxamide |
| A-35: | N-[4-chloro-3-(trifluoromethyl)pheny]-3-(4-{[2-(1,4,5,6-tetrahydropyrimidin-2-yl)pyridin-4-yl]oxy}phenyl)propanamide |
| A-36: | 3-(4-{[2-(aminomethyl)pyridin-4-yl]oxy}phenyl)-N-[4-chloro-3-(trifluoromethyl)phenyl]propanamide |
| A-37: | 4-[4-(3-{[4-chloro-3-(trifluoromethyl)phenyl]amino}-3-oxopropyl)phenoxy]pyridine-2-carboxylic acid |
| A-38: | 3-{4-[(2-aminopyrimidin-4-yl)oxy]phenyl}-N-[4-chloro-3-(trifluoromethyl)phenyl]propanamide |
| A-39: | 5-[4-(3-{[4-chloro-3-(trifluoromethyl)phenyl]amino}-3-oxopropyl)phenoxy]-N-methylpyridazine-3-carboxamide |
| A-40: | 5-[4-(3-{[4-chloro-3-(trifluoromethyl)phenyl]amino}-3-oxopropyl)phenoxy]-N-methylpyridazine-3-carboxamide |
| A-41: | 3-(4-{[5-(aminomethyl)-1H-pyrazol-4-yl]oxy}phenyl)-N-[4-chloro-3-(trifluoromethyl)phenyl]propanamide |
| A-42: | 3-(4-{[5-(aminomethyl)isoxazol-4-yl]oxy}phenyl)-N-[4-chloro-3-(trifluoromethyl)phenyl]propanamide |
| A-43: | 3-(4-{[2-(aminomethyl)-1,3-benzothiazol-5-yl]oxy}phenyl)-N-[4-chloro-3-(trifluoromethyl)phenyl]propanamide |
| A-44: | N-methyl-4-{4-[3-oxo-3-(quinoxalin-2-ylamino)propyl]phenoxy}pyridine-2-carboxamide |
| A-45: | N-methyl-4-[4-(3-oxo-3-{[4-(trifluoromethyl)pyridin-2-yl]amino}propyl)phenoxy]pyridine-2-carboxamide |
| A-46: | 4-{4-[3-(isoquinolin-3-ylamino)-3-oxopropyl]phenoxy}-N-methylpyridine-2-carboxamide |
| A-47: | N-methyl-4-[4-(3-oxo-3-{[2-(trifluoromethyl)pyridin-4-yl]amino}propyl)phenoxy]pyridine-2-carboxamide |
| A-48: | 4-(4-{3-[(5-tert-butylisoxazol-3-yl)amino]-3-oxopropyl}phenoxy)-N-methylpyridine-2-carboxamide |
| A-49: | 4-(4-{3-[(3-tert-butylisoxazol-5-yl)amino]-3-oxopropyl}phenoxy)-N-methylpyridine-2-carboxamide |
| A-50 | 4-[3-(3-{[4-(aminomethyl)-3-(trifluoromethyl)phenyl]amino}-3-oxopropyl)phenoxy]-N-methylpyridine-2-carboxamide |
| A-51 | 3-(3-{[2-(4,5-dihydro-1H-imidazol-2-yl)pyridin-4-yl]oxy}phenyl)-N-[3-(4,5-dihydro-1H-imidazol-2-yl)-5-(trifluoromethyl)phenyl]propanamide |
| A-52 | N-[4-chloro-3-(trifluoromethyl)phenyl]-3-[3-({2-[(ethanimidoylamino)methyl]pyridin-4-yl}oxy)phenyl]propanamide |
| A-53 | N-(3-tert-butylisoxazol-5-yl)-3-(3-{[2-(4,5-dihydro-1H-imidazol-2-yl)pyridin-4-yl]oxy}phenyl)propanamide |
| A-54 | N-[4-chloro-3-(trifluoromethyl)phenyl]-3-{4-[(2-{5-[4-(diethylamino)phenyl]-1H-imidazol-2-yl}pyridin-4-yl)oxy]phenyl}propanamide |
| A-55 | N-[4-chloro-3-(trifluoromethyl)phenyl]-3-(3-{[2-(4,5-dihydro-1H-imidazol-2-yl)pyridin-4-yl]oxy}phenyl)propanamide |
| A-56 | 3-(4-{[2-(aminomethyl)pyridin-4-yl]oxy}phenyl)-N-[3-(trifluoromethyl)phenyl]propanamide |

|   | Chemical Name |
|---|---|
| A-57 | N-[4-chloro-3-(trifluoromethyl)phenyl]-3-(4-{[2-(2H-tetrazol-5-yl)pyridin-4-yl]oxy}phenyl)propanamide |
| A-58 | N-[4-chloro-3-(trifluoromethyl)phenyl]-3-[3-({2-[5-({[2-(dimethylamino)ethyl]amino}methyl)-1H-imidazol-2-yl]pyridin-4-yl}oxy)phenyl]propanamide |
| A-59 | N-(3-tert-butylphenyl)-3-(3-{[2-(4,5-dihydro-1H-imidazol-2-yl)pyridin-4-yl]oxy}phenyl)propanamide |
| A-60 | 2-{4-[4-(3-{[4-chloro-3-(trifluoromethyl)phenyl]amino}-3-oxopropyl)phenoxy]pyridin-2-yl}-N-methyl-4,5-dihydro-1H-imidazole-4-carboxamide |
| A-61 | N-(3-tert-butyl-4-chlorophenyl)-3-(3-{[2-(4,5-dihydro-1H-imidazol-2-yl)pyridin-4-yl]oxy}phenyl)propanamide |
| A-62 | N-[4-chloro-3-(trifluoromethyl)phenyl]-3-(4-{[2-(4,5-dihydro-1H-imidazol-2-yl)pyridin-4-yl]oxy}-3-methylphenyl)propanamide |
| A-63 | 3-(3-{[2-(4,5-dihydro-1H-imidazol-2-yl)pyridin-4-yl]oxy}phenyl)-N-[4-(3-hydroxyprop-1-yn-1-yl)-3-(trifluoromethyl)phenyl]propanamide |
| A-64 | 4-(4-{3-[(2-fluoro-5-methylphenyl)amino]-3-oxopropyl}phenoxy)-N-methylpyridine-2-carboxamide |
| A-65 | 4-{[3-(3-{[2-(4,5-dihydro-1H-imidazol-2-yl)pyridin-4-yl]oxy}phenyl)propanoyl]amino}-N,N-dimethyl-2-(trifluoromethyl)benzamide |
| A-66 | 3-(3-{[2-(4,5-dihydro-1H-imidazol-2-yl)pyridin-4-yl]oxy}phenyl)-N-[4-[3-(dimethylamino)prop-1-yn-1-yl]-3-(trifluoromethyl)phenyl]propanamide |
| A-67 | 3-(3-{[2-(4,5-dihydro-1H-imidazol-2-yl)pyridin-4-yl]oxy}phenyl)-N-[4-(hydroxymethyl)-3-(trifluoromethyl)phenyl]propanamide |
| A-68 | tert-butyl (1-{4-[3-(3-{[4-chloro-3-(trifluoromethyl)phenyl]amino}-3-oxopropyl)phenoxy]pyrimidin-2-yl}piperidin-3-yl)carbamate |
| A-69 | 3-(3-{[2-(4,5-dihydro-1H-imidazol-2-yl)pyridin-4-yl]oxy}phenyl)-N-[4-(piperazin-1-ylcarbonyl)-3-(trifluoromethyl)phenyl]propanamide |
| A-70 | N-[4-chloro-3-(trifluoromethyl)phenyl]-3-{3-[(2-pyrrolidin-1-ylpyrimidin-4-yl)oxy]phenyl}propanamide |
| A-71 | N-methyl-4-(4-{3-[(3-methylphenyl)amino]-3-oxopropyl}phenoxy)pyridine-2-carboxamide |
| A-72 | N-(4-chloro-3-methylphenyl)-3-(3-{[2-(4,5-dihydro-1H-imidazol-2-yl)pyridin-4-yl]oxy}phenyl)propanamide |
| A-73 | N-[4-chloro-3-(trifluoromethyl)phenyl]-3-{3-[(2-{5-[(dimethylamino)methyl]-1H-imidazol-2-yl}pyridin-4-yl)oxy]phenyl}propanamide |
| A-74 | N-[4-chloro-3-(trifluoromethyl)phenyl]-3-(3-{[2-(1,4,5,6-tetrahydropyrimidin-2-yl)pyridin-4-yl]oxy}phenyl)propanamide |
| A-75 | 3-[({4-[3-(3-{[4-chloro-3-(trifluoromethyl)phenyl]amino}-3-oxopropyl)phenoxy]pyridin-2-yl}carbonyl)amino]propanoic acid |
| A-76 | N-(3-cyclopropylphenyl)-3-(3-{[2-(4,5-dihydro-1H-imidazol-2-yl)pyridin-4-yl]oxy}phenyl)propanamide |
| A-77 | tert-butyl {4-[3-(3-{[4-chloro-3-(trifluoromethyl)phenyl]amino}-3-oxopropyl)phenoxy]pyridin-2-yl}carbamate |
| A-78 | 4-[3-(3-{[4-chloro-3-(trifluoromethyl)phenyl]amino}-3-oxopropyl)phenoxy]-N-[2-(dimethylamino)ethyl]pyridine-2-carboxamide |
| A-79 | 4-[3-(3-{[4-chloro-3-(trifluoromethyl)phenyl]amino}-3-oxopropyl)phenoxy]-N-(2-morpholin-4-ylethyl)pyridine-2-carboxamide |
| A-80 | 3-(4-{[2-(4,5-dihydro-1H-imidazol-2-yl)pyridin-4-yl]oxy}phenyl)-N-[3-(trifluoromethyl)phenyl]propanamide |
| A-81 | 4-(3-{3-[(4-chloro-3-methylphenyl)amino]-3-oxopropyl}phenoxy)-N-methylpyridine-2-carboxamide |
| A-82 | 3-{3-[(2-aminopyrimidin-4-yl)oxy]phenyl}-N-[4-chloro-3-(trifluoromethyl)phenyl]propanamide |
| A-83 | 4-(3-{3-[(3-methoxyphenyl)amino]-3-oxopropyl}phenoxy)-N-methylpyridine-2-carboxamide |
| A-84 | N-[4-chloro-3-(trifluoromethyl)phenyl]-3-[4-(pyridin-4-ylmethyl)phenyl]propanamide |
| A-85 | N-[4-chloro-3-(trifluoromethyl)phenyl]-3-[4-({2-[(hydroxyamino)(imino)methyl]pyridin-4-yl}oxy)phenyl]propanamide |
| A-86 | 3-(4-{[2-(1,4,5,6-tetrahydropyrimidin-2-yl)pyridin-4-yl]oxy}phenyl)-N-[3-(trifluoromethyl)phenyl]propanamide |
| A-87 | N-[4-chloro-3-(trifluoromethyl)phenyl]-3-{3-[(2-piperidin-1-ylpyrimidin-4-yl)oxy]phenyl}propanamide |
| A-88 | 4-{4-[3-(1,3-dihydro-2-benzofuran-5-ylamino)-3-oxopropyl]phenoxy}-N-methylpyridine-2-carboxamide |
| A-89 | N-[2-chloro-5-(trifluoromethyl)phenyl]-3-(3-{[2-(4,5-dihydro-1H-imidazol-2-yl)pyridin-4-yl]oxy}phenyl)propanamide |
| A-90 | 4-(3-{3-[(5-tert-butyl-2-hydroxyphenyl)amino]-3-oxopropyl}phenoxy)pyridine-2-carboxamide |
| A-91 | N-[4-cyano-3-(trifluoromethyl)phenyl]-3-(3-{[2-(4,5-dihydro-1H-imidazol-2-yl)pyridin-4-yl]oxy}phenyl)propanamide |
| A-92 | 3-{3-[(2-aminopyridin-4-yl)oxy]phenyl}-N-[4-chloro-3-(trifluoromethyl)phenyl]propanamide |
| A-93 | 3-(3-{[2-(4,5-dihydro-1H-imidazol-2-yl)pyridin-4-yl]oxy}phenyl)-N-(3-ethylphenyl)propanamide |

| | Chemical Name |
|---|---|
| A-94 | 3-(3-{[2-(4,5-dihydro-1H-imidazol-2-yl)pyridin-4-yl]oxy}phenyl)-N-(3-isopropylphenyl)propanamide |
| A-95 | 3-(4-{[2-(4,5-dihydro-1H-imidazol-2-yl)pyridin-4-yl]oxy}phenyl)-N-(3-ethylphenyl)propanamide |
| A-96 | 3-(3-{[2-(acetylamino)pyridin-4-yl]oxy}phenyl)-N-(3-tert-butylphenyl)propanamide |
| A-97 | 3-(3-{[2-(aminomethyl)pyridin-4-yl]oxy}phenyl)-N-[4-chloro-3-(trifluoromethyl)phenyl]propanamide |
| A-98 | N-{4-[3-(3-{[4-chloro-3-(trifluoromethyl)phenyl]amino}-3-oxopropyl)phenoxy]pyridin-2-yl}cyclopropanecarboxamide |
| A-99 | N-[4-chloro-3-(trifluoromethyl)phenyl]-3-(4-{[2-(4-methyl-4,5-dihydro-1H-imidazol-2-yl)pyridin-4-yl]oxy}phenyl)propanamide |
| A-100 | 3-(3-{[2-(1,4,5,6-tetrahydropyrimidin-2-yl)pyridin-4-yl]oxy}phenyl)-N-[3-(trifluoromethyl)phenyl]propanamide |
| A-101 | N-[4-(aminomethyl)-3-(trifluoromethyl)phenyl]-3-(3-{[2-(4,5-dihydro-1H-imidazol-2-yl)pyridin-4-yl]oxy}phenyl)propanamide |
| A-102 | 5-{4-[3-(3-{[4-chloro-3-(trifluoromethyl)phenyl]amino}-3-oxopropyl)phenoxy]pyridin-2-yl}-1,3,4-oxadiazole-2-carboxamide |
| A-103 | 3-(3-{[2-(4,5-dihydro-1H-imidazol-2-yl)pyridin-4-yl]oxy}phenyl)-N-[2-fluoro-5-(trifluoromethyl)phenyl]propanamide |
| A-104 | 3-(3-{[2-(4,5-dihydro-1H-imidazol-2-yl)pyridin-4-yl]oxy}phenyl)-N-[3-(1-hydroxy-1-methylethyl)phenyl]propanamide |
| A-105 | N-[4-chloro-3-(trifluoromethyl)phenyl]-3-(3-{[2-(1H-imidazol-2-yl)pyridin-4-yl]oxy}phenyl)propanamide |
| A-106 | N-(4-chlorophenyl)-3-(4-{[2-(4,5-dihydro-1H-imidazol-2-yl)pyridin-4-yl]oxy}phenyl)propanamide |
| A-107 | N-[4-chloro-3-(trifluoromethyl)phenyl]-2-(3-{[2-(4,5-dihydro-1H-imidazol-2-yl)pyridin-4-yl]oxy}phenyl)cyclopropanecarboxamide |
| A-108 | 3-(3-{[2-(4,5-dihydro-1H-imidazol-2-yl)pyridin-4-yl]oxy}phenyl)-N-[3-fluoro-5-(trifluoromethyl)phenyl]propanamide |
| A-109 | N-[4-chloro-3-(trifluoromethyl)phenyl]-3-{3-[(2-{5-[(methylamino)methyl]-1H-imidazol-2-yl}pyridin-4-yl)oxy]phenyl}propanamide |
| A-110 | ethyl 2-{4-[3-(3-{[4-chloro-3-(trifluoromethyl)phenyl]amino}-3-oxopropyl)phenoxy]pyridin-2-yl}-1H-imidazole-5-carboxylate |
| A-111 | N-(4-bromo-3-tert-butylphenyl)-3-(3-{[2-(4,5-dihydro-1H-imidazol-2-yl)pyridin-4-yl]oxy}phenyl)propanamide |
| A-112 | N-[4-chloro-3-(trifluoromethyl)phenyl]-3-[4-({2-[(ethylamino)(imino)methyl]pyridin-4-yl}oxy)phenyl]propanamide |
| A-113 | 2-{4-[3-(3-{[4-chloro-3-(trifluoromethyl)phenyl]amino}-3-oxopropyl)phenoxy]pyridin-2-yl}-1H-imidazole-5-carboxylic acid |
| A-114 | N-[4-chloro-3-(trifluoromethyl)phenyl]-2-(3-{[2-(4,5-dihydro-1H-imidazol-2-yl)pyridin-4-yl]oxy}phenyl)cyclopropanecarboxamide |
| A-115 | N-(3-tert-butylphenyl)-3-(4-{[2-(4,5-dihydro-1H-imidazol-2-yl)pyridin-4-yl]oxy}phenyl)propanamide |
| A-116 | N-[4-chloro-3-(trifluoromethyl)phenyl]-3-[3-({2-[(2-pyrrolidin-1-ylethyl)amino]pyrimidin-4-yl}oxy)phenyl]propanamide |
| A-117 | N-[3-cyano-5-(trifluoromethyl)phenyl]-3-(3-{[2-(4,5-dihydro-1H-imidazol-2-yl)pyridin-4-yl]oxy}phenyl)propanamide |
| A-118 | 3-(3-{[2-(4-tert-butyl-1H-imidazol-2-yl)pyridin-4-yl]oxy}phenyl)-N-[4-chloro-3-(trifluoromethyl)phenyl]propanamide |
| A-119 | N-(2,3-dihydro-1H-inden-5-yl)-3-(4-{[2-(1,4,5,6-tetrahydropyrimidin-2-yl)pyridin-4-yl]oxy}phenyl)propanamide |
| A-120 | N-[4-chloro-2-hydroxy-3-(trifluoromethyl)phenyl]-3-(4-{[2-(4,5-dihydro-1H-imidazol-2-yl)pyridin-4-yl]oxy}phenyl)propanamide |
| A-121 | 3-(3-{[2-(4,5-dihydro-1H-imidazol-2-yl)pyridin-4-yl]oxy}phenyl)-N-(4-methylphenyl)propanamide |
| A-122 | N-[4-chloro-3-(trifluoromethyl)phenyl]-3-[3-({2-[(4S)-4-methyl-4,5-dihydro-1H-imidazol-2-yl]pyridin-4-yl}oxy)phenyl]propanamide |
| A-123 | methyl [({4-[3-(3-{[4-chloro-3-(trifluoromethyl)phenyl]amino}-3-oxopropyl)phenoxy]pyridin-2-yl}carbonyl)amino]acetate |
| A-124 | 3-(3-{[2-(3-aminopiperidin-1-yl)pyrimidin-4-yl]oxy}phenyl)-N-[4-chloro-3-(trifluoromethyl)phenyl]propanamide |
| A-125 | tert-butyl ({4-[3-(3-{[4-chloro-3-(trifluoromethyl)phenyl]amino}-3-oxopropyl)phenoxy]pyridin-2-yl}methyl)carbamate |
| A-126 | 3-(4-{[2-(4,5-dihydro-1H-imidazol-2-yl)pyridin-4-yl]oxy}phenyl)-N-(3-methylphenyl)propanamide |
| A-127 | 3-(3-chloro-4-{[2-(4,5-dihydro-1H-imidazol-2-yl)pyridin-4-yl]oxy}phenyl)-N-[4-chloro-3-(trifluoromethyl)phenyl]propanamide |
| A-128 | 3-(3-{[2-(4,5-dihydro-1H-imidazol-2-yl)pyridin-4-yl]oxy}phenyl)-N-[4-methoxy-3-(trifluoromethyl)phenyl]propanamide |
| A-129 | 3-(3-{[2-(4,5-dihydro-1H-imidazol-2-yl)pyridin-4-yl]oxy}phenyl)-N-[3-[2-(dimethylamino)ethoxy]-5-(trifluoromethyl)phenyl]propanamide |
| A-130 | 3-(3-{[2-(4,5-dihydro-1H-imidazol-2-yl)pyridin-4-yl]oxy}phenyl)-N-[3-(trifluoromethoxy)phenyl]propanamide |
| A-131 | 3-(3-{[2-(4,5-dihydro-1H-imidazol-2-yl)pyridin-4-yl]oxy}phenyl)-N-[4-(trifluoromethyl)phenyl]propanamide |

-continued

| | Chemical Name |
|---|---|
| A-132 | N-[4-chloro-3-(trifluoromethyl)phenyl]-3-(3-{[2-(4,5-dihydro-1H-imidazol-2-yl)pyridin-4-yl]oxy}phenyl)butanamide |
| A-133 | 4-[4-(3-{[3-methoxy-5-(trifluoromethyl)phenyl]amino}-3-oxopropyl)phenoxy]-N-methylpyridine-2-carboxamide |
| A-134 | 4-(3-{3-[(4-methoxyphenyl)amino]-3-oxopropyl}phenoxy)-N-methylpyridine-2-carboxamide |
| A-135 | 3-(4-chloro-3-{[2-(4,5-dihydro-1H-imidazol-2-yl)pyridin-4-yl]oxy}phenyl)-N-[4-chloro-3-(trifluoromethyl)phenyl]propanamide |
| A-136 | [({4-[3-(3-{[4-chloro-3-(trifluoromethyl)phenyl]amino}-3-oxopropyl)phenoxy]pyridin-2-yl}carbonyl)amino]acetic acid |
| A-137 | N-[4-chloro-3-(trifluoromethyl)phenyl]-3-(3-{[2-(5-hydroxy-1,4,5,6-tetrahydropyrimidin-2-yl)pyridin-4-yl]oxy}phenyl)propanamide |
| A-138 | 3-(4-{[2-(4,5-dihydro-1H-imidazol-2-yl)pyridin-4-yl]oxy}phenyl)-N-(2,3-dihydro-1H-inden-5-yl)propanamide |
| A-139 | N-[4-chloro-3-(trifluoromethyl)phenyl]-3-(3-{[2-(1-methyl-4,5-dihydro-1H-imidazol-2-yl)pyridin-4-yl]oxy}phenyl)propanamide |
| A-140 | N-[4-chloro-2-hydroxy-3-(trifluoromethyl)phenyl]-3-(3-{[2-(4,5-dihydro-1H-imidazol-2-yl)pyridin-4-yl]oxy}phenyl)propanamide |
| A-141 | N-methyl-4-[3-(3-{[3-nitro-5-(trifluoromethyl)phenyl]amino}-3-oxopropyl)phenoxy]pyridine-2-carboxamide |
| A-142 | 2-{4-[4-(3-{[4-chloro-3-(trifluoromethyl)phenyl]amino}-3-oxopropyl)phenoxy]pyridin-2-yl}-4,5-dihydro-1H-imidazole-4-carboxylic acid |
| A-143 | 2-{4-[3-(3-{[4-chloro-3-(trifluoromethyl)phenyl]amino}-3-oxopropyl)-phenoxy]pyridin-2-yl}-1,4,5,6-tetrahydropyrimidine-4-carboxylic acid |
| A-144 | 3-(3-{[2-(4,5-dihydro-1H-imidazol-2-yl)pyridin-4-yl]oxy}phenyl)-N-[4-ethynyl-3-(trifluoromethyl)phenyl]propanamide |
| A-145 | 3-(3-{[2-(4,5-dihydro-1H-imidazol-2-yl)pyridin-4-yl]oxy}phenyl)-N-[4-(3-hydroxypropyl)-3-(trifluoromethyl)phenyl]propanamide |
| A-146 | 3-(3-{[2-(4,5-dihydro-1H-imidazol-2-yl)pyridin-4-yl]oxy}phenyl)-N-(3-methylphenyl)propanamide |
| A-147 | N-[4-chloro-3-(trifluoromethyl)phenyl]-3-[3-({2-[5-(hydroxymethyl)-1H-imidazol-2-yl]pyridin-4-yl}oxy)phenyl]propanamide |
| A-148 | N-[3-(2-aminoethyl)-5-(trifluoromethyl)phenyl]-3-(3-{[2-(4,5-dihydro-1H-imidazol-2-yl)pyridin-4-yl]oxy}phenyl)propanamide |
| A-149 | 4-(3-{3-[(5-tert-butylisoxazol-3-yl)amino]-3-oxopropyl}phenoxy)-N-methylpyridine-2-carboxamide |
| A-150 | N-[4-chloro-3-(trifluoromethyl)phenyl]-3-[3-({2-[imino(morpholin-4-yl)methyl]pyridin-4-yl}oxy)phenyl]propanamide |
| A-151 | 3-(3-{[2-(4,5-dihydro-1H-imidazol-2-yl)pyridin-4-yl]oxy}phenyl)-N-[3-(trifluoromethyl)phenyl]propanamide |
| A-152 | tert-butyl ({4-[3-(3-oxo-3-{[3-(trifluoromethyl)phenyl]amino}propyl)phenoxy]pyridin-2-yl}methyl)carbamate |
| A-153 | N-[4-chloro-3-(trifluoromethyl)phenyl]-3-(3-{[2-({[imino(phenyl)methyl]amino}methyl)pyridin-4-yl]oxy}phenyl)propanamide |
| A-154 | N-(3-tert-butylphenyl)-3-(3-{[2-(1-methyl-4,5-dihydro-1H-imidazol-2-yl)pyridin-4-yl]oxy}phenyl)propanamide |
| A-155 | ethyl 4-[({4-[3-(3-{[4-chloro-3-(trifluoromethyl)phenyl]amino}-3-oxopropyl)phenoxy]pyridin-2-yl}carbonyl)amino]butanoate |
| A-156 | N-[4-chloro-3-(trifluoromethyl)phenyl]-3-(3-{[2-(4,5-dihydro-1H-imidazol-2-yl)pyridin-4-yl]amino}phenyl)propanamide |
| A-157 | N-[3,5-bis(trifluoromethyl)phenyl]-3-(3-{[2-(4,5-dihydro-1H-imidazol-2-yl)pyridin-4-yl]oxy}phenyl)propanamide |
| A-158 | N-[4-chloro-3-(trifluoromethyl)phenyl]-3-(3-{[2-(5-methyl-1H-imidazol-2-yl)pyridin-4-yl]oxy}phenyl)propanamide |
| A-159 | 3-[4-{[3-(3-{[2-(4,5-dihydro-1H-imidazol-2-yl)pyridin-4-yl]oxy}phenyl)propanoyl]amino}-2-(trifluoromethyl)phenyl]propanoic acid |
| A-160 | 4-[3-(3-{[4-chloro-3-(trifluoromethyl)phenyl]amino}-3-oxopropyl)phenoxy]-N,3-dimethylpyridine-2-carboxamide |
| A-161 | N-(4-tert-butylphenyl)-3-(3-{[2-(4,5-dihydro-1H-imidazol-2-yl)pyridin-4-yl]oxy}phenyl)propanamide |
| A-162 | N-(4-tert-butylphenyl)-3-(4-{[2-(4,5-dihydro-1H-imidazol-2-yl)pyridin-4-yl]oxy}phenyl)propanamide |
| A-163 | 4-(4-{3-[(4,6-dimethylpyridin-2-yl)amino]-3-oxopropyl}phenoxy)-N-methylpyridine-2-carboxamide |
| A-164 | N-[4-chloro-3-(trifluoromethyl)phenyl]-3-{3-[(2-{[3-(2-oxopyrrolidin-1-yl)propyl]amino}pyrimidin-4-yl)oxy]phenyl}propanamide |
| A-165 | 3-(3-{[2-(4,5-dihydro-1H-imidazol-2-yl)pyridin-4-yl]oxy}phenyl)-N-[3-[3-(dimethylamino)propyl]-5-(trifluoromethyl)phenyl]propanamide |
| A-166 | N-(3-tert-butylphenyl)-3-(3-{[2-(4,5-dihydro-1H-imidazol-2-yl)pyridin-4-yl]oxy}phenyl)-2-hydroxypropanamide |
| A-167 | N-[4-chloro-3-(trifluoromethyl)phenyl]-3-(3-{[2-(diethylamino)pyrimidin-4-yl]oxy}phenyl)propanamide |
| A-168 | N-(2,3-dihydro-1,4-benzodioxin-6-yl)-3-(3-{[2-(4,5-dihydro-1H-imidazol-2-yl)pyridin-4-yl]oxy}phenyl)propanamide |
| A-169 | 3-(3-{[2-(4,5-dihydro-1H-imidazol-2-yl)pyridin-4-yl]oxy}phenyl)-N-(3,3-dimethyl-1-oxo-1,3-dihydro-2-benzofuran-5-yl)propanamide |

-continued

| | Chemical Name |
|---|---|
| A-170 | methyl 2-{4-[3-(3-{[4-chloro-3-(trifluoromethyl)phenyl]amino}-3-oxopropyl)phenoxy]pyridin-2-yl}-1H-imidazole-5-carboxylate |
| A-171 | 2-{4-[3-(3-{[4-chloro-3-(trifluoromethyl)phenyl]amino}-3-oxopropyl)phenoxy]pyridin-2-yl}-N,N-dimethyl-1H-imidazole-5-carboxamide |
| A-172 | 3-[3-({2-[(benzylamino)(imino)methyl]pyridin-4-yl}oxy)phenyl]-N-[4-chloro-3-(trifluoromethyl)phenyl]propanamide |
| A-173 | tert-butyl ({4-[4-(3-{[4-chloro-3-(trifluoromethyl)phenyl]amino}-3-oxopropyl)phenoxy]pyridin-2-yl}methyl)carbamate |
| A-174 | 4-[({4-[3-(3-{[4-chloro-3-(trifluoromethyl)phenyl]amino}-3-oxopropyl)phenoxy]pyridin-2-yl}carbonyl)amino]butanoic acid |
| A-175 | 3-(3-{[2-(4,5-dihydro-1H-imidazol-2-yl)pyridin-4-yl]oxy}phenyl)-N-(3,5-dimethoxyphenyl)propanamide |
| A-176 | N-[2-bromo-5-(trifluoromethyl)phenyl]-3-(3-{[2-(4,5-dihydro-1H-imidazol-2-yl)pyridin-4-yl]oxy}phenyl)propanamide |
| A-177 | 3-(4-{[2-(4,5-dihydro-1H-imidazol-2-yl)pyridin-4-yl]oxy}phenyl)-N-(3-isopropylphenyl)propanamide |
| A-178 | N-[4-chloro-3-(trifluoromethyl)phenyl]-3-[3-({2-[4-(hydroxymethyl)-4,5-dihydro-1H-imidazol-2-yl]pyridin-4-yl}oxy)phenyl]propanamide |
| A-179 | N-[4-chloro-3-(trifluoromethyl)phenyl]-3-[3-(7H-pyrrolo[2,3-d]pyrimidin-4-yloxy)phenyl]propanamide |
| A-180 | methyl 2-{4-[3-(3-{[4-chloro-3-(trifluoromethyl)phenyl]amino}-3-oxopropyl)phenoxy]pyridin-2-yl}-4,5-dihydro-1H-imidazole-4-carboxylate |
| A-181 | tert-butyl ({4-[4-(3-oxo-3-{[3-(trifluoromethyl)phenyl]amino}propyl)phenoxy]pyridin-2-yl}methyl)carbamate |
| A-182 | 3-(3-{[2-(4,5-dihydro-1H-imidazol-2-yl)pyridin-4-yl]oxy}phenyl)-N-(3-fluoro-5-morpholin-4-ylphenyl)propanamide |
| A-183 | 3-(3-{[2-(acetylamino)pyridin-4-yl]oxy}phenyl)-N-[4-chloro-3-(trifluoromethyl)phenyl]propanamide |
| A-184 | N-[4-chloro-3-(trifluoromethyl)phenyl]-3-{3-[(2-{4-[(4-methylpiperazin-1-yl)carbonyl]-1H-imidazol-2-yl}pyridin-4-yl)oxy]phenyl}propanamide |
| A-185 | N-[4-chloro-2-methoxy-3-(trifluoromethyl)phenyl]-3-(3-{[2-(4,5-dihydro-1H-imidazol-2-yl)pyridin-4-yl]oxy}phenyl)propanamide |
| A-186 | N-[3-(aminomethyl)-5-(trifluoromethyl)phenyl]-3-(3-{[2-(4,5-dihydro-1H-imidazol-2-yl)pyridin-4-yl]oxy}phenyl)propanamide |
| A-187 | 2-{4-[3-(3-{[4-chloro-3-(trifluoromethyl)phenyl]amino}-3-oxopropyl)phenoxy]pyridin-2-yl}-N,N-dimethyl-4,5-dihydro-1H-imidazole-4-carboxamide |
| A-188 | tert-butyl 4-{[({4-[4-(3-oxo-3-{[3-(trifluoromethyl)phenyl]amino}propyl)phenoxy]pyridin-2-yl}methyl)amino]methyl}piperidine-1-carboxylate |
| A-189 | 3-(3-{[2-(4,5-dihydro-1H-imidazol-2-yl)pyridin-4-yl]oxy}phenyl)-N-[2-methyl-5-(trifluoromethyl)phenyl]propanamide |
| A-190 | 3-{[3-(3-{[2-(4,5-dihydro-1H-imidazol-2-yl)pyridin-4-yl]oxy}phenyl)propanoyl]amino}-N-[2-(dimethylamino)ethyl]-5-(trifluoromethyl)benzamide |
| A-191 | 3-{[3-(3-{[2-(4,5-dihydro-1H-imidazol-2-yl)pyridin-4-yl]oxy}phenyl)propanoyl]amino}-N-(2-methoxyethyl)-5-(trifluoromethyl)benzamide |
| A-192 | N-[4-chloro-3-(trifluoromethyl)phenyl]-3-{3-[(2-{[(4-ethylpiperazin-1-yl)acetyl]amino}pyridin-4-yl)oxy]phenyl}propanamide |
| A-193 | 3-(3-{[2-(4,5-dihydro-1H-imidazol-2-yl)pyridin-4-yl]oxy}phenyl)-N-[3-[3-(dimethylamino)prop-1-yn-1-yl]-5-(trifluoromethyl)phenyl]propanamide |
| A-194 | 3-(3-{[2-(4,5-dihydro-1H-imidazol-2-yl)pyridin-4-yl]oxy}phenyl)-N-(3-iodophenyl)propanamide |
| A-195 | 3-(3-{[2-(4,5-dihydro-1H-imidazol-2-yl)pyridin-4-yl]oxy}phenyl)-N-[4-methyl-3-(trifluoromethyl)phenyl]propanamide |
| A-196 | N-[4-chloro-3-(trifluoromethyl)phenyl]-2-(4-{[2-(4,5-dihydro-1H-imidazol-2-yl)pyridin-4-yl]oxy}phenyl)cyclopropanecarboxamide |
| A-197 | 4-(4-{3-[(3-chloro-4-fluorophenyl)amino]-3-oxopropyl}phenoxy)-N-methylpyridine-2-carboxamide |
| A-198 | 3-(3-{[2-(4,5-dihydro-1H-imidazol-2-yl)pyridin-4-yl]oxy}phenyl)-N-[6-(trifluoromethyl)pyridin-2-yl]propanamide |
| A-199 | 3-(3-{[2-(aminomethyl)pyridin-4-yl]oxy}phenyl)-N-[3-(trifluoromethyl)phenyl]propanamide |
| A-200 | N-[4-chloro-3-(trifluoromethyl)phenyl]-3-(3-{[2-(4-methyl-4,5-dihydro-1H-imidazol-2-yl)pyridin-4-yl]oxy}phenyl)propanamide |
| A-201 | 4-[3-(3-{[3-(2-aminoethyl)-5-trifluoromethyl)phenyl]amino}-3-oxopropyl)phenoxy]-N-methylpyridine-2-carboxamide |
| A-202 | N-[4-chloro-3-(trifluoromethyl)phenyl]-3-[3-(9H-purin-6-yloxy)phenyl]propanamide |
| A-203 | 3-(3-{[2-(4,5-dihydro-1H-imidazol-2-yl)pyridin-4-yl]oxy}phenyl)-N-[2-fluoro-3-(trifluoromethyl)phenyl]propanamide |
| A-204 | N-[4-chloro-3-(trifluoromethyl)phenyl]-3-[3-({2-[4-(morpholin-4-ylcarbonyl)-1H-imidazol-2-yl]pyridin-4-yl}oxy)phenyl]propanamide |
| A-205 | N-[4-chloro-3-(trifluoromethyl)phenyl]-3-(4-{[2-(4,4-dimethyl-4,5-dihydro-1H-imidazol-2-yl)pyridin-4-yl]oxy}phenyl)propanamide |

-continued

| | Chemical Name |
|---|---|
| A-206 | 3-{4-[(2-{[(piperidin-4-ylmethyl)amino]methyl}pyridin-4-yl)oxy]phenyl}-N-[3-(trifluoromethyl)phenyl]propanamide |
| A-207 | N-[4-chloro-3-(trifluoromethyl)phenyl]-3-{3-[(2-morpholin-4-ylpyrimidin-4-yl)oxy]phenyl}propanamide |
| A-208 | 2-{4-[3-(3-{[4-chloro-3-(trifluoromethyl)phenyl]amino}-3-oxopropyl)phenoxy]pyridin-2-yl}-4,5-dihydro-1H-imidazole-4-carboxylic acid |
| A-209 | 3-(3-{[2-(4,5-dihydro-1H-imidazol-2-yl)pyridin-4-yl]oxy}phenyl)-N-[3-methoxy-5-(trifluoromethyl)phenyl]propanamide |
| A-210 | 3-(3-{[2-(4,5-dihydro-1H-imidazol-2-yl)pyridin-4-yl]oxy}phenyl)-N-(2,3-dihydro-1H-inden-5-yl)propanamide |
| A-211 | 3-(3-{[2-(acetylamino)pyridin-4-yl]oxy}phenyl)-N-[3-[2-(dimethylamino)ethoxy]-5-(trifluoromethyl)phenyl]propanamide |
| A-212 | N-(6-chloro-5-methylpyridin-3-yl)-3-(3-{[2-(4,5-dihydro-1H-imidazol-2-yl)pyridin-4-yl]oxy}phenyl)propanamide |
| A-213 | 3-(3-{[2-(4,5-dihydro-1H-imidazol-2-yl)pyridin-4-yl]oxy}phenyl)-N-[4-fluoro-3-(trifluoromethyl)phenyl]propanamide |
| A-214 | N-[4-chloro-3-(trifluoromethyl)phenyl]-3-[3-(pyrimidin-5-yloxy)phenyl]propanamide |
| A-215 | N-[4-chloro-3-(trifluoromethyl)phenyl]-3-(3-{[2-(4,5-dihydro-1H-imidazol-2-yl)pyridin-4-yl]oxy}phenyl)-2-methylpropanamide |
| A-216 | methyl 4-{[3-(3-{[2-(4,5-dihydro-1H-imidazol-2-yl)pyridin-4-yl]oxy}phenyl)propanoyl]amino}-2-(trifluoromethyl)benzoate |
| A-217 | N-[4-chloro-3-(trifluoromethyl)phenyl]-3-{3-[(2-{[2-(dimethylamino)ethyl]amino}pyrimidin-4-yl)oxy]phenyl}propanamide |
| A-218 | N-[4-chloro-2-hydroxy-5-(trifluoromethyl)phenyl]-3-(3-{[2-(4,5-dihydro-1H-imidazol-2-yl)pyridin-4-yl]oxy}phenyl)propanamide |
| A-219 | N-(5-tert-butyl-2-methoxyphenyl)-3-(3-{[2-(4,5-dihydro-1H-imidazol-2-yl)pyridin-4-yl]oxy}phenyl)propanamide |
| A-220 | 3-(3-{[2-(4,5-dihydro-1H-imidazol-2-yl)pyridin-4-yl]oxy}phenyl)-N-[3-(2-pyrrolidin-1-ylethoxy)-5-(trifluoromethyl)phenyl]propanamide |
| A-221 | isobutyl {4-[3-(3-{[4-chloro-3-(trifluoromethyl)phenyl]amino}-3-oxopropyl)phenoxy]pyridin-2-yl}carbamate |
| A-222 | 3-(3-{[2-(4,5-dihydro-1H-imidazol-2-yl)pyridin-4-yl]oxy}phenyl)-N-(4-methylpyridin-2-yl)propanamide |
| A-223 | N-(4-chloro-3-methylphenyl)-3-(4-{[2-(4,5-dihydro-1H-imidazol-2-yl)pyridin-4-yl]oxy}phenyl)propanamide |
| A-224 | N-[4-chloro-3-(trifluoromethyl)phenyl]-3-[3-({2-[(4-methoxybenzyl)amino]pyrimidin-4-yl}oxy)phenyl]propanamide |
| A-225 | 4-[3-(3-{[3-amino-5-(trifluoromethyl)phenyl]amino}-3-oxopropyl)phenoxy]-N-methylpyridine-2-carboxamide |
| A-226 | N-[4-chloro-3-(trifluoromethyl)phenyl]-3-[3-({2-[5-(pyrrolidin-1-ylmethyl)-1H-imidazol-2-yl]pyridin-4-yl}oxy)phenyl]propanamide |
| A-227 | N-[4-chloro-3-(trifluoromethyl)phenyl]-3-{4-[(2-{imino[(2-morpholin-4-ylethyl)amino]methyl}pyridin-4-yl)oxy]phenyl}propanamide |
| A-228 | 3-[3-({2-[amino(imino)methyl]pyridin-4-yl}oxy)phenyl]-N-[4-chloro-3-(trifluoromethyl)phenyl]propanamide |
| A-229 | N-(3-chloro-4-fluorophenyl)-3-(3-{[2-(4,5-dihydro-1H-imidazol-2-yl)pyridin-4-yl]oxy}phenyl)propanamide |
| A-230 | N-(3,5-di-tert-butylphenyl)-3-(3-{[2-(4,5-dihydro-1H-imidazol-2-yl)pyridin-4-yl]oxy}phenyl)propanamide |
| A-231 | 3-(3-{[2-(4,5-dihydro-1H-imidazol-2-yl)pyridin-4-yl]oxy}phenyl)-N-[3-(2-morpholin-4-ylethoxy)-5-(trifluoromethyl)phenyl]propanamide |
| A-232 | N-[4-chloro-3-(trifluoromethyl)phenyl]-3-(4-{[2-(5-methyl-1H-imidazol-2-yl)pyridin-4-yl]oxy}phenyl)propanamide |
| A-233 | N-[3-amino-5-(trifluoromethyl)phenyl]-3-(3-{[2-(4,5-dihydro-1H-imidazol-2-yl)pyridin-4-yl]oxy}phenyl)propanamide |
| A-234 | methyl 3-[4-{[3-(3-{[2-(4,5-dihydro-1H-imidazol-2-yl)pyridin-4-yl]oxy}phenyl)propanoyl]amino}-2-(trifluoromethyl)phenyl]propanoate |
| A-235 | methyl 3-[({4-[3-(3-{[4-chloro-3-(trifluoromethyl)phenyl]amino}-3-oxopropyl)phenoxy]pyridin-2-yl}carbonyl)amino]propanoate |
| A-236 | N-[4-chloro-3-(trifluoromethyl)phenyl]-3-(3-{[2-(2H-tetrazol-5-yl)pyridin-4-yl]oxy}phenyl)propanamide |
| A-237 | 2-{4-[3-(3-{[4-chloro-3-(trifluoromethyl)phenyl]amino}-3-oxopropyl)phenoxy]pyridin-2-yl}-N-[2-(dimethylamino)ethyl]-4,5-dihydro-1H-imidazole-4-carboxamide |
| A-238 | N-methyl-4-[4-(3-oxo-3-{[4-(trifluoromethyl)phenyl]amino}propyl)phenoxy]pyridine-2-carboxamide |
| A-239 | 3-(3-{[2-(4,5-dihydro-1H-imidazol-2-yl)pyridin-4-yl]oxy}phenyl)-N-[4-iodo-3-(trifluoromethyl)phenyl]propanamide |
| A-240 | 3-amino-N-[4-chloro-3-(trifluoromethyl)phenyl]-3-(3-{[2-(4,5-dihydro-1H-imidazol-2-yl)pyridin-4-yl]oxy}phenyl)propanamide |
| A-241 | 3-(3-{[2-(4,5-dihydro-1H-imidazol-2-yl)pyridin-4-yl]oxy}phenyl)-N-[3-(methylsulfanyl)phenyl]propanamide |
| A-242 | N-(4-chlorophenyl)-3-(3-{[2-(4,5-dihydro-1H-imidazol-2-yl)pyridin-4-yl]oxy}phenyl)propanamide |
| A-243 | N-[4-chloro-3-(trifluoromethyl)phenyl]-3-[4-({2-[4-(hydroxymethyl)-4,5-dihydro-1H-imidazol-2-yl]pyridin-4-yl}oxy)phenyl]propanamide |

-continued

| | Chemical Name |
|---|---|
| A-244 | 3-(3-{[2-(4,5-dihydro-1H-imidazol-2-yl)pyridin-4-yl]oxy}phenyl)-N-[4-[3-(dimethylamino)propyl]-3-(trifluoromethyl)phenyl]propanamide |
| A-245 | 3-[4-({2-[amino(imino)methyl]pyridin-4-yl}oxy)phenyl]-N-[4-chloro-3-(trifluoromethyl)phenyl]propanamide |
| A-246 | N-[4-chloro-3-(trifluoromethyl)phenyl]-2-(4-{[2-(4,5-dihydro-1H-imidazol-2-yl)pyridin-4-yl]oxy}phenyl)cyclopropanecarboxamide |
| A-247 | 3-(3-{[2-(4,5-dihydro-1H-imidazol-2-yl)pyridin-4-yl]oxy}phenyl)-N-(4,6-dimethylpyridin-2-yl)propanamide |
| A-248 | N-[4-chloro-3-(trifluoromethyl)phenyl]-3-[3-({2-[(4S)-4-(methoxymethyl)-4,5-dihydro-1H-imidazol-2-yl]pyridin-4-yl}oxy)phenyl]propanamide |
| A-249 | N-(3-chlorophenyl)-3-(3-{[2-(4,5-dihydro-1H-imidazol-2-yl)pyridin-4-yl]oxy}phenyl)propanamide |
| A-250 | N-[4-chloro-3-(trifluoromethyl)phenyl]-3-(3-{[2-(isopropylamino)pyrimidin-4-yl]oxy}phenyl)propanamide |
| A-251 | N-[4-chloro-3-(trifluoromethyl)phenyl]-3-[3-({2-[(4R)-4-methyl-4,5-dihydro-1H-imidazol-2-yl]pyridin-4-yl}oxy)phenyl]propanamide |
| A-252 | 4-(4-{3-[(3,5-dimethoxyphenyl)amino]-3-oxopropyl}phenoxy)-N-methylpyridine-2-carboxamide |
| A-253 | 3-{3-[(6-aminopyrimidin-4-yl)oxy]phenyl}-N-[4-chloro-3-(trifluoromethyl)phenyl]propanamide |
| A-254 | N-(3-bromophenyl)-3-(3-{[2-(4,5-dihydro-1H-imidazol-2-yl)pyridin-4-yl]oxy}phenyl)propanamide |
| A-255 | N-[3-chloro-4-(trifluoromethyl)phenyl]-3-(3-{[2-(4,5-dihydro-1H-imidazol-2-yl)pyridin-4-yl]oxy}phenyl)propanamide |
| A-256 | methyl 3-({3-[3-({2-[(methylamino)carbonyl]pyridin-4-yl}oxy)phenyl]propanoyl}amino)benzoate |
| A-257 | N-[4-bromo-3-(trifluoromethyl)phenyl]-3-(3-{[2-(4,5-dihydro-1H-imidazol-2-yl)pyridin-4-yl]oxy}phenyl)propanamide |
| A-258 | 4-[3-(3-{[4-cyano-3-(trifluoromethyl)phenyl]amino}-3-oxopropyl)phenoxy]-N-methylpyridine-2-carboxamide |
| A-259 | 2-{4-[3-(3-{[4-chloro-3-(trifluoromethyl)phenyl]amino}-3-oxopropyl)phenoxy]pyridin-2-yl}-N-methyl-4,5-dihydro-1H-imidazole-4-carboxamide |
| A-260 | 4-[3-(3-{[4-chloro-3-(trifluoromethyl)phenyl]amino}-3-oxopropyl)phenoxy]-N-[3-(dimethylamino)propyl]pyridine-2-carboxamide |
| A-261 | 3-{3-[(2-aminopyridin-4-yl)oxy]phenyl}-N-(3-tert-butylphenyl)propanamide |
| A-262 | 4-{3-[3-(1,3-benzodioxol-5-ylamino)-3-oxopropyl]phenoxy}-N-methylpyridine-2-carboxamide |
| A-263 | 4-(4-{3-[3-chloro-4-cyanophenyl)amino]-3-oxopropyl}pheonoxy)-N-methylpyridin-2-carboxamide |
| A-264 | N-(2,3-dihydro-1H-inden-5-yl)-3-(3-{[2-(1,4,5,6-tetrahydropyrimidin-2-yl)pyridin-4-yl]oxy}phenyl)propanamide |
| A-265 | 3-(3-{[2-(4,5-dihydro-1H-imidazol-2-yl)pyridin-4-yl]oxy}phenyl)-N-[4-ethyl-3-(trifluoromethyl)phenyl]propanamide |
| A-266 | N-{4-[3-(3-{[4-ethyl-3-(trifluoromethyl)phenyl]amino}-3-oxopropyl)phenoxy]-pyridin-2-yl}cyclopropanecarboxamide |
| A-267 | N-{4-[3-(3-{[4-[(dimethylamino)methyl]-3-(trifluoromethyl)phenyl]amino}-3-oxopropyl)phenoxy]pyridin-2-yl}cyclopropanecarboxamide |
| A-268 | N-{4-[3-(3-{[3-(2-aminoethyl)-5-(trifluoromethyl)phenyl]amino}-3-oxopropyl)-phenoxy]pyridin-2-yl}cyclopropanecarboxamide |
| A-269 | 3-(3-{[2-(acetylamino)pyridin-4-yl]oxy}phenyl)-N-[4-ethyl-3-(trifluoromethyl)-phenyl]propanamide |
| A-270 | 3-(3-{[2-(acetylamino)pyridin-4-yl]oxy}phenyl)-N-[4-[(dimethylamino)methyl]-3-(trifluoromethyl)phenyl]propanamide |
| A-271 | 3-(3-{[2-(acetylamino)pyridin-4-yl]oxy}phenyl)-N-[3-(2-aminoethyl)-5-(trifluoromethyl)phenyl]propanamide |

Additional specific examples of compounds of formula (I) are shown below in
TABLE 2
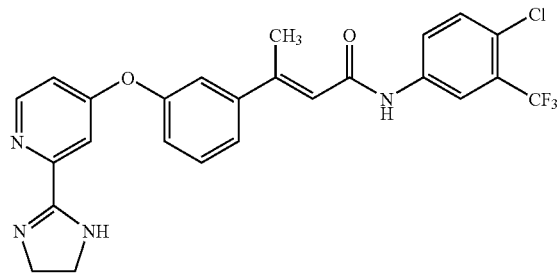
B-1
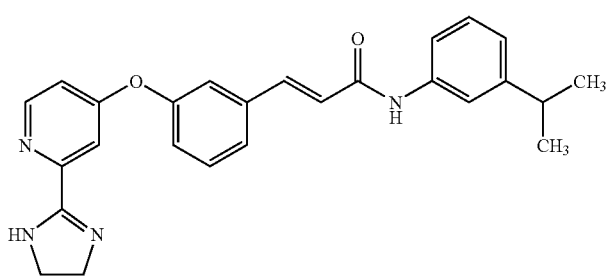
B-2
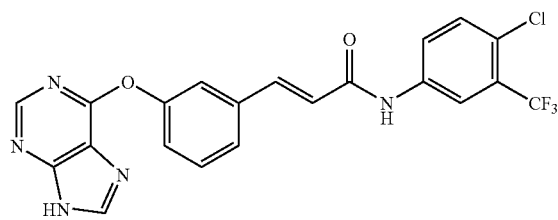
B-3
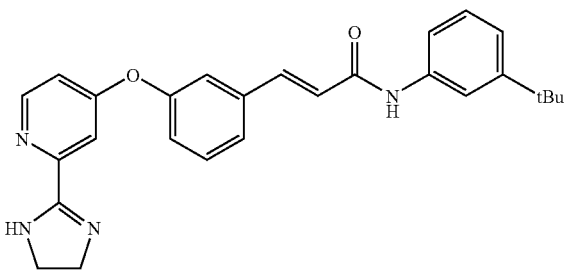
B-5
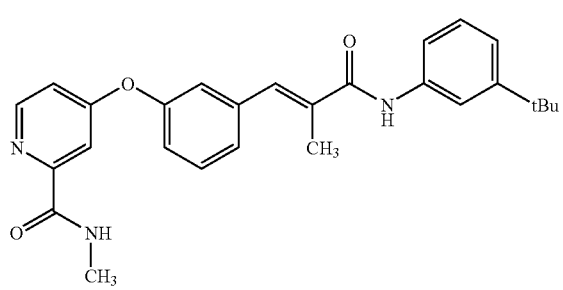
B-6

TABLE 2-continued
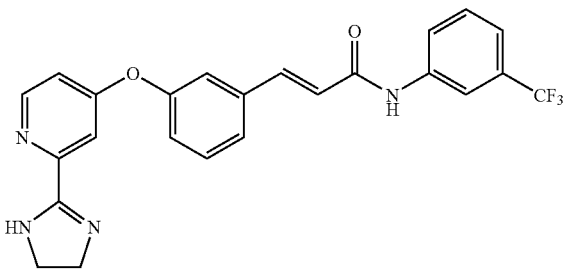
B-7
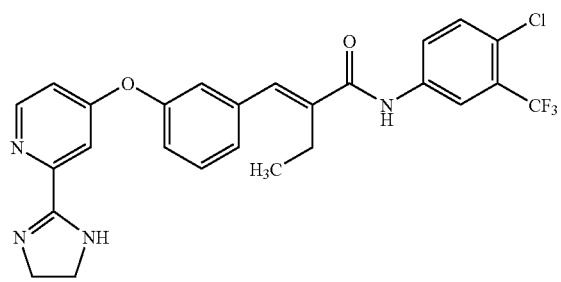
B-8
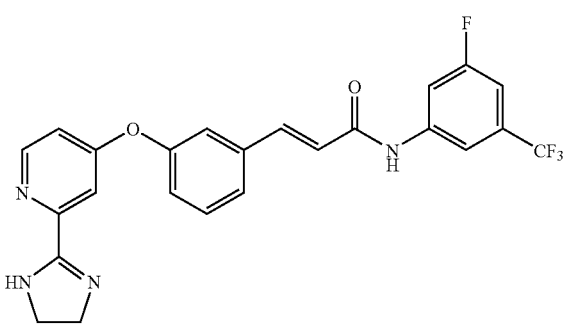
B-9
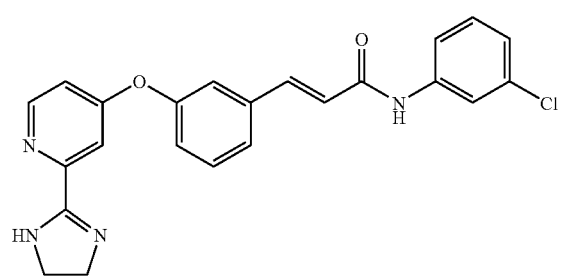
B-10
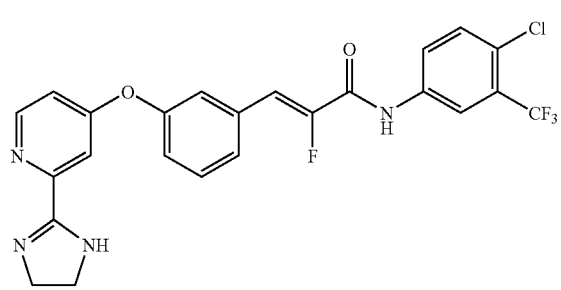
B-11

TABLE 2-continued
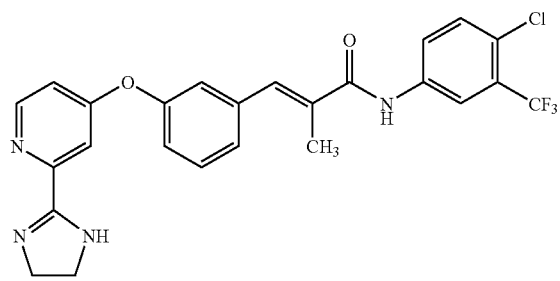
B-12
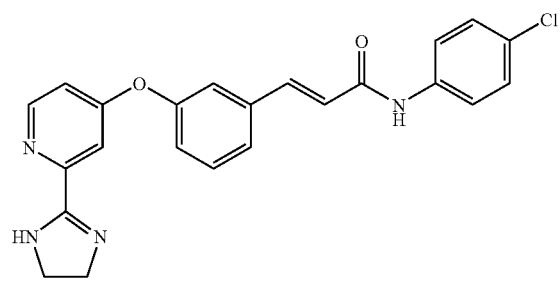
B-13
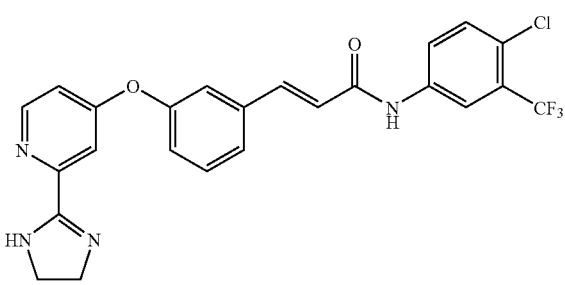
B-14
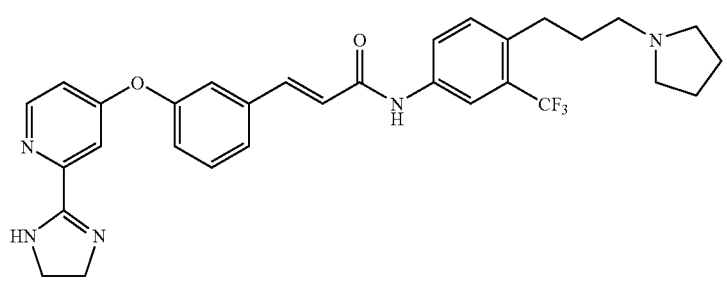
B-15
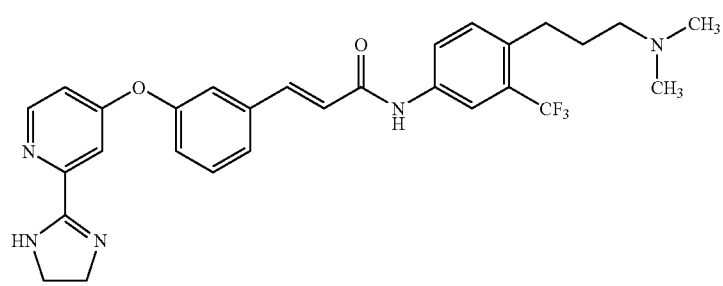
B-16

TABLE 2-continued
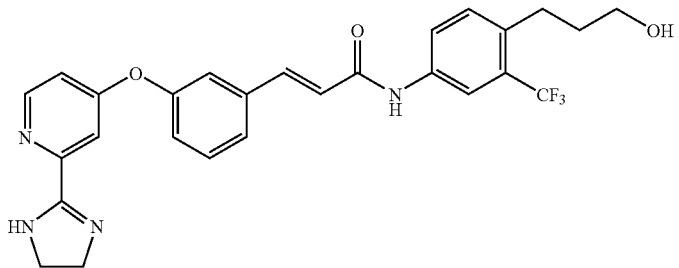
B-17
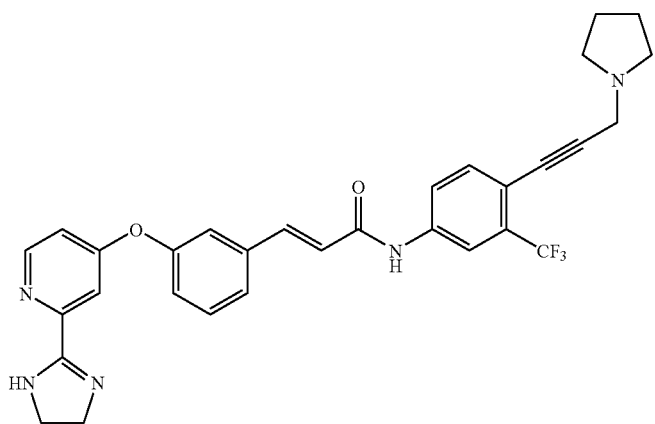
B-18
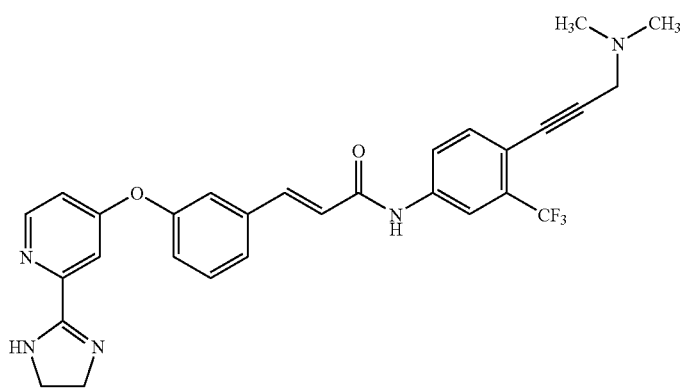
B-19
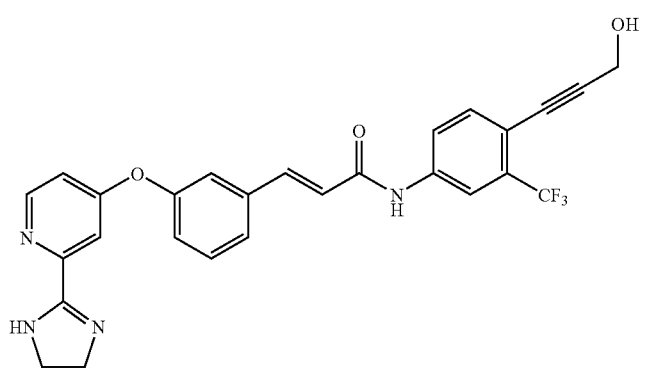
B-20

TABLE 2-continued
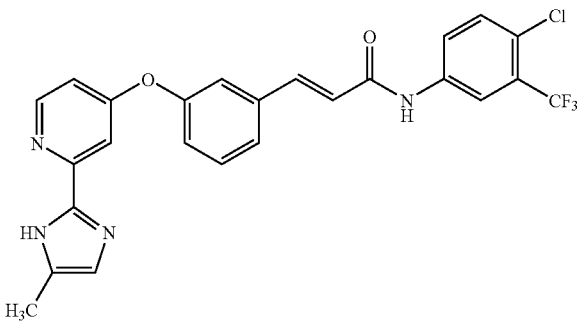
B-21
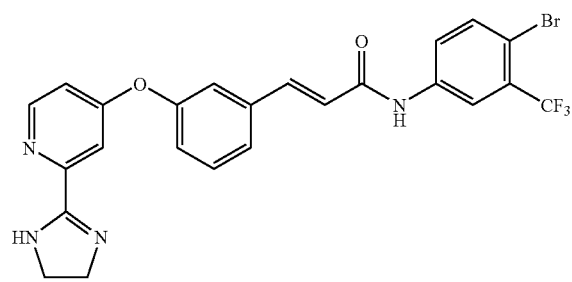
B-22
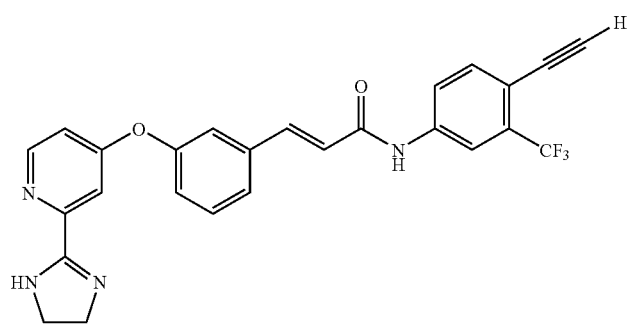
B-23
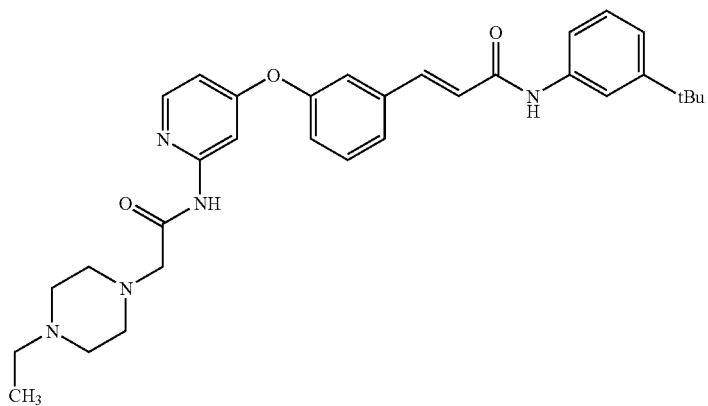
B-24

TABLE 2-continued
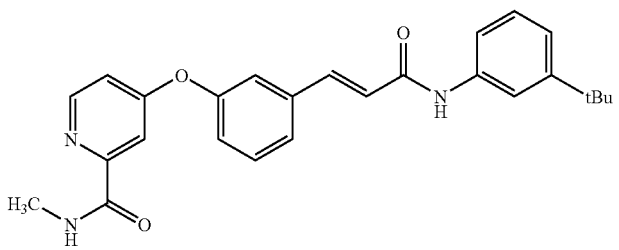
B-25
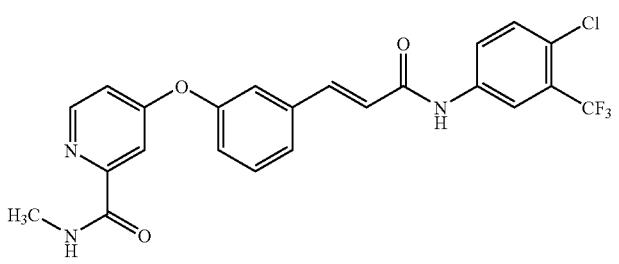
B-26
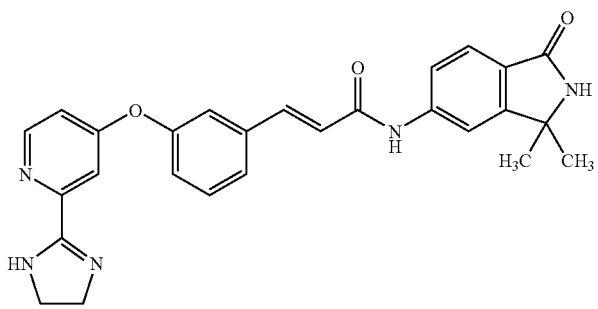
B-27
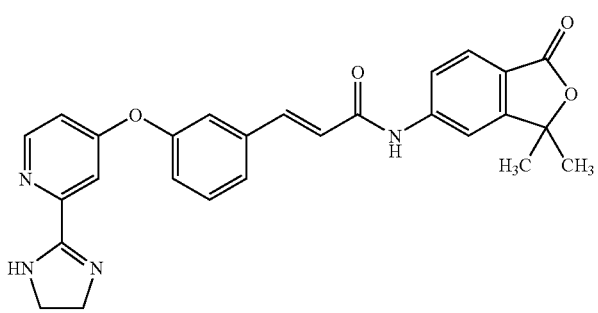
B-28
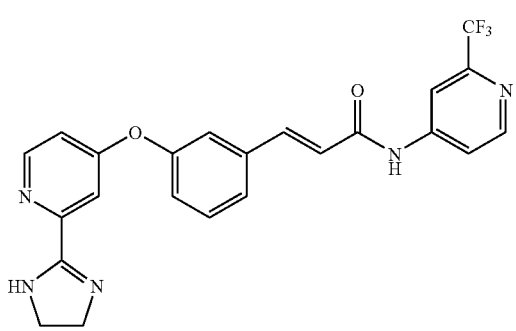
B-29

TABLE 2-continued
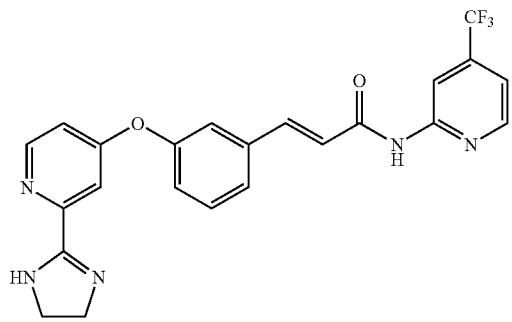
B-30
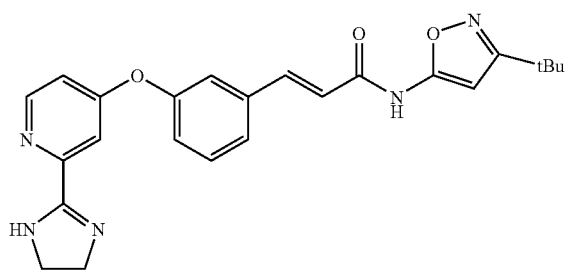
B-31
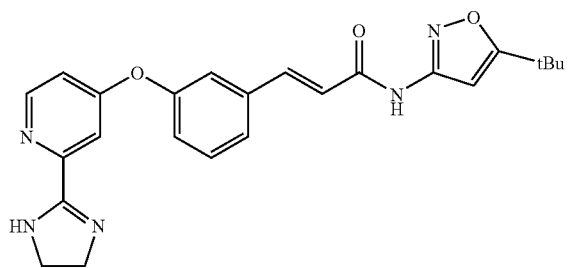
B-32
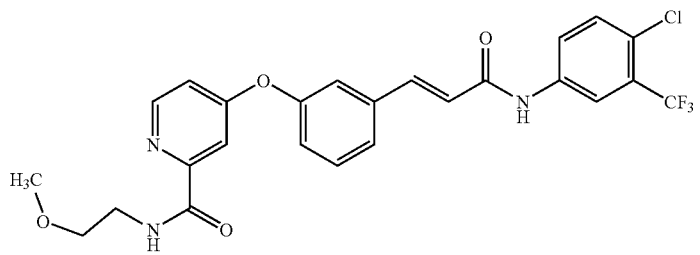
B-33
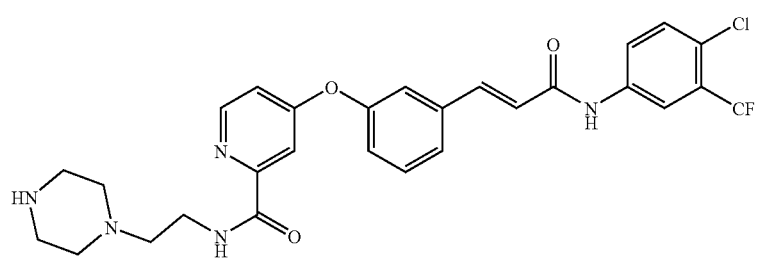
B-34

TABLE 2-continued
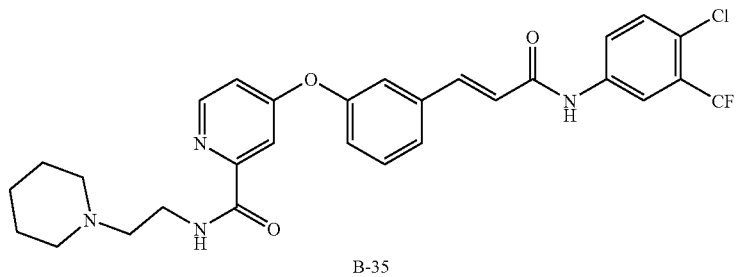
B-35
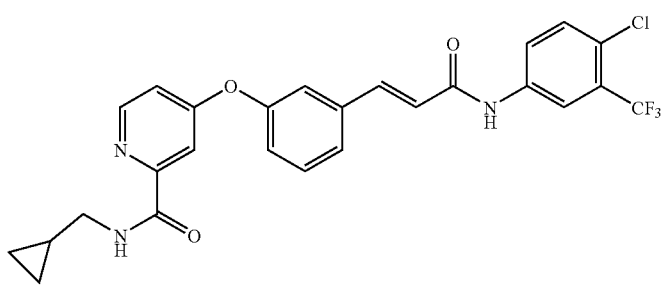
B-36
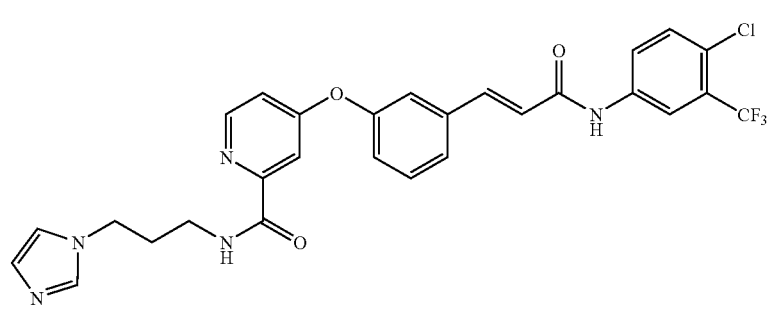
B-37
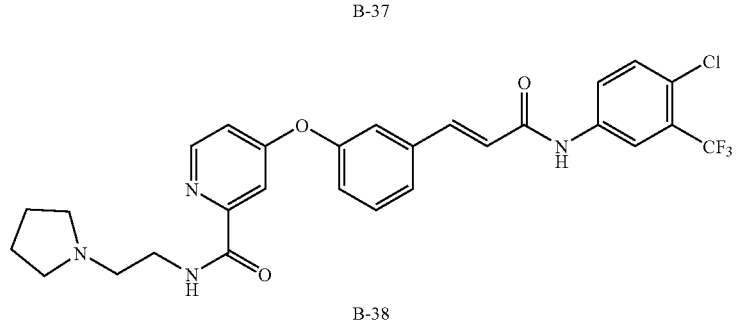
B-38
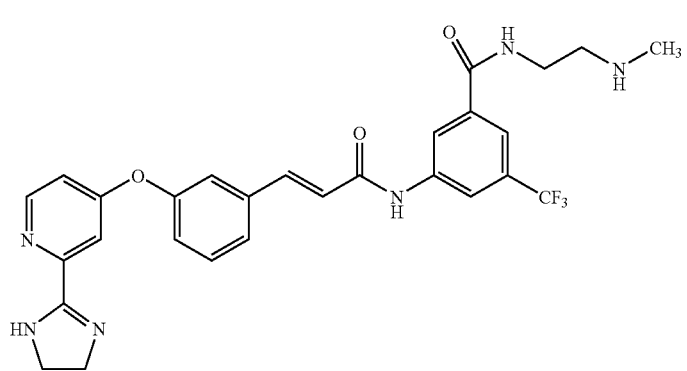
B-39

TABLE 2-continued
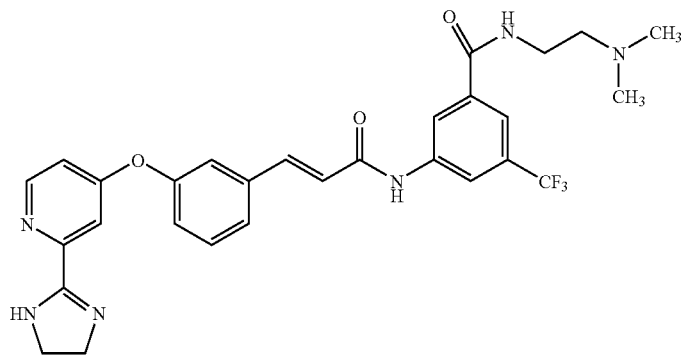
B-40
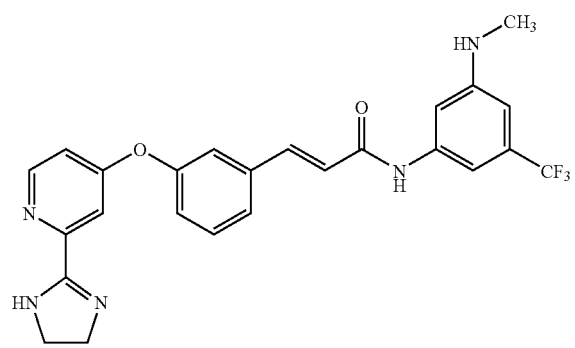
B-41
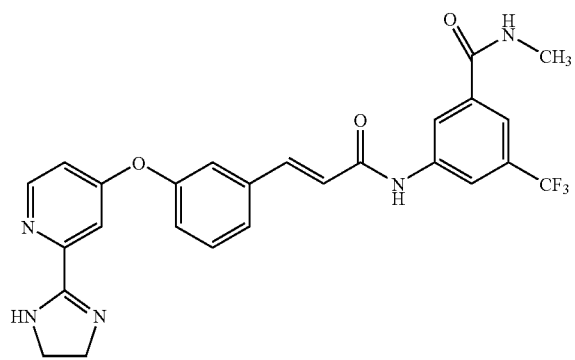
B-42
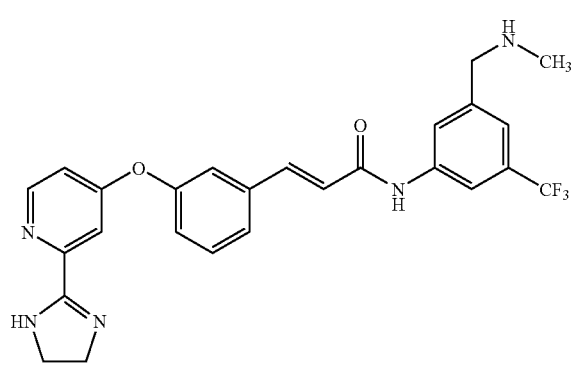
B-43

TABLE 2-continued
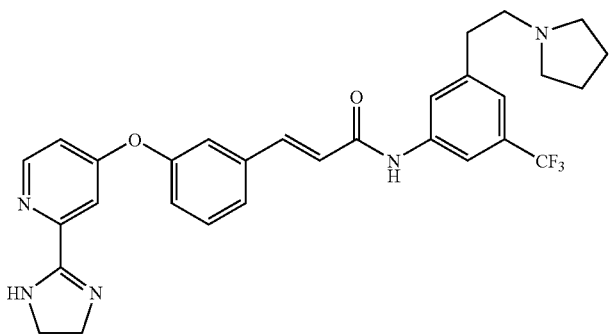
B-44
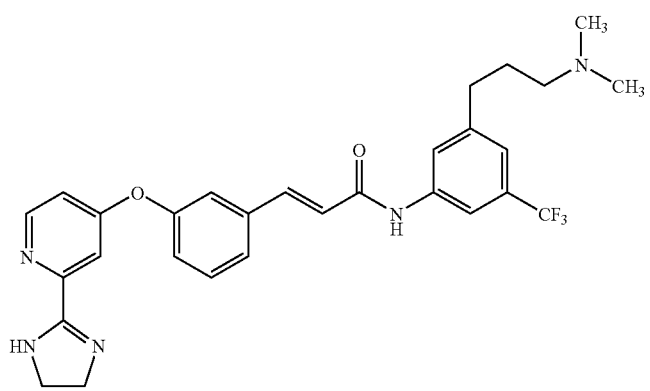
B-45
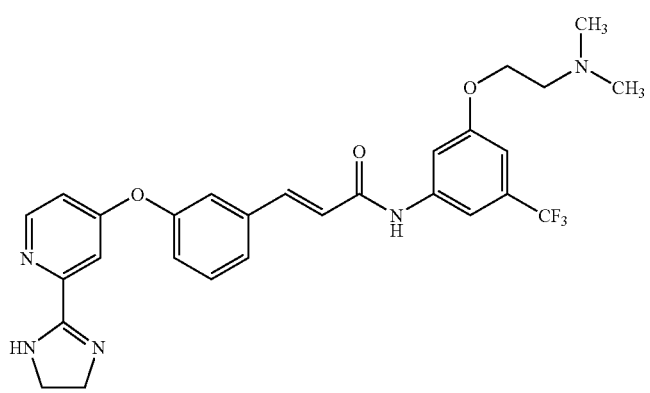
B-46
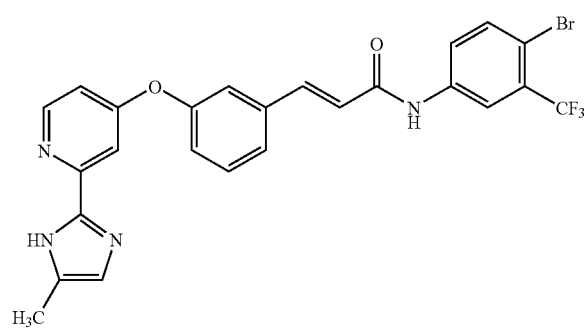
B-47

TABLE 2-continued
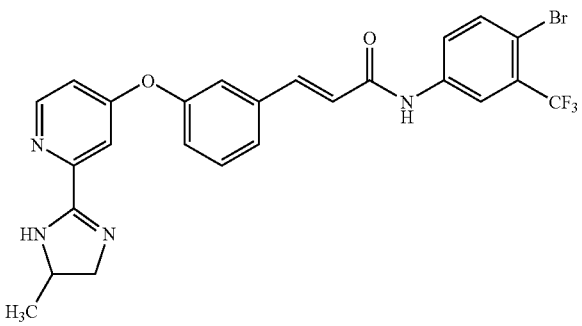
B-48
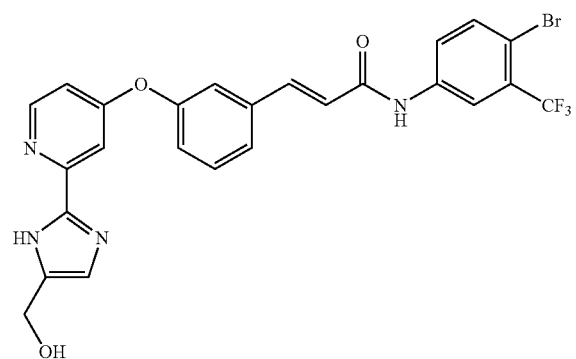
B-49
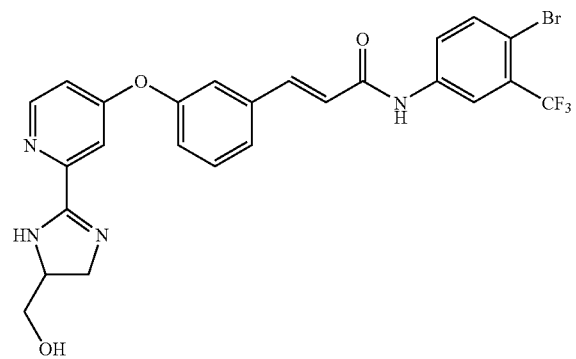
B-50
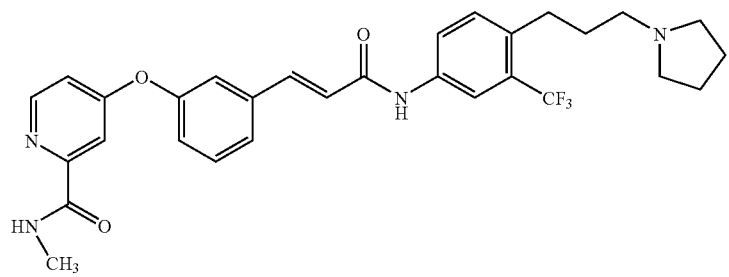
B-51

TABLE 2-continued
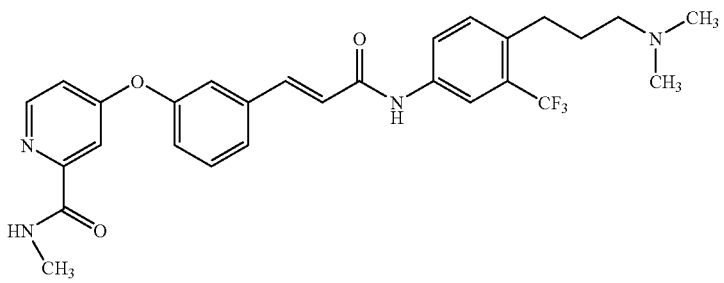
B-52
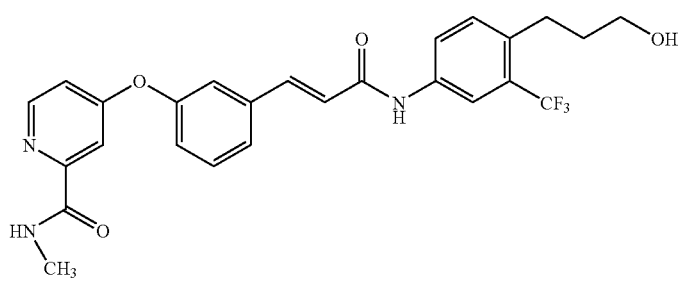
B-53
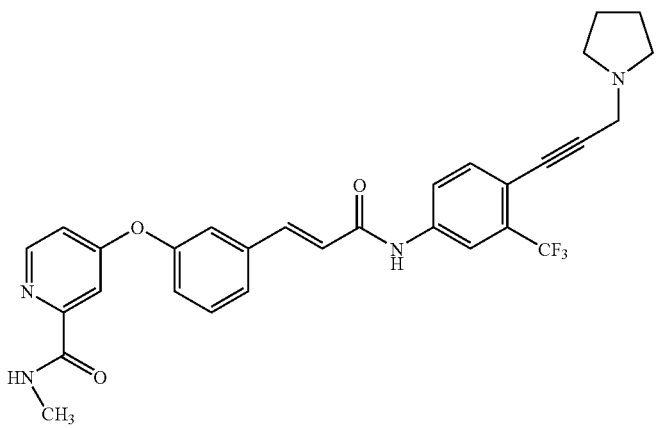
B-54
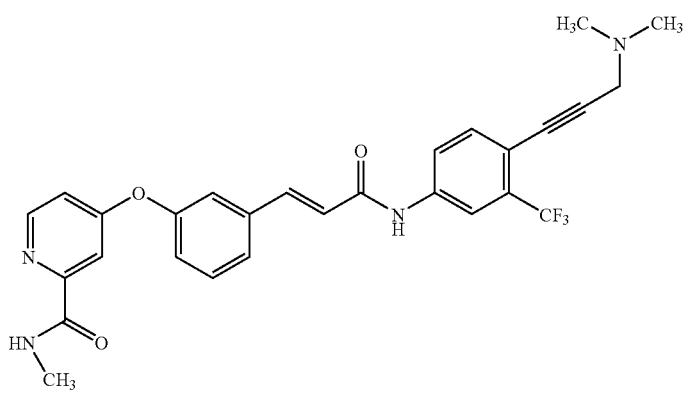
B-55

TABLE 2-continued
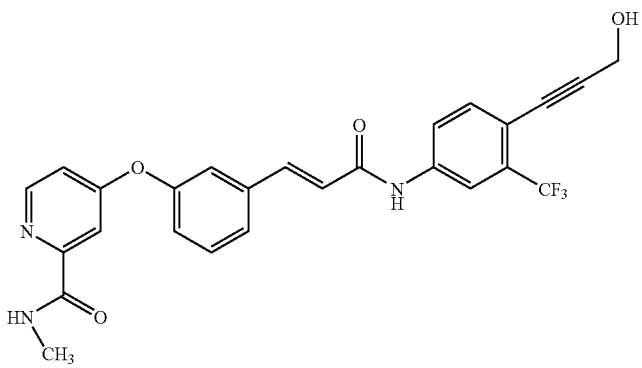
B-56
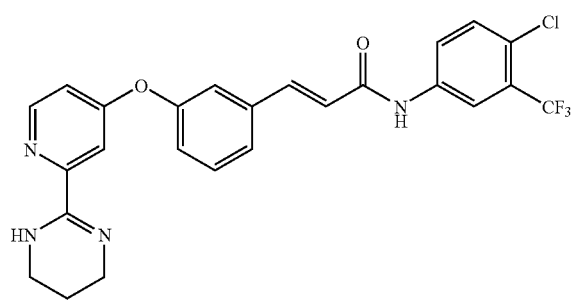
B-57
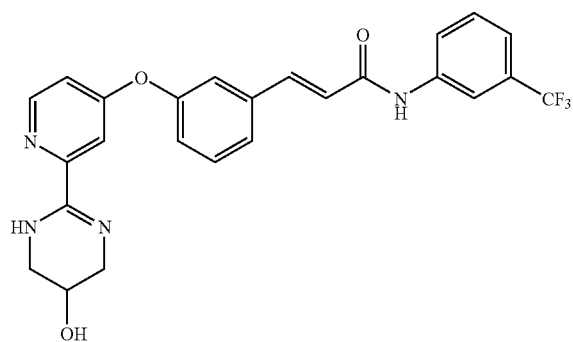
B-58
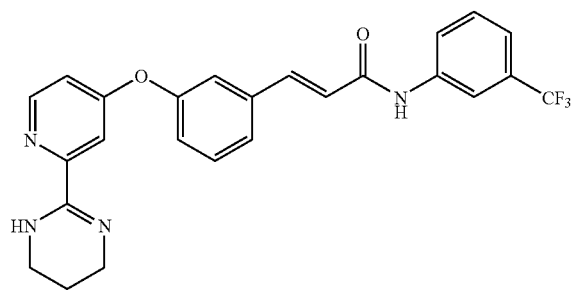
B-59

TABLE 2-continued
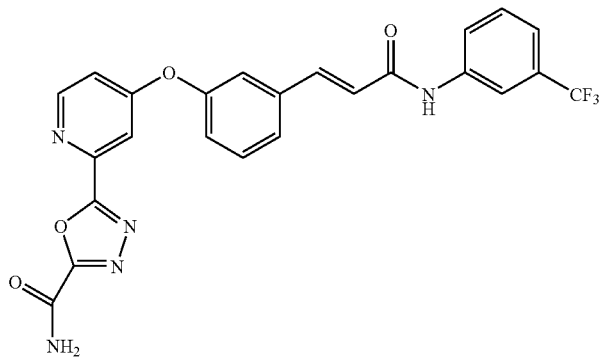
B-60
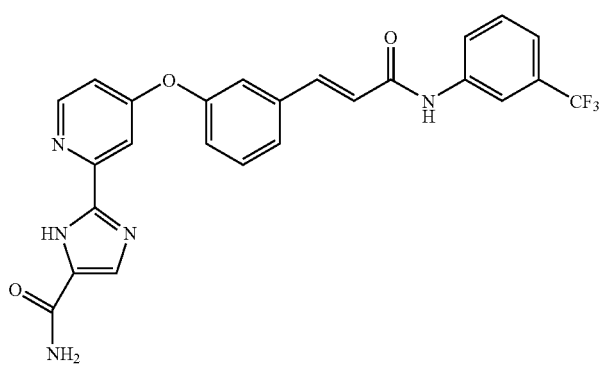
B-61
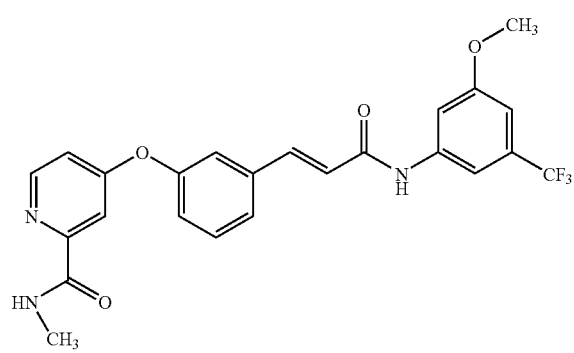
B-62
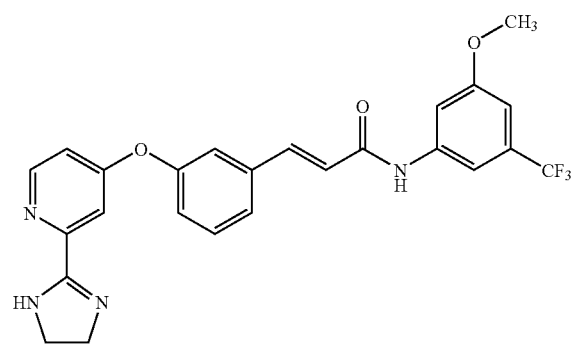
B-63

TABLE 2-continued
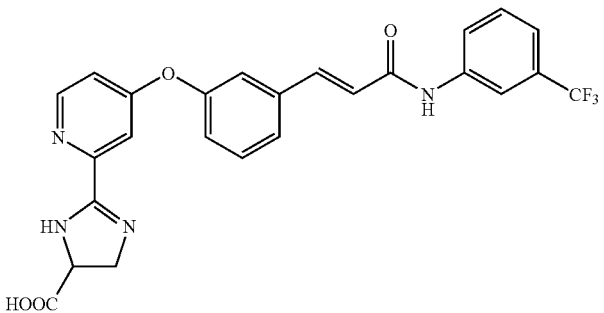
B-64
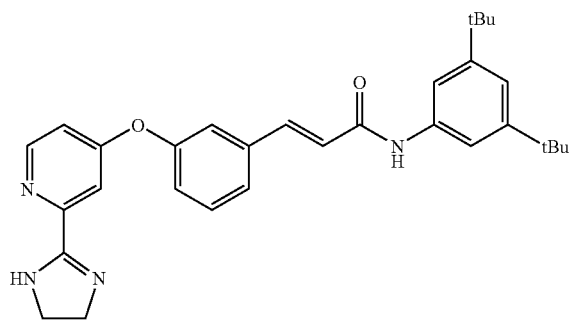
B-65
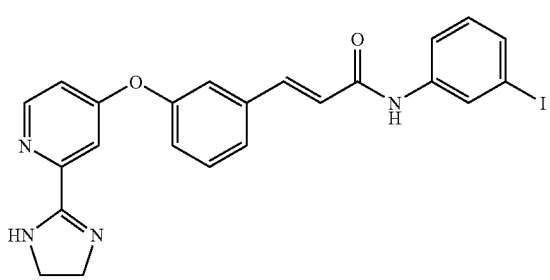
B-66
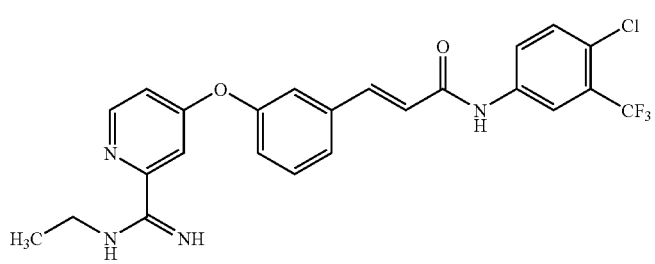
B-67
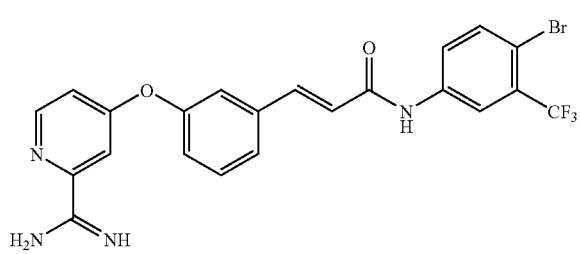
B-68

TABLE 2-continued
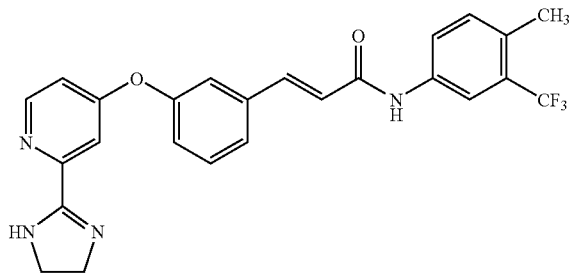
B-69
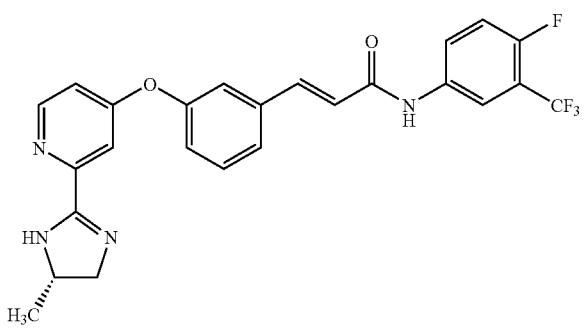
B-70
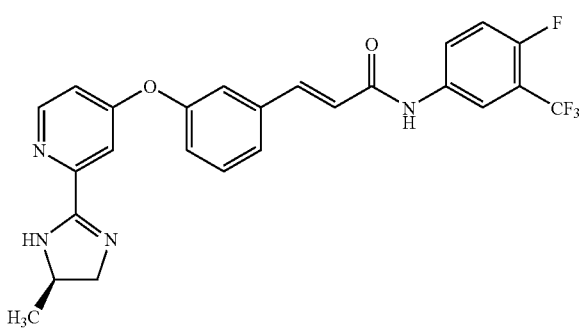
B-71
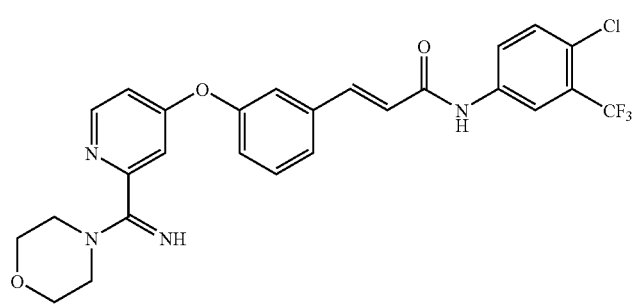
B-72
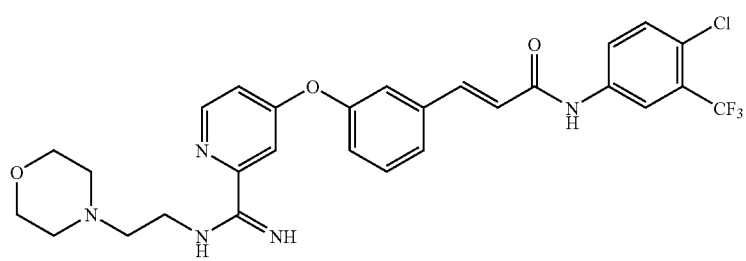
B-73

TABLE 2-continued
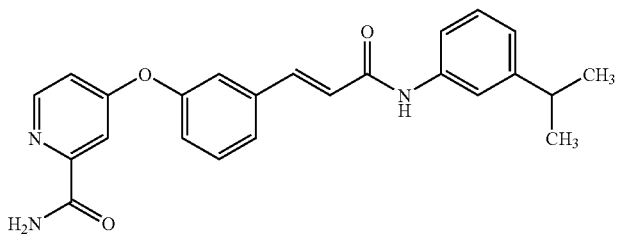
B-74
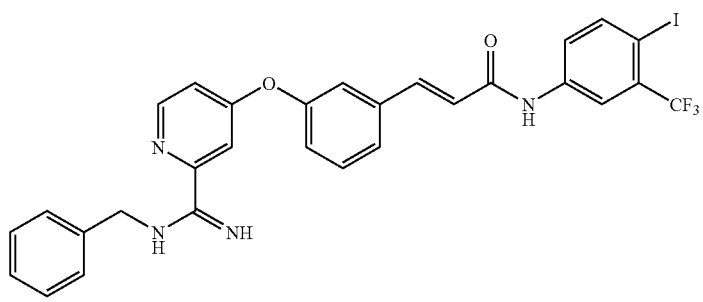
B-75
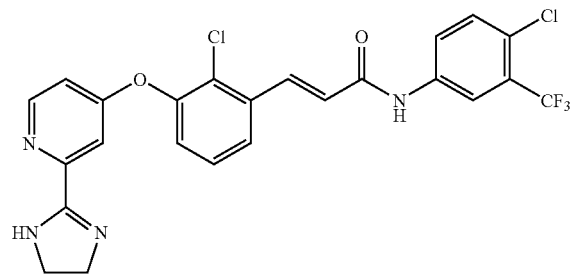
B-76
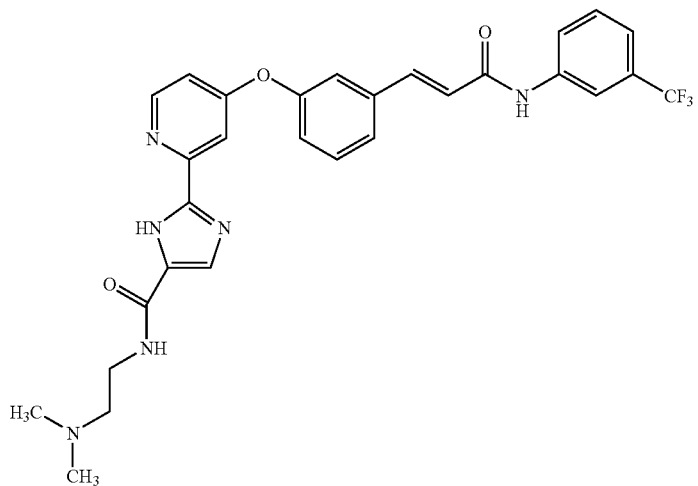
B-77

TABLE 2-continued
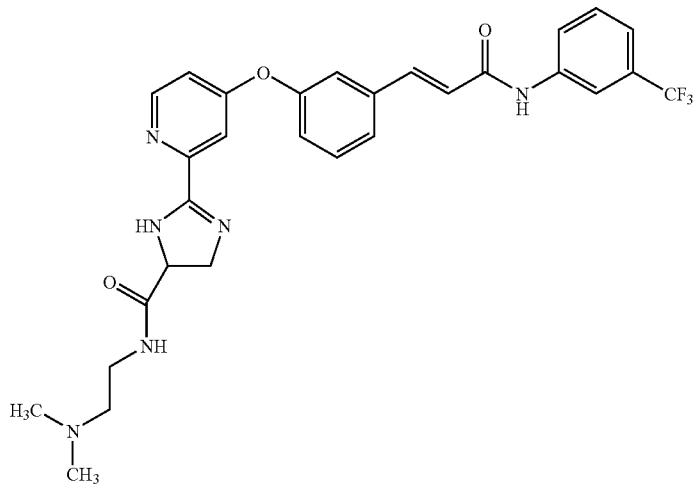
B-78
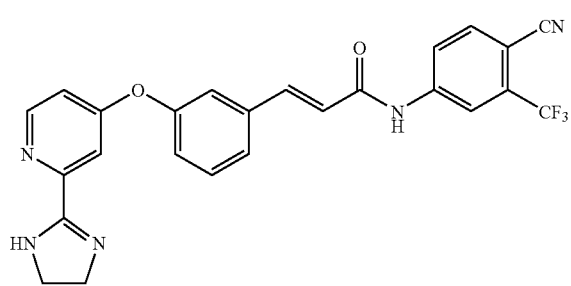
B-79
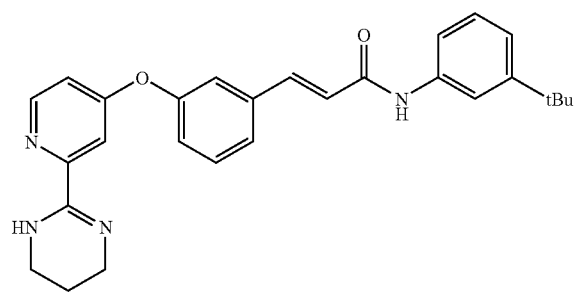
B-80
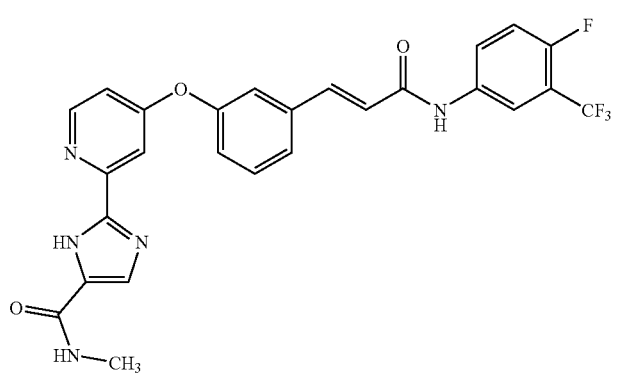
B-81

TABLE 2-continued
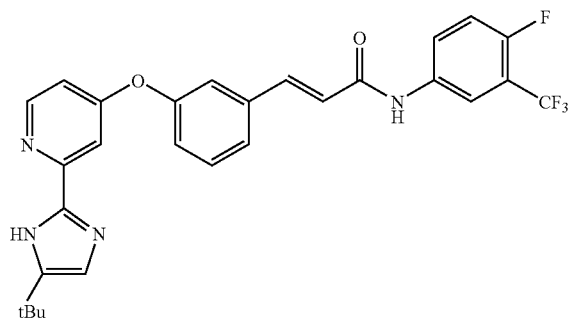
B-82
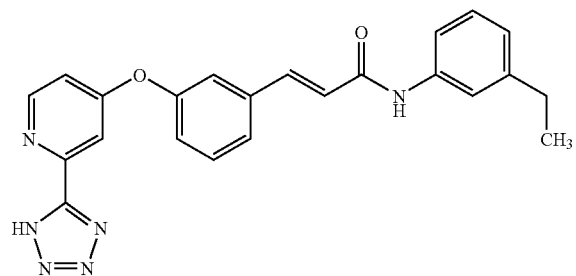
B-83
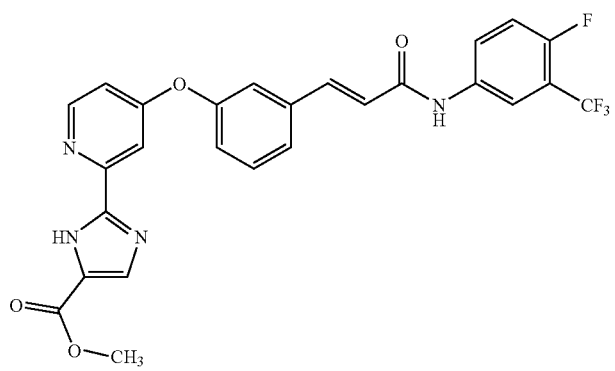
B-84
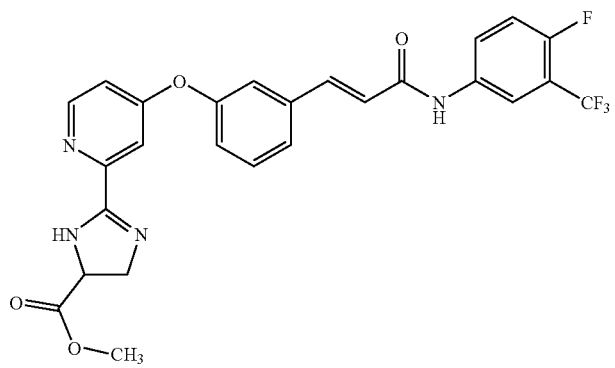
B-85

TABLE 2-continued
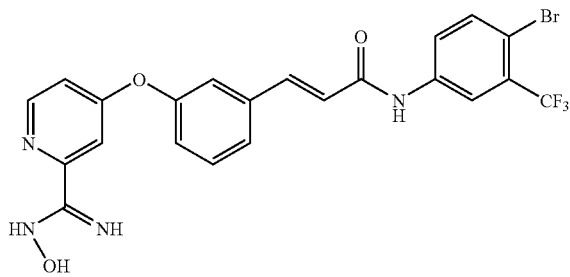
B-86
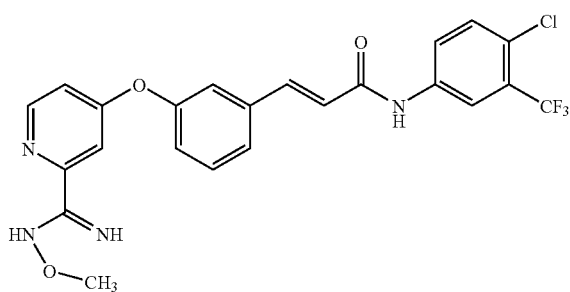
B-87
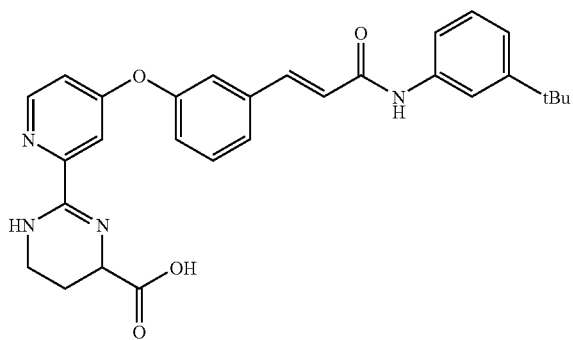
B-88
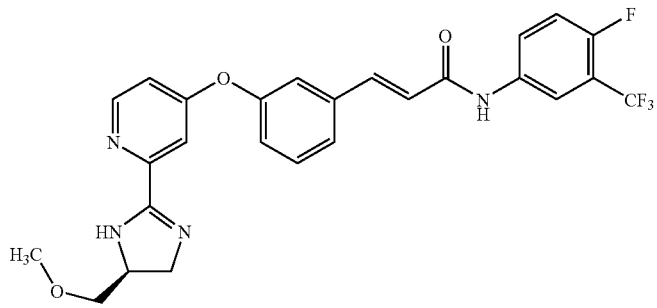
B-89

TABLE 2-continued
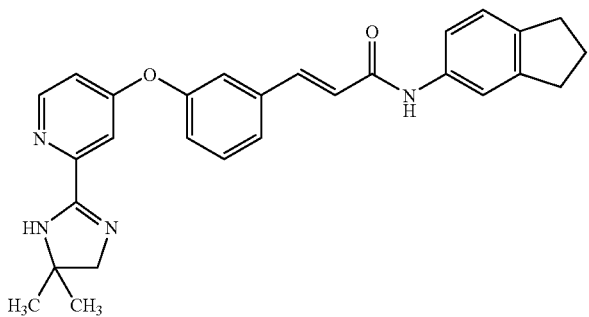
B-90
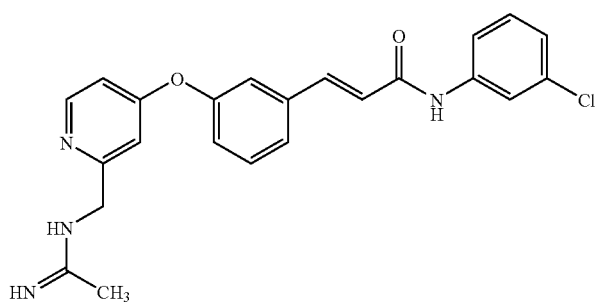
B-91
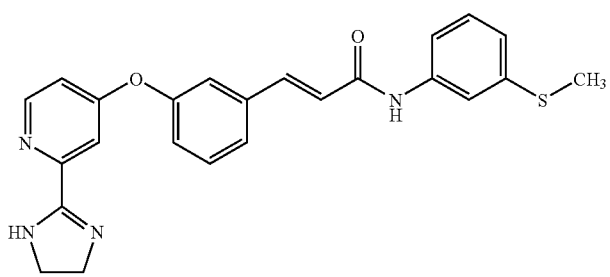
B-92
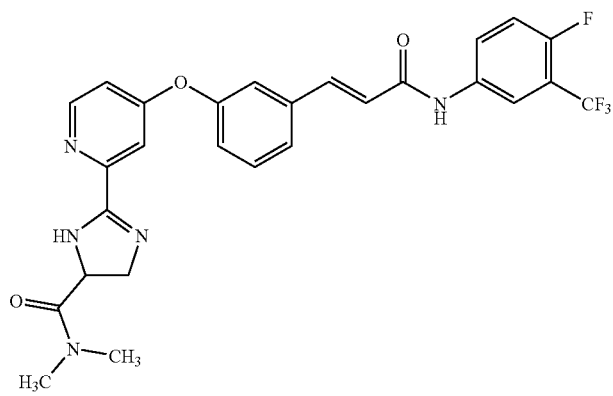
B-93

TABLE 2-continued
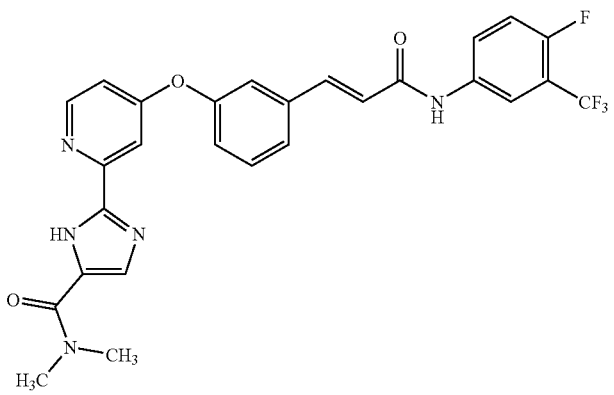
B-94
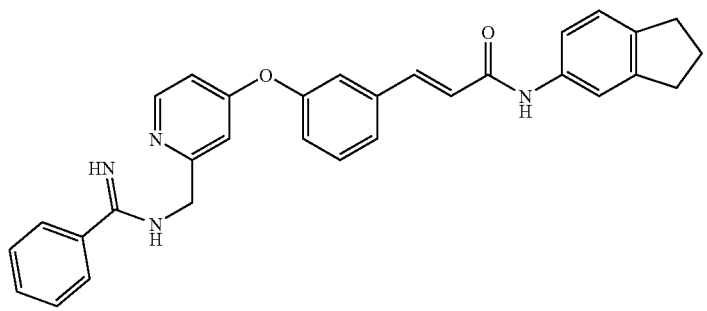
B-95
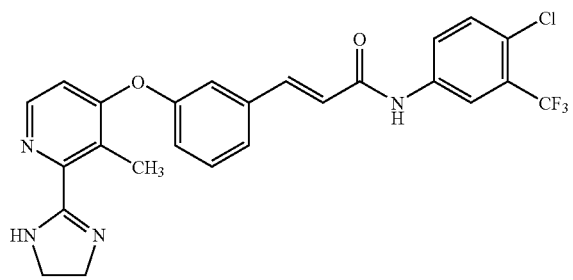
B-96
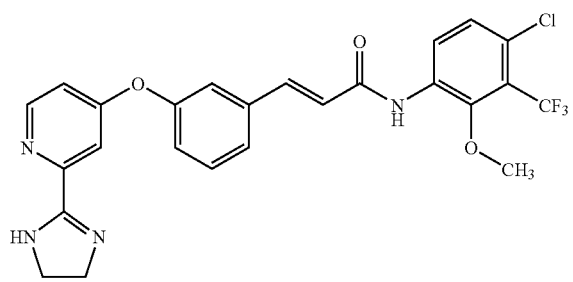
B-97

TABLE 2-continued
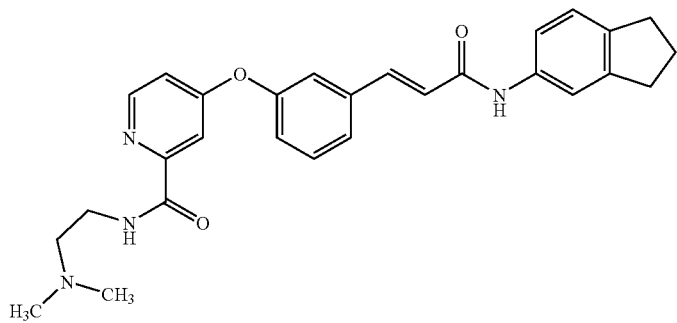
B-98
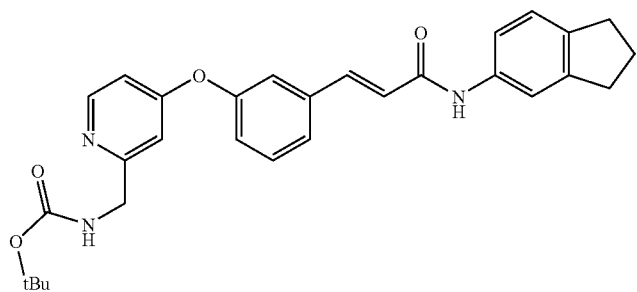
B-99
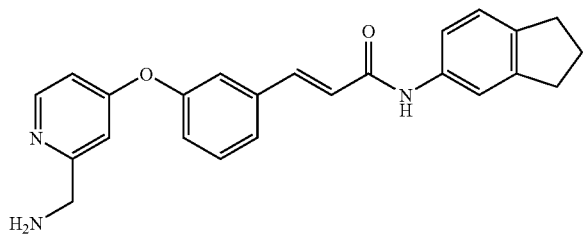
B-100
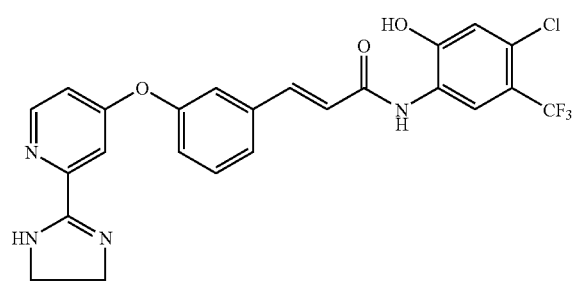
B-101
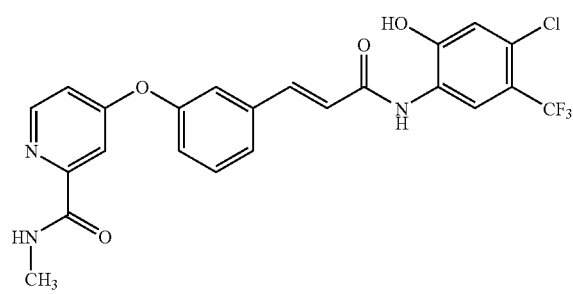
B-102

TABLE 2-continued
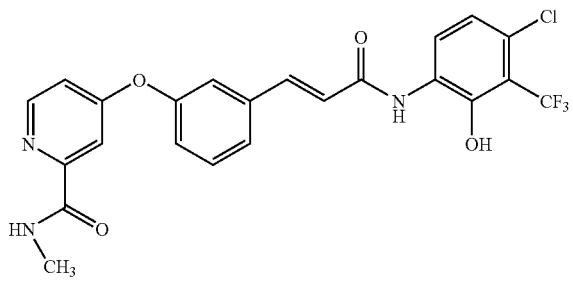
B-103
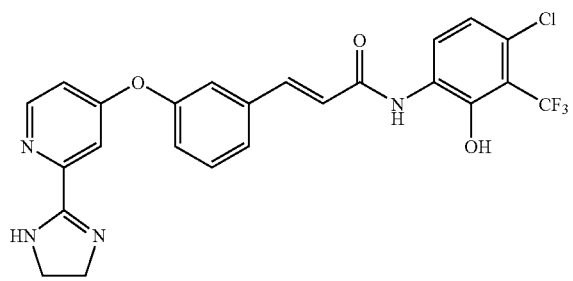
B-104
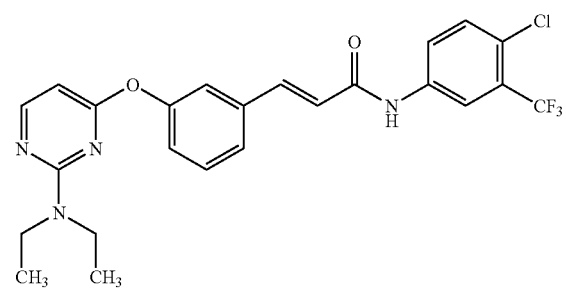
B-105
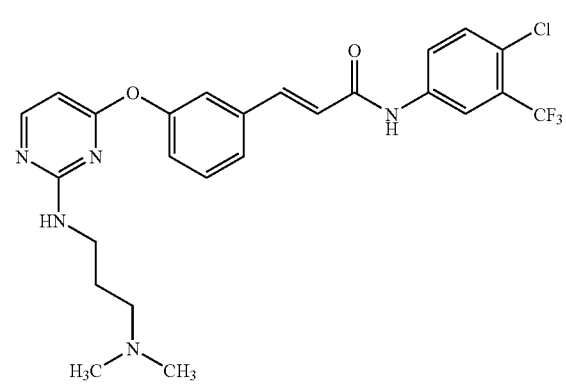
B-106
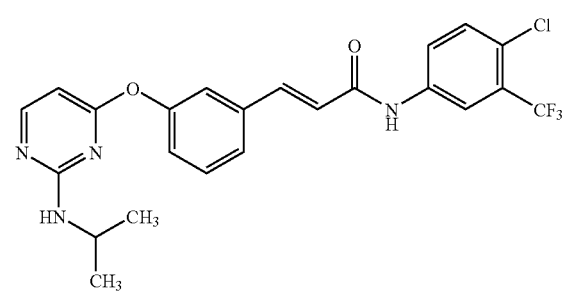
B-107

TABLE 2-continued
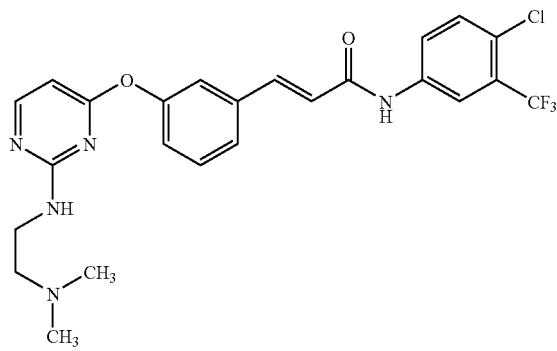
B-108
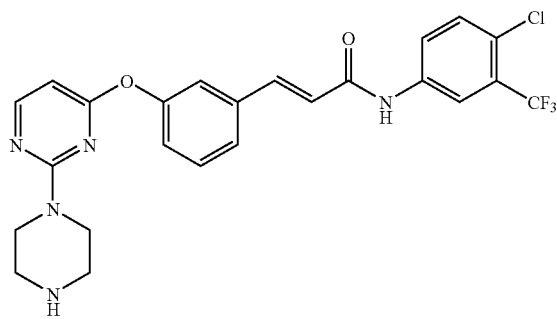
B-109
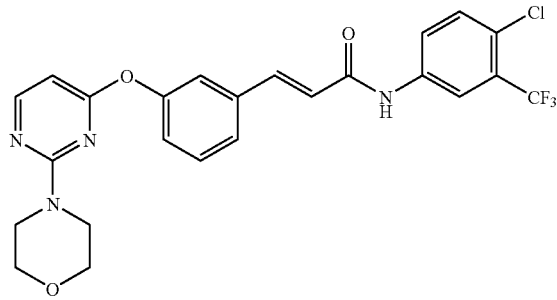
B-110
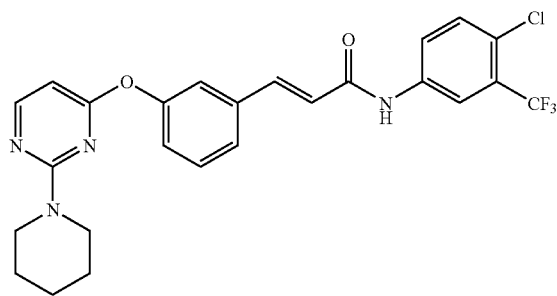
B-111

TABLE 2-continued
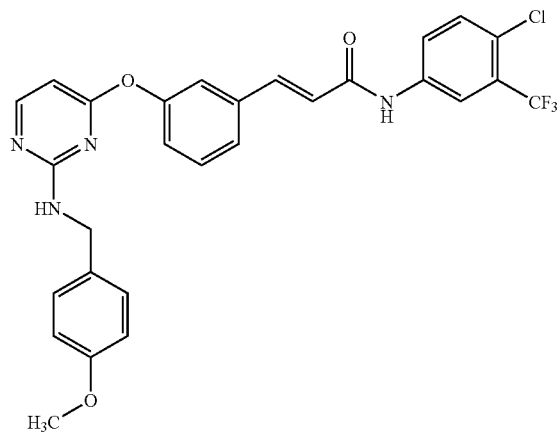
B-112
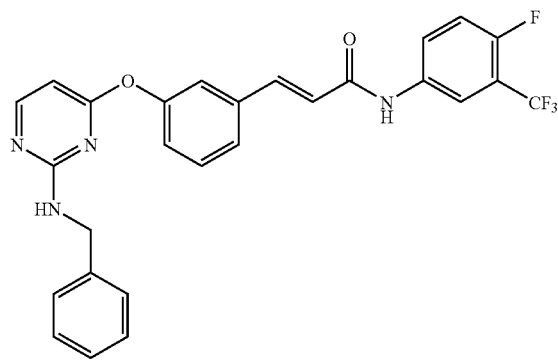
B-113
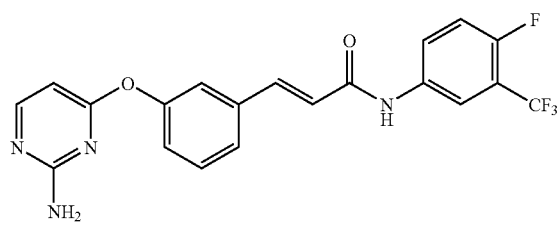
B-114
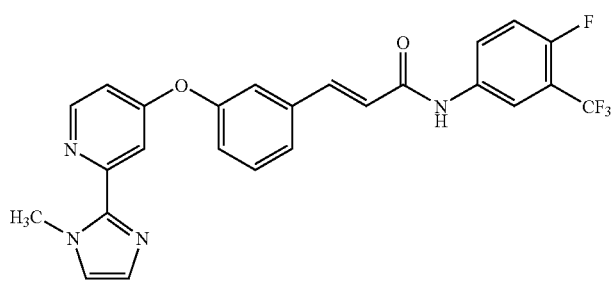
B-115

TABLE 2-continued
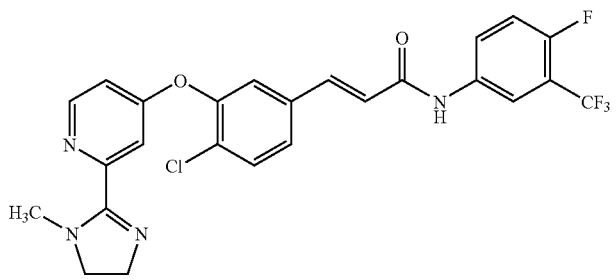
B-116
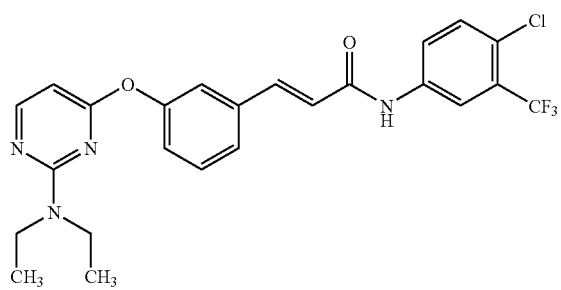
B-117
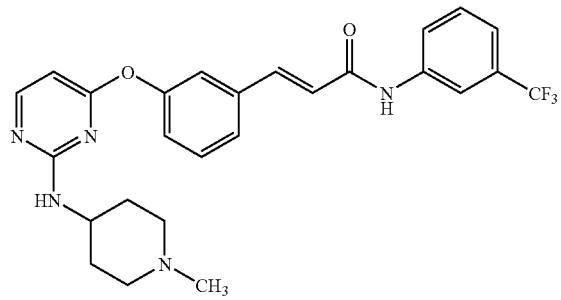
B-118
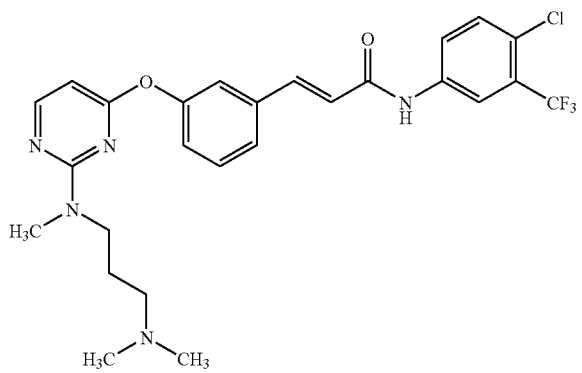
B-119

TABLE 2-continued
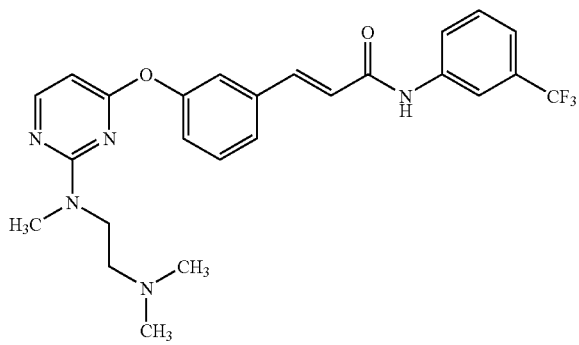
B-120
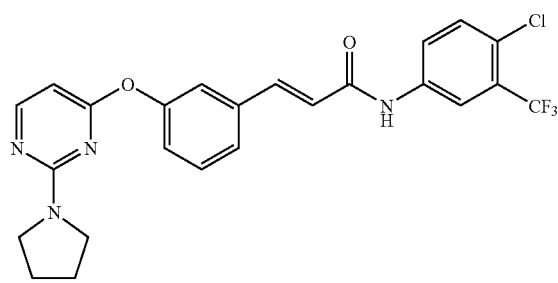
B-121
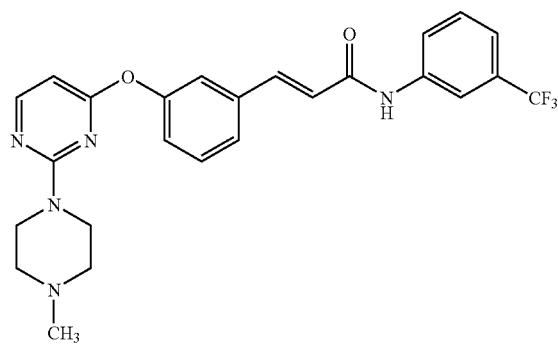
B-122
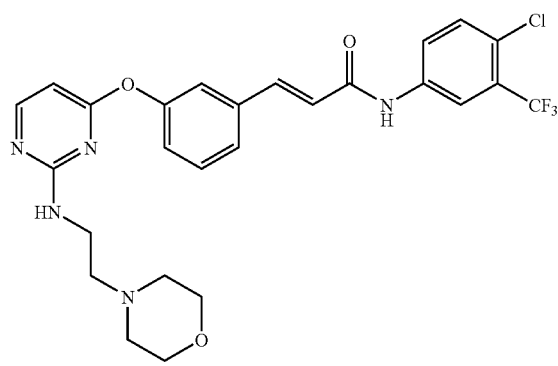
B-123

TABLE 2-continued
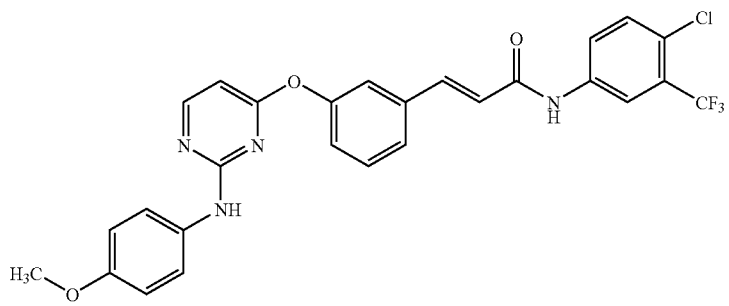
B-124
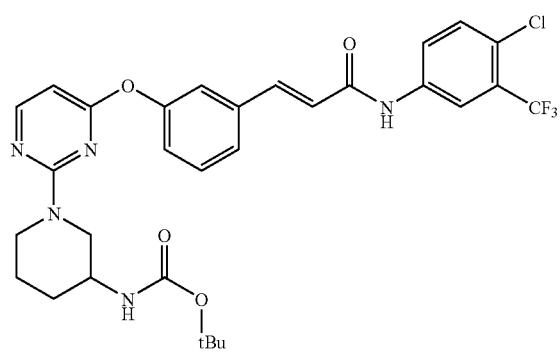
B-125
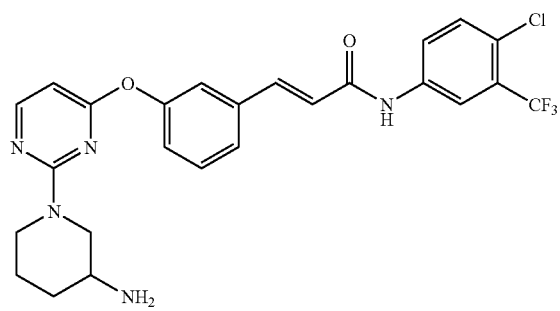
B-126
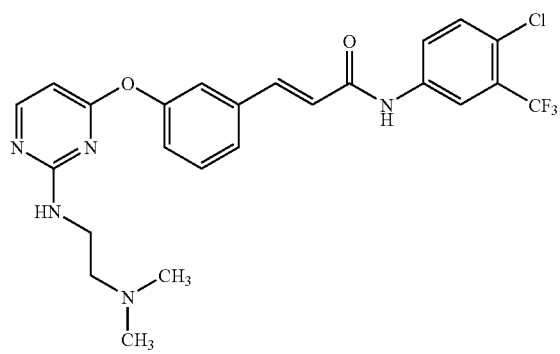
B-127

TABLE 2-continued
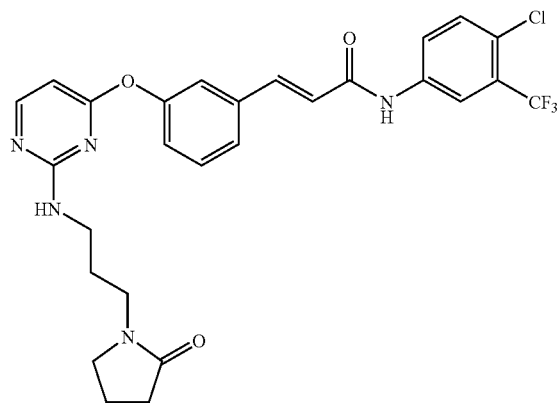
B-128
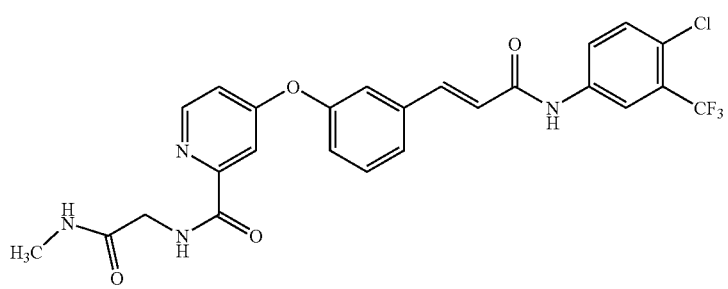
B-129
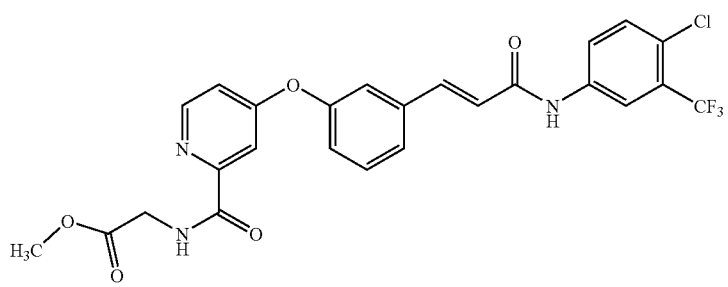
B-130
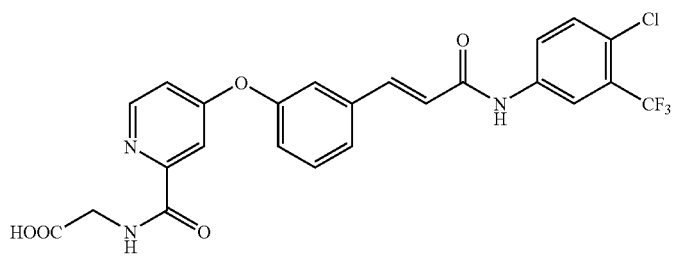
B-131

TABLE 2-continued
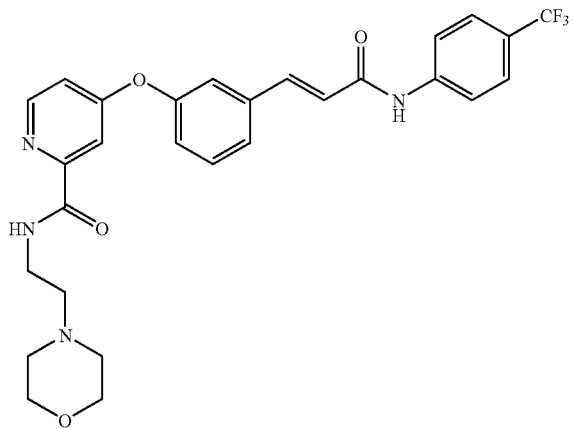
B-132
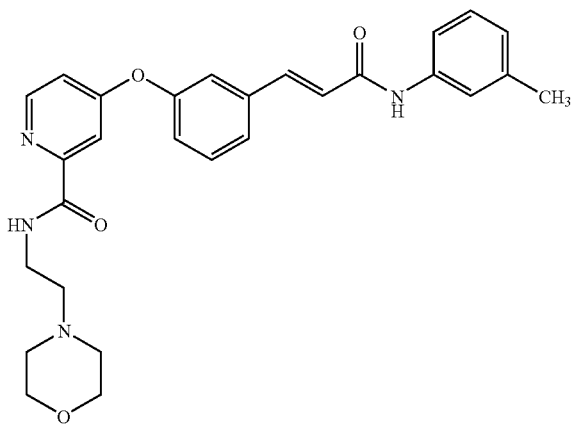
B-133
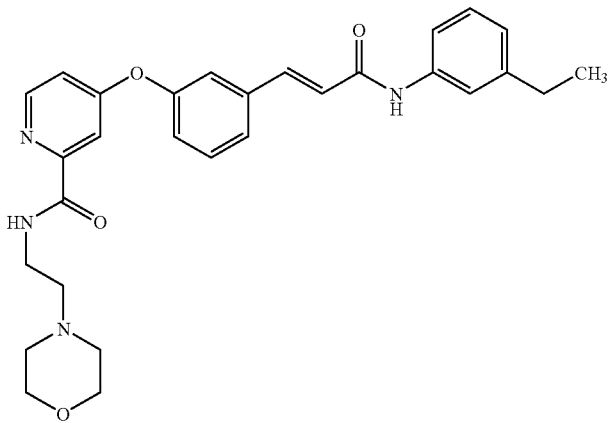
B-134

TABLE 2-continued
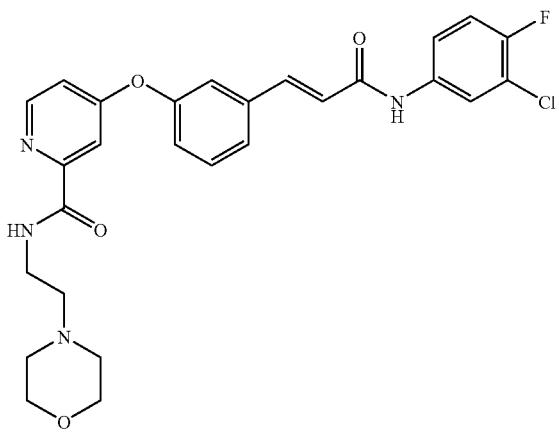
B-135
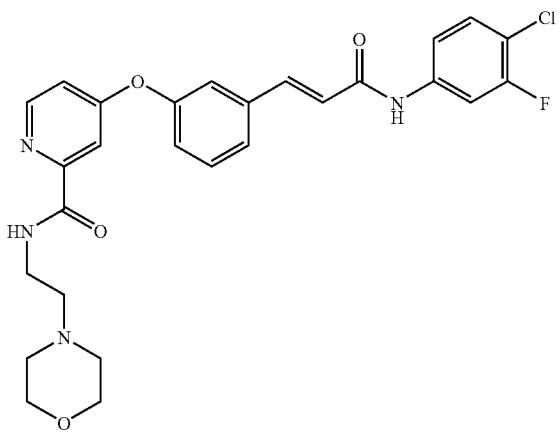
B-136
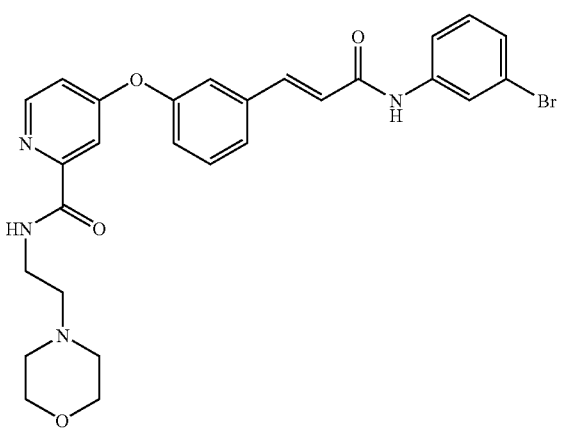
B-137

TABLE 2-continued
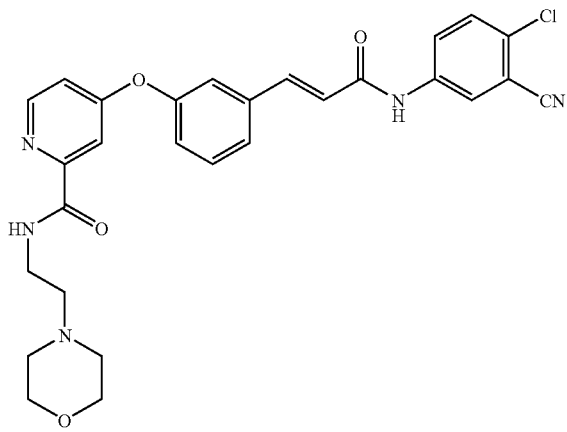
B-138
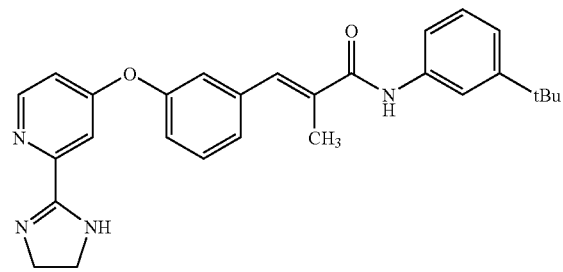
B-139
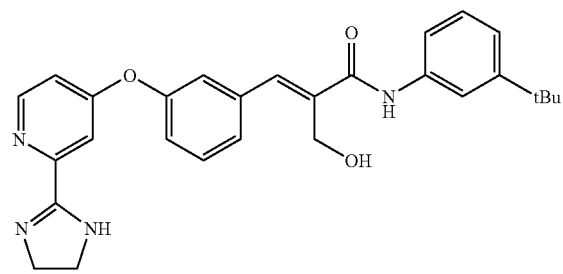
B-140
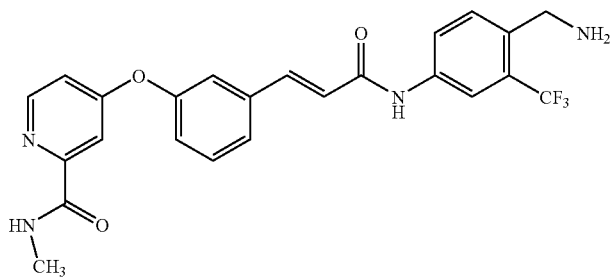
B-141

TABLE 2-continued
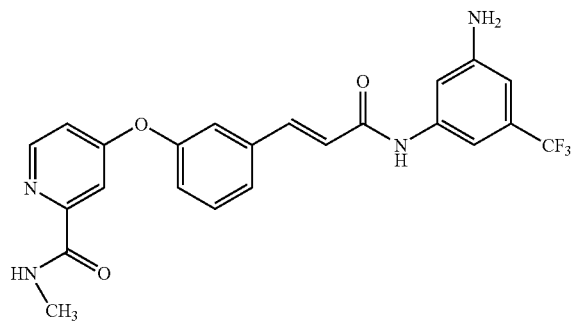
B-142
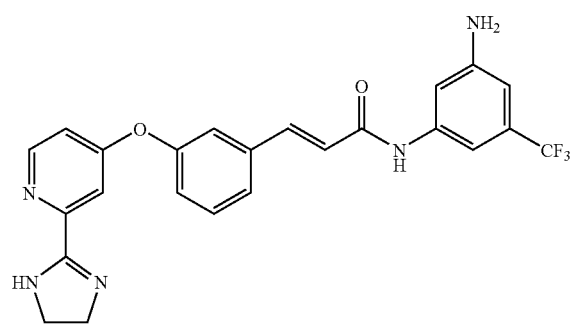
B-143
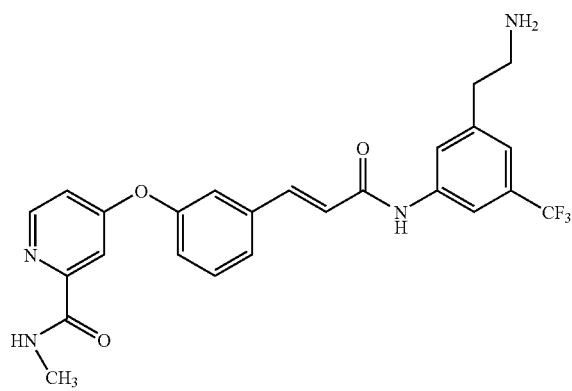
B-144
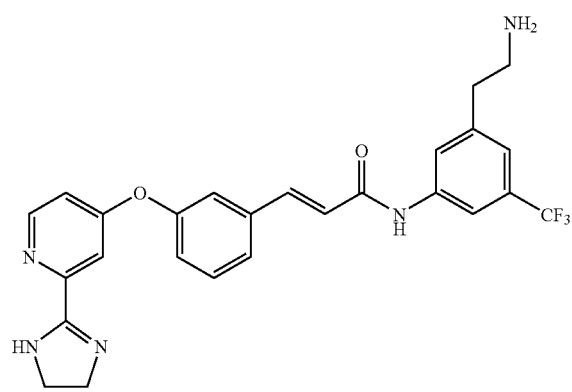
B-145

TABLE 2-continued
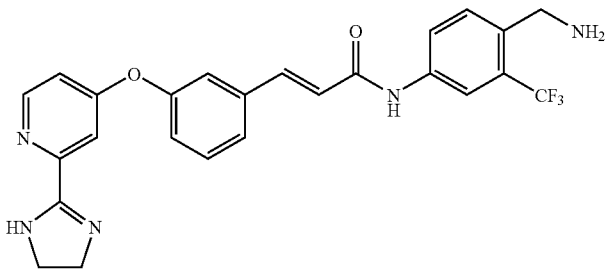
B-146
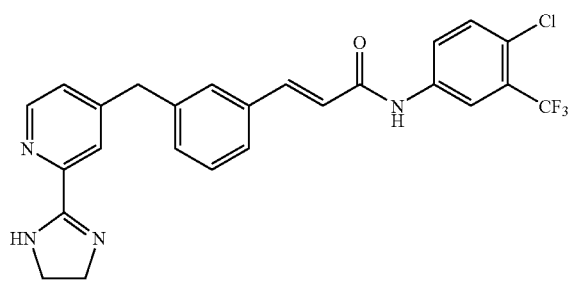
B-147
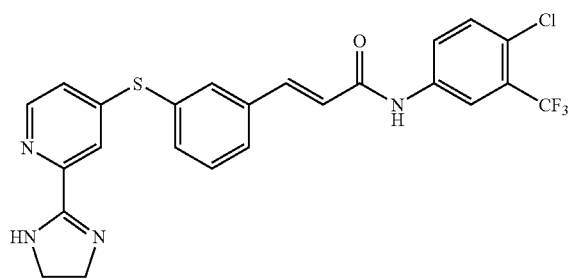
B-148
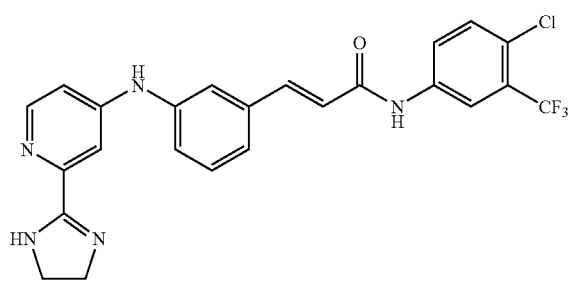
B-149
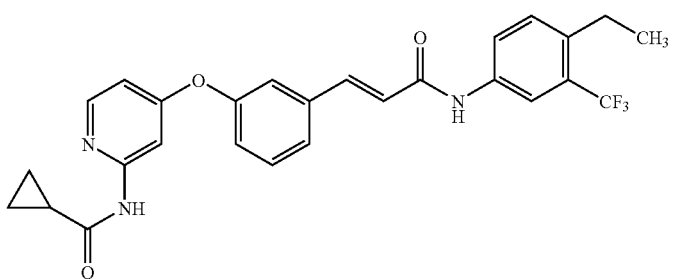
B-150

TABLE 2-continued
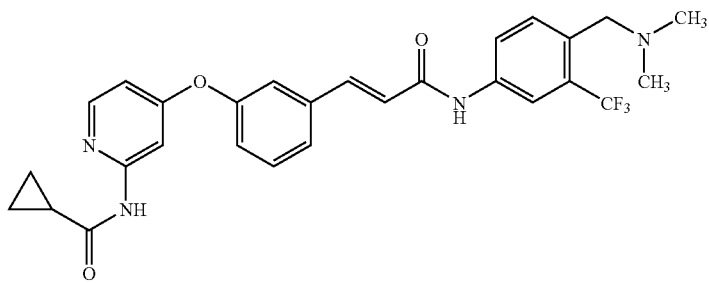
B-151
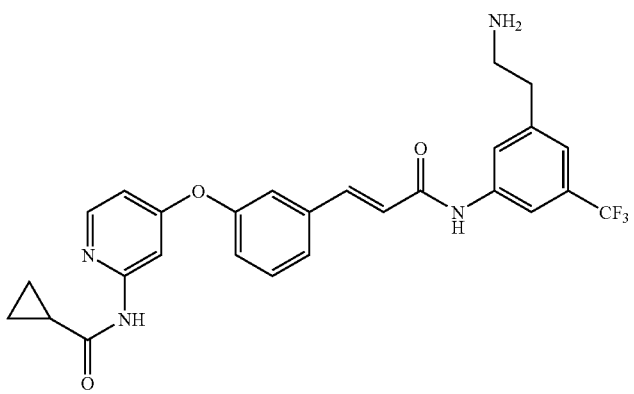
B-152
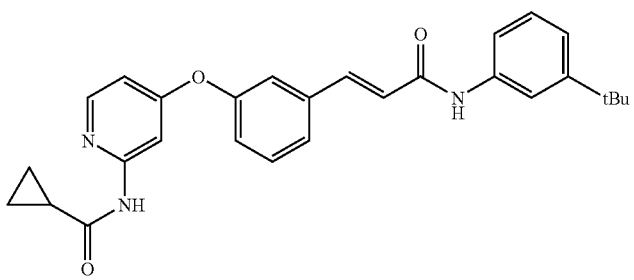
B-153
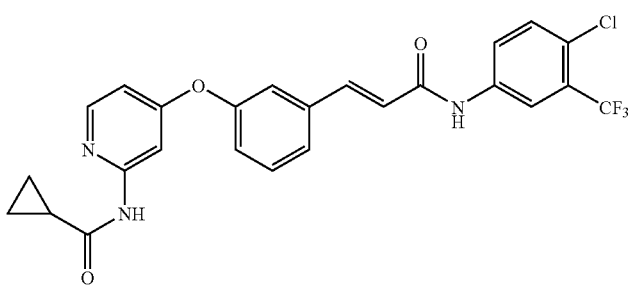
B-154
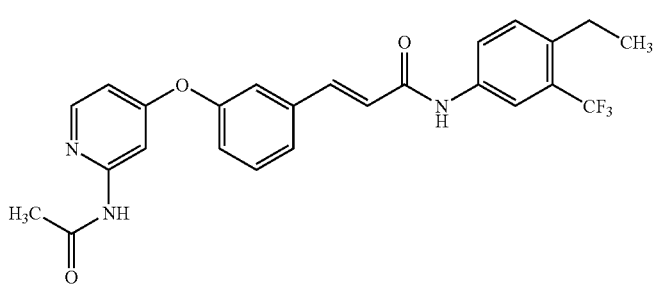
B-155

TABLE 2-continued

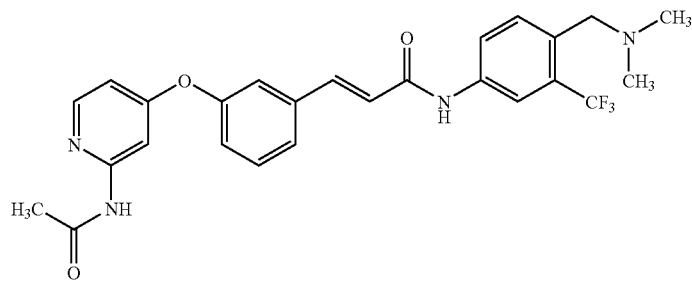

B-156

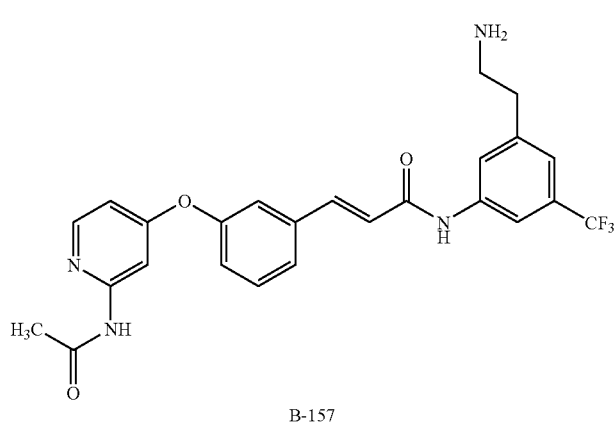

B-157

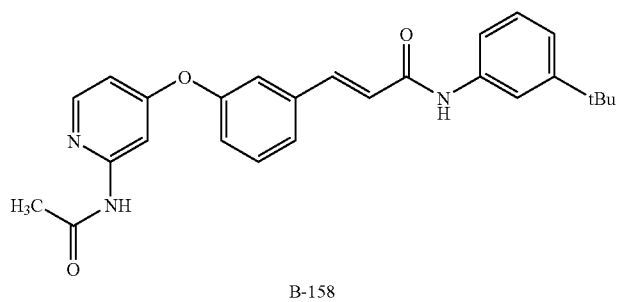

B-158

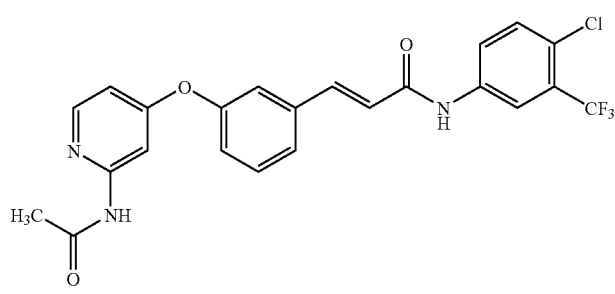

B-159

The compounds in Table 2 above also may be identified by the following chemical names:

Chemical Name

B-1: (2E)-N-[4-chloro-3-(trifluoromethyl)phenyl]-3-(3-{[2-(4,5-dihydro-1H-imidazol-2-yl)pyridin-4-yl]oxy}phenyl)but-2-enamide B-2: (2E)-3-(3-{[2-(4,5-dihydro-1H-imidazol-2-yl)pyridin-4-yl]oxy}phenyl)-N-(3-isopropylphenyl)acrylamide B-3: (2E)-N-[4-chloro-3-(trifluoromethyl)phenyl]-3-[3-(9H-purin-6-yloxy)phenyl]-acrylamide B-5: (2E)-N-(3-tert-butylphenyl)-3-(3-{[2-(4,5-dihydro-1H-imidazol-2-yl)pyridin-4-yl]oxy}phenyl)acrylamide B-6: 4-(3-{(1E)-3-[(3-tert-butylphenyl)amino]-2-methyl-3-oxoprop-1-en-1-yl}phenoxy)-N-methylpyridine-2-carboxamide B-7: (2E)-3-(3-{[2-(4,5-dihydro-1H-imidazol-2-yl)pyridin-4-yl]oxy}phenyl)-N-[3-(trifluoromethyl)phenyl]acrylamide B-8: (2E)-N-[4-chloro-3-(trifluoromethyl)phenyl]-2-(3-{[2-(4,5-dihydro-1H-imidazol-2-yl)pyridin-4-yl]oxy}benzylidene)butanamide B-9: (2E)-3-(3-{[2-(4,5-dihydro-1H-imidazol-2-yl)pyridin-4-yl]oxy}phenyl)-N-[3-fluoro-5-(trifluoromethyl)phenyl]acrylamide B-10: (2E)-N-(3-chlorophenyl)-3-(3-{[2-(4,5-dihydro-1H-imidazol-2-yl)pyridin-4-yl]oxy}phenyl)acrylamide B-11: (2Z)-N-[4-chloro-3-(trifluoromethyl)phenyl]-3-(3-{[2-(4,5-dihydro-1H-imidazol-2-yl)pyridin-4-yl]oxy}phenyl)-2-fluoroacrylamide B-12: (2E)-N-[4-chloro-3-(trifluoromethyl)phenyl]-3-(3-{[2-(4,5-dihydro-1H-imidazol-2-yl)pyridin-4-yl]oxy}phenyl)-2-methylacrylamide B-13: (2E)-N-(4-chlorophenyl)-3-(3-{[2-(4,5-dihydro-1H-imidazol-2-yl)pyridin-4-yl]oxy}phenyl)acrylamide B-14: (2E)-N-[4-chloro-3-(trifluoromethyl)phenyl]-3-(3-{[2-(4,5-dihydro-1H-imidazol-2-yl)pyridin-4-yl]oxy}phenyl)acrylamide B-15: (2E)-3-(3-{[2-(4,5-dihydro-1H-imidazol-2-yl)pyridin-4-yl]oxy}phenyl)-N-[4-(3-pyrrolidin-1-ylpropyl)-3-(trifluoromethyl)phenyl]acrylamide B-16: (2E)-3-(3-{[2-(4,5-dihydro-1H-imidazol-2-yl)pyridin-4-yl]oxy}phenyl)-N-[4-[3-(dimethylamino)propyl]-3-(trifluoromethyl)phenyl]acrylamide B-17: (2E)-3-(3-{[2-(4,5-dihydro-1H-imidazol-2-yl)pyridin-4-yl]oxy}phenyl)-N-[4-(3-hydroxypropyl)-3-(trifluoromethyl)phenyl]acrylamide B-18: (2E)-3-(3-{[2-(4,5-dihydro-1H-imidazol-2-yl)pyridin-4-yl]oxy}phenyl)-N-[4-(3-pyrrolidin-1-ylprop-1-yn-1-yl)-3-(trifluoromethyl)phenyl]acrylamide B-19: (2E)-3-(3-{[2-(4,5-dihydro-1H-imidazol-2-yl)pyridin-4-yl]oxy}phenyl)-N-[4-[3-(dimethylamino)prop-1-yn-1-yl]-3-(trifluoromethyl)phenyl]acrylamide B-20: (2E)-3-(3-{[2-(4,5-dihydro-1H-imidazol-2-yl)pyridin-4-yl]oxy}phenyl)-N-[4-(3-hydroxyprop-1-yn-1-yl)-3-(trifluoromethyl)phenyl]acrylamide B-21: (2E)-N-[4-chloro-3-(trifluoromethyl)phenyl]-3-(3-{[2-(5-methyl-1H-imidazol-2-yl)pyridin-4-yl]oxy}phenyl)acrylamide B-22: (2E)-N-[4-bromo-3-(trifluoromethyl)phenyl]-3-(3-{[2-(4,5-dihydro-1H-imidazol-2-yl)pyridin-4-yl]oxy}phenyl)acrylamide B-23: (2E)-3-(3-{[2-(4,5-dihydro-1H-imidazol-2-yl)pyridin-4-yl]oxy}phenyl)-N-[4-ethynyl-3-(trifluoromethyl)phenyl]acrylamide B-24: (2E)-N-(3-tert-butylphenyl)-3-{3-[(2-{[(4-ethylpiperazin-1-yl)acetyl]amino}pyridin-4-yl)oxy]phenyl}acrylamide B-25: 4-(3-{(1E)-3-[(3-tert-butylphenyl)amino]-3-oxoprop-1-en-1-yl}phenoxy)-N-methylpyridine-2-carboxamide B-26: 4-[3-((1E)-3-{[4-chloro-3-(trifluoromethyl)phenyl]amino}-3-oxoprop-1-en-1-yl)phenoxy]-N-methylpyridine-2-carboxamide B-27: (2E)-3-(3-{[2-(4,5-dihydro-1H-imidazol-2-yl)pyridin-4-yl]oxy}phenyl)-N-(3,3-dimethyl-1-oxo-2,3-dihydro-1H-isoindol-5-yl)acrylamide B-28: (2E)-3-(3-{[2-(4,5-dihydro-1H-imidazol-2-yl)pyridin-4-yl]oxy}phenyl)-N-(3,3-dimethyl-1-oxo-1,3-dihydro-2-benzofuran-5-yl)acrylamide B-29: (2E)-3-(3-{[2-(4,5-dihydro-1H-imidazol-2-yl)pyridin-4-yl]oxy}phenyl)-N-[2-(trifluoromethyl)pyridin-4-yl]acrylamide B-30: (2E)-3-(3-{[2-(4,5-dihydro-1H-imidazol-2-yl)pyridin-4-yl]oxy}phenyl)-N-[4-(trifluoromethyl)pyridin-2-yl]acrylamide B-31: (2E)-N-(3-tert-butylisoxazol-5-yl)-3-(3-{[2-(4,5-dihydro-1H-imidazol-2-yl)pyridin-4-yl]oxy}phenyl)acrylamide B-32: (2E)-N-(5-tert-butylisoxazol-3-yl)-3-(3-{[2-(4,5-dihydro-1H-imidazol-2-yl)pyridin-4-yl]oxy}phenyl)acrylamide B-33: 4-[3-((1E)-3-{[4-chloro-3-(trifluoromethyl)phenyl]amino}-3-oxoprop-1-en-1-yl)phenoxy]-N-(2-methoxyethyl)pyridine-2-carboxamide B-34: 4-[3-((1E)-3-{[4-chloro-3-(trifluoromethyl)phenyl]amino}-3-oxoprop-1-en-1-yl)phenoxy]-N-(2-piperazin-1-ylethyl)pyridine-2-carboxamide B-35: 4-[3-((1E)-3-{[4-chloro-3-(trifluoromethyl)phenyl]amino}-3-oxoprop-1-en-1-yl)phenoxy]-N-(2-piperidin-1-ylethyl)pyridine-2-carboxamide B-36: 4-[3-((1E)-3-{[4-chloro-3-(trifluoromethyl)phenyl]amino}-3-oxoprop-1-en-1-yl)phenoxy]-N-(cyclopropylmethyl)pyridine-2-carboxamide B-37: 4-[3-((1E)-3-{[4-chloro-3-(trifluoromethyl)phenyl]amino}-3-oxoprop-1-en-1-yl)phenoxy]-N-[3-(1H-imidazol-1-yl)propyl]pyridine-2-carboxamide B-38: 4-[3-((1E)-3-{[4-chloro-3-(trifluoromethyl)phenyl]amino}-3-oxoprop-1-en-1-yl)phenoxy]-N-(2-pyrrolidin-1-ylethyl)pyridine-2-carboxamide B-39: 3-{[(2E)-3-(3-{[2-(4,5-dihydro-1H-imidazol-2-yl)pyridin-4-yl]oxy}phenyl)prop-2-enoyl]amino}-N-[2-(methylamino)ethyl]-5-(trifluoromethyl)benzamide B-40: 3-{[(2E)-3-(3-{[2-(4,5-dihydro-1H-imidazol-2-yl)pyridin-4-yl]oxy}phenyl)prop-2-enoyl]amino}-N-[2-(dimethylamino)ethyl]-5-(trifluoromethyl)benzamide B-41: (2E)-3-(3-{[2-(4,5-dihydro-1H-imidazol-2-yl)pyridin-4-yl]oxy}phenyl)-N-[3-(methylamino)-5-(trifluoromethyl)phenyl]acrylamide B-42: 3-{[(2E)-3-(3-{[2-(4,5-dihydro-1H-imidazol-2-yl)pyridin-4-yl]oxy}phenyl)prop-2-enoyl]amino}-N-methyl-5-(trifluoromethyl)benzamide B-43: (2E)-3-(3-{[2-(4,5-dihydro-1H-imidazol-2-yl)pyridin-4-yl]oxy}phenyl)-N-[3-[(methylamino)methyl]-5-(trifluoromethyl)phenyl]acrylamide B-44: (2E)-3-(3-{[2-(4,5-dihydro-1H-imidazol-2-yl)pyridin-4-yl]oxy}phenyl)-N-[3-(2-pyrrolidin-1-ylethyl)-5-(trifluoromethyl)phenyl]acrylamide B-45: (2E)-3-(3-{[2-(4,5-dihydro-1H-imidazol-2-yl)pyridin-4-yl]oxy}phenyl)-N-[3-[3-(dimethylamino)propyl]-5-(trifluoromethyl)phenyl]acrylamide B-46: (2E)-3-(3-{[2-(4,5-dihydro-1H-imidazol-2-yl)pyridin-4-yl]oxy}phenyl)-N-[3-[2-(dimethylamino)ethoxy]-5-(trifluoromethyl)phenyl]acrylamide B-47: (2E)-N-[4-bromo-3-(trifluoromethyl)phenyl]-3-(3-{[2-(5-methyl-1H-imidazol-2-yl)pyridin-4-yl]oxy}phenyl)acrylamide B-48: (2E)-N-[4-bromo-3-(trifluoromethyl)phenyl]-3-(3-{[2-(5-methyl-4,5-dihydro-1H-imidazol-2-yl)pyridin-4-yl]oxy}phenyl)acrylamide B-49: (2E)-N-[4-bromo-3-(trifluoromethyl)phenyl]-3-[3-({2-[5-(hydroxymethyl)-1H-imidazol-2-yl]pyridin-4-yl}oxy)phenyl]acrylamide B-50: (2E)-N-[4-bromo-3-(trifluoromethyl)phenyl]-3-[3-({2-[5-(hydroxymethyl)-4,5-dihydro-1H-imidazol-2-yl]pyridin-4-yl}oxy)phenyl]acrylamide B-51: N-methyl-4-[3-((1E)-3-oxo-3-{[4-(3-pyrrolidin-1-ylpropyl)-3-(trifluoromethyl)phenyl]amino}prop-1-en-1-yl)phenoxy]pyridine-2-carboxamide B-52: 4-[3-((1E)-3-{[4-[3-(dimethylamino)propyl]-3-(trifluoromethyl)phenyl]amino}-3-oxoprop-1-en-1-yl)phenoxy]-N-methylpyridine-2-carboxamide B-53: 4-[3-((1E)-3-{[4-(3-hydroxypropyl)-3-(trifluoromethyl)phenyl]amino}-3-oxoprop-1-en-1-yl)phenoxy]-N-methylpyridine-2-carboxamide B-54: N-methyl-4-[3-((1E)-3-oxo-3-{[4-(3-pyrrolidin-1-yl-prop-1-yn-1-yl)-3-(trifluoromethyl)phenyl]amino}prop-1-en-1-yl)phenoxy]pyridine-2-carboxamide B-55: 4-[3-((1E)-3-{[4-[3-(dimethylamino)prop-1-yn-1-yl]-3-(trifluoromethyl)phenyl]amino}-3-oxoprop-1-en-1-yl)phenoxy]-N-methylpyridine-2-carboxamide B-56: 4-[3-((1E)-3-{[4-(3-hydroxyprop-1-yn-1-yl)-3-(trifluoromethyl)phenyl]amino}-3-oxoprop-1-en-1-yl)phenoxy]-N-methylpyridine-2-carboxamide B-57: (2E)-N-[4-chloro-3-(trifluoromethyl)phenyl]-3-(3-[2-(1,4,5,6-tetrahydropyrimidin-2-yl)pyridin-4-yl]oxy)phenyl)acrylamide B-58: (2E)-3-(3-{[2-(5-hydroxy-1,4,5,6-tetrahydropyrimidin-2-yl)pyridin-4-yl]oxy}phenyl)-N-[3-(trifluoromethyl)phenyl]acrylamide B-59: (2E)-3-(3-{[2-(1,4,5,6-tetrahydropyrimidin-2-yl)pyridin-4-yl]oxy}phenyl)-N-[3-(trifluoromethyl)phenyl]acrylamide B-60: 5-{4-[3-((1E)-3-oxo-3-{[3-(trifluoromethyl)phenyl]amino}prop-1-en-1-yl)phenoxy]pyridin-2-yl}-1,3,4-oxadiazole-2-carboxamide B-61: 2-{4-[3-((1E)-3-oxo-3-{[3-(trifluoromethyl)phenyl]amino}prop-1-en-1-yl)phenoxy]pyridin-2-yl}-1H-imidazole-5-carboxamide B-62: 4-[3-((1E)-3-{[3-methoxy-5-(trifluoromethyl)phenyl]amino}-3-oxoprop-1-en-1-yl)phenoxy]-N-methylpyridine-2-carboxamide B-63: (2E)-3-(3-{[2-(4,5-dihydro-1H-imidazol-2-yl)pyridin-4-yl]oxy}phenyl)-N-[3-methoxy-5-(trifluoromethyl)phenyl]acrylamide B-64: 2-{4-[3-((1E)-3-oxo-3-{[3-(trifluoromethyl)phenyl]amino}prop-1-en-1-yl)phenoxy]pyridin-2-yl}-4,5-dihydro-1H-imidazole-5-carboxylic acid B-65: (2E)-N-(3,5-di-tert-butylphenyl)-3-(3-{[2-(4,5-dihydro-1H-imidazol-2-yl)pyridin-4-yl]oxy}phenyl)acrylamide B-66: (2E)-3-(3-{[2-(4,5-dihydro-1H-imidazol-2-yl)pyridin-4-yl]oxy}phenyl)-N-(3-iodophenyl)acrylamide B-67: (2E)-N-[4-chloro-3-(trifluoromethyl)phenyl]-3-[3-({2-[(ethylamino)(imino)methyl]pyridin-4-yl}oxy)phenyl]acrylamide B-68: (2E)-3-[3-({2-[amino(imino)methyl]pyridin-4-yl}oxy)phenyl]-N-[4-bromo-3-(trifluoromethyl)phenyl]acrylamide B-69: (2E)-3-(3-{[2-(4,5-dihydro-1H-imidazol-2-yl)pyridin-4-yl]oxy}phenyl)-N-[4-methyl-3-(trifluoromethyl)phenyl]acrylamide B-70: (2E)-N-[4-fluoro-3-(trifluoromethyl)phenyl]-3-[3-({2-[(5S)-5-methyl-4,5-dihydro-1H-imidazol-2-yl]pyridin-4-yl}oxy)phenyl]acrylamide B-71: (2E)-N-[4-fluoro-3-(trifluoromethyl)phenyl]-3-[3-({2-[(5R)-5-methyl-4,5-dihydro-1H-imidazol-2-yl]pyridin-4-yl}oxy)phenyl]acrylamide B-72: (2E)-N-[4-chloro-3-(trifluoromethyl)phenyl]-3-[3-({2-[imino(morpholin-4-yl)methyl]pyridin-4-yl}oxy)phenyl]acrylamide B-73: (2E)-N-[4-chloro-3-(trifluoromethyl)phenyl]-3-{3-[(2-{imino[(2-morpholin-4-ylethyl)amino]methyl}pyridin-4-yl)oxy]phenyl}acrylamide B-74: 4-(3-{(1E)-3-[(3-isopropylphenyl)amino]-3-oxoprop-1-en-1-yl}phenoxy)pyridine-2-carboxamide B-75: (2E)-3-[3-({2-[(benzylamino)(imino)methyl]pyridin-4-yl}oxy)phenyl]-N-[4-iodo-3-(trifluoromethyl)phenyl]acrylamide B-76: (2E)-3-(2-chloro-3-{[2-(4,5-dihydro-1H-imidazol-2-yl)pyridin-4-yl]oxy}phenyl)-N-[4-chloro-3-(trifluoromethyl)phenyl]acrylamide B-77: N-[2-(dimethylamino)ethyl]-2-{4-[3-((1E)-3-oxo-3-{[3-(trifluoromethyl)phenyl]-amino}prop-1-en-1-yl)phenoxy]pyridin-2-yl}-1H-imidazole-5-carboxamide B-78: N-[2-(dimethylamino)ethyl]-2-{4-[3-((1E)-3-oxo-3-{[3-(trifluoromethyl)phenyl]amino}prop-1-en-1-yl)phenoxy]pyridin-2-yl}-4,5-dihydro-1H-imidazole-5-carboxamide B-79: (2E)-N-[4-cyano-3-(trifluoromethyl)phenyl]-3-(3-{[2-(4,5-dihydro-1H-imidazol-2-yl)pyridin-4-yl]oxy}phenyl)acrylamide B-80: (2E)-N-(3-tert-butylphenyl)-3-(3-{[2-(1,4,5,6-tetrahydropyrimidin-2-yl)pyridin-4-yl]oxy}phenyl)acrylamide B-81: 2-{4-[3-((1E)-3-{[4-fluoro-3-(trifluoromethyl)phenyl]amino}-3-oxoprop-1-en-1-yl)phenoxy]pyridin-2-yl}-N-methyl-1H-imidazole-5-carboxamide B-82: (2E)-3-(3-{[2-(5-tert-butyl-1H-imidazol-2-yl)pyridin-4-yl]oxy}phenyl)-N-[4-fluoro-3-(trifluoromethyl)phenyl]acrylamide B-83: (2E)-N-(3-ethylphenyl)-3-(3-{[2-(1H-tetrazol-5-yl)pyridin-4-yl]oxy}phenyl)acrylamide B-84: methyl 2-{4-[3-((1E)-3-{[4-fluoro-3-(trifluoromethyl)phenyl]amino}-3-oxoprop-1-en-1-yl)phenoxy]pyridin-2-yl}-1H-imidazole-5-carboxylate B-85: methyl 2-{4-[3-((1E)-3-{[4-fluoro-3-(trifluoromethyl)phenyl]amino}-3-oxoprop-1-en-1-yl)phenoxy]pyridin-2-yl}-4,5-dihydro-1H-imidazole-5-carboxylate B-86: (2E)-N-[4-bromo-3-(trifluoromethyl)phenyl]-3-[3-({2-[(hydroxyamino)(imino)methyl]pyridin-4-yl}oxy)phenyl]acrylamide B-87: (2E)-N-[4-chloro-3-(trifluoromethyl)phenyl]-3-[3-({2-[imino(methoxyamino)methyl]pyridin-4-yl}oxy)phenyl]acrylamide B-88: 2-[4-(3-{(1E)-3-[(3-tert-butylphenyl)amino]-3-oxoprop-1-en-1-yl}phenoxy)pyridin-2-yl]-1,4,5,6-tetrahydropyrimidine-4-carboxylic acid B-89: (2E)-N-[4-fluoro-3-(trifluoromethyl)phenyl]-3-[3-({2-[(5S)-5-(methoxymethyl)-4,5-dihydro-1H-imidazol-2-yl]pyridin-4-yl}oxy)phenyl]acrylamide B-90: (2E)-N-(2,3-dihydro-1H-inden-5-yl)-3-(3-{[2-(5,5-dimethyl-4,5-dihydro-1H-imidazol-2-yl)pyridin-4-yl]oxy}phenyl)acrylamide B-91: (2E)-N-(3-chlorophenyl)-3-[3-({2-[(ethanimidoylamino)methyl]pyridin-4-yl}oxy)phenyl]acrylamide B-92: (2E)-3-(3-{[2-(4,5-dihydro-1H-imidazol-2-yl)pyridin-4-yl]oxy}phenyl)-N-[3-(methylsulfanyl)phenyl]acrylamide B-93: 2-{4-[3-((1E)-3-{[4-fluoro-3-(trifluoromethyl)phenyl]amino}-3-oxoprop-1-en-1-yl)phenoxy]pyridin-2-yl}-N,N-dimethyl-4,5-dihydro-1H-imidazole-5-carboxamide B-94: 2-{4-[3-((1E)-3-{[4-fluoro-3-(trifluoromethyl)phenyl]amino}-3-oxoprop-1-en-1-yl)phenoxy]pyridin-2-yl}-N,N-dimethyl-1H-imidazole-5-carboxamide B-95: (2E)-N-(2,3-dihydro-1H-inden-5-yl)-3-(3-{[2-({[imino(phenyl)methyl]amino}methyl)pyridin-4-yl]oxy}phenyl)acrylamide B-96: (2E)-N-[4-chloro-3-(trifluoromethyl)phenyl]-3-(3-{[2-(4,5-dihydro-1H-imidazol-2-yl)-3-methylpyridin-4-yl]oxy}phenyl)acrylamide B-97: (2E)-N-[4-chloro-2-methoxy-3-(trifluoromethyl)phenyl]-3-(3-{[2-(4,5-dihydro-1H-imidazol-2-yl)pyridin-4-yl]oxy}phenyl)acrylamide B-98: 4-{3-[(1E)-3-(2,3-dihydro-1H-inden-5-ylamino)-3-oxoprop-1-en-1-yl]phenoxy}-N-[2-(dimethylamino)ethyl]pyridine-2-carboxamide B-99: tert-butyl[(4-{3-[(1E)-3-(2,3-dihydro-1H-inden-5-ylamino)-3-oxoprop-1-en-1-yl]phenoxy}pyridin-2-yl)methyl]carbamate B-100: (2E)-3-(3-{[2-(aminomethyl)pyridin-4-yl]oxy}phenyl)-N-(2,3-dihydro-1H-inden-5-yl)acrylamide B-101: (2E)-N-[4-chloro-2-hydroxy-5-(trifluoromethyl)phenyl]-3-(3-{[2-(4,5-dihydro-1H-imidazol-2-yl)pyridin-4-yl]oxy}phenyl)acrylamide B-102: 4-[3-((1E)-3-{[4-chloro-2-hydroxy-5-(trifluoromethyl)phenyl]amino}-3-oxoprop-1-en-1-yl)phenoxy]-N-methylpyridine-2-carboxamide B-103: 4-[3-((1E)-3-{[4-chloro-2-hydroxy-3-(trifluoromethyl)phenyl]amino}-3-oxoprop-1-en-1-yl)phenoxy]-N-methylpyridine-2-carboxamide B-104: (2E)-N-[4-chloro-2-hydroxy-3-(trifluoromethyl)phenyl]-3-(3-{[2-(4,5-dihydro-1H-imidazol-2-yl)pyridin-4-yl]oxy}phenyl)acrylamide B-105: (2E)-N-[4-chloro-3-(trifluoromethyl)phenyl]-3-(3-{[2-(diethylamino)pyrimidin-4-yl]oxy}phenyl)acrylamide B-106: (2E)-N-[4-chloro-3-(trifluoromethyl)phenyl]-3-{3-[(2-{[3-(dimethylamino)propyl]amino}pyrimidin-4-yl)oxy]phenyl}acrylamide B-107: (2E)-N-[4-chloro-3-(trifluoromethyl)phenyl]-3-(3-{[2-(isopropylamino)pyrimidin-4-yl]oxy}phenyl)acrylamide B-108: (2E)-N-[4-chloro-3-(trifluoromethyl)phenyl]-3-{3-[(2-{[2-(dimethylamino)ethyl]amino}pyrimidin-4-yl)oxy]phenyl}acrylamide B-109: (2E)-N-[4-chloro-3-(trifluoromethyl)phenyl]-3-{3-[(2-piperazin-1-ylpyrimidin-4-yl)oxy]phenyl}acrylamide B-110: (2E)-N-[4-chloro-3-(trifluoromethyl)phenyl]-3-{3-[(2-morpholin-4-ylpyrimidin-4-yl)oxy]phenyl}acrylamide B-111: (2E)-N-[4-chloro-3-(trifluoromethyl)phenyl]-3-{3-[(2-piperidin-1-ylpyrimidin-4-yl)oxy]phenyl}acrylamide B-112: (2E)-N-[4-chloro-3-(trifluoromethyl)phenyl]-3-[3-({2-[(4-methoxybenzyl)amino]pyrimidin-4-yl}oxy)phenyl]acrylamide B-113: (2E)-3-{3-[(2-(benzylamino)pyrimidin-4-yl]oxy}phenyl)-N-[4-fluoro-3-(trifluoromethyl)phenyl]acrylamide B-114: (2E)-3-{3-[(2-aminopyrimidin-4-yl)oxy]phenyl}-N-[4-fluoro-3-(trifluoromethyl)phenyl]acrylamide B-115: (2E)-N-[4-fluoro-3-(trifluoromethyl)phenyl]-3-(3-[2-(1-methyl-1H-imidazol-2-yl)pyridin-4-yl]oxy)phenyl)acrylamide B-116: (2E)-3-(4-chloro-3-{[2-(1-methyl-4,5-dihydro-1H-imidazol-2-yl)pyridin-4-yl]oxy}phenyl)-N-[4-fluoro-3-(trifluoromethyl)phenyl]acrylamide B-117: (2E)-N-[4-chloro-3-(trifluoromethyl)phenyl]-3-(3-{[2-(diethylamino)pyrimidin-4-yl]oxy}phenyl)acrylamide B-118: (2E)-3-[3-({2-[(1-methylpiperidin-4-yl)amino]pyrimidin-4-yl}oxy)phenyl]-N-[3-(trifluoromethyl)phenyl]acrylamide B-119: (2E)-N-[4-chloro-3-(trifluoromethyl)phenyl]-3-[3-({2-[[3-(dimethylamino)propyl](methyl)amino]pyrimidin-4-yl}oxy)phenyl]acrylamide B-120: (2E)-3-[3-({2-[[2-(dimethylamino)ethyl](methyl)amino]pyrimidin-4-yl}oxy)phenyl]-N-[3-(trifluoromethyl)phenyl]acrylamide B-121: (2E)-N-[4-chloro-3-(trifluoromethyl)phenyl]-3-{3-[(2-pyrrolidin-1-ylpyrimidin-4-yl)oxy]phenyl}acrylamide B-122: (2E)-3-(3-{[2-(4-methylpiperazin-1-yl)pyrimidin-4-yl]oxy}phenyl)-N-[3-(trifluoromethyl)phenyl]acrylamide B-123: (2E)-N-[4-chloro-3-(trifluoromethyl)phenyl]-3-[3-({2-[(2-morpholin-4-ylethyl)amino]pyrimidin-4-yl}oxy)phenyl]acrylamide B-124: (2E)-N-[4-chloro-3-(trifluoromethyl)phenyl]-3-[3-({2-[(4-methoxyphenyl)amino]pyrimidin-4-yl}oxy)phenyl]acrylamide B-125: tert-butyl(1-{4-[3-((1E)-3-{[4-chloro-3-(trifluoromethyl)phenyl]amino}-3-oxoprop-1-en-1-yl)phenoxy]pyrimidin-2-yl}piperidin-3-yl)carbamate B-126: (2E)-3-(3-{[2-(3-aminopiperidin-1-yl)pyrimidin-4-yl]oxy}phenyl)-N-[4-chloro-3-(trifluoromethyl)phenyl]acrylamide B-127: (2E)-N-[4-chloro-3-(trifluoromethyl)phenyl]-3-{3-[(2-{[2-(dimethylamino)ethyl]amino}pyrimidin-4-yl)oxy]phenyl}acrylamide B-128: (2E)-N-[4-chloro-3-(trifluoromethyl)phenyl]-3-{3-[(2-{[3-(2-oxopyrrolidin-1-yl)propyl]amino}pyrimidin-4-yl)oxy]phenyl}acrylamide B-129: 4-[3-((1E)-3-{[4-chloro-3-(trifluoromethyl)phenyl]amino}-3-oxoprop-1-en-1-yl)phenoxy]-N-[2-(methylamino)-2-oxoethyl]pyridine-2-carboxamide B-130: methyl[({4-[3-((1E)-3-{[4-chloro-3-(trifluoromethyl)phenyl]amino}-3-oxoprop-1-en-1-yl)phenoxy]pyridin-2-yl}carbonyl)amino]acetate B-131: [({4-[3-((1E)-3-{[4-chloro-3-(trifluoromethyl)phenyl]amino}-3-oxoprop-1-en-1-yl)phenoxy]pyridin-2-yl}carbonyl)amino]acetic acid B-132: N-(2-morpholin-4-ylethyl)-4-[3-((1E)-3-oxo-3-{[4-(trifluoromethyl)phenyl]amino}prop-1-en-1-yl)phenoxy]pyridine-2-carboxamide B-133: 4-(3-{(1E)-3-[(3-methylphenyl)amino]-3-oxoprop-1-en-1-yl}phenoxy)-N-(2-morpholin-4-ylethyl)pyridine-2-carboxamide B-134: 4-(3-{(1E)-3-[(3-ethylphenyl)amino]-3-oxoprop-1-en-1-yl}phenoxy)-N-(2-morpholin-4-ylethyl)pyridine-2-carboxamide B-135: 4-(3-{(1E)-3-[(3-chloro-4-fluorophenyl)amino]-3-oxoprop-1-en-1-yl}phenoxy)-N-(2-morpholin-4-ylethyl)pyridine-2-carboxamide B-136: 4-(3-{(1E)-3-[(4-chloro-3-fluorophenyl)amino]-3-oxoprop-1-en-1-yl}phenoxy)-N-(2-morpholin-4-ylethyl)pyridine-2-carboxamide B-137: 4-(3-{(1E)-3-[(3-bromophenyl)amino]-3-oxoprop-1-en-1-yl}phenoxy)-N-(2-morpholin-4-ylethyl)pyridine-2-carboxamide B-138: 4-(3-[(1E)-3-[(4-chloro-3-cyanophenyl)amino]-3-oxoprop-1-en-1-yl]phenoxy)-N-(2-morpholin-4-ylethyl)pyridine-2-carboxamide B-139: (2E)-N-(3-tert-butylphenyl)-3-(3-{[2-(4,5-dihydro-1H-imidazol-2-yl)pyridin-4-yl]oxy}phenyl)-2-methylacrylamide B-140: (2E)-N-(3-tert-butylphenyl)-3-(3-{[2-(4,5-dihydro-1H-imidazol-2-yl)pyridin-4-yl]oxy}phenyl)-2-(hydroxymethyl)acrylamide B-141: 4-[3-((1E)-3-{[4-(aminomethyl)-3-(trifluoromethyl)phenyl]amino}-3-oxoprop-1-en-1-yl)phenoxy]-N-methylpyridine-2-carboxamide B-142: 4-[3-((1E)-3-{[3-amino-5-(trifluoromethyl)phenyl]amino}-3-oxoprop-1-en-1-yl)phenoxy]-N-methylpyridine-2-carboxamide B-143: (2E)-N-[3-amino-5-(trifluoromethyl)phenyl]-3-(3-{[2-(4,5-dihydro-1H-imidazol-2-yl)pyridin-4-yl]oxy}phenyl)acrylamide B-144: 4-[3-((1E)-3-{[3-(2-aminoethyl)-5-(trifluoromethyl)phenyl]amino}-3-oxoprop-1-en-1-yl)phenoxy]-N-methylpyridine-2-carboxamide B-145: (2E)-N-[3-(2-aminoethyl)-5-(trifluoromethyl)phenyl]-3-(3-{[2-(4,5-dihydro-1H-imidazol-2-yl)pyridin-4-yl]oxy}phenyl)acrylamide B-146: (2E)-N-[4-(aminomethyl)-3-(trifluoromethyl)phenyl]-3-(3-{[2-(4,5-dihydro-1H-imidazol-2-yl)pyridin-4-yl]oxy}phenyl)acrylamide B-147: (2E)-N-[4-chloro-3-(trifluoromethyl)phenyl]-3-(3-{[2-(4,5-dihydro-1H-imidazol-2-yl)pyridin-4-yl]methyl}phenyl)acrylamide B-148: (2E)-N-[4-chloro-3-(trifluoromethyl)phenyl]-3-(3-{[2-(4,5-dihydro-1H-imidazol-2-yl)pyridin-4-yl]sulfanyl}phenyl)acrylamide B-149: (2E)-N-[4-chloro-3-(trifluoromethyl)phenyl]-3-(3-{[2-(4,5-dihydro-1H-imidazol-2-yl)pyridin-4-yl]amino}phenyl)acrylamide B-150: N-{4-[3-((1E)-3-{[4-ethyl-3-(trifluoromethyl)phenyl]amino}-3-oxoprop-1-en-1-yl)phenoxy]pyridin-2-yl}cyclopropanecarboxamide B-151: N-{4-[3-((1E)-3-{[4-[(dimethylamino)methyl]-3-(trifluoromethyl)phenyl]amino}-3-oxoprop-1-en-1-yl)phenoxy]pyridin-2-yl}cyclopropanecarboxamide B-152: N-{4-[3-((1E)-3-{[3-(2-aminoethyl)-5-(trifluoromethyl)phenyl]amino}-3-oxoprop-1-en-1-yl)phenoxy]pyridin-2-yl}cyclopropanecarboxamide B-153: N-[4-(3-{(1E)-3-[(3-tert-butylphenyl)amino]-3-oxoprop-1-en-1-yl}phenoxy)pyridin-2-yl]cyclopropanecarboxamide B-154: N-{4-[3-((1E)-3-{[4-chloro-3-(trifluoromethyl)phenyl]amino}-3-oxoprop-1-en-1-yl)phenoxy]pyridin-2-yl}cyclopropanecarboxamide B-155: (2E)-3-(3-{[2-(acetylamino)pyridin-4-yl]oxy}phenyl)-N-[4-ethyl-3-(trifluoromethyl)phenyl]acrylamide B-156: (2E)-3-(3-{[2-(acetylamino)pyridin-4-yl]oxy}phenyl)-N-[4-[(dimethylamino)methyl]-3-(trifluoromethyl)phenyl]acrylamide B-157: (2E)-3-(3-{[2-(acetylamino)pyridin-4-yl]oxy}phenyl)-N-[3-(2-aminoethyl)-5-(trifluoromethyl)phenyl]acrylamide B-158: (2E)-3-(3-{[2-(acetylamino)pyridin-4-yl]oxy}phenyl)-N-(3-tert-butylphenyl)acrylamide B-159 (2E)-3-(3-{[2-(acetylamino)pyridin-4-yl]oxy}phenyl)-N-[4-chloro-3-(trifluoromethyl)phenyl]acrylamide General Synthetic Methodology The compounds of the present invention can be prepared by methods known to one of ordinary skill in the art and/or by reference to the schemes shown below and the synthetic examples that follow. Exemplary synthetic routes are set forth in Schemes below, and in the Examples.

Compounds of formula (I) wherein $G^1$ is —O—, —S—, or —NH— may be prepared as outlined in Scheme 1 below:

Scheme 1

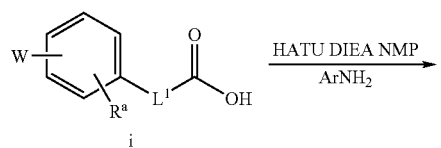

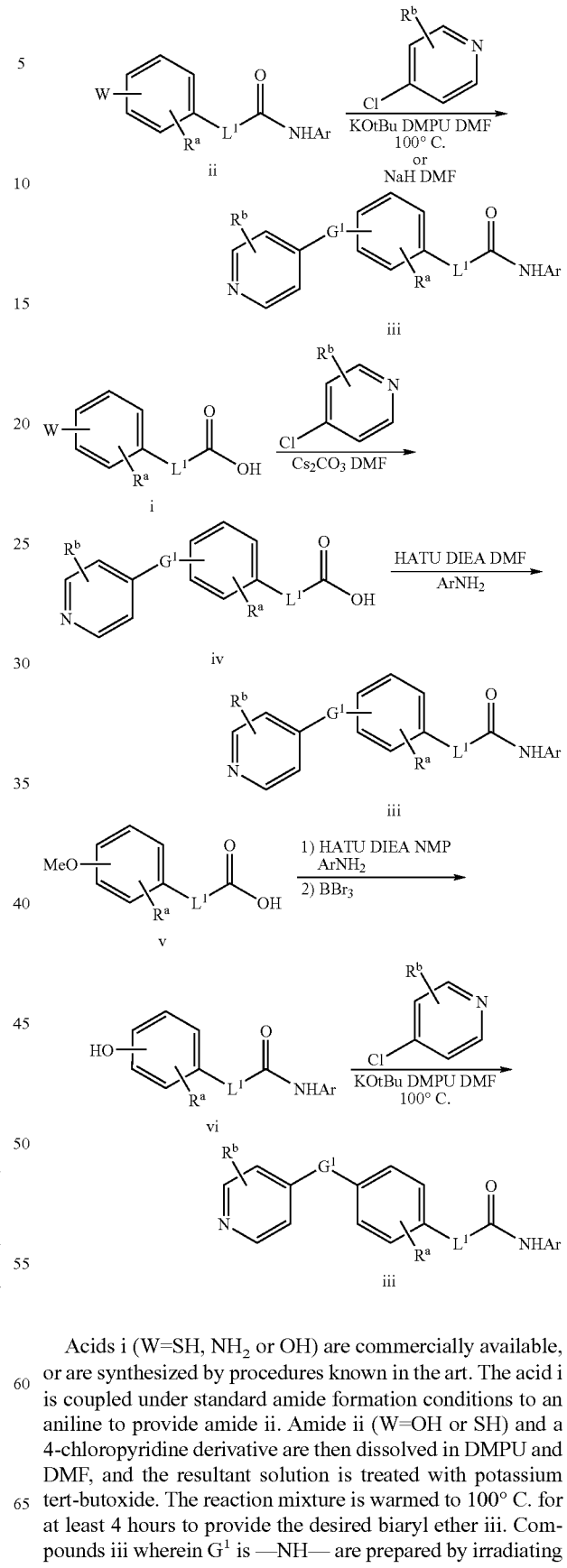

Acids i (W=SH, $NH_2$ or OH) are commercially available, or are synthesized by procedures known in the art. The acid i is coupled under standard amide formation conditions to an aniline to provide amide ii. Amide ii (W=OH or SH) and a 4-chloropyridine derivative are then dissolved in DMPU and DMF, and the resultant solution is treated with potassium tert-butoxide. The reaction mixture is warmed to 100° C. for at least 4 hours to provide the desired biaryl ether iii. Compounds iii wherein $G^1$ is —NH— are prepared by irradiating a solution of BOC protected aniline ii (W=NH$_2$) and a 4-chloropyridine derivative in NMP at elevated temperatures.

In an alternative approach, the biaryl ether bond can be formed first by reacting acid i with a 4-chloropyridine derivative in DMF in the presence of cesium carbonate or another base. This provides acid iv, which is then treated with an aryl or heteroaryl amine in the presence of coupling agents to give the desired amides iii. In some cases, the required acid i is not commercially available, but the corresponding methyl ether v is. For these cases acid v is converted to the amide under standard conditions and then treated with boron tribromide in methylene chloride to effect the deprotection of the phenol and provide amide vi. Ether formation is then accomplished as described above to provide the biaryl ether iii.

When the desired cinnamic amide is not commercially available, it can be prepared as shown in Scheme 2.

Scheme 2:

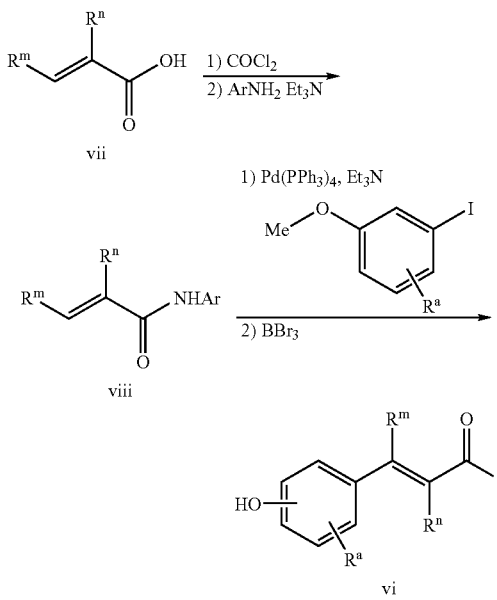

Acrylic acid vii is converted to the acid chloride with oxalyl chloride, and the resulting acid chloride is reacted with an aniline in the presence of base. The resulting acrylamide viii is then reacted with an appropriately substituted aryl iodide ix in the presence of a palladium catalyst and a base to give the cinnamide vi.

Compounds of formula (I) wherein L$^1$ is saturated and ring B is a heteroaromatic ring represented by Ar' can be prepared from the cinnamic amide iii by reduction in the presence of palladium and hydrogen as shown in Scheme 3.

Scheme 3

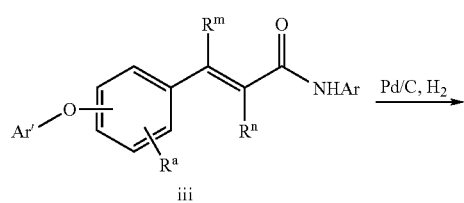

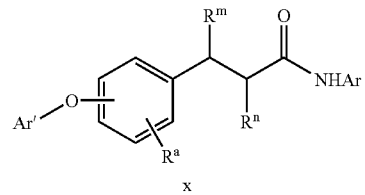

Compounds of formula (I) wherein L$^1$ is substituted with nitrogen can be prepared as shown in Scheme 4.

Scheme 4:

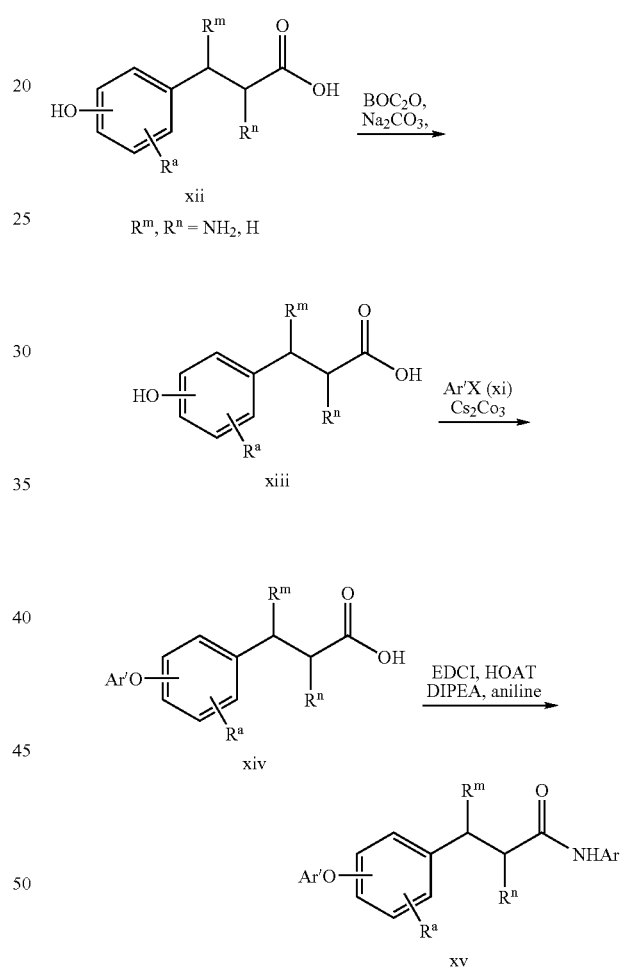

An appropriately substituted β-amino acid xii is treated with di-t-butoxycarbonyl anhydride to protect the amine. This protected amine is then dissolved in DMF and treated with a 4-chloropyridine in the presence of Cs$_2$CO$_3$ as described above to provide biaryl ether xiv. Amide coupling and BOC deprotection afford β-amino amides xv which are further elaborated using standard amide formation conditions, reductive amination, or sulfonamide formation conditions to provide N-substituted derivatives of xv.

Compounds of formula (I) wherein G$^1$ is —CH$_2$— may be prepared as shown in Scheme 5.

Scheme 5:

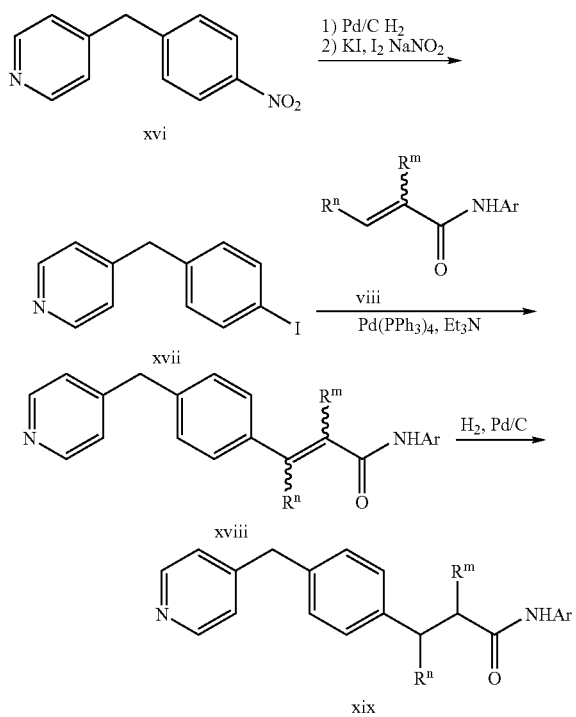

Commercially available nitrobenzyl pyridine xvi is reduced to the aniline in the presence of hydrogen and catalytic palladium on carbon. The resulting aniline is then converted to the iodide. Heck coupling of xvii with an acrylamide viii provides cinnamide xviii, which can be reduced by catalytic hydrogenation to provide the desired hydrocinnamides xix.

Compounds of formula (I) wherein $G^1$ is —$CH_2$— may also be prepared as depicted in Scheme 6.

Scheme 6:

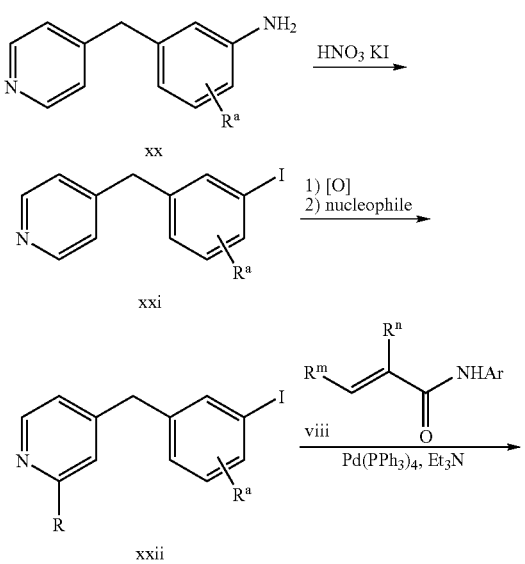

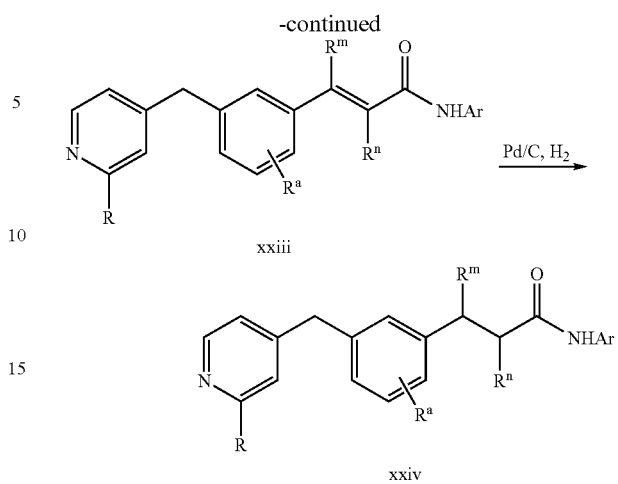

Known aniline xx can be converted to iodide xxi under standard Sandmeyer conditions. Oxidation of the pyridine nitrogen, followed by treatment with an appropriate nucleophile results in substituted pyridine xxii. Heck coupling of this iodide with an acrylamide viii results in cinnamide xxiii which can be reduced by catalytic hydrogenation to provide the desired hydrocinnamides xxiv.

One of ordinary skill in the art will recognize that additional compounds of formula (I) may be prepared by methods analogous to those depicted in Schemes 1-6 by changing the starting materials or reagents.

Uses, Formulation, and Administration

As discussed above, the present invention provides compounds that are inhibitors of Raf kinases. The compounds can be assayed in vitro or in vivo for their ability to bind to and/or inhibit a Raf kinase. In vitro assays include assays to determine inhibition of the ability of the kinase to phosphorylate a substrate protein or peptide. Alternate in vitro assays quantitate the ability of the compound to bind to the kinase. Inhibitor binding may be measured by radiolabelling the inhibitor prior to binding, isolating the inhibitor/kinase complex and determining the amount of radiolabel bound. Alternatively, inhibitor binding may be determined by running a competition experiment in which new inhibitors are incubated with the kinase bound to a known radioligand. The compounds also can be assayed for their ability to affect cellular or physiological functions mediated by protein kinase activity. Assays for each of these activities are described in the Examples and/or are known in the art.

In another aspect, therefore, the invention provides a method for inhibiting Raf kinase activity in a cell, comprising contacting a cell in which inhibition of a Raf kinase is desired with a compound of formula (I). In some embodiments, the compound of formula (I) interacts with and reduces the activity of more than one Raf kinase enzyme in the cell. By way of example, when assayed against B-Raf and C-Raf, some compounds of formula (I) show inhibition of both enzymes. In some embodiments, the compound of formula (I) is selective, i.e., the concentration of the compound that is required for inhibition of one Raf kinase enzymes is lower, preferably at least 2-fold, 5-fold, 10-fold, or 50-fold lower, than the concentration of the compound required for inhibition of another Raf kinase enzyme.

In some embodiments, the compound of formula (I) inhibits one or more Raf kinase enzymes at a concentration that is lower than the concentration of the compound required for inhibition of other, unrelated, kinase enzymes. In some other embodiments, in addition to inhibiting Raf kinase, the compound formula (I) also inhibits one or more other kinase enzymes, preferably other kinase enzymes involved in tumor cell proliferation.

The invention thus provides a method for inhibiting cell proliferation, comprising contacting a cell in which such inhibition is desired with a compound of formula (I). The phrase "inhibiting cell proliferation" is used to denote the ability of a compound of formula (I) to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a kinase inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, formate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of the invention preferably are formulated for administration to a patient having, or at risk of developing or experiencing a recurrence of, a Raf kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in protein kinase activity or the severity of a Raf kinase-mediated disorder. The amount of Raf kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a Raf kinase-mediated disorder. As used herein, the term "Raf kinase-mediated disorder" includes any disorder, disease or condition which is caused or characterized by an increase in Raf kinase expression or activity, or which requires Raf kinase activity. The term "Raf kinase-mediated disorder" also includes any disorder, disease or condition in which inhibition of Raf kinase activity is beneficial.

The Raf kinase inhibitors of the invention can be used to achieve a beneficial therapeutic or prophylactic effect, for example, in subjects with a proliferative disorder. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed Raf kinase inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies that can be treated with the disclosed Raf kinase inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

The compounds of formula (I) are particularly useful in the treatment of cancers or cell types characterized by aberrant activation of the Ras-Raf-MEK-ERK pathway, including, without limitation, those characterized by an activating Ras and/or Raf mutation. In some embodiments, the compound or composition of the invention is used to treat a patient having or at risk of developing or experiencing a recurrence in a cancer selected from the group consisting of melanoma, colon, lung, breast, ovarian, sarcoma and thyroid cancer. In certain embodiments, the cancer is a melanoma.

In some embodiments, the Raf kinase inhibitor of the invention is administered in conjunction with another therapeutic agent. In some embodiments, the other therapeutic agent is one that is normally administered to patients with the disease or condition being treated. The Raf kinase inhibitor of the invention may be administered with the other therapeutic agent in a single dosage form or as a separate dosage form. When administered as a separate dosage form, the other therapeutic agent may be administered prior to, at the same time as, or following administration of the protein kinase inhibitor of the invention.

In some embodiments, a Raf kinase inhibitor of formula (I) is administered in conjunction with an anticancer agent. As used herein, the term "anticancer agent" refers to any agent that is administered to a subject with cancer for purposes of treating the cancer. Nonlimiting examples anticancer agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

| | Definitions |
|---|---|
| AcOH | acetic acid |
| ACN | acetonitrile |
| ATP | adenosine triphosphate |
| BCA | bicinchoninic acid |
| BSA | bovine serum albumin |
| Boc | tert-butoxycarbonyl |
| DABCO | 1,4-diazabicyclo[2.2.2]octane |
| DCE | dichloroethane |
| DCM | dichloromethane |
| DIPEA | diisopropyl ethyl amine |
| DMEM | Dulbecco's Modified Eagle's Medium |
| DMF | dimethylformamide |
| DMPU | 1,3-dimethyl-3,4,5,6-tetrahydro-2(1H)-pyrimidinone |
| DTT | dithiothreitol |
| EDTA | ethylenediaminetetraacetic acid |
| EtOAc | ethyl acetate |
| FA | formic acid |
| FBS | fetal bovine serum |
| HATU | O-(7-Azabenzotriazol-1-yl)-N,N,N',N'-tetramethyluronium hexafluorophosphate |
| HEPES | N-(2-Hydroxyethyl)piperazine-N'-(2-ethanesulfonic acid) |
| KHMDS | potassium bis(trimethylsilyl)amide |

-continued

Definitions

| | |
|---|---|
| KOt-Bu | potassium tert-butoxide |
| LDA | lithium diisopropyl amide |
| Me | methyl |
| MeOH | methanol |
| MTT | methylthiazoletetrazolium |
| MWI | microwave irradiation |
| NMP | 1-Methyl-2-pyrrolidinone |
| PBS | phosphate buffered saline |
| PKA | cAMP-dependent protein kinase |
| p-TSA | para-toluene sulfonic acid |
| TBS | tert-butyldimethyl silyl |
| TBTU | O-(1H-benzotriazol-1-yl)-N,N,N',N'-tetramethyluronium tetrafluoroborate |
| TEA | triethylamine |
| TFFH | Fluoro-N,N,N'-tetramethylformamidinium hexafluorophosphate |
| THF | tetrahydrofuran |
| TMB | 3,3',5,5'-Tetramethylbenzidine |
| WST | (4-[3-(4-iodophenyl)-2-(4-nitrophenyl)-2H-5-tetrazolio]-1,3-benzene disulfonate sodium salt) |
| h | hours |
| min | minutes |
| rt | room temperature |
| m/z | mass to charge |
| MS | mass spectrum |
| LCMS | liquid chromatography mass spectrum |
| HRMS | high resolution mass spectrum |

Analytical LC-MS Methods

LCMS Conditions
  Spectra were run on a Phenominex Luna 5 μm C18 50×4.6 mm column on a Hewlett-Packard HP1100 at 2.5 ml/min for a 3 minute run using the following gradients:
  Method Formic Acid (FA): Acetonitrile containing zero to 100 percent 0.1% formic acid in water.
  Method Polar Ammonium Acetate (PAA): Acetonitrile containing zero to 50 percent 10 mM ammonium acetate in water.
  Method Ammonium Acetate (AA): Acetonitrile containing zero to 100 percent 10 mM ammonium acetate in water.

Example 1

Preparation of Phenols and Phenol Equivalents 3-(3-chloro-4-hydroxyphenyl)-N-[4-chloro-3-(trifluoromethyl)phenyl]-propanamide

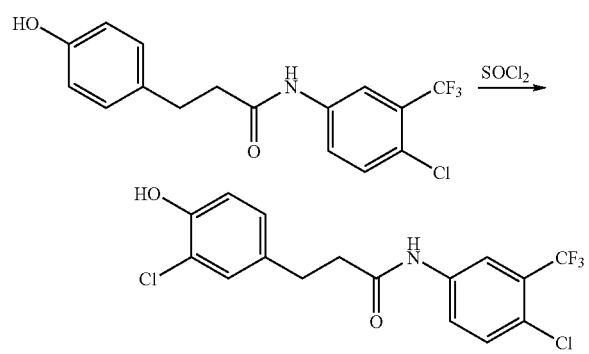

To a solution of N-[4-chloro-3-(trifluoromethyl)phenyl]-3-(4-hydroxyphenyl)propanamide (1.33 g, 3.89 mmol) in DCE was added sulfuryl chloride (4.28 mL, 4.28 mmol) slowly over 45 min. The reaction mixture was heated at 84° C. overnight and then additional sulfuryl chloride was added. After heating for 2 h, the reaction mixture was cooled to rt and diluted with EtOAc. The combined organic solutions were washed with water and brine, dried over $MgSO_4$, filtered and concentrated. The residue was purified by column chromatography to give the title compound (0.66 g, 45%).

2-(3-methoxyphenyl)cyclopropanecarboxylic acid

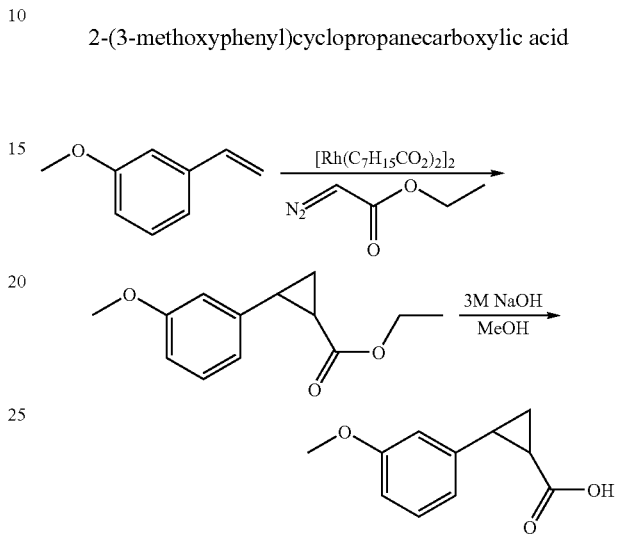

Step 1: Preparation of ethyl 2-(3-methoxyphenyl)cyclopropanecarboxylate

To a mixture of 1-methoxy-3-vinylbenzene (3.10 g, 23.1 mmol) and dioxomethane-diheptylrhodium (4:2) (0.090 g, 0.12 mmol) in DCM (100 mL) under an atmosphere of argon at rt was added a solution of ethyl diazoacetate (1.22 mL, 11.6 mmol) in DCM (6 mL) dropwise via syringe. The reaction mixture as allowed to stir at rt for 2 h and then concentrated. The residue was purified by column chromatography to give the desired product (1.63 g) as a mixture of cis and trans isomers, along with recovered starting material (1.50 g). LCMS: (FA) ES+ 221.2 (M+1).

Step 2: Preparation of 2-(3-methoxyphenyl)cyclopropanecarboxylic acid

A solution of ethyl 2-(3-methoxyphenyl)cyclopropanecarboxylate (1.63 g, 7.4 mmol) in 3N NaOH (35 mL) and MeOH (35 mL) was heated at 60° C. for 1 h. After cooling to rt, the reaction mixture was concentrated. The residue was dissolved in 1N HCl and extracted with DCM. The organic solutions were dried over $Na_2SO_4$, filtered, and concentrated to give the desired product (1.23 g, 87%) which was used without further fication. The cis and trans isomers were separated at a later stage of analog synthesis. LCMS: (FA) ES– 191.3 (M+1).

2-(4-methoxyphenyl)cyclopropanecarboxylic acid

The title compound was prepared from the appropriate starting materials in a manner analogous to that described for 2-(3-methoxyphenyl)cyclopropanecarboxylic acid.
  LCMS: (FA) ES– 191.3 (M–1).

3-(4-chloro-3-methoxyphenyl)-N-[3-chloro-4-(trifluoromethyl)phenyl]-propanamide

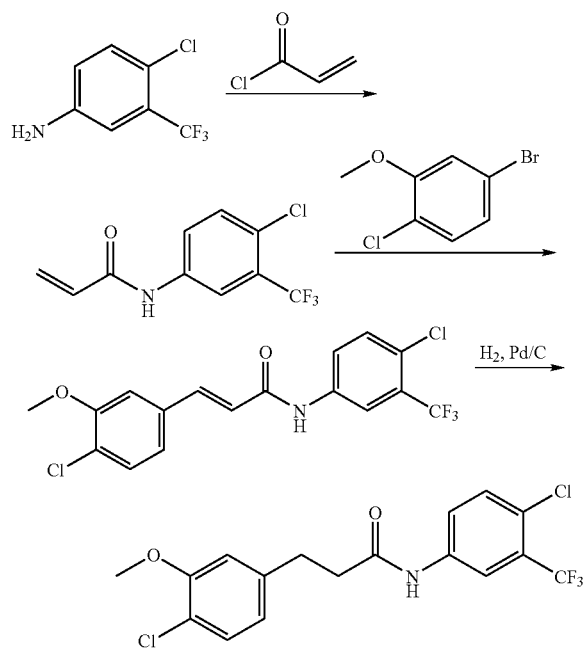

Step 1: Preparation of N-[3-chloro-4-(trifluoromethyl)phenyl]acrylamide

To a stirred solution of the aniline (0.655 g, 3.3 mmol) in DCM (35 mL) was added TEA (0.604 mL, 4.4 mmol) and acryloyl chloride (0.286 mL, 3.5 mmol) at rt. After 20 min, the reaction was quenched by the addition of water and the mixture was extracted with DCM. The combined organic solutions were washed with water, dried over $Na_2SO_4$, filtered, and concentrated. The residue was purified by column chromatography to give the desired amide (0.535 g, 65%) as a white solid. LCMS: (FA) ES+ 250.2 (M+1), ES– 248.4 (M–1).

Step 2: Preparation of (2E)-3-(4-chloro-3-methoxyphenyl)-N-[3-chloro-4-(trifluoromethyl)phenyl]acrylamide To a suspension of $K_2CO_3$ (0.936 g, 6.77 mmol) and n-$Bu_4$NCl (0.753 g, 2.71 mmol) in DMF under an atmosphere of argon were added 4-bromo-1-chloro-2-methoxybenzene (0.600 g, 2.71 mmol), the amide from Step 1 (0.809 g, 3.25 mmol), and molecular sieves. The mixture was stirred for 10 min at rt before adding $PPh_3$ (0.071 g, 0.271 mmol) and Pd(OAc)$_2$ (0.0304 g, 0.135 mmol). The reaction mixture was heated at 80° C. overnight and then cooled to rt and filtered through Celite. The filtrate was diluted with EtOAc and washed with sat. NaHCO3 solution, water, and brine. The organic solution was dried over $MgSO_4$, filtered, and concentrated. The residue was purified by column chromatography to give the desired acrylamide (0-0.755 g, 72%).

Step 3: Preparation of 3-(4-chloro-3-methoxyphenyl)-N-[3-chloro-4-(trifluoromethyl)phenyl]propanamide The alkene from Step 2 (0.755 g, 1.80 mmol) was suspended in MeOH. To this suspension was added Pd/C (10 wt %). The reaction was placed under an atmosphere of hydrogen gas and allowed to stir at rt for 3 h. The mixture was filtered through Celite and concentrated. The residue was purified by column chromatography to give the desired product (0.546 g, 72%). LCMS: (FA) ES+ 392.0 (M+1), ES– 390.0 (M–1).

N-[4-chloro-3-(trifluoromethyl)phenyl]-3-(4-hydroxy-3-methylphenyl)-propanamide

The title compound was prepared from the appropriate starting materials in a manner analogous to that described for N-[3-chloro-4-(trifluoromethyl)phenyl]acrylamide.
LCMS: (FA) ES+ 358.2 (M+1), ES– 356.3 (M–1).

Example 2

Preparation of pyridines 4-chloro-N,3-dimethylpyridine-2-carboxamide

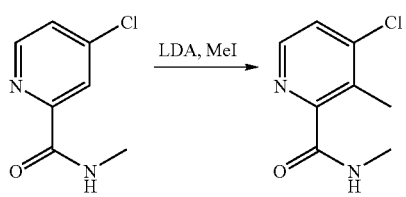

To a solution of 4-chloro-N-methylpyridine-2-carboxamide (0.700 g, 4.12 mmol) in THF was added LDA (4.12 mL, 2M in THF, 8.24 mmol) dropwise at –78° C. under an atmosphere of argon. The mixture was allowed to stir for 90 min at –78° C. and then methyl iodide (1.51 mL, 24.71 mmol) was added. After stirring for 90 min, the solution was allowed to warm to 0° C. The reaction was quenched at 0° C. with sat. sodium hydrogen sulfite and extracted with EtOAc. The combined organic solutions were washed with water, dried over $MgSO_4$, filtered and concentrated. The residue was purified by column chromatography to give the desired product (0.070 g, 23%).

4-chloro-2-(4,5-dihydro-1H-imidazol-2-yl)pyridine

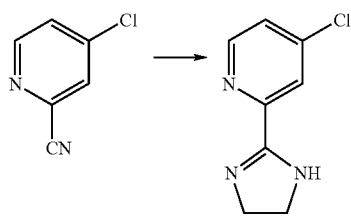

To a solution of 4-chloropyridine-2-carbonitrile (20.0 g, 121 mmol, prepared as described by Sakamoto et al. *Chem. Pharm. Bull.* 1985, 33, 565-571) in MeOH (240 mL), was added sodium methoxide (0.655 g, 12.1 mmol). The reaction mixture was stirred at rt under an atmosphere of argon for 2 h. Ethylene diamine (40.0 mL, 597 mmol) was added to the reaction mixture was stirred at 50° C. for 20 h. The solution was allowed to cool to rt and concentrated. The residue was partitioned between water and DCM. The organic layer was separated, dried over $MgSO_4$, filtered and concentrated to give the desired product as a light brown solid (21.9 g, >99%). LCMS: (FA) ES$^+$ 182.09 (M+1).

4-chloro-N-[2-(dimethylamino)ethyl]pyridine-2-carboxamide

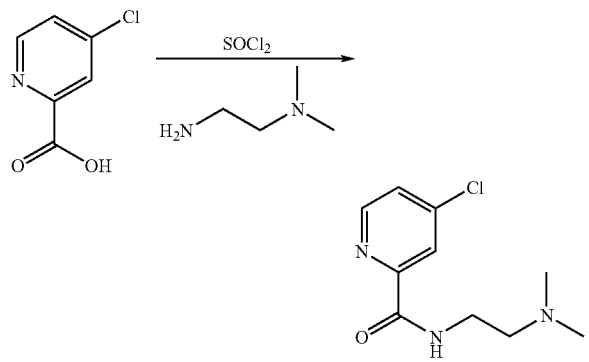

To a solution of thionyl chloride (7.4 mL, 101 mmol) in DMF was added pyridine-2-carboxylic acid (2.5 g, 20.3 mmol). The reaction mixture was heated at 95° C. for 12 h and then concentrated. The residue was redissolved in DMF (7 mL) and N,N-dimethylethane-1,2-diamine (11 mL, 101.5 mmol) was added. After stirring for 15 min, the mixture was concentrated and the residue was purified by column chromatography (0-10% methanol/dichloromethane) to yield 2.11 g of the title compound (46%). LCMS: (FA) ES+ 227.9 (M+1)

4-chloro-N-[3-(dimethylamino)propyl]pyridine-2-carboxamide

The title compound was prepared from the appropriate starting materials in a manner analogous to that described for 4-chloro-N-[2-(dimethylamino)ethyl]pyridine-2-carboxamide. LCMS: (FA) ES+ 241.9 (M+1)

4-chloro-N-(2-morpholin-4-ylethyl)pyridine-2-carboxamide

The title compound was prepared from the appropriate starting materials in a manner analogous to that described for 4-chloro-N-[2-(dimethylamino)ethyl]pyridine-2-carboxamide. LCMS: (FA) ES+ 270.0 (M+1).

Example 3

Synthesis of Anilines

2-{2-[3-amino-5-(trifluoromethyl)phenyl]ethyl}-1H-isoindole-1,3(2H)-dione

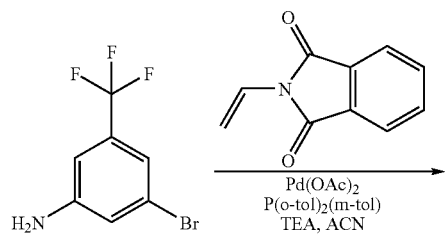

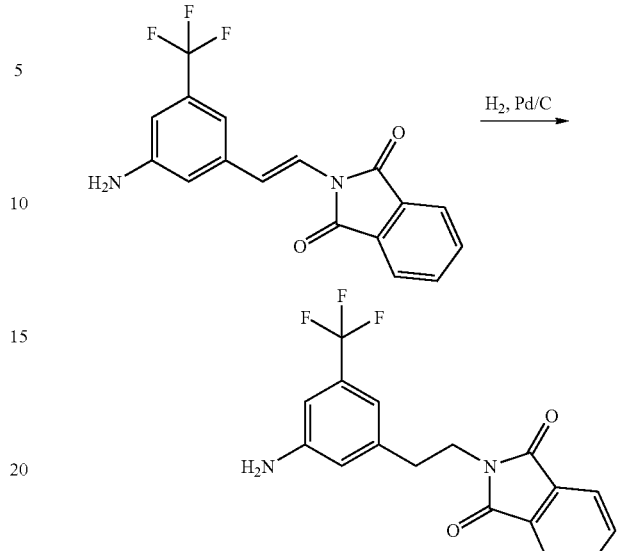

Step 1: Preparation of 2-{(E)-2-[3-amino-5-(trifluoromethyl)phenyl]vinyl}-1H-isoindole-1,3(2H)-dione To a degassed solution of 3-bromo-5-(trifluoromethyl) aniline (1.00 g, 4.17 mmol) and ACN (40 mL) was added Pd(OAc)₂ (0.46 g, 0.20 mmol), bis(2-methylphenyl)(3-methylphenyl)phosphine (0.13 g, 0.40 mmol), and TEA (1.15 mL, 8.25 mmol). After stirring for 1 h, 2-vinyl-1H-isoindole-1,3(2H)-dione (0.72 g, 4.17 mmol) was added. The solution was heated at reflux for 20 h and then allowed to cool to rt and filtered through Celite. The filtrate was washed with water and brine. The organic layer was dried over Na₂SO₄, filtered and concentrated. The residue was purified by column chromatography to yield the title compound as a yellow solid (0.90 g, 62%). LCMS: (FA) ES+ 333.2 (M+1).

Step 2: Preparation of 2-{2-[3-amino-5-(trifluoromethyl)phenyl]ethyl}-1H-isoindole-1,3(2H)-dione Pd/C (10% by wt, 0.090 g) was added to a degassed solution of 2-{(E)-2-[3-amino-5-(trifluoromethyl)phenyl]vinyl}-1H-isoindole-1,3(2H)-dione (0.900 g, 2.71 mmol) in EtOH (56 mL) and THF (40 mL). The mixture was hydrogenated (50 psi) at rt until LC/MS indicated reaction was complete. The mixture was filtered through Celite and the filtrate was concentrated. The residue was purified by column chromatography (SiO₂, 1:1 EtOAc:hexanes) to afford the desired product as a white solid (0.371 g, 40%). LCMS: (FA) ES+ 335.3 (M+1).

3-tert-butyl-4-chloroaniline

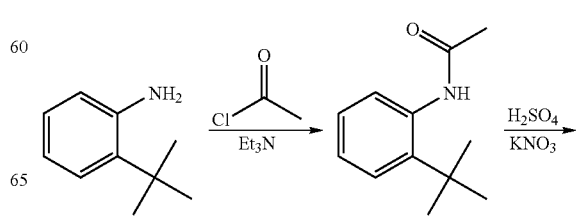

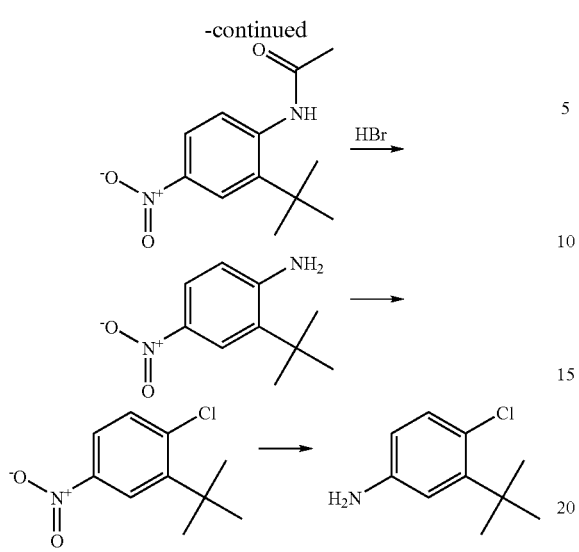

Step 1: Preparation of N-(2-tert-butylphenyl)acetamide

A solution of 2-tert-butylaniline (2.0 g, 2.1 mL, 13.4 mmol) and TEA (2.8 mL, 20.1 mmol) in DCM (100 mL) was cooled to 0° C. Acetyl chloride (1.0 mL, 14.7 mmol) was added dropwise. The resulting solution was allowed to stir and warm to rt over 2 h. The reaction mixture was diluted with water and DCM. The organic phase was washed with 1N HCl and brine, dried over Na$_2$SO$_4$, filtered and concentrated to give the title compound as a white solid (2.73 g, >100%). $^1$H NMR (400 MHz, CDCl$_3$) δ: 7.51-7.53 (m, 1H), 7.39-7.41 (m, 1H), 7.14-7.24 (m, 2H), 2.21 (s, 2.2H), 1.92 (s, 0.9H), and 1.41 (s, 9H).

Step 2: Preparation of N-(2-tert-butyl-4-nitrophenyl)acetamide

Concentrated sulfuric acid (30 mL) was cooled to 0° C. and solid N-(2-tert-butylphenyl)acetamide (1.0 g, 5.2 mmol) was added in several portions. To the resulting solution was added KNO$_3$ (578 mg, 5.7 mmol). The reaction mixture was allowed to warm to rt over 2 h and then stirred at rt overnight. The reaction mixture was poured over ice and a white precipitate formed. The precipitate was isolated by filtration (1.04 g, 84%). LCMS: (FA) ES+ 237.2 (M+1), ES− 235.1 (M−1).

Step 3: Preparation of 2-tert-butyl-4-nitroaniline

N-(2-tert-butyl-4-nitrophenyl)acetamide (840 mg, 3.57 mmol) was dissolved in concentrated HBr (48%, 20 mL). The resulting solution was heated at 110° C. for 3 h. The reaction mixture was cooled to rt, diluted with EtOAc, and poured into sat. NaHCO$_3$ solution. The organic phase was extracted with sat. NaHCO$_3$ solution and brine, dried over Na$_2$SO$_4$, filtered and concentrated to give the desired product as a yellow-green oil (710 mg, >100%). $^1$H NMR (400 MHz, CD$_3$OD) δ: 7.52 (d, 1H), 7.40 (dd, 1H), 7.33 (d, 1H), and 1.42 (s, 9H).

Step 4: Preparation of 2-tert-butyl-1-chloro-4-nitrobenzene

The title compound was prepared as described by Nguyen, P. et al. *J. Org. Chem.* 2003, 68, 10195.

Step 5: Preparation of 3-tert-butyl-4-chloroaniline

To a solution of 2-tert-butyl-1-chloro-4-nitrobenzene (505 mg, 2.36 mmol) in EtOAc (25 mL) was added SnCl$_2$ hydrate (906 mg, 3.55 mmol). This mixture was heated at reflux and the solids dissolved. After 2 h, additional SnCl$_2$ hydrate (906 mg, 3.55 mmol) was added and the solution was heated at reflux for another 2 h. The reaction mixture was purified by column chromatography (SiO$_2$, 20% EtOAc/Hex) to give 210 mg of the title compound as a yellow oil (48%). $^1$H NMR (400 MHz, CD$_3$OD) δ: 6.68 (d, 1H), 6.16 (d, 1H), 6.02 (dd, 1H), and 0.92 (s, 9H).

3-tert-butyl-4-bromoaniline

The title compound was prepared from the appropriate starting materials in a manner analogous to that described for 3-tert-butyl-4-chloroaniline. $^1$H NMR (300 MHz, CDCl$_3$) δ: 7.25 (d, 1H), 7.01-7.06 (m, 1H), 7.60-7.67 (m, 1H), and 1.46 (s, 9H).

3-[2-(dimethylamino)ethoxy]-5-(trifluoromethyl)aniline

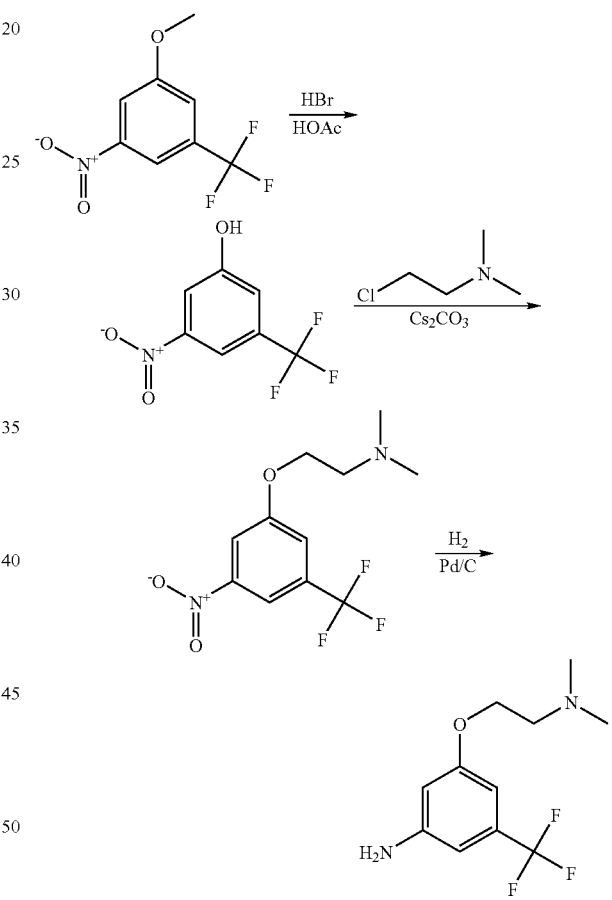

Step 1: Preparation of 3-nitro-5-(trifluoromethyl)phenol

A solution of 3-nitro-5-(trifluoromethyl)phenyl ether (20.0 g, 0.090 mol) in HBr (74.7 mL, 1.38 mmol) and HOAc (279.8 mL, 4.92 mol) was heated at reflux until reaction was judged to be complete by LCMS. The reaction was concentrated to tan solid to yield the desired product (18.7 g, 96% yield). LCMS: (FA) ES− 206.2 (M−1).

Step 2: Preparation of N,N-dimethyl-2-[3-nitro-5-trifluoromethyl)phenoxy]-ethanamine A mixture of 2-chloro-N$_1$N-dimethylethanamine (0.355 g, 2.66 mmol), 3-nitro-5-(trifluoromethyl)phenol (0.500 g, 2.41 mmol) and Cs$_2$CO$_3$ (2.36 g, 7.24 mmol) in DMF (19 mL) was stirred at rt until reaction complete by TLC (1:1 EtOAc: Hexane). The mixture was diluted with EtOAc and washed with water. The organic solution was dried over $Na_2SO_4$, filtered, and concentrated to give the desired product as a brown oil (0.490 g, 63%). LCMS: (FA) ES+ 304.3 (M+1).

Step 3: Preparation of 3-[2-(dimethylamino)ethoxy]-5-(trifluoromethyl)aniline

A mixture of N,N-dimethyl-2-[3-nitro-5-(trifluoromethyl)phenoxy]-ethanamine (490 mg, 1.61 mmol) and Pd/C (10 wt %, 49 mg) in EtOAc (15 mL) was stirred under an atmosphere of hydrogen until reaction complete was judged to be complete by LCMS. The mixture was filtered through Celite and rinsed with EtOAc. The filtrate was concentrated to yield the desired product as a brown solid (329 mg, 71%). LCMS: (FA) ES+ 275.2 (M+1).

3-(2-morpholin-4-ylethoxy)-5-(trifluoromethyl)aniline

The title compound was prepared from the appropriate starting materials in a manner analogous to that described for 3-[2-(dimethylamino)ethoxy]-5-(trifluoromethyl)aniline.
LCMS: (FA) ES+ 291.2 (M+1).

3-(2-pyrrolidin-1-ylethoxy)-5-(trifluoromethyl)aniline

The title compound was prepared from the appropriate starting materials in a manner analogous to that described for 3-[2-(dimethylamino)ethoxy]-5-(trifluoromethyl)aniline.
LCMS: (FA) ES+ 275.2 (M+1).

2-(3-aminophenyl)propan-2-ol

Step 1: Preparation of 1-(3-bromophenyl)-2,5-dimethyl-1H-pyrrole

A solution of 3-bromoaniline (2.50 mL, 23.0 mmol) in acetonylacetone (3.00 mL, 25.6, mmol) containing a small amount of p-TSA was heated at reflux in a round bottom flask fitted with a Dean Stark trap and a reflux condenser for 5 h. The reaction mixture was allowed to cool to rt and diluted with EtOAc. The solution was washed with 1N HCl and sat. $NaHCO_3$ solution. The organic solutions were dried over $Na_2SO_4$, filtered, and concentrated to give the desired product as a light brown solid (5.5 g, 96%) which was used without further purification.

LCMS: (FA) ES+ 260.0 (M+1).

Step 2: Preparation of 2-[3-(2,5-dimethyl-1H-pyrrol-1-yl)phenyl]propan-2-ol

A solution of 1-(3-bromophenyl)-2,5-dimethyl-1H-pyrrole (1.50 g, 6.00 mmol) in THF (25 mL) was cooled to −78° C. under an atmosphere of argon. To this solution was added n-BuLi (2.50 M in hexane, 2.76 mL, 6.90 mmol) dropwise via syringe. After 30 min, acetone (0.572 mL, 7.8 mmol) was added to the cold solution dropwise via syringe. After 10 min, the cold bath was removed and the reaction mixture was allowed to warm to rt. After 5.5 h, the reaction was quenched by the addition of water. The mixture was extracted with EtOAc and the organic solutions dried over $Na_2SO_4$, filtered, and concentrated. The residue was purified by column chromatography to give the desired product (0.84 g, 61%). LCMS: (FA) ES+ 230.1 (M+1).

Step 3: Preparation of 2-(3-aminophenyl)propan-2-ol

To a solution of hydroxylamine hydrochloride (7.42 g, 107 mmol) and potassium hydroxide (5.41 g, 82.0 mmol) in ethanol (65 mL) and water (30 mL) was added 2-[3-(2,5-dimethyl-1H-pyrrol-1-yl)phenyl]propan-2-ol (0.840 g, 3.66 mmol). The heterogeneous mixture was heated at 120° C. overnight and then concentrated. The residue was purified by column chromatography to give the desired product (0.55 g, 65%). $^1$H NMR (400 MHz, $CDCl_3$) δ: 7.11-7.15 (m, 1H), 6.85-6.87 (m, 1H), 6.84 (ddd, 1H), 6.58 (ddd, 1H), and 1.55 (s, 6H). LCMS: (FA) ES+ 152.0 (M+1).

3-amino-N-(2-methoxyethyl)-5-(trifluoromethyl)-benzamide

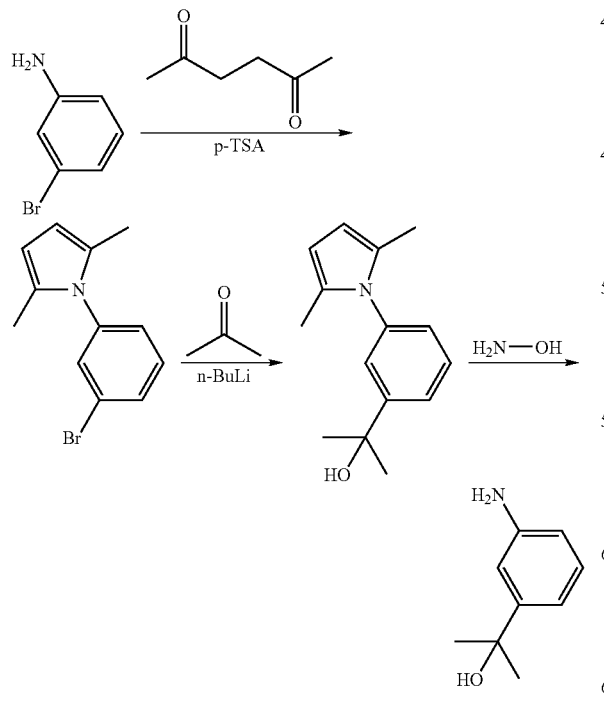

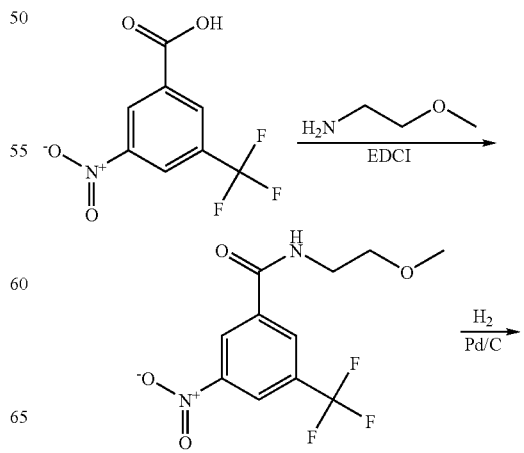

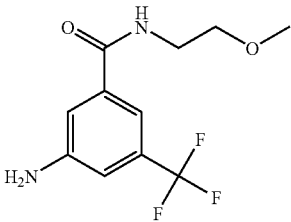

Step 1: Preparation of N-(2-methoxyethyl)-3-nitro-5-(trifluoromethyl)benzamide

To a stirred solution of 3-nitro-5-(trifluoromethyl)benzoic acid (1.00 g, 0.42 mmol) in DCM (20 mL), were added 2-methoxyethanamine (0.41 mL, 0.47 mmol), DMAP (620 mg, 0.51 mmol) and EDCI (900 mg, 0.47 mmol). The reaction mixture was allowed to stir at rt overnight and then concentrated. The residue was diluted with EtOAc and washed with water. The organic solution was dried (MgSO$_4$) and evaporated. The residue was purified by chromatography (SiO$_2$, MeOH/DCM) to yield the title compound as a white solid (780 mg, 63%). LCMS: (FA) ES$^+$ 293.2 (M+1), ES$^-$ 291.2 (M−1).

Step 2: Preparation of 3-amino-N-(2-methoxyethyl)-5-(trifluoromethyl)-benzamide

To a stirred solution of N-(2-methoxyethyl)-3-nitro-5-(trifluoromethyl)benzamide (760 mg, 0.26 mmol) in EtOAc (20 mL) was added Pd on carbon (10% wt, 76 mg). The mixture was allowed to stir at rt overnight under an atmosphere of hydrogen. The mixture was diluted with EtOAc and filtered through Celite. The filtrate was evaporated and the residue was purified by column chromatography (SiO$_2$, MeOH/DCM) to yield the title compound as a white solid (630 mg, 92%). LCMS: (FA) ES$^+$ 263.2 (M+1)

3-amino-N-[2-(dimethylamino)ethyl]-5-(trifluoromethyl)benzamide

The title compound was prepared from the appropriate starting materials in a manner analogous to that described for 3-amino-N-(2-methoxyethyl)-5-(trifluoromethyl)benzamide.

LCMS: (FA) ES$^+$ 276.23 (M+1).

4-chloro-2-methoxy-3-(trifluoromethyl)aniline

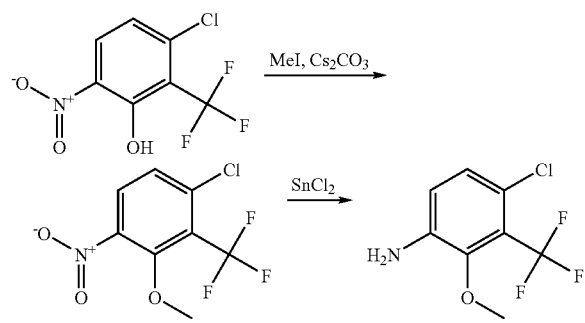

Step 1: Preparation of 1-chloro-3-methoxy-4-nitro-2-(trifluoromethyl)benzene

A mixture of 3-chloro-6-nitro-2-(trifluoromethyl)phenol (1.00 g, 4.14 mmol), cesium carbonate (4.05 g, 12.4 mmol), and iodomethane (465 μL, 7.45 mmol) in DMF (20 mL) was allowed to stir at rt overnight. The reaction mixture was diluted with EtOAc and poured into water. The mixture was extracted 3 times with EtOAc and the organic solution was dried over Na$_2$SO$_4$, filtered and concentrated. The residue was purified by column chromatography (SiO$_2$, EtOAc in hexanes) provided the title compound. $^1$H NMR (300 MHz, CDCl$_3$) δ: 7.90 (d, 1H), 7.40 (d, 1H), and 3.97 (s, 3H).

Step 2: Preparation of 4-chloro-2-methoxy-3-(trifluoromethyl)aniline

To a solution of 1-chloro-3-methoxy-4-nitro-2-(trifluoromethyl)benzene (1.73 g, 6.74 mmol) in EtOAc (40 mL) was added tin chloride dihydrate (3.04 g, 13.5 mmol). The reaction mixture was heated at reflux for 3 h. The crude reaction mixture was purified by column chromatography (SiO$_2$, EtOAc in hexanes) to give the title compound. LCMS: (FA) ES$^+$ 226.0 (M+1).

6-amino-3-chloro-2-(trifluoromethyl)phenol

The title compound was prepared from the appropriate starting materials in a manner analogous to that described 4-chloro-2-methoxy-3-(trifluoromethyl)aniline (step 2).

LCMS: (FA) ES− 210.3 (M−1).

4-chloro-2-methoxy-5-(trifluoromethyl)aniline

The title compound was prepared from the appropriate starting materials in a manner analogous to that described 4-chloro-2-methoxy-3-(trifluoromethyl)aniline (step 2). $^1$H NMR (300 MHz, CDCl$_3$) δ: 8.25 (s, 1H), 7.23 (s, 1H), 4.04 (s, 3H), and 1.55 (s, 1H).

[4-amino-2-(trifluoromethyl)phenyl]methanol

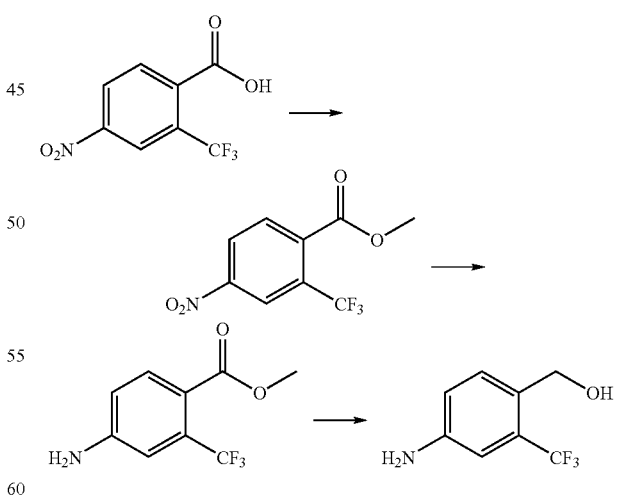

Step 1: Preparation of methyl 4-nitro-2-(trifluoromethyl)benzoate

A solution of 4-amino-2-(trifluoromethyl)benzoic acid (5.00 g, 21.6 mmol) in MeOH (30 mL) was cooled to 0° C. Trimethylsilyl diazomethane (2.0 M in Et$_2$O, 31.9 mL, 63.8 mmol) was slowly added and the reaction mixture was allowed to warm to rt. The solvent was removed and the white powder redissolved in EtOAc. The organic solution was washed with sat. NaHCO$_3$ solution, dried over Na$_2$SO$_4$, filtered, and concentrated to give the title compound.

LCMS: (FA) ES$^-$ 249.1 (M−1).

Step 2: Preparation of methyl 4-amino-2-(trifluoromethyl)benzoate

Methyl 4-nitro-2-(trifluoromethyl)benzoate (5.20 g, 20.9 mmol) was dissolved in EtOAc (100 mL) and tin chloride dihydrate (9.41 g, 41.7 mmol) was added to the reaction mixture. The reaction was heated at reflux for 2 h. The crude reaction mixture was purified by column chromatography (SiO$_2$, EtOAc/hexanes) to give the title compound. LCMS: (FA) ES$^-$ 218.4 (M−1).

Step 3: Preparation of [4-amino-2-(trifluoromethyl)phenyl]methanol (AN-13)

The title compound was synthesized from methyl 4-amino-2-(trifluoromethyl)benzoate as described by *J. Med. Chem.* 2002, 45(15), 3280-3285. LCMS: (FA) ES$^+$ 192.2 (M+1).

Example 4

Synthesis of Additional Reactants (2S)-3-methoxypropane-1,2-diamine dihydrochloride

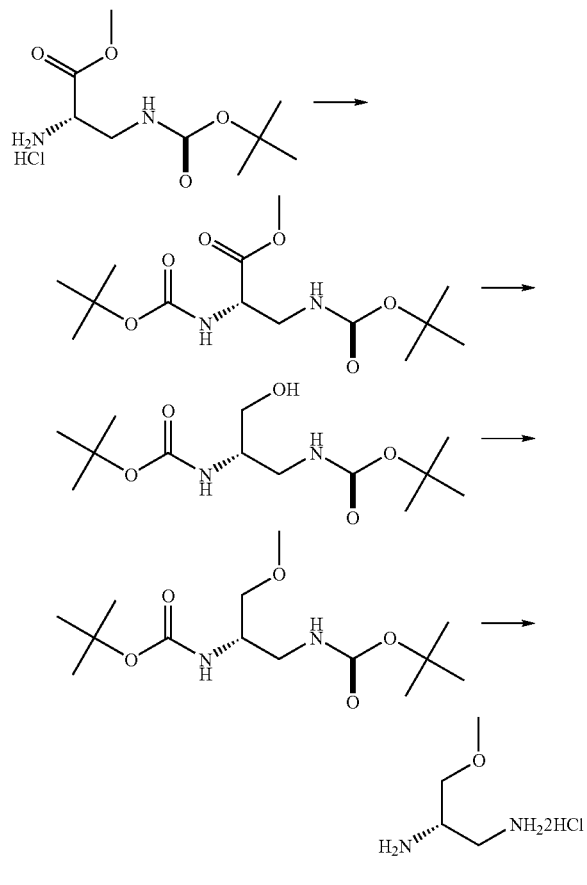

Step 1: Preparation of methyl (2S)-2,3-bis[(tert-butoxycarbonyl)amino]-propanoate To a solution of methyl (2S)-2-amino-3-[(tert-butoxycarbonyl)amino]-propanoate hydrochloride (3.00 g, 11.8 mmol) and TEA (3.30 mL, 23.6 mmol) in DCM (60 mL), was added (Boc)$_2$O (3.08 g, 14.1 mmol). The reaction was stirred for 18 h then diluted with DCM and washed with 1N HCl and brine. The organic phase was dried (Na$_2$SO$_4$) and evaporated to yield the title compound as a white solid (4.10 g, 100%). $^1$H NMR (400 MHz, CDCl$_3$) δ: 5.42 (s, 1H), 4.83 (s, 1H), 4.35 (s, 1H), 3.75 (s, 3H), 3.54-3.48 (m, 2H), and 1.44 (s, 18H).

Step 2: Preparation of di-tert-butyl [(2S)-3-hydroxypropane-1,2-diyl]biscarbamate To a solution of methyl (2S)-2,3-bis[(tert-butoxycarbonyl)amino]-propanoate (3.57 g, 11.2 mmol) in THF (60 mL) at 0° C. was added lithium chloride (523 mg, 12.3 mmol) and then sodium borohydride (467 mg, 12.3 mmol) portionwise. Ethanol (30 mL) was added slowly. The reaction mixture was allowed to warm to rt and stirred for 18 h. Acetic acid (0.707 mL, 12.3 mmol) was added and the solvents were evaporated. The residue was purified by chromatography (SiO$_2$, EtOAc/hexane) to yield the title compound as a white solid (2.35 g, 72.2%). LCMS: (FA) ES+ 291.2 (M+1).

Step 3: Preparation of di-tert-butyl [(2S)-3-methoxypropane-1,2-diyl]-biscarbamate To a solution of di-tert-butyl [(2S)-3-hydroxypropane-1,2-diyl]biscarbamate (2.45 g, 8.10 mmol) in THF (80 mL) at 0° C., was added NaH (60%, 357 mg, 8.91 mmol). The reaction was allowed to stir at 0° C. for 30 min, and then methyl iodide (0.556 mL, 8.91 mmol) was added dropwise. The reaction was stirred at 0° C. for 1 h and then allowed to warm to rt and stirred for 3 h. Water was added and the reaction was extracted into EtOAc. The combined organic solutions were washed with brine, dried (Na$_2$SO$_4$) and evaporated. The residue was purified by chromatography (SiO$_2$, EtOAc/hexane) to yield the title compound as a white solid (895 mg, 36%).

LCMS: (FA) ES+ 305.2 (M+1).

Step 4: Preparation of (2S)-3-methoxypropane-1,2-diamine dihydrochloride

To a solution of di-tert-butyl [(2S)-3-methoxypropane-1,2-diyl]biscarbamate (895 mg, 2.94 mmol) in MeOH (30 mL), was added 2N HCl in Et$_2$O (15 mL, 29.4 mmol). The reaction was stirred at rt for 18 h and the solvents evaporated to yield the title compound as a white solid (478 mg, 92%). LCMS: (FA) ES+ 105.0 (M+1).

Example 5

4-[4-(3-{[4-chloro-3-(trifluoromethyl)phenyl]amino}-3-oxopropyl)phenoxy]-N-methylpyridine-2-carboxamide (A-9)

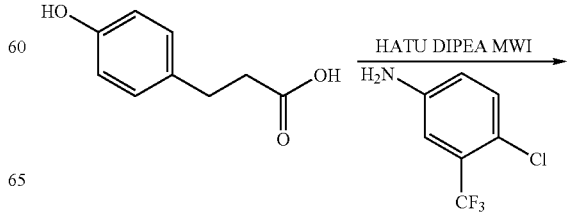

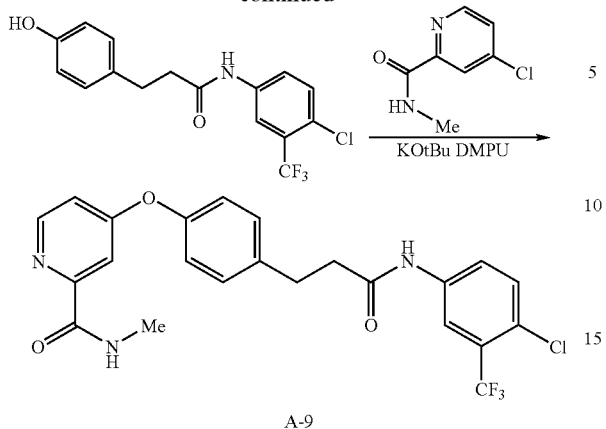

A-9

| A-6 | $^1$H NMR(300MHz, CD$_3$OD, HCl salt) δ: 8.26(dd, J$_1$=1.5Hz, J$_2$=5.1Hz, 2H), 7.98(d, J=2.4Hz, 1H), 7.65(dd, J$_1$=2.6Hz, J$_2$=9.0Hz, 1H), 7.43(d, J=8.7Hz, 1H), 7.28(bd, J=8.5Hz, 2H), 6.97(bd, J=8.7Hz, 2H), 6.79(dd, J$_1$=1.5Hz, J$_2$=4.9Hz, 2H), 2.95(t, J=7.2Hz, 2H), and 2.63(t, J=7.5Hz, 2H). |
|---|---|
| A-71 | $^1$H NMR(400MHz, CD$_3$OD) δ: 8.03(d, 1H), 7.14(d, 1H), 6.98-7.02(m, 2H), 6.94-6.96(m, 1H), 6.89-6.93(m, 1H), 6.75-6.80(m, 1H), 6.66-6.71(m, 2H), 6.59(dd, 1H), 6.50-6.54(m, 1H), 2.66(t, 2H), 2.54(s, 3H), 2.30(t, 2H), and 1.91(s, 3H). LCMS, FA: R$_t$=1.72min, [MH$^+$ 390.4]. |

Step 1: Preparation of N-[4-chloro-3-(trifluoromethyl)phenyl]-3-(4-hydroxyphenyl)propanamide A mixture of 3-(4-hydroxyphenyl)propanoic acid (4×250 mg, 24.1 mmol total), 4-chloro-3-(trifluoromethyl)aniline (4×190 mg, 15.5 mmol total) and HATU (4×0.58 g, 24.1 mmol total) were added to four microwave-safe vials. To each vial, NMP (5 mL) and DIPEA (0.425 mL, 9.7 mmol) were added. The vials were then sealed and subjected to MWI at 220° C. for 15 min. The reaction vessels were unsealed and the mixtures were combined and diluted with EtOAc. The organic solution was extracted with 1N HCl and brine, dried over Na$_2$SO$_4$, filtered, and concentrated to give a brown oil. Purification by column chromatography (SiO$_2$, EtOAc/hexane) provided 960 mg of a yellow oil that solidified upon exposure to DCM (47%, <95% pure). $^1$H NMR (300 MHz, CDCl$_3$) δ: 7.74 (br d, J=2.4 Hz, 1H), 7.65 (br dd, J$_1$=8.5 Hz, J$_2$=2.3 Hz, 1H), 7.42 (d, J=8.7 Hz, 1H), 7.16 (br s, 1H), 7.10 (d, J=8.5 Hz, 2H), 6.79 (d, J=8.5 Hz, 2H), 2.99 (t, J=7.4 Hz), and 2.65 (t, J=7.4 Hz).

Step 2: Preparation of 4-[4-(3-{[4-chloro-3-(trifluoromethyl)phenyl]amino}-3-oxopropyl)phenoxy]-N-methylpyridine-2-carboxamide (A-9)

To a mixture of DMPU (0.7 mL) and DMF (2.8 mL) was added N-[4-chloro-3-(trifluoromethyl)phenyl]-3-(4-hydroxyphenyl)propanamide (600 mg, 1.75 mmol) and 4-chloro-N-methylpyridine-2-carboxamide (prepared as described in Bankston, D. et al. *Organic Process Research and Development* 2002, 6, 777-781; 328 mg, 1.92 mmol). To this solution was added KOt-Bu (590 mg, 5.25 mmol). The reaction mixture was stirred at 100° C. for 18 h and then cooled to rt, diluted with water and extracted with EtOAc and DCM. The combined organic solutions were washed with water and brine, dried over Na$_2$SO$_4$, filtered and concentrated to give a brown oil. Purification by column chromatography provided 100 mg of a colorless solid. $^1$H NMR (300 MHz, CD$_3$OD) δ: 10.11 (br s, 0.34H), 8.41 (d, J=5.6 Hz, 1H), 8.07 (br d, J=2.2 Hz, 1H), 7.74 (br dd, J$_1$=8.7 Hz, J$_2$=2.1 Hz, 1H), 7.48-7.51 (m, 2H), 7.36 (d, J=8.5 Hz, 1H), 7.05 (d, J=8.5 Hz, 2H), 6.98 (dd, J1=5.6 Hz, J2=2.5 Hz, 1H), 3.34 (s, 0.84H), 3.04 (t, J=7.5 Hz), 2.92 (s, 3H), and 2.71 (t, J=7.5 Hz).

Compounds in the following table were prepared from the appropriate starting materials in a method analogous to that of Example 5:

Example 6

Preparation of 4-[3-(3-{[4-chloro-3-(trifluoromethyl)phenyl]amino}-3-oxopropyl)phenoxy]-N-methylpyridine-2-carboxamide (A-7)

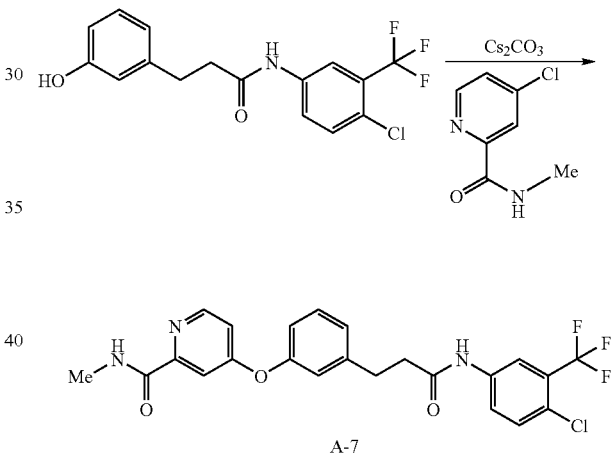

A-7

A mixture of N-[4-chloro-3-(trifluoromethyl)phenyl]-3-(3-hydroxyphenyl)propanamide (585 mg, 1.70 mmol), 4-chloro-N-methylpyridine-2-carboxamide (318 mg, 1.87 mmol), and Cs$_2$CO$_3$ (7.76 g, 8.5 mmol) in DMF (3.4 mL) was heated at 100° C. overnight. The reaction mixture was concentrated and diluted with EtOAc. The organic solution was washed with brine, dried over MgSO$_4$, filtered, and concentrated. The residue was purified by column chromatography (SiO$_2$, 0-30% EtOAc in hexanes) to give the product as a white solid. $^1$H NMR (400 MHz, CD$_3$OD) δ: 8.62 (d, 1H), 8.26 (m, 1H), 7.89-7.96 (m, 1H), 7.71-7.74 (m, 1H), 7.63 (t, 1H), 7.41-7.47 (m, 1H), 7.28 (br s, 1H), 7.17-7.24 (m, 2H), 2.58 (t, 2H), 3.15 (s, 3H), and 2.93 (t, 2H). LCMS, AA: R$_t$=2.05 min, [MH$^+$ 478.3].

Compounds in the following table were prepared from the appropriate starting materials in a method analogous to that of Example 6:

| | |
|---|---|
| A-202 | ¹H NMR(400MHz, CD₃OD) δ: 8.40(s, 1H), 8.32(s, 1H), 8.03(d, 1H), 7.69(dd, 1H), 7.45(d, 1H), 7.36(t, 1H), 7.15-7.20(m, 2H), 7.09(dd, 1H), 3.04(t, 2H), and 2.71(t, 2H). LCMS, FA: $R_t$=1.66min, [MH⁺ 462.1]. |
| A-214 | ¹H NMR(300MHz, d6 DMSO) δ: 9(s, 1H), 8.58(s, 2H), 7.81-7.85(m, 1H), 7.65-7.76(m, 2H), 7.32-7.45(m, 2H), 7.14(d, 1H), 6.91-7.01(m, 2H), 3.07(t, 2H), 2.7(t, 2H), and 3.07(t, 2H). LCMS, FA: $R_t$=1.91min, [MH⁺ 422.0]. |
| A-253 | ¹H NMR(400MHz, d₆DMSO) δ: 11.96(s, 1H), 10.37(s, 1H), 8.15(d, 1H), 8.03(s, 1H), 7.79(dd, 1H), 7.63(d, 1H), 7.32(t, 1H), 7.11(d, 1H), 7.01-7.04(m, 1H), 6.95(dd, 1H), 6.83(s, 2H), 5.69-5.72(m, 1H), 2.92(t, 2H), 2.66(t, 2H), and 2.92(t, 2H). LCMS, FA: $R_t$=1.65min, [MH⁺ 437.9]. |
| A-179 | ¹H NMR(300MHz, CD₃OD) δ: 8.22(s, 1H), 8.03(d, 1H), 7.7(dd, 1H), 7.45(d, 1H), 7.36(t, 1H), 7.22(d, 1H), 7.2(d, 1H), 7.15(s, 1H), 7.06(dd, 1H), 6.22(d, 1H), 4.9(s, 4H), 3.04(t, 2H), 2.71(t, 2H). LCMS: (FA)ES+461.14(M+1), ES−459.18(M−1). |
| A-160 | ¹H NMR(400MHz, CD₃OD) δ: 8.09(d, 1H), 8.04(d, 1H), 7.74(dd, 1H), 7.5(d, 1H), 7.39(t, 1H), 7.17-7.21(m, 1H), 6.98-7.01(m, 1H), 6.93(ddd, 1H), 6.61(d, 1H), 3.03(t, 2H), 2.93(s, 3H), 2.7(t, 2H), 2.47(s, 3H), and 2.7(t, 2H). LCMS, FA: $R_t$=1.90min, [MH⁺ 493.2]. |
| A-141 | ¹H NMR(400MHz, CDCl₃) δ: 9.24(bs, 1H), 8.78(t, 1H), 8.45(s, 1H), 8.44(d, 1H), 8.12(bs, 1H), 7.56(d, 1H), 7.34(t, 1H), 7.15-7.19(m, 2H), 7.06(t, 1H), 6.96-6.99(m, 1H), 3.09-3.12(m, 2H), 3.08(d, 3H), and 2.70-2.73(m, 2H). |
| A-258 | ¹H NMR(400MHz, CDCl₃) δ: 9.04(bs, 1H), 8.44(d, 1H), 8.11-8.18(m, 2H), 8.04-8.05(m, 1H), 7.70(d, 1H), 7.57(d, 1H), 7.33(t, 1H), 7.13-7.16(m, 2H), 7.02(t, 1H), 6.95-6.98(m, 1H), 3.08(t, 2H), 3.03(d, 3H), and 2.70(t, 2H). |
| A-117 | ¹H NMR(300MHz, CD₃OD) δ: 8.38(d, 1H), 8.15(s, 1H), 8.11(s, 1H), 7.73(s, 1H), 7.44(d, 1H), 7.39(t, 1H), 7.21(d, 1H), 7.05(t, 1H), 7.00-6.96(m, 2H), 3.75(s, 4H), 3.06(t, 2H), and 2.73(t, 2H). LCMS: (FA)ES⁺ 480.3(M+1), ES⁻ 478.3(M−1). |
| A-91 | ¹H NMR(400MHz, CD₃OD) δ: 8.57(d, 1H), 8.42(d, 1H), 8.17(d, 1H), 8.03(dd, 1H), 7.89-7.87(m, 1H), 7.56(dd, 1H), 7.49(d, 1H), 7.41(t, 1H), 7.23(d, 1H), 7.06(t, 1H), 6.99(dd, 2H), 3.83(s, 4H), 3.06(t, 2H), 2.76(t, 2H). LCMS: (FA) ES+ 480.11(M+1), ES− 478.01(M−1). |
| A-24 | ¹H NMR(300MHz, CD₃OD) δ: 8.44(d, 1H), 8.10(d, 1H), 7.74(dd, 1H), 7.53(dd, 2H), 7.39(dd, 2H), 7.08(d, 2H), 7.02(dd, 1H), 3.56(dd, 2H), 3.07(dd, 2H), 2.63-2.77(m, 4H), and 2.39(s, 6H). LCMS: (FA)ES+ 535.3(M+1), ES− 533.5(M−1). |
| A-78 | ¹H NMR(400MHz, d₆ DMSO) δ: 10.37(s, 1H), 8.49(d, 1H), 8.13(s, 1H), 7.77(dd, 1H), 7.61(d, 1H), 7.43(dd, 1H), 7.36(d, 1H), 7.23(d, 1H), 7.13(dd, 1H), 7.11(dd, 1H), 7.04(dd, 1H), 3.37(dd, 2H), 3.32(br. s, 2H), 2.96(dd, 2H), 2.68(dd, 2H), and 2.24(s, 6H). LCMS: (FA)ES+ 535.9(M+1), ES− 533.1(M−1). |
| A-260 | ¹H NMR(400MHz CD₃OD) δ: 8.38(d, 1H), 8.03(d, 1H), 7.69(dd, 1H), 7.52(d, 1H), 7.49(d, 1H), 7.41(dd, 1H), 7.23(d, 1H), 7.05(dd, 1H), 6.99(d, 1H), 6.98(d, 1H), 3.46(dd, 2H), 2.93(dd, 2H), 2.71(dd, 2H), 2.69(s, 6H), and 1.94(dddd, 2H). LCMS: (FA)ES+ 549.1(M+1), ES− 547.1(M−1). |
| A-79 | ¹H NMR(400MHz, CD₃OD; HCOOH salt) δ: 10.36(s, 1H), 8.69(dd, 1H), 8.46(d, 1H), 8.13(d, 1H), 7.77(dd, 1H), 7.62(dd, 1H), 7.43(dd, 1H), 7.22(d, 1H), 7.10-7.13(m, 2H), 7.04(dd, 1H), 3.55(dd, 4H), 3.37(ddd, 2H), 2.96(dd, 2H), 2.68(dd, 2H), 2.51(dd, 2H), 2.44(dd, 2H), and 2.38(dd, 2H). LCMS: (FA)ES+ 577.1(M+1), ES− 575.0(M−1). |

Example 7

Preparation of 4-[4-(4-{[4-chloro-3-(trifluoromethyl)phenyl]amino}-4-oxobutyl)phenoxy]-N-methylpyridine-2-carboxamide (A-8)

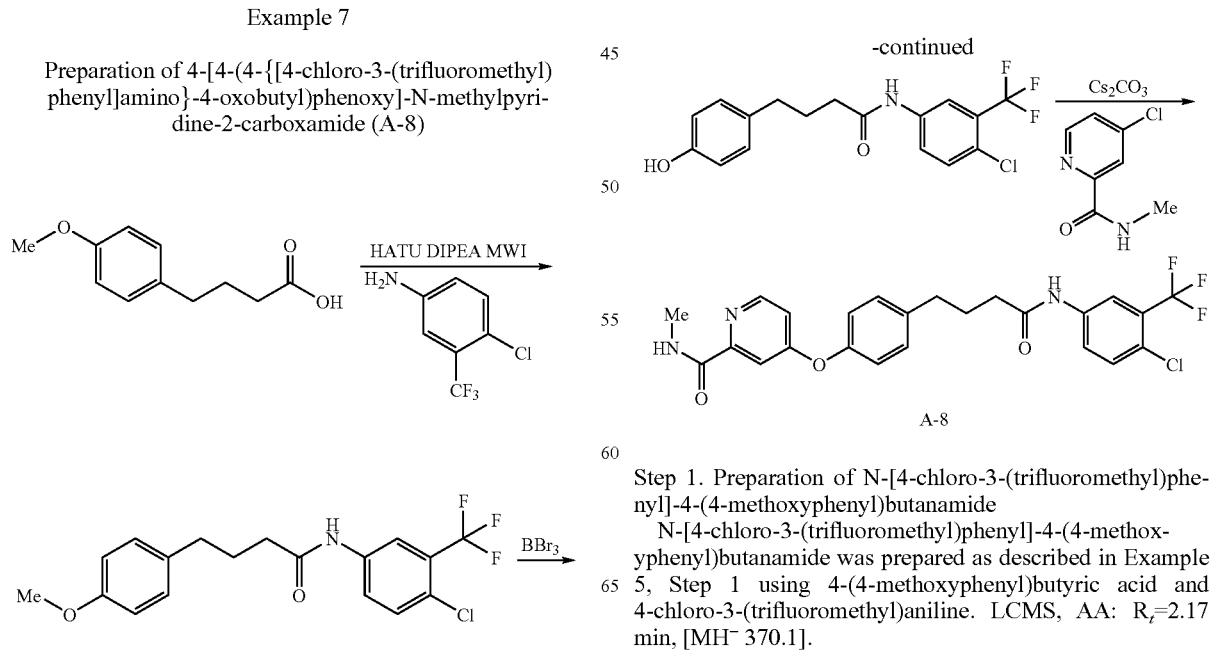

Step 1. Preparation of N-[4-chloro-3-(trifluoromethyl)phenyl]-4-(4-methoxyphenyl)butanamide N-[4-chloro-3-(trifluoromethyl)phenyl]-4-(4-methoxyphenyl)butanamide was prepared as described in Example 5, Step 1 using 4-(4-methoxyphenyl)butyric acid and 4-chloro-3-(trifluoromethyl)aniline. LCMS, AA: $R_t$=2.17 min, [MH⁻ 370.1].

Step 2. Preparation of N-[4-chloro-3-(trifluoromethyl)phenyl]-4-(4-hydroxyphenyl)butanamide To a solution of N-[4-chloro-3-(trifluoromethyl)phenyl]-4-(4-methoxyphenyl)butanamide (460 mg, 1.23 mmol) in DCM (6 mL) at 0° C. was added BBr$_3$ (1.0 M in DCM, 0.40 mL, 0.4 mmol) dropwise. The solution was allowed to warm to rt. Upon reaction completion, the solution was poured onto ice and neutralized with NH$_4$OH. The yellow solid was filtered off and rinsed with hexanes and Et$_2$O to give the product as a white solid (356 mg, 81%). LCMS, AA: R$_t$=1.94 min, [MH$^-$ 356.1].

Step 3. Preparation of 4-[4-(4-{[4-chloro-3-(trifluoromethyl)phenyl]amino}-4-oxobutyl)phenoxy]-N-methylpyridine-2-carboxamide (A-8)

The title compound was prepared as described in Example 6. $^1$H NMR (400 MHz, CD$_3$OD) δ: 8.38 (d, 1H), 8.03 (d, 1H), 7.66-7.73 (m, 1H), 7.41-7.48 (m, 2H), 7.23-7.32 (m, 2H), 6.92-7.03 (m, 3H), 2.85 (s, 3H), 2.68 (t, 2H), 2.37 (t, 2H), and 1.91-2.04 (m, 2H). LCMS, AA: R$_t$=2.10 min, [MH$^+$ 492.1].

Example 8

Preparation of 4-[4-(3-anilino-3-oxopropyl)phenoxy]-N-methylpyridine-2-carboxamide (A-12)

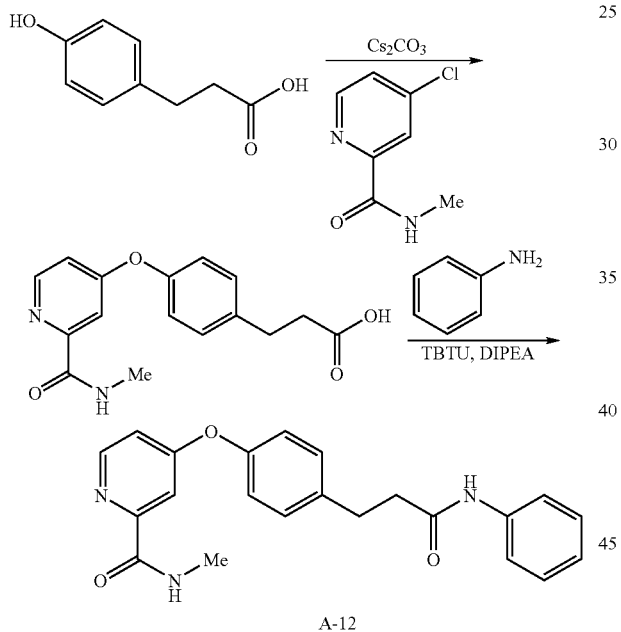

Step 1. Preparation of 3-(4-(2-(methylcarbamoyl)pyridin-4-yloxy)phenyl)propanoic acid A mixture of 3-(4-hydroxyphenyl)propanoic acid (10.7 g, 64.5 mmol), 4-chloro-N-methylpicolinamide (10.0 g, 58.6 mmol) and cesium carbonate (57.3 g, 175.8 mmol) was stirred in DMF and heated at 100° C. overnight. After cooling to rt, the mixture was filtered and washed with EtOAc to remove cesium carbonate. The remaining solid was dissolved in a minimal amount of water and the pH of the solution was adjusted to 4 by the dropwise addition of a sat. oxalic acid solution. The solution was extracted with DCM, the organic solutions washed with water and brine, dried over MgSO$_4$, filtered, and concentrated. The resulting solid was recrystallized from EtOAc to give the desired product as a pale cream solid (5.07 g, 37%). $^1$H NMR (400 MHz, d$_6$-DMSO) δ: 12.13 (s, 1H), 8.70-8.78 (m, 1H), 8.49 (d, J=5.6 Hz, 1H), 7.34-7.39 (m, 3H), 7.11-7.14 (m, 3H), 2.87 (br t, J=7.6 Hz, 2H), 2.77 (d, J=4.8 Hz, 3H), and 2.57 (br t, J=7.6 Hz, 2H).

Step 2. Preparation of 4-[4-(3-anilino-3-oxopropyl)phenoxy]-N-methylpyridine-2-carboxamide (A-12)

A mixture of 3-(4-(2-(methylcarbamoyl)pyridin-4-yloxy)phenyl)-propanoic acid (100 mg, 0.33 mmol), aniline (0.033 mL, 0.36 mmol), and TBTU (117 mg, 0.36 mmol) in DCM (5 mL) was stirred at rt. To this slurry was added DIPEA (0.20 mL, 1.16 mmol). The mixture was allowed to stir at rt overnight and then diluted with water. The aqueous phase was separated and extracted with DCM. The organic solutions were combined, washed with brine, dried over MgSO$_4$, filtered, and concentrated. The resulting solid was treated with MeOH and filtered to give 45 mg of a white solid. $^1$H NMR (400 MHz, d$_6$-DMSO) δ: 9.90 (br s, 1H), 8.71-8.78 (m, 1H), 8.48 (d, J=5.6 Hz, 1H), 7.55-7.60 (m, 2H), 7.36-7.40 (m, 2H), 7.36 (d, J=2.4 Hz, 1H), 7.25-7.31 (m, 2H), 7.12-7.16 (m, 2H), 7.11 (dd, J=5.2, 2.4 Hz, 1H), 6.99-7.04 (m, 1H), 2.93-2.98 (m, 2H), 2.77 (d, J=4.8 Hz, 3H), and 2.64-2.69 (m, 2H).

Compounds in the following table were prepared from the appropriate starting materials in a method analogous to that of Example 8:

| | |
|---|---|
| A-11 | $^1$H NMR (400 MHz, d$_6$-DMSO): δ 10.04 (br s, 1H), 8.71-8.77 (m, 1H), 8.48 (d, J=5.6 Hz, 1H), 7.58-7.63 (m, 2H), 7.36-7.40 (m, 2H), 7.35 (d, J=2.8 Hz, 1H), 7.31-7.35 (m, 2H), 7.12-7.15 (m, 2H), 7.11 (dd, J=5.6, 2.4 Hz, 1H), 2.96 (dd, J=8.0, 7.6 Hz, 2H), 2.77 (d, J=5.2 Hz, 3H), and 2.64-2.69 (m, 2H). |

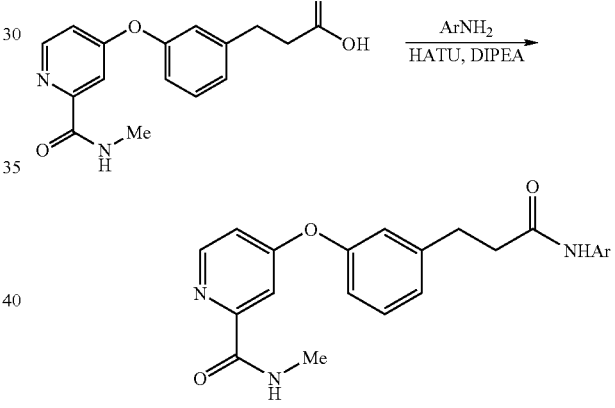

Example 9

Preparation of N-methyl-4-[4-(3-oxo-3-{[3-(trifluoromethyl)phenyl]amino}-propyl)phenoxy]pyridine-2-carboxamide (A-4)

A solution of 3-[4-({2-[(methylamino)carbonyl]pyridin-4-yl}oxy)phenyl]-propanoic acid (270 mg, 0.90 mmol), 3-(trifluoromethyl)aniline (158 mg, 0.98 mmol), HATU (409 mg, 1.07 mmol), and DIPEA (348 mg, 2.69 mmol) in DMF (5 mL) was stirred at rt for 16 h. The reaction mixture was diluted with EtOAc and washed with 1N HCl and brine. The organic solution was dried over MgSO$_4$, filtered, and concentrated to give A-4 as a white solid (127 mg, 32%). $^1$H NMR (300 MHz, d$_6$-DMSO) δ: 10.28 (s, 1H), 8.76 (m, 1H), 8.47 (d, 1H), 8.08 (br s, 1H), 7.75 (br d, 1H), 7.53 (t, 1H), 7.31-7.42 (m, 4H), 7.08-7.19 (m, 3H), 2.97 (t, 2H), 2.76 (d, 3H), and 2.71 (d, 2H). LCMS, FA: R$_t$=1.89 min, [MH$^+$ 444.1].

Compounds in the following table were prepared from the appropriate starting materials in a method analogous to that of Example 9:

| | |
|---|---|
| A-5 | $^1$H NMR(400MHz, $d_6$-DMSO) δ: 10.00(s, 1H), 8.43-8.55(m, 1H), 8.22(d, 1H), 7.82(s, 1H), 7.46-7.52(m, 1H), 7.28(t, 1H), 7.20(t, 1H), 7.11-7.18(m, 2H), 6.98-7.03(m, 1H), 6.84-6.91(m, 2H), 6.78-6.83(m, 1H), 2.74(t, 2H), 2.54(d, 3H), and 2.45(t, 2H). LCMS, PAA:$R_t$=2.63min, [M+H 444.2]. |
| A-13 | LCMS: (AA)ES$^+$ 410.0(M+1). |
| A-149 | $^1$H NMR(400MHz, $d_6$-DMSO; HCOOH salt) δ: 10.91(s, 1H), 8.81-8.70(m, 1H), 8.47(d, 1H), 7.47-7.35(m, 2H), 7.26-7.16(m, 1H), 7.16-6.99(m, 3H), 6.57(s, 1H), 2.92(t, 2H), 2.77(d, 3H), 2.67(t, 2H), and 1.35-1.16(m, 9H). LCMS: (FA)ES$^+$ 423.2(M+1), ES$^-$ 421.2(M−1). |
| A-18 | $^1$H NMR(300MHz, $d_6$-DMSO; MeCOOH salt) δ: 9.76(s, 1H), 8.81-8.72(m, 1H), 8.45(d, 1H), 7.48-7.36(m, 3H), 7.25-7.18(m, 2H), 7.13-7.06(m, 3H), 7.06-7.00(m, 1H), 2.94(t, 2H), 2.83-2.72(m, 7H), 2.61(t, 2H), and 2.03-1.90(m, 2H). LCMS: (FA)ES$^+$ 416.3(M+1), ES$^-$ 414.3(M−1). |
| A-81 | $^1$H NMR(300MHz, $d_6$-DMSO; HCl salt) δ: 10.00(s, 1H), 8.85-8.75(m, 1H), 8.46(d, 1H), 7.55-7.50(m, 1H), 7.47-7.35(m, 3H), 7.31-7.19(m, 2H), 7.14-7.07(m, 2H), 7.08-6.99(m, 1H), 2.94(t, 2H), 2.78(d, 3H), 2.64(t, 2H), and 2.25(s, 3H). LCMS: (FA)ES$^+$ 424.2(M+1), ES$^-$ 422.5(M−1). |
| A-83 | $^1$H NMR(300MHz, $d_6$-DMSO; HCl salt) δ: 9.93(s, 1H), 8.86-8.76(m, 1H), 8.45(d, 1H), 7.48-7.38(m, 2H), 7.30-7.19(m, 2H), 7.2-7.00(m, 5H), 6.63-6.55(m, 1H), 3.69(s, 3H), 2.94(t, 2H), 2.78(d, 3H), and 2.63(t, 2H). LCMS: (FA)ES$^+$ 406.3(M+1), ES$^-$ 404.4(M−1). |
| A-256 | $^1$H NMR(300MHz, $d_6$-DMSO; HCl salt) δ: 10.16(s, 1H), 8.82-8.72(m, 1H), 8.45(d, 1H), 8.26-8.20(m, 1H), 7.83-7.75(m, 1H), 7.64-7.57(m, 1H), 7.48-7.37(m, 3H), 7.26-7.20(m, 1H), 7.15-7.00(m, 3H), 3.83(s, 3H), 2.96(t, 2H), 2.78(d, 3H), and 2.67(t, 2H). LCMS: (FA)ES$^+$ 434.7(M+1), ES$^-$ 432.0(M−1). |
| A-262 | $^1$H NMR(400MHz, CD$_3$OD; HCl salt) δ: 8.49-8.44(m, 1H), 7.71-7.67(m, 1H), 7.43(t, 1H), 7.31-7.25(m, 2H), 7.09-7.00(m, 2H), 6.97-6.93(m, 1H), 6.70-6.65(m, 1H), 6.64-6.59(m, 1H), 5.84(s, 2H), 3.01(t, 2H), 2.85(s, 3H), and 2.61(t, 2H). LCMS: (FA)ES$^+$ 420.5(M+1), ES$^-$ 417.9(M−1). |
| A-13 | $^1$H NMR(400MHz, CD$_3$OD; HCl salt) δ: 8.55-8.51(m, 1H), 7.79-7.75(m, 1H), 7.51-7.45(m, 3H), 7.34-7.23(m, 4H), 7.16-7.12(m, 1H), 7.11-7.06(m, 1H), 3.08(t, 2H), 2.95(s, 3H), and 2.72(t, 2H). LCMS: (FA)ES$^+$ 410.0(M+1), ES$^-$ 407.7(M−1). |
| A-134 | $^1$H NMR(400MHz, $d_6$-DMSO; HCl salt) δ: 9.51(s, 1H), 8.58-8.50(m, 1H), 8.22(d, 1H), 7.25-7.15(m, 4H), 7.02-6.96(m, 1H), 6.89-6.84(m, 2H), 6.83-6.77(m, 1H), 6.65-6.56(m, 2H), 3.46(s, 3H), 2.71(t, 2H), 2.55(d, 3H), and 2.36(t, 2H). LCMS: (FA)ES$^+$ 406.5(M+1), ES$^-$ 404.1(M−1). |
| A-238 | LCMS: (FA)ES$^+$ 444.4(M+1) |
| A-64 | LCMS: (AA)ES$^+$ 408.5(M+1). ES$^-$ 406.5(M−1). |
| A-88 | LCMS: (AA)ES$^+$ 417.5(M+1). |
| A-252 | LCMS: (AA)ES$^+$ 436.5(M+1), ES$^-$ 434.5(M−1). |
| A-197 | LCMS: (AA)ES$^+$ 428.1(M+1), ES$^-$ 426.4(M−1). |
| A-163 | LCMS: (AA)ES$^+$ 405.5(M+1), ES$^-$ 403.5(M−1). |
| A-263 | LCMS: (AA)ES$^+$ 435.4(M+1), ES$^-$ 433.4(M−1). |
| A-133 | LCMS: (AA)ES$^+$ 474.6(M+1), ES$^-$ 472.4(M−1). |

Example 10

Preparation of 4-[4-(3-{[4-chloro-3-(trifluoromethyl)phenyl]amino}-3-oxopropyl)phenoxy]pyridine-2-carboxamide (A-3)

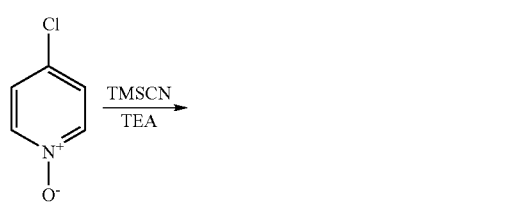

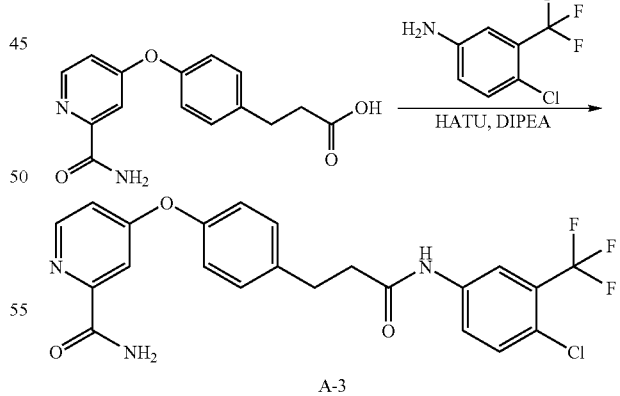

Step 1. Preparation of 4-chloropyridine-2-carbonitrile

To a solution of 4-chloropyridine N-oxide (5.0 g, 38.6 mmol) in CAN (100 mL) was added trimethylsilyl cyanide (7.7 g, 77.2 mmol) and TEA (8.1 mL, 57.9 mmol). The solution was heated at reflux for 48 h. The reaction was then concentrated and diluted with DCM and water before adding 1N HCl (caution!). The mixture was extracted with DCM and the organic solutions were combined and washed with brine, dried over Na$_2$SO$_4$ and concentrated to yield the title compound as a brown solid (4.62 g, 87%). $^1$H NMR (300 MHz, d$_6$-DMSO) δ: 8.67 (dd, J$_1$=0.57 Hz, J$_2$=5.5 Hz, 1H), 8.29 (dd, J=0.75 Hz, J$_2$=2.1, 1H), and 7.88 (dd, J$_1$=0.2.1 Hz, J$_2$=5.5 m, 1H).

Step 2. Preparation of 3-(4-{[2-(aminocarbonyl)pyridin-4-yl]oxy}phenyl)-propanoic acid To a suspension of 4-chloropyridine-2-carbonitrile (2.0 g, 14.5 mmol) in DMF (70 mL) was added cesium carbonate (14.0 g, 43.5 mmol) and 3-(4-hydroxyphenyl)propanoic acid (2.6 g, 15.9 mmol). The reaction mixture was heated at reflux overnight. The mixture was cooled to rt, concentrated, and then taken up in 300 mL of water. The pH was adjusted to 3 by the dropwise addition of oxalic acid and a precipitate formed. The precipitate was filtered to yield the title compound as a brown solid (1.2 g, 28%). LCMS: Method FA, R$^t$=1.27 min, [MH$^+$=287].

Step 3. Preparation 4-[4-(3-{[4-chloro-3-(trifluoromethyl)phenyl]amino}-3-oxopropyl)phenoxy]pyridine-2-carboxamide (A-3)

A solution of 3-(4-{[2-(aminocarbonyl)pyridin-4-yl]oxy}phenyl)-propanoic acid (200 mg, 0.70 mmol), HATU (319 mg, 0.84 mmol), DIPEA (0.24 mL, 1.4 mmol), and 4-chloro-3-(trifluoromethyl)aniline (136 mg, 0.70 mmol) in DMF (5 mL) was stirred overnight at rt. EtOAc was added to the reaction and the mixture was washed with 1N HCl, 1N NaOH, and brine, dried over Na$_2$SO$_4$ and concentrated. Purification by column chromatography (SiO$_2$, 20-100% EtOAc in hexane) followed by recrystallization in EtOAc/hexane provided A-3 (37 mg, 11%). $^1$H NMR (300 MHz, d$_6$-DMSO) δ: 10.36 (s, 1H), 8.48 (d, J=5.7 Hz, 1H), 8.18 (d, J=2.5 Hz, 1H), 8.09 (bs, 1H), 7.81 (dd, J$_1$=2.5 Hz, J$_2$=8.8, 1H), 7.7 (bs, 1H), 7.64 (d, J=8.8 Hz, 1H), 7.35-7.40 (m, 3H), 7.12-7.16 (m, 3H), 2.97 (t, J=7.3 Hz, 2H), and 2.70 (t, J=7.8 Hz, 2H).

Compounds in the following table were prepared from the appropriate starting materials in a method analogous to that of Example 10:

| | |
|---|---|
| A-2 | $^1$H NMR(300MHz, d$_6$-DMSO): δ 10.26(s, 1H), 8.48(d, J=5.7Hz, 1H), 8.10(bs, 2H), 7.75(d, J=8.5Hz, 1H), 7.67(bs, 1H), 7.53(t, J=7.8Hz, 1H), 7.36-7.41(m, 4H), 7.11-7.16(m, 3H), 2.97(t, J=7.5Hz, 2H), and 2.70(t, J=8.0Hz, 2H). |
| A-1 | $^1$H NMR(300MHz, d$_6$-DMSO): δ 10.04(s, 1H), 8.48(d, J=5.8Hz, 1H), 8.09(bd, J=1.8Hz, 1H), 7.67(bd, J=1.8Hz), 7.58-7.62(m, 2H), 7.31-7.40(m, 5H), 7.11-7.76(m, 3H), 2.96(t, J=7.3Hz, 2H), and 2.66(t, J=8.0Hz, 2H). |

Example 11

Preparation of N-(4-chlorophenyl)-3-{4-[(2-cyanopyridin-4-yl)oxy]phenyl}propanamide (A-21)

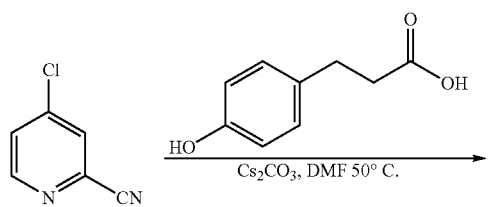

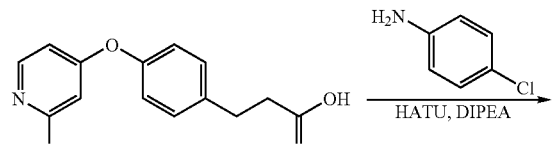

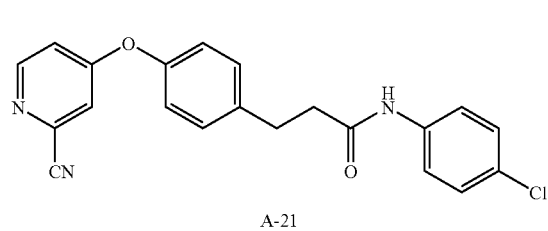

A-21

Step 1. Preparation of 3-{4-[(2-cyanopyridin-4-yl)oxy]phenyl}propanoic acid

To a suspension of 4-chloropyridine-2-carbonitrile (2.3 g, 16.6 mmol) in DMF (100 mL) was added cesium carbonate (16.3 g, 50.0 mmol) and 3-(4-hydroxy-phenyl)propanoic acid (3.03 g, 18.3 mmol). The reaction was heated to 50° C. for 3 days. The mixture was cooled to rt, concentrated, and then taken up in 300 mL of water. The pH was adjusted to 3 by the dropwise addition of oxalic acid and a precipitate formed. The precipitate was filtered to give the title compound as a cream solid (4.17 g, 95%). LCMS: Method FA, R$_t$=1.49 min, [MH$^+$=269].

Step 2. Preparation of N-(4-chlorophenyl)-3-{4-[(2-cyanopyridin-4-yl)oxy]-phenyl}propanamide (A-21)

A solution of 3-{4-[(2-cyanopyridin-4-yl)oxy]phenyl}propanoic acid (400 mg, 1.49 mmol), HATU (681 mg, 1.79 mmol), DIPEA (0.5 mL, 2.98 mmol), and 4-chloroaniline (209 mg, 1.63 mmol) in DMF (5 mL) was stirred overnight at rt. The reaction mixture was diluted with EtOAc and washed with 1N HCl, 1N NaOH and brine, dried over Na$_2$SO$_4$ and concentrated. The resulting solid was triturated with DCM and filtered to give A-21 (187 mg, 33%). $^1$H NMR (300 MHz, d$_6$-DMSO): δ 10.02 (s, 1H), 8.56 (dd, J$_1$=0.50 Hz, J$_2$=5.8 Hz, 1H), 7.57-7.63 (m, 3H), 7.31-7.40 (m, 4H), 7.10-7.17 (m, 3H), 2.95 (t, J=7.5 Hz, 2H), and 2.65 (t, J=7.8 Hz, 2H).

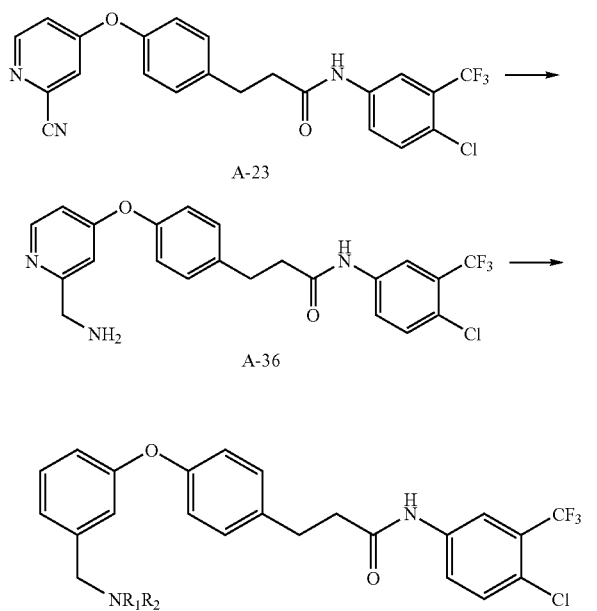

Example 12

Preparation of N-[4-chloro-3-(trifluoromethyl)phenyl]-3-[4-({2-[(methylamino)methyl]pyridin-4-yl}oxy)phenyl]propanamide (A-30)

Step 1. Preparation of 3-(4-{[2-(aminomethyl)pyridin-4-yl]oxy}phenyl)-N-[4-chloro-3-(trifluoromethyl)phenyl]propanamide (A-36)

A solution of A-23 (65 mg, 0.17 mmol) in 7N ammonia in MeOH (10 mL) was treated with 5% Rainey Nickel and exposed to a hydrogen atmosphere at rt for 2 h. The reaction mixture was diluted with water, and MeOH was removed in vacuo. The mixture was acidified with 2M HCl in dioxane and taken up in MeOH and DMF, filtered through a pad of Celite® and concentrated. The mixture is taken up in water and treated with TEA to form a precipitate that is filtered, treated with 2M HCl in ether, and recrystallized from MeOH and ether to yield A-36.

Step 2. Preparation of N-[4-chloro-3-(trifluoromethyl)phenyl]-3-[4-({2-[(methylamino)methyl]pyridin-4-yl}oxy)phenyl]propanamide (A-30)

To A-36 (1.0 eq) in ACN at rt was added formaldehyde (1.5 eq) followed by sodium cyanoborohydride (3.1 eq), and a few drops of acetic acid. The mixture was allowed to stir for 5 h and then concentrated. The residue was dissolved in sat. sodium carbonate solution and the mixture was extracted into EtOAc. The organic solutions were combined, washed with brine, dried over $Na_2SO_4$, and concentrated. Purification by column chromatography gave A-30.

Example 13

Preparation of 1-(4-Chloro-3-trifluoromethyl-phenyl)-4-{4-[2-(4,5-dihydro-1H-imidazol-2-yl)-pyridin-4-yloxy]-phenyl}-butan-2-one (A-27)

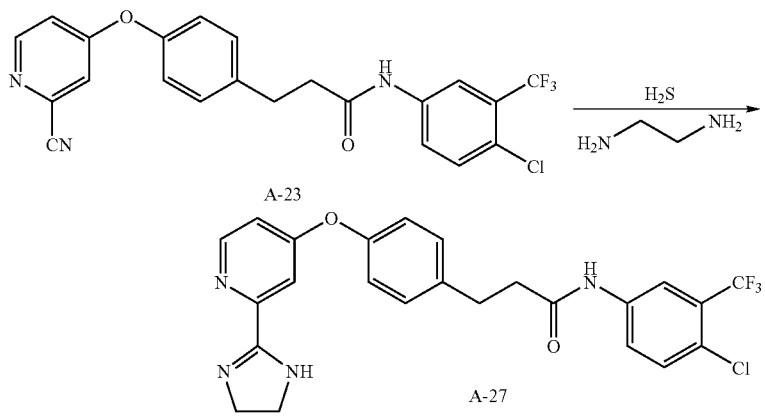

$H_2S$ was bubbled into a solution of A-23 (107 mg, 0.2 mmol) in ethylenediamine (1 mL) for 15 min. The solution stirred for 72 hr at 60° C. and then diluted with water. The solution was extracted with DCM and the organic solution was washed with brine, dried over MgSO4, filtered, and concentrated. The residue was purified by flash chromatography (MeOH/DCM) and then crystallized with 1N HCl/$Et_2O$ to give A-27 (46 mg, 44%). $^1$H NMR (300 MHz, $d_6$-$CD_3OD$): δ 8.62 (d, J=5.0 Hz, 1H), 8.10 (s, 1H), 7.75 (d, J=8.3 Hz, 1H), 7.65 (s, 1H), 7.52 (d, J=8.3 Hz, 1H), 7.42 (d, J=7.5 Hz, 2H), 7.07-7.13 (m, 3H), 4.12 (s, 4H), 3.07 (t, J=7.0 Hz), and 2.76 (t, J=7.0 Hz). LCMS FA: $R_t$=1.09 min, [MH$^+$ 498.3].

Compounds in the following table were prepared from the appropriate starting materials in a method analogous to that of Example 13:

| | |
|---|---|
| A-35 | ¹H NMR(300MHz, CD₃OD, HCl salt): δ 8.59(d, J=5.5Hz, 1H), 8.12(s, 1H), 7.77(d, J=5.0Hz, 1H), 7.65(s, 1H), 7.54(d, J=8.5Hz, 1H), 7.42(d, J=7.5Hz, 1H), 7.12(d, J=7.8Hz, 3H), 3.63(br t, J=5.3Hz, 4H), 3.08(t, J=7.0Hz, 2H), 2.77(t, J=7.0, 2H), and 2.12(t, J=4.0Hz, 2H). LCMS FA: R$_f$=1.53min, [MH⁺ 503.0]. |
| A-103 | ¹H NMR(400MHz, d6 DMSO; HCl salt) δ: 10.82(s, 1H), 10.09(s, 1H), 8.63(d, 1H), 8.38-8.33(m, 1H), 7.91-7.89(m, 1H), 7.53-7.42(m, 3H), 7.27-7.23(m, 1H), 7.21-7.18(m, 1H), 7.15-7.13(m, 1H), 7.09-7.05(m, 1H), 3.99(s, 4H), 2.97(t, 2H), and 2.79(t, 2H); LCMS: (FA)ES⁺ 473.3(M+1), ES⁻ 471.3(M−1). |
| A-182 | ¹H NMR(400MHz, d6 DMSO; HCl salt) δ: 10.87-10.77(m, 2H), 10.14-10.06(m, 1H), 8.67-8.57(m, 1H), 7.94-7.86(m, 1H), 7.44(t, 1H), 7.29-7.14(m, 2H), 7.15-6.86(m, 3H), 6.53-6.41(m, 1H), 4.05-3.93(m, 4H), 3.77-3.65(m, 4H), 3.10-2.99(m, 4H), 2.95(t, 2H), and 2.65(t, 2H). LCMS: (FA)ES⁺ 490.3(M+1), ES⁻ 488.2(M−1). |
| A-223 | ¹H NMR(300MHz, CD₃OD; HCOOH salt) δ: 8.58(d, 1H), 8.42(br s, 1H), 7.65-7.62(m, 1H), 7.49-7.32(m, 4H), 7.29-7.23(m, 1H), 7.14-7.07(m, 3H), 4.09(s, 4H), 3.05(t, 2H), 2.70(t, 2H), and 2.32(s, 3H). LCMS: (FA)ES+ 435.9(M+1), ES− 433.0(M−1). |
| A-249 | ¹H NMR(300MHz, CD₃OD; HCOOH salt) δ: 8.44(d, 1H), 7.67-7.62(m, 1H), 7.53-7.50(m, 1H), 7.45-7.37(m, 1H), 7.32-7.18(m, 3H), 7.08-6.96(m, 4H), 3.93(s, 4H), 3.03(t, 2H), and 2.69(t, 2H). LCMS: (FA)ES+ 421.0(M+1), ES− 419.0(M−1). |
| A-219 | ¹H NMR(400MHz, CD₃OD; HCl salt) δ: 8.51(d, 1H), 7.65-7.63(m, 1H), 7.54-7.53(m, 1H), 7.48-7.43(m, 1H), 7.33-7.28(m, 1H), 7.20-7.14(m, 3H), 7.05-7.00(m, 1H), 6.90-6.86(m, 1H), 3.92(s, 4H), 3.69(s, 3H), 3.08(t, 2H), 2.78(t, 2H), and 1.23(s, 9H). LCMS: (FA)ES+ 473.4(M+1). |
| A-93 | ¹H NMR(400MHz, CD₃OD; HCl salt) δ: 8.48(d, 1H), 7.58-7.55(m, 1H), 7.45(t, 1H), 7.30-7.08(m, 6H), 7.04-6.99(m, 1H), 6.96(m, 1H), 4.04(s, 4H), 3.07(t, 2H), 2.72(t, 2H), 2.55(q, 2H), and 1.17(t, 3H). LCMS: (FA)ES+ 415.1(M+1), ES− 413.1(M−1). |
| A-210 | ¹H NMR(400MHz, CD₃OD; HCOOH salt) δ: 8.49(d, 1H), 7.48-7.41(m, 2H), 7.30-7.25(m, 1H), 7.19(br s, 1H), 7.15-7.12(m, 1H), 7.09-7.04(m, 3H), 7.02-6.99(m, 1H), 4.00(s, 4H), 3.06(t, 2H), 2.83(t, 2H), 2.76(t, 2H), 2.68(t, 2H), and 2.10-2.00(m, 2H). LCMS: (FA)ES+ 427.3(M+1). |
| A-162 | ¹H NMR(300MHz, CD₃OD; HCl salt) δ: 8.58(d, 1H), 7.64-7.60(m, 1H), 7.45-7.36(m, 4H), 7.35-7.29(m, 2H), 7.14-7.03(m, 3H), 4.10(s, 4H), 3.06(t, 2H), 2.70(t, 2H), and 1.29(s, 9H). LCMS: (FA)ES+ 443.7(M+1), ES− 441.2(M−1). |
| A-241 | ¹H NMR 300MHz, CD₃OD; HCOOH salt) δ: 8.49(d, 1H), 7.54-7.50(m, 1H), 7.47-7.39(m, 2H), 7.28-7.23(m, 1H), 7.19-7.06(m, 4H), 7.03-6.92(m, 2H), 4.04(s, 4H), 3.05(t, 2H), 2.70(t, 2H), and 2.41(s, 3H). LCMS: (FA)ES+ 433.5(M+1), ES− 430.9(M−1). |
| A-86 | ¹H NMR 400MHz, CD₃OD HCOOH salt) δ: 8.56(d, 1H), 8.00(br s, 1H), 7.72-7.69(m, 1H), 7.62-7.60(m, 1H), 7.52-7.46(m, 1H), 7.43-7.35(m, 3H), 7.12-7.08(m, 3H), 3.62-3.58(m, 4H), 3.07(t, 2H), 7.74(t, 2H), and 2.15-2.06(m, 2H). LCMS: (FA)ES+ 469.9(M+1), ES− 467.1(M−1). |
| A-119 | ¹H NMR 400MHz, CD₃OD; HCOOH salt) δ: 8.40(d, 1H), 7.47-7.44(m, 1H), 7.28-7.23(m, 3H), 7.06-7.02(m, 1H), 6.99-6.92(m, 4H), 3.45(t, 4H), 2.91(t, 2H), 2.70(q, 4H), 2.54(t, 2H), and 1.20-1.87(m, 4H). LCMS: (FA)ES+ 441.7(M+1). |
| A-161 | ¹H NMR 300MHz, CD₃OD; HCl salt) δ: 8.50(d, 1H), 7.55-7.53(m, 1H), 7.44(t, 1H), 7.32-7.24(m, 5H), 7.15-7.07(m, 2H), 7.04-6.98(m, 1H), 4.04(s, 4H), 3.06(t, 2H), 2.70(t, 2H), and 1.28(s, 9H). LCMS: (FA)ES+ 443.2(M+1), ES− 441.1(M−1). |
| A-72 | ¹H NMR 300MHz, CD₃OD) δ: 8.50(d, 1H), 7.55-7.51(m, 1H), 7.43(t, 1H), 7.34(br s, 1H), 7.28-7.19(m, 3H), 7.13-6.98(m, 3H), 4.05(s, 4H), 3.05(t, 2H), 2.69(t, 2H), and 2.27(s, 3H). LCMS: (FA)ES+ 435.9(M+1), ES− 433.0(M−1). |
| A-138 | ¹H NMR 400MHz, CD₃OD; HCOOH salt) δ: 8.57(d, 1H), 7.65-7.63(m, 1H), 7.42-7.36(m, 3H), 7.20-7.17(m, 1H), 7.13-7.07(m, 4H), 4.08(s, 4H), 3.05(t, 2H), 2.86-2.81(m, 4H), 2.68(t, 2H), and 2.11-2.00(m, 2H). LCMS: (FA)ES+ 427.5(M+1). |
| A-264 | ¹H NMR 400MHz, CD₃OD; HCl salt) δ: 8.46(d, 1H), 7.46-4.42(m, 2H), 7.28-7.25(m, 1H), 7.20(br s, 1H), 7.12-7.05(m, 4H), 7.03-6.99(m, 1H), 3.51(t, 4H), 306.00(t, 2H), 2.82(t, 2H), 2.77(t, 2H), 2.68(t, 2H), and 2.10-1.99(m, 4H). LCMS: (FA)ES+ 441.2(M+1). |
| A-254 | ¹H NMR 400MHz, CD₃OD; HCl salt) δ: 8.52(d, 1H), 7.81-7.78(m, 1H), 7.58-7.56(m, 1H), 7.44(t, 1H), 7.35-7.32(m, 1H), 7.28-7.25(m, 2H), 7.24-7.15(m, 2H), 7.12-7.06(m, 2H), 7.04-7.00(m, 1H), 4.08(s, 4H), 3.06(t, 2H), and 2.71(t, 2H). LCMS: (FA)ES+ 465.2(M+1), ES− 463.3(M−1). |
| A-95 | ¹H NMR 300MHz, CD₃OD) δ: 8.58(d, 1H), 7.66-7.63(m, 1H), 7.44-7.27(m, 4H), 7.19(t, 1H), 7.13-7.08(m, 3H), 6.95-6.90(m, 1H), 4.10(s, 4H), 3.06(t, 2H), 2.71(t, 2H), 2.59(q, 2H), and 1.21(t, 3H). LCMS: (FA)ES+ 415.9(M+1), ES− 413.1(M−1). |
| A-131 | ¹H NMR 300MHz, CD₃OD; HCOOH salt) δ: 8.53(d, 1H), 7.72-7.67(m, 2H), 7.63-7.53(m, 3H), 7.47-7.38(m, 1H), 7.30-7.22(m, 1H), 7.12-7.08(m, 2H), 7.03-7.00(m, 1H), 4.09(s, 4H), 3.07(t, 2H), and 2.75(t, 2H). LCMS: (FA)ES+ 455.6(M+1), ES− 453.1(M−1). |
| A-106 | ¹H NMR 300MHz, CD₃OD; HCOOH salt) δ: 8.59(d, 1H), 7.65-7.62(m, 1H), 7.55-7.50(m, 2H), 7.43-7.37(m, 2H), 7.31-7.23(m, 2H), 7.15-7.06(m, 3H), 4.10(s, 4H), 3.05(t, 2H), and 2.71(t, 2H). LCMS: (FA)ES+ 421.9(M+1), ES− 419.0(M−1). |
| A-146 | ¹H NMR 300MHz, CD₃OD) δ: 8.48(d, 1H), 7.54-7.52(m, 1H), 7.44(t, 1H), 7.29-7.25(m, 1H), 7.22-7.07(m, 5H), 7.04-6.98(m, 1H), 6.94-6.89(m, 1H), 4.02(s, 4H), 3.06(t, 2H), 2.70(t, 2H), and 2.25(s, 3H). LCMS: (FA)ES+ 401.1(M+1), ES− 399.1(M−1). |

-continued

A-126 ¹H NMR 300MHz, CD₃OD; HCOOH salt) δ: 8.58(d, 1H), 7.65-7.60(m, 1H), 7.44-7.38(m, 2H), 7.34-7.26(m, 2H), 7.20-7.06(m, 4H), 6.92-6.86(m, 1H), 4.09(s, 4H), 3.06(t, 2H), 2.70(t, 2H), and 2.30(s, 3H). LCMS: (FA)ES+ 401.1(M+1), ES− 399.1(M−1).

A-168 ¹H NMR 400MHz, CD₃OD; HCOOH salt) δ: 8.53-8.50(m, 1H), 7.47-7.41(m, 2H), 7.27-7.24(m, 1H), 7.14-7.12(m, 1H), 7.05-6.99(m, 2H), 6.93-6.91(m, 1H), and 6.74-6.67(m, 2H). LCMS: (FA)ES+ 445.1(M+1), ES− 443.1(M−1).

A-242 ¹H NMR 300MHz, CD₃OD; HCOOH salt) δ: 8.52(d, 1H), 7.58-7.57(m, 1H), 7.47-7.40(m, 3H), 7.28-7.21(m, 3H), 7.11-7.08(m, 1H), 7.06-6.90(m, 2H), 4.07(s, 4H), 3.05(t, 2H), and 2.70(t, 2H). LCMS: (FA)ES+ 421.9(M+1), ES− 419.0(M−1).

A-121 ¹H NMR 400MHz, CD₃OD; HCL salt) δ: 8.50(d, 1H), 7.49(d, 1H), 7.44(t, 1H), 7.29-7.22(m, 3H), 7.14-7.12(m, 1H), 7.08-7.00(m, 4H), 4.03(s, 4H), 3.06(t, 2H), 2.69(t, 2H), and 2.28(s, 3H). LCMS: (FA)ES+ 401.2(M+1), ES− 399.1(M−1).

A-177 ¹H NMR(300MHz, CD₃OD; HCl salt) δ: 8.58(d, 1H), 7.65-7.61(m, 1H), 7.45-7.37(m, 3H), 7.36-7.29(m, 1H), 7.23-7.15(m, 1H), 7.13-7.07(m, 3H), 6.99-6.93(m, 1H), 4.01(s, 4H), 3.06(t, 2H), 2.92-2.80(m, 1H), 2.71(t, 2H), and 1.22(d, 6H). LCMS: (FA)ES+ 429.9(M+1), ES− 427.0(M−1).

A-80 ¹H NMR(400MHz, CD₃OD; HCl salt) δ: 8.48(d, 1H), 7.99(br s, 1H), 7.76-7.69(m, 1H), 7.56-7.46(m, 2H), 7.42-7.35(m, 3H), 7.12-7.07(m, 2H), 7.04-7.00(m, 1H), 3.84(s, 4H), 3.07(t, 2H), and 2.74(t, 2H). LCMS: (FA)ES+ 455.5(M+1), ES− 453.1(M−1).

A-94 ¹H NMR(300MHz, CD₃OD; HCl salt) δ: 8.47(d, 1H), 7.62−7.58(m, 1H), 7.45(t, 1H), 7.32-7.23(m, 3H), 7.18(t, 1H), 7.12-7.07(m, 2H), 7.06-6.95(m, 2H), 4.05(s, 4H), 3.07(t, 2H), 2.89-2.76(m, 1H), 2.72(t, 2H), and 1.19(d, 6H). LCMS: (FA) ES+ 429.2(M+1), ES− 427.1(M−1).

A-100 ¹H NMR(400MHz, CD₃OD) δ: 8.48(d, 1H), 8.20(br s, 2H), 7.94(br s, 1H), 7.66-7.63(m, 1H), 7.61-7.59(m, 1H), 7.49-7.40(m, 2H), 7.37-7.33(m, 1H), 7.29-7.25(m, 1H), 7.10-7.04(m, 2H), 7.02-6.99(m, 1H), 3.62-3.56(m, 4H), 3.07(t, 2H), 2.74(t, 2H), and 2.13-2.04(m, 2H). LCMS: (FA)ES+ 469.8(M+1), ES− 467.1(M−1).

A-230 ¹H NMR(400MHz, CD₃OD; HCl salt) δ: 8.40(d, 1H), 7.65-7.62(m, 1H), 7.47-7.42(m, 1H), 7.32-7.26(m, 3H), 7.21(br s, 1H), 7.11(br s, 1H), 7.07-7.05(m, 1H), 7.03-6.98(m, 1H), 4.04(s, 4H), 3.06(t, 2H), 2.71(t, 2H), and 1.27(s, 18H). LCMS: (FA) ES+ 429.2(M+1).

A-151 ¹H NMR(300MHz, CD₃OD; HCOOH salt) δ: 8.51(d, 1H), 8.18(br s, 4H), 7.94(br s, 1H), 7.66-7.61(m, 1H), 7.61-7.59(m, 1H), 7.49-7.40(m, 2H), 7.39-7.25(m, 2H), 7.11-7.09(m, 2H), 7.03-7.00(m, 1H), 4.08(s, 4H), 3.07(t, 2H), and 2.74(t, 2H). LCMS: (FA)ES+ 455.6(M+1).

A-194 ¹H NMR(300MHz, CD₃OD; HCOOH salt) δ: 8.53(br s, 1H), 8.48(d, 1H), 7.55-7.52(m, 1H), 7.46-7.35(m, 3H), 7.29-7.22(m, 1H), 7.09-6.97(m, 4H), 4.00(s, 4H), 3.05(t, 2H), and 2.69(t, 2H). LCMS: (FA)ES+ 513.30(M+1).

A-115 ¹H NMR(300MHz, CD₃OD; HCl salt) δ: 8.58(d, 1H), 7.63-7.61(m, 1H), 7.55-7.51(m, 1H), 7.45-7.38(m, 2H), 7.37-7.31(m, 1H), 7.26-7.17(m, 1H), 7.16-7.06(m, 4H), 4.10(s, 4H), 3.06(t, 2H), 2.71(t, 2H), and 1.30(s, 9H). LCMS: (FA)ES+ 443.40(M+1).

A-59 ¹H NMR(300MHz, CD₃OD; HCl salt) δ: 8.46(d, 1H), 7.59-7.55(m, 1H), 7.48-7.41(m, 2H), 7.32-7.07(m, 4H), 7.05-6.98(m, 1H), 4.04(s, 4H), 3.06(t, 2H), 2.71(t, 2H), and 1.26(s, 9H).

A-255 ¹H NMR(400MHz, CDCl₃) δ: 9.5(br s, 1H), 8.45(d, 1H), 7.70-7.75(m, 1H), 7.49-7.54(m, 2H), 7.42-7.47(m, 1H), 7.28(t, 1H), 7.08(dd, 1H), 7.04-7.07(m, 1H), 6.98-7.01(m, 1H), 6.92-6.96(m, 1H), 3.77(br s, 4H), 3.004(t, 2H), and 2.62(t, 2H). LCMS FA: R₁=2.05min, [MH⁺ 489.1].

A-203 ¹H NMR(400MHz, CDCl₃) δ: 8.4(d, 1H), 8.27-8.35(m, 1H), 8.05(br s, 1H), 7.61(d, 1H), 7.28-7.37(m, 2H), 7.15-7.22(m, 1H), 7.09-7.14(m, 1H), 7.00-7.04(m, 1H), 6.94-7.00(m, 2H), 3.73(br s, 4H), 3.06(t, 2H), and 2.74(t, 2H). LCMS, FA: R₁=1.93min, [MH⁺ 471.1].

A-108 ¹H NMR(400MHz, CDCl₃) δ: 9.66(br s, 1H), 8.44(d, 1H), 7.58-7.63(m, 1H), 7.52-7.54(m, 1H), 7.45-7.48(m, 1H), 7.24-7.30(m, 1H), 7.03-7.11(m, 2H), 6.96-7.00(m, 2H), 6.91-6.95(m, 1H), 3.76(br s, 4H), 2.98-3.07(m, 2H), and 2.55-2.65(m, 2H). LCMS, FA: R₁=1.22min, [MH⁺ 473.8].

A-189 ¹H NMR(400MHz, CDCl₃) δ: 8.56(br s, 1H), 8.43(d, 1H), 7.67(br s, 1H), 7.62(d, 1H), 7.28-7.38(m, 2H), 7.20-7.25(m, 1H), 7.11-7.17(m, 1H), 7.05-7.09(m, 2H), 6.97-7.02(m, 1H), 3.65(br s, 4H), 3.08(t, 2H), 2.7(t, 2H), and 2.02(s, 3H). LCMS, FA: R₁=1.17min, [MH⁺ 469.8].

A-53 ¹H NMR(400MHz, CDCl₃; HCOOH salt) δ: 11.98(br s, 1H), 8.38(d, 1H), 8.31(s, 1H), 7.68(br s, 2H), 7.48-7.54(m, 1H), 7.36(t, 1H), 7.09-7.18(m, 2H), 6.88(d, 1H), 6.84(br s, 1H), 6.09(s, 1H), 4.05(s, 4H), 3.00-3.09(m, 2H), 2.69-2.79(m, 2H), and 1.16(s, 9H). LCMS, FA: R₁=1.08min, [MH⁺ 434.3].

A-130 ¹H NMR(400MHz, CDCl₃) δ: 8.98(br s, 1H), 8.43(d, 1H), 7.57(d, 1H), 7.44(br s, 1H), 7.32-7.38(m, 1H), 7.28(t, 1H), 7.23(t, 1H), 7.07-7.11(m, 2H), 7.05(dd, 1H), 7(br s, 1H), 6.87-6.96(m, 2H), 3.76(br s, 4H), 3.04(t, 2H), and 2.62(t, 2H). LCMS, FA:[MH⁺ 472.3].

A-128 ¹H NMR(400MHz, CDCl₃) δ: 9.05(br s, 1H), 8.42(d, 1H), 7.59(dd, 1H), 7.55(d, 1H), 7.49(d, 1H), 7.29(t, 1H), 7.06(br d, 1H), 7.05(dd, 1H), 6.99(br s, 1H), 6.93-6.96(m, 1H), 6.86(d, 1H), 3.85(s, 3H), 3.74(br s, 4H), 3.02(t, 2H), and 2.59(t, 2H). LCMS, FA: R₁=1.18min, [MH⁺ 485.8].

A-195 ¹H NMR(400MHz, CDCl₃) δ: 9.02(br s, 1H), 8.42(d, 1H), 7.59(dd, 1H), 7.55(d, 1H), 7.49(d, 1H), 7.29(t, 1H), 7.08(br d, 1H), 7.05(dd, 1H), 6.99(br s, 1H), 6.93-6.96(m, 1H), 6.86(d, 1H), 3.85(s, 3H), 3.74(br s, 4H), 3.02(t, 2H), and 2.59(t, 2H). LCMS, FA: R₁=1.18min, [MH⁺ 469.8].

|   |   |
|---|---|
| | -continued |
| A-176 | ¹H NMR(400MHz, CDCl₃) δ: 8.41(br s, 1H), 8.4(d, 1H), 8.32(br s, 1H), 7.67(d, 1H), 7.62(d, 1H), 7.37(t, 1H), 7.2(dd, 1H), 7.14-7.18(m, 1H), 7.00-7.04(m, 2H), 6.93-6.96(m, 2H), 3.84(s, 4H), 3.1(t, 2H), and 2.79(t, 2H). LCMS, FA: R$_r$=2.03min, [MH⁺ 533.1]. |
| A-89 | ¹H NMR(400MHz, CDCl₃) δ: 8.59(br s, 1H), 8.39(d, 1H), 7.81(br s, 1H), 7.71(d, 1H), 7.45(d, 1H), 7.35(t, 1H), 7.27-7.32(m, 1H), 7.11-7.15(m, 1H), 7.00-7.03(m, 1H), 6.94-6.97(m, 1H), 6.93(dd, 1H), 3.78(br s, 4H), 3.1(t, 2H), and 2.77(t, 2H). LCMS, FA:[MH⁺ 489.1]. |
| A-157 | ¹H NMR(400MHz, CDCl₃) δ: 9.84(br s, 1H), 8.46(d, 1H), 7.98(br s, 2H), 7.54(d, 1H), 7.51(br s, 1H), 7.27-7.33(m, 1H), 7.05-7.16(m, 2H), 6.93-6.99(m, 1H), 3.76(br s, 4H), 3.06(t, 2H), and 2.64(t, 2H). LCMS, FA: R$_r$=1.31min, [MH⁺ 523.8]. |
| A-257 | ¹H NMR(400MHz, d₆-DMSO) δ: 10.4(s, 1H), 8.55(d, 1H), 8.18(s, 1H), 7.8(d, 1H), 7.75(d, 1H), 7.5(s, 1H), 7.42(t, 1H), 7.22(d, 1H), 7.1-7.08(m, 2H), 7.02(d, 1H), 3.7(s, 4H), 2.95(t, 2H), 2.65(t, 2H), 1.78(d, 1H). LCMS: (FA)ES+ 491.86(M+1), ES− 489.81(M−1). |
| A-213 | ¹H NMR(400MHz, CD₃OD) δ: 8.42(d, 1H), 7.95-7.90(m, 1H), 7.7-7.65(m, 1H), 7.55-7.53(m, 1H), 7.42(t, 1H), 7.25-7.20(m, 2H), 7.07(t, 1H), 7-6.98(m, 2H), 3.85(s, 4H), 3.06(t, 2H), 2.71(t, 2H). LCMS: (FA)ES+ 473.16(M+1), ES− 470.98(M−1). |
| A-239 | ¹H NMR(400MHz, CD₃OD) δ: 8.4(s, 1H), 7.99(s, 1H), 7.95(s, 1H), 7.48(d, 1H), 7.45-7.40(m, 2H), 7.25(d, 1H), 7(s, 1H), 7-6.95(m, 2H), 3.8(s, 4H), 3.05(t, 2H), 2.71(t, 2H). LCMS: (FA)ES+ 581.06(M+1), ES− 578.87(M−1). |
| A-127 | ¹H NMR(400MHz, CD₃OD) δ: 8.46(d, 1H), 8.06(d, 1H), 7.13(dd, 1H), 7.48-7.53(m, 2H), 7.42(d, 1H), 7.32(dd, 1H), 7.21(d, 1H), 6.97(dd, 1H), 3.77(br s, 4H), 3.05(t, 2H), 2.73(t, 2H), and 3.05(t, 2H). LCMS, FA: R$_r$=1.33min, [MH⁺ 524.1]. |
| A-137 | ¹H NMR(300MHz, CD₃OD); bisHCl salt) δ: 8.53(d, 1H), 8.05(d, 1H), 7.71(dd, 1H), 7.64(d, 1H), 7.53-7.42(m, 2H), 7.27(d, 1H), 7.10-7.07(m, 2H), 7.03(dd, 1H), 4.42-4.38(m, 1H), 3.68-3.52(m, 4H), 3.07(t, 2H), and 2.74(t, 2H). LCMS: (FA)ES+ 519.94(M+1), ES− 516.97(M−1). |
| A-143 | ¹H NMR(300MHz, d₆-DMSO) δ: 11.36(s, 1H), 10.22(br s, 1H), 8.62(d, 1H), 8.37(d, 1H), 8.03(dd, 1H), 7.81(d, 1H), 7.59(d, 1H), 7.42(t, 1H), 7.28(dd, 1H), 7.22-7.18(m, 2H), 7.07(dd, 1H), 4.02(t, 1H), 3.57-3.30(m, 2H), 2.92(t, 2H), 2.77-2.67(m, 2H), and 2.11-2.02(m, 2H). LCMS: (FA)ES+ 547.04(M+1), ES− 545.00(M−1). |
| A-154 | ¹H(400MHz, d₆-DMSO) δ: 8.6(d, 1H), 7.55-7.42(m, 4H), 7.26-7.03(m, 6H), 3.69(s, 4H), 3.19(s, 3H), 2.96(t, 2H), 2.65(t, 2H) and 1.23(s, 9H). LCMS: (FA)ES⁺ 457.18(M+1). |
| A-61 | ¹H NMR(300MHz, CD₃OD; HCl salt) δ: 8.35(d, 1H), 7.59(d, 1H), 7.47(d, 1H), 7.25-7.41(m, 3H), 7.19(d, 1H), 7.03(t, 1H), 6.94-6.98(m, 1H), 6.91(dd, 1H), 3.74(s, 4H), 3.02(t, 2H), 2.65(t, 2H), and 1.43(s, 9H). |
| A-111 | ¹H NMR(300MHz, CD₃OD) δ: 8.37(d, 1H), 7.81-7.82(m, 1H), 7.47(d, 1H), 7.40(t, 1H), 7.34-7.35(m, 2H), 7.21(d, 2H), 7.04-7.05(m, 1H), 6.93-6.99(m, 2H), 3.77(s, 4H), 3.03(t, 2H), 2.66(t, 2H), and 1.47(s, 9H). |
| A-129 | ¹H NMR(300MHz, CD₃OD; HCl salt) δ: 8.56(d, 1H), 7.68-7.60(m, 2H), 7.50-7.40(m, 2H), 7.28-7.23(m, 1H), 7.17-7.08(m, 2H), 7.06-6.98(m, 2H), 4.46-4.73(m, 2H), 4.11(s, 4H), 3.67-3.56(m, 2H), 3.06(t, 2H), 2.99(s, 6H), and 2.75(t, 3H). LCMS: (FA)ES+ 542.3(M+1). |
| A-231 | ¹H NMR(300MHz, CD₃OD; 3*HCl salt) δ: 8.56(d, 1H), 7.67-7.62(m, 2H), 7.48-7.40(m, 2H), 7.29-7.23(m, 1H), 7.15-7.10(m, 2H), 7.07-6.98(m, 2H), 4.48-4.42(m, 2H), 4.14-4.03(m, 6H), 3.90-3.79(m, 2H), 3.70-3.54(m, 4H), 3.09-3.00(m, 2H), and 2.78-2.71(m, 2H). LCMS: (FA)ES+ 584.40(M+1), ES− 582.40(M−1). |
| A-220 | ¹H NMR(300MHz, CD₃OD; HCl salt) δ: 8.56(d, 1H), 7.67-7.60(m, 2H), 7.51-7.40(m, 2H), 7.29-7.25(m, 1H), 7.16-7.10(m, 2H), 7.04-6.98(m, 2H), 4.12-4.35(m, 2H), 4.10(s, 4H), 3.78-3.67(m, 4H), 3.27-3.18(m, 2H), 3.10-3.00(m, 2H), 2.79-2.70(m, 2H), and 2.26-1.99(m, 4H). LCMS: (FA)ES+ 568.4(M+1), ES− 566.4(M−1). |
| A-104 | ¹H NMR(400MHz, CDCl₃) δ: 8.69(s, 1H), 8.35(d, 1H), 7.56(d, 1H), 7.50-7.52(m, 1H), 7.37-7.41(m, 1H), 7.27(t, 1H), 7.2(t, 1H), 7.12-7.15(m, 1H), 7.04-7.08(m, 1H), 6.96(dd, 1H), 6.93-6.95(m, 1H), 6.86-6.93(m, 1H), 3.72(br s, 4H), 3.00(t, 2H), 2.58(t, 2H), and 1.5(s, 6H). LCMS, FA: R$_r$=0.99min, [MH⁺ 445.2]. |
| A-190 | ¹H(400MHz, CD₃OD; HCOOH salt) δ: 8.54(d, 1H), 8.44(s, 1H), 8.21(s, 1H), 8.09(s, 1H), 7.85(s, 1H), 7.6(d, 1H), 7.43(t, 1H), 7.27-7.25(m, 1H), 7.12-7.08(m, 2H), 7.02-6.99(m, 1H), 4.07(s, 4H), 3.7(t, 2H), 3.15-3.06(m, 4H), and 2.78-2.74(m, 8H). LCMS: (FA)ES⁺ 569.4(M+1), ES⁻ 567.4(M−1). |
| A-191 | ¹H(300MHz, d₆-DMSO) δ: 10.47(s, 1H), 8.78(s, 1H), 8.48(d, 1H), 8.2(d, 1H), 7.86(s, 1H), 7.47-7.39(m, 2H), 7.23-7.01(m, 4H), 3.65(s, 4H), 3.45-3.41(m, 4H), 3.25(s, 3H), 2.96(t, 2H), and 2.69(t, 2H). LCMS: (FA)ES⁺ 556.41(M+1), ES⁻ 554.45(M−1). |
| A-248 | ¹H NMR(300MHz, CD₃OD; HCOOH salt) δ: 8.55(d, 1H), 8.27(s, 2H), 8.05(d, 1H), 7.70(dd, 1H), 7.65(d, 1H), 7.52-7.42(m, 2H), 7.27(d, 1H), 7.13-7.08(m, 2H), 7.03(dd, 1H), 4.65-4.55(m, 1H), 4.15(t, 1H), 3.91(dd, 1H), 3.64-3.53(m, 2H), 3.41(s, 3H), 3.07(t, 2H), and 2.74(t, 2H). LCMS: (FA)ES+ 533.31(M+1), ES− 531.41(M−1). |
| A-166 | ¹H NMR(300MHz, d₆-DMSO; bisHCl salt) δ: 10.83(s, 2H), 9.68(s, 1H), 8.55(d, 1H), 7.92(d, 1H), 7.63(t, 1H), 7.54-7.50(m, 1H), 7.43(t, 1H), 7.27(d, 1H), 7.22-7.06(m, 5H), 4.29(dd, 1H), 3.99(s, 4H), 3.10(dd, 1H), 2.91(dd, 1H), and 1.23(s, 9H). LCMS: (FA)ES+ 459.26(M+1), ES− 457.36(M−1). |
| A-169 | ¹H NMR(300MHz, d₆-DMSO; bisHCl salt) δ: 10.92(s, 2H), 10.79(s, 1H), 8.60(d, 1H), 8.01-7.99(m, 2H), 7.71(d, 1H), 7.63(dd, 1H), 7.44(t, 1H), 7.25(d, 1H), |

| | -continued |
|---|---|
| | 7.18-7.14(m, 2H), 7.06(dd, 1H), 3.99(s, 4H), 2.98(t, 2H), 2.76(t, 2H), and 1.56(s, 6H). LCMS: (FA)ES+ 471.69(M+1), ES− 469.40(M−1). |
| A-76 | ¹H NMR(300MHz, d₆-DMSO; bisHCl salt) δ: 10.90(s, 2H), 9.98(s, 1H), 8.59(d, 1H), 7.98(d, 1H), 7.43(t, 1H), 7.34-7.23(m, 3H), 7.17-7.03(m, 4H), 6.72(d, 1H), 3.99(s, 4H), 2.95(t, 2H), 2.65(t, 2H), 1.87-1.78(m, 1H), 0.94-0.87(m, 2H), and 0.60-0.55(m, 2H). LCMS: (FA)ES+ 427.59(M+1). |
| A-142 | ¹H NMR(300MHz, d₆-DMSO; HCl salt) δ: 10.70(s, 1H), 8.68(d, 1H), 8.24(d, 1H), 7.96(d, 1H), 7.88(dd, 1H), 7.64(d, 1H), 7.42-7.39(m, 2H), 7.25(d, 1H), 7.18-7.15(m, 2H), 5.07-5.00(m, 1H), 4.26(t, 1H), 4.16-4.09(m, 1H), 2.97(t, 2H), and 2.73(t, 2H). LCMS: (FA)ES+ 533.04(M+1), ES− 530.94(M−1). |
| A-208 | ¹H NMR(400MHz, d₆-DMSO; HCl salt) δ: 11.34(s, 1H), 11.23(s, 1H), 10.71(s, 1H), 8.66(d, 1H), 8.21(d, 1H), 8.01(d, 1H), 7.85(dd, 1H), 7.63(d, 1H), 7.44(t, 1H), 7.26-7.22(s, 2H), 7.15(s, 1H), 7.06(dd, 1H), 5.05(dd, 1H), 4.27(t, 1H), 4.13(dd, 1H), 2.97(t, 2H), and 2.72(t, 2H). LCMS: (FA)ES+ 533.00(M+1), ES− 530.97(M−1). |
| A-67 | ¹H NMR(400MHz, d₆-DMSO) δ: 10.36(s, 1H), 8.47(d, 1H), 8.00(s, 1H), 7.75-7.63(m, 2H), 7.50(d, 1H), 7.42(t, 1H), 7.22(d, 1H), 7.09-7.01(m, 3H), 3.69(s, 4H), 2.96(t, 2H), and 2.68(t, 2H). LCMS: (FA)ES⁺ 499.3(M+1). |
| A-216 | ¹H NMR(400MHz, CD₃OD) δ: 8.36(d, 1H), 8.04(d, 1H), 7.82-7.76(m, 2H), 7.45(d, 1H), 7.38(t, 1H), 7.19(d, 1H), 7.04(t, 1H), 6.98-6.92(m, 2H), 3.87(s, 3H), 3.73(s, 4H), 3.04(t, 2H), 2.72(t, 2H), and 3.04(t, 2H). LCMS: (FA)ES⁺ 513.4(M+1), ES⁻ 511.3(M−1). |
| A-140 | ¹H NMR(400MHz, d₆-DMSO) δ: 8.78(s, 1H), 8.65(d, 1H), 7.93(s, 1H), 7.81(d, 1H), 7.36(d, 1H), 7.26(t, 1H), 7.09(s, 1H), 7.00(d, 2H), 6.20(d, 1H), 3.85(s, 4H), 2.90(t, 2H), and 2.60(t, 2H). LCMS: (FA)ES⁺ 505.0(M+1), ES⁻ 503.0(M−1). |
| A-120 | ¹H NMR(400MHz, CD₃OD) δ: 8.58(d, 1H), 7.98(d, 1H), 7.62(d, 1H), 7.34(s, 1H), 7.32(s, 1H), 7.21-7.19(m, 1H), 7.04(s, 1H), 7.02(s, 1H), 6.38(d, 1H), 4.00(s, 4H), 3.05(t, 2H), and 2.70(t, 2H). LCMS: (FA)ES⁺ 505.9(M+1), ES⁻ 503.0(M−1). |
| A-185 | ¹H NMR(300MHz, CD₃OD) δ: 6.88(d, 1H), 6.53(d, 1H), 5.93(d, 1H), 5.85(t, 1H), 5.74(d, 1H), 5.68(d, 1H), 5.54(s, 1H), 5.46-5.42(m, 2H), 2.21(s, 4H), 2.07(s, 3H), 1.52(t, 1H), and 1.27(t, 2H). LCMS: (FA)ES⁺ 519.0(M+1). |
| A-212 | ¹H NMR(300MHz, CD₃OD) δ: 8.39(d, 1H), 8.32(d, 1H), 7.91(d, 1H), 7.44(d, 1H), 7.40(t, 1H), 7.20(d, 1H), 7.04(s, 1H), 7.00-6.96(m, 2H), 3.76(s, 4H), 3.04(t, 2H), and 2.70(t, 2H). LCMS: (FA)ES⁺ 436.3(M+1), ES⁻ 34.3(M−1). |
| A-222 | ¹H NMR(300MHz, CD₃OD) δ: 8.35(d, 1H), 8.08(d, 1H), 7.86(s, 1H), 7.49(d, 1H), 7.38(t, 1H), 7.21(d, 1H), 7.06(s, 1H), 6.98-6.91(m, 3H), 3.74(s, 4H), 3.04(t, 2H), 2.74(t, 2H), and 2.32(s, 3H). LCMS: (FA)ES⁺ 402.3(M+1). |
| A-240 | ¹H NMR(400MHz, CD₃OD) δ: 8.39(d, 1H), 8.02(d, 1H), 7.70-7.66(m, 1H), 7.48-7.42(m, 3H), 7.34(d, 1H), 7.23-7.22(m, 1H), 7.05-7.01(m, 1H), 6.98-6.95(m, 1H), 4.45(t, 1H), 3.74(s, 4H), and 2.77-2.74(m, 2H). LCMS: (FA)ES⁺ 504.0(M+1), ES⁻ 502.0(M−1). |
| A-218 | ¹H NMR(300MHz, d₆-DMSO) δ: 8.82(s, 1H), 8.57(d, 1H), 8.39(s, 1H), 7.62(d, 1H), 7.33(t, 1H), 7.27-7.25(m, 1H), 7.15(s, 1H), 7.12(d, 1H), 6.99-6.96(m, 1H), 6.72(s, 1H), 3.77(s, 4H), 2.92(t, 2H), and 2.72(t, 2H). LCMS: (FA)ES⁺ 506.2(M+1), ES⁻ 503.2(M−1). |
| A-51 | ¹H NMR(400MHz, CD₃OD) δ: 8.35(d, 1H), 8.09-8.03(m, 2H), 7.75(s, 1H), 7.46(d, 1H), 7.40(t, 1H), 7.21(d, 1H), 7.07(t, 1H), 7.00-6.96(dd, 1H), 6.95-6.93(dd, 1H), 3.76(s, 4H), 3.74(s, 4H), 3.06(t, 2H), and 2.73(t, 2H). LCMS: (FA)ES⁺ 523.3(M+1), ES⁻ 521.3(M−1). |
| A-55 | ¹H NMR(400MHz, CD₃OD; bisHCl salt): δ 8.19(d, 1H), 7.68(s, 1H), 7.31(d, 1H), 7.28(d, 1H), 7.13(d, 1H), 7.08(dd, 1H), 6.91(d, 1H), 7.91(m, 1), 6.71-6.79(m, 1H), 6.67(d, 1H), 3.72(s, 4H), 2.69(dd, 2H), 2.38(dd, 2H). LCMS: (FA)ES+ 489.87(M+1), ES− 486.98(M−1). |
| A-175 | ¹H NMR(300MHz, CD₃OD) δ: 8.50(d, 1H), 7.51(s, 1H), 7.44(dd, 1H), 7.25(d, 1H), 7.11(d, 1H), 7.06(s, 1H), 7.01(d, 1H), 6.65(s, 1H), 6.21(s, 1H), 4.05(s, 4H), 3.70(s, 6H), 3.05(dd, 2H), and 2.70(dd, 2H). LCMS: (FA)ES+ 447.8(M+1), ES− 445.0(M−1). |
| A-74 | ¹H NMR(400MHz, d₆-DMSO; HCOOH salt) δ: 8.50(d, 1H), 8.43(s, 1H), 8.03(d, 1H), 7.71(d, 1H), 7.67(d, 1H), 7.59(d, 1H), 7.39-7.52(m, 2H), 7.24(d, 1H), 7.06-7.09(m, 2H), 7.05(d, 1H), 7.01(dd, 1H), 3.59(dd, 4H), 3.06(dd, 2H), 2.73(dd, 2H), and 2.09(dddd, 2H). LCMS: (FA)ES+ 504.0(M+1), ES− 501.0(M−1). |
| A-200 | ¹H NMR(300MHz, CD₃OD) δ: 8.51(d, 1H), 8.06(d, 1H), 7.71(dd, 1H), 7.59(d, 1H), 7.52(d, 1H), 7.37(dd, 1H), 7.27(d, 1H), 7.05-7.12(m, 2H), 7.03(dd, 1H), 4.37-4.49(m, 1H), 4.12(dd, 1H), 3.57(dd, 1H), 3.08(dd, 2H), 2.75(dd, 2H), and 1.39(d, 3H). LCMS: (FA)ES+ 503.01(M+1), ES− 500.99(M−1). |
| A-99 | ¹H NMR(400MHz, CD₃OD; bisHCl salt) δ: 8.63(d, 1H), 8.11(d, 1H), 7.74(dd, 1H), 7.61(s, 1H), 7.53(d, 1H), 7.41(d, 2H), 7.12-7.15(dd, 1H), 7.11(d, 2H), 4.50-4.63(m, 1H), 4.24(dd, 1H), 3.69(dd, 1H), 3.09(dd, 2H), 2.75(dd, 2H), and 1.46(d, 3H). LCMS: (FA)ES+ 503.9(M+1), ES− 503.0(M−1). |
| A-205 | ¹H NMR(400MHz, d₆-DMSO; bisHCl salt) δ: 8.61(d, 1H), 8.11(d, 1H), 7.75(dd, 1H), 7.62(d, 1H), 7.52(d, 1H), 7.39(d, 2H), 7.11(dd, 1H), 7.09(d, 2H), 3.85(s, 2H), 3.08(dd, 2H), 2.61(dd, 2H), and 1.50(s, 6H). LCMS: (FA)ES+ 517.9(M+1), ES− 515.0(M−1). |
| A-209 | ¹H NMR(300MHz, CD₃OD) δ: 8.57(d, 1H), 8.07(s, 1H), 7.71(d, 1H), 7.64(s, 1H), 7.42-7.54(m, 2H), 7.27(d, 1H), 7.11(d, 2H), 7.03(d, 1H), 4.56(br. s, 1H), 4.23(dd, 1H), 3.69(dd, 1H), 3.07(dd, 2H), 2.76(dd, 2H), and 1.48(d, 3H). LCMS: (FA)ES+ 483.1(M+1), ES− 485.1(M−1). |
| A-122 | ¹H NMR(300MHz, CD₃OD) δ: 8.56(d, 1H), 8.07(d, 1H), 7.71(dd, 1H), 7.63(d, 1H), 7.52(d, 1H), 7.46(dd, 1H), 7.27(d, 1H), 7.09-7.15(m, 2H), 7.04(dd, 1H), |

-continued

| | |
|---|---|
| | 4.51-4.62(m, 1H), 4.23(dd, 1H), 3.68(dd, 1H), 3.08(dd, 2H), 2.76(dd, 2H), and 1.46(d, 3H). LCMS: (FA)ES+ 503.9(M+1), ES– 501.0(M–1). |
| A-251 | ¹H NMR(300MHz, CD₃OD) δ: 8.34(d, 1H), 7.47(d, 1H), 7.34-7.42(m, 3H), 7.19(d, 1H), 7.04(dd, 1H), 6.96(dd, 1H), 6.91(dd, 1H), 6.86(dd, 1H), 3.79(s, 3H), 3.73(s, 4H), 3.03(dd, 2H), and 2.68(dd, 2H). LCMS: (FA)ES+ 503.9(M+1), ES– 501.0(M–1). |
| A-229 | ¹H NMR(400MHz, d₆-DMSO) δ: 8.54(d, 1H), 8.52(s, 1H), 7.75(dd, 1H), 7.58(dd, 1H), 7.43(d, 1H), 7.29-7.35(dd, 1H), 7.27(m, 1H), 7.17(d, 1H), 7.06-7.14(m, 2H), 7.03(dd, 1H), 4.06(s, 4H), 3.07(dd, 2H), and 2.71(dd, 2H). LCMS: (FA)ES+ 439.2(M+1), ES– 436.7(M–1). |
| A-139 | ¹H NMR(300MHz, d₆-DMSO; HCl salt) δ: 10.65(s, 1H), 10.61(s, 1H), 8.63(d, 1H), 8.19(s, 1H), 7.84(dd, 1H), 7.64(d, 1H), 7.48(d, 1H), 7.44(dd, 1H), 7.24(d, 1H), 7.18(dd, 1H), 7.14(dd, 1H), 7.07(dd, 1H), 4.07(dd, 2H), 3.91(dd, 2H), 3.20(s, 3H), 2.97(dd, 2H), and 2.71(dd, 2H). LCMS: (FA)ES+ 503.9(M+1), ES– 501.1(M–1). |
| A-247 | ¹H NMR(300MHz, CD₃OD) δ: 8.54(d, 1H), 8.47(s, 1H), 7.64(s, 1H), 7.61(d, 1H), 7.44(dd, 1H), 7.27(dd, 1H), 7.14(d, 1H), 7.10-7.13(m, 1H), 7.02(dd, 1H), 6.83(s, 1H), 4.09(s, 4H), 3.07(dd, 2H), 2.76(dd, 2H), 2.29(s, 3H), and 2.34(s, 3H). LCMS: (FA)ES+ 416.1(M+1). |
| A-156 | ¹H NMR(300MHz, CD₃OD) δ: 8.54(s, 1H), 8.23(d, 1H), 7.99(d, 1H), 7.67(dd, 1H), 7.40-7.52(m, 2H), 7.32(dd, 1H), 7.15(dd, 1H), 7.07(dd, 2H), 7.68-7.03(m, 1H), 0.01(s, 4H), 3.03(dd, 2H), and 2.72(dd, 2H). LCMS: (FA)ES+ 488.3(M+1), ES– 486.39(M–1). |
| A-35 | ¹H NMR(400MHz, CD₃OD) δ: 8.59(d, 1H), 8.12(s, 1H), 7.77(d, 1H), 7.65(d, 1H), 7.54(d, 1H), 7.42(d, 2H), 7.26-7.39(m, 3H), 3.63(dd, 4H), 3.08(dd, 2H), 2.77(dd, 2H), and 2.12(dddd, 2H). LCMS: (FA)ES+ 503.10(M+1), ES– 501.02(M–1). |
| A-60 | ¹H NMR(300MHz, d₆-DMSO; bisHCl salt) δ: 11.18(s, 1H), 11.10(s, 1H), 10.59(s, 1H), 8.68(d, 1H), 8.47-8.42(m, 1H), 8.22(d, 1H), 7.91(d, 1H), 7.86(dd, 1H), 7.65(d, 1H), 7.40(d, 2H), 7.24(dd, 1H), 7.17(d, 2H), 4.86(dd, 1H), 4.24(t, 1H), 3.98(dd, 1H), 2.97(t, 2H), 2.72(t, 2H), and 2.65(d, 3H). LCMS: (FA)ES+ 546.08(M+1), ES– 544.0(M–1). |
| A-259 | ¹H NMR(300MHz, CD₃OD; HCOOH salt) δ: 8.48(d, 1H), 8.39(s, 1H), 8.03(d, 1H), 7.72(dd, 1H), 7.61(d, 1H), 7.49(d, 1H), 7.42(t, 1H), 7.24(d, 1H), 7.07-7.04(m, 2H), 7.00(dd, 1H), 4.73(dd, 1H), 4.19(t, 1H), 3.94(dd, 1H), 3.05(t, 2H), 2.78(s, 3H), and 2.72(t, 2H). LCMS: (FA)ES+ 546.30(M+1), ES– 544.02(M–1). |

Example 14

Preparation of 4-{4-[4-(4-chloro-3-trifluoromethyl-phenyl)-3-oxo-butyl]-phenoxy}-pyridine-2-carboxy-lic acid (2-pyrrolidin-1-yl-ethyl)-amide (A-26)

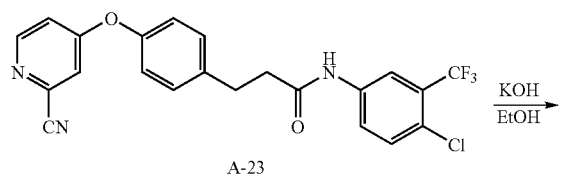

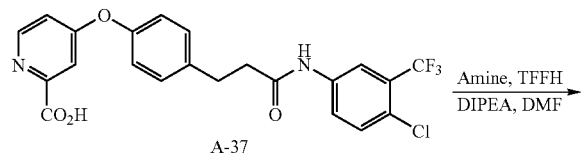

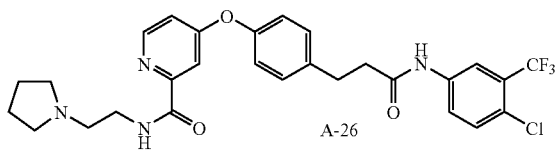

Step 1. Preparation of 4-[4-(3-{[4-chloro-3-(trifluoromethyl)phenyl]amino}-3-oxopropyl)phenoxy]pyridine-2-carboxy-lic acid (A-37).

To a solution of A-23 (570 mg, 1.3 mmol) in ethanol (2.6 mL) was added 1N KOH (2.6 mL, 2.6 mmol). The solution was stirred overnight at 85° C. and then concentrated. The residue was taken up in water and extracted with EtOAc, washed with 1N HCl and brine, dried over MgSO₄, filtered and concentrated to give A-37 as a yellow solid (159 mg, 27%). LCMS FA: $R_t$=1.48 min, [MH⁺ 465.3]. ¹H NMR (300 MHz, CD₃OD): δ 8.59 (d, J=5.5 Hz, 1H), 8.1 (d, J=4.5 Hz, 1H), 7.28-7.35 (m, 3H), 7.16 (d, J=2.4 Hz, 1H), 6.88 (d, J=8.7 Hz, 1H), 3.71 (s, 3H), 3.14 (br t, J=7.5 Hz, 2H), and 2.75 (br t, J=7.5 Hz, 2H).

Step 2. Preparation of 4-{4-[4-(4-Chloro-3-trifluoromethyl-phenyl)-3-oxo-butyl]-phenoxy}-pyridine-2-carboxylic acid (2-pyrrolidin-1-yl-ethyl)-amide (A-26).

To a solution A-37 (52 mg, 0.1 mmol) in DMF (1.1 mL) were added TFFH (41 mg, 0.1 mmol) and DIPEA (280 µL, 0.2 mmol). After stirring for 1 h at rt, 2-pyrrolidin-1-yl-ethylamine (71 µL, 0.6 mmol) was added and the solution was stirred for 12 h. The reaction mixture was diluted with water and extracted with EtOAc, washed with brine, dried over MgSO₄, filtered and concentrated. The residue was purified by column chromatography to give A-26.

Compounds in the following table were prepared from the appropriate starting materials in a method analogous to that of Example 14:

| | |
|---|---|
| A-237 | ¹H NMR(300MHz, CD₃OD; HCOOH salt) δ: 8.46(d, 1H), 8.38(s, 1H), 8.04(d, 1H), 7.69(dd, 1H), 7.58(d, 1H), 7.50(d, 1H), 7.42(t, 1H), 7.23(d, 1H), 7.07-6.98(m, 3H), 4.73(dd, 1H), 4.12(t, 1H), 3.94(dd, 1H), 3.59-3.53(m, 2H), 3.13-3.03(m, 4H), 2.78(s, 6H), and 2.72(t, 2H). LCMS: (FA) ES+ 603.22(M+1), ES− 600.87(M−1). |
| A-187 | ¹H NMR(300MHz, CD₃OD; HCOOH salt) δ: 8.51(d, 1H), 8.05(d, 1H), 7.70(dd, 1H), 7.63(d, 1H), 7.52(d, 1H), 7.43(t, 1H), 7.25(d, 1H), 7.09-7.07(m, 2H), 7.02(dd, 1H), 5.31(dd, 1H), 4.28(t, 1H), 4.05(dd, 1H), 3.13(s, 3H), 3.06(t, 2H), 3.00(s, 3H), and 2.73(t, 2H). LCMS: (FA) ES+ 560.33(M+1). |
| A-75 | ¹H NMR(400MHz, CD₃OD) δ: 8.38(d, 1H), 8.03(m, 1H), 7.66(d, 1H), 7.48(m, 2H), 7.41(t, 1H), 7.21(d, 1H), 7.06(m, 1H), 6.98(m, 2H), 3.63(t, 2H), 3.05(t, 2H), 2.70(t, 2H), and 2.61(t, 2H).LCMS: (FA) ES⁺ 536.17(M+1). |
| A-174 | ¹H NMR(400MHz, CD₃OD) δ: 8.41(d, 1H), 8.03(m, 1H), 7.70(dd, 1H), 7.54(d, 1H), 7.46(d, 1H), 7.41(t, 1H), 7.22(d, 1H), 7.07(m, 1H), 7.01(m, 2H), 3.43(t, 2H), 3.05(t, 2H), 2.71(t, 2H), 2.36(t, 2H), and 1.89(q, 2H). LCMS: (FA) ES⁺ 550.11(M+1). |
| A-136 | ¹H NMR(300MHz, CD₃OD) δ: 8.45(d, 1H), 8.06(d, 1H), 7.72(dd, 1H), 7.56(d, 1H), 7.50(d, 1H), 7.44(t, 1H), 7.24(d, 1H), 7.08(br, 2H), 7.04(m, 1H), 4.13(s, 2H), 3.07(t, 2H), and 2.73(t, 2H). LCMS: (FA) ES⁺ 522.21(M+1). |
| A-235 | ¹H NMR(400MHz, CD₃OD) δ: 8.38(d, 1H), 8.05(d, 1H), 7.70(dd, 1H), 7.50(m, 2H), 7.42(t, 1H), 7.22(d, 1H), 7.07(m, 1H), 6.99(m, 2H), 3.69(s, 3H), 3.65(t, 2H), 3.06(t, 2H), 2.72(t, 2H), and 2.65(t, 2H). LCMS: (FA) ES⁺ 550.18(M+1). |
| A-155 | ¹H NMR(400MHz, CD₃OD) δ: 8.38(d, 1H), 8.04(d, 1H), 7.70(dd, 1H), 7.51(d, 1H), 7.47(d, 1H), 7.40(t, 1H), 7.21(d, 1H), 7.06(m, 1H), 6.98(m, 2H), 4.08(q, 2H), 3.43(t, 2H), 3.05(t, 2H), 2.71(t, 2H), 2.38(t, 2H), 1.91(q, 2H), and 1.22(t, 3H). LCMS: (FA) ES⁺ 578.38(M+1). |
| A-123 | ¹H NMR(300MHz, CD₃OD) δ: 8.43(d, 1H), 8.05(d, 1H), 7.70(dd, 1H), 7.50(m, 2H), 7.41(t, 1H), 7.22(d, 1H), 7.07(m, 1H), 6.99(m, 2H), 4.14(s, 2H), 3.74(s, 3H), 3.05(t, 2H), and 2.71(t, 2H). LCMS: (FA) ES⁺ 536.27(M+1). |
| A-26 | ¹H NMR(400MHz, d₆-DMSO; HCl salt) δ: 8.51(d, 1H), 8.03(d, 1H), 7.71(d, 1H), 7.68(dd, 1H), 7.45(d, 1H), 7.37(d, 2H), 7.18(d, 1H), 7.07(d, 2H), 3.63-3.42(m, 4H), 3.39(dd, 2H), 3.07(dd, 2H), 2.99(dd, 2H), 2.68(dd, 2H), 2.08(dd, 2H), and 1.90-1.99(m, 2H). LCMS : (FA) ES+ 560.9(M+1), ES− 559.2(M−1). |

Example 15

Preparation of 3-{3-[(2-aminopyrimidin-4-yl)oxy]phenyl}-N-[4-chloro-3-(trifluoromethyl)phenyl]propanamide (A-82)

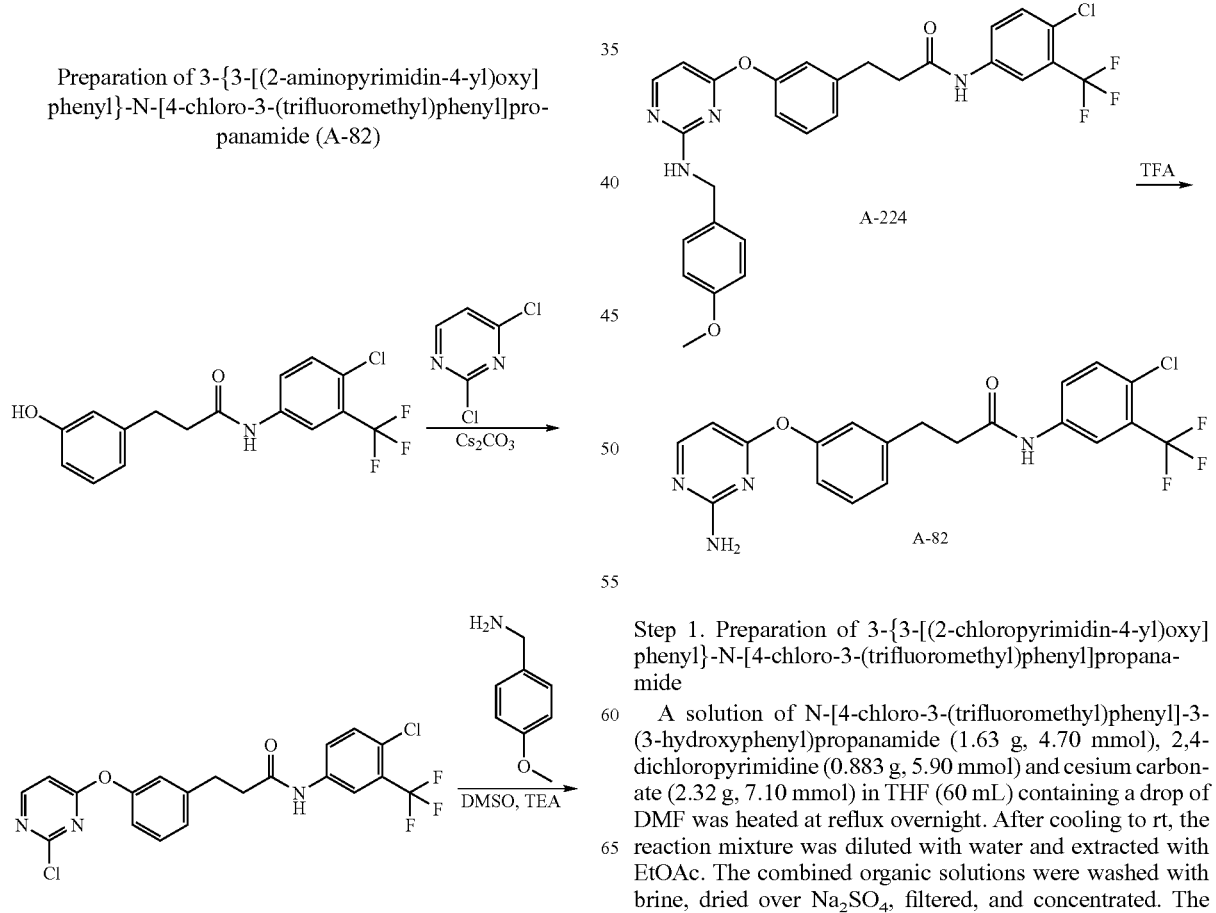

Step 1. Preparation of 3-{3-[(2-chloropyrimidin-4-yl)oxy]phenyl}-N-[4-chloro-3-(trifluoromethyl)phenyl]propanamide A solution of N-[4-chloro-3-(trifluoromethyl)phenyl]-3-(3-hydroxyphenyl)propanamide (1.63 g, 4.70 mmol), 2,4-dichloropyrimidine (0.883 g, 5.90 mmol) and cesium carbonate (2.32 g, 7.10 mmol) in THF (60 mL) containing a drop of DMF was heated at reflux overnight. After cooling to rt, the reaction mixture was diluted with water and extracted with EtOAc. The combined organic solutions were washed with brine, dried over Na₂SO₄, filtered, and concentrated. The residue was purified by column chromatography to give the title compound (1.60 g, 77%). LCMS, FA: $R_t$=1.28 min, [MH⁺ 520.2].

Step 2. Preparation of N-[4-chloro-3-(trifluoromethyl)phenyl]-3-[3-({2-[(4-methoxybenzyl)amino]pyrimidin-4-yl}oxy)phenyl]propanamide (A-224)

To a solution of 3-{3-[(2-chloropyrimidin-4-yl)oxy]phenyl}-N-[4-chloro-3-(trifluoromethyl)phenyl]propanamide (0.200 g, 0.44 mmol) in DMSO (1 mL) were added 1-(4-methoxyphenyl)methanamine (0.056 mL, 0.44 mmol) and TEA (0.061 mL, 0.44 mmol). The reaction mixture was heated at 95° C. overnight and then cooled to rt, diluted with water and extracted with EtOAc. The combined organic solutions were washed with brine, dried over $Na_2SO_4$, filtered, and concentrated. The residue was purified by column chromatography to give A-224. ¹H NMR (400 MHz, d6 DMSO) δ: 10.35 (s, 1H), 8.11-8.15 (m, 1H), 8.05-8.11 (m, 1H), 7.75-7.81 (m, 1H), 7.62 (d, 1H), 7.30-7.39 (m, 1H), 7.09-7.26 (m, 2H), 7.04-7.07 (m, 1H), 6.67-7.00 (m, 4H), 6.05 (d, 1H), 4.25-4.43 (br m, 1H), 3.96-4.10 (br m, 1H), 3.67 (s, 3H), 2.93 (t, 2H), and 2.67 (t, 2H). LCMS, FA: $R_t$=1.88 min, [MH⁺ 557.3].

Step 3. Preparation of 3-{3-[(2-aminopyrimidin-4-yl)oxy]phenyl}-N-[4-chloro-3-(trifluoromethyl)phenyl]propanamide (A-82)

A solution of A-224 (0.060 g, 0.11 mmol) in TFA (1 mL) was heated at 80° C. for 4 h. The mixture was allowed to cool to rt, quenched with sat. aqueous $NaHCO_3$ and extracted with EtOAc. The combined organic solutions were washed with brine, dried over $Na_2SO_4$, filtered, and concentrated. The residue was purified by column chromatography to give A-82.

¹H NMR (400 MHz, d₆ DMSO) δ: 10.41 (s, 1H), 8.2 (d, 1H), 8.16 (d, 1H), 7.89 (br s, 1H), 7.8 (d, 1H), 7.63 (d, 1H), 7.37 (t, 1H), 7.18 (d, 1H), 7.11-7.13 (m, 1H), 7.06 (dd, 1H), 6.41 (d, 1H), 2.94 (t, 2H), and 2.68 (t, 2H). LCMS, FA: $R_t$=1.40 min, [MH⁺ 437.1].

Compounds in the following table were prepared from the appropriate starting materials in a method analogous to that of Example 15:

| | |
|---|---|
| A-87 | ¹H NMR(400MHz, CDCl₃) δ: 8.12(d, 1H), 7.75(d, 1H), 7.65(dd, 1H), 7.42(d, 1H), 7.29-7.34(m, 1H), 7.17(br s, 1H), 7.09(d, 1H), 7.01-7.06(m, 2H), 5.9(d, 1H), 3.63-3.69(m, 4H), 3.07(t, 2H), 2.68(t, 2H), 1.52-1.64(m, 6H), and 2.68(t, 2H). LCMS, FA: $R_t$=2.09min, [MH⁺ 505.2]. |
| A-167 | ¹H NMR(300MHz, CDCl₃) δ: 8.12(dd, 1H), 7.75(d, 1H), 7.64(dd, 1H), 7.37-7.43(m, 2H), 7.26-7.34(m, 1H), 6.98-7.09(m, 3H), 5.93(dd, 1H), 3.37-3.51(m, 4H), 3.05(t, 2H), 2.67(t, 2H), 0.99-1.12(m, 6H), and 2.67(t, 2H). LCMS, FA: $R_t$=1.90min, [MH⁺ 493.3]. |
| A-124 | LCMS, FA: $R_t$=1.28min, [MH⁺ 520.2]. |
| A-217 | ¹H NMR(300MHz, CDCl₃) δ: 9.8(br s, 1H), 8.49(br s, 1H), 8.09(d, 1H), 7.84(br s, 2H), 7.36(d, 1H), 7.22-7.30(m, 1H), 7.02-7.12(m, 2H), 6.88-6.98(m, 1H), 6.16(d, 1H), 3.46-3.65(m, 2H), 3.03(t, 2H), 2.75-7.92(m, 2H), 2.7(t, 2H), 2.45(br s, 6H), and 2.7(t, 2H). LCMS, FA: $R_t$=1.21min, [MH⁺ 508.3]. |
| A-70 | ¹H NMR(400MHz, CDCl₃) δ: 8.13(d, 1H), 7.75(d, 1H), 7.64(dd, 1H), 7.41(d, 1H), 7.30-7.34(m, 1H), 7.23(br s, 1H), 7.08(d, 1H), 7.02-7.07(m, 2H), 5.89(d, 1H), 3.46(br s, 4H), 3.07(t, 2H), and 2.68(t, 2H). LCMS, FA: $R_t$=1.66min, [MH⁺ 492.3]. |
| A-250 | ¹H NMR(400MHz, CDCl₃) δ: 8.08(d, 1H), 7.73(d, 1H), 7.63(dd, 1H), 7.4(d, 1H), 7.29-7.35(mm, 2H), 7.08(dm, 1H), 6.98-7.03(mm, 2H), 5.99(d, 1H), 4.93(br s, 1H), 3.91-4.03(mm, 1H), 3.06(t, 2H), 2.68(t, 2H), and 1.13(d, 6H). LCMS, FA: $R_t$=1.68min, [MH⁺ 438.2]. |
| A-207 | ¹H NMR(400MHz, d₆-DMSO) δ: 10.34(s, 1H), 8.2(d, 1H), 8.12-8.16(d, 1H), 7.78(d, 1H), 7.62(d, 1H), 7.38(t, 1H), 7.13(d, 1H), 7.06-7.10(m, 1H), 7(dm, 1H), 6.09(d, 1H), 3.46-3.58(m, 8H), 2.93(t, 2H), and 2.66(t, 2H). LCMS, FA: $R_t$=2.05min, [MH⁺ 508.1]. |
| A-164 | ¹H NMR(400MHz, CDCl₃) δ: 9.61(br s, 1H), 8.1(d, 1H), 7.93(d, 1H), 7.75(br s, 1H), 7.38(d, 1H), 7.24-7.31(m, 1H), 7.06-7.17(m, 2H), 6.88-6.95(m, 1H), 6.19(d, 1H), 5.62(br s, 1H), 3.36(t, 2H), 3.22(br s, 2H), 3.05(t, 2H), 2.75(t, 2H), 2.33(t, 2H), 2.13(br s, 2H), 2.01(quint, 2H), and 1.67(br s, 2H). LCMS, FA: $R_t$=1.50min, [MH⁺ 563.3]. |
| A-68 | LCMS, FA: $R_t$=2.24min, [MH⁺ 621.3]. |
| A-116 | LCMS, FA: $R_t$=1.25min, [MH⁺ 535.1]. |

Example 16

Preparation of N-[4-chloro-3-(trifluoromethyl)phenyl]-3-(4-{[2-(2H-tetrazol-5-yl)pyridin-4-yl]oxy}phenyl)propanamide (A-57)

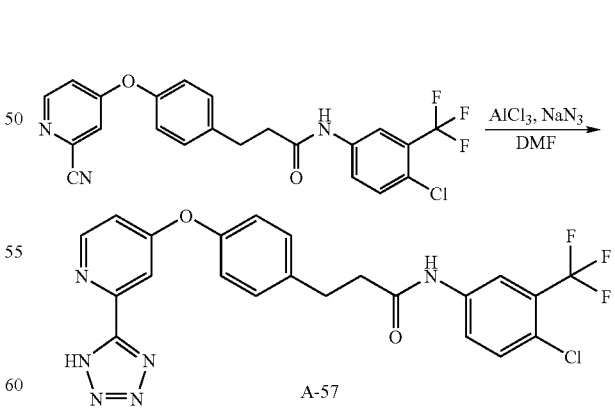

A-57

A solution of N-[4-chloro-3-(trifluoromethyl)phenyl]-3-{4-[(2-cyanopyridin-4-yl)oxy]phenyl}propanamide (0.300 g, 0.67 mmol), aluminum trichloride (1.0 M in hexanes, 2.0 mL, 2.0 mmol), and sodium azide (0.131 g, 2.0 mmol) in DMF was heated at 100° C. for 3 days. The mixture was concentrated and purified by column chromatography to give A-57 which was converted to the bishydrochloride salt (29 mg). $^1$H NMR (400 MHz, CD$_3$OD; bis HCl salt) δ: 8.66 (d, 1H), 8.03 (d, 1H), 7.93 (d, 1H), 7.66 (dd, 1H), 7.52 (t, 1H), 7.45 (d, 1H), 7.41 (dd, 1H), 7.37 (d, 1H), 7.21-7.24 (m, 1H), 7.12-7.17 (m, 1H), 3.10 (t, 2H), and 2.75 (t, 2H). LCMS, FA: R$_t$=1.48 min, [MH$^+$ 489.3].

Compounds in the following table were prepared from the appropriate starting materials in a method analogous to that of Example 16:

| | |
|---|---|
| A-236 | $^1$H NMR(300MHz, d$_6$-DMSO; bisHCl salt) δ: 10.37(s, 1H), 8.60(d, 1H), 8.12(d, 1H), 7.76(dd, 1H), 7.59(d, 1H), 7.55(d, 1H), 7.45(t, 1H), 7.25(d, 1H), 7.15-7.18(m, 1H), 7.08-7.14(m, 2H), 2.97(t, 2H), and 2.69(t, 2H). LCMS, FA: Rt=1.52min, [MH+ 489.3]. |

Example 17

Preparation of N-[4-chloro-3-(trifluoromethyl)phenyl]-3-[4-({2-[(hydroxyamino)(imino)methyl]pyridin-4-yl}oxy)phenyl]propanamide (A-85)

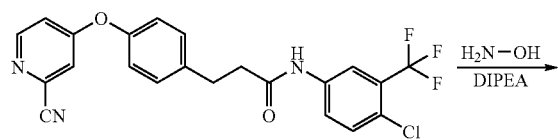

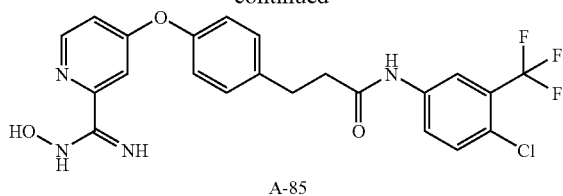

A solution of N-[4-chloro-3-(trifluoromethyl)phenyl]-3-{4-[(2-cyanopyridin-4-yl)oxy]phenyl}propanamide (0.300 g, 0.67 mmol), hydroxylamine hydrochloride (0.117 g, 1.69 mmol), and DIPEA (0.117 mL, 0.67 mmol) in MeOH was allowed to stir at rt overnight. The mixture was concentrated and purified by column chromatography to give A-85 (68 mg). $^1$H NMR (300 MHz, d$_6$ DMSO) δ: 10.48 (br s, 1H), 10.17 (br s, 1H), 8.50 (d, 1H), 8.14-8.20 (m, 1H), 7.77-7.85 (m, 1H), 7.60-7.66 (m, 1H), 7.50-7.56 (m, 1H), 7.39-7.47 (m, 1H), 7.20-7.26 (m, 1H), 7.01-7.13 (m, 3H), 2.92-3.01 (m, 2H), and 2.65-2.72 (m, 2H). LCMS, FA: R$_t$=1.98 min, [MH$^+$ 479.3].

Example 18

Preparation of N-[4-chloro-3-(trifluoromethyl)phenyl]-3-[4-({2-[(ethylamino)(imino)methyl]pyridin-4-yl}oxy)phenyl]propanamide (A-112)

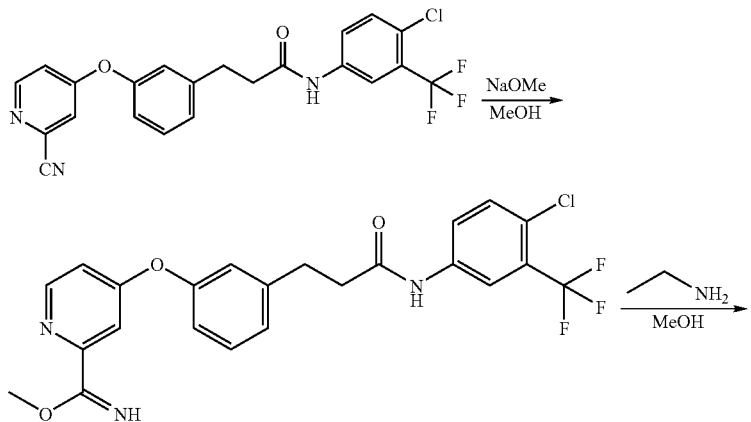

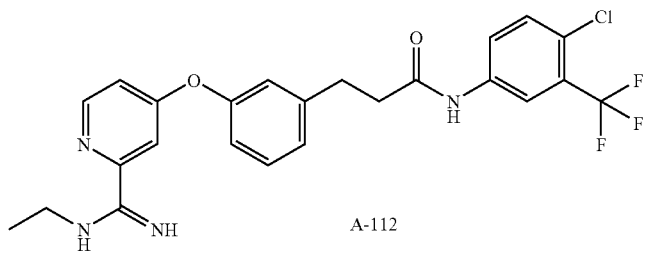

Step 1. Preparation of methyl 4-[4-(3-{[4-chloro-3-(trifluoromethyl)phenyl]-amino}-3-oxopropyl)phenoxy]pyridine-2-carboximidoate To a solution of N-[4-chloro-3-(trifluoromethyl)phenyl]-3-{4-[(2-cyanopyridin-4-yl)oxy]phenyl}propanamide (0.500, 1.12 mmol) in MeOH was added NaOMe (0.006 g, 0.11 mmol) in one portion. The reaction mixture was allowed to stir at rt overnight and then concentrated. The crude material was used without further purification.

Step 2. Preparation of N-[4-chloro-3-(trifluoromethyl)phenyl]-3-[4-({2-[(ethylamino)(imino)methyl]pyridin-4-yl}oxy)phenyl]propanamide (A-112)

A mixture of the methyl 4-[4-(3-{[4-chloro-3-(trifluoromethyl)phenyl]-amino}-3-oxopropyl)phenoxy]pyridine-2-carboximidoate (0.150 g, 0.31 mmol) and ethylamine (2.0 M in MeOH, 0.155 mL, 0.31 mmol) in MeOH was heated at 50° C. for 3 days. The reaction mixture was concentrated and purified by column chromatography to give A-112 (94 mg). $^1$H NMR (300 MHz, CD$_3$OD) δ: 8.33 (d, 1H), 8.02 (d, 1H), 7.68 (dd, 1H), 7.56 (d, 1H), 7.46 (d, 1H), 7.37 (t, 1H), 7.15-7.21 (m, 1H), 7.01-7.05 (m, 1H), 6.93-6.99 (m, 1H), 6.88 (dd, 1H), 3.27 (q, 2H), 3.03 (t, 2H), 2.69 (t, 2H), and 1.24 (t, 3H). LCMS, FA: R$_t$=1.58 min, [MH$^+$ 491.3].

Compounds in the following table were prepared from the appropriate starting materials in a method analogous to that of Example 18:

| | |
|---|---|
| A-172 | $^1$H NMR(400MHz, CD$_3$OD; HCOOH salt) δ: 8.52(d, 1H), 8.02(d, 1H), 7.74(d, 1H), 7.67(dd, 1H), 7.31-7.51(m, 7H), 7.22-7.28(m, 1H), 7.05-7.09(m, 2H), 7.02(ddd, 1H), 4.71(s, 2H), 3.05(t, 2H), and 2.71(t, 2H). LCMS, FA: R$_t$=1.73min, [MH$^+$ 553.3]. |
| A-227 | $^1$H NMR(400MHz, CD$_3$OD) δ: 8.35(d, 1H), 8.03(d, 1H), 7.69(dd, 1H), 7.57(d, 1H), 7.48(d, 1H), 7.39(t, 1H), 7.18-7.22(m, 1H), 7.03-7.06(m, 1H), 6.96-7.00(m, 1H), 6.90(dd, 1H), 3.69(dd, 4H), 3.40(t, 2H), 3.04(t, 2H), 2.70(t, 2H), 2.65(t, 2H), and 2.49-2.56(m, 4H). LCMS, FA: R$_t$=1.60min, [MH$^+$ 576.3]. |
| A-150 | $^1$H NMR(300MHz, d$_6$-DMSO; HCOOH salt) δ: 8.54(s, 1H), 8.46(d, 1H), 8.05(d, 1H), 7.70(dd, 1H), 7.51(d, 1H), 7.43(t, 1H), 7.24-7.31(m, 2H), 7.07-7.10(m, 1H, 6.98-7.05(m, 2H), 3.75-3.82(m, 2H), 3.50-3.60(m, 2H), 3.05(t, 2H), and 2.72(t, 2H). LCMS, FA: R$_t$=1.59min, [MH$^+$ 533.3]. |

Example 19: Preparation of N-[4-chloro-3-(trifluoromethyl)phenyl]-3-{4-[(2-{5-[4-(diethylamino)phenyl]-1H-imidazol-2-yl}pyridin-4-yl)oxy]phenyl}propanamide (A-54)

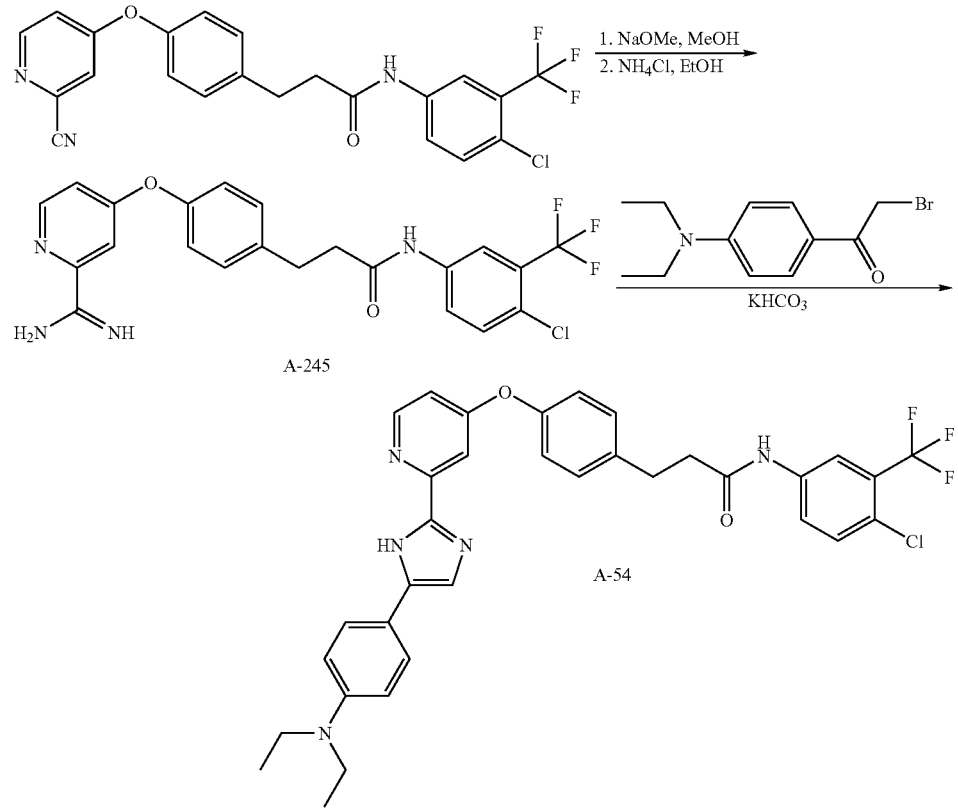

Step 1. Preparation of 3-[4-({2-[amino(imino)methyl]pyridin-4-yl}oxy)phenyl]-N-[4-chloro-3-(trifluoromethyl)phenyl]propanamide (A-245)

To a solution of N-[4-chloro-3-(trifluoromethyl)phenyl]-3-{4-[(2-cyanopyridin-4-yl)oxy]phenyl}propanamide (0.200 g, 0.45 mmol) in MeOH was added NaOMe (2.4 mg, 0.045 mmol) in one portion. The mixture was allowed to stir at rt for 2 days and then ammonium chloride (35 mg, 0.50 mmol) was added. The reaction mixture was heated at reflux for 30 min and then cooled to rt and concentrated. The residue was recrystallized from ETOH to give A-245. $^1$H NMR (300 MHz, $d_6$-DMSO) δ: 10.39 (br s, 1H), 8.47 (d, 1H), 8.14 (d, 1H), 7.58-7.82 (m, 1H), 7.70-7.74 (m, 1H), 7.42 (t, 1H), 7.21 (d, 1H), 7.08-7.13 (m, 1H), 6.98-7.06 (m, 2H), 2.96 (t, 2H), and 2.68 (t, 2H). LCMS, FA: $R_t$=1.83 min, [MH$^+$ 463.2].

Step 2. Preparation of N-[4-chloro-3-(trifluoromethyl)phenyl]-3-{4-[(2-{5-[4-(diethylamino)phenyl]-1H-imidazol-2-yl}pyridin-4-yl)oxy]phenyl}propanamide (A-54)

A solution of A-245 (30 mg, 0.06 mmol) and KHCO$_3$ (24 mg, 0.24 mmol) in THF (4 mL) and water (1 mL) was heated at reflux. Reflux was maintained while adding the bromide (16 mg, 0.06 mmol). The mixture was heated at reflux overnight and then concentrated. The residue was purified by column chromatography to give A-54 (8 mg). $^1$H NMR (400 MHz, $d_6$-DMSO) δ: 10.37 (s, 1H), 8.43 (d, 1H), 8.14 (d, 1H), 7.75-7.83 (m, 1H), 7.54-7.66 (m, 3H), 7.37-7.52 (m, 2H), 7.19-7.25 (m, 1H), 7.13-7.17 (m, 1H), 7.05-7.11 (m, 1H), 6.87-6.92 (m, 1H), 6.61-6.67 (m, 2H), 3.28-3.37 (m, 4H), 2.94-3.01 (m, 2H), 2.65-2.73 (m, 2H), and 1.03-1.11 (m, 4H). LCMS, FA: $R_t$=2.36 min, [MH$^+$ 634.3].

Compounds in the following table were prepared from the appropriate starting materials in a method analogous to that of Example 19:

| | |
|---|---|
| A-228 | $^1$H NMR(400MHz, CD$_3$OD; HCl salt) δ: 8.53(d, 1H), 8.05(d, 1H), 7.78(d, 1H), 7.69(dd, 1H), 7.49(d, 1H), 7.43(t, 1H), 7.23-7.28(m, 1H), 7.05-7.10(m, 2H), 6.99-7.04(m, 1H), 3.06(t, 2H), and 2.74(t, 2H). LCMS, FA: $R_t$=1.61min, [MH$^+$ 463.1]. |
| A-232 | $^1$H NMR(400MHz, CD$_3$OD) δ: 8.34-8.41(m, 1H), 8.01-8.09(m, 1H), 7.63-7.76(m, 1H), 7.35-7.52(m, 3H), 6.98-7.23(m, 3H), 6.79-6.87(m, 2H), 3.05(t, 2H), 2.68-2.76(m, 2H), and 2.24(d, 3H). LCMS, FA: $R_t$=1.33min, [MH$^+$ 501.9]. |
| A-158 | $^1$H NMR(400MHz, CD$_3$OD) δ: 8.36(d, 1H), 8.01(d, 1H), 7.65(dd, 1H), 7.38-7.46(m, 3H), 7.19-7.23(m, 1H), 7.06-7.08(m, 1H), 7.00(ddd, 1H), 6.84-6.86(m, 1H), 6.82(dd, 1H), 3.05(t, 2H), 2.71(t, 2H), and 2.25(d, 3H). LCMS, FA: $R_t$=1.97min, [MH$^+$ 501.0]. |
| A-118 | $^1$H NMR(400MHz, CD$_3$OD) δ: 8.54(d, 1H), 8.01(d, 1H), 7.70(d, 1H), 7.66(dd, 1H), 7.45(dd, 2H), 7.37(s, 1H), 7.27(d, 1H), 7.10(s, 1H), 7.01-7.07(m, 2H), 3.07(dd, 2H), 2.74(dd, 2H), and 1.41(s, 9H). LCMS: (FA) ES+ 543.1(M+1), ES− 541.2(M−1). |

Example 20

Preparation of 5-{4-[3-(3-{[4-chloro-3-(trifluoromethyl)phenyl]amino}-3-oxopropyl)phenoxy]pyridin-2-yl}-1,3,4-oxadiazole-2-carboxamide (A-102)

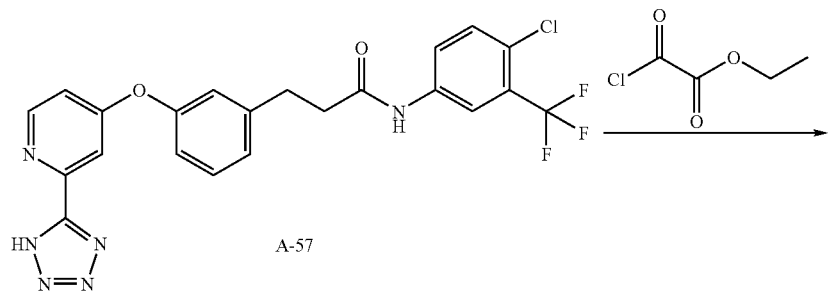

-continued

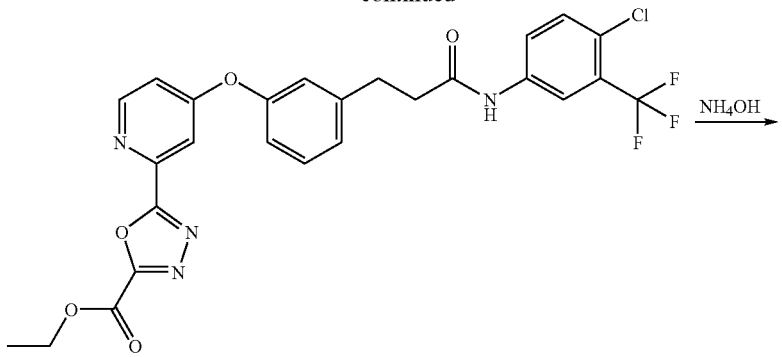

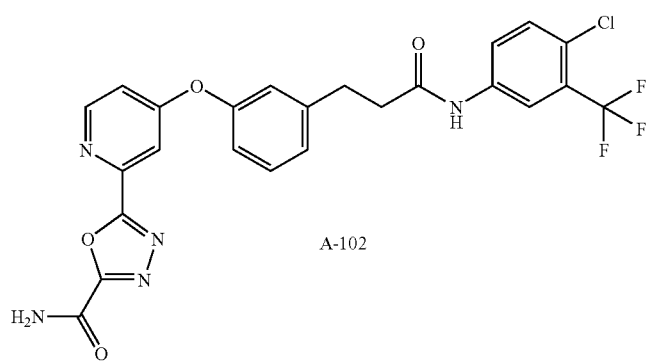

Step 1. Preparation of ethyl 5-{4-[3-(3-{[4-chloro-3-(trifluoromethyl)phenyl]-amino}-3-oxopropyl)phenoxy]pyridin-2-yl}-1,3,4-oxadiazole-2-carboxylate A mixture of A-57 (50 mg, 0.11 mmol) and ethyl oxalyl chloride (11 mg, 0.11 mmol) in toluene was heated at reflux for 2 h. The reaction mixture was concentrated and the residue purified by column chromatography to give the desired product. LCMS, FA: [MH⁺ 561.2].

Step 2. Preparation of 5-{4-[3-(3-{[4-chloro-3-(trifluoromethyl)phenyl]amino}-3-oxopropyl)phenoxy]pyridin-2-yl}-1,3,4-oxadiazole-2-carboxamide (A-102)

A solution of ethyl 5-{4-[3-(3-{[4-chloro-3-(trifluoromethyl)phenyl]-amino}-3-oxopropyl)phenoxy]pyridin-2-yl}-1,3,4-oxadiazole-2-carboxylate (100 mg) in NH₄OH (10 mL) was allowed to stir at rt for 90 min. The reaction mixture was concentrated and the residue recrystallized from MeOH to give A-102. $^1$H NMR (300 MHz, d₆-DMSO) δ: 8.70 (br s, 1H), 8.62 (d, 1H), 8.29 (br s, 1H), 8.13 (d, 1H), 7.76 (dd, 1H), 7.58-7.64 (m, 2H), 7.45 (t, 1H), 7.23-7.28 (m, 1H), 7.14-7.19 (m, 2H), 7.07-7.13 (m, 1H), 2.97 (t, 2H), and 2.69 (t, 2H). LCMS, FA: R$_t$=1.77 min, [MH⁺ 532.1].

Example 21

Preparation of 4-[3-(3-{[3-an-no-5-(trifluoromethyl)phenyl]amino}-3-oxopropyl)phenoxy]-N-methylpyridine-2-carboxamide (A-225)

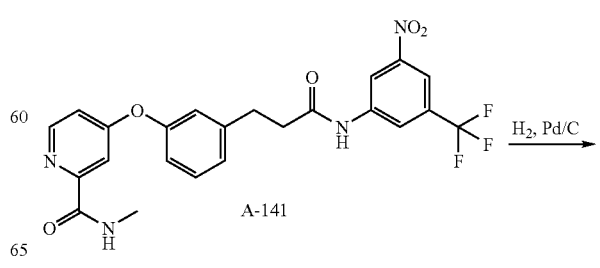

-continued

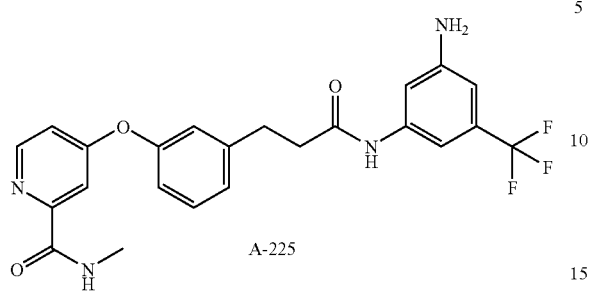

A-141 (0.143 g, 0.293 mmol) was dissolved in EtOAc (4 mL). The solution was purged with nitrogen and Pd/carbon (10% wt., 14 mg) was added. The mixture was stirred under an atmosphere of hydrogen overnight. The reaction mixture was filtered through Celite and washed with EtOAc and MeOH. The filtrate was concentrated to a yellow solid. Purification by column chromatography (SiO$_2$, 60% EtOAc/Hex) provided A-225 as an off white solid (80 mg). $^1$H NMR (400 MHz, CD$_3$OD) δ: 8.44 (d, 1H), 7.54 (d, 1H), 7.39 (t, 1H), 7.21 (d, 1H), 7.05-7.08 (m, 3H), 6.93-6.98 (m, 2H), 6.64 (bs, 1H), 3.02 (t, 2H), 2.92 (s, 3H), and 2.66 (t, 2H).

Compounds in the following table were prepared from the appropriate starting materials in a method analogous to that of Example 21:

| | |
|---|---|
| A-233 | $^1$H NMR(400MHz, CD$_3$OD; 3*HCl salt) δ: 8.40(d, 1H), 7.50(d, 1H), 7.41(t, 1H), 7.22(d, 1H), 7.06(d, 2H), 7.02(s, 1H), 6.97(m, 2H), 6.64(s, 1H), 3.83(s, 4H), 3.02(t, 2H), and 2.66(t, 2H). LCMS: (FA) ES$^+$ 470.1(M+1). |

Example 22

Preparation of 4-[3-(3-{[4-(aminomethyl)-3-(trifluoromethyl)phenyl]amino}-3-oxopropyl)phenoxy]-N-methylpyridine-2-carboxamide (A-50)

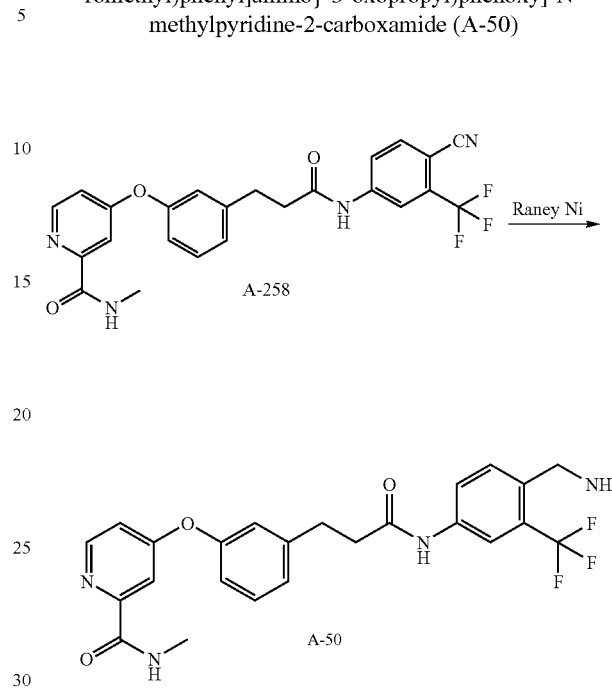

A-258 (115 mg, 0.246 mmol) was dissolved in a solution of NH$_3$ in MeOH (7.0 M, 3 mL) and EtOAc (1 mL). Raney 2800 nickel (slurry in water, 50% v/v, about 1 mL) was added to the reaction mixture. This slurry was stirred under an atmosphere of hydrogen overnight. THF (1 mL) and more Raney 2800 nickel (ca. 1 mL) were added and the reaction mixture was sonicated under an atmosphere of hydrogen overnight. The reaction mixture was then filtered through a pad of Celite washing well with MeOH. The filtrate was concentrated to give A-50 as a yellow oil. $^1$H NMR (400 MHz, CD$_3$OD) δ: 8.37 (d, 1H), 7.99 (bs, 1H), 7.78-7.81 (m, 1H), 7.55 (d, 1H), 7.50 (d, 1H), 7.39 (t, 1H), 7.20-7.22 (m, 1H), 7.03-7.06 (m, 1H), 6.93-6.98 (m, 2H), 4.09 (s, 2H), 3.05 (t, 2H), 2.92 (s, 3H), and 2.71 (t, 2H).

Compounds in the following table were prepared from the appropriate starting materials in a method analogous to that of Example 22:

| | |
|---|---|
| A-186 | $^1$H NMR(300MHz, CD$_3$OD) δ: 8.58(d, 1H), 7.96(d, 2H), 7.66(d, 1H), 7.51(s, 1H), 7.43(t, 1H), 7.27(d, 1H), 7.15-7.12(m, 2H), 7.02(dd, 1H), 4.18(s, 2H), 4.11(s, 4H), 3.08(t, 2H), and 2.78(t, 2H). LCMS: (FA) ES$^+$ 484.2(M+1), ES$^-$ 482.3(M−1). |
| A-101 | $^1$H NMR(400MHz, CD$_3$OD) δ: 8.38(d, 1H), 7.92(d, 1H), 7.71(dd, 1H), 7.53(d, 1H), 7.48(d, 1H), 7.41(t, 1H), 7.23(d, 1H), 7.07(t, 1H), 7.00-6.95(m, 2H), 3.91(s, 2H), 3.81(s, 4H), 3.06(t, 2H), 2.71(t, 2H). LCMS: (FA) ES+ 484(M+1), ES− 482.27(M−1). |

Example 23

Preparation of N-[4-chloro-3-(trifluoromethyl)phenyl]-3-[3-({2-[(ethanimidoylamino)methyl]pyridin-4-yl}oxy)phenyl]propanamide (A-52)

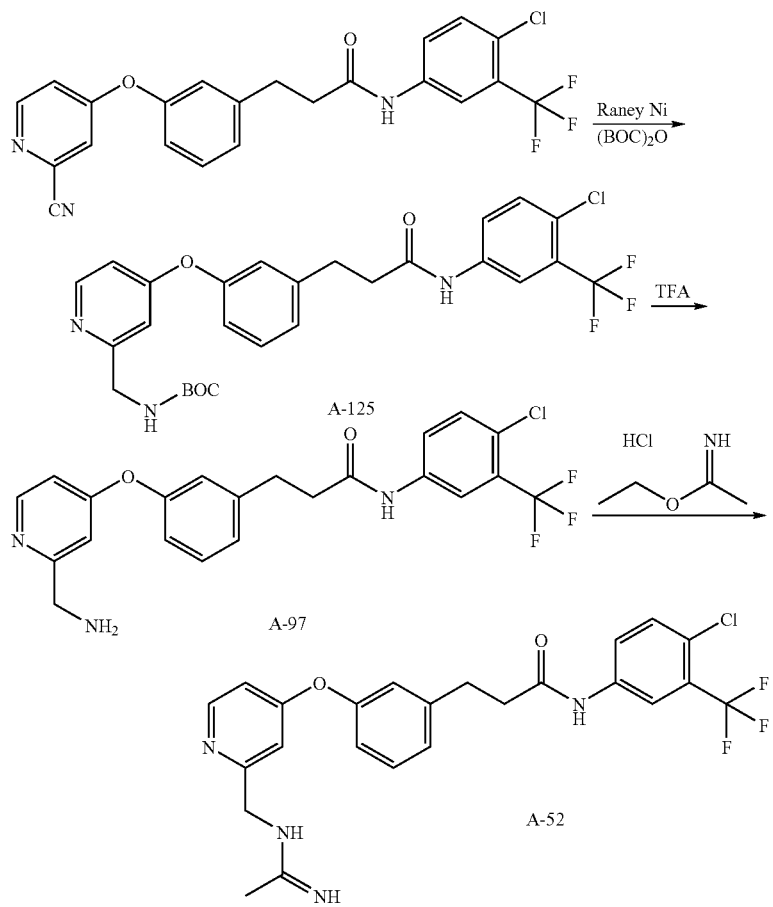

Step 1. Preparation of tert-butyl ({4-[3-(3-{[4-chloro-3-(trifluoromethyl)phenyl]-amino}-3-oxopropyl)phenoxy]pyridin-2-yl}methyl)carbamate (A-125)

Boc$_2$O (4.16 g, 19.08 mmol) was added to a degassed solution of N-[4-chloro-3-(trifluoromethyl)phenyl]-3-{3-[(2-cyanopyridin-4-yl)oxy]phenyl}propanamide (2.83 g, 6.35 mmol), THF (65 mL), and TEA (4.41 mL, 31.75 mmol). Raney nickel (aqueous solution) was added and the solution was degassed. The mixture stirred under a hydrogen atmosphere for 24 h and then filtered through Celite, eluting with ETOH. The filtrate was concentrated and the residue purified by column chromatography (SiO$_2$, 0-50% EtOAc in hexanes) to give A-125 (0.581 mg, 16%). $^1$H NMR (300 MHz, d$_6$-DMSO) δ: 10.35 (s, 1H), 8.29 (d, 1H), 8.14 (d, 1H), 7.80 (dd, 1H), 7.63 (d, 1H), 7.39 (t, 2H), 7.17 (d, 1H), 7.05 (s, 1H), 6.96 (dd, 1H), 6.74 (m, 2H), 4.12 (d, 2H), 2.94 (t, 2H), 2.67 (t, 2H), and 1.32 (s, 9H). LCMS: (FA) ES$^+$ 550.5 (M+1).

Step 2. Preparation of 3-(3-{[2-(aminomethyl)pyridin-4-yl]oxy}phenyl)-N-[4-chloro-3-(trifluoromethyl)phenyl]propanamide (A-97)

A solution of A-125 (0.58 g, 1.06 mmol) in TFA (2 mL) and DCM (10 mL) was stirred at rt for 5 h. The reaction was concentrated and the residue was purified by column chromatography (SiO$_2$, 10:1:89 MeOH: FA: DCM) to give A-97 (0.43 mg, 90%). $^1$H NMR (300 MHz, CD$_3$OD) δ: 8.25 (d, 1H), 8.03 (d, 1H), 7.70 (dd, 1H), 7.48 (d, 1H), 7.39 (t, 1H), 7.19 (d, 1H), 7.03 (br, 1H), 6.95 (d, 2H), 6.70 (dd, 1H), 3.82 (s, 2H), 3.04 (t, 2H), and 2.71 (t, 2H). LCMS: (FA) ES$^+$ 516.4 (M+1).

Step 3. Preparation of N-[4-chloro-3-(trifluoromethyl)phenyl]-3-[3-({2-[(ethanimidoylamino)methyl]pyridin-4-yl}oxy)phenyl]propanamide (A-52)

A solution of A-97 (0.107 g, 0.22 mmol), ethyl ethanimidoate hydrochloride (0.054 g, 0.44 mmol), and TEA (120 mL) in DMF (5 mL) was stirred at 0° C. for 15 min and then concentrated. The residue was partitioned between EtOAc and water. The aqueous layer was extracted with EtOAc, and the combined organic solutions were washed with brine and concentrated. The residue was purified by HPLC eluting with 85% (95% water/5% FA):15% (99% ACN:1% FA) to 20% (95% water/5% FA):15% (99% ACN:1% FA) (20 min gradient) to give A-52. The HCl salt was prepared by dissolving the residue in MeOH and adding 2.0 M HCl in Et$_2$O and concentrating to white solid. $^1$H NMR (300 MHz, CD$_3$OD; HCl salt) δ: 8.31 (d, 1H), 8.09-8.03 (m, 1H), 7.73-7.67 (m, 1H), 7.54-7.35 (m, 2H), 7.26-7.19 (m, 1H), 7.04 (br s, 1H), 7.00-6.93 (m, 2H), 6.83-6.76 (m, 1H), 4.49 (s, 2H), 3.04 (t, 2H), 2.72 (t, 2H), and 2.78 (s, 3H). LCMS: (FA) ES+ 491.2 (M+1), ES– 489.1 (M–1).

Compounds in the following table were prepared from the appropriate starting materials in a method analogous to that of Example 23:

| | |
|---|---|
| A-153 | $^1$H NMR 300MHz, CD$_3$OD; HCl salt) δ: 8.35(d, 1H), 8.06-8.04(m, 1H), 7.88-7.82(m, 2H), 7.76-7.67(m, 4H), 7.63-7.35(m, 5H), 7.26-7.19(m, 1H), 7.04(br s, 1H), 6.99-6.94(m, 2H), 6.84-6.81(m, 1H), 4.69(s, 2H), 3.02(t, 2H), and 2.70(t, 2H). LCMS: (FA) ES+ 553.1(M+1), ES− 551.1(M−1). |
| A-199 | $^1$H NMR(300MHz, CD$_3$OD) δ: 8.20(d, 1H), 7.95(s, 1H), 7.66(d, 1H), 7.43(t, 1H), 7.33(m, 2H), 7.19(d, 1H), 7.02(m, 1H), 6.91(m, 2H), 6.67(dd, 1H), 3.79(s, 2H), 3.02(t, 2H), and 2.70(t, 2H). LCMS: (FA) ES$^+$ 416.30(M+1). |
| A-152 | $^1$H NMR(300MHz, CD$_3$OD) δ: 8.19(d, 1H), 7.97(s, 1H), 7.68(d, 1H), 7.42(m, 1H), 7.35(m, 2H), 7.31(d, 1H), 7.02(s, 1H), 6.93(d, 1H), 6.85(s, 1H), 6.72(br, 1H), 4.26(s, 2H), 3.02(t, 2H), 2.70(t, 2H), and 1.33(s, 9H). LCMS: (FA) ES$^+$ 516.44(M+1). |

Example 24

Preparation of 4-(3-{3-[(5-tert-butyl-2-hydroxyphenyl)amino]-3-oxopropyl}phenoxy)pyridine-2-carboxamide (A-90)

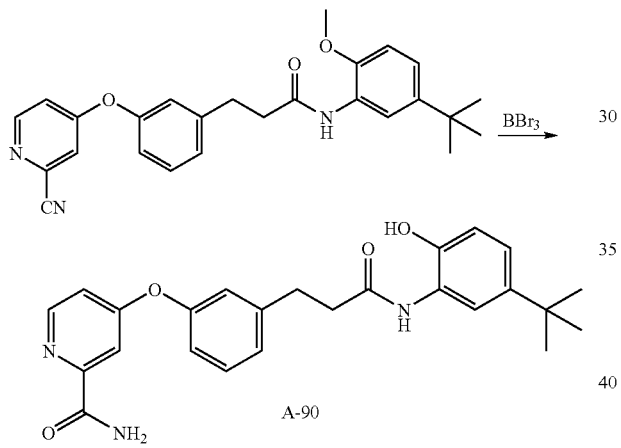

A solution of BBr$_3$ (1 M in DCM, 2.46 mL, 2.46 mmol) was added to a solution of N-(5-tert-butyl-2-methoxyphenyl)-3-{3-[(2-cyanopyridin-4-yl)oxy]phenyl}propanamide (0.53 g, 1.23 mmol) in DCM (13 mL) at 0° C. The solution was warmed to rt and stirred for 16 h. The reaction was poured onto ice slowly, the pH was adjusted to 7, and the solution extracted three times with Et$_2$O. The combined organic solutions were washed with brine and sat. Na$_2$S$_2$O$_3$, dried over Na$_2$SO$_4$ and concentrated to orange solid. The residue was purified by column chromatography to give A-90 (0.16 g, 32% yield). $^1$H NMR (300 MHz, CD$_3$OD) δ: 8.31 (d, 1H), 7.58 (d, 1H), 7.48 (d, 1H), 7.41 (t, 1H), 7.27-7.21 (m, 1H), 7.09-6.90 (m, 4H), 6.78-6.73 (m, 1H), 3.06 (t, 2H), 2.76 (t, 2H), and 1.25 (s, 9H). LCMS: (FA) ES+ 435.2 (M+1), ES− 432.2 (M−1).

Example 25

Preparation of N-[3-(2-aminoethyl)-5-(trifluoromethyl)phenyl]-3-(3-{[2-(4,5-dihydro-1H-imidazol-2-yl)pyridin-4-yl]oxy}phenyl)propanamide (A-148)

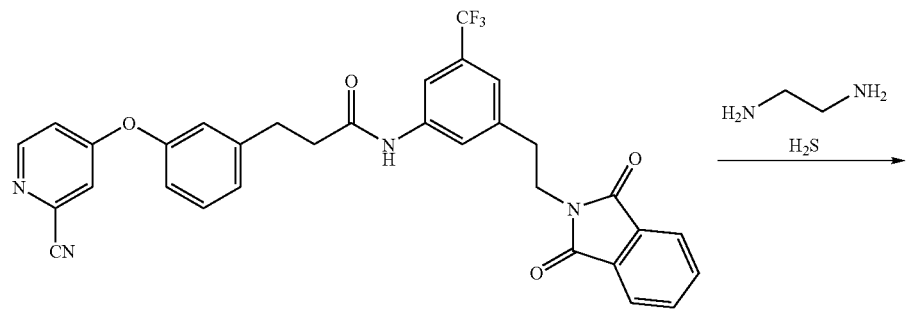

-continued

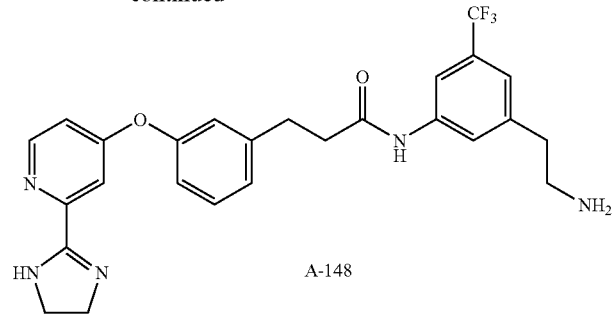

A-148

A-148 was prepared by the procedure of Example 13. Deprotection occurred concurrently with the amidine ring formation. $^1$H NMR (300 MHz, d$_6$-DMSO; HCl salt) δ: 10.88 (s, 1H), 10.58 (s, 1H), 8.62 (d, 1H), 8.07 (br s, 2H), 7.96 (s, 2H), 7.72 (s, 1H), 7.47-7.37 (m, 1H), 7.31-7.15 (m, 4H), 7.07-7.03 (m, 1H), 4.00 (s, 4H), 3.10-2.90 (m, 6H), and 2.76-2.69 (m, 2H). LCMS: (FA) ES+ 498.3 (M+1).

A-201 was prepared from 4-[3-(3-{[3-[2-(1,3-dioxo-1,3-dihydro-2H-isoindol-2-yl)ethyl]-5-(trifluoromethyl)phenyl]amino}-3-oxopropyl)phenoxy]-N-methylpyridine-2-carboxamide in a method analogous to that of Example 25. $^1$H NMR (300 MHz, CD$_3$OD; HCOOH salt) δ: 8.52 (br s, 1H), 8.37 (d, 1H), 7.74 (s, 2H), 7.52-7.48 (m, 1H), 7.43-7.35 (m, 1H), 7.31 (br s, 1H), 7.25-7.19 (m, 1H), 7.10-7.04 (m, 1H), 7.02-6.94 (m, 2H), 3.21-3.15 (m, 2H), 3.09-2.94 (s, 4H), 2.91 (s, 3H), and 2.76-2.69 (m, 2H). LCMS: (FA) ES+ 487.3 (M+1).

Example 26

Preparation of Substituted Aminomethyl Imidazoles

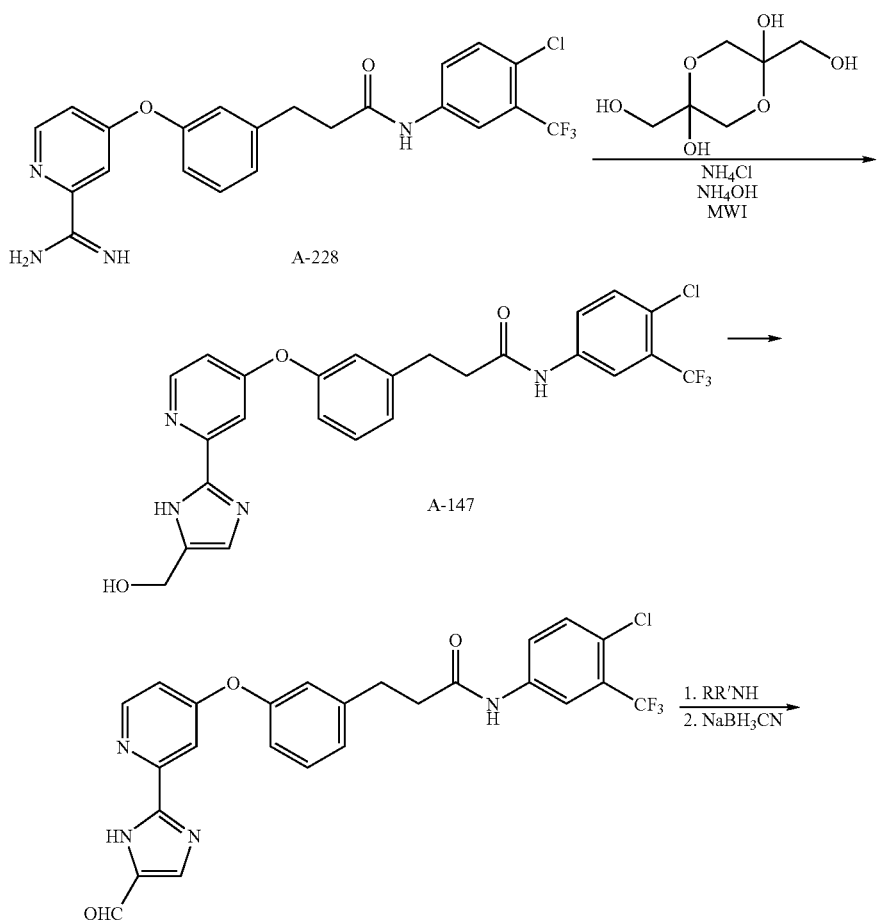

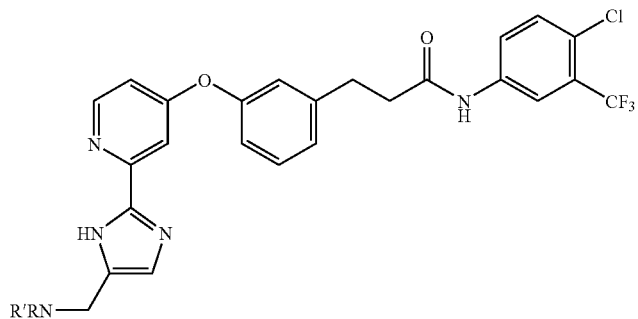

Step 1. Preparation of N-[4-chloro-3-(trifluoromethyl)phenyl]-3-[3-({2-[5-(hydroxymethyl)-1H-imidazol-2-yl]pyridin-4-yl}oxy)phenyl]propanamide (A-147)

A solution of A-228 (150 mg, 0.32 mmol), 1,3-dihydroxyacetone dimer (80 mg, 0.44 mmol) and NH$_4$Cl (80 mg, 1.50 mmol) in NH$_4$OH (3 mL) and NH$_3$ in MeOH (7M, 3 mL) was subjected to MWI at 120° C. for 5 mins. The reaction mixture was poured into ice-water and extracted with DCM. The combined organic solutions were washed with brine and dried over Na$_2$SO$_4$. The residue was purified by reverse phase HPLC [20% water with ACN (contained 0.1% FA) to 100% ACN (contained 0.1% FA) over 25 mins]. The HCl salt of A-147 was obtained as a white solid after adding 1M HCl in ether into the MeOH solution of product and followed by removal of solvent. $^1$H NMR (300 MHz, CD$_3$OD): δ 8.53 (d, 1H), 8.02 (d, 1H), 7.66 (dd, 1H), 7.61 (d, 1H), 7.50 (s, 1H), 7.42 (d, 1H), 7.39 (d, 1H), 7.24 (d, 1H), 7.08 (m, 1H), 7.02 (m, 2H), 4.66 (s, 2H), 3.04 (t, 2H), 2.73 (t, 2H). LCMS: (FA) ES$^+$ 517.2 (M+1).

Step 2. Preparation of N-[4-chloro-3-(trifluoromethyl)phenyl]-3-(3-{[2-(5-formyl-1H-imidazol-2-yl)pyridin-4-yl]oxy}phenyl)propanamide Dess-Martin periodinane (354 mg, 0.84 mmol) was added to a suspension of A-147 (360 mg, 0.70 mmol) in DCM (3 mL) at rt. The resulting suspension was stirred at rt for 30 min, and then quenched by the addition of aq. NaHCO$_3$/Na$_2$SO$_3$ (1:1). The mixture was extracted with DCM and the combined organic solutions were washed with brine and dried over Na$_2$SO$_4$, filtered, and concentrated to give the title compound as an off-white foam and directly used in the next step. LCMS: (FA) ES$^+$ 515.3 (M+1).

Step 3. Preparation of Imidazoles

An amine (4.0 eq) was added to a solution of the appropriate aldehyde (1.0 eq) in MeOH at rt. The reaction was stirred for 2 h, and then sodium cyanoborohydride (4.0 eq) was added and the reaction was stirred overnight. DCM was added into the reaction mixture and the mixture was washed with brine. The residue was purified by reverse phase HPLC [80% water with ACN (contained 0.1% FA) to 100% ACN (contained 0.1% FA) over 25 mins]. The HCl salt of the imidazole was obtained as a white solid after adding 1M HCl in ether into the MeOH solution of product and followed by removal of solvent.

Compounds in the following table were prepared from the appropriate starting materials in a method analogous to that of Example 26:

| | |
|---|---|
| A-109 | $^1$H NMR(300MHz, CD$_3$OD; 3*HCl salt): δ8.59(d, 1H), 8.07(d, 1H), 7.76(d, 1H), 7.72(s, 1H), 7.68(d, 1H), 7.51(s, 1H), 7.48(d, 1H), 7.34(d, 1H), 7.26(dd, 1H), 7.14(m, 1H), 7.12(dd, 1H), 4.33(s, 2H), 3.10(t, 2H), 2.80(s, 3H), 2.78(t, 2H). LCMS: (FA) ES$^+$ 530.24(M+1). |
| A-73 | $^1$H NMR(400MHz, CD$_3$OD; 3*HCl salt): δ8.59(d, 1H), 8.05(d, 1H), 7.78(d, 1H), 7.75(s, 1H), 7.69(dd, 1H), 7.52(d, 1H), 7.48(d, 1H), 7.35(d, 1H), 7.28(dd, 1H), 7.20(m, 1H), 7.12(dd, 1H), 4.43(s, 2H), 3.11(t, 2H), 2.95(s, 6H), 2.78(t, 2H). LCMS: (FA) ES$^+$ 544.69(M+1). |
| A-226 | $^1$H NMR(400MHz, CD$_3$OD; 3*HCl salt): δ8.59(d, 1H), 8.05(d, 1H), 7.77(d, 1H), 7.75(s, 1H), 7.69(dd, 1H), 7.52(d, 1H), 7.48(d, 1H), 7.35(d, 1H), 7.28(dd, 1H), 7.20(m, 1H), 7.12(dd, 1H), 4.50(s, 2H), 3.62(m, 2H), 3.11(t, 2H), 2.78(t, 2H), 2.10(m, 4H). LCMS: (FA) ES$^+$ 570.61(M+1). |
| A-58 | $^1$H NMR(400MHz, CD$_3$OD; 4*HCl salt): δ8.61(d, 1H), 8.06(d, 1H), 7.76(m, 2H), 7.70(dd, 1H), 7.50(m, 2H), 7.34(d, 1H), 7.28(dd, 1H), 7.20(m, 1H), 7.12(dd, 1H), 4.46(s, 2H), 3.67(m, 4H), 3.11(t, 2H), 3.01(s, 6H), 2.78(t, 2H). LCMS: (FA) ES$^+$ 587.63(M+1). |

Example 27

Preparation of Amide-substituted Imidazoles

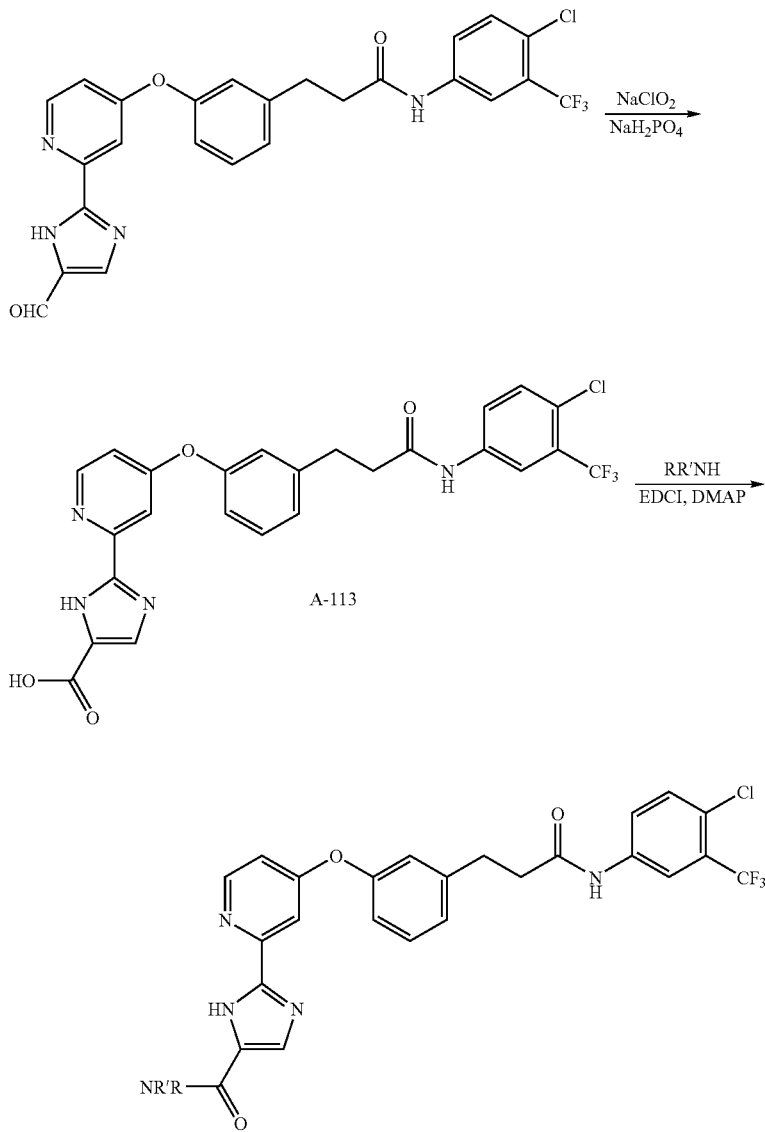

Step 1. Preparation of 2-{4-[3-(3-{[4-chloro-3-(trifluoromethyl)phenyl]amino}-3-oxopropyl)phenoxy]pyridin-2-yl}-1H-imidazole-4-carboxylic acid (A-113)

A solution of N-[4-chloro-3-(trifluoromethyl)phenyl]-3-(3-{[2-(5-formyl-1H-imidazol-2-yl)pyridin-4-yl]oxy}phenyl)propanamide (210 mg, 0.41 mmol) in 2-methyl-2-butene (1 mL), ACN (2 mL) and tert-butyl alcohol (2 mL) was cooled to 0° C., and a solution of sodium chlorite (228 mg, 2.02 mmol) and sodium dihydrogenphosphate (240 mg, 2.0 mmol) in water (1 mL) was added. The yellow solution was stirred at 0° C. overnight. The reaction was quenched with brine and extracted with EtOAc. The combined organic solutions were washed with brine, dried over $Na_2SO_4$, filtered, and concentrated to give A-113 as a white solid, which was directly used in the next step. $^1$H NMR (300 MHz, $CD_3OD$) δ: 6.96 (d, 1H), 6.49 (s, 1H), 6.42 (d, 1H), 6.19 (m, 1H), 6.05 (dd, 1H), 5.79-5.88 (m, 2H), 5.68 (d, 1H), 5.58 (d, 1H), 5.53 (s, 1H), 5.45 (d, 1H), 1.46 (dd, 2H), and 1.14 (22, 2H). LCMS: (FA) ES+ 531.1 (M+1), ES− 529.1 (M−1).

Step 2. Preparation of Amide Substituted Imidazoles

A solution of the appropriate carboxylic acid (1.0 eq), amine (1.2 eq) and DMAP (1.2 eq) in DCM was cooled to 0° C. and then EDCI (1.3 eq) was added. The reaction mixture was stirred at rt for 16 h and then diluted with DCM and washed with brine. The crude product was purified by reverse phase HPLC [80% water with ACN (contained 0.1% FA) to 100% ACN (contained 0.1% FA) over 25 mins]. The HCl salt of the title compound was obtained as a white solid after adding 1M HCl in ether into the MeOH solution of product and followed by removal of solvent.

Compounds in the following table were prepared from the appropriate starting materials in a method analogous to that of Example 27:

| | |
|---|---|
| A-184 | ¹H NMR(400MHz, CD₃OD; 3*HCl salt): δ8.62(d, 1H), 8.07(d, 1H), 8.04(s, 1H), 7.83(d, 1H), 7.70(dd, 1H), 7.52(t, 1H), 7.46(d, 1H), 7.37(m, 2H), 7.24(br, 1H), 7.15(dd, 1H), 3.65(d, 4H), 3.26(m, 4H), 3.11(t, 2H), 2.99(s, 3H), 2.80(t, 2H). LCMS: (FA) ES⁺ 613.34(M+1). |
| A-204 | ¹H NMR(400MHz, CD₃OD; bisHCl salt): δ8.61(d, 1H), 8.06(d, 1H), 7.99(s, 1H), 7.81(d, 1H), 7.68(dd, 1H), 7.50(t, 1H), 7.46(d, 1H), 7.34(d, 1H), 7.29(dd, 1H), 7.21(br, 1H), 7.12(d, 1H), 4.11(br, 4H), 3.75(m, 4H), 3.10(t, 2H), 2.79(t, 2H). LCMS: (FA) ES⁺ 600.26(M+1). |
| A-171 | ¹H NMR(300MHz, CD₃OD)•: 8.37(d, 1H), 8.02(d, 1H), 7.65(dd, 1H), 7.62(s, 1H), 7.56(d, 1H), 7.44(d, 1H), 7.38(d, 1H), 7.20(d, 2H), 7.07(dd, 1H), 7.00(dd, 1H), 6.81(s, 1H), 3.37(s, 3H), 3.01-3.13(m, 5H), and 2.70(dd, 2H). LCMS: (FA) ES+ 558.31(M+1), ES− 556.28(M−1). |

Example 28

Preparation of N-[4-chloro-3-(trifluoromethyl)phenyl]-3-[4-({2-[4-(hydroxymethyl)-4,5-dihydro-1H-imidazol-2-yl]pyridin-4-yl}oxy)phenyl]propanamide (A-243)

Step 1. Preparation of methyl 2-{4-[4-(3-{[4-chloro-3-(trifluoromethyl)phenyl]amino}-3-oxopropyl)phenoxy]pyridin-2-yl}-4,5-dihydro-1H-imidazole-4-carboxylate To a solution of A-142 (300 mg, 0.56 mmol) in MeOH (1.00 mL) were added a few drops of 6N HCl. The mixture was stirred at rt for 5 h. The solvents were evaporated and the residue was purified by chromatography (SiO₂, 90:10:1

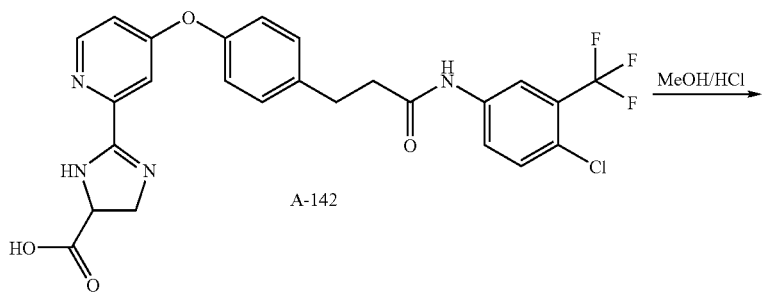

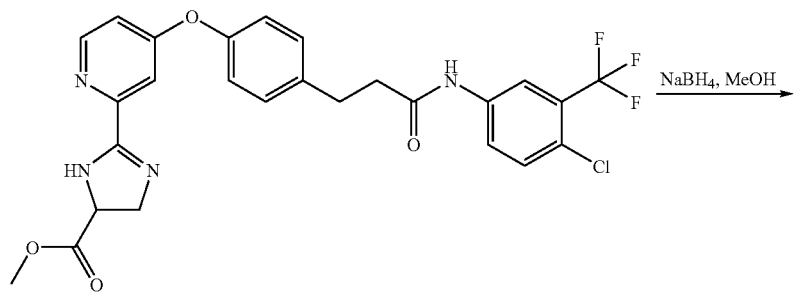

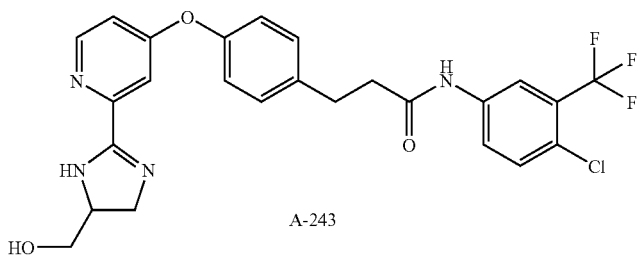

DMC:MeOH:H₂O) to yield the title compound (107 mg, 35%). LCMS: (FA) ES+ 547.1 (M+1), ES– 545.3 (M–1).

Step 2. Preparation of N-[4-chloro-3-(trifluoromethyl)phenyl]-3-[4-({2-[4-(hydroxymethyl)-4,5-dihydro-1H-imidazol-2-yl]pyridin-4-yl}oxy)phenyl]propanamide (A-243)

To a solution of methyl 2-{4-[4-(3-{[4-chloro-3-(trifluoromethyl)phenyl]amino}-3-oxopropyl)phenoxy]pyridin-2-yl}-4,5-dihydro-1H-imidazole-4-carboxylate (107 mg, 0.20 mmol) in MeOH (2 mL), at 0° C., was added sodium borohydride (8.0 mg, 0.22 mmol) portionwise. The reaction mixture was stirred at 0° C. for 45 min, and then warmed to rt and stirred for 18 h. After this time additional sodium borohydride (8.0 mg, 0.22 mmol) was added and the mixture was heated at 60° C. for 18 h. The reaction was then cooled to rt, and 1N HCl was added. The solvents were evaporated and the residue was purified by HPLC (250 mm C18 column) eluting with ACN containing 30% to 100% of 0.1% FA in water (20 min gradient) to give A-243 (6.0 mg, 5.8%). ¹H NMR (300 MHz, CD₃OD) δ: 8.55 (d, 1H), 8.08 (d, 1H), 7.76-7.72 (m, 1H), 7.61 (d, 1H), 7.53 (d, 1H), 7.41-7.38 (m, 2H), 7.11-7.08 (m, 3H), 4.45-4.35 (m, 1H), 4.06 (t, 1H), 3.90-3.83 (m, 1H), 3.74-3.61 (m, 2H), 3.06 (t, 2H), and 2.73 (t, 2H). LCMS: (FA) ES+ 519.1 (M+1).

Compounds in the following table were prepared from the appropriate starting materials in a method analogous to that of Example 28:

| | |
|---|---|
| A-180 | ¹H NMR(400MHz, d₆-DMSO; bisHCl salt) δ: 11.41(s, 1H), 11.33(s, 1H), 10.67(s, 1H), 8.66(d, 1H), 8.20(d, 1H), 8.01(d, 1H), 7.84(dd, 1H), 7.63(d, 1H), 7.44(t, 1H), 7.26-7.21(m, 2H), 7.15(s, 1H), 7.06(dd, 1H), 5.17(dd, 1H), 4.34-4.16(m, 2H), 3.75(s, 3H), 2.97(t, 2H), and 2.72(t, 2H). LCMS: (FA)ES+ 547.3(M+1), ES– 545.4(M–1). |
| A-178 | ¹H NMR(300MHz, CD₃OD; HCOOH salt) δ: 8.54(d, 1H), 8.47(s, 1H), 8.04(d, 1H), 7.69(dd, 1H), 7.64(d, 1H), 7.51(d, 1H), 7.44(t, 1H), 7.26(d, 1H), 7.11-7.08(m, 2H), 7.02(dd, 1H), 4.52-4.45(m, 1H), 4.13(t, 1H), 3.94(dd, 1H), 3.79-3.64(m, 2H), 3.06(t, 2H), and 2.73(t, 2H). LCMS: (FA)ES+ 519.1(M+1), ES– 517.0(M–1). |

Example 29

Preparation of 3-(3-{[2-(4,5-dihydro-1H-imidazol-2-yl)pyridin-4-yl]oxy}phenyl)-N-[4-(piperazin-1-ylcarbonyl)-3-(trifluoromethyl)phenyl]propanamide (A-69)

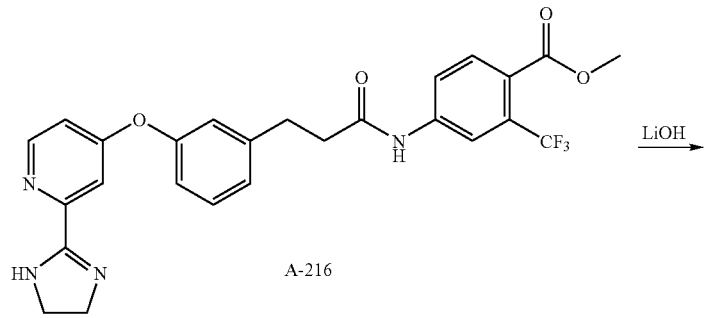

A-216

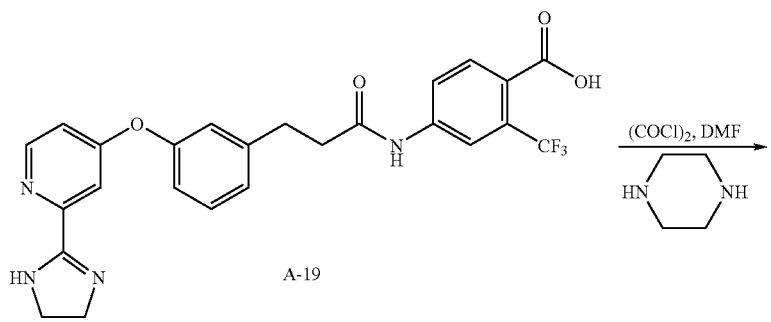

A-19

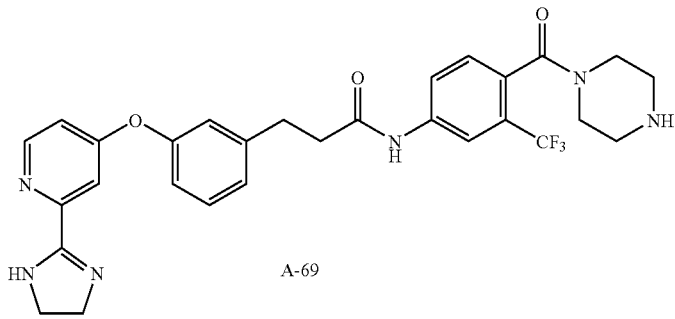

A-69

Step 1. Preparation of 4-{[3-(3-{[2-(4,5-dihydro-1H-imidazol-2-yl)pyridin-4-yl]-oxy}phenyl)propanoyl]amino}-2-(trifluoromethyl)benzoic acid (A-19)

A-19 was prepared by refluxing A-216 (900 mg, 1.76 mmol) with lithium hydroxide (84.0 mg, 3.51 mmol) in THF (15 mL) and water (200 μL) for 72 h. The reaction mixture was concentrated and purified by reverse phase HPLC [water with 20% ACN (contained 0.1% FA) to 100% ACN (contained 0.1% FA) over 25 mins]. $^1$H NMR (400 MHz, d$_6$-DMSO) δ: 10.36 (s, 1H), 8.47 (d, 1H), 8.00 (s, 1H), 7.75-7.63 (m, 2H), 7.50 (d, 1H), 7.42 (t, 1H), 7.22 (d, 1H), 7.09-7.01 (m, 3H), 3.69 (s, 4H), 2.96 (t, 2H), and 2.68 (t, 2H). LCMS: (FA) ES$^+$ 499.3 (M+1).

Step 2. Preparation of 3-(3-{[2-(4,5-dihydro-1H-imidazol-2-yl)pyridin-4-yl]oxy}phenyl)-N-[4-(piperazin-1-ylcarbonyl)-3-(trifluoromethyl)phenyl]propanamide (A-69)

A-69 was prepared by treating A-19 (100 mg, 0.20 mmol) with oxalyl chloride (60 μL, 0.66 mmol) and DMF (100 μL) in methylene chloride (3 mL) at rt. After stirring for 1 h, piperazine (125 mg, 1.45 mmol) was added. The reaction mixture was concentrated and purified by reverse phase HPLC [water with 5% ACN (contained 0.1% FA) to 100% ACN (contained 0.1% FA) over 25 mins]. $^1$H NMR (400 MHz, CD$_3$OD; HCl salt) δ: 8.55 (d, 1H), 8.06 (s, 1H), 7.80 (dd, 1H), 7.62 (d, 1H), 7.45-7.39 (m, 2H), 7.26 (d, 1H), 7.12-7.08 (m, 2H), 7.01 (dd, 1H), 4.08 (s, 4H), 3.94-3.80 (m, 2H), 3.40-3.32 (m, 2H), 3.18-3.11 (m, 2H), 3.07 (t, 2H), 3.02-2.90 (m, 2H), and 2.75 (t, 2H). LCMS: (FA) ES$^+$ 567.0 (M+1).

Compounds in the following table were prepared from the appropriate starting materials in a method analogous to that of Example 29:

| | |
|---|---|
| A-65 | $^1$H NMR(400MHz, CD$_3$OD) δ: 8.51(d, 1H), 8.04(s, 1H), 7.77(dd, 1H), 7.61(d, 1H), 7.42(t, 1H), 7.32(d, 1H), 7.25(d, 1H), 7.09-7.07(m, 2H), 7.02-6.99(m, 1H), 4.03(s, 4H), 3.09-3.05(m, 5H), 2.81(s, 3H), and 2.74(t, 2H). LCMS: (FA)ES$^+$ 526.3(M+1). |
| A-159 | $^1$H NMR(400MHz, CD$_3$OD) δ: 8.44(t, 2H), 7.81(d, 1H), 7.58-7.54(m, 2H), 7.44(t, 1H), 7.38(d, 1H), 7.26(d, 1H), 7.05-7.00(m, 3H), 4.07(s, 4H), 3.09-3.01(m, 4H), 2.71(t, 2H), 2.52(t, 2H). LCMS: (AA)ES+ 527.29(M+1), ES− 525.39(M−1). |

Example 30
Preparation of 3-(3-{[2-(4,5-dihydro-1H-imidazol-2-yl)pyridin-4-yl]oxy}phenyl)-N-[3-[3-(dimethylamino)propyl]-5-(trfluoromethyl)phenyl]propanamide (A-165)
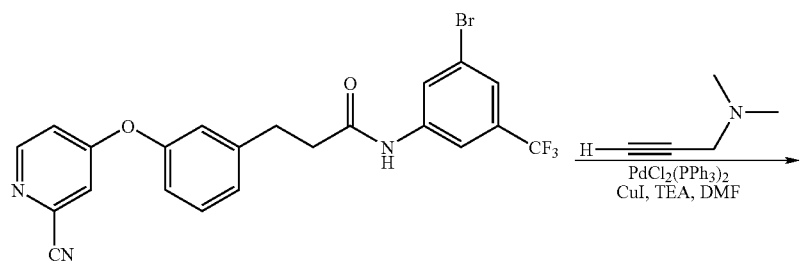
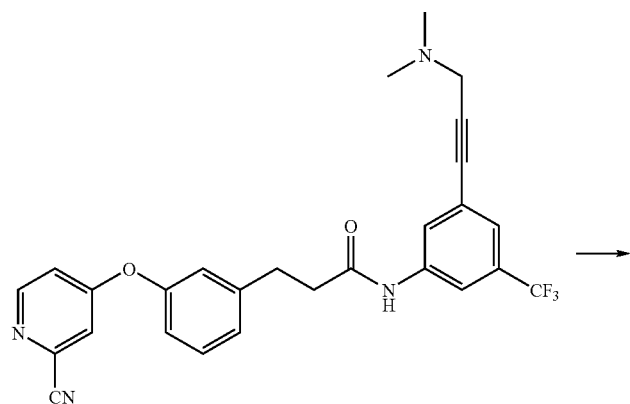
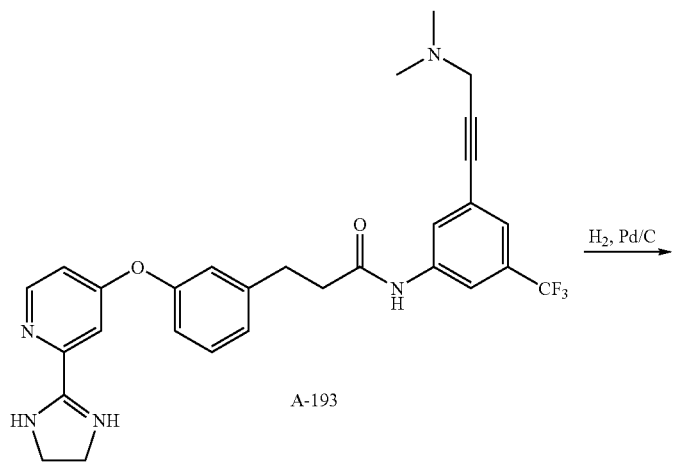

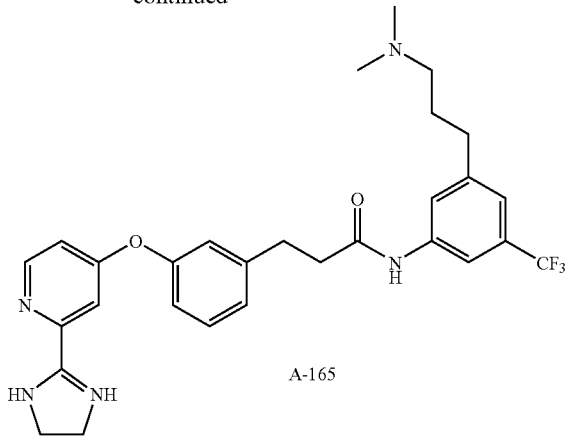

A-165

Step 1. Preparation of 3-{3-[(2-cyanopyridin-4-yl)oxy]phenyl}-N-[3-[3-(dimethylamino)prop-1-yn-1-yl]-5-(trifluoromethyl)phenyl-]propanamide A solution of N-[3-bromo-5-(trifluoromethyl)phenyl]-3-{3-[(2-cyanopyridin-4-yl)oxy]phenyl}propanamide (prepared following the procedures described in Example 11, 0.500 g, 1.02 mmol), TEA (569 μL, 4.08 mmol), and copper iodide (19.0 mg, 0.10 mmol) in DMF (3 mL) was degassed for 15 min. To this solution was added 1-dimethylamino-2-propyne (240 μL, 4.08 mmol) and the reaction degassed for an additional minute. Dichlorobis(triphenylphosphine)-palladium(II) (36 mg, 0.05 mmol) was added to the reaction mixture and the reaction heated at 60° C. for 6 h. The crude reaction mixture was purified by column chromatography to give the title compound. LCMS: (FA) ES$^+$ 493.1 (M+1), ES$^-$ 491.1 (M−1).

Step 2. Preparation of 3-(3-{[2-(4,5-dihydro-1H-imidazol-2-yl)pyridin-4-yl]oxy}phenyl)-N-[3-[3-(dimethylamino)prop-1-yn-1-yl]-5-(trifluoromethyl)phenyl]propanamide (A-193)

A-193 was prepared from 3-{3-[(2-cyanopyridin-4-yl)oxy]phenyl}-N-[3-[3-(dimethylamino)prop-1-yn-1-yl]-5-(trifluoromethyl)phenyl-]propanamide following the procedures described in Example 13. $^1$H NMR (300 MHz, CD$_3$OD) δ: 8.37 (d, 1H), 7.88 (s, 1H), 7.79 (s, 1H), 7.47 (d, 1H), 7.42-7.37 (m, 2H), 7.20 (d, 1H), 7.06 (t, 1H), 6.99-6.93 (m, 2H), 3.74 (s, 4H), 3.50 (s, 2H), 3.04 (t, 2H), 2.70 (t, 2H), and 2.37 (s, 6H). LCMS: (FA) ES$^+$ 536.3 (M+1), ES$^-$ 534.4 (M−1).

Step 3. Preparation of 3-(3-{[2-(4,5-dihydro-1H-imidazol-2-yl)pyridin-4-yl]oxy}phenyl)-N-[3-[3-(dimethylamino)propyl]-5-(trifluoromethyl)phenyl]propanamide (A-165)

A-196 (247 mg, 0.46 mmol) was dissolved in MeOH (10 mL) and the reaction mixture was degassed. Under argon, Pd (5 wt. % on activated carbon, 10 mol %) was added to the reaction mixture which was then stirred under an atmosphere of hydrogen at rt. The reaction was filtered through Celite and the solvent was evaporated to give A-165. $^1$H NMR (400 MHz, CD$_3$OD) δ: 8.34 (d, 1H), 7.75 (s, 1H), 7.54 (s, 1H), 7.49 (d, 1H), 7.39 (t, 1H), 7.21-7.20 (m, 2H), 7.05 (s, 1H), 6.98-6.92 (m, 2H), 3.75 (s, 4H), 3.05 (t, 2H), 2.71-2.63 (m, 4H), 2.35-2.29 (m, 2H), 2.23 (s, 6H), 1.83-1.75 (m, 2H), and 2.23 (s, 6H). LCMS: (FA) ES+ 540.4 (M+1), ES$^-$ 538.5 (M−1).

Compounds in the following table were prepared from the appropriate starting materials in a method analogous to that of Example 30:

| | |
|---|---|
| A-144 | $^1$H NMR(400MHz, CD$_3$OD) δ: 7.94(d, 1H), 7.55(d, 1H), 7.25(dd, 1H), 7.13(d, 1H), 7.04(d, 1H), 6.96(t, 1H), 6.76(d, 1H), 6.65(t, 1H), 6.55-6.50(m, 2H), 4.5(s, 4H), 2.92(s, 1H), 2.89-2.87(m, 2H), 2.61(t, 2H), 2.28(t, 2H). LCMS: (FA)ES+ 479.2(M+1), ES− 477.3(M−1). |
| A-63 | $^1$H NMR(400MHz, CD$_3$OD) δ: 8.41(d, 1H), 7.96(d, 1H), 7.67(dd, 1H), 7.53(d, 1H), 7.49(d, 1H), 7.41(t, 1H), 7.22(d, 1H), 7.07(t, 1H), 7.00-6.97(m, 2H), 4.41(s, 2H), 3.81(s, 4H), 3.06(t, 2H), 2.72(t, 2H). LCMS: (FA)ES+ 509.2(M+1), ES− 507.2(M−1). |
| A-145 | $^1$H NMR(400MHz, CD$_3$OD) δ: 8.4(d, 1H), 7.86(s, 1H), 7.62(d, 1H), 7.5(s, 1H), 7.39(t, 1H), 7.32(d, 1H), 7.21(d, 1H), 7.05(s, 1H), 6.96(s, 2H), 3.83(s, 4H), 3.6(t, 2H), 3.04(t, 2H), 2.79(t, 2H), 2.69(t, 2H). LCMS: (FA)ES+ 513.8(M+1), ES− 511.3(M−1). |
| A-66 | $^1$H NMR(400MHz, CD$_3$OD) δ: 8.3(d, 1H), 7.98(d, 1H), 7.68(dd, 1H), 7.51(d, 1H), 7.46(d, 1H), 7.37(t, 1H), 7.2(d, 1H), 7.03(t, 1H), 6.96-6.92(m, 2H), 3.73(s, 4H), 3.52(s, 2H), 3.02(t, 2H), 2.69(t, 2H), 2.36(s, 6H). LCMS: (FA)ES$^+$ 536.0(M+1), ES− 534.3(M−1). |
| A-244 | $^1$H NMR(400MHz, CD$_3$OD) δ: 8.34(d, 1H), 7.89(s, 1H), 7.65(d, 1H), 7.47(s, 1H), 7.38-7.31(m, 2H), 7.18(d, 1H), 7.03(s, 1H), 6.96-6.89(m, 2H), 3.72(s, 4H), 3.02(t, 2H), 2.68(q, 4H), 2.36(t, 2H), 2.22(s, 6H), 1.78-1.72(m, 2H). LCMS: (FA)ES+ 540.0(M+1), ES− 538.3(M−1). |
| A-265 | $^1$H NMR(400MHz, CD$_3$OD; HCl salt) δ: 8.37(d, 1H), 7.85(t, 1H), 7.62(dd, 1H), 7.48(d, 1H), 7.39(t, 1H), 7.33(d, 1H), 7.22(d, 1H), 7.06(s, 1H), 6.99-6.93(m, |

| | |
|---|---|
| | 2H), 3.75(s, 4H), 3.04(t, 2H), 2.75(dd, 2H), 2.69(t, 2H), 1.21(t, 3H). LCMS: (FA)ES+ 483.2(M+1), ES− 481.1(M−1). |
| A-234 | $^1$H NMR(400MHz, CD$_3$OD) δ: 8.38(d, 1H), 7.88(d, 1H), 7.62(dd, 1H), 7.49(d, 1H), 7.4(t, 1H), 7.35(d, 1H), 7.23(d, 1H), 7.06(t, 1H), 7(dd, 1H), 6.97-6.95(m, 1H), 3.81(s, 4H), 3.67(s, 3H), 3.07-3.01(m, 4H), 2.69(t, 2H), 2.6(t, 2H). LCMS: (FA)ES+ 541.4(M+1), ES− 539.4(M−1). |

Example 31

Preparation of 3-{3-[(2-aminopyridin-4-yl)oxy]phenyl}-N-(3-tert-butylphenyl)propanamide (A-261)

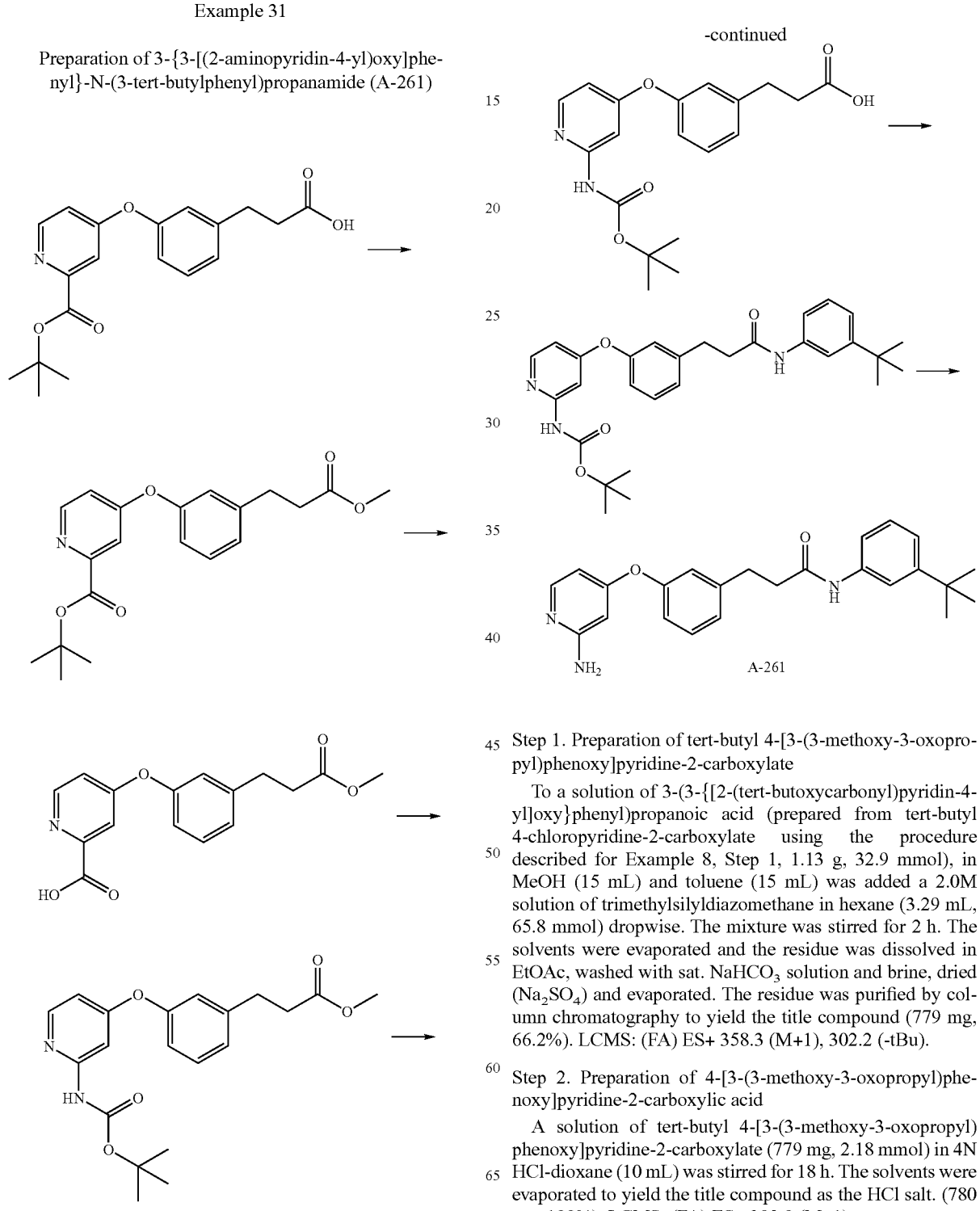

Step 1. Preparation of tert-butyl 4-[3-(3-methoxy-3-oxopropyl)phenoxy]pyridine-2-carboxylate To a solution of 3-(3-{[2-(tert-butoxycarbonyl)pyridin-4-yl]oxy}phenyl)propanoic acid (prepared from tert-butyl 4-chloropyridine-2-carboxylate using the procedure described for Example 8, Step 1, 1.13 g, 32.9 mmol), in MeOH (15 mL) and toluene (15 mL) was added a 2.0M solution of trimethylsilyldiazomethane in hexane (3.29 mL, 65.8 mmol) dropwise. The mixture was stirred for 2 h. The solvents were evaporated and the residue was dissolved in EtOAc, washed with sat. NaHCO$_3$ solution and brine, dried (Na$_2$SO$_4$) and evaporated. The residue was purified by column chromatography to yield the title compound (779 mg, 66.2%). LCMS: (FA) ES+ 358.3 (M+1), 302.2 (-tBu).

Step 2. Preparation of 4-[3-(3-methoxy-3-oxopropyl)phenoxy]pyridine-2-carboxylic acid A solution of tert-butyl 4-[3-(3-methoxy-3-oxopropyl)phenoxy]pyridine-2-carboxylate (779 mg, 2.18 mmol) in 4N HCl-dioxane (10 mL) was stirred for 18 h. The solvents were evaporated to yield the title compound as the HCl salt. (780 mg, 100%). LCMS: (FA) ES+ 302.0 (M+1).

Step 3. Preparation of methyl 3-[3-({2-[(tert-butoxycarbonyl)amino]pyridin-4-yl}oxy)phenyl]propanoate To a solution of 4-[3-(3-methoxy-3-oxopropyl)phenoxy]pyridine-2-carboxylic acid (736 mg, 2.18 mmol) in THF (20 mL) at 0° C., was added TEA (1.09 mL, 7.84 mmol) then diphenylphosphonic azide (610 μL, 2.83 mmol) dropwise. The reaction was stirred at 0° C. for 10 min and then allowed to warm to rt. After 2 h, the solvents were evaporated and the residue was taken up in EtOAc, washed with sat. NaHCO₃ solution, then brine, dried (Na₂SO₄), and evaporated. 2-methylpropan-2-ol (10.0 mL) was added and the solution was heated at 85° C. for 40 min, and then allowed to cool to rt. The solvents were evaporated and the residue was purified by chromatography to yield the title compound as an oil (427 mg, 52.6%). LCMS: (FA) ES+ 327.1 (M+1).

Step 4. Preparation of 3-[3-({2-[(tert-butoxycarbonyl)amino]pyridin-4-yl}oxy)phenyl]propanoic acid To a solution of methyl 3-[3-({2-[(tert-butoxycarbonyl)amino]pyridin-4-yl}oxy)phenyl]propanoate (427 mg, 1.15 mmol) in MeOH (10 mL) and THF (5 mL), was added 1M NaOH solution (4.59 mL, 4.49 mmol). The reaction was stirred for 18 h. The solvents were evaporated and the residue was dissolved in water. The solution was acidified to pH=3 by addition of 1N HCl. The precipitate was filtered off and washed with water and then hexane, then dried under vacuum to yield the title compound as a white solid (333 mg, 81%). LCMS: (FA) ES⁺ 359.1 (M+1), ES⁻ 357.0 (M−1).

Step 5. Preparation of tert-butyl [4-(3-{3-[(3-tert-butylphenyl)amino]-3-oxopropyl}phenoxy)pyridin-2-yl]carbamate To a solution of 3-[3-({2-[(tert-butoxycarbonyl)amino]pyridin-4-yl}oxy)phenyl]propanoic acid (333 mg, 0.93 mmol) in DCM (10 mL), were added 3-tert-butylaniline (152 mg, 1.02 mmol), DMAP (125 mg, 1.02 mmol) and then EDCI (196 mg, 1.02 mmol). The reaction was stirred for 18 h., and then diluted with DCM and washed with water and brine. The organic solution was dried over Na₂SO₄, filtered and concentrated. The residue was purified by column chromatography to yield the title compound as a white solid (389 mg, 86%). LCMS: (FA) ES⁺ 490.2 (M+1), ES⁻ 488.2 (M−1).

Step 6. Preparation of 3-{3-[(2-aminopyridin-4-yl)oxy]phenyl}-N-(3-tert-butylphenyl)propanamide (A-261)

A solution of tert-butyl [4-(3-{3-[(3-tert-butylphenyl)amino]-3-oxopropyl}phenoxy)pyridin-2-yl]carbamate (389 mg, 0.79 mmol) in 4M HCl-dioxane (10 mL) was stirred under nitrogen for 18 h. The solvents were evaporated to yield A-261 as the HCl salt (341 mg, 100%). ¹H NMR (400 MHz, d₆-DMSO; HCl salt) δ: 9.92 (s, 1H), 7.91 (d, 1H), 7.78 (s, 2H), 7.53 (t, 1H), 7.46 (t, 2H), 7.27 (d, 1H), 7.21-7.15 (m, 2H), 7.07 (dd, 2H), 6.60 (dd, 1H), 6.09 (d, 1H), 2.96 (t, 2H), 2.64 (t, 2H), and 1.24 (s, 9H). LCMS: (FA) ES+ 390.16 (M+1), ES− 388.12 (M−1). LCMS: (FA) ES⁺ 390.2 (M+1), ES⁻ 388.1 (M−1).

Compounds in the following table were prepared from the appropriate starting materials in a method analogous to that of Example 31:

Example 32

Preparation of 3-(3-{[2-(acetylamino)pyridin-4-yl]oxy}phenyl)-N-[3-[2-(dimethylamino)ethoxy]-5-(trifluoromethyl)phenyl]propanamide (A-211)

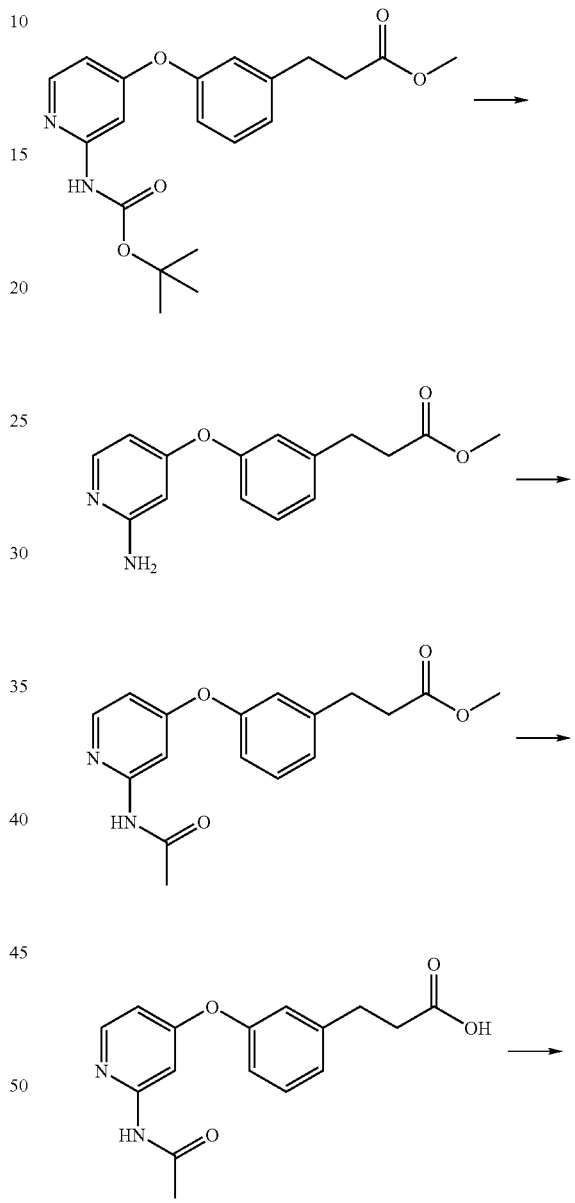

---

A-77  ¹H NMR(300MHz, CD₃OD) δ: 8.02(m, 2H), 7.69(dd, 1H), 7.44(m, 2H), 7.34(t, 1H), 7.13(dd, 1H), 7.03(br, 1H), 6.93(dd, 1H), 6.47(dd, 1H), 3.02(t, 2H), 2.70(t, 2H), and 1.45(s, 9H). LCMS: (FA)ES⁺ 536.21(M+1).

A-92  ¹H NMR(400MHz, CD₃OD) δ: 8.04(d, 1H), 7.71(dd, 1H), 7.69(d, 1H), 7.46(d, 1H), 7.33(t, 1H), 7.13(d, 1H), 7.00(m, 1H), 6.91(m, 1H), 6.14(dd, 1H), 5.99(d, 1H), 3.01(t, 2H), and 2.70(t, 2H). LCMS: (FA)ES⁺ 436.11(M+1).

-continued

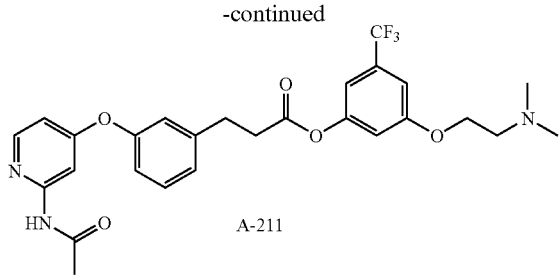

A-211

Step 1. Preparation of methyl 3-{3-[(2-aminopyridin-4-yl)oxy]phenyl}propanoate

Methyl 3-[3-({2-[(tert-butoxycarbonyl)amino]pyridin-4-yl}oxy)phenyl]propanoate (960 mg, 0.25 mmol), trifluoroacetic acid (5.00 mL) and few drops of water were stirred for 3.5 h. at rt. The reaction mixture was concentrated and purified by column chromatography to give the title compound as white solid (790 mg, 100%). LCMS: (FA) ES+ 273.3 (M+1)

Step 2. Preparation of methyl 3-(3-{[2-(acetylamino)pyridin-4-yl]oxy}phenyl)-propanoate Methyl 3-{3-[(2-aminopyridin-4-yl)oxy]phenyl}propanoate (390 mg, 0.14 mmol) was dissolved in pyridine (5 mL) and the reaction mixture was cooled at 0° C. and stirred for 1 h. Acetic anhydride (135 µL, 0.14 mmol) was added dropwise and the reaction mixture was allowed to stir for 1 h. The reaction mixture was allowed to warm to rt and to stir overnight. The reaction was quenched with water and extracted with EtOAc. The organic solutions were dried (MgSO$_4$), filtered and concentrated. The residue was purified column chromatography to give the title compound (340 mg, 76%) as a white solid. LCMS: (FA) ES+ 315.29 (M+1).

Step 3. Preparation of 3-(3-{[2-(acetylamino)pyridin-4-yl]oxy}phenyl)propanoic acid To a solution of methyl 3-(3-{[2-(acetylamino)pyridin-4-yl]oxy}phenyl)propanoate (184 mg, 0.59 mmol) in MeOH (5 mL) was added 1N NaOH solution (702 µL, 0.70 mmol). The reaction was stirred for 18 h. The solvents were evaporated and the residue was dissolved in water and acidified to pH=1 by addition of 1N HCl solution. The precipitate was filtered off and washed with water then hexane and dried under vacuum to yield the title compound as a white solid (112 mg, 63.7%). LCMS: (FA) ES+ 301.2 (M+1), ES− 299.3 (M−1).

Step 4. Preparation of 3-(3-{[2-(acetylamino)pyridin-4-yl]oxy}phenyl)-N-[3-[2-(dimethylamino)ethoxy]-5-(trifluoromethyl)phenyl]propanamide (A-211)

A-211 was prepared from 3-(3-{[2-(acetylamino)-4-yl]oxy}phenyl)propanoic acid, using the procedure described in Example 9. The HCl salt was prepared by dissolving the compound in DCM/MeOH and adding 1M HCl in Et$_2$O, and immediately evaporating the solvents. $^1$H NMR (400 MHz, d6 DMSO) δ: 10.49 (s, 1H), 10.27 (br s, 1H), 8.18 (d, 1H), 7.59 (d, 2H), 7.41 (t, 2H), 7.22 (d, 1H), 7.12 (s, 1H), 7.03 (dd, 1H), 6.98 (s, 1H), 6.79-6.76 (1, mH), 4.38 (t, 2H), 3.52-3.48 (m, 2H), 2.95 (t, 2H), 2.83 (s, 3H), 2.82 (s, 3H), 2.69 (t, 2H), and 2.08 (s, 3H). LCMS: (FA) ES+ 531.2 (M+1).

Compounds in the following table were prepared from the appropriate starting materials in a method analogous to that of Example 32:

| | |
|---|---|
| A-96 | $^1$H NMR(400MHz, d$_6$-DMSO; HCl salt) δ: 11.21(br s, 1H), 9.88(s, 1H), 8.15(d, 1H), 7.51-7.54(m, 1H), 7.39-7.46 (m, 2H), 7.32-7.36(m, 1H), 7.22(d, 1H), 7.18(t, 1H), 7.09-7.13(m, 1H), 7.01-7.07(m, 1H), 6.76-6.81(m, 1H), 2.94(dd, 2H), 2.63(dd, 2H), 2.09(s, 3H), and 1.22(s, 9H). |

Example 33

Preparation of N-[4-chloro-3-(trifluoromethyl)phenyl]-3-{3-[(2-{[(4-ethylpiperazin-1-yl)acetyl]amino}pyridin-4-yl)oxy]phenyl}propanamide (A-192)

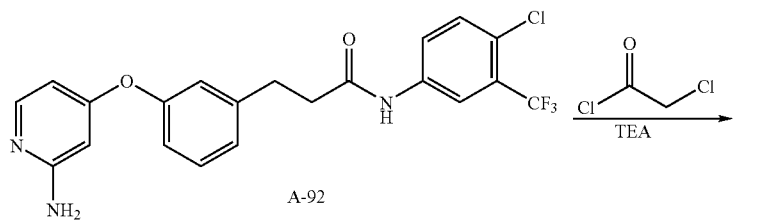

A-92

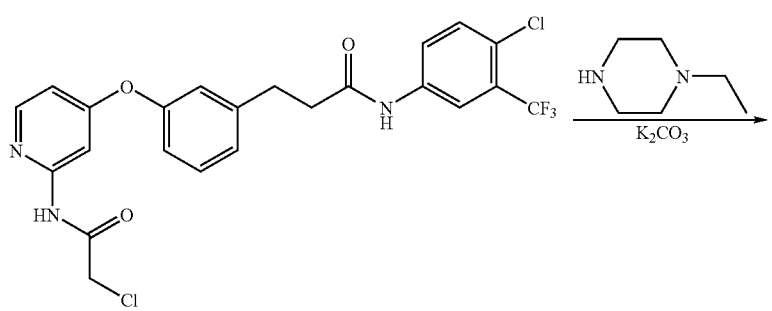

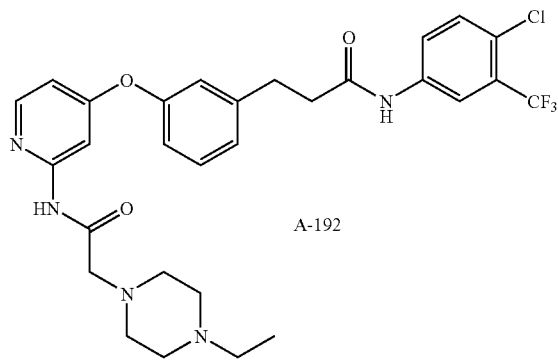

A-192

Step 1. Preparation of 3-[3-({2-[(chloroacetyl)amino]pyridin-4-yl}oxy)phenyl]-N-[4-chloro-3-(trifluoromethyl)phenyl]-propanamide To a solution of A-92 (0.100 g, 0.22 mmol) and TEA (0.020 mL, 0.25 mmol) in THF (5 mL) was added 2-chloroacetyl chloride (0.060 mL, 0.44 mmol). The reaction mixture was allowed to stir for 15 min at rt and then concentrated. The residue was redissolved in EtOAc, washed with water and brine, dried over $Na_2SO_4$, filtered, and concentrated. The resulting oil was purified by column chromatography to give the title compound as a white solid.

Step 2. Preparation of N-[4-chloro-3-(trifluoromethyl)phenyl]-3-{3-[(2-{[(4-ethylpiperazin-1-yl)acetyl]amino}pyridin-4-yl)oxy]phenyl}propanamide (A-192)

A mixture of 3-[3-({2-[(chloroacetyl)amino]pyridin-4-yl}oxy)phenyl]-N-[4-chloro-3-(trifluoromethyl)phenyl]-propanamide (0.050 g, 0.090 mmol), 1-ethylpiperazine (0.040 mL, 0.29 mmol), and $K_2CO_3$ (0.050 g, 0.36 mmol) was stirred at 60° C. in DMF for 1 h. The mixture was concentrated and partitioned between EtOAc and water. The organic solution was concentrated and the residue was purified by column chromatography to give A-192. $^1$H NMR (400 MHz, $d_6$-DMSO) δ: 10.98 (m, 1H), 10.60 (m, 1H), 8.21 (m, 2H), 7.83 (dd, 1H), 7.63 (d, 1H), 7.60 (m, 1H), 7.41 (t, 1H), 7.21 (d, 1H), 7.10 (m, 1H), 7.01 (m, 1H), 6.75 (dd, 1H), 4.85 (br, 6H), 3.84 (br, 1H), 3.39 (br, 1H), 3.22 (br, 2H), 3.13 (m, 2H), 2.95 (t, 2H), 2.70 (t, 2H), and 1.23 (t, 3H). LCMS: (FA) $ES^+$ 590.3 (M+1).

Compounds in the following table were prepared from the appropriate starting materials in a method analogous to that of Example 33:

Example 34

Preparation of ethyl 2-{4-[3-(3-{[4-chloro-3-(trifluoromethyl)-phenyl]amino}-3-oxopropyl)phenoxy]pyridin-2-yl}-1H-imidazole-5-carboxylate (A-110)

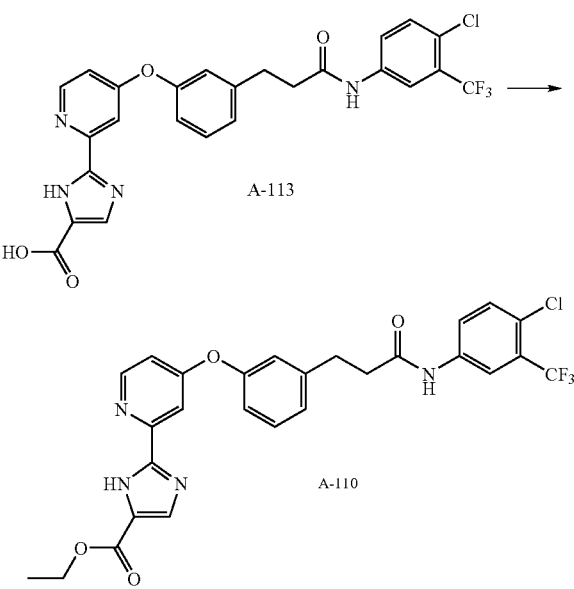

To a solution of A-113 (450 mg, 0.847 mmol) in ethanol (4 mL) was added 1N NaOH (5 mL) dropwise. The solution

| | |
|---|---|
| A-20 | $^1$H(400MHz, $d_6$-DMSO; HCl salt) δ: 9.86(s, 1H), 8.15(d, 1H), 7.51(t, 1H), 7.44-7.33(m, 3H), 7.22-7.16(m, 2H), 7.1(t, 1H), 7.05-7.01(m, 2H), 6.78-6.75(m, 1H), 2.94(t, 2H), 2.62(t, 2H), 1.97-1.9(m, 1H), 1.23(s, 9H), and 0.86-0.81(m, 4H). LCMS: (FA)ES+ 458.86(M+1), ES− 456.3(M−1). |
| A-183 | $^1$H NMR(300MHz, $CD_3OD$) δ: 8.01-8.0(m, 2H), 7.71(dd, 1H), 7.48(dd, 1H), 7.36(dd, 1H), 7.16(dd, 1H), 7.04(s, 1H), 6.95(dd, 1H), 6.58(dd, 1H), 3.03(dd, 2H), 2.69(dd, 2H), and 2.11(s, 3H). LCMS: (FA)ES+ 478.28(M+1), ES− 476.19(M−1). |
| A-98 | $^1$H NMR(300MHz, $CD_3OD$) δ: 8.05(d, 1H), 8.02(d, 1H), 7.67(dd, 1H), 7.63(d, 1H), 7.48(d, 1H), 7.35(dd, 1H), 7.17(d, 1H), 7.03(dd, 1H), 6.95(dd, 1H), 6.58(dd, 1H), 3.02(dd, 2H), 2.69(dd, 2H), 1.78-1.87(m, 1H), and 0.80-0.95(m, 4H). LCMS: (FA)ES+ 504.3(M+1), ES− 502.2(M−1). | stirred at 70° C. for 10 h and then extracted with EtOAc. The organic solutions were combined, washed with 1N HCl, dried over MgSO₄, filtered and concentrated. The residue was purified by column chromatography (1% NH₄OH/DCM containing 0-10% MeOH) to give A-110 (10 mg, 2%). ¹H NMR (300 MHz, CD₃OD) δ: 8.41 (d, 1H), 7.99 (d, 1H), 7.80 (s, 1H), 7.64 (dd, 1H), 7.59 (s, 1H), 7.37-7.43 (m, 1H), 7.21 (d, 2H), 7.07 (dd, 1H), 7.00 (dd, 1H), 6.89 (dd, 1H), 4.32 (dd, 1H), 3.05 (dd, 2H), 2.71 (dd, 22H), and 1.35 (dd, 3H). LCMS: (FA) ES+ 559.3 (M+1), ES- 557.3 (M-1).

Example 35

Preparation of isobutyl {4-[3-(3-{[4-chloro-3-(trifluoromethyl)-phenyl]amino}-3-oxopropyl)phenoxy]pyridin-2-yl}carbamate (A-221)

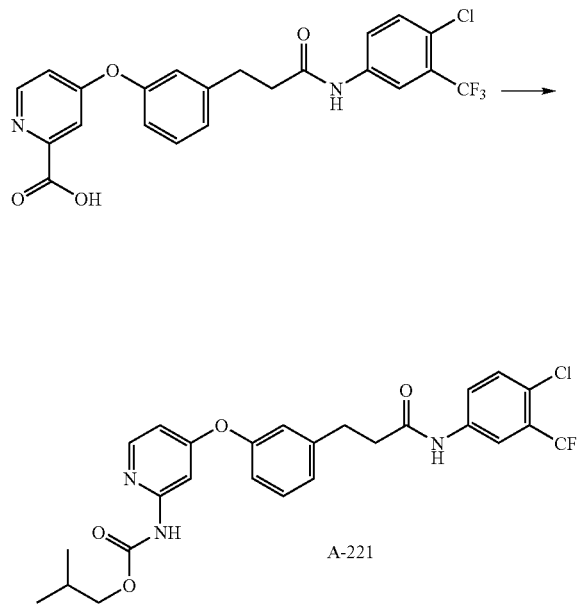

A solution of 4-[3-(3-{[4-chloro-3-(trifluoromethyl)phenyl]amino}-3-oxopropyl)phenoxy]pyridine-2-carboxylic acid (8.0 mmol) in THF (66 mL) was cooled to 0° C. TEA (2.8 mL, 19.9 mmol) was added, followed by isobutylchloroformate (1.04 mL, 8.0 mmole) and the solution was allowed to stir for 1 h at 0° C. The reaction mixture was concentrated, diluted with DCM, washed with sat. NaHCO₃, extracted with DCM, washed with brine, dried over NaSO₄, filtered, and concentrated. The residue was redissolved in toluene (30 mL) and t-butanol (1.3 mL, 13.9 mmol) was added. The solution was heated to 100° C. for 1.5 h and then cooled to rt. The solution was diluted with DCM, washed with NaHCO₃ and brine, dried over MgSO₄, filtered and concentrated. The residue was purified by column chromatography (hexane/ethyl EtOAc) to give A-221 (600 mg, 17%). ¹H NMR (300 MHz, CD₃OD) δ: 8.02-8.07 (m, 2H), 7.69 (dd, 1H), 7.49 (dd, 1H), 7.40 (dd, 1H), 7.19-7.24 (m, 2H), 7.07 (dd, 1H), 6.99 (dd, 1H), 6.66 (dd, 1H), 3.91 (dd, 2H), 3.04 (dd, 2H), 2.71 (dd, 2H), 1.94 (ddd, 1H), and 0.94 (d, 6H). LCMS: (FA) ES+ 536.3 (M+1), ES- 534.2 (M-1).

Example 36

Preparation of methyl 2-{4-[3-(3-{[4-chloro-3-(trifluoromethyl)phenyl]amino}-3-oxopropyl)phenoxy]pyridin-2-yl}-1H-imidazole-5-carboxylate (A-170)

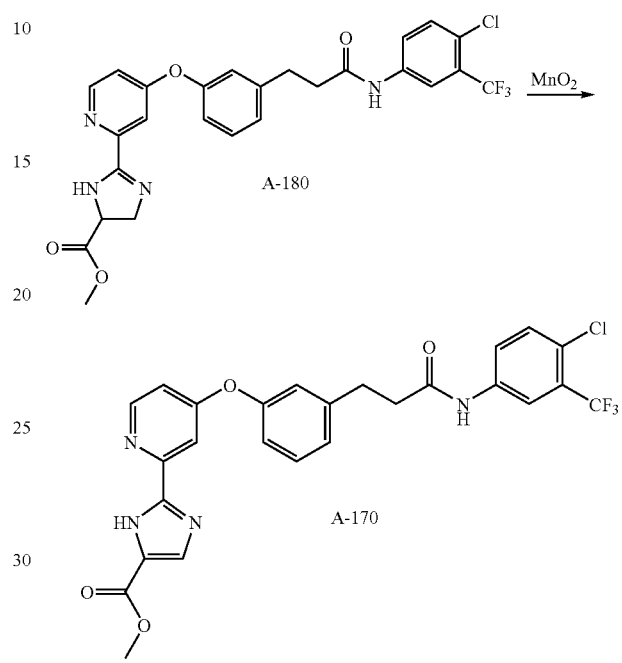

To a solution of A-180 (0.190 g, 0.36 mmol) in DCM (4 mL) was added activated MnO₂ (0.364 g, 3.6 mmol). The reaction mixture was allowed to stir for 72 h and then filtered through Celite and concentrated. The residue was purified by column chromatography to give A-170 (35 mg, 18%).

¹H NMR (300 MHz, d6 DMSO; HCl salt) δ: 7.00 (d, 1H), 6.54 (s, 1H), 6.46 (d, 1H), 6.21 (d, 1H), 6.1.1 (dd, 1H), 5.86-5.96 (m, 2H), 5.76 (d, 1H), 5.64 (dd, 1H), 5.61 (dd, 1H), 5.54 (dd, 1H), 2.38 (s, 3H), 1.51 (dd, 2H), and 1.21 (dd, 2H). LCMS: (FA) ES+ 546.2 (M+1), ES- 543.2 (M-1).

Example 37

Preparation of N-[4-chloro-3-(trifluoromethyl)phenyl]-3-(3-{[2-(1H-imidazol-2-yl)pyridin-4-yl]oxy}phenyl)propanamide (A-105)

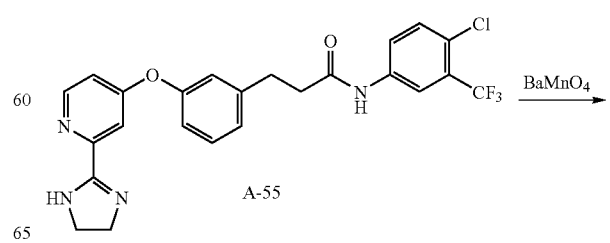

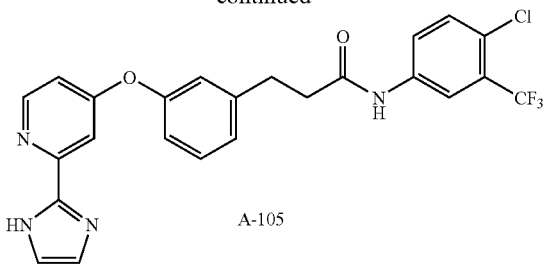

A-105

To a solution of A-55 (66 mg, 0.13 mmol) in DCM (5 mL) of was added BaMnO₄ (600 mg). The solution was allowed to stir for 15 h at 80° C. and then filtered through Celite and concentrated. The residue was purified by reversed phase HPLC (formic in acetonitrile/water) to give A-105 (15 mg, 23%). ¹H NMR (300 MHz, CD₃OD) δ: 8.42 (d, 1H), 8.14 (s, 1H), 7.77 (dd, 1H), 7.60 (d, 1H), 7.42 (dd, 1H), 7.37 (d, 1H), 7.20 (d, 1H), 7.19 (dd, 1H), 7.13 (dd, 1H), 7.05 (dd, 1H), 6.98 (s, 1H), 6.91 (dd, 1H), 2.97 (dd, 2H), and 2.69 (dd, 2H). LCMS: (FA) ES+ 487.90 (M+1), ES− 484.99 (M−1).

Example 38

Preparation of N-[4-chloro-3-(trifluoromethyl)phenyl]-3-[4-(pyridin-4-ylmethyl)phenyl]propanamide (A-84)

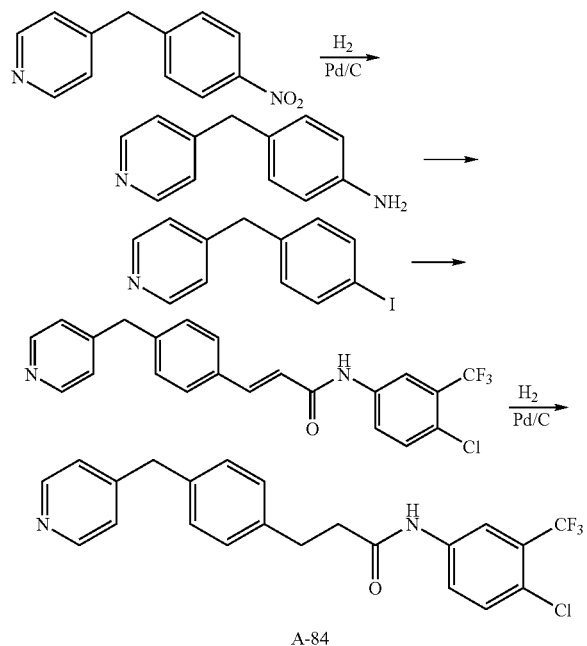

Step 1. Preparation of 4-(pyridin-4-ylmethyl)aniline

To a solution of 4-(4-nitrobenzyl)pyridine (2.0 g, 9.3 mmol) in MeOH (93 mL) was added Pd on carbon (10% by wt, 0.20 g). The reaction mixture was placed under an atmosphere of hydrogen and allowed to stir for 12 h at rt. The reaction mixture was filtered through Celite and the filtrate concentrated to give the title compound (1.73 g, 100%). LCMS: (FA) ES+ 185.1 (M+1)

Step 2. Preparation of 4-(4-iodobenzyl)pyridine

A solution of 4-(pyridin-4-ylmethyl)aniline (679 mg, 3.7 mmol) in acetic acid (1.84 mL) and concentrated hydrochloric acid (0.787 mL) was cooled to 0° C. NaNO₂ (280 mg, 40.7 mmol) in water (1.23 mL) was added dropwise and the reaction mixture was allowed to stir for 30 min. A solution of KI (737 mg, 4.44 mmol) and iodine (563 mg, 2.22 mmole) in water (3.7 mL) was added dropwise to the above solution. The solution stirred for 30 min at 0° C. and for 1 h at rt. The reaction was quenched by the addition of aq. NaS₂O₄ and the solution was extracted with EtOAc. The combined organic solutions were washed with sat. NaHCO₃, brine and 1% NaOH, dried over MgSO₄, filtered and concentrated. The residue was purified by column chromatography to give the title compound (140 mg, 18%). LCMS: (FA) ES+ 296.1 (M+1).

Step 3. Preparation of (2E)-N-[4-chloro-3-(trifluoromethyl)phenyl]-3-[4-(pyridin-4-ylmethyl)phenyl]acrylamide A mixture of 4-(4-iodobenzyl)pyridine (129 mg, 0.44 mmol), TEA (67 µL, 0.48 mmol), Pd(PPh₃)₄ (254 mg, 0.222 mmol) and N-[4-chloro-3-(trifluoromethyl)-phenyl]acrylamide (0.120 g, 0.44 mmol) in DMF (4.4 mL) was heated at 95° C. for 3 h. The reaction mixture was cooled to rt, diluted with water, extracted with EtOAc, washed with brine, dried over NaSO₄, filtered and concentrated. The residue was purified by column chromatography to give the title compound (161 mg, 40%). LCMS: (FA) ES+ 417.2 (M+1).

Step 4. Preparation of N-[4-chloro-3-(trifluoromethyl)phenyl]-3-[4-(pyridin-4-ylmethyl)phenyl]propanamide (A-84)

To a solution of (2E)-N-[4-chloro-3-(trifluoromethyl)phenyl]-3-[4-(pyridin-4-ylmethyl)phenyl]acrylamide (70 mg, 0.17 mmol) in MeOH (2 mL) and EtOAc (2 mL) was added Pd/C (10 wt %, 20 mg). The mixture was stirred under hydrogen (60 psi) for 18 h and then filtrated through Celite. The filtrate was concentrated and purified by column chromatography to give A-84 (28 mg, 41%). ¹H NMR (300 MHz, CD₃OD) δ: 8.35 (d, 2H), 8.03 (d, 1H), 7.70 (dd, 1H), 7.48 (d, 1H), 7.10-7.24 (m, 6H), 3.96 (s, 2H), 2.97 (dd, 2H), and 2.65 (dd, 2H). LCMS: (FA) ES+ 419.2 (M+1), ES− 417.2 (M−1).

Example 39

Preparation of (E)-3-(3-(2-(4,5-dihydro-1H-imidazol-2-yl)pyridin-4-yloxy)phenyl)-N-(3-isopropylphenyl)acrylamide (B-2)

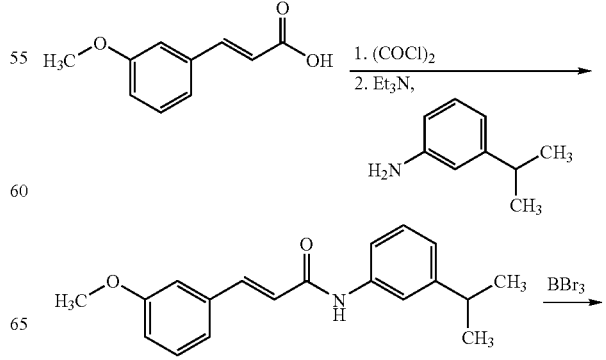

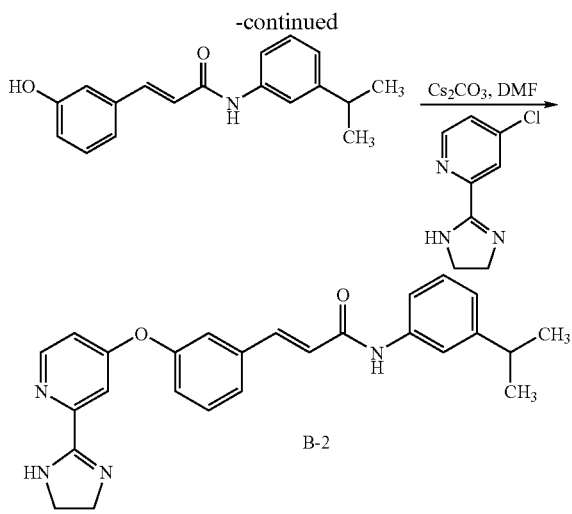

B-2

Step 1. Preparation of (E)-N-(3-isopropylphenyl)-3-(3-methoxyphenyl)acrylamide

To a solution of (E)-3-(3-methoxyphenyl)acrylic acid (1.50 g, 8.30 mmol) in DCM (80 mL) under an atmosphere of argon was added oxalyl chloride (1.45 mL, 16.6 mmol) at rt. The reaction was allowed to stir at rt for 2 h and then concentrated. The residue was dissolved in DCM (80 mL). To this solution were added 3-isopropyl-benzenamine (1.24 g, 9.2 mmol) and TEA (2.31 mL, 16.6 mmol). The reaction was allowed to stir at rt for 15 min and then quenched by the addition of water. The mixture was extracted with DCM and the organic solutions were combined, washed with water and brine, dried over $Na_2SO_4$, filtered, and concentrated to give the desired amide which was used without further purification. $^1$H NMR (400 MHz, $CDCl_3$): δ 7.71 (d, J=15.2 Hz, 1H), 7.64-7.69 (m, 1H), 7.51-7.58 (m, 1H), 7.44-7.50 (m, 1H), 7.20-7.31 (m, 1H), 7.11 (d, J=7.6 Hz, 1H), 6.99-7.05 (m, 2H), 6.89-6.93 (m, 1H), 6.60 (d, J=15.6 Hz, 1H), 3.82 (s, 3H), 2.90 (sept, J=7.2 Hz, 1H), and 1.24 (t, J=7.2 Hz, 6H).

Step 2. Preparation of (E)-3-(3-hydroxyphenyl)-N-(3-isopropylphenyl)acrylamide

A solution of (E)-N-(3-isopropylphenyl)-3-(3-methoxyphenyl)acrylamide (8.30 mmol) in DCM (50 mL) was cooled to 0° C. under an atmosphere of argon. To this solution was added boron tribromide (1M in DCM, 16.5 mL). The reaction mixture was allowed to come to rt and stir for 2 hr before being quenched by the addition of water. The mixture was extracted with EtOAc and the combined organic solutions were washed with water and brine, dried over $Na_2SO_4$, filtered, and concentrated. The residue was triturated with DCM and filtered to give the desired phenol (1.22 g, 52% for 2 steps).

Step 3. Preparation of (E)-3-(3-(2-(4,5-dihydro-1H-imidazol-2-yl)pyridin-4-yloxy)phenyl)-N-(3-isopropylphenyl)acrylamide (B-2)

To a solution of (E)-3-(3-hydroxyphenyl)-N-(3-isopropylphenyl)acrylamide (3.20 mmol) in DMF (40 mL) was added 4-chloro-2-(4,5-dihydro-1H-imidazol-2-yl)pyridine (11.2 mmol) and cesium carbonate (16.0 mmol). The heterogeneous mixture was heated at 100° C. for 18 h and then cooled to rt. The mixture was diluted with water and extracted with EtOAc. The combined organic solutions were washed with water and brine, dried over $Na_2SO_4$, filtered, and concentrated. The residue was purified by column chromatography (90:10:1 DCM:MeOH:$NH_4OH$) to give B-2. $^1$H NMR (300 MHz, $d_6$-DMSO): δ 10.13 (s, 1H), 8.52 (d, J=5.6 Hz, 1H), 7.56-7.61 (m, 3H), 7.50-7.54 (m, 2H), 7.44-7.47 (m, 1H), 7.41 (d, J=2.8 Hz, 1H), 7.20-7.29 (m, 2H), 7.17 (dd, J=6.8, 2.8 Hz, 1H), 6.93-6.99 (m, 2H), 6.85 (d, J=15.6 Hz, 1H), 3.32 (s, 4H), 2.85 (sept, J=6.8 Hz, 1H), and 1.18 (d, J=7.2 Hz, 6H).

Compounds in the following table were prepared from the appropriate starting materials in a method analogous to that of Example 39:

| | |
|---|---|
| B-7 | $^1$H NMR(400MHz, $d_6$-DMSO): δ 10.56(s, 1H), 8.52(d, J=5.6Hz, 1H), 8.18(br s, 1H), 7.81-7.89(m, 1H), 7.53-7.70(m, 4H), 7.39-7.52(m, 2H), 7.24-7.33(m, 1H), 7.15-7.21(m, 1H), 6.82(d, J=15.6Hz, 1H), and 3.59(s, 4H). |
| B-9 | $^1$H NMR(400MHz, $d_6$-DMSO): δ 10.76(s, 1H), 8.54(d, J=5.6Hz, 1H), 8.17(br s, 1H), 7.84-7.84(m, 2H), 7.57-7.70(m, 2H), 7.50-7.52(m, 1H), 7.44(d, J=2.4Hz, 1H), 7.36-7.40(m, 1H), 7.27-7.31(m, 1H), 7.19(dd, J=5.6, 2.4Hz, 1H), 6.80(d, J=15.6Hz, 1H), and 3.61(s, 4H). |
| B-13 | $^1$H NMR(400MHz, $d_6$-DMSO): δ 10.34(s, 1H), 8.52(d, J=6.0Hz, 1H), 7.66-7.75(m, 2H), 7.54-7.65(m, 3H), 7.34-7.49(m, 4H), 7.24-7.29(m, 1H), 7.17(dd, J=5.6, 2.4Hz, 1H), 6.83(d, J=15.6Hz, 1H), and 3.59(s, 4H). |
| B-14 | $^1$H NMR(400MHz, $CDCl_3$): δ 10.33(br s, 1H), 8.45(d, J=5.7Hz, 1H), 7.93(d, J=2.7Hz, 1H), 7.80(dd, J=8.7, 2.4Hz, 1H), 7.54(d, J=15.6Hz, 1H), 7.34-7.39(m, 2H), 7.15-7.24(m, 2H), 7.02(dd, J=5.7, 2.4Hz, 1H), 6.94-6.97(m, 1H), 6.86-6.91(m, 1H), 6.38(d, J=15.6Hz, 1H), and 3.78(s, 4H). |
| B-5 | $^1$H NMR(400MHz, $CD_3OD$): δ 8.65(d, J=5.6Hz, 1H), 7.68-7.70(m, 2H), 7.63(d, J=15.6Hz, 1H), 7.44-7.61(m, 3H), 7.41-7.44(m, 1H), 7.14-7.27(m, 4H), 6.84(d, J=15.6Hz, 1H), 4.09(s, 4H), and 1.31(s, 9H). |
| B-10 | $^1$H NMR(400MHz, $d_6$-DMSO): δ 10.41(s, 1H), 8.53(d, J=5.6Hz, 1H), 7.91(br s, 1H), 7.55-7.69(m, 3H) 7.46-7.54(m, 2H), 7.43(d, J=2.4Hz, 1H), 7.35(t, J=8.0Hz, 1H), 7.25-7.31(m, 1H), 7.18(dd, J=5.6, 2.8Hz, 1H), 7.10-7.15(m, 1H), 6.83(d, J=15.6Hz, 1H), and 3.60(s, 4H). |
| A-114 | $^1$H NMR(400MHz, $CDCl_3$) δ: 8.51(d, 1H), 8.18(s, 1H), 8.07(d, 1H), 7.84(dd, 1H), 7.73(d, 1H), 7.34-7.42(m, 2H), 7.12-7.17(m, 1H), 6.89-6.94(m, 1H), 6.65-6.80(m, 1H), 3.99-4.08(m, 4H), 2.34-2.43(m, 1H), 2.01-2.11(m, 1H), 1.80-1.90(m, 1H), and 1.30-1.40(m, 1H). LCMS, FA: $R_t$=1.31min, [MH$^+$ 502.3]. |

| | |
|---|---|
| A-107 | $^1$H NMR(400MHz, CDCl$_3$) δ: 9.21(br s, 1H), 8.35(d, 1H), 7.58-7.69(m, 2H), 7.25-7.33(m, 2H), 7.11-7.17(m, 1H), 7.02-7.08(m, 1H), 6.94-7.01(m, 1H), 6.85-6.93(m, 1H), 3.82-3.90(m, 4H), 2.47-2.57(m, 1H), 2.21-2.31(m, 1H), 1.72-1.83(m, 1H), and 1.34-1.46(m, 1H). LCMS, FA: R$_t$=1.42min, [MH$^+$ 502.3]. |
| A-246 | $^1$H NMR(400MHz, CDCl$_3$) δ: 10.32(br s, 1H), 8.46(dd, 1H), 8.08-8.12(m, 1H), 7.84-7.89(m, 1H), 7.62-7.66(m, 1H), 7.35(d, 1H), 7.18(dd, 1H), 7.12(d, 1H), 6.93(d, 1H), 3.96(br s, 4H), 2.39-2.46(m, 1H), 2.10-2.17(m, 1H), .77-1.84(m, 1H), and 1.34-1.42(m, 1H). LCMS, FA: R$_t$=1.19min, [MH$^+$ 501.0]. |
| A-196 | $^1$H NMR(400MHz, CDCl$_3$) δ: 8.47(d, 1H), 8.17-8.19(m, 1H), 7.94(d, 1H), 7.56(dd, 1H), 7.41(d, 1H), 7.28(d, 2H), 7.08(d, 2H), 7.01(dd, 1H), 4.04(br s, 1H), 2.79-7.87(m, 1H), 2.59-2.75(m, 2H), 2.16-2.24(m, 1H). LCMS, FA: R$_t$=1.34min, [MH$^+$ 501.0]. |
| A-135 | $^1$H NMR(400MHz, CD$_3$OD) δ: 8.42(d, 1H), 8.03(d, 1H), 7.67(dd, 1H), 7.49-7.51(m, 1H), 7.46-7.49(m, 1H), 7.40(d, 1H), 7.24(dd, 1H), 7.19(d, 1H), 6.95(dd, 1H), 3.78(s, 4H), 3.04(t, 2H), 2.70(t, 2H), and 3.04(t, 2H). LCMS, FA: R$_t$=1.33min, [MH$^+$ 523.1]. |
| A-62 | $^1$H NMR(400MHz, CD$_3$OD) δ: 8.42(d, 1H), 8.05(d, 1H), 7.73(dd, 1H), 7.50(d, 1H), 7.40(d, 1H), 7.22-7.25(m, 1H), 7.15-7.20(m, 1H), 6.97(d, 1H), 6.92(dd, 1H), 3.77(s, 4H), 3.01(t, 2H), 2.70(t, 2H) and 2.09(s, 3H). LCMS, FA: R$_t$=1.31min, [MH$^+$ 503.3]. |

Example 40

Preparation of (2E)-N-[4-chloro-3-(trifluoromethyl)phenyl]-3-[3-(9H-purin-6-yloxy)phenyl]acrylamide (B-3)

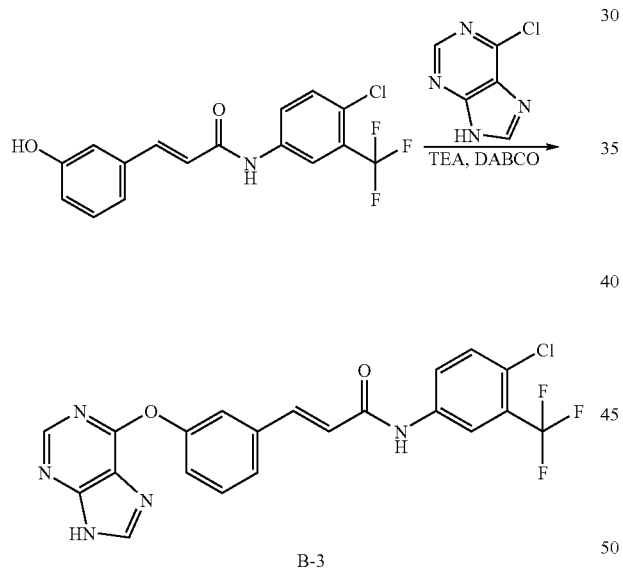

B-3

To a mixture of 1,4-diazabicyclo[2.2.2]octane (0.098 g, 0.87 mmol) in DCE (25 mL) was added (2E)-N-[4-chloro-3-(trifluoromethyl)phenyl]-3-(3-hydroxyphenyl)-acrylamide (300 mg, 0.87 mmol) and 6-chloro-9H-purine (1.95 mmol). TEA (366 μL, 2.61 mmol) was added, and the resulting solution was stirred at 60° C. The solution was diluted with brine and extracted with EtOAc. The combined organic solutions were dried over Na$_2$SO$_4$, filtered and concentrated. Purification by column chromatography (SiO$_2$, 10-80% EtOAc in hexanes) provided the title compound as a white solid (45 mg). $^1$H NMR (400 MHz, d$_6$-DMSO): 813.68 (br s, 1H), 10.67 (s, 1H), 8.55 (bs, 1H), 8.45 (s, 1H), 8.30 (s, 1H), 7.92 (dd, 1H), 7.70 (d, 1H), 7.65 (s, 1H), 7.60 (m, 2H), 7.38 (d, 1H) and 6.80 (d, 1H). LCMS, AA: R$_t$=1.71 min, [MH$^+$ 460.0].

Example 41

Preparation of (E)-N-(4-chloro-3-(trifluoromethyl)phenyl)-3-(3-(2-(4,5-dihydro-1H-imidazol-2-yl)pyridin-4-yloxy)phenyl)-2-methylacrylamide (B-12)

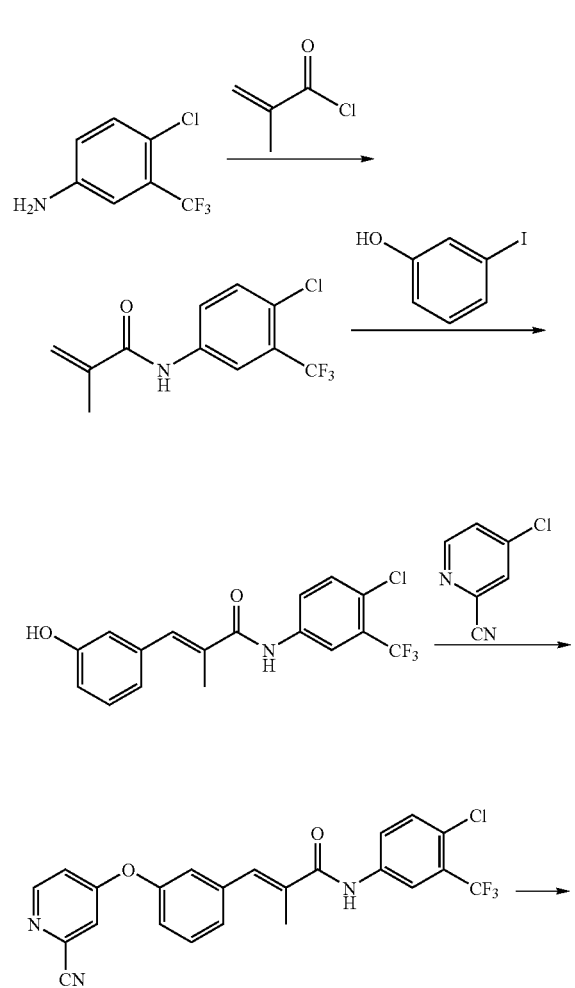

-continued

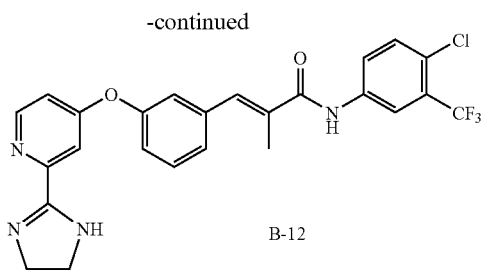

B-12

Step 1. Preparation N-(4-chloro-3-(trifluoromethyl)phenyl) methacrylamide

4-Chloro-3-(trifluoromethyl) aniline (2.60 mL, 26.8 mmol) was dissolved in DCM (120 mL) and TEA (4.64 mL, 33.3 mmol) was added. The solution was cooled to 0° C. and methacryloyl chloride (5.0 g, 25.6 mmol) was slowly added. The reaction was stirred for 5 h while warming to rt. The organic phase was washed with 0.5M $KHSO_4$ solution, sat. $NaHCO_3$ solution and brine, dried over $Na_2SO_4$, filtered, and concentrated to provide the title compound (6.51 g) as a light yellow oil. LCMS, FA: $R_f$=1.88 min, [MH+ 264.0].

Step 2. Preparation of (E)-N-(4-chloro-3-(trifluoromethyl) phenyl)-3-(3-hydroxyphenyl)-2-methylacrylamide To a flame-dried flask, $NaHCO_3$ (5.20 g, 61.88 mmol), 3 Å molecular sieves (10.9 g), N-(4-chloro-3-(trifluoromethyl) phenyl)methacrylamide (6.51 g, 24.75 mmol), and 3-iodophenol (5.99 g, 27.23 mmol) were added under an atmosphere of argon. The solids were then dissolved in ACN (100 mL) and stirred at rt for 10 min. PPh (650 mg, 2.48 mmol) was added and argon bubbled through the reaction mixture. $Pd(OAc)_2$ (278 mg, 1.24 mmol) was added and the reaction mixture was heated at 60° C. for 12 h. Additional palladium acetate was added and the reaction mixture was heated for 24 h. The mixture was cooled to rt and filtered through a pad of Celite. The filtrate was washed with sat. $NaHCO_3$ and the aqueous solution extracted with EtOAc. The combined organic solutions were dried over $Na_2SO_4$, filtered, and concentrated to provide a brown oil. Purification by column chromatography ($SiO_2$, 0-10% $Et_2O$ in DCM) provided the titled compound. LCMS, FA: $R_f$=1.94 min, [MH+ 356.0].

Step 3. Preparation of (E)-N-(4-chloro-3-(trifluoromethyl) phenyl)-3-(3-(2-cyanopyridin-4-yloxy)phenyl)-2-methylacrylamide (E)-N-(4-Chloro-3-(trifluoromethyl)phenyl)-3-(3-hydroxyphenyl)-2-methylacrylamide (1.0 g, 2.81 mmol), 4-chloropicolinonitrile (428 mg, 3.09 mmol) and cesium carbonate (2.75 g, 8.43 mmol) were combined and stirred in DMF. The reaction mixture was heated at 100° C. overnight and then cooled to rt. The mixture was filtered to remove cesium carbonate, the collected precipitate was washed with EtOAc, and the combined filtrate was concentrated. Purification by column chromatography ($SiO_2$, 0-80% EtOAc in hexanes) provided the title compound (883 mg). LCMS, FA: $R_f$=2.15 min, [MH+ 458.0].

Step 4. Preparation of (E)-N-(4-Chloro-3-(trifluoromethyl) phenyl)-3-(3-(2-(4,5-dihydro-1H-imidazol-2-yl)pyridine-4-yloxy)phenyl)-2-methylacrylamide (B-12)

(E)-N-(4-Chloro-3-(trifluoromethyl)phenyl)-3-(3-(2-cyanopyridin-4-yloxy)phenyl)-2-methylacrylamide (500 mg, 1.09 mmol) and TEA (456 µL, 3.27 mmol) were combined and stirred in ethanol. $H_2S$ was bubbled into the solution for 2 min then the reaction mixture was sealed and allowed to stir at rt. Reaction completion was checked by LCMS and TLC. The mixture was diluted with EtOAc and washed with brine. The aqueous phase was extracted with EtOAc, and the organic solutions were combined, dried over $Na_2SO_4$, filtered, and concentrated to provide a yellow residue. The residue was redissolved in ethylene diamine (3 mL), heated to 60° C. for 5 min, and then allowed to cool to rt. The mixture was diluted with EtOAc and washed with brine. The aqueous phase was extracted with EtOAc, and the organic solutions were combined, dried over $Na_2SO_4$, filtered, and concentrated. Purification by column chromatography ($SiO_2$, 0-10% MeOH with 1% $NH_4OH$ in DCM) provided B-12 (415 mg). LCMS, FA: $R_f$=1.34 min, [MH+ 501.0]. $^1$H NMR (400 MHz, $CD_3OD$): δ 8.49 (d, 1H), 8.18 (d, 1H), 7.91-7.89 (dd, 1H), 7.57-7.53 (m, 3H), 7.40 (d, 1H), 7.35 (s, 1H), 7.23 (m, 1H), 7.16-7.13 (dd, 1H), 7.09-7.07 (m, 1H), 3.77 (s, 4H), and 2.16 (d, 3H).

Compounds in the following table were prepared from the appropriate starting materials in a method analogous to that of Example 41:

| | |
|---|---|
| B-1 | $^1$H NMR(300MHz, $CD_3OD$): δ 8.50(d, 1H), 8.19(d, 1H), 7.85-7.80(dd, 1H), 7.57-7.50(m, 4H), 7.36(m, 1H), 7.21-7.17(m, 1H), 7.09-7.07(dd, 1H), 6.35(d, 1H), 4.87(s, 4H), and 2.61(d, 3H). LCMS, FA: $R_f$=1.37min, [MH+ 501.0]. |
| B-139 | $^1$H NMR(400MHz, $CD_3OD$): δ 8.65(d, 1H), 8.49(br s, 1H), 7.68-7.66(m, 2H), 7.58(t, 1H), 7.47-7.44(m, 2H), 7.32(br s, 1H), 7.28-7.22(m, 3H), 7.20-7.16(m, 2H), 4.09(s, 4H), 2.17(d, 3H), and 1.32(s, 9H). LCMS, FA: Rt=2.06min, [MH+ 444.0]. |
| B-6 | $^1$H NMR(400MHz, $CD_3OD$): δ 8.48(d, 1H), 7.67(s, 1H), 7.57(s, 1H), 7.53(d, 1H), 7.45(d, 1H), 7.39(d, 1H), 7.31(s, 1H), 7.27-7.22(m, 2H), 7.18-7.13(m, 2H), 7.10-7.08(dd, 1H), 2.93(s, 3H), 2.15(s, 3H), and 1.32(s, 9H). LCMS, FA: Rt=2.06min, [MH+ 444.0]. |

Example 42

Preparation of (E)-2-(3-(2-(4,5-Dihydro-1H-imidazol-2-yl)pyridin-4-yloxy)benzylidene)-N-(4-chloro-3-(trifluoromethyl)phenyl)butanamide (B-8)

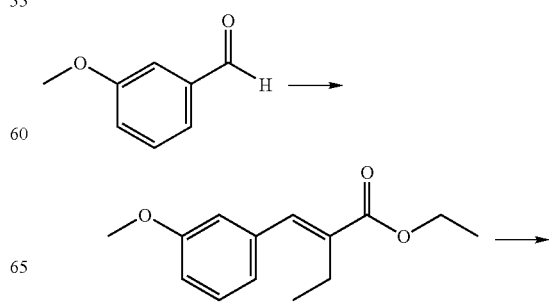

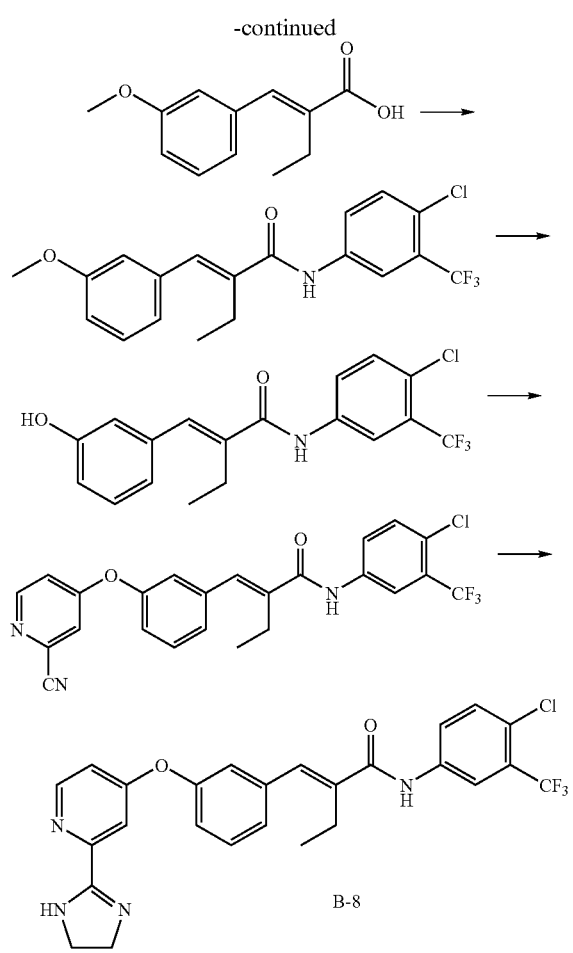

Step 1. Preparation of (E)-Ethyl 2-(3-methoxybenzylidene)butanoate

Under an atmosphere of argon, to a flame-dried flask were added KHMDS (2.55 g, 12.78 mmol) and THF (40 mL). The mixture was cooled to −78° C. and a solution of triethyl-2-phosphonobutyrate (3.00 ml, 12.7 mmol) in THF (10 mL) was slowly added. The reaction mixture was allowed to stir at −78° C. for 1 h. To the cold reaction mixture was added a solution of 3-anisaldehyde (1.54 mL, 12.66 mmol) in THF (10 mL). After 10 min, the cooling bath was removed and the reaction was allowed to warm slowly to rt over 3 h. The reaction was quenched by pouring onto ice. The aqueous phase was extracted with EtOAc and the combined organic solutions were dried over $Na_2SO_4$, filtered, and concentrated. Purification by column chromatography ($SiO_2$, 0-8% EtOAc in hexanes) provided the title compound (2.17 g). $^1$H NMR (300 MHz, $d_6$-DMSO): δ 7.61 (s, 1H), 7.33-7.26 (dd, 1H), 6.97 (d, 1H), 6.91-6.86 (m, 2H), 4.27 (q, 2H), 3.82 (s, 3H), 2.55 (q, 2H), 1.35 (t, 3H), and 1.17 (t, 3H).

Step 2. Preparation of (2E)-2-(3-methoxybenzylidene)butanoic acid (E)-Ethyl-2-(3-methoxybenzylidene)butanoate (300 mg, 1.28 mmol) was dissolved in THF (30 mL), and LiOH (61 mg, 2.56 mmol), and water (100 µL) were added. The reaction mixture was heated to reflux for 48 h and then cooled to rt. The reaction was diluted with EtOAc and 1N HCl. The aqueous phase was extracted with EtOAc and the combined organic solutions were dried over $Na_2SO_4$, filtered, and concentrated. Purification by column chromatography ($SiO_2$, 0-70% EtOAc with 1% acetic acid in DCM) provided the title compound (190 mg). $^1$H NMR (400 MHz, $d_6$-DMSO): δ 7.52 (s, 1H), 7.37-7.33 (dd, 1H), 6.99 (d, 1H), 6.95-6.93 (m, 2H), 3.77 (s, 3H), 2.43 (q, 2H), and 1.10 (t, 3H).

Step 3. Preparation of (2E)-N-[4-chloro-3-(trifluoromethyl)phenyl]-2-(3-methoxybenzylidene)butanamide (2E)-2-(3-methoxybenzylidene)butanoic acid (190 mg, 0.92 mmol), 4-chloro-3-(trifluoromethyl)aniline (189 mg, 0.97 mmol) and DMAP (135 mg, 1.11 mmol) were mixed together and stirred in DCM (15 mL). The reaction mixture was cooled to 0° C. and EDCI (118 mg, 1.29 mmol) was added. The reaction was allowed to warm slowly to rt overnight. The mixture was diluted with DCM and washed with 1N HCl, sat. $NaHCO_3$ and brine, dried over $Na_2SO_4$, filtered, and concentrated. The residue was purified by column chromatography ($SiO_2$, 0-15% EtOAc in hexanes) to give the title compound (216 mg). $^1$H NMR (400 MHz, $d_6$-DMSO): δ 10.44 (s, 1H), 8.29 (d, 1H), 8.05-8.02 (dd, 1H), 7.68 (d, 1H), 7.39-7.35 (m, 1H), 7.22 (s, 1H), 6.99 (d, 1H), 6.95-6.93 (m, 2H), 3.77 (s, 3H), 2.54 (q, 2H), and 1.08 (t, 3H).

Step 4. Preparation of (E)-2-(3-hydroxybenzylidene)-N-(4-chloro-3-(trifluoromethyl) phenyl)butanamide A solution of (2E)-N-[4-chloro-3-(trifluoromethyl)phenyl]-2-(3-methoxybenzylidene)butanamide (216 mg, 0.54 mmol) in DCM (15 mL) was cooled to 0° C. under an atmosphere of argon. To this solution was added $BBr_3$ (1M in DCM, 1.18 mL). The cooling bath was removed and the reaction mixture was allowed to warm to rt. After stirring for 2 h, the reaction was quenched by the addition of water. The mixture was extracted with EtOAc and the combined organic solutions were washed with water and brine, dried over $Na_2SO_4$, filtered, and concentrated. The residue was triturated with DCM and filtered to give the desired phenol (189 mg). $^1$H NMR (400 MHz, $d_4$-MeOH): δ 8.19 (d, 1H), 7.91-7.87 (dd, 1H), 7.55 (d, 1H), 7.24-7.16 (m, 2H), 6.87-6.85 (m, 2H), 6.77-6.74 (dd, 1H), 2.63 (q, 2H), and 1.14 (t, 3H).

Step 5. Preparation of (E)-2-(3-(2-(4,5-dihydro-1H-imidazol-2-yl)pyridin-4-yloxy)benzylidene)-N-(4-chloro-3-(trifluoromethyl)phenyl)butanamide (B-8)

B-8 was prepared from (E)-2-(3-hydroxybenzylidene)-N-(4-chloro-3-(trifluoromethyl)phenyl)butanamide by the methods described above. LCMS, FA: $R_f$=1.41 min, [MH$^+$ 515.0]. $^1$H NMR (400 MHz, $d_4$-MeOH): δ 8.53 (d, 1H), 8.19 (d, 1H), 7.91-7.88 (dd, 1H), 7.59-7.53 (m, 3H), 7.36 (d, 1H), 7.22 (s, 1H), 7.17-7.10 (m, 3H), 3.84 (s, 4H), 2.65-2.60 (m, 2H), and 1.11 (t, 3H).

Compounds in the following table were prepared from the appropriate starting materials in a method analogous to that of Example 42:

| | |
|---|---|
| B-11 | $^1$H NMR(300MHz, $d_6$-DMSO): δ 10.81(s, 1H), 8.52(d, 1H), 8.33(s, 1H), 8.10(d, 1H), 7.74-7.59(m, 3H), 7.53(s, 1H), 7.42(s, 1H), 7.29(d, 1H), 7.22-7.09(m, 2H), and 3.58(s, 4H). LCMS, FA: $R_f$=1.32min, [MH$^+$ 505.0]. |

Example 43

Preparation of (E)-N-(3-Tert-butylphenyl)-3-(3-(2-(4,5-dihydro-1H-imidazol-2-yl)pyridin-4-yloxy)phenyl)-2-(hydroxymethyl)acrylamide (1-140)

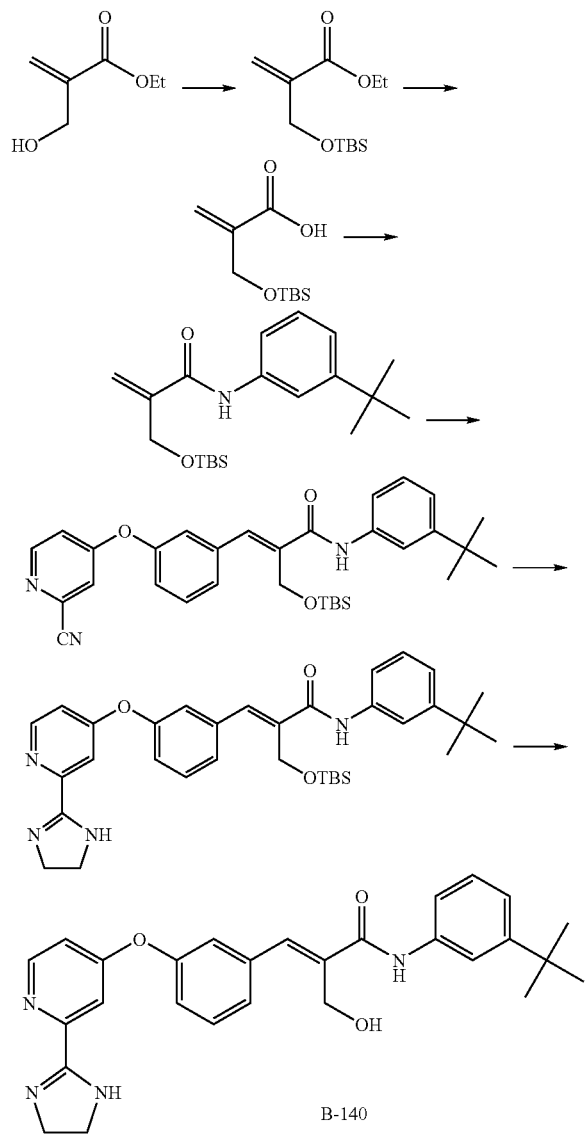

B-140

Step 1. Preparation of ethyl 2-((tert-butyldimethylsilyloxy)methyl)acrylate

Ethyl-2(hydroxymethyl)acrylate (2.0 mL, 17.12 mmol), imidazole (2.3 g, 34.24 mmol), and tert-butyl dimethylsilyl chloride (3.1 g, 20.54 mmol) were stirred in a solution of DMF (10 mL) at rt overnight. The reaction was diluted with EtOAc and washed with a 10% solution of LiCl. The aqueous phase was extracted with EtOAc, the organic solutions combined, dried over $Na_2SO_4$, filtered, and concentrated. Purification by column chromatography ($SiO_2$, 0-10% EtOAc in hexanes) provided the title compound (2.69 g). $^1$H NMR (300 MHz, $d_6$-DMSO): δ 6.13 (d, 1H), 5.82 (d, 1H), 4.30 (s, 2H), 4.14 (q, 2H), 1.21 (t, 3H), 0.87 (s, 9H), and 0.05 (s, 6H).

Step 2. Preparation of (E)-2-((tert-butyldimethylsilyloxy)methyl)-3-(3-methoxyphenyl) acrylic acid Ethyl 2-((tert-butyldimethylsilyloxy)methyl)acrylate (2.15 g, 8.8 mmol) and LiOH (421 mg, 17.6 mmol) were dissolved in THF (100 mL) and water (100 μL). The reaction mixture was heated to reflux for 48 h then cooled to rt. The reaction mixture was diluted with EtOAc and 1N HCl. The aqueous phase was extracted with EtOAc and the combined organic solutions were dried over $Na_2SO_4$, filtered, and concentrated. Purification by column chromatography ($SiO_2$, 0-10% EtOAc with 1% acetic acid in DCM) provided the title compound (1.04 g). $^1$H NMR (400 MHz, $d_6$-DMSO): δ 12.57 (s, 1H), 6.13-6.09 (dd, 1H), 5.81-5.76 (dd, 1H), 4.28 (d, 2H), 0.88 (s, 9H), and 0.05 (s, 6H).

Step 3. Preparation of 2-((tert-butyldimethylsilyloxy)methyl)-N-(3-tert-butylphenyl) acrylamide The title compound was prepared as described in Example 10, Step 3, using (E)-2-((tert-butyldimethylsilyloxy)methyl)-3-(3-methoxyphenyl)acrylic acid and 3-tert-butyl aniline. LCMS, FA: $R_t$=2.51 min, [MH$^+$ 348.0].

Step 4. Preparation of (E)-2-((tert-butyldimethylsilyloxy)methyl)-N-(3-tert-butylphenyl)-3-(3-(2-cyanopyridin-4-yloxy)phenyl)acrylamide The title compound was prepared as described in Example 36, Step 2, using 2-((tert-butyldimethylsilyloxy)methyl)-N-(3-tert-butylphenyl)acrylamide and 4-(3-iodophenoxy)picolinonitrile (prepared as described in Example 11, Step 1 using 3-iodophenol and 4-chloropicolinonitrile). LCMS, FA: $R_t$=2.61 min, [MH$^+$542.0].

Step 5. Preparation of (E)-2-((tert-butyldimethylsilyloxy)methyl)-N-(3-tert-butylphenyl)-3-(3-(2-(4,5-dihydro-1H-imidazol-2-yl)pyridin-4-yloxy)phenyl)acrylamide The title compound was prepared as described in Example 13. $^1$H NMR (300 MHz, $d_4$-MeOH): δ 8.47 (d, 1H), 7.61 (t, 1H), 7.57-7.54 (m, 2H), 7.49-7.46 (m, 2H), 7.40-7.37 (m, 2H), 7.25 (t, 1H), 7.21-7.16 (m, 2H), 7.06-7.04 (dd, 1H), 4.59 (s, 2H), 3.75 (s, 4H), and 1.31 (s, 9H), 0.81 (s, 9H), 0.01 (s, 6H).

Step 6. Preparation of (E)-N-(3-tert-butylphenyl)-3-(3-(2-(4,5-dihydro-1H-imidazol-2-yl)pyridin-4-yloxy)phenyl)-2-(hydroxymethyl)acrylamide (B-140)

(E)-2-((tert-butyldimethylsilyloxy)methyl)-N-(3-tert-butylphenyl)-3-(3-(2-(4,5-dihydro-1H-imidazol-2-yl)pyridin-4-yloxy)phenyl)acrylamide (107 mg, 0.18 mmol) was dissolved in a 1:1 mixture of THF/pyridine (3 mL). The reaction mixture was cooled to 0° C. and 20 drops of HF/pyridine were added. The reaction was sealed and allowed to warm to rt over 5 h. The mixture was diluted with EtOAc and washed with sat. $NaHCO_3$, dried over $Na_2SO_4$, filtered, and concentrated. Purification by column chromatography ($SiO_2$, 0-10% MeOH with 1% $NH_4OH$ in DCM) provided B-140 (32 mg). LCMS, FA: $R_t$=1.21 min, [MH$^+$ 471.0]. $^1$H NMR (300 MHz, $d_4$-MeOH): δ 8.48 (d, 1H), 7.68 (t, 1H), 7.56-7.51 (m, 3H), 7.48-7.44 (m, 1H), 7.41 (d, 1H), 7.31 (t, 1H), 7.25 (t, 1H), 7.19-7.15 (m, 2H), 7.08-7.05 (dd, 1H), 4.52 (s, 2H), 3.75 (s, 4H), and 1.32 (s, 9H).

Example 44

Preparation of N-[4-chloro-3-(trifluoromethyl)phenyl]-3-(3-{[2-(4,5-dihydro-1H-imidazol-2-yl)pyridin-4-yl]oxy}phenyl)butanamide (A-132)

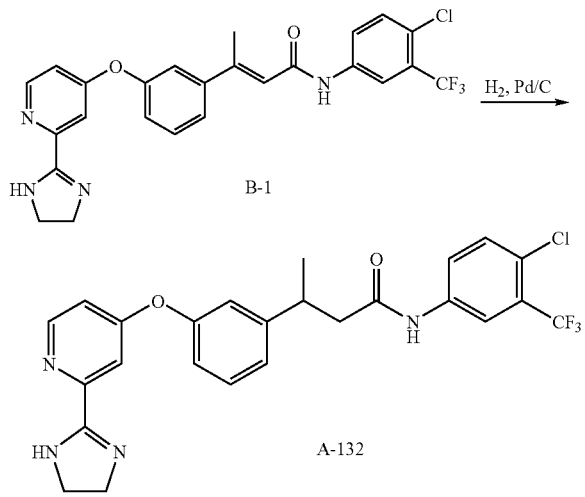

B-1 (25 mg, 0.05 mmol) was dissolved in MeOH (10 mL) and the reaction mixture was degassed. Under argon, 5 wt. % Pd on activated carbon (10 mol %) was added to the reaction mixture which was then stirred under 1 atmosphere of hydrogen at rt. The reaction was filtered over Celite. The solvent was evaporated to obtain A-132. $^1$H NMR (400 MHz, d$_6$-DMSO) δ: 10.37 (s, 1H), 8.45 (d, 1H), 8.23 (s, 1H), 8.11 (d, 1H), 7.75 (d, 1H), 7.61 (d, 1H), 7.44-7.40 (m, 2H), 7.23 (d, 1H), 7.12 (s, 1H), 7.04-7.01 (m, 2H), 3.34-3.29 (m, 1H), 2.68-2.57 (m, 2H), and 1.26 (d, 3H). LCMS: (FA) ES$^+$ 503.0 (M+1), ES$^-$ 501.0 (M−1).

Compounds in the following table were prepared from the appropriate starting materials in a method analogous to that of Example 44:

| | |
|---|---|
| A-215 | $^1$H NMR(400MHz, CD$_3$OD) δ: 8.32(d, 1H), 7.98(d, 1H), 7.62(dd, 1H), 7.44(d, 1H), 7.42(d, 1H), 7.36(t, 1H), 7.13-7.18(m, 1H), 6.98-7.01(m, 1H), 6.93-6.97(m, 1H), 6.87(dd, 1H), 3.74(s, 4H), 3.01(dd, 1H), 2.73-2.82(m, 2H), and 1.24(d, 3H). |
| A-135 | $^1$H NMR(400MHz, CD$_3$OD) δ: 8.42(d, 1H), 8.03(d, 1H), 7.67(dd, 1H), 7.49-7.51(m, 1H), 7.46-7.49(m, 1H), 7.40(d, 1H), 7.24(dd, 1H), 7.19(d, 1H), 6.95(dd, 1H), 3.78(s, 4H), 3.04(t, 2H), 2.70(t, 2H), and 3.04(t, 2H). LCMS, FA: R$_t$=1.33min, [MH$^+$ 523.1]. |
| A-62 | $^1$H NMR(400MHz, CD$_3$OD) δ: 8.42(d, 1H), 8.05(d, 1H), 7.73(dd, 1H), 7.50(d, 1H), 7.40(d, 1H), 7.22-7.25(m, 1H), 7.15-7.20(m, 1H), 6.97(d, 1H), 6.92(dd, 1H), 3.77(s, 4H), 3.01(t, 2H), 2.70(t, 2H) and 2.09(s, 3H). LCMS, FA: R$_t$=1.31min, [MH$^+$ 503.3]. |

Example 45

Expression and Purification of Raf Kinase Enzymes

Wild-Type B-Raf

Enzymatically active wild-type B-Raf was purchased from Upstate (cat# 14-530).

V599E B-Raf

Enzymatically active mutant B-Raf(V599E) was purchased from Upstate (cat# 14-557).

Wild Type C-Raf

Enzymatically active C-Raf was purchased from Upstate (cat# 14-352).

Example 46

Raf Kinase Enzyme Assays

B-Raf Flash Plate® Assay

Enzyme mix (15 µL), containing 50 mM HEPES pH 7.5, 0.025% Brij 35, 10 mM DTT, 4 nM B-Raf (V599E or Wild Type), was added to the wells of an assay plate and incubated for 20 minutes. Substrate mix (15 µL), containing 50 mM HEPES pH 7.5, 0.025% Brij 35, 10 mM MnCl$_2$, 2 µM Peptide 118 (Biotin-DRGFPRARYRARTTNYNSSR-SRFYSGFN-SRPRGRVYRGRARATSWYSPY-NH$_2$, New England Peptide), 1 µM ATP, 0.2 mg/mL BSA, $^{33}$P ATP 0.5 µCi/reaction was then added. Final reagent concentrations in the reaction mixture were 50 mM HEPES pH 7.5, 0.025% Brij 35, 5 mM DTT, 5 mM MnCl$_2$, 1 µM Peptide 118, 0.5 µM ATP, 0.1 mg/mL BSA, 2 nM B-Raf Wild Type, and $^{33}$P ATP 0.5 µCi/reaction. The reaction mixture, with or without Raf kinase inhibitor, was incubated for 60 minutes, and then stopped by the addition of 50 µL of 100 mM EDTA. The stopped reaction mixture (65 µL) was transferred to a Flash Plate® (Perkin Elmer) and incubated for 2 hours. The wells were washed three times with 0.02% Tween-20. Plates were read on a TopCount analyzer.

The following compounds exhibited IC$_{50}$ values less than or equal to 50 nM in this assay: A-5, A-7, A-20, A-27, A-35, A-51, A-53, A-55, A-58, A-59, A-63, A-73, A-74, A-89-91, A-96, A-98, A-99, A-100-103, A-105, A-108-110, A-112, A-113, A-115, A-108-110, A-112, A-113, A-115, A-117, A-122, A-128-130, A-137, A-141, A-142, A-144, A-145, A-147-149, A-151, A-154, A-156-158, A-164-166, A-170, A-171, A-176, A-178, A-183, A-184, A-186, A-189-195, A-200, A-201, A-203, A-204, A-209, A-211, A-216, A-220, A-221, A-225, A-226, A-228, A-230-234, A-237, A-239, A-243, A-245, A-255, A-257, A-258, A-265, B-2, B-5-7, B-9, B-11, B-12, B-139, B-140

The following compounds exhibited IC$_{50}$ values of greater than 50 nM and less than 500 nM in this assay: A-2-4, A-6, A-8, A-9, A-18, A-24, A-36, A-50, A-52, A-60-62, A-65-68, A-70, A-72, A-75-78, A-80-82, A-84-86, A-93, A-94, A-97, A-118-120, A-123, A-124, A-127, A-132, A-135, A-136, A-138, A-139, A-143, A-150, A-152, A-153, A-159-162, A-169, A-172-174, A-177, A-180, A-181, A-185, A-187, A-199, A-202, A-205, A-207, A-208, A-210, A-213, A-215, A-217-219, A-223, A-224, A-227, A-229, A-235, A-236, A-238, A-240, A-241, A-244, A-248-251, A-259-261, A-264, B-1, B-3, B-8, B-10.

The following compounds exhibited $IC_{50}$ values greater than 500 nM in this assay: A-1, A-6, A-11-13, A-19, A-21, A-23, A-54, A-56, A-57, A-64, A-69, A-71, A-79, A-83, A-87, A-88, A-92, A-95, A-104, A-105, A-107, A-111, A-114, A-116, A-121, A-125, A-126, A-131, A-134, A-140, A-146, A-155, A-163, A-167, A-175, A-177, A-182, A-188, A-196-198, A-206, A-212, A-214, A-222, A-242, A-246, A-252-254, A-256, A-262, A-263, B-13.

C-Raf Flash Plate® Assay

Enzyme mix (15 µL), containing 50 mM HEPES pH 7.5, 0.025% Brij 35, 10 mM DTT, 20 nM C-Raf (Wild Type), was added to the wells of an assay plate and incubated for 20 minutes. Substrate mix (15 µL), containing 50 mM HEPES pH 7.5, 0.025% Brij 35, 10 mM $MnCl_2$, 4 µM Peptide 118, 1 µM ATP, 0.1 mg/mL BSA, $^{33}P$ ATP 0.5 µCi/reaction was then added. Final reagent concentrations in the reaction mixture were 50 mM HEPES pH 7.5, 0.025% Brij 35, 5 mM DTT, 5 mM $MnCl_2$, 2 µM Peptide 118, 1.0 µM ATP, 0.1 mg/mL BSA, 10 nM C-Raf Wild Type, and $^{33}P$ ATP 0.5 µCi/reaction. The reaction mixture was incubated for 40 minutes, and then stopped by the addition of 50 µL of 100 mM EDTA. The stopped reaction mixture (65 µL) was transferred to a Flash Plate® (Perkin Elmer) and incubated for 2 hours. The wells were washed three times with 0.02% Tween-20. Plates were read on a TopCount analyzer.

Example 47

Raf Kinase Cellular Assays

Phospho-ERK ELISA Assay

Inhibition of Raf kinase activity in whole cell systems can be assessed by determining the decrease in phosphorylation of Raf kinase substrates. Any known Raf kinase substrate can be used to measure inhibition of Raf kinase activity in a whole cell system.

In a specific example, A375 cells were seeded in a 96-well cell culture plate ($12 \times 10^3$ cells/100 µL/well) and incubated overnight at 37° C. Medium was removed, and cells were incubated with Raf kinase inhibitors for 3 hours at 37° C. Medium was removed, and cells were fixed with 4% paraformaldehyde for 15 minutes at room temperature.

Methanol was added for 15 min. Cells were removed and blocked with 10% sheep serum and 1% BSA in PBS overnight at 4° C. Cells were incubated with anti-p44/42MAPK antibody (1:100, Cell Signaling Technologies, #9101L) (20 µL/well) for one hour at room temperature. After washing with PBS three times, cells were stained with anti-rabbit horseradish peroxidase-linked antibody from donkey (1:100, Amersham Bioscience #NA934V) for 1 hour at room temperature. Cells were washed three times with 0.5% Tween-20 in PBS and twice with PBS. 3,3',5,5'-Tetramethylbenzidine (TMB) liquid substrate system (Sigma, #T8665) (50 µL/well) was added, and cells were incubated for 30-45 minutes at room temperature. Optical density was read at 650 nm. Cells were then washed 3-5 times with PBS to remove color solution. Results were normalized for the protein content in each well using a BCA protein assay kit (Pierce).

The following compounds exhibited $IC_{50}$ values less than or equal to 1 µM in this assay: A-59, A-96, A-115, A-144, A-171, A-184, A-219, A-265, B-2, B-5, B-7-9, B-11, B-12, B-139, B-140.

The following compounds exhibited $IC_{50}$ values greater than 1 µM and less than 10 µM in this assay: A-12, A-27, A-35, A-51, A-55, A-58, A-61-63, A-72-74, A-76, A-89-91, A-98, A-99, A-101, A-103, A-104, A-108-110, A-113, A-117, A-122, A-124, A-127-130, A-132, A-145, A-147-149, A-151, A-153, A-154, A-156, A-157, A-161, A-165, A-166, A-169, A-170, A-176, A-178, A-183, A-186, A-189, A-190, A-192, A-193, A-195, A-200, A-204, A-205, A-209, A-211, A-216, A-218, A-220, A-223, A-226, A-228, A-230-233, A-237, A-239, A-243-245, A-248, A-251, A-255, A-257, B-3, B-6, B-10.

The following compounds exhibited $IC_{50}$ values greater than 10 µM and less than 25 µM in this assay: A-11, A-24, A-26, A-50, A-52, A-66, A-67, A-78, A-86, A-102, A-105, A-106, A-112, A-137, A-158, A-180, A-187, A-191, A-201, A-203, A-213, A-225, A-227, A-234, A-249, A-259, B-1.

Example 48

Anti-Proliferation Assays

WST Assay

A375 cells (4000) in 100 µL of 1% FBS-DMEM were seeded into wells of a 96-well cell culture plate and incubated overnight at 37° C. Test compounds were added to the wells and the plates were incubated for 48 hours at 37° C. Test compound solution was added (100 µL/well in 1% FBS DMEM), and the plates were incubated at 37° C. for 48 hours. WST-1 reagent (Roche #1644807, 10 µL) was added to each well and incubated for four hours at 37° C. as described by the manufacturer. The optical density for each well was read at 450 nm and 600 nm. A well containing medium only was used as a control.

Example 49

In Vivo Assays

In Vivo Tumor Efficacy Model

Raf kinase inhibitors are tested for their ability to inhibit tumor growth in standard xenograft tumor models.

For example, HCT-116 cells ($1 \times 10^6$) in 100 µL of phosphate buffered saline are aseptically injected into the subcutaneous space in the right dorsal flank of female CD-1 nude mice (age 5-8 weeks, Charles River) using a 23-ga needle. Beginning at day 7 after inoculation, tumors are measured twice weekly using a vernier caliper. Tumor volumes are calculated using standard procedures ($0.5 \times length \times width^2$). When the tumors reach a volume of approximately 200 $mm^3$, mice are injected i.v. in the tail vein with test compound (100 µL) at various doses and schedules. All control groups receive vehicle alone. Tumor size and body weight are measured twice a week, and the study is terminated when the control tumors reach approximately 2000 mm. Analogous procedures are followed for melanoma (A375 or A2058 cells), colon (HT-29 or HCT-116 cells), and lung (H460 cells) tumor models.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A compound of formula (I):

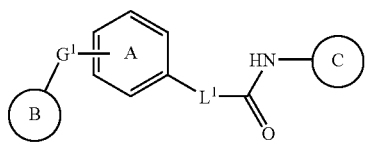

or a pharmaceutically acceptable salt thereof;
wherein:
$G^1$ is —C($R^{e'}$)($R^e$)—, —O—, —S—, or —N($R^f$)—, wherein $G^1$ is attached to Ring A at the position meta or para to $L^1$;
$L^1$ is —[C($R^g$)($R^h$)]$_m$—C($R^j$)($R^k$)— or —C($R^m$)=C($R^n$)—;
Ring A is substituted with 0-2 $R^a$;
Ring B is an optionally substituted mono- or bicyclic aromatic ring system having one to four ring nitrogen atoms and optionally one or two additional ring heteroatoms independently selected from oxygen and sulfur;
Ring C is an optionally substituted 5- or 6-membered aryl or heteroaryl ring having 0-3 ring nitrogen atoms and optionally one additional ring heteroatom selected from oxygen and sulfur;
$R^a$ is halo, —NO$_2$, —CN, —OR$^5$, —SR$^6$, —S(O)R$^6$, —SO$_2$R$^6$, —SO$_2$N(R$^4$)$_2$, —N(R$^4$)$_2$, —OC(O)R$^5$, —CO$_2$R$^5$, —C(O)N(R$^4$)$_2$, —N(R$^4$)SO$_2$R$^6$, —N(R$^4$)SO$_2$N(R$^4$)$_2$, or an optionally substituted C$_{1-4}$ aliphatic;
$R^{e'}$ is hydrogen, fluoro, C$_{1-4}$ aliphatic, C$_{1-4}$ fluoroaliphatic, —NH$_2$, —NH(C$_{1-4}$alkyl), —N(C$_{1-4}$ alkyl)$_2$, OH, or —O(C$_{1-4}$ alkyl);
$R^e$ is hydrogen, fluoro, C$_{1-4}$ aliphatic, or C$_{1-4}$ fluoroaliphatic; or $R^{e'}$ and $R^e$, taken together with the carbon atom to which they are attached, form a 3- to 6-membered cycloaliphatic or heterocyclyl ring;
$R^f$ is —H, —C(O)R$^5$, —C(O)N(R$^4$)$_2$, —CO$_2$R$^6$, —SO$_2$R$^6$, —SO$_2$N(R$^2$)$_2$, or an optionally substituted C$_{1-6}$ aliphatic;
$R^g$ is hydrogen, fluoro, C$_{1-4}$ aliphatic, or C$_{1-4}$ fluoroaliphatic; and
$R^h$ is hydrogen, fluoro, C$_{1-4}$ aliphatic, C$_{1-4}$ fluoroaliphatic, —OH, —O(C$_{1-4}$ alkyl), —N(R$^4$)$_2$, —N(R$^4$)C(O)(C$_{1-4}$ aliphatic), —C(O)(C$_{1-4}$ alkyl), —CO$_2$H, —CO$_2$(C$_{1-4}$ alkyl), or —C(O)N(R$^4$)$_2$; or
$R^g$ and $R^h$ taken together with the carbon atom to which they are attached, form a 3- to 6-membered cycloaliphatic ring;
$R^j$ is hydrogen, fluoro, C$_{1-4}$ aliphatic, or C$_{1-4}$ fluoroaliphatic; and
$R^k$ is hydrogen, fluoro, C$_{1-4}$ aliphatic, C$_{1-4}$ fluoroaliphatic, —OH, —O(C$_{1-4}$ alkyl), —C(O)(C$_{1-4}$ alkyl), —CO$_2$H, —CO$_2$(C$_{1-4}$ alkyl), or —C(O)N(R$^4$)$_2$; or $R^j$ and $R^k$, taken together with the carbon atom to which they are attached, form a 3- to 6-membered cycloaliphatic ring; or
each of $R^g$ and $R^j$ is hydrogen, fluoro, C$_{1-4}$ aliphatic, or C$_{1-4}$ fluoroaliphatic; and
$R^h$ and $R^k$, taken together with the intervening carbon atoms, form a 3- to 6-membered cycloaliphatic ring;
$R^m$ is hydrogen, fluoro, —OR$^5$, —C(O)R$^5$, —C(O)N(R$^4$)$_2$, —CO$_2$R$^5$, —SO$_2$R$^6$, —SO$_2$N(R$^4$)$_2$, or an optionally substituted C$_{1-4}$ aliphatic;
$R^n$ is hydrogen, fluoro, —C(O)R$^5$, —C(O)N(R$^4$)$_2$, —CO$_2$R$^5$, —SO$_2$R$^6$, —SO$_2$N(R$^4$)$_2$, or an optionally substituted C$_{1-4}$ aliphatic;
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;
each $R^5$ independently is hydrogen or an optionally substituted aliphatic, aryl, heteroaryl, or heterocyclyl group; and
each $R^6$ independently is an optionally substituted aliphatic, aryl, or heteroaryl group; and
m is 1 or 2;
provided that $G^1$ is attached to Ring A at the position meta to $L^1$ when $L^1$ is —C($R^m$)=C($R^n$)—;
further provided that Ring B is other than imidazolyl when $L^1$ is —[C($R^g$)($R^h$)]$_m$—C($R^j$)($R^k$)—, Ring C is substituted or unsubstituted phenyl and $G^1$ is —CH$_2$— in the para position; and
further provided that the compound of formula (I) is other than:
N-(3-chloro-2-ethyl-4-pyridinyl)-4-[[5-(trifluoromethyl)-2-pyridinyl]oxy]-benzenepropanamide;
4-[[3-cyano-6-(1-methylethyl)$_2$-pyridinyl]oxy]-N-(2,6-diethylphenyl)-benzenepropanamide;
4[[5-bromo-4-(2-propynyloxy)-2-pyrimidinyl]amino-N-(4-hydroxyphenyl)-benzenebutanamide;
4-[(4,5-dihydro-2-thiazolyl)amino]-N-phenyl-benzenebutanamide;
N-(3-chloro-2-ethyl-4-pyridinyl)-4-[[5-(trifluoromethyl)-2-pyridinyl]oxy]-benzenebutanamide; or
4-[[4,6-bis-(3,5-diamino-1-piperidinyl)-1,3,5-triazin-2-yl]amino]-☐-hydroxy-N-[2-(trifluoromethyl)phenyl]benzenebutanamide.

2. The compound of claim 1, wherein one or more of the following features are satisfied:
(a) each $R^a$ independently is —F, —Cl, —CN, —NO$_2$, C$_{1-4}$ alkyl, —CF$_3$, —O(C$_{1-4}$ alkyl), —OCF$_3$, —S(C$_{1-4}$ alkyl), —SO$_2$(C$_{1-4}$ alkyl), —NH$_2$, —NH(C$_{1-4}$ alkyl), —N(C$_{1-4}$ alkyl)$_2$, —CO$_2$H, —C(O)NH$_2$, or —C(O)NH(C$_{1-4}$ alkyl);
(b) $R^h$ and $R^k$ are each independently hydrogen, fluoro, C$_{1-4}$ alkyl, or C$_{1-4}$ fluoroalkyl;
(c) $L^1$ is —C($R^m$)=C($R^n$)—, and $R^m$ and $R^n$ are trans to each other;
(d) $R^m$ and $R^n$ are each independently hydrogen, fluoro, C$_{1-4}$ fluoroaliphatic, or a C$_{1-4}$ aliphatic optionally substituted with one substituent selected from —NH$_2$, —NH(C$_{1-4}$ alkyl), —N(C$_{1-4}$ alkyl)$_2$, —OH, or —O(C$_{1-4}$ alkyl);
(e) $L^1$ is —CH$_2$—CH$_2$— or —CH$_2$—CH$_2$—CH$_2$—; and
(f) $G^1$ is —O— or —NH—.

3. The compound of claim 1, wherein:

Ring B is substituted on its substitutable ring carbon atoms with 0-2 $R^b$ and 0-2 $R^{8b}$;

each $R^b$ independently is halo, $-NO_2$, $-CN$, $-C(R^5)$ $=C(R^5)_2$, $-C\equiv C-R^5$, $-OR^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-N(R^4)C(=NR^4)-N(R^4)_2$, $N(R^4)C(=NR^4)-R^6$, $-NR^4CO_2R^6$, $-N(R^4)$ $SO_2R^6$, $-N(R^4)SO_2N(R^4)_2$, $-O-C(O)R^5$, $-OC(O)N(R^4)_2$, $-C(O)R^5$, $-CO_2R^5$, $-C(O)N(R^4)_2$, $-C(O)N(R^4)-OR^5$, $-C(O)N(R^4)C(=NR^4)-N(R^4)_2$, $-N(R^4)C(=NR^4)-N(R^4)-C(O)R^5$, $-C(=NR^4)-N(R^4)_2$, $-C(=NR^4)-OR^5$, $-C(=NR^4)-N(R^4)-OR^5$, $-C(R^6)=N-OR^5$, or an optionally substituted aliphatic, aryl, heteroaryl, or heterocyclyl;

each $R^{8b}$ independently is selected from the group consisting of $C_{1-4}$ aliphatic, $C_{1-4}$ fluoroaliphatic, halo, $-OH$, $-O(C_{1-4}$ aliphatic), $-NH_2$, $-NH(C_{1-4}$ alkyl), and $-N(C_{1-4}$ alkyl)$_2$;

each substitutable ring nitrogen atom in Ring B is unsubstituted or is substituted with $-C(O)R^5$, $-C(O)N(R^4)_2$, $-CO_2R^6$, $-SO_2R^6$, $-SO_2N(R^4)_2$, $C_{1-4}$ aliphatic, an optionally substituted $C_{6-10}$ aryl, or a $C_{6-10}$ ar($C_{1-4}$) alkyl, the aryl portion of which is optionally substituted; and one ring nitrogen atom in Ring B optionally is oxidized.

4. The compound of claim 3, wherein each $R^b$ independently is selected from the group consisting of $C_{1-6}$ aliphatic, $C_{1-6}$ fluoroaliphatic, halo, $-R^{1b}$, $-R^{2b}$, $-T^1-R^{1b}$, $-T^1-R^{2b}$, $-V^1-T^1-R^{1b}$, and $-V^1-T^1-R^{2b}$;

$T^1$ is a $C_{1-6}$ alkylene chain optionally substituted with $R^{3a}$ or $R^{3b}$, wherein the alkylene chain optionally is interrupted by $-C(R^5)=C(R^5)-$, $-C\equiv C-$, $-O-$, $-S-$, $-S(O)-$, $-S(O)_2-$, $-SO_2N(R^4)-$, $-N(R^4)-$, $-N(R^4)C(O)-$, $-NR^4C(O)N(R^4)-$, $-N(R^4)C(=NR^4)-N(R^4)-$, $-N(R^4)-C(=NR^4)-$, $-N(R^4)CO_2-$, $-N(R^4)SO_2-$, $-N(R^4)SO_2N(R^4)-$, $-OC(O)-$, $-OC(=NR^4)-O-$, or $-C(R^6)=N-O-$, and wherein $T^1$ or a portion thereof optionally forms part of a 3-7 membered ring;

$V^1$ is $-C(R^5)=C(R^5)-$, $-C\equiv C-$, $-O-$, $-S-$, $-S(O)-$, $-S(O)_2-$, $-SO_2N(R^4)-$, $-N(R^4)-$, $-N(R^4)C(O)-$, $-NR^4C(O)N(R^4)-$, $-N(R^4)C(=NR^4)-N(R^4)-$, $-N(R^4)C(=NR^4)-$, $-N(R^4)CO_2-$, $-N(R^4)SO_2-$, $-N(R^4)SO_2N(R^4)-$, $-OC(O)-$, $-OC(O)N(R^4)-$, $-C(O)-$, $-CO_2-$, $-C(O)N(R^4)-$, $-C(O)N(R^4)-O-$, $-C(O)N(R^4)C(=NR^4)-N(R^4)-$, $-N(R^4)C(=NR^4)-N(R^4)-C(O)-$, $-C(=NR^4)-N(R^4)-$, $-C(NR^4)=N(R^4)-$, $-C(=NR^4)-O-$, or $-C(R^6)=N-O-$;

each $R^{1b}$ independently is an optionally substituted aryl, heteroaryl, heterocyclyl, or cycloaliphatic ring;

each $R^{2b}$ independently is $-NO_2$, $-CN$, $C(R^5)=C(R^5)_2$, $-C\equiv C-R^5$, $-OR^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-N(R^4)C(=NR^4)-N(R^4)_2$, $-N(R^4)C(=NR^4)-R^6$, $-NR^4CO_2R^6$, $-N(R^4)SO_2R^6$, $-N(R^4)SO_2N(R^4)_2$, $-O-C(O)R^5$, $-OC(O)N(R^4)_2$, $-C(O)R^5$, $-CO_2R^5$, $-C(O)N(R^4)_2$, $-C(O)N(R^4)-OR^5$, $-C(O)N(R^4)C(=NR^4)-N(R^4)_2$, $-N(R^4)C(=NR^4)-N(R^4)-C(O)R^5$, $-C(=NR^4)-N(R^4)_2$, $-C(=NR^4)-OR^5$, $-C(=NR^4)-N(R^4)-OR^5$, or $-C(R^6)=N-OR^5$;

each $R^{3a}$ independently is selected from the group consisting of $-F$, $-OH$, $-O(C_{1-4}$ alkyl), $-CN$, $-N(R^4)_2$, $-C(O)(C_{1-4}$ alkyl), $-CO_2H$, $-CO_2(C_{1-4}$ alkyl), $-C(O)NH_2$, and $-C(O)NH(C_{1-4}$ alkyl);

each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring; and each $R^7$ independently is an optionally substituted aryl or heteroaryl ring.

5. The compound of claim 4, wherein:

Ring B is a radical derived from an aromatic ring system selected from the group consisting of pyrrole, oxazole, thiazole, imidazole, pyrazole, isoxazole, isothiazole, oxadiazole, triazole, thiadiazole, pyridine, pyridazine, pyrimidine, pyrazine, triazine, indolizine, indole, isoindole, indazole, benzimidazole, benzthiazole, benzoxazole, pyrrolopyridine, imidazopyridine, oxazolopyridine, thiazolopyridine, triazolopyridine, pyrrolopyrimidine, purine, triazolopyrimidine, quinoline, isoquinoline, cinnoline, phthalazine, quinazoline, quinoxaline, naphthyridine, and pteridine, wherein the point of attachment connecting Ring B to $G^1$ may be on either ring when Ring B is a radical derived from a bicyclic ring system;

Ring B optionally is substituted on any substitutable ring carbon atom or ring nitrogen atom; and one ring nitrogen atom in Ring B optionally is oxidized.

6. The compound of claim 5, wherein the substitutable ring carbon atoms in Ring B are substituted with 0-1 $R^b$ and 0-1 $R^{8b}$;

$R^b$ is selected from the group consisting of $C_{1-4}$ aliphatic, $C_{1-4}$ fluoroaliphatic, halo, $-R^{1b}$, $-R^{2b}$, $-T^1-R^{1b}-T^1-R^{2b}$, $-V^1-T^1-R^{1b}$, and $-V^1-T^1-R^{2b}$;

$T^1$ is a $C_{1-4}$ alkylene chain optionally substituted with one or two substituents independently selected from the group consisting of $C_{1-3}$ aliphatic, $C_{1-3}$ fluoroaliphatic, $-F$, $-OH$, $-O(C_{1-4}$ alkyl), $-CO_2H$, $-CO_2(C_{1-4}$ alkyl), $-C(O)NH_2$, and $-C(O)NH(C_{1-4}$ alkyl), wherein the alkylene chain optionally is interrupted with $-N(R^4)-$, $-C(=NR^4)-N(R^4)-$, $-C(NR^4)=N(R^4)-$, $-N(R^4)-C(=NR^4)-$, $-N(R^4)-C(O)-$, or $-C(O)N(R^4)-$;

$V^1$ is $-C(R^5)=C(R^5)-$, $-C\equiv C-$, $-O-$, $-N(R^4)-$, $-N(R^4)C(O)-$, $-C(O)N(R^4)-$, $-C(=NR^4)-N(R^4)-$, $-C(NR^4)=N(R^4)-$, Or $-N(R^4)-C(=NR^4)-$;

each $R^{1b}$ independently is an optionally substituted aryl, heteroaryl, heterocyclyl, or cycloaliphatic ring;

each $R^{2b}$ independently is $-NO_2$, $-CN$, $-C(R^5)=C(R^5)_2$, $-C\equiv C-R^5$, $-OR^5$, $-SO_2R^6$, $-SO_2N(R^4)_2$, $-N(R^4)_2$, $-NR^4C(O)R^5$, $-NR^4C(O)N(R^4)_2$, $-N(R^4)C(=NR^4)-N(R^4)_2$, $-N(R^4)C(=NR^4)-R^6$, $-NR^4CO_2R^6$, $-N(R^4)SO_2R^6$, $-N(R^4)SO_2N(R^4)_2$, $-O-C(O)R^5$, $-OC(O)N(R^4)_2$, $-C(O)R^5$, $-CO_2R^5$, $-C(O)N(R^4)_2$, $-C(O)N(R^4)-OR^5$, $-C(O)N(R^4)C(=NR^4)-N(R^4)_2$, $-N(R^4)C(=NR^4)-N(R^4)-C(O)R^5$, $-C(=NR^4)-N(R^4)_2$, $-C(=NR^4)-OR^5$, $-C(=NR^4)-N(R^4)-OR^5$, or $-C(R^6)=N-OR^5$; and $R^{8b}$ is selected from the group consisting of $C_{1-4}$ aliphatic, $C_{1-4}$ fluoroaliphatic, halo, $-OH$, $-O(C_{1-4}$ aliphatic), $-NH_2$, $-NH(C_{1-4}$ aliphatic), and $-N(C_{1-4}$ aliphatic)$_2$.

7. The compound of claim 6, wherein:

Ring B is a radical derived from pyrrole, oxazole, thiazole, imidazole, pyrazole, isoxazole, pyridine, pyridazine, pyrimidine, pyrazine, pyrrolopyridine, imidazolopyridine, pyrazolopyridine, triazolopyridine, pyrrolopyrimidine, purine, pyrazolopyrimidine, triazolopyrimidine, benzimidazole, or benzthiazole, wherein the point of attachment connecting Ring B to $G^1$ may be on either ring when Ring B is a radical derived from a bicyclic ring system;

Ring B optionally is substituted on any substitutable ring carbon atom or ring nitrogen atom; and one ring nitrogen atom in Ring B optionally is oxidized.

8. The compound of claim 7, wherein Ring B is an optionally substituted pyrimidinyl, pyridyl, or N-oxidopyridyl.

9. The compound of claim 1, having formula (III):

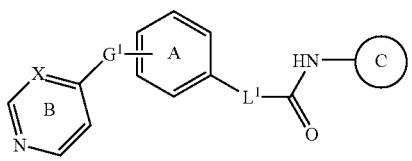

(III)

or a pharmaceutically acceptable salt thereof;
wherein:
X is CH or N;
Ring B is substituted with 0-1 $R^b$ and 0-1 $R^{8b}$, and one nitrogen atom in Ring B optionally is oxidized;
$R^b$ is selected from the group consisting of $C_{1-4}$ aliphatic, $C_{1-4}$ fluoroaliphatic, halo, -$R^{1b}$, -$R^{2b}$, -$T^1$-$R^{1b}$-$T^1$-$R^{2b}$, —$V^1$-$T^1$-$R^{1b}$, and —$V^1$-$T^1$-$R^{2b}$;
$T^1$ is a $C_{14}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —$CO_2H$, —$CO_2(C_{1-4}$ alkyl), —C(O)$NH_2$, and —C(O)NH($C_{1-4}$ alkyl), wherein the alkylene chain optionally is interrupted with —N($R^4$)—, —C(=N$R^4$)—N($R^4$)—, —C(N$R^4$)=N($R^4$)—, —N($R^4$)—C(=N$R^4$)—, —N($R^4$)—C(O)—, or —C(O)N($R^4$)-;
$V^1$ is —C($R^5$)=C($R^5$)—, —C≡C—, —O—, —N($R^4$)—, —N($R^4$)C(O)—, —C(O)N($R^4$)—, —C(=N$R^4$)—N($R^4$)—, —C(N$R^4$)=N($R^4$)—, or —N($R^4$)—C(=N$R^4$)-;
each $R^{1b}$ independently is an optionally substituted aryl, heteroaryl, heterocyclyl, or cycloaliphatic ring;
each $R^{2b}$ independently is —$NO_2$, —CN, —C($R^5$)=C($R^5$)$_2$, —C≡C—$R^5$, —$OR^5$, —$SO_2R^6$, —$SO_2N(R^4)_2$, —N($R^4$)$_2$, —$NR^4C(O)R^5$, —$NR^4C(O)N(R^4)_2$, —N($R^4$)C(=N$R^4$)—N($R^4$)$_2$, —N($R^4$)C(=N$R^4$)-$R^6$, —$NR^4CO_2R^6$, —N($R^4$)$SO_2R^6$, —N($R^4$)$SO_2N(R^4)_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—$OR^5$, —C(=N$R^4$)—N($R^4$)—$OR^5$, or —C($R^6$)=N—$OR^5$; and $R^{8b}$ is selected from the group consisting of $C_{1-4}$ aliphatic, $C_{1-4}$ fluoroaliphatic, halo, —OH, —O($C_{1-4}$ aliphatic), —$NH_2$, —NH($C_{1-4}$ aliphatic), and —N($C_{1-4}$ aliphatic)$_2$.

10. The compound of claim 9, having the formula (IV):

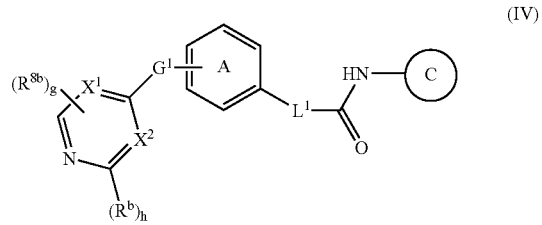

(IV)

or a pharmaceutically acceptable salt thereof;
wherein:
$G^1$ is —O— or —NH—;
$X^1$ and $X^2$ are each independently CH or N, provided that $X^1$ and $X^2$ are not both N;
$R^b$ is selected from the group consisting of halo, —N($R^4$)$_2$, —$CO_2R^5$, —C(O)—N($R^4$)$_2$, —C(O)—N($R^4$)—$OR^5$, —N($R^4$)C(O)$R^5$, —N($R^4$)C(O)—$OR^5$, —N($R^4$)C(O)—N($R^4$)$_2$, —N($R^4$)$SO_2R^6$, —C(=N$R^4$)N($R^4$)$_2$, and —C(=N$R^4$)N($R^4$)—$OR^5$;
$R^{8b}$ is selected from the group consisting of $C_{1-4}$ aliphatic, $C_{1-4}$ fluoroaliphatic, halo, —OH, —O($C_{1-4}$ aliphatic), —$NH_2$, —NH($C_{1-4}$ aliphatic), and —N($C_{1-4}$ aliphatic)$_2$;
g is 0 or 1; and
h is 0 or 1.

11. The compound of claim 10, wherein:
$R^b$ is selected from the group consisting of halo, —N($R^{4x}$)($R^{4z}$), —$CO_2R^{5x}$, —C(O)—N($R^{4x}$)($R^{4z}$), —C(O)—N($R^{4x}$)—$OR^{5x}$, —N($R^{4x}$)C(O)$R^{5x}$, —N($R^{4x}$)C(O)—$OR^{5x}$, —N($R^{4x}$)C(O)—N($R^{4x}$)($R^{4z}$), —N($R^{4x}$)$SO_2R^{6x}$, —C(=N$R^{4x}$)N($R^{4x}$)($R^{4z}$), and —C(=N$R^{4x}$)N($R^{4x}$)—$OR^{5x}$;
$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted;
$R^{4z}$ is hydrogen, $C_{1-4}$ alkyl, $C_{1-4}$ fluoroalkyl, $C_{6-10}$ ar($C_{1-4}$) alkyl, the aryl portion of which may be optionally substituted, or an optionally substituted 5- or 6-membered aryl, heteroaryl, or heterocyclyl ring; or
$R^{4x}$ and $R^{4z}$, taken together with the nitrogen atom to which they are attached, form an optionally substituted 4- to 8-membered heterocyclyl ring having, in addition to the nitrogen atom, 0-2 ring heteroatoms independently selected from N, O, and S;
each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; and
each $R^{6x}$ independently is $C_{1-4}$ alkyl, $C_{1-4}$ fluoroalkyl, $C_{6-10}$ ar($C_{1-4}$)alkyl, the aryl portion of which maybe optionally substituted, or an optionally substituted 5- or 6-membered aryl, heteroaryl, or heterocyclyl ring.

12. The compound of claim 11, wherein $R^b$ is —N($R^{4x}$)($R^{4z}$), —C(O)—N($R^{4x}$)($R^{4z}$), or —C(=NH)N($R^{4x}$)($R^{4z}$), and $R^{4x}$ and $R^{4z}$, taken together with the nitrogen atom to which they are attached, form a morpholinyl, piperidinyl, piperazinyl, or pyrrolidinyl ring.

13. The compound of claim 11, wherein $R^b$ is selected from the group consisting of halo, —NH($R^{4z}$), —N($R^{4x}$)($R^{4z}$), —$CO_2R^{5x}$, —C(O)—NH($R^{4z}$), —C(O)—N($R^{4x}$)($R^{4z}$), —C(O)—NH—$OR^{5x}$, —NHC(O)$R^{5x}$, —NHC(O)—$OR^{5x}$, —NHC(O)—N($R^{4x}$)($R^{4z}$), —NHSO$_2$$R^{6x}$, —C(=NH)N($R^{4x}$)($R^{4z}$), —C(=NH)N($R^{4x}$)($R^{4z}$), and —C(=NH)NH—O$R^{5x}$.

14. The compound of claim 9, having the formula (IV):

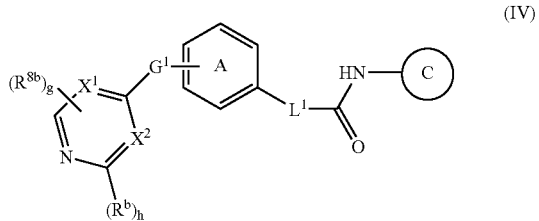

or a pharmaceutically acceptable salt thereof;
wherein:
$G^1$ is —O— or —NH—;
$X^1$ and $X^2$ are each independently CH or N, provided that $X^1$ and $X^2$ are not both N;
$R^b$ is —$V^1$-$T^1$-$R^{1b}$ or —$V^1$-$T^1$-$R^{2b}$;
  $V^1$ is —N($R^4$)—, —N($R^4$)—C(O)—, —N($R^4$)SO$_2$$R^6$, —N($R^4$)C(O)—O$R^5$, —C(O)N($R^4$)—, —C(=N$R^4$)N($R^4$)—, or —N($R^4$)—C(=N$R^4$)-;
  $T^1$ is a C$_{1-4}$ alkylene chain optionally substituted with —F, C$_{1-3}$ alkyl, or C$_{1-3}$ fluoroalkyl;
  $R^{1b}$ is an optionally substituted C$_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring;
  $R^{2b}$ is —N($R^4$)$_2$, —N$R^4$C(O)$R^5$, —C(O)N($R^4$)$_2$, —CO$_2$$R^5$, or —O$R^5$;
$R^{8b}$ is selected from the group consisting of C$_{1-4}$ aliphatic, C$_{1-4}$ fluoroaliphatic, halo, —OH, —O(C$_{1-4}$ aliphatic), —NH$_2$, —NH(C$_{1-4}$ aliphatic), and —N(C$_{1-4}$ aliphatic)$_2$;
g is 0 or 1; and
h is 0 or 1.

15. The compound of claim 14, wherein:
$V^1$ is —N($R^{4x}$)—, —N($R^{4x}$)—C(O)—, —C(O)N($R^{4x}$)—, —C(=N$R^{4x}$)N($R^{4x}$)—, or —N($R^{4x}$)—C(=N$R^{4x}$)-;
$R^{1b}$ is an optionally substituted C$_{3-6}$ cycloaliphatie or an optionally substituted pyrrolidinyl, piperidinyl, morpholinyl, or piperazinyl; and
$R^{2b}$ is —N($R^{4x}$)($R^{4z}$), —N$R^{4x}$C(O)$R^{5x}$, —C(O)N($R^{4x}$)($R^{4z}$), —CO$_2$$R^{5x}$, or —O$R^{5x}$;
$R^{4x}$ is hydrogen, C$_{1-4}$ alkyl, C$_{1-4}$ fluoroalkyl, or C$_{6-10}$ ar(C$_{1-4}$)alkyl, the aryl portion of which may be optionally substituted;
$R^{4z}$ is hydrogen, C$_{1-4}$ alkyl, C$_{1-4}$ fluoroalkyl, C$_{6-10}$ ar(C$_{1-4}$) alkyl, the aryl portion of which may be optionally substituted, or an optionally substituted 5- or 6-membered aryl, heteroaryl, or heterocyclyl ring; or
$R^{4x}$ and $R^{4z}$, taken together with the nitrogen atom to which they are attached, form an optionally substituted 4- to 8-membered heterocyclyl ring having, in addition to the nitrogen atom, 0-2 ring heteroatoms independently selected from N, O, and S; and
each $R^{5x}$ independently is hydrogen, C$_{1-4}$ alkyl, C$_{1-4}$ fluoroalkyl, C$_{6-10}$ ar(C$_{1-4}$)alkyl, the aryl portion of which may be optionally substituted, or an optionally substituted 5- or 6-membered aryl, heteroaryl, or heterocyclyl ring.

16. The compound of claim 15, wherein $X^1$ and $X^2$ are each CH and $V^1$ is —C(O)—NH— or —NH—C(O)—.

17. The compound of claim 16, wherein $R^b$ is selected from the group consisting of:

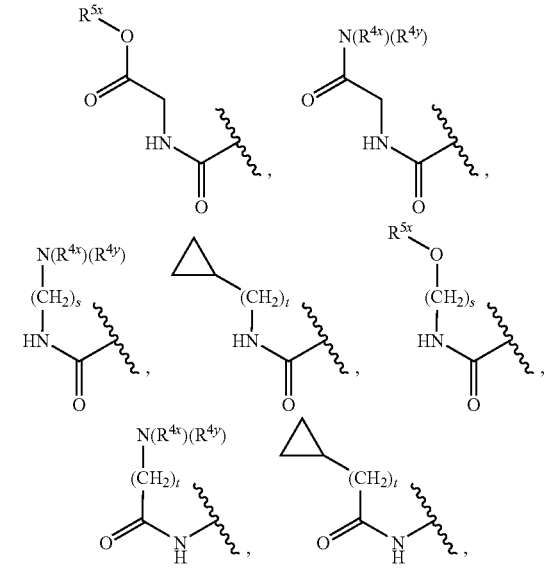

s is 2 or 3; and
t is 1, 2, or 3.

18. The compound of claim 9, having the formula (IV):

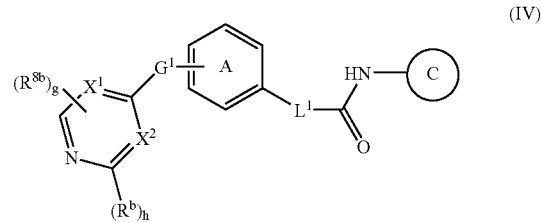

or a pharmaceutically acceptable salt thereof;
wherein:
$G^1$ is —O— or —NH—;
$X^1$ and $X^2$ are each independently CH or N, provided that $X^1$ and $X^2$ are not both N;
$R^b$ is -$T^1$-$R^{1b}$ or -$T^1$-$R^{2b}$;
  $T^1$ is a C$_{1-6}$ alkylene chain optionally substituted with —F, C$_{1-3}$ alkyl, or C$_{1-3}$ fluoroalkyl, wherein the alkylene chain optionally is interrupted by —N($R^4$)—, —C(O)—N($R^4$)—, —C(=N$R^4$)—N($R^4$)—, —N($R^4$)—C(O)—, or —N($R^4$)—C(=N$R^4$)-;
  $R^{1b}$ is an optionally substituted C$_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahyclropyrimidinyl ring;
  $R^{2b}$ is —O$R^5$, —N($R^4$)$_2$, —N$R^4$C(O)$R^5$, —N$R^4$C(O)N($R^4$)$_2$, —C(O)N($R^4$)—O$R^5$, —C(O)N($R^4$)$_2$, —N($R^4$)—CO$^2$$R^5$, —N($R^4$)—C(=N$R^4$)-$R^5$ or —C(=N$R^4$)—N($R^4$)$_2$;

$R^{8b}$ is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$;

g is 0 or 1; and h is 0 or 1.

19. The compound of claim 18, wherein:

$R^b$ is selected from the group consisting of —(CH$_2$)$_q$—R$^{1x}$, —(CH$_2$)$_q$—R$^{2x}$, —(CH$_2$)$_q$—R$^{2y}$—(CH$_2$)$_q$—N(R$^{4x}$)—(CH$_2$)$_q$—R$^{1x}$, —(CH$_2$)$_q$—N(R$^{4x}$)—(CH$_2$)$_q$—R$^{2x}$, —(CH$_2$)$_q$—N(R$^{4x}$)—(CH$_2$)$_s$—R$^{2y}$—(CH$_2$)$_q$—N(R$^{4x}$)C(=NR$^{4x}$)—(CH$_2$)$_q$—R$^{1x}$, —(CH$_2$)$_q$—N(R$^{4x}$)C(=NR$^{4x}$)—(CH$_2$)$_q$—R$^{2x}$, —(CH$_2$)$_q$—N(R$^{4x}$)C(=NR$^{4x}$)—(CH$_2$)$_q$—R$^{2y}$;

$R^{1x}$ is an optionally substituted phenyl, piperidinyl, piperazinyl, morpholinyl, or pyrrolidinyl ring;

$R^{2x}$ is —C(O)N(R$^{4x}$)(R$^{4z}$);

$R^{2y}$ is —N(R$^{4x}$)(R$^{4z}$), —NR$^{4x}$C(O)R$^{5x}$, —N(R$^{4x}$)—CO$_2$R$^{5x}$, —N(R$^{4x}$)—C(=NR$^{4x}$)—R$^{5x}$ or —OR$^{5x}$;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted;

$R^{4z}$ is hydrogen, $C_{1-4}$ alkyl, $C_{1-4}$ fluoroalkyl, $C_{6-10}$ ar($C_{1-4}$) alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted morpholinyl, piperidinyl, piperazinyl, or pyrrolidinyl ring;

$R^{5x}$ is hydrogen, $C_{1-4}$ alkyl, $C_{1-4}$ fluoroalkyl, or $C_{6-10}$ ar($C_{1-4}$)alkyl, the aryl portion of which may be optionally substituted;

$R^{8b}$ is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$;

q is 1, 2, or 3; and s is 2 or 3.

20. The compound of claim 9, having the formula (V):

(V)

(R$^{8b}$)$_g$—X$^1$—G$^1$—A—L$^1$—C(O)—HN—C

N—X$^2$

D or a pharmaceutically acceptable salt thereof;

wherein:

G$^1$ is —O— or —NH—;

X$^1$ and X$^2$ are each independently CH or N, provided that X$^1$ and X$^2$ are not both N;

Ring D is an aryl, heteroaryl, heterocyclyl, or cycloaliphatic ring;

each substitutable saturated ring carbon atom in Ring D is unsubstituted or is substituted with =O, =S, =C(R$^5$)$_2$, =N—OR$^5$, =N—R$^5$, or —R$^d$;

each substitutable unsaturated ring carbon atom in Ring D is unsubstituted or is substituted with —Rhu d;

each substitutable ring nitrogen atom in Ring D is unsubstituted or is substituted with —C(O)R$^5$, —C(O)N(R$^4$)$_2$, —CO$_2$R$^6$, —SO$_2$R$^6$, —SO$_2$(NR$^4$)$_2$, an optionally substituted $C_{6-10}$ aryl, or a $C_{1-4}$ aliphatic optionally substituted with R$^3$ or R$^7$;

one ring nitrogen atom in Ring D optionally is oxidized;

each Rd independently is halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, —C(R$^6$)=N—OR$^5$, or an optionally substituted aliphatic, aryl, heteroaryl, or heterocyclyl;

$R^{8b}$ is selected from the group consisting of $C_{1-4}$ aliphatic, $C_{1-4}$ fluoroaliphatie, halo, —OH, —O($C_{1-4}$ aliphatic), —NH$_2$, —NH($C_{1-4}$ aliphatic), and —N($C_{1-4}$ aliphatic)$_2$; and g is 0 or 1.

21. The compound of claim 20, wherein Ring D is an optionally substituted heteroaryl or heterocyclyl selected from the group consisting of azetidinyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, and tetrahydropyritnidinyl.

22. The compound of claim 21, wherein:

Ring D is substituted with 0-1 R$^d$ and 0-1 R$^{8d}$;

$R^d$ is selected from the group consisting of $C_{1-4}$ aliphatic, $C_{1-4}$ fluoroaliphatic, halo, —R$^{1d}$, —R$^{2d}$, -T$^3$-R$^{1d}$, -T$^3$-R$^{2d}$, —V$^3$-T$^3$-R$^{1d}$, and —V$^3$-T$^3$-R$^{2d}$;

T$^3$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —CO$_2$H, —CO$_2$($C_{1-4}$ alkyl), —C(O)N$_2$, and —C(O)NH($C_{1-4}$ alkyl);

V$^3$ is —O—, —N(R$^4$)—, —N(R$^4$)C(O)—, —C(O)N(R$^4$)—, —C(=NR$^4$)—N(R$^4$)—, —C(NR$^4$)=N(R$^4$)—, or —N(R$^4$)C(=NR$^4$)-;

each $R^{1d}$ independently is an optionally substituted aryl, heteroaryl, heterocyclyl, or cycloaliphatic ring;

each $R^{2d}$ independently is —NO$_2$, —CN, —C(R$^5$)=C(R$^5$)$_2$, —C≡C—R$^5$, —OR$^5$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)N(R$^4$)$_2$, —C(=NR$^4$)—OR$^5$, —C(=NR$^4$)—N(R$^4$)—OR$^5$, or —C(R$^6$)=N—OR$^5$; and $R^{8d}$ is $C_{1-4}$ aliphatic, $C_{1-4}$ fluoroaliphatic, halo, —OH, —O($C_{1-4}$ aliphatic), —NH$_2$, —NH($C_{1-4}$ aliphatic), or —N($C_{1-4}$ aliphatic)$_2$.

23. The compound of claim 22, wherein each $R^{2d}$ independently is selected from the group consisting of —OR$^5$, —N(R$^4$)$_2$, —NR$^4$C(O)R$^5$, —NR$^4$C(O)N(R$^4$)$_2$, —O—C(O)R$^5$, —C)O$_2$R$^5$, —C(O)R$^5$, —C(O)N(R$^4$)$_2$, —C(O)N(R$^4$)—OR$^5$, and —C(=NR$^4$)—N(R$^4$)$_2$.

24. The compound of claim 20, wherein Ring D is selected from the group consisting of:

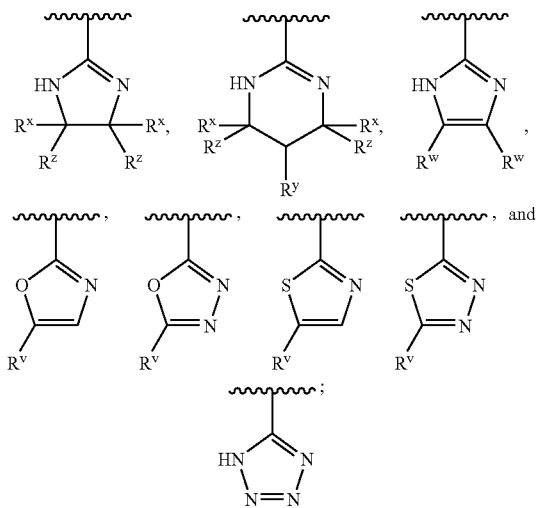

$R^v$ is hydrogen, halo, $C_{1-4}$ aliphatic, $C_{1-4}$ fluoroaliphatic, —$OR^5$, —$N(R^4)_2$, —$CO_2R^5$, —$C(O)N(R^4)_2$, -$T^3$-$OR^5$, -$T^3$-$N(R^4)_2$, -$T^3$-$CO_2R^5$, -$T^3$-$C(O)N(R^4)_2$, or an optionally substituted 5- or 6-membered aryl or heteroaryl;

each $R^w$ independently is hydrogen, halo, $C_{1-4}$ aliphatic, $C_{1-4}$ fluoroaliphatic, —$OR^5$, —$N(R^4)_2$, —$CO_2R^5$, —$C(O)N(R^4)_2$, -$T^3$-$OR^5$, -$T^3$-$N(R^4)_2$, -$T^3$-$CO_2R^5$, -$T^3$-$C(O)N(R^4)_2$, or an optionally substituted 5- or 6-membered aryl or heteroaryl;

each $R^x$ independently is hydrogen, fluoro, $C_{1-4}$ aliphatic, $C_{1-4}$ fluoroaliphatic, —$CO_2R^5$, —$C(O)N(R^4)_2$, -$T^3$-$N(R^4)_2$, -$T^3$-$OR^5$, -$T^3$-$CO_2R^5$, or -$T^3$-$C(O)N(R^4)_2$;

$R^y$ is hydrogen, halo, $C_{1-4}$ aliphatic, $C_{1-4}$ fluoroaliphatic, —$OR^5$, —$N(R^4)_2$, —$CO_2R^5$, —$C(O)N(R^4)_2$, -$T^3$-$OR^5$, -$T^3$-$N(R^4)_2$, -$T^3$-$CO_2R^5$, or -$T^3$-$C(O)N(R^4)_2$;

each $R^z$ independently is hydrogen, fluoro, $C_{1-4}$ aliphatic, or $C_{1-4}$ fluoroaliphatic; and $T^3$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —$CO_2H$, —$CO_2(C_{1-4}$ alkyl), —C(O)NH2, and —C(O)NH($C_{1-4}$ alkyl).

25. The compound of claim 20, wherein Ring D is selected from the group consisting of:

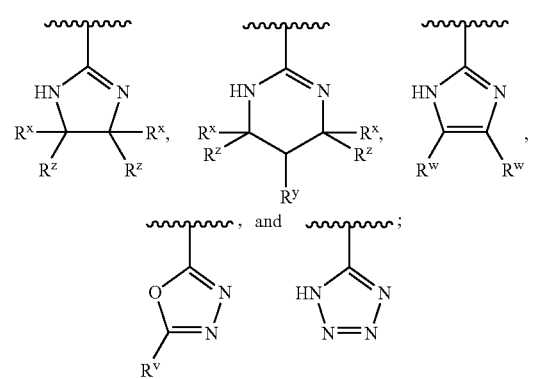

$R^v$ is hydrogen, halo, $C_{1-4}$ aliphatic, $C_{1-4}$ fluoroaliphatic, —$(CH_2)_p$—$OR^{5x}$, —$(CH_2)_p$—$N(R^{4x})(R^{4z})$, —$(CH_2)_p$—$CO_2R^{5x}$, —$(CH_2)_p$—$C(O)N(R^{4x})(R^{4z})$, or an optionally substituted phenyl, pyridyl, or pyrimidinyl group;

each $R^w$ independently is hydrogen, an optionally substituted phenyl, pyridyl, or pyrimidinyl group, halo, $C_{1-4}$ aliphatic, $C_{1-4}$ fluoroaliphatic, —$(CH_2)_p$—$OR^{5x}$, —$(CH_2)_p$—$N(R^{4x})(R^{4z})$, —$(CH_2)_p$—$CO_2R^{5x}$, —$(CH_2)_p$—$C(O)N(R^{4X})(R^{4Z})$, —$(CH_2)_q$—$N(R^{4X})$—$(CH_2)_q$—$R^{1x}$, —$(CH_2)_q$—$N(R^{4x})$—$(CH_2)_q$—$R^{2x}$, —$(CH_2)_q$—$N(R^{4X})$—$(CH_2)_s$—$R^{2y}$—$CH_2)_q$—$N(R^{4x})C(=NR^{4x})$—$(CH_2)_q$—$R^{1x}$, —$(CH_2)_q$—$N(R^{4x})C(=NR^{4x})$—$(CH_2)_q$—$R^{2x}$, or —$(CH_2)_q$—$N(R^{4x})C(=NR^{4x})$—$(CH_2)_q$—$R^{2y}$;

each $R^x$ independently is hydrogen, fluoro, $C_{1-4}$ aliphatic, $C_{1-4}$ fluoroaliphatic, —$(CH_2)_p$—$CO_2R^{5x}$, —$(CH_2)_p$—$C(O)N(R^{4x})(R^{4z})$, —$(CH_2)_r$—$N(R^{4x})(R^{4z})$, or —$(CH_2)_r$—$OR^{5x}$;

$R^y$ is hydrogen, fluoro, $C_{1-4}$ aliphatic, $C_{1-4}$ fluoroaliphatic, —$(CH_2)_p$—$N(R^{4x})(R^{4z})$, —$(CH_2)_p$—$OR^{5x}$, —$(CH_2)_p$—$CO_2R^{5x}$, —$(CH_2)_p$—$C(O)N(R^{4x})(R^{4z})$;

each $R^z$ independently is hydrogen, fluoro, $C_{1-4}$ aliphatic, or $C_{-4}$ fluoroaliphatic;

each $R^{1x}$ independently is an optionally substituted phenyl, piperidinyl, piperazinyl, morpholinyl, or pyrrolidinyl ring;

each $R^{2x}$ independently is —$C(O)N(R^{4x})(R^{4z})$;

each $R^{2y}$ independently is —$N(R^{4x})(R^{4z})$, —$NR^{4x}C(O)R^{5x}$, —$N(R^{4x})$—$CO_2R^{5x}$, —$N(R^{4x})$—$C(=NR^{4x})$—$R^{5x}$ or —$OR^{5x}$;

each $R^{4x}$ independently is hydrogen, $C_{1-4}$ alkyl, $C_{1-4}$ fluoroalkyl, or $C_{6-10}$ ar($C_{1-4}$)alkyl, the aryl portion of which may be optionally substituted;

each $R^{4z}$ independently is hydrogen, $C_{1-4}$ alkyl, $C_{-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted 4 to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring;

p is 0, 1, or 2;

q is 1, 2, or 3;

r is 1 or 2; and s is 2 or 3.

26. The compound of claim 25, wherein:

$X^1$ and $X^2$ are each CH; and

Ring D is selected from the group consisting of:

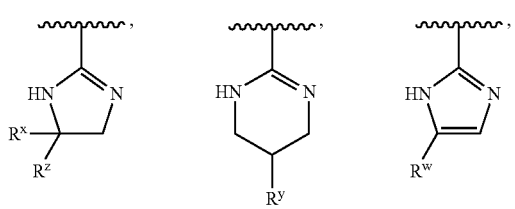

-continued

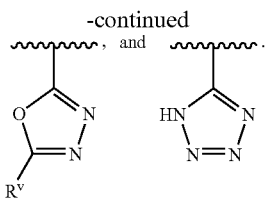

27. The compound of claim 1, wherein:

Ring C is substituted on its substitutable ring carbon atoms with 0-2 $R^c$ and 0-2 $R^{8c}$;

each $R^c$ independently is halo, —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—$C(O)R^5$, —$OC(O)N(R^4)_2$, —$C(O)R^5$, —$CO_2R^5$, —$C(O)N(R^4)_2$, —$C(O)N(R^4)$—$OR^5$, —$C(O)N(R^4)C(=NR)$—$N(R^4)_2$, —$N(R^4)C(=NR^4)$—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, —$C(R^6)$=N—$OR^5$, or an optionally substituted aliphatic, aryl, heteroaryl, or heterocyclyl; or two adjacent $R^c$, taken together with the intervening ring atoms, form an optionally substituted fused 5- or 6 membered aromatic or non-aromatic ring having 0-3 ring heteroatoms independently selected from the group consisting of O, N, and S;

each $R^{8c}$ independently is selected from the group consisting of $C_{1-4}$ aliphatic, $C_{1-4}$ fluoroaliphatic, —$O(C_{1-4}$ alkyl), —$O(C_{1-4}$ fluoroalkyl), and halo;

each substitutable ring nitrogen atom in Ring C is unsubstituted or is substituted with —$C(O)R^5$, —$C(O)N(R^4)_2$, —$CO_2R^6$, —$SO_2R^6$, —$SO_2N(R^4)_2$, an optionally substituted $C_{6-10}$ aryl, or a $C_{1-4}$ aliphatic optionally substituted with —F, —OH, —$O(C_{1-4}$ alkyl), —CN, —$N(R^4)_2$, —$C(O)(C_{1-4}$ alkyl), —$CO_2H$, —$CO_2(C_{1-4}$ alkyl), —$C(O)NH_2$, —$C(O)NH(C_{1-4}$ alkyl), or an optionally substituted $C_{6-10}$ aryl ring; and one ring nitrogen atom in Ring C optionally is oxidized.

28. The compound of claim 27, wherein each $R^c$ independently is selected from the group consisting of $C_{1-6}$ aliphatic, $C_{1-6}$ fluoroaliphatic, halo, —$R^{1c}$, —$R^{2c}$, -$T^2$-$R^{2c}$, and -$T^2$-$R^{1c}$;

$T^2$ is a $C_{1-6}$ alkylene chain optionally substituted with $R^{3a}$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$N(R^4)SO_2$—, —$C(O)N(R^4)$—, —C(O)—, —$CO_2$—, —OC(O)—, or —$OC(O)N(R^4)$—, and wherein $T^2$ or a portion thereof optionally forms part of a 3-7 membered ring;

each $R^{1c}$ independently is an optionally substituted aryl, heteroaryl, heterocyclyl, or cycloaliphatic ring;

each $R^{2c}$ independently is —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—$C(O)R^5$, —$OC(O)N(R^4)_2$, —$C(O)R^5$, —$CO_2R^5$, —$C(O)N(R^4)_2$, —$C(O)N(R^4)$—$OR^5$, —$C(O)N(R^4)C(=NR^4)$—$N(R^4)_2$, —$N(R^4)C(=NR^4)$—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, or —$C(R^4)$=N—$OR^5$;

each $R^{3a}$ independently is selected from the group consisting of —F, —OH, —$O(C_{1-4}$alkyl), —CN, —$N(R^4)_2$, —$C(O)(C_{1-4}$ alkyl), —$CO_2H$, —$CO_2(C_{1-4}$ alkyl), —$C(O)NH_2$, and —$C(O)NH(C_{1-4}$ alkyl);

each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4 to 8-membered heterocyclyl ring having, in addition to the nitrogen atom, 0-2 ring heteroatoms independently selected from N, O, and S;

each $R^5$ independently is hydrogen or an optionally substituted aliphatic, aryl, heteroaryl, or heterocyclyl group;

each $R^6$ independently is an optionally substituted aliphatic, aryl, or heteroaryl group; and each $R^7$ independently is an optionally substituted aryl or heteroaryl ring.

29. The compound of claim 28, wherein Ring C is an optionally substituted phenyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, or triazinyl, wherein one ring nitrogen atom in Ring C is optionally oxidized.

30. The compound of claim 28, wherein:

Ring C is a 5- or 6-membered heteroaryl substituted with 0-2 $R^c$; and each $R^c$ independently is selected from the group consisting of -halo, $C_{1-4}$ alkyl, $C_{1-4}$ fluoroalkyl, —$O(C_{1-4}$ alkyl), and —$O(C_{1-4}$ fluoroalkyl), or two adjacent $R^c$, taken together with the intervening ring atoms, form an optionally substituted fused 5- or 6-membered aromatic or non-aromatic ring having 0-3 ring heteroatoms selected from the group consisting of O, N, and S.

31. The compound of claim 28, wherein:

Ring C is phenyl substituted with 0-2 $R^c$ and 0-1 $R^{8c}$;

each $R^c$ independently is selected from the group consisting of $C_{1-4}$ aliphatic, $C_{1-4}$ fluoroaliphatic, halo, —$R^{2c}$ and -$T^2$-$R^{2c}$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$T^2$ is a $C_{1-4}$ alkylene chain optionally substituted with one or two groups independently selected from —F, $C_{1-4}$ aliphatic, and $C_{1-4}$ fluoroaliphatic; and each $R^{2c}$ c independently is —CN, —$C(R^4)$=$C(R^5)_2$, —C≡C—$R^5$, —$OR^5$, —$SR^6$, —$N(R^4)_2$, —$NR^4C(O)R^5$, —$NR^4C(O)N(R^4)_2$, —$NR^4CO_2R^6$, —$CO_2R^5$, or —$C(O)N(R^4)_2$; and each $R^{8c}$ independently is selected from the group consisting of $C_{1-4}$ aliphatic, $C_{1-4}$ fluoroaliphatic, —$O(C_{1-4}$ alkyl), —$O(C_{1-4}$ fluoroalkyl), and halo.

32. The compound of claim 30, wherein:

each $R^c$ independently is halo, —CN, —$C(R^{5x})$=$C(R^{5x})(R^{5y})$, —C≡C—$R^{5y}$, —$OR^{5y}$, —$SR^{6x}$, —$CO_2R^{5x}$, —$C(O)N(R^{4x})(R^{4y})$, or a $C_{1-4}$ aliphatic or $C_{1-4}$ fluoroaliphatic optionally substituted with one or two substituents independently selected from the group consisting of —$OR^{5x}$, —$N(R^{4x})(R^{4y})$, —$SR^{6x}$, —$CO_2R^{5x}$, or —$C(O)N(R^{4x})(R^{4y})$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted, or two $R^{4x}$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

$R^{4y}$ is hydrogen, $C_{6-10}$ ar($C_{1-4}$)alkyl, the aryl portion of which may be optionally substituted, an optionally substituted 5- or 6-membered aryl, heteroaryl, or heterocyclyl ring, or a $C_{1-4}$ alkyl or $C_{1-4}$ fluoroalkyl optionally substituted with one or two substituents independently selected from the group consisting of —$OR^{5x}$, —$N(R^{4x})_2$, —$CO_2R^{5x}$, or —$C(O)N(R^{4x})_2$; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring;

each $R^{5y}$ independently is hydrogen, an optionally substituted $C_{6-10}$ aryl, a $C_{6-10}$ar($C_{1-4}$)alkyl, the aryl portion of which may be optionally substituted, or a $C_{1-4}$ alkyl or $C_{1-4}$ fluoroalkyl optionally substituted with one or two substituents independently selected from the group consisting of —$OR^{5x}$, —$N(R^{4x})_2$, —$CO_2R^{5x}$, or —$C(O)N(R^{4x})_2$; and each $R^{6x}$ independently is $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

33. The compound of claim 32, wherein Ring C is selected from the group consisting of:

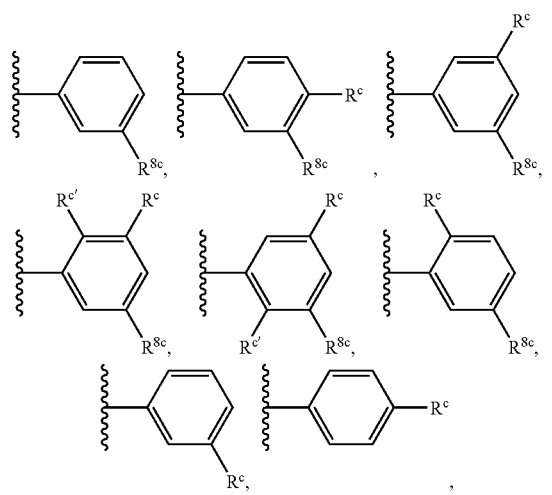

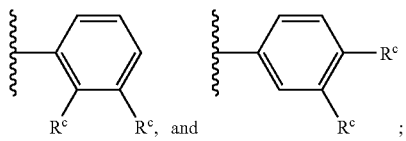

each $R^c$ independently is halo, —CN, —$C(R^{5x})$=$C(R^{5x})(R^{5y})$, —C≡C—$R^{5y}$, —$OR^{5y}$, —$SR^{6x}$, —$N(R^{4x})(R^{4y})$, —$CO_2R^{5x}$, —$C(O)N(R^{4x})(R^{4y})$, or a $C_{1-4}$ aliphatic or $C_{1-4}$ fluoroaliphatic optionally substituted with one or two substituents independently selected from the group consisting of —$OR^{5x}$, —$N(R^{4x})(R^{4y})$, —$SR^{6x}$, —$CO_2R^{5x}$, or —$C(O)N(R^{4x})(R^{4y})$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$R^{c'}$ is $C_{1-4}$ aliphatic, $C_{1-4}$ fluoroaliphatic, halo, —CN, —OH, —O($C_{1-4}$ alkyl), —O($C_{1-4}$ fluoroalkyl), —S($C_{1-4}$ alkyl), —$NH_2$, —NH($C_{1-4}$ alkyl), or —N($C_{1-4}$ alkyl)$_2$; and $R^{8c}$ is $C_{1-4}$ aliphatic, $C_{1-4}$ fluoroaliphatic, or halo.

34. The compound of claim 33, wherein Ring C is selected from the group consisting of:

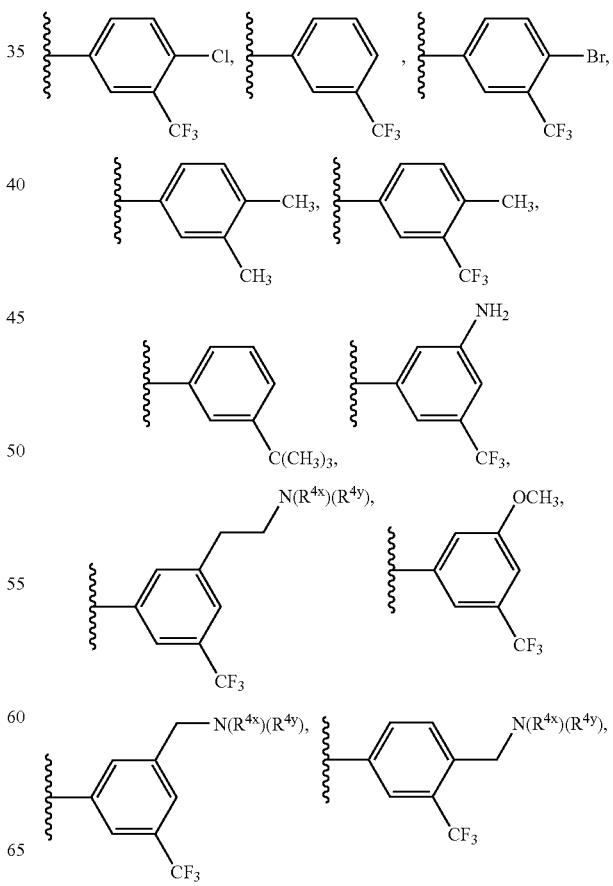

-continued

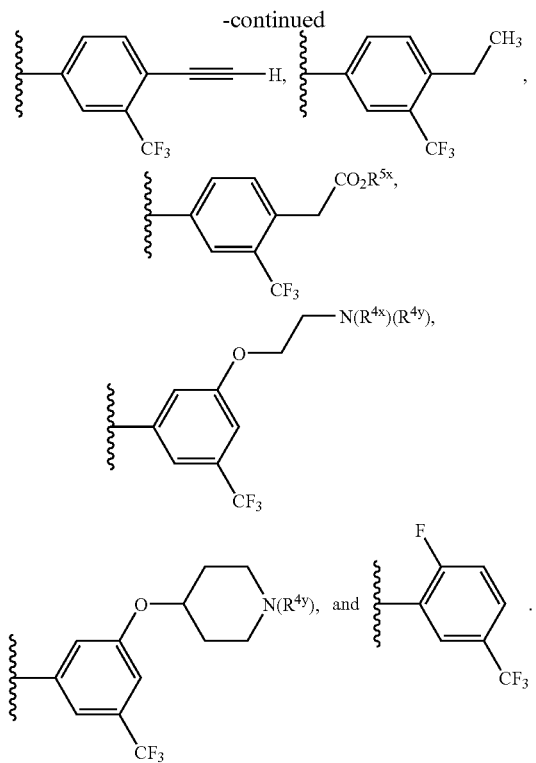

35. A compound of claim 1, having the formula (VI):

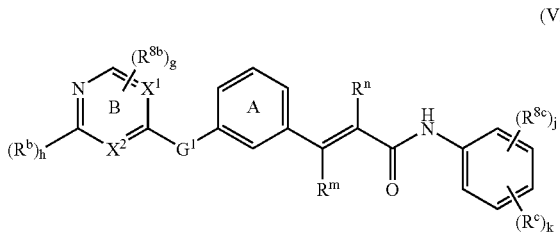
(VI)

or a pharmaceutically acceptable salt thereof;
wherein:
$G^1$ is —O— or —NH—;
$X^1$ and $X^2$ are each independently CH or N, provided that $X^1$ and $X^2$ are not both N;
one ring nitrogen atom in Ring B optionally is oxidized;
$R^m$ is hydrogen, fluoro, —$OR^5$, —$C(O)R^5$, —$C(O)N(R^4)_2$, —$CO_2R^5$, —$SO_2R^6$, —$SO_2N(R^4)_2$, or an optionally substituted $C_{1-4}$ aliphatic;
$R^n$ is hydrogen, fluoro, —$C(O)R^5$, —$C(O)N(R^4)_2$, —$CO_2R^5$, —$SO_2R^6$, —$SO_2N(R^4)_2$, or an optionally substituted $C_{1-4}$ aliphatic;
Ring A is substituted with 0-2 $R^a$;
each $R^a$ independently is —F, —Cl, —$NO_2$, —$CH_3$, —$CF_3$, —$OCH_3$, —$OCF_3$, —$SCH_3$, —$SO_2CH_3$—CN, —$CO_2H$, —$C(O)NH_2$, or —$C(O)NHCH_3$;
$R^b$ is selected from the group consisting of $C_{1-4}$ aliphatic, $C_{1-4}$ fluoroaliphatic, halo, —$R^{1b}$, —$R^{2b}$, -$T^1$-$R^{1b}$, -$T^1$-$R^{2b}$, —$V^1$-$T^1$-$R^{1b}$ and —$V^1$-$T^1$-$R^{2b}$;
$T^1$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —$CO_2H$, —$CO_2(C_{1-4}$ alkyl), —$C(O)NH_2$, and —$C(O)NH$ ($C_{1-4}$ alkyl), wherein the alkylene chain optionally is interrupted with —$N(R^4)$—, —$C(=NR^4)$—N ($R^4$)—, —$C(NR^4)=N(R^4)$—, —$N(R^4)$—C (=$NR^4$)—, —$N(R^4)$—C(O)—, or —$C(O)N(R^4)$—;
$V^1$ is —$C(R^5)=C(R^5)$—, —C≡C—, —O—, —$N(R^4)$—, —$N(R^4)C(O)$—, —$C(O)N(R^4)$—, —$C(=NR^4)$—$N(R^4)$—, or —$C(NR^4)=N(R^4)$—;
each $R^{1b}$ independently is an optionally substituted aryl, heteroaryl, heterocyclyl, or cycloaliphatic ring;
each $R^{2b}$ independently is —$NO_2$, —CN, —$C(R^5)=C$ $(R^5)_2$, —C≡C—$R^5$, —$OR^5$, —$SO_2R^6$, —$SO_2N$ $(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N$ $(R^4)_2$, —O—$C(O)R^5$, —$OC(O)N(R^4)_2$, —C(O) $R^5$, —$CO_2R^5$, —$C(O)N(R^4)_2$, —$C(O)N(R^4)$—$OR^5$, —$C(O)N(R^4)C(=NR^4)$—$N(R^4)_2$, —$N(R^4)C$ (=$NR^4$)—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, or —$C(R^6)=N$—$OR^5$;
$R^{8b}$ is selected from the group consisting of $C_{1-4}$ aliphatic, $C_{1-4}$ fluoroaliphatic, halo, —OH, —O($C_{1-4}$ aliphatic), —$NH_2$, —NH($C_{1-4}$ aliphatic), and —N($C_{1-4}$ aliphatic)$_2$;
each $R^c$ independently is selected from the group consisting of $C_{1-6}$ aliphatic, $C_{1-6}$ fluoroaliphatic, halo, —$R^{1c}$, —$R^{2c}$, -$T^2$-$R^{2c}$, and -$T^2$-$R^{1c}$;
$T^2$ is a $C_{1-6}$ alkylene chain optionally substituted with $R^{3a}$ or $R^{3b}$, wherein the alkylene chain optionally is interrupted by —$C(R^5)=C(R^5)$—, —C≡C—, —O—, —S—, —S(O)—, —$S(O)_2$—, —$SO_2N$ $(R^4)$—, —$N(R^4)$—, —$N(R^4)C(O)$—, —$NR^4C(O)N$ $(R^4)$—, —$N(R^4)CO_2$—, —$N(R^4)SO_2$—, —$C(O)N$ $(R^4)$—, —C(O)—, —$CO_2$—, —OC(O)—, or —OC $(O)N(R^4)$—, and wherein $T^2$ or a portion thereof optionally forms part of a 3-7 membered ring;
each $R^{1c}$ independently is an optionally substituted aryl, heteroaryl, heterocyclyl, or cycloaliphatic ring;
each $R^{2c}$ independently is —$NO_2$, —CN, $(R^5)=C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)$ $SO_2R^6$, —$N(R^4)SO_2N(R^4)_2$, —O—$C(O)R^5$, —OC $(O)N(R^4)_2$, —$C(O)R^5$, —$CO_2R^5$, —$C(O)N(R^4)_2$, —$C(O)N(R^4)$—$OR^5$, —$C(O)N(R^4)C(=NR^4)$—N $(R^4)_2$, —$N(R^4)C(=NR^4)$—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, or —$C(R^6)=N$—$OR^5$;
each $R^{3a}$ independently is selected from the group consisting of —F, —OH, —O($C_{1-4}$ alkyl), —CN, —$N(R^4)_2$—$C(O)(C_{1-4}$ alkyl), —$CO_2H$, —$CO_2(C_{1-4}$ alkyl), —$C(O)NH_2$, and —$C(O)NH(C_{1-4}$ alkyl);
each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring;
each $R^{8c}$ independently is selected from the group consisting of $C_{1-4}$ aliphatic, $C_{1-4}$ fluoroaliphatic, —O($C_{1-4}$ alkyl), —O($C_{1-4}$ fluoroalkyl), and halo;
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic, aryl, or heteroaryl group;

each $R^7$ independently is an optionally substituted aryl or heteroaryl ring;

g is 0 or 1;

h is 0 or 1;

j is 0 or 1; and k is 0, 1, or 2.

36. The compound of claim 35, wherein:

$R^m$ is hydrogen, and $R^n$ is hydrogen, fluoro, —CH$_3$, or —CH$_2$OH;

$X^1$ and $X^2$ are each CH;

Ring A has no substituents $R^a$;

each $R^c$ independently is halo, —CN, —C($R^{5x}$)=C($R^{5x}$)($R^{5y}$), —C≡C—$R^{5y}$, —O$R^{5y}$, —S$R^{6x}$, —CO$_2R^{5x}$, —C(O)N($R^{4x}$)($R^{4y}$), or a $C_{1-4}$ aliphatic or $C_{1-4}$ fluoroaliphatic optionally substituted with one or two substituents independently selected from the group consisting of —O$R^{5x}$, —N($R^{4x}$)($R^{4y}$), —S$R^{6x}$, —CO$_2R^{5x}$, or —C(O)N($R^{4x}$)($R^{4y}$); or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted, or two $R^{4x}$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

$R^{4y}$ is hydrogen, $C_{6-10}$ ar($C_{1-4}$)alkyl, the aryl portion of which may be optionally substituted, an optionally substituted 5- or 6-membered aryl, heteroaryl, or heterocyclyl ring, or a $C_{1-4}$ alkyl or $C_{1-4}$ fluoroalkyl optionally substituted with one or two substituents independently selected from the group consisting of —O$R^{5x}$, —N($R^{4x}$)$_2$, —CO$_2R^{5x}$, or —C(O)N($R^{4x}$)$_2$; or $R^{4x}$ and $R^{4y}$, taken together with the nitrogen atom to which they are attached, form an optionally substituted 4 to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring;

each $R^{5y}$ independently is hydrogen, an optionally substituted $C_{6-10}$ aryl, a $C_{6-10}$ar($C_{1-4}$)alkyl, the aryl portion of which may be optionally substituted, or a $C_{1-4}$ alkyl or $C_{1-4}$ fluoroalkyl optionally substituted with one or two substituents independently selected from the group consisting of —O$R^{5x}$, —N($R^{4x}$)$_2$, —CO$_2R^{5x}$, or —C(O)N($R^{4x}$)$_2$; and each $R^{6x}$ independently is $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring.

37. A compound selected from the group consisting of 4-(4-{3-[(4-chlorophenyl)amino]-3-oxopropyl}phenoxy)pyridino-2-carboxamide;

4-[4-(3-oxo-3-{[3-(trifluoromethyl)phenyl]amino}propyl)phenoxy]pyridino-2-carboxamido:

4-[4-(3-{[4-chloro-3-(trifluoromethyl)phenyl]amino}-3-oxopropyl)phenoxy]pyridine-2-carboxamide:

N-methyl-4-[4-(3-oxo-3-{[3-(trifluoromethyl)phenyl]amino}propyl)phenoxy]pyridine-2-carboxamide:

N-methyl-4-[3-(3-oxo-3-{[3-trifluoromethyl)phenyl]amino}propyl)phenoxy]pyridine-2-carboxamide;

N-[4-chloro-3-(trifluoromethyl)phenyl]-3-[4-(pyridin-4-yloxy)phenyl]propanamide:

4-[3-(3-{[4-chloro-3-(trifluoromethyl)phenyl]amino}-3-oxopropyl)phenoxy]-N-methylpyridine-2-carboxamide:

4-[4-(4-{[4-chloro-3-(trifluoromethyl)phenyl]amino}-4-oxobutyl)phenoxy]-N-methylpyridine-2-carboxamide:

4-[4-(3-{[4-chloro-3-(trifluoromethyl)phenyl]amino}-3-oxopropyl)phenoxy]-N-methylpyridine-2-carboxamide:

4-[4-(3-{[2-fluoro-5-(trifluoromethyl)phenyl]amino}-3-oxopropyl)phenoxy]-N-methylpyridine-2-carboxamide:

4-(4-{3-[(4-chlorophenyl)amino]-3-oxopropyl}phenoxy)-N-methylpyridine-2-carboxamide;

4-[4-(3-anilino-3-oxopropyl)phenoxy]-N-methylpyridine-2-carboxamide:

4-(3-{3-[(4-chlorophenyl)amino]-3-oxopropyl}phenoxy)-N-methylpyridine-2-carboxamide:

4-[3-(3-anilino-3-oxopropyl)phenoxyl]-N-methylpyridine-2-carboxamide:

N-methyl-4-(3-{3-[(3-chlorophenyl)amino]-3-oxopropyl}phenoxy)pyridine-2-carboxamide:

4-(3-{3-[(3,4-dimethylphenyl)amino]-3-oxopropyl}phenoxy)-N-methylpyridine-2-carboxamide:

4-(3-{3-[(4-chloro-3-methoxyphenyl)amino]-3-oxopropyl}phenoxy)-N-methylpyridine-2-carboxamide:

4-{3-[3-(2,3-dihydro-1H-inden-5-ylamino)-3-oxopropyl]phenoxy}-N-methylpyridine-2-carboxamide:

4-{[3-(3-{[2-4,5-dihydro-1H-imidazol-2-yl)pyridin-4-yl]oxy}phenyl)propanoyl]amino}-2-(trifluoromethyl)benzoic acid;

N-[4-(3-{3-[(3-tert-butylphenyl)amino]-3-oxonpropyl}phenoxy)pyridin-2-yl]cyclopropanecarboxamide;

N-(4-chlorophenyl)-3-{4-[(2-cyanopyridin-4-yl)oxy]phenyl}propanamide;

3-{4-[(2-cyanopyridin-4-yl)oxy]phenyl}-N-[3-(trifluoromethyl)phenyl]propanamide;

N-[4-chloro-3-(trifluoromethyl)phenyl]-3-{4-[2-cyanopyridin-4-yl)oxy]-phenyl}propanamide;

4-[4-(3-{[4-chloro-3-(trifhxoromethyl)phenyl]amino}-3-oxopropyl)phenoxy]-N-[2-(dimethylamino)ethyl]pyridine-2-carboxamide;

4-[4-(3-{[4-chloro-3-(trifluoromethyl)phenyl]amino}-3-oxopropyl)phenoxy]-N-(2-morpholin-4-ylethyl)pyridine-2-carboxamide;

4-[4-(3-{[4-chloro-3-(trifluoromethyl)phenyl]amino}-3-oxopropyl)phenoxy]-N-(2-pyrrolidin-1-ylethyl)pyridine-2-carboxamide;

N-[4chloro-3-(trifluoromethyl)phenyl]-3-(4-{[2-(4,5-dihydro-1H-imidazol-2-yl)pyridin-4-yl]oxy}phenyl)propanamide;
N-[4-chloro-3-(trifluoromethyl)phenyl]-3-(4-{[2-(1H-imidazol-2-yl)pyridin-4-yl]oxy}phenyl)propanamide;
3-[4-({2-[(methylamino)methyl]pyridin-4-yl}oxy)phenyl]-N-[3-(trifluoromethyl)phenyl]propanamide;
3-[4-({2[(dimethylamino)methyl]pyridin-4-yl}oxy)phenyl]-N-[3-(trifluoromethyl)phenyl]propanamide;
3-[4-({2-[(dimethylamino)methyl]pyridin-4-yl}oxy)phenyl]-N-[3-(trifluoromethyl)phenyl]propanamide;
5-[4-(3-{[4-chloro-3-(trifluoromethyl)phenyl]amino}-3-oxopropyl)phenoxy]-N-methylnicotinamide;
4-[4-(3-{[4-chloro-3-(trifluoromethyl)phenyl]amino}-3-oxopropyl)-3-fluorophenoxy]-N-methylpyridine-2-carboxamide;
4-[2-chloro-4-(3-{[4-chloro-3-(trifluoromethyl)phenyl]amino}-3-oxopropyl)phenoxy]-N-methylpyridine-2-carboxamide;
N-[4-chloro-3-(trifluoromethyl)phenyl]-3-(4-{[2-(1,4,5,6-tetrahydropyrimidin-2-yl)pyridin-4-yl]oxy}phenyl)propanamide;
3-(4-{[2-(aminomethyl)pyridin-4-yl]oxy}phenyl)-N-[4-chloro-3-(trifluoromethyl)phenyl]propanamide;
4-[4-(3-{[4-chloro-3-(trifluoromethyl)phenyl]amino}-3-oxopropyl)phenoxy]pyridine-2-carboxylic acid;
3-{4-[(2-aminopyrimidin-4-yl)oxy]phenyl}-N-[4-chloro-3-(trifluoromethyl)phenyl]propanamide;
5-[4-(3-{[4-chloro-3-(trifluoromethyl)phenyl]amino}-3-oxopropyl)phenoxy]-N-methylpyridazine-3-carboxamide;
5-[4-(3-{[4-chloro-3-(trifluoromethyl)phenyl]amino}-3-oxopropyl)phenoxy]-N-methylpyridazine-3-carboxamide;
3-(4-{[5-(aminomethyl)-1H-pyrazol-4-yl]oxy}phenyl)-N-[4-chloro-3-(trifluoromethyl)phenyl]propanamide;
3-(4-{[5-(aminomethyl)isoxazol-4-yl]oxy}phenyl)-N-[4-chloro-3-(trifluoromethyl)phenyl]propanamide;
3-(4-{[2-(aminomethyl)-1,3-benzothiazol-5-yl]oxy}phenyl)-N-[4-chloro-3-(trifluoromethyl)phenyl]propanamide;
N-methyl-4-{4-[3-oxo-3-(quinoxalin-2-ylamino)propyl]phenoxy}pyridine-2-carboxamide;
N-methyl-4-[4-(3-oxo-3-{[4-(trifluoromethyl)pyridin-2-yl]amino}propyl)phenoxy]pyridine-2-carboxamide;
4-{4-[3-(isoquinolin-3-ylamino)-3-oxopropyl]phenoxyl}-N-methylpyridine-2-carboxamide;
N-methyl-4-[4-(3-oxo-3-{[2-(trifluoromethyl)pyridin-4-yl]amino}propyl)phenoxy]pyridine-2-carboxamide;
4-(4-{3-[(5-tert-butylisoxazol-3-yl)amino]-3-oxopropyl}phenoxy)-N-methylpyridine-2-carboxamide;
4-(4-{3-[3-tert-butylisoxazol-5-yl)amino]-3-oxopropyl}phenoxy)-N-methylpyridine-2-carboxamide;
4-[3-(3-{[4-(aminomethyl)-3-(trifluoromethyl)phenyl]amino}-3-oxopropyl)phenoxy]-N-methylpyridine-2-carboxamide;
3-(3-{[2-(4,5-dihydro-1H-imidazol-2-yl)pyridin-4-yl]oxy}phenyl)-N-[3-(4,5-dihydro-1H-imidazol-2-yl-5-(trifluoromethyl)phenyl]propanamide;
N-[4-chloro-3 4trifluoromethyl)phenyl]-3-[3-({2-[(ethanimidoylamino)methyl]pyridin-4-yl}oxy)phenyl]propanamide;
N-(3-tert-butylisoxazol-5-yl)-3-(3-{[2-(4,5-dihydro-1H-imidazol-2-yl)pyridin-4-yl]oxy}phenyl)propanamide;
N-[4-chloro-3-(trifluoromethyl)phenyl]-3-{4-[2-{5-[4-(diethylamino)phenyl]-1H-imidazol-2-yl}pyridin-4-yl)oxy]phenyl}propanamide;
N-[4chloro-3-(trifluoromethyl)phenyl]-3-(3-{[2-(4,5-dihydro-1H-imidazol-2-yl)pyridin-4-yl]oxy}phenyl)propanamide;
3-(4-{[2-(aminomethyl)pyridin-4-yl]oxy}phenyl)-N-[3-(trifluoromethyl)phenyl]propanamide;
N-[4-chloro-3-(trifluoromethyl)phenyl]-3-(4-{[2-(2H-tetrazol-5-yl)pyridin-4-yl]oxy}phenyl)propanamide;
N-[4-chloro-3-(trifluoromethyl)phenyl]-3-[3-({2-[5-({[2-(dimethylamino)ethyl]amino}methyl)-1H-imidazol-2-yl]pyridin-4-yl}oxy)phenyl]propanamide;
N-(3-tert-butylphenyl)-3-(3-{[2-(4,5-dihydro-1H-imidazol-2-yl)pyridin-4-yl]oxy}phenyl)propanamide;
2-{4-[4-(3-{[4-chloro-3-(trifluoromethyl)phenyl]amino}-3-oxopropyl)phenoxy]pyridin-2-yl}-N-methyl-4,5-dihydro-1H-imidazol-4-carboxamide;
N-(3-tert-butyl-4-chlorophenyl)-3-(3-{[2-(4,5-dihydro-1H-imidazol-2-yl)pyridin-4-yl]oxy}phenyl)propanamide;
N-[4-chloro-3-(trifluoromethyl)phenyl]-3-(4-{[2-(4,5-dihydro-1H-imidazol-2-yl)pyridin-4-yl]oxy}-3-methylphenyl)propanamide;
3-(3-{[2-(4,5-dihydro-1H-imidazol-2-yl)pyridin-4-yl]oxy}phenyl)-N-[4-(3-hydroxyprop-1-yn-1-yl-3-(trifluoromethyl)phenyl]propanamide;
4-(4-{3-[2-fluoro-5-methylphenyl)amino]-3-oxopropyl}phenoxy)-N-methylpyridine-2-carboxamide;
4-{([3-(3-{[2-(4,5-dihydro-1H-imidazol-2-yl)pyridin-4-yl]oxy}phenyl)propanoyl]amino}-N,N-dimethyl-2-(trifluoromethyl)benzamide;
3-(3-{[2-(4,5-dihydro-1H-imidazol-2-yl)pyridin-4-yl]oxy}phenyl-N-[4-[3-(dimethylamino)prop-1-yn-1-yl]-3-(trifluoromethyl)phenyl]propanamide;
3-(3-{[2-(4,5-dihydro-1H-imidazol-2-yl)pyridin-4-yl]oxy}phenyl)-N-[4-(hydroxymethyl)-3-(trifluoromethyl)phenyl]propanamide;
tert-butyl(1-{4-[3-(3-{[4-chloro-3-(trifluoromethyl)phenyl]amino}-3-oxopropyl)phenoxy]pyrimidin-2-yl}piperidin-3-yl)carbamate;
3-(3-{[2-(4,5-dihydro-1H-imidazol-2-yl)pyridin-4-yl]oxy}phenyl)-N-[4-(piperazin-1-ylcarbonyl)-3-(trifluoromethyl)phenyl]propanamide;
N-[4-chloro-3-(trifluoromethyl)phenyl]-3-{3-[(2-pyrrolidin-1-ylpyrimidin-4-yl)oxy]phenyl}propanamide;
N-methyl-4-(4-{3-[(3-methylphenyl)amino]-3-oxopropyl}phenoxy)pyridine-2-carboxamide;
N-(4-chloro-3-methylphenyl)-3-(3-{([2-(4,5-dihydro-1H-imidazol-2-yl)pyridin-4-yl]oxy}phenyl)propanamide;
N-[4-chloro-3-(trifluoromethyl)phenyl]-3-{(3-[(2-{(5-[(dimethylamino)methyl]-1H-imidazol-2-yl}pyridin-4-yl)oxy]phenyl}propanamide;
N-[4-chloro-3-(trifluoromethyl)phenyl]-3-(3-{[2-(1,4,5,6-tetrahydropyrinddin-2-yl)pyridin-4-yl]oxy}phenyl)propanamide;
3-[({4-[3-(3-{[4-chloro-3-(trifluoromethyl)phenyl]amino}-3-oxopropyl)phenoxy]pyridin-2-yl}carbonyl)amino]propanoic acid;
N-(3-cvclopropylphenyl)-3-(3-{[2-(4,5-dihydro-1H-imidazol-2-yl)pyridin-4-yl]oxy}phenyl)propanamide;
tert-butyl{4-[3-(3-{[4-chloro-3-(trifluoromethyl)phenyl]amino}-3-oxopropyl)phenoxy]pyridin-2-yl}carbamate;

4-[3-(3-{[4-chloro-3-(trifluoromethyl)phenyl]amino}-3-oxopropyl)phenoxy]-N-[2-(dimethylamino)ethyl]pyridine-2-carboxamide;

4-[3-(3-{[4-chloro-3-(trifluoromethyl)phenyl]amino}-3-oxopropyl)phenoxy]-N-2-morpholin-4-ylethyl)pyridine-2-carboxamide;

3-(4-{[2-(4,5-dihydro-1H-imidazol-2-yl)pyridin-4-yl]oxy}phenyl)-N-[3-(trifluoromethyl)phenyl]propanamide;

4-3-{3-[(4-chloro-3-methylphenyl)amino]-3-oxopropyl}phenoxy)-N-methylpyridine-2-carboxamide;

3-{(3-[(2-aminopyrimidin-4-yl)oxy]phenyl}-N-[4-chloro-3-(trifluoromethyl)phenyl]propanamide;

4-(3-{3[(3-methoxyphenyl)amino]-3-oxopropyl}phenoxy)-N-methylpyridine-2-carboxamide;

N-[4-chloro-3-(trifluoromethyl)phenyl]-3-[4-(pyridin-4-ylmethyl)phenyl]propanamide;

N-[4-chloro-3-(trifluoromethyl)phenyl]-3-[4-({2-[(hydroxyamino)(imino)methyl]pyridin-4-yl}oxy)phenyl]propanamide;

3-(4-{[2-(1,4,5,6-tetrahydropyrimidin-2-yl)pyridin-4-yl]oxy}phenyl)-N-[3-(trifluoromethyl)phenyl]propanamide;

N-[4-chloro-3-(trifluoromethyl)phenyl]3-{3[(2-piperidin-ylpyrimidin-4-yl)oxy]phenyl}propanamide;

4-{4-[3-(1,3-dihydro-2-benzofuran-5-ylamino)-3-oxopropyl]phenoxy}-N-methylpyridine-2-carboxamide;

N-[2-chloro-5 4(trifluoromethyl)phenyl]-3-(3-{[2-(4,5-dihydro-1H-imidazol-2-yl)pyridin-4-yl]oxy}phenyl)propanamide;

4-(3-{3-[(5-tert-butyl-2-hydroxyphenyl)amino]-3-oxopropyl}phenoxy)pyridine-2-carboxamide;

N-[4-cyano-3-(trifluoromethyl)phenyl]-3-(3-{[2-(4,5-dihydro-1H-imidazol-2-yl)pyridin-4-yl]oxy}phenyl)propanamide;

3-{3-[(2-aminopyridin-4-yl)oxy]phenyl}-N-[4-chloro-3-(trifluoromethyl)phenyl]propanamide;

3-(3-{[2-(4,5-dihydro-1H-imidazol-2-yl)pyridin-4-yl]oxy}phenyl)-N-(3-ethyphenyl)propanamide;

3-(3-{[2-(4,5-dihydro-1H-imidazol-2-yl)pyridin-4-yl]oxy}phenyl)-N-(3-isopropylphenyl)propanamide;

3-(4-{[2-(4,5-dihydro-1H-imidazol-2-yl)pyridin-4-yl]oxy}phenyl)-N-(3-ethyphenyl)propanamide;

3-(3-{[2-(acetylamino)pyridin-4-yl]oxy}phenyl)-N-(3-tert-butylphenyl)propanamide;

3-(3-{[2-(aminomethyl)pyridin-4-yl]oxy}phenyl)-N-[4-chloro-3-(trifluoromethyl)phenyl]propanamide;

N-{4-[3-(3-{[4-chloro-3-(trifluoromethyl)phenyl]amino}-3-oxopropyl)phenoxy]pyridin-2-yl}cyclopropanecarboxamide;

N-[4-chloro-3-(trifluoromethyl)phenyl]-3-(4-{[2-(4-methyl-4,5-dihydro-1H-imidazol-2-yl)pyridin-4-yl]oxy}phenyl)propanamide;

3-(3-{[2-(1,4,5,6-tetrahydropyrimidin-2-yl)pyridin-4-yl]oxy}phenyl)-N-[3-(trifluoromethyl)phenyl]propanamide;

N-[4-(aminomethyl)-3-(trifluoromethyl)phenyl]-3-(3-{[2-(4,5-dihydro-1H-imidazol-2-yl)pyridin-4-yl]oxy}phenyl)propanamide;

5-{(4-[3-(3-{[4-chloro-3-(trifluoromethyl)phenyl]amino}-3-oxopropyl)phenoxy]pyridin -2-yl}-1,3,4-oxadiazole-2-carboxamide;

3-(3-{[2-(4,5-dihydro-1H-imidazol-2-yl)pyridin-4-yl]oxy}phenyl)-N-[2-fluoro-5-(trifluoromethyl)phenyl]propanamide;

3-(3-{[2-4,5-dihydro-1H-imidazol-2-yl)pyridin-4-yl]oxy}phenyl)-N-[3-(1-hydroxy-1-methylethyl)phenyl]propanamide;

N-[4-chloro-3-(trifluoromethyl)phenyl]-3-(3-{[2-(1H-imidazol-2-yl)pyridin-4-yl]oxy}phenyl)propanamide;

N-(4chlorophenyl)-3-(4-{[2-(4,5-dihydro-1H-imidazol-2-yl)pyridin-4-yl]oxy}phenyl)propanamide;

N-[4-chloro-3-(trifluoromethyl)phenyl]-2-(3-{[2-(4,5-dihydro-1H-imidazol-2-yl)pyridin-4-yl]oxy}phenyl)cyclopropanecarboxamide;

3-(3-{[2-(4,5-dihydro-1H-imidazol-2-yl)pyridin-4-yl]oxy}phenyl)-N-[3-fluoro-5-(trifluoromethyl)phenyl]propanamide;

N-[4-chloro-3-(trifluoromethyl)phenyl]-3-{3-[(2-{5-[(methylamino)methyl]-1H-imidazol-2-yl}pyridin-4-yl)oxy]phenyl}propanamide;

ethyl 2-{4-[3-(3-{[4-chloro-3-(trifluoromethyl)phenyl]amino}-3-oxopropyl)phenoxy]pyridin-2-yl}-1H-imidazole-5-carboxylate;

N-(4-bromo-3-ten-butylphenyl)-3-(3-{[2-(4,5-dihydro-1H-imidazol-2-yl)pyridin-4-yl]oxy}phenyl)propanamide;

N-[4-chloro-3-(trifluoromethyl)phenyl]-3-[4-({2-[(ethylamino)(imino)methyl]pyridin-4-yl}oxy)phenyl]propanamide;

2-{4-[3-(3-{[4-chloro-3-(trifluoromethyl)phenyl]amino}-3-oxopropyl)phenoxy]pyridin-2-yl}-1H-imidazole-5-carboxylic acid;

N-[4-chloro-3-(trifluoromethyl)phenyl]-2-(3-{[2-(4,5-dihydro-1H-imidazol-2-yl)pyridin-4-yl]oxy}phenyl)cyclopropanecarboxamide;

N-(3-tert-butylphenyl)-3-(4-{[2-(4,5-dihydro-1H-imidazol-2-yl)pyridin-4-yl]oxy}phenyl)propanamide;

N-[4-chloro-3-(trifluoromethyl)phenyl]-3-[3-({2-[(2-pyrrolidin-1-ylethyl)amino]pyrimidin-4-yl}oxy)phenyl]propanamide;

N-[3-cyano-5-(trifluoromethyl)phenyl]-3-(3-{[2-(4,5-dihydro-1H-imidazol-2-yl)pyridin-4-yl]oxy}phenyl)propanamide;

3-(3-{[2-(4-tert-butyl-1H-imidazol-2-yl)pyridin-4-yl]oxy}phenyl)-N-[4-chloro-3-(trifluoromethyl)phenyl]propanamide;

N-(2,3-dihydro-1H-inden-5-yl)-3-(4-{[2-(1 ,4,5,6-tetrahydropyrimidin-2-yl)pyridin-4-yl]oxy}phenyl)propanamide;

N-[4-chloro-2-hydroxy-3-(trifluoromethyl)phenyl]-3-(4-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl-N-(4-methylphenyl)propanamide;

N-[4-chloro-3-(trifluoromethyl)phenyl]-3-[3-({2-[(4S)-4-methyl-4,5-dihydro-1H-imidazol-2-yl]pyridin-4-yl}oxy)phenyl]propanamide;

methyl[({4-[3-(3-{[4-chloro-3-(trifluoromethyl)phenyl]amino}-3-oxopropyl)phenoxy]pyridin-2-yl}carbonyl)amino]acetate;

3-(3-{[2-(3-aminopiperidin-1-yl)pyrimidin-4-yl]oxy}phenyl)-N-[4-chloro-3-(trifluoromethyl)phenyl]propanamide;

tert-butyl({4-[3-(3-{[4-chloro-3-(trifluoromethyl)phenyl]amino}-3-oxopropyl)phenoxy]pyridin-2-yl}methyl)carbamate;

3-(4-{[2-(4,5-dihydro-1H-imidazol-2-yl)pyridin-4-yl]oxy}phenyl)-N-(3-methylphenyl)propanamide;

3-(3-chloro-4-{[2-(4,5-dihydro-1H-imidazol-2-yl)pyridin-4-yl]oxy}phenyl)-N-[4-chloro-3-(trifluoromethyl)phenyl]propanamide;

3-(3-{[2-(4,5-dihydro-1H-imidazol-2-yl)pyridin-4-yl]oxy}phenyl)-N-[4-methoxy-3-(trifluoromethyl)phenyl]propanamide;

3-(3-{[2-(4,5-dihydro-1H-imidazol-2-yl)pyridin-4-yl]oxy}phenyl)-N-[3-[2-(dimethylamino)ethoxy]-5-(trifluoromethyl)phenyl]propanamide;

3-(3-{[2-(4,5-dihydro-1H-imidazol-2-yl)pyridin-4-yl]oxy}phenyl)-N-[3-(trifluoromethoxy)phenyl]propanamide;

3-(3-{[2-(4,5-dihydro-1H-imidazol-2-yl)pyridin-4-yl]oxy}phenyl)-N-[4-(trifluoromethyl)phenyl]propanamide;

N-[4-chloro-3-(trifluoromethyl)phenyl]-3-(3-{[2-(4,5-dihydro-1H-imidazol-2-yl)pyridin-4-yl]oxy}phenyl)butanamide;

4-[4-(3-{[3-methoxy-5-(trifluoromethyl)phenyl]amino}-3-oxopropyl)phenoxy]-N-methylpyridine-2-carboxamide;

4-(3-{3-[(4-methoxyphenyl)amino]-3-oxopropyl}phenoxy)-N-methylpyridine-2-carboxamide;

3-(4-chloro-3-{[2-(4,5-dihydro-1H-imidazol-2-yl)pyridin-4-yl]oxy}phenyl)-N-[4-chloro-3-(trifluoromethyl)phenyl]propanamide;

[({4-[3-(3-{[4-chloro-3-(trifluoromethyl)phenyl]amino}-3-oxopropyl)phenoxy]pyridin-2-yl}carbonyl)amino]acetic acid;

N-[4-chloro-3-(trifluoromethyl)phenyl]-3-(3-{[2-(5-hydroxy-1,4,5,6-tetrahydropyrimidin-2-yl)pyridin-4-yl]oxy}phenyl)propanamide;

3-(4-{[2-(4,5-dihydro-1H-imidazol-2-yl)pyridin-4-yl]oxy}phenyl)-N-(2,3-dihydro-1H-inden-5-yl)propanamide;

N-[4-chloro-3-(trifluoromethyl)phenyl]-3-(3-{[2-(1-methyl-4,5-dihydro-1H-imidazol-2-yl)pyridin-4-yl]oxy}phenyl)propanamide;

N-[4-chloro-2-hydroxy-3-(trifluoromethyl)phenyl]-3-(3-{[2-(4,5-dihydro-1H-imidazol-2-yl)pyridin-4-yl]oxy}phenyl)propanamide;

N-methyl-4-[3-(3-{[3-nitro-5-(trifluoromethyl)phenyl]amino}-3-oxopropyl)phenoxy]pyridine-2-carboxamide;

2-{4-[4-(3-{[4-chloro-3-(trifluoromethyl)phenyl]amino}-3-oxopropyl)phenoxy]pyridin-2-yl}-4,5-dihydro-1H-imidazole-4-carboxylic acid;

2-{4-[3-(3-{[4-chloro-3-(trifluoromethyl)phenyl]amino}-3-oxopropyl)phenoxy]pyridin-2-yl}-1,4,5,6-tetrahydropyrimidine-4-carboxylic acid;

3-(3-{[2-(4,5-dihydro-1H-imidazol-2-yl)pyridin-4-yl]oxy}phenyl)-N-[4-ethynyl-3-(trifluoromethyl)phenyl]propanamide;

3-(3-{[2-(4,5-dihydro-1H-imidazol-2-yl)pyridin-4-yl]oxy}phenyl)-N-[4-(3-hydroxypropyl)-3-(trifluoromethyl)phenyl]propanamide;

3-(3-{[2-(4,5-dihydro-1H-imidazol-2-yl)pyridin-4-yl]oxy}phenyl)-N-(3-methylphenyl)propanamide;

N-[4-chloro-3-(trifluoromethyl)phenyl]-3-[3-({2-[(5-(hydroxymethyl)-1H-imidazol-2-yl]pyridin-4-yl}oxy)phenyl]propanamide;

N-[3-(2-aminoethyl)-5-(trifluoromethyl)phenyl]-3-(3-{[2-(4,5-dihydro-1H-imidazol-2-yl)pyridin-4-yl]oxy}phenyl)propanamide;

4-(3-{3-[(5-tert-butylisoxazol-3-yl)amino]-3-oxopropyl}phenoxy)-N-methylpyridine-2-carboxamide;

N-[4-chloro-3-(trifluoromethyl)phenyl]-3-[3-({2-[imino(morpholin-4-yl)methyl]pyridin-4-yl}oxy)phenyl]propanamide;

3-(3-{[2-(4,5-dihydro-1H-imidazol-2-yl)pyridin-4-yl]oxy}phenyl)-N-[3-(trifluoromethyl)phenyl]propanamide;

tert-butyl({4-[3-(3-oxo-3-{[3-(trifluoromethyl)phenyl]amino}propyl)phenoxy]pyridin-2-yl}methyl)carbamate;

N-[4-chloro-3-(trifluoromethyl)phenyl]-3-(3-{[2-({[imino(phenyl)methyl]amino}methyl)pyridin-4-yl]oxy}phenyl)propanamide;

N-(3-tert-butylphenyl)-3-(3-{[2-(1-methyl-4,5-dihydro-1H-imidazol-2-yl)pyridin-4-yl]oxy}phenyl)propanamide;

ethyl 4-[({4-[3-(3-{[4-chloro-3-(trifluoromethyl)phenyl]amino}-3-oxopropyl)phenoxy]pyridin-2-yl}carbonyl)amino]butanoate;

N-[4chloro-3-(trifluoromethyl)phenyl]-3-(3-{[2-(4,5-dihydro-1H-imidazol-2-yl)pyridin-4-yl]amino}phenyl)propanamide;

N-[3,5-bis(trifluoromethyl)phenyl]-3-(3-{[2-(4,5-dihydro-1H-imidazol-2-yl)pyridin-4-yl]oxy}phenyl)propanamide;

N-[4-chloro-3-(trifluoromethyl)phenyl]-3-(3-{[2-(5-methyl-1H-imidazol-2-yl)pyridin-4-yl]oxy}phenyl)propanamide;

3-[4-{[3-(3-{[2-(4,5-dihydro-1H-imidazol-2-yl)pyridin-4-yl]oxy}phenyl)propanoyl]amino}-2-(trifluoromethyl)phenyl]propanoic acid;

4-[3-(3-{[4-chloro-3-(trifluoromethyl)phenyl]amino}-3-oxopropyl)phenoxyl]-N-3-dimethylpyridine-2-carboxamide;

N-(4-tert-butylphenyl)-3-(3-{[2-(4,5-dihydro-1H-imidazol-2-yl)pyridin-4-yl]oxy}phenyl)propanamide;

N-(4-tert-butylphenyl)-3-(4-{[2-(4,5-dihydro-1H-imidazol-2-yl)pyridin-4-yl]oxy}phenyl)propanamide;

4-(4-{3-[(4,6-dimethylpyridin-2-yl)amino]-3-oxopropyl}phenoxy)-N-methylpyridine-2-carboxamide;

N-[4-chloro-3-(trifluoromethyl)phenyl]-3-{3-[(2-{[3-(2-oxopyrrolidin-1-yl)propyl]amino}pyrimidin-4-yl)oxy]phenyl}propanamide;

3-(3-{[2-(4,5-dihydro-1H-imidazol-2-yl)pyridin-4-yl]oxy}phenyl)-N-[3-[3-(dimethylamino)propyl]-5-(trifluoromethyl)phenyl]propanamide;

N-(3-tert-butylphenyl)-3-(3-{[2-(4,5-dihydro-1H-imidazol-2-yl)pyridin-4-yl]oxy}phenyl)-2-hydroxypropanamide;

N-[4-chloro-3-(trifluoromethyl)phenyl]-3-(3-{[2-(diethylamino)pyrimidin-4-yl]oxy}phenyl)propanamide;

N-(2,3-dihydro-1,4-benzodioxin-6-yl)-3-(3-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl)-N-(3,3-dimethyl-1-oxo-1,3-dihydro-2-benzofuran-5-yl)propanamide;

methyl 2-{4-[3-(3-{[4-chloro-3-(trifluoromethyl)phenyl]amino}-3-oxopropyl)phenoxy]pyridin-2-yl}-1H-imidazole-5-carboxylate;

2-{4-[3-(3-{[4-chloro-3-(trifluoromethyl)phenyl]amino}-3-oxopropyl)phenoxy]pyridin-2-yl}-N,N-dimethyl-1H-imidazole-5-carboxamide;

3-[3-({2-[(benzylamino)(imino)methyl]pyridin-4-yl}oxy)phenyl]-N-[4-chloro-3-(trifluoromethyl)phenyl]propanamide;

tert-butyl({4-[4-(3-{[4-chloro-3-(trifluoromethyl)phenyl]amino}-3-oxopropyl)phenoxy]pyridin-2-yl}methyl)carbamate;

4-[({4-[3-(3-{[4-chloro-3-(trifluoromethyl)phenyl]amino}-3-oxopropyl)phenoxy]pyridin-2-yl}carbonyl)amino]butanoic acid;

3-(3-{[2-(4,5-dihydro-1H-imidazol-2-yl)pyridin-4-yl]oxy}phenyl)-N-(3,5-dimethoxyphenyl)propanamide;

N-[2-bromo-5-(trifluoromethyl)phenyl]-3-(3-{[2-(4,5-dihydro-1H-imidazol-2-yl)pyridin-4-yl]oxy}phenyl)propanamide;

3-(4-{[2-(4,5-dihydro-1H-imidazol-2-yl)pyridin-4-yl]oxy}phenyl)-N-(3-isopropylphenyl)propanamide;

N-[4-chloro-3-(trifluoromethyl)phenyl]-3-[3-({2-[4hydroxymethyl)-4,5-dihydro-1H-imidazol-2-yl]pyridin-4-yl}oxy)phenyl]propanamide;

N-[4-chloro-3-(trifluoromethyl)phenyl]-3-[3-(7H-pyrrolo[2,3-d]pyrimidin-4-yloxy)phenyl]propanamide;

methyl 2-{4-[3-(3-{[4-chloro-3-(trifluoromethyl)phenyl]amino}-3-oxopropyl)phenoxy]pyridin-2-yl}-4,5-dihydro-1H-imidazole-4-carboxylate;

tert-butyl({4-[4-(3-oxo-3-{[-(trifluoromethyl)phenyl]amino}propyl)phenoxy]pyridin-2-yl}methyl)carbamate;

3-(3-{[2-(4,5-dihydro-1H-imidazol-2-yl)pyridin-4-yl]oxy}phenyl)-N-(3-fluoro-5-morpholin-4-ylphenyl)propanamide;

3-(3-{[2-(acetylamino)pyridin-4-yl]oxy}phenyl)-N-[4-chloro-3-(trifluoromethyl)phenyl]propanamide;

N-[4-chloro-3-(trifluoromethyl)phenyl]-3-{3-[(2-{4-[(4-methylpiperazin-1-yl)carbonyl]-1H-imidazol-2-yl}pyridin-4-yl)oxy]phenyl}propanamide;

N-[4-chloro-2-methoxy-3-(trifluoromethyl)phenyl]-3-(3-{[2-(4,5-dihydro-1H-imidazol-2-yl)pyridin-4-yl]oxy}phenyl)propanamide;

N-[3-(aminomethyl)-5-(trifluoromethyl)phenyl]-3-(3-{[2-(4,5-dihydro-1H-imidazol-2-yl)pyridin-4-yl]oxy}phenyl)propanamide;

2-{4-[3-(3-{[4-chloro-3-(trifluoromethyl)phenyl]amino}-3-oxopropyl)phenoxy]pyridin-2-yl}-N,N-dimethyl-4,5dihydro-1H-imidazole-4-carboxamide;

tert-butyl4-{[({4-[4-(3-oxo-3-{[3-(trifluoromethyl)phenyl]amino}propyl)phenoxy]pyridin-2-yl}methyl)amino]methyl}piperidine-1-carboxylate;

3-(3-{[2-(4,5-dihydro-1H-imidazol-2-yl)pyridin-4-yl]oxy}phenyl)-N-[2-methyl-5-(trifluoromethyl)phenyl]propanamide;

3-{[3-(3-{[2-(4,5-dihydro-1H-imidazol-2-yl)pyridin-4-yl]oxy}phenyl)propanoyl]amino}-N-[2-(dimethylamino)ethyl]-5-(trifluoromethyl)benzamide;

3-{[3-(3-{[2-(4,5-dihydro-1H-imidazol-2-yl)pyridin-4-yl]oxy}phenyl)propanoyl]amino}-N-(2-methoxyethyl)-5-(trifluoromethyl)benzamide;

N-[4-chloro-3(trifluoromethyl)phenyl]-3-{3-[(2-{[(4-ethylpiperazin-1-yl)acetyl]amino}pyridin-4-yl)oxy]phenyl}propanamide;

3-(3-{[2-(4,5-dihydro-1H-imidazol-2-yl)pyridin-4-yl]oxy}phenyl)-N-[3-[3-(dimethylamino)prop-1-yn-1-yl]-5-(trifluoromethyl)phenyl]propanamide;

3-(3-{[2-(4,5-dihydro-1H-imidazol-2-yl)pyridin-4-yl]oxy}phenyl)-N-(3-iodophenyl)propanamide;

3-(3-{[2-(4,5-dihydro-1H-imidazol-2-yl)pyridin-4-yl]oxy}phenyl)-N-[4-methyl-3-(trifluoromethyl)phenyl]propanamide;

N-[4-chloro-3-(trifluoromethyl)phenyl]-2-(4-{[2-(4,5-dihydro-1H-imidazol-2-yl)pyridin-4-yl]oxy}phenyl)cyclopropanecarboxamide;

4-(4-{3-[(3-chloro-4-fluorophenyl)amino]-3-oxopropyl}phenoxy)-N-methylpyridine-2-carboxamide;

3-(3-{[2-(4,5-dihydro-1H-imidazol-2-yl)pyridin-4-yl]oxy}phenyl)-N-[6-(trifluoromethyl)pyridin-2-yl]propanamide;

3-(3-{[2-(aminomethyl)pyridin-4-yl]oxy}phenyl)-N-[3-(trifluoromethyl)phenyl]propanamide;

N-[4-chloro-3-(trifluoromethyl)phenyl]-3-(3-{[2-(4-methyl-4,5-dihydro-1H-imidazol-2-yl)pyridin-4-yl]oxy}phenyl)propanamide;

4-[3-(3-{[3-(2-aminoethyl)-5-(trifluoromethyl)phenyl]amino}-3-oxopropyl)phenoxy]-N-methylpyridine-2-carboxamide;

N-[4-chloro-3-(trifluoromethyl)phenyl]-3-[3-(9H-purin-6-yloxy)phenyl]propanamide;

3-(3-{[2-(4,5-dihydro-1H-imidazol-2-yl)pyridin-4-yl]oxy}phenyl)-N-[2-fluoro-3-(trifluoromethyl)phenyl]propanamide;

N-[4-chloro-3-(trifluoromethyl)phenyl]-3-[3-({2-[4-(morpholin-4-ylcarbonyl)-1H-imidazol-2-yl]pyridin-4-yl}oxy)phenyl]propanamide;

N-[4-chloro-3-(trifluoromethyl)phenyl]-3-(4-{[2-(4,4-dimethyl-4,5-dihydro-1H-imidazol-2-yl)pyridin-4-yl]oxy}phenyl)propanamide;

3-{4[(2-{[(piperidin-4-ylmethyl)amino]methyl}pyridin-4-yl)oxy]phenyl}-N-[3-(trifluoromethyl)phenyl]propanamide;

N-[4-chloro-3-(trifluoromethyl)phenyl]-3-{3-[(2-morpholin-4-ylpyrimidin-4-yl)oxy]phenyl}propanamide;

2-{4-[3-(3-{[4-chloro-3-(trifluoromethyl)phenyl]amino}-3-oxopropyl)phenoxy]pyridin -2-yl}-4,5-dihydro-1H-imidazole-4-carboxylic acid;

3-(3-{[2-(4,5-dihydro-1H-imidazol-2-yl)pyridin-4-yl]oxy}phenyl)-N-[3-methoxy-5-(trifluoromethyl)phenyl]propanamide;

3-(3-{[2-(4,5-dihydro-1H-imidazol-2-yl)pyridin-4-yl]oxy}phenyl)-N-(2,3-dihydro-1H-inden-5-yl)propanamide;

3-(3-{[2-(acetylamino)pyridin-4-yl]oxy}phenyl)-N-[3-[2-(dimethylamino)ethoxy]-5-(trifluoromethyl)phenyl]propanamide;

N-(6-chloro-5-methylpyridin-3-yl)-3-(3-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl)-N-[4-fluoro-3-(trifluoromethyl)phenyl]propanamide;

N-[4-chloro-3-(trifluoromethyl)phenyl]-3-[3-(pyrimidin-5-yloxy)phenyl]propanamide;

N-[4-chloro-3-(trifluoromethyl)phenyl]-3-(3-{[2-(4,5-dihydro-1H-imidazol-2-yl)pyridin-4-yl]oxy}phenyl)-2-methylpropanamide;

methyl 4-{[3-(3-{[2-(4,5-dihydro-1H-imidazol-2-yl)pyridin-4-yl]oxy}phenyl)propanoyl]amino}-2-(trifluoromethyl)benzoate;

N-[4-chloro-3-(trifluoromethyl)phenyl]-3-{3-[(2-{[2-(dimethylamino)ethyl]amino}pyrimidin-4-yl)oxy]phenyl}propanamide;

N-[4-chloro-2-hydroxy-5-(trifluoromethyl)phenyl]-3-(3-{[2-(4,5-dihydro-1H-imidazol-2-yl)pyridin-4-yl]oxy}phenyl)propanamide;

N-(5-tert-butyl-2-methoxyphenyl)-3-(3-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl)-N-[3-(2-pyrrolidin 1-ylethoxy)-5-(trifluoromethyl)phenyl]propanamide;

isobutyl{4-[3-(3-{[4-chloro-3-(trifluoromethyl)phenyl]amino}-3-oxopropyl)phenoxy]pyridin-2-yl}carbamate;

3-(3-{[2-(4,5-dihydro-1H-imidazol-2-yl)pyridin-4-yl]oxy}phenyl)-N-(4-methylpyridin-2-yl)propanamide;

N-(4-chloro-3-methylphenyl)3-(4-{[2-(4,5-dihydro-1H-imidazol-2-yl)pyridin-4-yl]oxy}phenyl)propanamide;

N-[4-chloro-3-(trifluoromethyl)phenyl]-3-[3-({2-[(4-methoxybenzyl)amino]pyrimidin-4-yl}oxy)phenyl]propanamide;

4-[3-(3-{[3-amino-5(trifluoromethyl)phenyl]amino}-3-oxopropyl)phenoxy]-N-methylpyridine-2-carboxamide;

N-[4-chloro-3-(trifluoromethyl)phenyl]-3-[3-({2-[5-(pyrrolidin-1-ylmethyl)-1H-imidazol-2-yl]pyridin-4-yl}oxy)phenyl]propanamide;

N-[4-chloro-3-(trifluoromethyl)phenyl]-3-{4-[(2-{imino[(2-morpholin-4-ylethyl)amino]methyl}pyridin-4-yl)oxy]phenyl}propanamide;

3-[3-({2-[amino(imino)methyl]pyridin-4-yl}oxy)phenyl]-N-[4-chloro-3-(trifluoromethyl)phenyl]propanamide;

N-(3-chloro-4-fluorophenyl)-3-(3-{[2-(4,5-dihydro-1H-imidazol-2-yl)pyridin-4-yl]oxy}phenyl)propanamide;

N-(3,5-di-tert-butylphenyl)-3-(3-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl)-N-[3-(2-morpholin-4-ylethoxy)-5-(trifluoromethyl)phenyl]propanamide;

N-[4-chloro-3-(trifluoromethyl)phenyl]-3-(4-{[2-(5-methyl-1H-imidazol-2-yl)pyridin-4-yl]oxy}phenyl)propanamide;

N-[3-amino-5(trifluoromethyl)phenyl]-3-(3-{[2-(4,5-dihydro-1H-imidazol-2-yl)pyridin-4-yl]oxy}phenyl)propanamide;

methyl 3-[4-{[3-(3-{[2-(4,5-dihydro-1H-imidazol-2-yl)pyridin-4-yl]oxy}phenyl)propanoyl]amino}-2-(trifluoromethyl)phenyl]propanoate;

methyl 3-[({4-[3-(3-{[4-chloro-3-(trifluoromethyl)phenyl]amino}-3-oxopropyl)phenoxy]pyridin-2-yl}carbonyl)amino]propanoate;

N-[4-chloro-3-(trifluoromethyl)phenyl]-3-(3-{[2-(2H-tetrazol-5-yl)pyridin-4-yl]oxy}phenyl)propanamide;

2-{4-[3-(3-{[4-chloro-3-(trifluoromethyl)phenyl]amino}-3-oxopropyl)phenoxy]pyridin -2yl}-N-[2-(dimethylamino)ethyl]-4,5-dihydro-1H-imidazole4carboxamide;

N-methyl-4-[4-(3-oxo-3-{[4-(trifluoromethyl)phenyl]amino}propyl)phenoxy]pyridine-2-carboxamide;

3-(3-{[2-(4,5-dihydro-1H-imidazol-2-yl)pyridin-4-yl]oxy}phenyl)-N-[4-iodo-3-(trifluoromethyl)phenyl]propanamide;

3-amino-N-[4-chloro-3-(trifluoromethyl)phenyl]-3-(3-{[2-(4,5-dihydro-1H-imidazol-2-yl)pyridin-4-yl]oxy}phenyl)propanamide;

3-(3-{[2-(4,5-dihydro-1H-imidazol-2-yl)pyridin-4-yl]oxy}phenyl)-N-[3-(methylsulfanyl)phenyl]propanamide;

N-(4-chlorophenyl)-3-(3-{[2-(4,5-dihydro-1H-imidazol-2-yl)pyridin-4-yl]oxy}phenyl)propanamide;

N-[4-chloro-3-(trifluoromethyl)phenyl]-3-[4-({2-[4-(hydroxymethyl)-4,5-dihydro-1H-imidazol-2-yl]pyridin-4-yl}oxy)phenyl]propanamide;

3-(3-{[2-(4,5-dihydro-1H-imidazol-2-yl)pyridin-4-yl]oxy}phenyl)-N-[4-[3-(dimethylamino)propyl]-3-(trifluoromethyl)phenyl]propanamide;

3-[4-({2-[amino(imino)methyl]pyridin-4-yl}oxy)phenyl]-N-[4-chloro-3-(trifluoromethyl)phenyl]propanamide;

N-[4-chloro-3-(trifluoromethyl)phenyl]2-(4-{[2-(4,5-dihydro-1H-imidazol-2-yl)-pyridin-4-yl]oxy}phenyl)cyclopropanecarboxamide;

3-(3-{[2-(4,5-dihydro-1H-imidazol-2-yl)pyridin-4-yl]oxy}phenyl)-N-(4,6-dimethylpyridin-2-yl)propanamide;

N-[4-chloro-3-(trifluoromethyl)phenyl]-3-[3-({2-[(4S)-4-(methoxymethyl)-4,5-dihydro-1H-imidazol-2-yl]pyridin-4-yl}oxy)phenyl]propanamide;

N-(3-chlorophenyl)-3-(3-{[2-(4,5-dihydro-1H-imidazol-2-yl)pyridin4 yl]oxy}phenyl)propanamide;

N-[4-chloro-3-(trifluoromethyl)phenyl]-3-(3-{[2-(isopropylamino)pyrimidin-4-yl]oxy}phenyl)propanamide;

N-[4-chloro-3-(trifluoromethyl)phenyl]-3-[3-({2-[(4R)-4-methyl-4,5-dihydro-1H-imidazol-2-yl]pyridin-4-yl}oxy)phenyl]propanamide;

4-(4-{3-[(3,5-dimethoxyphenyl)amino]-3-oxopropyl}phenoxy)-N-methylpyridine-2-carboxamide;

3-{3-[(6-aminopyrimidin-4-yl)oxy]phenyl}-N-[4-chloro-3-(trifluoromethyl)phenyl]propanamide;

N-(3-bromophenyl)-3-(3-{[2-(4,5-dihydro-1H-imidazol-2-yl)pyridin-4-yl]oxy}phenyl))propanamide;

N-[3-chloro-4-(trifluoromethyl)phenyl]-3-(3-{[2-(4,5-dihydro-1H-imidazol-2-yl)pyridin-4-yl]oxy}phenyl)propanamide;

methyl 3-({3-[3-({2-[(methylamino)carbonyl]pyridin-4-yl}oxy)phenyl]pronanoyl}amino)benzoate;

N-[4-bromo-3-(trifluoromethyl)phenyl]-3-(3-{[2-4,5-dihydro-1H-imidazol-2-yl)pyridin-4-yl]oxy}phenyl)propanamide;

4-[3-(3-{[4-cyano-3-(trifluoromethyl)phenyl]amino}-3-oxopropyl)phenoxy]-N-methylpyridine-2-carboxamide;

2-{4-[3-(3-{[4-chloro-3-(trifluoromethyl)phenyl]amino}-3-oxopropyl)phenoxy]pyridin -2-yl}-N-methyl-4,5-dihydro-1H-imidazole-4-carboxamide;

4-[3-(3-{[4-chloro-3-(trifluoromethyl)phenyl]amino}-3-oxopropyl)phenoxy]-N-[3-(dimethylamino)propyl]pyridine-2-carboxamide;

3-{3-[(2-aminopyridin-4-yl)oxy]phenyl}-N-(3-tert-butylphenyl)propanamide;

4-{3-[3-(1,3-benzodioxol-5-ylamino)-3-oxopropyl]phenoxy}-N-methylpyridine-2-carboxamide;

4-(4-{3-[(3-chloro-4-cyanophenyl)amino]-3-oxopropyl}phenoxy)-N-methylpyridine-2-carboxamide;

N-(2,3-dihydro-1H-inden-5-yl)-3-(3-{[2-(1,4,5,6-tetrahydropyrimidin-2-yl)pyridin-4-yl]oxy}phenyl)propanamide;

3-(3-{[2-(4,5-dihydro-1H-imidazol-2-yl)pyridin-4yl]oxy}phenyl)-N-[4-ethyl-3-(trifluoromethyl)phenyl]propanamide;

N-{4-[3-(3-{[4-ethyl-3-(trifluoromethyl)phenyl]amino}-3-oxopropyl)phenoxy]pyridin-2-yl}cyclopropanecarboxamide;

N-{4-[3-(3-{[4-[(dimethylamino)methyl]-3-(trifluoromethyl)phenyl]amino}-3-oxopropyl)phenoxy]pyridin-2-yl}cyclopropanecarboxamide;

N-{4-[3-(3-{[3-(2-aminoethyl)-5-(trifluoromethyl)phenyl]amino}-3-oxopropyl)-phenoxy]pyridin-2-yl}cyclopropanecarboxamide;

3-(3-{[2-(acetylamino)pyridin-4-yl]oxy}phenyl)-N-[4-ethyl-3-(trifluoromethyl)phenyl]-propanamide;

3-(3-{[2-(acetylamino)pyridin-4-yl]oxy}phenyl)-N-[4-[(dimethylamino)methyl]-3-(trifluoromethyl)phenyl]propanamide;

3-(3-{[2-(acetylamino)pyridin-4-yl]oxy}phenyl)-N-[3-(2-aminoethyl)-5-(trifluoromethyl)phenyl]propanamide;

(2E)-N-[4-chloro-3-(trifluoromethyl)phenyl]-3-(3-{[2-(4,5-dihydro-1H-imidazol-2-yl)pyridin-4-yl]oxy}phenyl)but-2-enamide;

(2E-3-(3-{[2-(4,5-dihydro-1H-imidazol-2-yl)pyridin-4-yl]oxy}phenyl)-N-(3-isopropylphenyl)acrylamide;

(2E)-N-[4-chloro-3-(trifluoromethyl)phenyl]-3-[3-(9H-purin-6-yloxy)phenyl]-acrylamide;

(2E)-N-(3-tert-butylphenyl)-3-(3-{[2-(4,5-dihydro-1H-imidazol-2-yl)pyridin-4-yl]oxy}phenyl)acrylamide;

4-(3-{(1E)-3-[(3-tert-butylphenyl)amino]-2-methyl-3-oxoprop-1-en-1-yl}phenoxy)-N-methylpyridine-2-carboxamide;

(2E)-3-(3-{[2-(4,5-dihydro-1H-imidazol-2-yl)pyridin-4-yl]oxy}phenyl)-N-[3-(trifluoromethyl)phenyl]acrylamide;

(2E)-N-[4-chloro-3-(trifluoromethyl)phenyl]-2-(3-{[2-(4,5-dihydro-1H-imidazol-2-yl)pyridin-4-yl]oxy}benzylidene)butanamide;

(2E)-3-(3-{[2-(4,5-dihydro-1H-imidazol-2-yl)pyridin-4-yl]oxy}phenyl)-N-[3-fluoro-5-(trifluoromethyl)phenyl]acrylamide;

(2E)-N-(3-chlorophenyl)-3-(3-{[2-(4,5-dihydro-1H-imidazol-2-yl)pyridin-4-yl]oxy}phenyl)acrylamide;

(2Z)-N-[4-chloro-3-(trifluoromethyl)phenyl]-3-(3-{[2-(4,5-dihydro-1H-imidazol-2-yl)pyridin-4-yl]oxy}phenyl)-2-fluoroacrylamide;

(2E-N-[4-chloro-3-(trifluoromethyl)phenyl]-3-(3-{[2-4,5-dihydro-1H-imidazol-2-yl)pyridin-4-yl]oxy}phenyl)-2-methylacrylamide;

(2E)-N-(4-chlorophenyl)-3-(3-{[2-(4,5-dihydro-1H-imidazol-2-yl)pyridin-4-yl]oxy}phenyl)acrylamide;

(2E)-N-[4-chloro-3-(trifluoromethyl)phenyl]-3-(3-{[2-(4,5-dihydro-1H-imidazol-2-yl)pyridin-4-yl]oxy}phenyl)acrylamide;

(2E)-3-(3-{[2-(4,5-dihydro-1H-imidazol-2-yl)pyridin-4-yl]oxy}phenyl)-N-[4-(3-pyrrolidin-1-ylpropyl)-3-(trifluoromethyl)phenyl]acrylanmide;

(2E-3-(3-{[2-(4,5-dihydro-1H-imidazol-2-yl)pyridin-4-yl]oxy}phenyl-N-[4-[3-(dimethylamino)propyl]-3-(trifluoromethyl)phenyl]acrylamide;

(2E)-3-(3-{[2-(4,5-dihydro-1H-imidazol-2-yl)pyridin-4-yl]oxy}phenyl)-N-[4-(3-hydroxypropyl)-3-(trifluoromethyl)phenyl]acrylamide;

(2E)-3-(3-{[2-(4,5-dihydro-1H-imidazol-2-yl)pyridin-4-yl]oxy}phenyl)-N-[4-(3-pyrrolidin-1-ylprop-1-yn-1-yl)-3-(trifluoromethyl)phenyl]acrylamide;

(2E-3-(3-{[2-(4,5-dihydro-1H-imidazol-2-yl)pyridin-4-yl]oxy}phenyl)-N-[4-[3-(dimethylamino)prop-1-yn-1-yl]-3-(trifluoromethyl)phenyl]acrylamide;

(2E)-3-(3-{[2-(4,5-dihydro-1H-imidazol-2yl)pyridin-4yl]oxy}phenyl)-N-[4-(3-hydroxyprop-1-yn-1-yl)-3-(trifluoromethyl)phenyl]acrylamide;

(2E)-N-[4-chloro-3-(trifluoromethyl)phenyl]-3-(3-{[2-(5-methyl-1H-imidazol-2-yl)pyridin-4-yl]oxy}phenyl)acrylamide;

(2E)-N-[4-bromo-3-(trifluoromethyl)phenyl]-3-(3-{[2-(4,5-dihydro-1H-imidazol-2-yl)pyridin-4-yl]oxy}phenyl)acrylamide;

(2E)-3-(3-{[2-(4,5-dihydro-1H-imidazol-2-yl)pyridin-4-yl]oxy}phenyl)-N-[4-ethynyl-3-(trifluoromethyl)phenyl]acrylamide;

(2E)-N-(3-tert-butylphenyl)-3-{3-[(2-{[(4-ethylpiperazin-1-yl)acetyl]amino}pyridin-4-yl)oxy]phenyl}acrylamide;

4-(3-{(1E)-3-[(3-tert-butylphenyl)amino]-3-oxoprop-1-en-1-yl}phenoxy)-N-methylpyridine-2-carboxamide;

4-[3-((1E)-3-{[4-chloro-3-(trifluoromethyl)phenyl]amino}-3-oxoprop-1-en-1-yl)phenoxy]-N-methylpyridine-2-carboxamide;

(2E)-3-(3-{[2-(4,5-dihydro-1H-imidazol-2-yl)pyridin-4-yl]oxy}phenyl)-N-(3 ,3-dimethyl-1-oxo-2,3-dihydro-1H-isoindol-5-yl)acrylamide;

(2E)-3-(3-{[2-(4,5-dihydro-1H-imidazol-2-yl)pyridin-4-yl]oxy}phenyl)-N-(3,3-dimethyl-1-oxo-1,3-dihydro-2-benzofuran-5-yl)acrylamide;

(2E)-3-(3-{[2-(4,5-dihydro-1H-imidazol-2-yl)pyridin-4-yl]oxy}phenyl)-N-[2-(trifluoromethyl)pyridin-4-yl]acrylamide;

(2E)-3-(3-{[2-(4,5-dihydro-1H-imidazol-2-yl)pyridin-4-yl]oxy}phenyl)-N-[4-(trifluoromethyl)pyridin-2-yl]acrylamide;

(2E)-N-(3-tert-butylisoxazol-5-yl)-3-(3-{[2-(4,5-dihydro-1H-imidazol-2-yl)pyridin-4-yl]oxy}phenyl)acrylamide;

(2E)-N-(5-tert-butylisoxazol-3-yl)-3-(3-{[2-(4,5-dihydro-1H-imidazol-2-yl)pyridin-4-yl]oxy}phenyl)acrylamide;

4-[3-((1E)-3-{[4-chloro-3-(trifluoromethyl)phenyl]amino}-3-oxoprop-1-en-1-yl)phenoxy]-N-(2-(methoxyethyl)pyridine-2-carboxamide;

4-[3-((1E)-3-{[4-chloro-3-(trifluoromethyl)phenyl]amino}-3-oxoprop-1-en-1-yl)phenoxy]-N-(2-piperazin-1-ylethyl)pyridine-2-carboxamide;

4-[3-((1E)-3-{[4-chloro-3-(trifluoromethyl)phenyl]amino}-3-oxoprop-1-en-1-yl)phenoxy]-N-(2-piperidin-1-ylethyl)pyridine-2-carboxamide;

4-[3-((1E)-3-{[4-chloro-3-(trifluoromethyl)phenyl]amino}-3-oxoprop-1-en-1-yl)phenoxy]-N-(cyclopropylmethyl)pyridine-2-carboxamide;

4-[3-((1E)-3-{[4-chloro-3-(trifluoromethyl)phenyl]amino}-3-oxoprop-1-en-1-yl)phenoxy]-N-[3-(1H-imidazol-1-yl)propyl]pyridine-2-carboxamide;

4-[3-((1E)-3-{[4-chloro-3-(trifluoromethyl)phenyl]amino}-3-oxoprop-1-en-1-yl)phenoxy]-N-(2pyrrolidin-1-ylethyl)pyridine-2-carboxamide;

3-{[(2E)-3-(3-{[2-(4,5-dihydro-1H-imidazol-2-yl)pyridin-4-yl]oxy}phenyl)prop-2-enoyl]amino}-N-[2-(methylamino)ethyl]-5-(trifluoromethyl)benzamide;

3-{[(2E)-3-(3-{[2-(4,5-dihydro-1H-imidazol-2-yl)pyridin-4-yl]oxy}phenyl)prop-2-enoyl]amino}-N-[2-(dimethylamino)ethyl]-5-(trifluoromethyl)benzamide;

(2E)-3-(3-{[2-(4,5-dihydro-1H-imidazol-2-yl)pyridin-4-yl]oxy}phenyl)-N-[3-(methylamino)-5-(trifluoromethyl)phenyl]acrylamide;

3-{[(2E)-3-(3-{[2-(4,5-dihydro-1H-imidazol-2-yl)pyridin-4-yl]oxy}phenyl)prop-2-enoyl]amino}-N-methyl-5-(trifluoromethyl)benzamide;

(2E)-3-(3-{[2-(4,5-dihydro-1H-imidazol-2-yl)pyridin-4-yl]oxy}phenyl)-N-[3-[(methylamino)methyl]-5-(trifluoromethyl)phenyl]acrylamide;

(2E)-3-(3-{[2-(4,5-dihydro-1H-imidazol-2-yl)pyridin-4-yl]oxy}phenyl)-N-[3-(2-pyrrolidin-1-ylethyl-5-(trifluoromethyl)phenyl]acrylamide;

(2E)-3-(3-{[2-(4,5-dihydro-1H-imidazol-2-yl)pyridin-4-yl]oxy}phenyl)-N-[3-[3-(dimethylamino)propyl]-5-(trifluoromethyl)phenyl]acrylamide;

(2E)-3-(3-{[2-(4,5-dihydro-1H-imidazol-2-yl)pyridin-4-yl]oxy}phenyl)-N-[3-[2-(dimethylamino)ethoxy]-5-(trifluoromethyl)phenyl]acrylamide;

(2E)-N-[4-bromo-3-(trifluoromethyl)phenyl]-3-(3-{[2-(5-methyl-1H-imidazol-2-yl)pyridin-4-yl]oxy}phenyl)acrylamide;

(2E)-N-[4-bromo-3-(trifluoromethyl)phenyl]-3-(3-{[2-(5-methyl-4,5-dihydro-1H-imidazol-2-yl)pyridin-4-yl]oxy}phenyl)acrylamide;

(2E)-N-[4-bromo-3-(trifluoromethyl)phenyl]-3-[3-({2-[5-(hydroxymethyl)-1H-imidazol-2-yl]pyridin-4-yl}oxy)phenyl]acrylamide;

(2E)-N-[4-bromo-3-(trifluoromethyl)phenyl]-3-[3-({2-[5-(hydroxymethyl)-4,5-dihydro-1H-imidazol-2-yl]pyridin-4-yl}oxy)phenyl]acrylamide;

N-methyl-4-[3-((1E)-3-oxo-3-{[4-(3-pyrrolidin-1-ylpropyl-3-(trifluoromethyl)-phenyl]amino}prop-1-en-1-yl)phenoxy]pyridine-2-carboxamide;

4-[3-((1E)-3-{[4-[3-(dimethylamino)propyl]-3-(trifluoromethyl)phenyl]amino}-3-oxoprop-1-en-1-yl)phenoxy]-N-methylpyridine-2-carboxamide;

4-[3-((1E)-3-{[4-(3-hydroxypropyl)-3-(trifluoromethyl)phenyl]amino}-3-oxoprop-1-en-1-yl)phenoxy]-N-methylpyridine-2-carboxamide;

N-methyl-4-[3-((1E)-3-oxo-3-{[4-(3-pyrrolidin-1-yl-prop-1-yn-1-yl)-3-(trifluoromethyl)phenyl]amino}prop-1-en-1-yl)phenoxy]pyridine-2-carboxamide;

4-[3-((1E)-3-{[4-[3-(dimethylamino)prop-1-yn-1-yl]-3-(trifluoromethyl)phenyl]amino}-3-oxoprop-1-en-1-yl)phenoxy]-N-methylpyridine-2-carboxamide;

4-[3-((1E)-3-{[4-(3-hydroxyprop-1-yn-1-yl)-3-(trifluoromethyl)phenyl]amino}-3-oxoprop-1-en-1-yl)phenoxy]-N-methylpyridine-2-carboxamide;

(2E)-N-[4-chloro-3-(trifluoromethyl)phenyl]-3-(3-{[2-(1,4,5,6-tetrahydropyrimidin-2-yl)pyridin-4-yl]oxy}phenyl)acrylamide;

(2E)-3-(3-{[2-(5-hydroxy-1,4,5,6-tetrahydropyrimidin-2-yl)pyridin-4-yl]oxy}phenyl)-N-[3-(trifluoromethyl)phenyl]acrylamide;

(2E)-3-(3-{[2-(1,4,5,6-tetrahydropyrimidin-2-yl)pyridin-4-yl]oxy}phenyl)-N-[3-(trifluoromethyl)phenyl]acrylamide;

5-{4-[3-((1E)-3-oxo-3-{[3-(trifluoromethyl)phenyl]amino}prop-1-en-1-yl)phenoxy]pyridin-2-yl}-1,3,4-oxadiazole-2-carboxamide;

2-{4-[3-((1E)-3-oxo-3-{[3-(trifluoromethyl)phenyl]amino}prop-1-en-1-yl)phenoxy]pyridin-2-yl}-1H-imidazole-5-carboxamide;

4-[3-((1E)-3-{[3-methoxy-5-(trifluoromethyl)phenyl]amino}-3-oxoprop-1-en-1-yl)phenoxy]-N-methylpyridine-2-carboxamide;

(2E)-3-(3-{[2-(4,5-dihydro-1H-imidazol-2-yl)pyridin-4-yl]oxy}phenyl)-N-[3-methoxy-5-(trifluoromethyl)phenyl]acrylamide;

2-{4-[3-((1E)-3-oxo-3-{[3-(trifluoromethyl)phenyl]annino}prop-1-en-1-yl)phenoxy]pyridin-2-yl}-4,5-dihydro-1H-imidazole-5-carboxylic acid;

(2E)-N-(3,5-di-tert-butylphenyl)-3-(3-{[2-(4,5-dihydro-1H-imidazol-2-yl)pyridin-4-yl]oxy}phenyl)acrylamide;

(2E)-3-(3-{[2-(4,5-dihydro-1H-imidazol-2-yl)pyridin-4-yl]oxy}phenyl)-N-(3-iodophenyl)acrylamide;

(2E)-N-[4-chloro-3-(trifluoromethyl)phenyl]-3--[3-({2-[(ethylamino)-(imino)methyl]pyridin-4-yl}oxy)phenyl]acrylamide;

(2E)-3-[3-({2-[amino(imino)methyl]pyridin-4-yl}oxy)phenyl]-N-[4-bromo-3-(trifluoromethyl)phenyl]acrylamide;

(2E)-3-(3-{[2-(4,5-dihydro-1H-imidazol-2-yl)pyridin-4-yl]oxy}phenyl)-N-[4-methyl-3-(trifluoromethyl)phenyl]acrylamide;

(2E)-N-[4-fluoro-3-(trifluoromethyl)phenyl]-3-[3-({2-[(5S)-5-methyl-4,5-dihydro-1H-imidazol-2-yl]pyridin-4-yl}oxy)phenyl]acrylamide;

(2E)-N-[4-fluoro-3-(trifluoromethyl)phenyl]-3-[3-({2-[(5R)-5-methyl-4,5-dihydro-1H-imidazol-2-yl]pyridin-4-yl}oxy)phenyl]acrylamide;

(2E)-N-[4-chloro-3-(trifluoromethyl)phenyl]-3-[3-({2-[imino(morpholin-4-yl)methyl]pyridin-4-yl}oxy)phenyl]acrylamide;

(2E)-N-[4-chloro-3-(trifluoromethyl)phenyl]-3-{3-[2-{imino[(2-morpholin-4-ylethyl)amino]methyl}pyridin-4-yl)oxy]phenyl}acrylamide;

4-(3-{(1E)-3-[(3-isopropylphenyl)amino]-3-oxoprop-1-en-1-yl}phenoxy)pyridine-2-carboxamide;

(2E)-3-[3-({2-[(benzylamino)(imino)methyl]pyridin-4-yl}oxy)phenyl]-N-[4-iodo-3-(trifluoromethyl)phenyl]acrylamide;

(2E)-3-(2-chloro-3-{[2-(4,5-dihydro-1H-imidazol-2-yl)pyridin-4-yl]oxy}phenyl)-N-[4-chloro-3-(trifluoromethyl)phenyl]acrylamide;

N-[2-(dimethylamino)ethyl]-2-{4-[3-((1E)-3-oxo-3-{[3-(trifluoromethyl)phenyl]amino}prop-1-en-1-yl)phenoxy]pyridin-2-yl}-1H-imidazole-5-carboxamide;

N-[2-(dimethylamino)ethyl]-2-{4-[3-((1E)-3-oxo-3-{[3-(trifluoromethyl)-phenyl]amino}prop-1-en-1-yl)phenoxy]pyridin-2-yl}-4,5-dihydro-1H-imidazole-5-carboxamide;

(2E)-N-[4-cyano-3-(trifluoromethyl)phenyl]-3-(3-{[2-(4,5-dihydro-1H-imidazol-2-yl)pyridin-4-yl]oxy}phenyl)acrylamide;

(2E)-N-(3-tert-butylphenyl)-3-(3-{[2-(1,4,5,6-tetrahydropyrimidin-2-yl)pyridin-4-yl]oxy}phenyl)acrylamide;

2-{4-[3-((1E)-3-{[4-fluoro-3-(trifluoromethyl)phenyl]amino}-3-oxoprop-1-en-1-yl)phenoxy]pyridin-2-yl}-N-methyl-1H-imidazole-5-carboxamide;

(2E)-3-(3-{[2-(5-tert-butyl-1H-imidazol-2-yl)pyridin-4-yl]oxy}phenyl)-N-[4-fluoro-3-(trifluoromethyl)phenyl]acrylamide;

(2E)-N-(3-ethylphenyl)-3-(3-{[2-(1H-tetrazol-5-yl)pyridin-4-yl]oxy}phenyl)acrylamide;

methyl 2-{4-[3-((1E)-3-{[4-fluoro-3-(trifluoromethyl)phenyl]amino}-3-oxoprop-1-en-1-yl)phenoxy]pyridin-2-yl}-1H-imidazole-5-carboxylate;

methyl 2-{4-[3-((1E)-3-{[4-fluoro-3-(trifluoromethyl)phenyl]amino}-3-oxoprop-1-en-1-yl)phenoxy]pyridin-2-yl}-4,5-dihydro-1H-imidazole-5-carboxylate;

(2E)-N-[4-bromo-3-(trifluoromethyl)phenyl]-3-[3-({2-[(hydroxyamino)-(imino)methyl]pyridin-4-yl}oxy)phenyl]acrylamide;

(2E)-1-N-[4-chloro-3-(trifluoromethyl)phenyl]-3-[3-({2-[imino(methoxyamino)-methyl]pyridin-4-yl}oxy)phenyl]acrylamide;

2-[4-(3-{(1E)-3-[(3-tert-butylphenyl)amino]-3-oxoprop-1-en-1-yl}phenoxy)pyridin-2-yl]-1,4,5,6-tetrahydropyrimidine-4-carboxylic acid;

(2E)-N-[4-fluoro-3-(trifluoromethyl)phenyl]-3-[3-({2-[(5S)-5-(methoxymethyl)-4,5-dihydro-1H-imidazol-2-yl]pyridin-4-yl}oxy)phenyl]acrylamide;

(2E)-N-(2,3-dihydro-1H-inden-5-yl)-3-(3-{[2-(5,5-dimethyl-4,5-dihydro-1H-imidazol-2-yl)pyridin-4-yl]oxy}phenyl)acrylamide;

(2E)-N-(3-chlorophenyl)-3-[3-({2-[(ethanimidoylamino)methyl]pyridin-4-yl}oxy)phenyl]acrylamide;

(2E)-3-(3-{[2-(4,5-dihydro-1H-imidazol-2-yl)pyridin-4-yl]oxy}phenyl)-N-[3-(methylsulfanyl)phenyl]acrylamide;

2-{4-[3-((1E)-3-{[4-fluoro-3-(trifluoromethyl)phenyl]amino}-3-oxoprop-1-en-1-yl)phenoxy]pyridin-2-yl}-N,N-dimethyl-4,5-dihydro-1H-imidazole-5-carboxamide;

2-{4-[3-((1E)-3-{[4-fluoro-3-(trifluoromethyl)phenyl]amino}-3-oxoprop-1-en-1-yl)phenoxy]pyridin-2-yl}-N,N-dimethyl-1H-imidazole-5-carboxamide;

(2E)-N-(2,3-dihydro-1H-inden-5-yl)-3-(3-{[2-({[imino(phenyl)methyl]amino}methyl)pyridin-4-yl]oxy}phenyl)acrylamide;

(2E)-N-[4-chloro-3-(trifluoromethyl)phenyl]-3-(3-{[2-(4,5-dihydro-1H-imidazol-2-yl)-3-methylpyridin-4-yl]oxy}phenyl)acrylamide;

(2E)-N-[4-chloro-2-methoxy-3-(trifluoromethyl)phenyl]-3-(3-{[2-(4,5-dihydro-1H-imidazol-2-yl)pyridin-4-yl]oxy}phenyl)acrylamide;

4-{3-[(1E)-3-(2,3-dihydro-1H-inden-5-ylamino)-3-oxoprop-1-en-1-yl]phenoxy}-N-[2-(dimethylamino)ethyl]pyridine-2-carboxamide;

tert-butyl[(4-{3-[(1E)-3-(2,3-dihydro-1H-inden-5-ylamino)-3-oxoprop-1-en-1-yl]phenoxy}pyridin-2-yl)methyl]carbamate;

(2E)-3-(3-{[2-(aminomethyl)pyridin-4-yl]oxy}phenyl)-N-(2,3-dihydro-1H-inden-5-yl)acrylamide;

(2E)-N-[4-chloro-2-hydroxy-5-(trifluoromethyl)phenyl]-3-(3-{[2-(4,5-dihydro-1H-imidazol-2-yl)pyridin-4-yl]oxy}phenyl)acrylamide;

4[3-((1E)-3-{[4-chloro-2-hydroxy-5-(trifluoromethyl)phenyl]amino}-3-oxoprop-1-en-1-yl)phenoxy]-N-methylpyridine-2-carboxamide;

4-[3-((1E)-3-{[4-chloro-2-hydroxy-3-(trifluoromethyl)phenyl]amino}-3-oxoprop-1-en-1-yl)phenoxy]-N-methylpyridine-2-carboxamide;

(2E)-N-[4-chloro-2-hydroxy-3-(trifluoromethyl)phenyl]-3-(3-{[2-(4,5-dihydro-1H-imidazol-2-yl)pyridin-4-yl]oxy}phenyl)acrylamide;

(2E)-N-[4-chloro-3-(trifluoromethyl)phenyl]-3-(3-{[2-(diethylamino)pyridin-4-yl]oxy}phenyl)acrylamide;

(2E)-N-[4-chloro-3-(trifluoromethyl)phenyl]-3-{3-[(2{[3-(dimethylamino)propyl]amino}pyrimidin-4-yl)oxy]phenyl}acrylamide;

(2E)-N-[4-chloro-3-(trifluoromethyl)phenyl]-3-(3-{[2-(isopropylamino)pyrimidin-4-yl]oxy}phenyl)acrylamide;

(2E)-N-[4-chloro-3-(trifluoromethyl)phenyl]-3-{3-[2-{[2-(dimethylamino)ethyl]amino}pyrimidin-4-yl)oxy]phenyl}acrylamide;

(2E)-N-[4-chloro-3-(trifluoromethyl)phenyl]-3-{3-[(2-piperazin-1-ylpyrimidin-4-yl)oxy]phenyl}acrylamide;

(2E)-N-[4-chloro-3-(trifluoromethyl)phenyl]-3-{3-[(2-morpholin-4-ylpyrimidin-4-yl)oxy]phenyl}acrylamide;

(2E)-N-[4-chloro-3-(trifluoromethyl)phenyl]-3-{3-[(2-piperidin-1-ylpyrimidin-4-yl)oxy]phenyl}acrylamide;

(2E)-N-[4-chloro-3-(trifluoromethyl)phenyl]-3-[3-({2-[(4-methoxybenzyl)amino]pyrimidin-4-yl}oxy)phenyl]acrylamide;

(2E)-3-(3-{[2benzylamino)pyrimidin-4-yl]oxy}phenyl-N-[4-fluoro-3-(trifluoromethyl)phenyl]acrylamide;

(2E)-3-{3-[(2-aminopyrimidin-4-yl)oxy]phenyl}-N-[4-fluoro-3-(trifluoromethyl)phenyl]acrylamide;

(2E)-N-[4-fluoro-3-(trifluoromethyl)phenyl]-3-(3-{[2-(1-methyl-1H-imidazol-2-yl)pyridin-4-yl]oxy}phenyl)acrylamide;

(2E)-3-(4-chloro-3-{[2-(1-methyl-4,5-dihydro-1H-imidazol-2-yl)pyridin-4-yl]oxy}phenyl)-N-[4-fluoro-3-(trifluoromethyl)phenyl]acrylamide;

(2E)-N-[4-chloro-3-(trifluoromethyl)phenyl]-3-(3-{[2-(diethylamino)pyrimidin-4-yl]oxy}phenyl)acrylamide;

(2E)-3-[3-({2-[(1-methylpiperidin-4-yl)amino]pyrimidin-4-yl}oxy)phenyl]-N-[3-(trifluoromethyl)phenyl]acrylamide;

(2E)-N-[4-chloro-3-(trifluoromethyl)phenyl]-3-[3-({2-[[3-(dimethylamino)propyl](methyl)amino]pyrimidin-4-yl}oxy)phenyl]acrylamide;

(2E)-3-[3-({2-[[2-(dimethylamino)ethyl](methyl)amino]pyrimidin-4-yl}oxy)phenyl]-N-[3-(trifluoromethyl)phenyl]acrylamide;

(2E)-N-[4-chloro-3-(trifluoromethyl)phenyl]-3-{3-[(2-pyrrolidin-1-ylpyrimidin-4-yl)oxy]phenyl}acrylamide;

(2E)-3-(3-{[2-(4-methylpiperazin-1-yl)pyrimidin-4-yl]oxy}phenyl)-N-[3-(trifluoromethyl)phenyl]acrylamide;

(2E)-N-[4-chloro-3-(trifluoromethyl)phenyl]-3-[3-({2-[(2-morpholin-4-ylethyl)amino]pyrimidin-4-yl}oxy)phenyl]acrylamide;

(2E)-N-[4-chloro-3-(trifluoromethyl)phenyl]-3-[3({2-[(4-methoxyphenyl)amino]pyrimidin-4-yl}oxy)phenyl]acrylamide;

tert-butyl(1-{4-[3-((1E)-3-{[4-chloro-3-(trifluoromethyl)phenyl]amino}-3-oxoprop-1-en-1-yl)phenoxy]pyrimidin-2-yl}piperidin-3-yl)carbamate;

(2E)-3(3-{[2-(3-aminopiperidin-1-yl)pyrimidin-4-yl]oxy}phenyl)-N-[4-chloro-3-(trifluoromethyl)phenyl]acrylamide;

(2E)-N-[4-chloro-3-(trifluoromethyl)phenyl]-3-{3-[(2-{[2-(dimethylamino)ethyl]amino}pyrimidin-4-yl)oxy]phenyl}acrylamide;

(2E)-N-[4-chloro-3-(trifluoromethyl)phenyl]-3-{3-[(2-{[3-(2-oxopyrrolidin-1-yl)propyl]amino}pyrimidin-4-yl)oxy]phenyl}acrylamide;

4-[3-((1E)-3-{[4-chloro-3-(trifluoromethyl)phenyl]amino}-3-oxoprop-1-en-1-yl)phenoxy]-N-[2-(methylamino)-2-oxoethyl]pyridine-2-carboxamide;

methyl[({4-[3-((1E)-3-{[4-chloro-3-(trifluoromethyl)phenyl]amino}-3-oxoprop-1-en-1-yl)phenoxy]pyridin-2-yl}carbonyl)amino]acetate;

[({4-[3-((1E)-3-{[4-chloro-3-(trifluoromethyl)phenyl]amino}-3-oxoprop-1-en-1-yl)phenoxy]pyridin-2-yl}carbonyl)amino]acetic acid;

N-(2-morpholin-4-ylethyl)-4-[3-((1E)-3-oxo-3-{[4-(trifluoromethyl)phenyl]amino}prop-1-en-1-yl)phenoxy]pyridine-2-carboxamide;

4-(3-{(1E)-3-[(3-methylphenyl)amino]-3-oxoprop-1-en-1-yl}phenoxy)-N-(2-morpholin-4-ylethyl)pyridine-2-carboxamide;

4-(3-{(1E)-3-[(3-ethylphenyl)amino]-3-oxoprop-1-en-1-yl}phenoxy)-N-(2-morpholin-4-ylethyl)pyridine-2-carboxamide;

4-(3-{(1E)-3-[(3-chloro-4-fluorophenyl)amino]-3-oxo-prop-1-en-1-yl}phenoxy)-N-(2-morpholin-4-ylethyl)pyridine-2-carboxamide;
4-(3-{(1E)-3-[(4-chloro-3-fluorophenyl)amino]-3-oxo-prop-1-en-1-yl}phenoxy)-N-(2-morpholin-4-ylethyl)pyridine-2-carboxamide;
4-(3-{(1E)-3-[(3-bromophenyl)amino]-3-oxoprop-1-en-1-yl}phenoxy)-N-(2-morpholin-4-ylethyl)pyridine-2-carboxamide;
4-(3-{(1E)-3-[(4-chloro-3-cyanophenyl)amino]-3-oxo-prop-1-en-1-yl}phenoxy)-N-(2-morpholin-4-ylethyl)pyridine-2-carboxamide;
(2E)-N-(3-tert-butylphenyl)-3-(3-{[2-(4,5-dihydro-1H-imidazol-2-yl)pyridin-4-yl]oxy}phenyl)-2-methylacrylamide;
(2E)-N-(3-tert-butylphenyl)-3-(3-{[2-(4,5-dihydro-1H-imidazol-2-yl)pyridin-4-yl]oxy}phenyl)-2-(hydroxymethyl)acrylamide;
4-[3-((1E)-3-{[4-(aminomethyl)-3-(trifluoromethyl)phenyl]amino}-3-oxoprop-1-en-1-yl)phenoxy]-N-methylpyridine-2-carboxamide;
4-[3-((1E)-3-{[3-amino-5-(trifluoromethyl)phenyl]amino}-3-oxoprop-1-en-1-yl)phenoxy]-N-methylpyridine-2-carboxamide;
(2E)-N-[3-amino-5-(trifluoromethyl)phenyl]-3-(3-{[2-(4,5-dihydro-1H-imidazol-2-yl)pyridin-4-yl]oxy}phenyl)acrylamide;
4-[3-((1E)-3-{[3-(2-aminoethyl)-5-(trifluoromethyl)phenyl]amino}-3-oxoprop-1-en-1-yl)phenoxy]-N-methylpyridine-2-carboxamide;
(2E)-N-[3-(2-aminoethyl)-5-(trifluoromethyl)phenyl]-3-(3-{[2-(4,5-dihydro-1H-imidazol-2-yl)pyridin-4-yl]oxy}phenyl)acrylamide;
(2E)-N-[4-(aminomethyl)-3-(trifluoromethyl)phenyl]-3-(3-{[2-(4,5-dihydro-1H-imidazol-2-yl)pyridin-4-yl]oxy}phenyl)acrylamide;
(2E)-N-[4-chloro-3-(trifluoromethyl)phenyl]-3-(3-{[2-(4,5-dihydro-1H-imidazol-2-yl)pyridin-4-yl]methyl}phenyl)acrylamide;
(2E)-N-[4-chloro3-(trifluoromethyl)phenyl]-3-(3-{[2-(4,5-dihydro-1H-imidazol-2-yl)pyridin-4-yl]sulfanyl}phenyl)acrylamide;
(2E)-N-[4-chloro-3-(trifluoromethyl)phenyl]-3-(3-{[2-(4,5-dihydro-1H-imidazol-2-yl)pyridin-4-yl]amino}phenyl)acrylamide;
N-{4-[3-((1E)-3-{[4-ethyl-3-(trifluoromethyl)phenyl]amino}-3-oxoprop-1-en-1-yl)phenoxy]pyridin-2-yl}cyclopropanecarboxamide;
N-{4-[3-((1E)-3-{[4[(dimethylamino)methyl]-3-(trifluoromethyl)phenyl]amino}-3-oxoprop-1-en-1-yl)phenoxy]pyridin-2-yl}cyclopropanecarboxamide;
N-{4-[3-((1E)-3-{[3-(2-aminoethyl)-5-(trifluoromethyl)phenyl]amino}-3-oxoprop-1-en-1-yl)phenoxy]pyridin-2-yl}cyclopropanecarboxamide;
N-[4-(3-{(1E)-3-[(3-tert-butylphenyl)amino]-3-oxoprop-1-en-1-yl}phenoxy)pyridin-2-yl]cyclopropanecarboxamide;
N-{4-[3-((1E)-3-{[4-chloro-3-(trifluoromethyl)phenyl]amino}-3-oxoprop-1-en-1-yl)phenoxy]pyridin-2-yl}cyclopropanecarboxamide;
(2E)-3-(3-{[2-(acetylamino)pyridin-4-yl]oxy}phenyl)-N-[4-ethyl-3-(trifluoromethyl)-phenyl]acrylamide;
(2E)-3-(3-{[2-(acetylamino)pyridin-4-yl]oxy}phenyl)-N-[4-[(dimethylamino)methyl]-3-(trifluoromethyl)phenyl]acrylamide;
(2E)-3-(3-{[2-(acetylamino)pyridin-4-yl]oxy}phenyl)-N-[3-(2-aminoethyl)-5-(trifluoromethyl)phenyl]acrylamide;
(2E)-3-(3-{[2-(acetylamino)pyridin-4-yl]oxy}phenyl)-N-(3-tert-butylphenyl)-acrylamide; and
(2E)-3-(3-{[2-(acetylamino)pyridin-4-yl]oxy}phenyl)-N-[4-chloro-3-(trifluoromethyl)phenyl]acrylamide;
or a pharmaceutically acceptable salt thereof.

38. A pharmaceutical composition comprising a compound according to claim 1 and a pharmaceutically acceptable carrier.

39. The pharmaceutical composition according to claim 38, formulated for administration to a human patient.

* * * * *

UNITED STATES PATENT AND TRADEMARK OFFICE
CERTIFICATE OF CORRECTION

PATENT NO. : 7,652,041 B2  Page 1 of 1
APPLICATION NO. : 11/332674
DATED : January 26, 2010
INVENTOR(S) : Adams et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 955 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,652,041 B2
APPLICATION NO. : 11/332674
DATED : January 26, 2010
INVENTOR(S) : Ruth S. Adams et al.

It is certified that error appears in the above-identified patent and that said Letters Patent is hereby corrected as shown below:

In Column 350, Claim 1, Line 39, please delete, "(1-methylethyl)$_2$" and replace with -- (1-methylethyl)2 --

In Column 350, Claim 1, Line 47, please delete, "-☐-" and replace with -- -β- --

In Column 350, Claim 1, Line 58, please delete, "trans" and replace with -- *trans* --

In Column 351, Claim 1, Line 5, please delete, "C==C-R$^5$" and replace with -- C≡C-R$^5$ --

In Column 351, Claim 3, Line 39, please delete,"—OC(==NR$^4$)—O—," and replace with -- —OC(O)N(R$^4$)— --

In Column 353, Claim 1, Line 32, please delete, "C$_{14}$" and replace with -- C$_{1-4}$ --

In Column 354, Claim 9, Line 56, please delete, "maybe" and replace with -- may be --

In Column 355, Claim 14, Line 46, please delete, "cycloaliphatie" and replace with -- cycloaliphatic --

In Column 356, Claim 18, Line 63, please delete, "tetrahyclropyrimidinyl" and replace with -- tetrahydropyrimidinyl --

In Column 356, Claim 18, Line 66, please delete, "CO$^2$R$^5$," and replace with -- CO$_2$R$^5$ --

In Column 357, Claim 20, Line 65, please delete, "—Rhu d" and replace with -- R$^d$ --

In Column 358, Claim 20, Line 5, please delete, "Rd" and replace with -- R$^d$ --

In Column 358, Claim 21, Line 29, please delete, "tetrahydropyritnid-nyl." and replace with -- tetrahydropyrimidinyl. --

Signed and Sealed this
Twenty-fifth Day of January, 2011

David J. Kappos
*Director of the United States Patent and Trademark Office*

CERTIFICATE OF CORRECTION (continued)

U.S. Pat. No. 7,652,041 B2

In Column 358, Claim 22, Line 40, please delete, "—C(O)N$_2$," and replace with -- —C(O)NH$_2$, --

In Column 358, Claim 22, Line 44, please delete, "(R$^4$)—," and replace with -- N(R$^4$)—, --

In Column 358, Claim 22, Line 55, please delete, "—C(== NR$^4$)N(R$^4$)$_2$," and replace with -- —C(== NR$^4$)—N(R$^4$)$_2$, --

In Column 359, Claim 24, Line 46, please delete, "C(O)NH2" and replace with -- C(O)NH$_2$ --

In Column 360, Claim 25, Line 21, delete, "C$_{-4}$" and replace with -- C$_{1-4}$ --

In Column 360, Claim 25, Line 33, please delete, "C$_{-4}$" and replace with -- C$_{1-4}$ --

In Column 362, Claim 28, Line 2, please delete, "—C(R$^4$)==N—OR$^5$" and replace with -- —C(R$^6$)==N—OR$^5$ --

In Column 362, Claim 31, Line 53, please delete, "—C(R$^4$)==C(R$^5$)$_2$" and replace with -- —C(R$^5$)==C(R$^5$)$_2$ --

In Column 368, Claim 37, Line 3, please delete, "pyridino" and replace with -- pyridine --

In Column 368, Claim 37, Line 5, please delete, "]pyridino-2-carboxamido:" and replace with -- ]pyridine-2-carboxamide;--

In Column 368, Claim 37, Line 7, please delete, "-2-carboxamide:" and replace with -- -2-carboxamide; --

In Column 368, Claim 37, Line 9, please delete, "-2-carboxamide:" and replace with -- -2-carboxamide; --

In Column 368, Claim 37, Line 13, please delete, "yloxy)phenyl]propanamide:" and replace with -- yloxy)phenyl]propanamide; --

In Column 368, Claim 37, Line 16, please delete, "ide:" and replace with -- ide; --

In Column 368, Claim 37, Line 18, please delete, "carboxamide:" and replace with -- carboxamide; --

In Column 368, Claim 37, Line 21, please delete, "ide:" and replace with -- ide; --

In Column 368, Claim 37, Line 24, please delete, "ide:" and replace with -- ide; --

In Column 368, Claim 37, Line 29, please delete, "dine-2-carboxamide:" and replace with -- dine-2-carboxamide; --

In Column 368, Claim 37, Line 32, please delete, "ide:" and replace with -- ide; --

CERTIFICATE OF CORRECTION (continued)

U.S. Pat. No. 7,652,041 B2

In Column 368, Claim 37, Line 34, please delete "-carboxanide:" and replace with -- -carboxamide; --

In Column 368, Claim 37, Line 37, please delete, "ide:" and replace with -- ide; --

In Column 368, Claim 37, Line 40, please delete, "ide:" and replace with -- ide; --

In Column 368, Claim 37, Line 43, please delete, "ide:" and replace with -- ide; --

In Column 368, Claim 37, Line 45, please delete, "ide:" and replace with -- ide; --

In Column 368, Claim 37, Line 46, please delete "{[2-4,5-dihydro-1H-imidazol-2-yl)" and replace with -- {[2-(4,5-dihydro-1H-imidazol-2-yl) --

In Column 369, Claim 37, Line 8, please delete "(dimethylamino)" and replace with -- (methylamino) --

In Column 370, Claim 37, Line 58, please delete "6-tetrahydropyrinddin-2-yl)" and replace with -- 6-tetrahydropyrimidin-2-yl --

In Column 371, Claim 37, Line 27, please delete "din-ylpyrimidin-4-yl) and replace with -- din-1-ylpyrimidin-4-yl) --

In Column 371, Claim 37, Line 56, please delete "tetrahvdropyrimidin" and replace with -- tetrahydropyrimidin --

In Column 372, Claim 37, Line 6, please delete "N-(4chlorophenyl)" and replace with -- N-(4-chlorophenyl) --

In Column 372, Claim 37, Line 20, please delete "N-(4-bromo-3-ten-butylphenyl)" and replace with -- N-(4-bromo-3-tert-butylphenyl) --

In Column 373, Claim 37, Line 49, please delete "drpyrimidine-4-carboxylic acid;" and replace with -- dropyrimidine-4-carboxylic acid; --

In Column 375, Claim 37, Line 14, please delete "[4hy-" and replace with -- [4(hy- --

In Column 375, Claim 37, Line 41, please delete "5dihydro-1H-imidazole-4-carboxamide;" and replace with -- 5-dihydro-1H-imidazole-4-carboxamide; --

In Column 377, Claim 37, Line 51, please delete "imidazole4carboxamide;" and replace with -- imidazole-4-carboxamide; --

In Column 378, Claim 37, Line 17, please delete "2-yl)pyridin4yl]oxy}phenyl)propanamide;" and replace with -- 2-yl)pyridin-4-yl]oxy}phenyl)propanamide; --

CERTIFICATE OF CORRECTION (continued)
U.S. Pat. No. 7,652,041 B2

In Column 379, Claim 37, Line 15, please delete "(2E" and replace with -- (2E) --

In Column 379, Claim 37, Line 18, please delete "purin-6-yloxy)phenyl]-acrylamide;" and replace with -- purin-6-yloxy)phenyl] acrylamide; --

In Column 379, Claim 37, Line 39, please delete "(2E-N-[4-chloro-3-(trifluoromethyl)phenyl]-3-(3-{[2-4," and replace with -- (2E)-N-[4-chloro-3-(trifluoromethyl)phenyl]-3-(3-{[2-(4, --

In Column 379, Claim 37, Line 49, please delete "acrylanmide;" and replace with -- acrylamide; --

In Column 379, Claim 37, Line 50, please delete "(2E" and replace with -- (2E) --

In Column 379, Claim 37, Line 59, please delete "(2E" and replace with -- (2E) --

In Column 380, Claim 37, Line 35, please delete "(meth-" and replace with -- meth- --

In Column 381, Claim 37, Line 42, please delete "4,5,6-tetrahvdropyrimidin-2-yl)" and replace with -- 4,5,6-tetrahydropyrimidin-2-yl) --

In Column 381, Claim 37, Line 47, please delete "(1,4,5,6,-tetrahvdropyrimidin-2-yl)" and replace with -- (1,4,5,6,-tetrahydropyrimidin-2-yl) --

In Column 381, Claim 37, Line 63, please delete "annino" and replace with -- amino --

In Column 382, Claim 37, Line 36, please delete "(trifluoromethyl)-phenyl]amino}" and replace with -- (trifluoromethyl)phenyl]amino} --

In Column 382, Claim 37, Line 61, please delete "(2E)-1-N-" and replace with -- (2E)-N- --